US006265211B1

(12) United States Patent
Choo et al.

(10) Patent No.: US 6,265,211 B1
(45) Date of Patent: Jul. 24, 2001

(54) NUCLEIC ACID MOLECULES COMPRISING A NEOCENTROMERE

(75) Inventors: Kong-Hong Andy Choo, Doncaster East; Desiree Du Sart, Doncaster; Michael Robert Cancilla, Maribyrnong, all of (AU)

(73) Assignee: AMRAD Operations Pty. Ltd., Victoria (AU)

( * ) Notice: Subject to any disclaimer, the term of this patent is extended or adjusted under 35 U.S.C. 154(b) by 0 days.

(21) Appl. No.: 09/078,294

(22) Filed: May 13, 1998

(30) Foreign Application Priority Data

May 13, 1997 (AU) ........................................ PO 6784
Aug. 26, 1997 (AU) ........................................ PO 8791

(51) Int. Cl.$^7$ ........................ C12N 15/63; C07H 21/04

(52) U.S. Cl. .................. 435/320.1; 536/23.1; 536/24.1

(58) Field of Search ........................ 514/44; 536/23.1, 536/24.1; 435/320.1

(56) References Cited

U.S. PATENT DOCUMENTS 5,712,134 1/1998 Hadlaczky ........................ 435/465
5,721,118 2/1998 Scheffler ........................ 435/69.1

FOREIGN PATENT DOCUMENTS

WO 96/40965 12/1996 (WO) .
WO 98/08964 3/1998 (WO) .

OTHER PUBLICATIONS

Du Sart, D., et al., (1997) "A functional neo–centromere formed through activation of a latent human centromere and consisting of non–alpha–satellite DNA", *Nature Genetics*, 16:144–153.

Harrington J.J., et al., (1997) "Formation of de novo centromeres and construction of first–generation human artificial microchromosomes", *Nature Genetics*, 15:345–355.

Ikeno, M., et al., (1998) "Construction of YAC–based mammalian artificial chromosomes", *Nature Biotechnology* 16:431–439.

Voullaire, L.E., et al., (1993) "A Functional Marker Centromerme with No Detectable Alpha–Satellite, Satellite III, or CENP–B Protein: Activation of a Latent Centromere?", *Am J. Hum. Genet* 52:1153–1163.

Callos, M. The potential of extrachromosomal relicating vectore for gene therapy. TIG. vol. 12(1):463–466, Nov. 1996.*

Marshall, E. Gene therapy's growing pains. Science vol. 269:1050–1055, Aug. 1995.*

Verma et al. Gene therapy—promises, problems and prospects. Nature vol. 389:239–242, Sep. 1997.*

Anderson, WF Human gene therapy. Nature vol. 392:25–30, Apr. 1998.*

Orkin et al. Report and recommendations of the panel to assess the NIH investment in research on gene therapy, Dec. 1995.*

* cited by examiner

*Primary Examiner*—Robert A. Schwartzman
*Assistant Examiner*—William Sandals
(74) *Attorney, Agent, or Firm*—Scully, Scott, Murphy & Presser

(57) ABSTRACT

The present invention is directed generally to an isolated nucleic acid molecule encompassing a neocentromere or a functional derivative thereof or a latent, synthetic or hybrid form thereof and its use inter alia in developing a range of eukaryotic artificial chromosomes including mammalian (e.g. human) and non-mammalian artificial chromosomes. Such artificial chromosomes are useful in a range of genetic therapies.

34 Claims, 224 Drawing Sheets

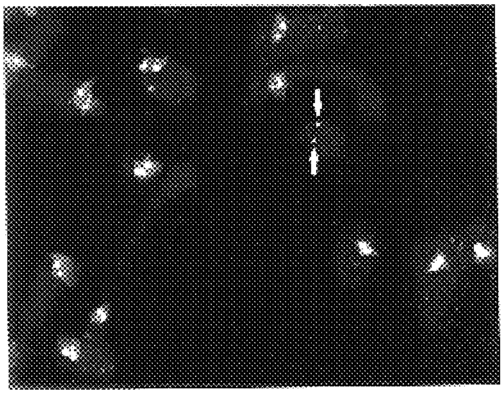
FIG. 2A(1)
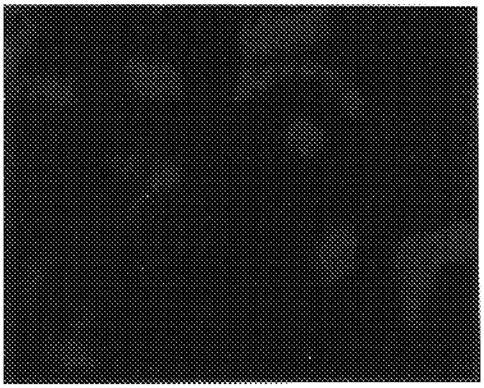
FIG. 2A(2)
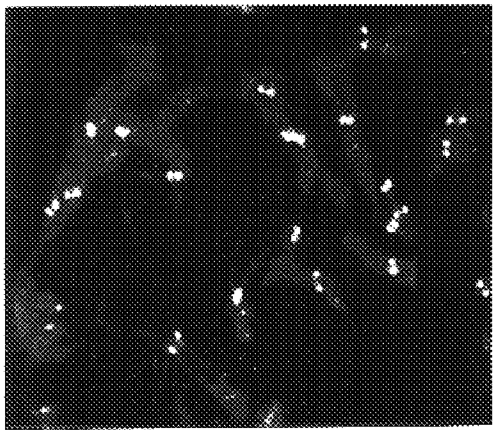
FIG. 2B(1)
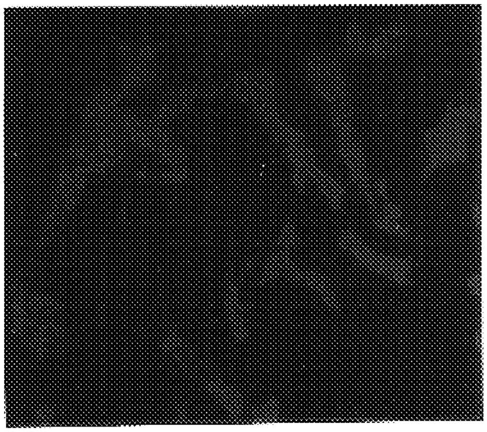
FIG. 2B(2)

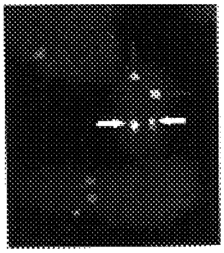
FIG. 3A(a1)
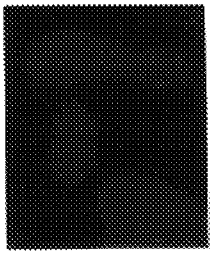
FIG. 3A(a2)
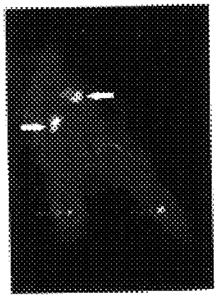
FIG. 3A(b1)
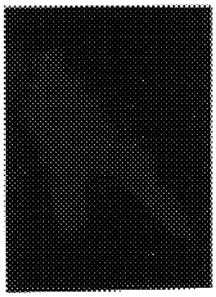
FIG. 3A(b2)
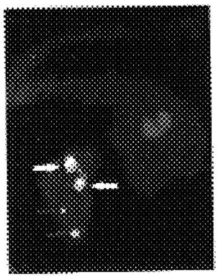
FIG. 3A(c1)
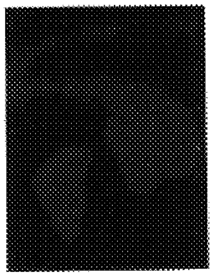
FIG. 3A(c2)
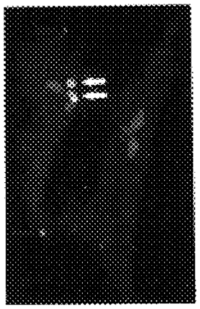
FIG. 3A(d1)
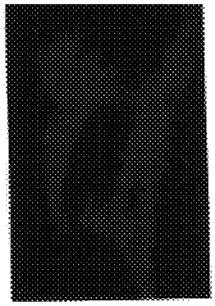
FIG. 3A(d2)

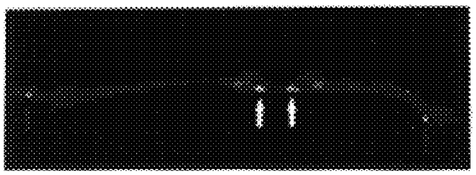
FIG. 3A(e1)
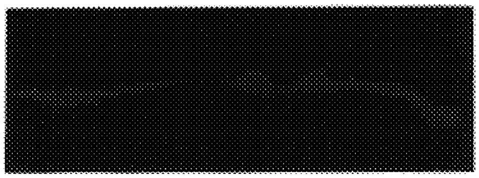
FIG. 3A(e2)
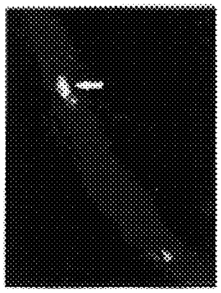
FIG. 3A(f1)
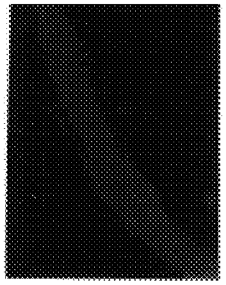
FIG. 3A(f2)
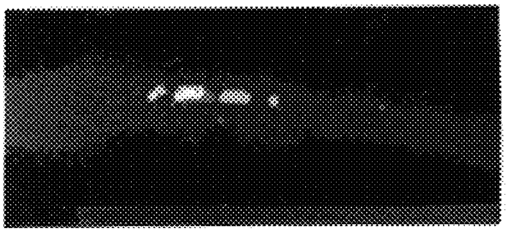
FIG. 3B(1)
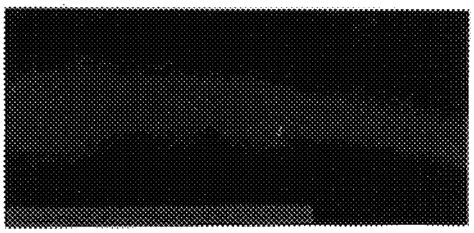
FIG. 3B(2)

GAATTCTCCT GCCTCAGCCT CCCAAGTAGC TGAGGTTACA GGTGCCAGCC ACCACGTCCA
GCTAATTTTT GTATTTTAGT AGAGACGGGG TTTCACCGTG TTTGCCAGGC TGGTATCAAA
CTCCTGACCT CAAGTGATCT GCCTGCCTCA GCCTCCCAAA ATGCTAGGAT TACAGGTGTG
AGTCACCGCA CCCAGCCCTT CTTTCAGTTC TATCACCTCT TTTTGCTATA TTTGTATGAG
AGCTTTATTA TTAGGGGCAC ATACATTTAA AATTGTTATG TCTTATTGAT AGATTGATCT
GTCATTATGA ATGTCTGTAT TCATTCCCTG ATAGTATTTC TTTTTCTAAA TATTTTTCTG
AATGTGTCTG CTATTAACAT AGCCACTCTG GCTTTTTAAA ATTAGTATTT TTATGGTATA
TATTTTTCCT TTTTTTTTTT TTTAAGTTTT AGATGTTATG TTTCCTTATA CTTAAAGTGG
GTGTCTTATA GGCAGCATAT ATCTGGGTCT TGATGTATTA TTTAATCTGA TAATCTCAAC
CTTTTTGTTG GAGTGTTTAG GCCATTTACA TTTAGTGTAA TTATAGACAT GGTTTGATTT
GCTATACCAT CTTTTCATTT GTTTTATATG TGAGCCATCT TTTCATTGTT CTTTTTTCAT

```
CTTTGACCAT TTTCTTTAGT ACTGAATACT TTTTTTGTAT TTCATTATAT CTATTGGCTT
TTTAGTTATA CCTCTTAAAA TTTTTTTTTC TGTTTTATGT AGGATTTATA ATATACATCT
TTAACTTATC ACAGATTACC TTCAAATAGT ATTTTACCAG CTCAAGTGTA ATGTAGAAAC
CTTACAAGAG TATATTTTCA TTTCTGTCTC CTAATTTTTA TGCTATGTCT ATAATACATT
AGGTTTGTTG TTGTTTGTTT TTACCTTATT GCTGTTGGCT GGGGTCAGCA AACATTTTCT
GTAAAGGGCT AGATAGTACA GGCATACCTT GGAGATACTG TGGGTTTGGT TCCATACCAC
CACAATAATA CAAATATGCA AGAAGTGGAT ATCACAATAA AGTGAGTCAC ACAAGTCTTT
TGGCTTCCCA GTGCATATAA AAGTTTTGCT TATACTACAC TGTAGTCTGT TAAGTGTGCA
ATAGTGTTAT GTCTAAAAAA ACACATACCT TAATTTTAAA ATGCTTTATT ACTAAAAAAT
GCTAACAATC ATTTGAGCAT TCAGTGAGTT GTAATCTTTT TGCTGGTGGA AGGTCTTTTC
TTATTGATGA CTGATCGGGG GTCAGGTGCT GAAGCTTAGG GTGGCTGTGG CAGTTTCTTA
```

AAACAACAGT GAAGATTGCA ATATCAGTTG ACTCTTCCTT TCATGAAAGA TTTCTCTCTA

GTGTGTGATG CTTTTTGATA GCATTTTATG CACAGTAGAA CTTCTTTGAA AATTGGATCA

ATCCTCTCAA ACCCTGCTCT GCTTTAACAA CCTAAGTTAA TATAATATTC TGAATCCATT

GTTGTCATTT CAACAATTTT CACAGTGTCT TCACCAGGAG TAGATTCCAT CTCATTTCCT

GAGATGGAAT CTTTGCTCAT CCATAAGAAG AAATTCCTCA TCTGTTCAAG TTTTATCATG

AGATTGCAGC AATACAGTCA TGTCTTCAGG CCTCACTTCA CTTTTAATTC CAGTTCTCTT

GCTGTTTCTA CCACATCTGT GGTTCCTTCC TCCATTGAAG TCTTGAACCT CTCCAAGTCA

TCCATGAGGG TTGGAATCGA CTTCTTCCAA ATTCCTGTTA ATATTTATAT TTTGACCTCC

CATGAATCAT GAATGTTCTT AATGGCACCT GGAATGGTGA ATCCTTTCCA AAAGGTTTTC

AATTTACTTA GTCCAGATCC ATCCATCCAG AGGATCCACT TTCAATGCCA GTTATAGCCT

TATGGAATGT ATTTCTTCAA TAATAAGGCT TGAAAGTTGA AATTACTCCT TGATCCATTT

TCTGCAAAAT AGATGTTGTG TTAGCAGGCA TGAAAGCAAC ATTAATCTTT TTGTACATGT

CCATCAGAGC TCTTGGGTGA CCAGGTATAT TGCCAGTGAG CAGTAATACT TTGAAAGGAA

TTATTTTTCT TAGCAGTAGG TCTCAACAAT GGGCTTAAAA TATTTGGTCC ACCATTCTGT

AAACTGATGT GCTGTCATCT AAACTTTGTA GTTTCATTTA TAGAGCACAG GCAGAGTAGA

TGTAGCATAA TTCTTAAGGG ACTTAGGATT TTCAGAATGG TAAATGAACA TTGGCATCAA

TTTAAATCAC TAGCTGTATT AGCCCCCAAC AAGAGAGTCA GCCTATTTTT TGAAGCTTTG

AAGCCAAGCG TCGACTTCTC CTCCCTGGTT ACAAAAGTCC TAAATGGCAT CTTCTTCCAA

TATAAGGCTG TTTTATCTAC ATTGAAAATC TGTTGTTTAG TGTAGCCACC TTCATCAATG

ATACTATCTA GATCTCTTGG ATAACTTGTG CAGCTTCTAC ATCAGCATTT GCTACTTCAC

CTTGTACTCT TATGTAATGG AGTGGCATCT TTCCTCGTAC CTCATGAACC AACCTCTGCT

AGCTTCCAAC TTTTCTTCTG TAGTTTCCTC GCCTCTCTCA GCCTTCATAG ACTTGAGGAT

AGTTAGAGAC TTGCTTTGGA TTAGATTTTG GCTTCAGGAA ATGTTGTGGC TGGTTTGATC

TTCTATCCAG ACCACTAAAA CTTTATCCAT ATCAGCAATA AGGCTGTTTT GCTTTCTTAT

TATTTGTGTG TTCACTGGAG TAGCACTTTT AATTTGCTTC AAGATATATT TCTTTGCATT

CACAACTTGG CTGACTGGTG CAAGAGGCCT AGCTTTCAGA CTATCTTGGC TTTTGACATG

CCTTCCTCAC TAAGCTTAAT CATTTCTAGC TTTTGATTTA AAATGAGAGA TGTAGGCCAG

GCACAGTGGC AGGCACAGTG GCATATGCCT GTAATTCCAA CACATTAAGA GGCCAAGGTG

GGAGGATTGC TTGAACCCAG GAGGTGGAGG TTGTAGAGAT CACACCACTG CATTCCGTCC

TGGATGACAG AGCAAGACCT TTCTCAAAAT AAAATGAGAG GTGTGCTTCT TCTTTTTGTT

TGAGCCCATA GAAGCCATAG TATGATTTTT AATTGGCCTA ATTTCAATAC TGTTGTGTCT

CAGAGAATAG GGAGGTCTGA AGAGAGGGAG AGAGGTGGGG GAATGGCTGG TCAGTGGAGC

AGTCAGAACA CACATAACAC TAATAAATTG TTTGCTGTCT TATATGGATG TGGTTTGTGA

TGCCCCCAAA CAATTACAAT AGTTACAGCA AATATCACTG ATCACAGATC ACCATAACAG

ATATAAGAAT CATGGCAAAG TTTGAAATAT TCTTGAGAAT TAGCAAAGTG TGACACAGAG

AAACAAAGTG AGCACATGCC GTTGGAAAAA ATTGGTGTTG ATAGACTTGC TCCATCGCAA

GTTTGCCATA CGCCTTCAAT TTATAAAAAA CACAATATCT AGGAAGTTCA ATAAAGTGAA

GTGCAATAAG ATGAAGTATG CCTGTAAATA TTTCAGGCTT TCCAGACCAT AGGGTTTCTG

TTGCAACTGC TCACCTCTGC CATTATAGCA TGAAAGCAGC TATAGAAAAT ATACATAAAT

GAGGCCTGTA ATCCCAACAC TTTGGGAGCC CAAGGTGGAT GGATCACTTG AGGTCAGGAA

TTCGAGACCA GCTTGGCCAA CATGGCAAAA CCCCGTCTCT ACTAAAAATA CAAAAATGAG

CCAGGACTAC GCATGCCTGT AGTCCCAGCT ACTTGGGAGG CTGAGGCAGG AGAATCTCTT

GAACCCGGGA AGGGGAGGTT ACAGTGAGCC AAGATTGTGC CACTGCACTC CAGCCTGGGC

AACAGAGTGA GACTGTCTCA CAAAAAAAAA AAAAGGAAAA GAAAATACAC ATAAATGAAT

GTATGTGGCT GTGTACCAGT ATATCCTCAT GCTCTAGCTT GCCAACCCTT GCTTTACACT
GTCAGTTACC TTCTAAAGAG ATTAAAAATC ATAACAATAT CTATTACGTT TATTCACATC
CTAGTGTCAT TTCTTCCTTA TGTAGAATCA AATTTCATTC TGGTATCATA TTTCTTCTTT
CTAAATAATT TCCTTTAATA TTTTTTATAG CACAGGTCTA ATAGCAATGC ATTATGCAAT
TCATTGCTAT TAGACCTGTG CTATAAAATA GCAATGAATT ATGTCAGTTT TTATTTGTCT
GAAAAAGTTT TTTGTTTTTG AAATATACTT TTGCTGGGTA TATAAATCCA TGTTGCATAA
CTTCTCTTTT CTTCAGCACT TTAATGAAGT CACTCAGTTA TCTTCTGGCT TGTATAGTTT
CTCTGGCTGC CTTCAAGATT TTTTCATTGT CTTTAATTTT TAGCAGTTTG ATGTGTCTAG
GAGTGATTTT CTTTGTATTT ATCCTTTTGG GGGCCTCTTA ATTTCTTTGA TCCTTTTTTT
CTTTTTTTTT TTTTTTTAAT CAGTTTTGGT CTGTCTCCTC AAGTGGGCTG AAAAAAAAAG
AAAAATAAAA TCATAGTTTA AAAAACTAAT TTTGGAAAAT TTTCAGCTAT CATTTCTTCA

AATATTTATC CTACTCTATG CTCCCCTCCT CCCCTTTCCT TCTGTGACTC AAATTACAGG

TATATTTAAC CATTTTATTT GTTCACGGCA CTTGGATGCT CTGCTTTCTT ATTTTTTGTC

TTTCATTTTG GATAATTTCT ACTGACCTAT CTTCAAGTTC ACTGATTCTT TTCTCAGTCA

TATCTAGTGT GCTCAACGCC TGTTGAAGAA ATCCTTTGTC TTTAATATCA TGTTTTTTAT

TTCTAGCATT TTCATGTAAC TCTTTGTTCT GGTTTCCATC TCTCTACTCA CTTTTTTTTT

TTTTTTTTTT TTTTTTTGAG ACAGAGTCTC GCTCTGTCAC CCAGGCTGGA GTGTAGTGGC

GCGATCTCGG CTCACTGCAA CTTCCGTCCC CTGGGTTCAA GTGATTCTCC TGCCTCATCC

TCCCGAGTAG TTGGAATTAC AGGTGCCCAC CACCGTGGCT GGCTAATTTT TGTATTTTTT

TAGTGGAAAC AGGGTTTCAC CATGTTGGCC AGGCTGGTCT TGAATTCCTG ACCTCAGGTG

ATCCACCTGC CTCAGCCTCC CCAATTGCTG AAATTACTGG CATGAGGCAC TGCACCCAGC

TCTGCTGACA TTTTTTATCT TTTGCTGCAT TTTGTCTACC TTTTCCATGA AATCCTTTAA

CATAGTAGTC ATAGTTACTT TCAATTCCTT GTCTGACAGT TCTGACATTC AAGTCTAGGT

CTGTTAATAG CTTTGTGAGT CTGTTAACAG CTTTTTTTCA TTCTTGTCTG TGTGTTTTGT

ATTTCTTGAT TGTATGCCAA ATATTGCCTG TAAAATAAAC TTAGATAAGT CATACTTCTA

TCCAGAAATA GGCACATTTT TTGTGTCCAG TCATTAGTGT GGAGGGAGGT TGGGGCAGTC

TAGTCAGTGG CTGAACTAGG TTTGGATTTG TTGATGCTAT ACTTAGAATG CACCAGACTT

CCATTCACTG CAAGAGTGGG CTGCTGCGCT TTGTGATTCA TGTGAGGCCT GAATTGTGGG

TTTTTCCTTA GTGTGTCCCT CCATGCTCAG ATTTCAGCAA GTCTTCATAT CTGTGCCACA

GAAGGAATCT GACCCATGCT CTTTTTGACC TCCCCAAGTG ATCAACTGTT GCTTGTTATA

GCTTGTCATG GAGTAAGAGG GTGTTTTTTT AGTTTTCATC CTCCAGCCTT GGTCTTGGGC

CCTGAGCTCC TAGACTCCAG GAGTGGATGG AATCCAGTGA TTTCTCAGTA ATTCAGCCCC

TTCTCCAGTA GTGGCAGATC TCTGCTTTGT ATCAGTGCAA GATCCTGGGC TGAGCTCATT

TTCTGCCCTT CCTCGAGTGG CAGACAGCTC TTGCTTTCAC CCTTCTACCA AAGGCAGTGC

ATCTTTTCTT GGGCCTCTCC CCATTGAACT TATGACTTTC ACATAAGAGA AGGGCTCATG

TATCAGAGAA TTCTGTGACT TTGTGCCACA TACAGAGTCT CTCAGTTCTC TTGCCCTGCC

CCAGTCTTTT TTGTGAGCAC CTAGTAGAGA CCCTTGGAGA AGAGCAAGGA AGCGAGTATG

GACTTCTTTT GTGTCTGTCG ATTGCTTTGT TTCTCAACTG CTACTCTTGG ACTTTAAGAA

TTCATTAAAA TTTCAGCTGT TTTCTTTTAT TCTTTTTGTT TTTCTTTTTT TTTTTTTTTT

TTTTTAGATG GAGTCTTGCT CTGTTGCCCA GGCTGGAGTG CAGTGGTGTG ATCTTGGCTT

GCTGCAACCT CCGCCTCCCG GGTTCAAGCG ATTCTCCTGC CTCAGCCTCC CAAGTAGTTG

GGATTACAGG TGCCCACCAC CACACCTGGC TAATTTTTGT ATTTTTAGTA GACACAGGGT

TTCACCATTT TGGTCAGGCT TGTCTCAAAC TCCTGACCTC ATGATCTGCC CGCCTCAGCC

TCCCAAAGTG CTGGGATTAC AGGCATGAGC CACCGCGCCA GGCCTCAGCT GTTCTCTTTT

TACCTGCTGG GATGGCTAGT TTTCTGTGTC AACTTGACTG GGCCATGGGA TGTCCAGATA

TGTAATTAAA CAGTATTTCT GGGTGTTTCT GTGAGGGTGT CTTCAGAAGA GATTTGCATT

TGAATTGGTG AACTAAGTAA AGCAGAGGGC CCTGTCTAGT AGGGGTAGGC ATCATCCAGT

CTGTTGAGGA CTTGAATAGA ACAAAAGGCA GGGGAAGGTT GGAATTGCCC CCTCTCTGCT

TGAGCTGAGA CATCTATCCT GCCCTTGGCA CTCCTGGTTC TCAGGGGTTC AGACCTGGAT

TCCTGGTCTC CACCTTGCCC ATGGCAGACT GTGGGACTTC TCAGCCTCCT ATCTAATTAA

TAAATCTCTT CATACACACA CACACACACA CACACACACA CACACACACA CACACACACA

CCCTATGTAT CCTTCTGTTT CTCTGCAGAA CCATATCTAA TACACCTGCT TTTATGACGA

TTACCTATCG ATTCTGTATT CTGCCAAAAC TGAAAACAGT TCATTTTTCC ATCTCTTCTC

AGAGAGGCTT GTCAGCCATT AGTTCTCTGA TGGGCTCAAG AAGTTATGCA GTTTTTTTTT

TCTCACTGTT AGGATGGAAT TGATATTCTG TTGAAACTTT CTATACCTAA GTGGAAACTT

GTTTTGAGGT TATTTTCTCT ACTTACTTTT GCTGGAAATG GAACACTCTG TATCTAGTTA
AGACACATAA ACTGACTTGT GATACCATAA TGTTGTGTTG AATTTTATAT TCTTAGAAAA
TCATCTGTCA AGGTGTTAAC TAATGGCAAA GCATTTAATA AATCAGCATT CATGTATTCA
GGTGCTCTGA ATTATCTGAC TTTTAAATTC TTACTTTATA AATGAGAAAA TTGGGGCATG
GAAAAGTTAA CTCTCCTAAC CCCGAATTAT TACATTATTA AGGACAGGAC TTAGAGGCCA
GATATCTTAA GTCATTAATA TTCTTTGGCT CACAGAATTG GCAGTATAAC CTAAAGGTAA
TAACTAGGTG ATTTTCTTTT ATATCAATTA AATATGTCAG TTTTCAAATA TTCATAAGTA
CCTACTGTGC AGGGAAAGAA CATGCCATAC AAAAGATGTA GTCCAGGCCT TTAAGAAACT
TTCATTTAAT GGGAACTCAA GAAGTGTACA TATAAGGAGG GAAGTAGCAG TATGGTACAA
GATAATACAT ACATATCAGT GAATGATATT GCCAAAAAGT GCTATTGATA GAGAAATAAT
TCATTTCTGC AAACAGCTGC TGATCTCCTA CTGAAAACAG AGGAGGGAGA ACAGGACGCC

TCGTGGTCAG GATAGAAGAG AAAGACCTTG AGTTGAGCCT TGAACAGTAT TTAATATTCA

AAAGGTTAAG AGAGGAGAGC AATTGAGGAG GGGAGAATAG TTCCAGCACA AATGATGGTG

TACAAGATGA ACACAGTCAG TAAAGAGCAG ACTGGTCTGG ATGGAGAGGA GGATTTGCAT

CATTTGGGAT TACGTCATTT AGACCCTTGA AAGCCAGGAT TGAGTAAAGC CACAGTGAAG

CGACTGGCTC GTATGGAAGC TTTATTTTAA GAAGATTAAT CTGGTAGTGA CATGTGCCAA

AAACTGAATA GGTAGAAATG AGATGCAGAG AGCCCAGTTA GAACTAAGTC TGGTGCAGTA

ATGCAGGATT GAGGCAATAA ACACCAAACT ACAGTATCAC CAGATAATGG ATGTTTGAAC

GGACGGTTTA AAGGAAAATT GATGGTATTT GGTAATTTAT TAGATAATCC AGGGCCATGG

AATGAGAGGG GAAAATGACT AACCATAGTC ATCAAATGGT TTTTCTTAAT GAATCTGAAT

TTTGGTGTAA GAGCAACATT TTCTTAGGCC TTGCCTAGTT GGTACAGCTG ACTATGATAA

TGACTGCTAC CATGCTTGTT CCTCTTTTAG CAGCTGTGAG TCCCCCACCA GCCAAACAAT

GAGCCTCTTG AAAAGGACGA TGCCTTTTCA CTTCTCTCCA AGTGCTTGGC AAATAGGAGG

CCTTTTGAAG TTACTTTATA GTTAGGGGTT CCCAGTGAGT ATTTGAAATA TTAAGTCATG

CCCGTGGTTG ACAGCATGGC CCTACTGCTC ATCATCAGCT ATTAACCTTA GGCAAGTTAA

TGAACTTTTC TAAGCCCCAG TCTACTCATT TATAAAGTGG GATTATTAAT AATGTCTACT

TCATAAAATT ATGAAGCCTG AGTTAGGTCA TTCAGATAGT GTTTAGTCTG ATTCTTCGAA

CCTAGTAAAC AGTCAGTAAA CAGAAGCAAA TGCCACATGC CTGATTTATA TCCAAGGGGA

GAAAGGTAAA AGTGAAATTT TCATGATTTA TGGATTCAAA TTATACATTT CAAAGATGCT

TTATAAGCTA TTGTTTTGGT AAGAAGAATT GAGCTGAAAC AGAATTTTCT GACAGCAGTG

ATTATTAAAT GGTGAAATAG GCTATTGATG TCTTTAGAGG ATATAGATGT TCACCTTTTG

CATATAAGTG CACAAAAATT CACTAAGTAG ATATGTCTGT CTACACAGAG AGAGAGAGCG

TGAGAGCATT AAAGTTAGTA AACATCCCCC TCGCTTTTTT TTTTTTGAGA CAGGGTCTTA

CTCTGTTGCC TAGGCTGGAG TGCAGTGGTG CAATCGTGGC TCACTGCAGT CTCAACATCC

TGGGCTCAAG CGATCCTCTC GCTCAGCCTC CTGAGTAGCT GAGGTGTGCA CCACCACACC

CGGCTAATTT TTAAATTTTT TTATTGTAAA GGTGAGGTTT CACCATGTTG CCCAGGTCTC

AAACTCCTGA GCTCAAGCAA TCTGCTCACT TCAGCCTCCA AAAATGCTGG GATTACAGGC

GTGAGCCACC ACGCCTGGCC AGTAAACCCC ATTCATTTAC ATCATCTTAC TTGTCCCTCC

AAAATCCTGC AAAGTAGGTA GGTTCTGTCT TTATTTGTTA TTTAGGTGAA GAACTTGAAG

TGGTGTTGAG GAATAGGTGT TTTGCCAAGA GTCACGCAGC TGGAGTGGCA GAGCTGTATA

CTCTTCTGAT TCCACCAACG CTGTTTACAT CACATCTGGA GAAAAGTGCT CTGAGGCACA

GATGTTTAGT GGGAGGGATG AGACACAGGC TGCAATGCCT AAAGATAATC GGGAATAAAA

GCAGAAAACA AGACGTTTGT TTCTGTTAAA ATGAGACAGA AAATAAGGCG TTTGTTGTTT

GGGATTGAGC ACTTGGAGAA GTGGGGAGCG ATTTGATTTG GGTGAGACTG CTCCTGGAAT

```
GCTGCATCTG  GTTCTGGACT  ACTCATTACT  AGGCTTATAG  AAACTAGCTG  GAGGAGGTTC

AAAGAAAAGC  TCCAAAATGA  TTAGCGGGCT  GACGGGATTG  ATTTATAAGA  AATATTAAAA

GAATTAAATG  TGTATAGCTC  AGCTAAGCAA  AGATGAAAGA  GACCAGCTAA  ATGTATACAA

ATATCTGAAA  CGTGCAAACT  TTAAAAAGAG  AGATTAATTA  TTTAACATGA  TACACGGGGG

CACAATATGC  AGTCACAGGA  TGAAAATTTC  AGCTGAGTAT  CTAGAAGAAT  TCCCCGATAG

TGAATCTGTT  AAGGCTGTCT  GTAGTGTGGC  CTTTCCCTGG  AGAGGCAATA  GAAATTTCAA

GTCTTACGAT  TTTAAAAGTT  TCTTGGGAAC  TAGGTATTAG  ATGATGTTAG  AGAATTATTA

TTAATTTGGT  CAGGTATGAT  AATGGTATTG  TAGTTCTATA  AGAAAAATTG  TATTTTTTAG

AGTTACATAC  CCTGAAATAT  AAGCATAGAA  TATGATGTAG  GAGATTTGCT  TTAAAATACC

ACAGTAAGGA  AAGAAAGGAA  GGAGGAAGAA  AAGAAAGGAA  GGGGAAGAAA  GGGAAAAAGA

GGCAAAGAAG  GAAGAGAAGG  TAAGAGAAAG  AAAAGAATG  AAGGAAGAAG  GCTGGGCACT
```

GTGGCTCATG CCTATAATCC CAGCATTTAG GAGGCCAAGT TGGGAGGATC ACTTAATTAA

GCCCAGGAGT TCAAGGCTGC AGTGAGCTGT GATTGCGCCA CTGCACTCCA GCCTGGGTGG

CAGAGTGAAG CCCTGTCTCT AAAAAAAAAA AATAAGTTAA AAAGAAAGAA AAGGATAGAT

GAAGTATGGC AAGATGTTGG TAATGTTGAA CCTGAAGGAA GTTAATATGT GAGTTCACTT

TCCTCTTCAG TCTTCTTTAT GTATGTTTGC CAACTTTCAT AATAAACAAT TTAAATTATA

TTTTCCTGAT CAAAACTTAG TAGCAGTATT AATCCCTGGG CTTCCTGACT AGAACAGCCT

CATTACCACA TGGGCAGAGT TCTGGCCGAC CAGGGACCAC GTAGTGGTTC ACCATCTTGC

TCTGGTAATG TGGTCTGGGC TGAAGGGCCC TTTCTAAGGT TGTAGATAGA AATCCAGGAA

ACTTGTTAGA ACTGCAGACC TATCAGGGTA CCTGCAGGAG GTGAGTCTAC TAAGGTGAAA

AAGCAGAGGG CAGAGGTCGT GATTAGCAGC TGACCGCCCC CTGCTTTTCT GTCCCTCATT

CGTGGAAAAT TGAGTGGAGC TCAATTTTGA GTGGAGCTCT AAGTAGCTCC ACTTGTAGAC

ATTGAGTGGA GCTCTAAGTG TCTTCAGAAT AGCAAAACAC TAGTTTTCTT TTTCTTTTCT

TTTTTTTTTT TTTTGGAGAC AGAGTCTTGG TCTGTCGCCC AGGCTGGAGT GCAATGGCAC

GATCTCCGCT CACTGAACTC TGCCTCCCGG GTTCAAGCGA CTCTCCTGCC TCAGCCTCCC

GAGTAGCTGG GATTACAGGT GCCCACCACC ACGCCCAGCT AATTTTCCTA TTTTTAGTAG

AGATGAGGTT TCACCGTGTT GGCCAGGCTG GTCTCAAACT CCTGGCCTCA AGTGATCCGC

CTGCCTTGGC CTCCCAAAGT CCTGGGATTA CAGGTGTGAG CCACCACACC CAGCTGCAAA

ACCCTATTTT TCTTGAATGG AGAAACACTT TCCCCTTATT TATTGAGTTT GGGAAGCAAG

AAGAGGGGTA ATTCATTAAG TGAAAATTTC CAAAATCCAG AAAACATCGA TAAAGCAGCA

GCTTAATTTT TTTAAGGAAG AATTTTTTAA ACTATCTTCT TTTGAGCCTC TTTAGGAAGA

CCTCACGTCC TTGCCTTGAA TGTTGAGAGT GGGAAATCCA GGGAGTTTTG GAATGCATGC

CTTATGTCTG CTTTTTTGTT TGTTAGAGAA ATATAAATAT TTTATCTAGG TTTTGCTGAT

GGCAGTCAAG CATGAACACA ACCCACTGTT TGAGAAGCTG TAATTTCTGA ATTTCTGCAG

AGTGCACATC TAGGCCAGCA AATGGCAGTA AGAGTGAGGT GGATTTAGCT CAGTGTAAGG

ATGAACTCCA GAACCATCGG CTCTGACTGA AAGTGAAGCG GCAGCCGCGT TGTGGGAAAG

CTGGCTGGAG TCTCTCTCAT AAGCAGGCAT TCTTTTTCTC CAGCCCGTCA CTGTGTTGGT

TTGGGCCCAC GGTAAGCCTC CTGGCCTCTA GGCTGTAACC CCCACCATCC TCCTCTGCCT

CGCCTCCAGA GTGATTGTTC TGAAGCACAA CTGGATGTCA TTCCCCTTCC TGAACTCCTA

GCACCTACAG GGACTCCATC CCTTGTGCCC CACATACCTC ACACGTAGAC ATTCCTAATG

AAGATTTGAT TGAATTATTG TAAACTCAGT GCCTCCCACT CTTCTAGTTG CCTCTCTGCC

TGCCTTTGTA CATTTATTTA TTTATTTATT TATTTATTTA TTTATGAGAC AGAGTCTTAC

TGTATCACCC AGGCTGGAGT TTAGTGGCAC CATCTCAGCT CACTGCAACT TACCTCCCAG

ATCAAGCAAT CCTCCCACCT CAGCCTCCCG AGGAGCTGGG ACCATAGGCA CGTGCCATAT

GCCCGGTTAA TTTATTGTAA TTTTTGTAGA GATGGGGTTT CATCGTGTTG CCCAGGCTAG
TCTTGAACTC CTGGACTCAG GCGATTCGCC CGTCTCAGTC TCCCAAAGTG CTGGGATTAT
AGGCGTGAGC CACCATGCCC AGCCGCTAGC ACTCATCTTA ATCGTATATT TACTTATCTG
GCTTTCCCAC CAGACTGCGG GCTCTTCAAG AGTAAATGCC ATGTTTTCAC CTTTATTTCC
CCAGTTTGTG GCACATTCTA GGCACTCGCC ATCATGAAAT AAACCTCTGG AGCTGTGATA
TTACAAACGT GGAAAGATGA CGAGCACTCA GCAACTTTCA GTGAGTAAAC AAAGGCTTTC
ATTCAGCATG ATTTATTGAC TGCCCAAATC TGGGCTGCTT CCTGTCTGTG GTTCAAGGAG
AGCATAGTCT ACAGAACCAG AGACCTGGCT ACTCTGGAAG TTAGACTTAA GCCCACCCCG
GTCCTTGAAT GGGGAAATAT TTCCCTTCAT TCCTGTGTTT TAGGGACAGA AAGATGAGTA
ATGCAGTGAT ACATGCTGGA AATGTTTATT CCACTACCCG AAGCTGCCTC TCAACTTAAC
AATCCATGAA AGAAACAAGA TGGTATATAA CTTTTTCTAA TTTGTGATGC CTTTGTTTAT

TTGTTTCCGG TTAAAAGAGG AGGTGGCATT GAATTGTTTG TTTGGTTTGG TTTCTTCTTC

AATAAGAAGC ATCTTAATAT AACTAGACTG GACATCTGTC CCATTTTCAA AAATTACAAG

TTTCGATCAT TGCTAAATTG TACAGATCCC AATCTGTCTG CTCTGCATAC ATTTGCATTT

ATAAAAGCAG AAGCAGACTA GCAGTCTTTC TAATGCAATC CCCCAAATGC ATGAAGTATT

AGATTGCTTC TCCCTATTGG TTCATGCATT GCTAAAGGCT TAAAAGGATC ATTGATTTTA

ATTATTTAAT GTGTACAGCA GGCTGAGCTT CCTTTCTTTT TTAAGGGAAG AACCTTCAGG

GGCATTGCTT TAGTTTTTTA ATGTTAAATC TCATTTTTCT TTGAAAATAA GAAGTTAAAG

CTGTATTCAC ACAAGCTCTC AAAGTGCCAG ATTTTCATTG TGTTTTTAAA CCATCTAGGA

AATGTTTGAT TCTAATGAAA CATTACTGCT GAAAATTGGG CTGAAATTGC TGGGCTGGAA

ATATTGTTAT AACTTCACAT GATTCCAGTG TTGTATTATT ATTTTTTCTT TTTCTTTTTT

TGACCCGATA TAGATGAAGC GAAGAGACAA GGAGCAATCC CATGTGTAAT AGAAAAAGGC

AGCCTGAATT GTTGTTGCTG TTTTTGAAAT TTAAGCTGGT TTTCGATTAA ATTCAGTAAA

TGGTCCAGGA CTATAAATGT TGAACATTTT TTACCGTGTG ATTTAAATTT TAGTCTTATT

GTTTTTTTTT TTTTTGATGG TTTACATTTT CCCCATGGGA AGCAGCTATG TCATGTCGGC

ATGATTCATC ATGGTAACAT CTCGGGTTAT TTTGGTTTGT GTTATGTTCA GAAAGCGGAA

TGCCAAAAAT AAAGAGTGGT TTGTGATGTC TAGTGTGTCT TCCTTTAACA AATCAAAGGC

TTTTATTTAA TCCACTTAAT GGGACACTGC AGAAATTTAA AAAATGGAAG TCCCATCCAC

AGAAGGCAGG TACTATGATG TAAAAAGTTT AGGTGGGGGA TTAATAGAGT GATCATATAA

TTTATGAGCT AAACCGGAGG CACTTTTTTT TTTGAGATCG AGTCTCACTG TTGCCTAGGC

TGGAGTGCAG TGACGTGATC ACAGCTCACT GCAACCTCCG CCTCCCGGGT TCAAGCGATT

CTCATGCCTC AGCCTCCTGA GTAGCTGGGA CTATAGGCGC CCACCACCAT GCCCAGCTAA

TTTTTGTGTT TTTTGTAGAG ATGGGGTTTC ACCATGTTGG CCAGGCTTGT CTCAAACTCC

TGACCTCAGG TGATCCGCCC ACCTCGACCT CCTAAACTGC TGGGATTACA GGCGTAAGCC

ACCATGCCTG GCCCAGAGAC ACTTTTGAGA GTGAAGAGGA AGCTGAGAAT AATTCACTGA

TCTACAACTG GGACCATCCA GGGCAAGCCA GATGCCATTA CCACTAGCTA GAAAGCTTGC

CAAGGTCTCA TTTACCTTGG TATATAGCAA ATTCTTCTTT TGAATTCTGG AAATTCTGGT

AAGTCATTGA GGTAGCTCTG TGCCAAGGAG CAATATGGTA GAATTCTAAT ATTTCAGGCA

GACAACACTT TCCTGCATTT GTAGCAGGTA AAGGGAGGTC AGGGCAGAAG ACAAAACCAC

TGGGACTCGA CAAAGGGCAT AAACGTCTAA TGCACCTGAT GTAGCTGATG GTAAATTGTT

ATCAGCTAAA GATCTTTCAT AATAAATAAA CTTATCATTT GTAGGAGGGC ACAGAAATCG

TGGAAAGCTG GGATTCAGGT TGCCTGTGGC TTTAATTCTG GAATCAGAAA TATTAGTCAA

GGATATCAGT CTATGAAGTA AGTTTTCAAT GTTATATGCC ACAAGATGCA GCTGTCCTAT

TTTCACTTCC AGTAATTCCT TCTGAATTAA TACACCTTAA AAATAGCTGC AGCTTCTCAA

ATCTGTGAGA ATCGTATGTG CTGCTTGCTA CACTTTCTTT TTCCTGAAGG CTCTTTGAGG
TCTTTCAAGA ACTCAATTCA ATTCAGCAAC AATTAGGGGG TCTAAGGTAT ACAGACGCTG
TGCAAGATGC TCCTGAGACA CAAAGAGGAG GTCAAGCCCC TGCCTTCAGG CACCTCTCTA
TAATATAGGA GGAGAAAGAG AAGAAACACT AATACACATA GGTAGGTGCC ATTAAAAGGG
TACATACATT AAAGCCAGGT GGTAGGTGTA AGAAGATTTG TAACATGAGA ATTTTCTGCA
TGTTTGAAAT ATCTTATAAT TTTTAAAAAT TAAAATGGGA GATACATATA TATGTATTTA
TGTATGTATA TATGTATGTA CATATACACA CATATATACA TAAATATATA CATAAATATG
TATATATGTG TATATAGACA TAAATATGTA TATATGTGTA TATATACATA AATATGTATA
TATGTGTATA TAGACATAAA TATGTATATA TGTGTATATA GACATAAATA TGTATATATG
TGTATATAGA CATAAATATG TATATATGTG TATATAGACA TAAATATGTA TATATGTGTA
TATAGACATA AATATGTATA TATGTGTATA TAGACATAAA TATGTATATA TGTGTATATA

GACATAAATA TGTATATATG TGTATATAGA CATAAATATG TATATATGTG TATATAGACA

TAAATATGTA TATATGTGTA TATAGACATA AATATGTATA TATGTGTATA TAGACATAAA

TATGTATATA TGTGTATATA GACATAAATA TGTATATATG TGTATATAGA CATAAATATG

TATATATGTT GTATATAGAC ATAAATATGT ATATATGTGT GTATATAATA ATGTGTGTCA

TATACACACA TATATACATA CATAAACATT CTGCATTATA CCATTCACTT TGTAACCCAT

CTTCCCTAAA AACTGTCTCA TAAAGAGTCT TCTTTTCCCT GTACCTATGC AATGGTAAGT

AGCAAAACAC ACATTCTTTT GGGTCCCCAT AACATTCCCT GTAGTTTGCC CTTAACAGTC

TTTGATGTGA AATTTACTGT TTCTGTCTTA ACCTTGCCTG TCTCGCGTAC ATGGAGTTTT

GGCTCCTGGC TCCTAGTCTG CATCTTCACC CCATCCCTTG CCCAAAGAAT CTGGTTATGT

GACCACTGCT CATCTTTTCT GCTGCCACAA CTCCAGTCCA AGCCACAAAC CTCTCTCTCC

TGGACTCCTG CGGGGAGTTC CTTTCTCTCC CTGCATGAGT CTATTCTCCG CACAACTGGC

ATAGGTAAGT GAGACTGCGG AAGAGGCAAG TTTGCAAGTC CAGAGGAAAT GAAGACTCTG

CTTGTGCACA TGCTGGGTTT GACGGGTGCT GGATATCCGA TGGATGGCCC TTAAGGTGAG

CTCAAGGCTT AAGGGAGAGA TAGGGGCTGA TGATCTGAGA TTCATCAGTG TGTGGCTGAT

GTTTAAACCC AGGGGACAGG ATAAGAAGGT TATTCCAGGG AGAGCGTAGA TAAAGAAGCT

AAATGGCTTC TGGGTCCTTA GTCATTCAAA ATCGGACCTC TGAGGCAGGA GGAAAGCCCA

GAAAGAGTAG ATTCCTGGGA CTCACGGGAT AAAGACTTTC AAAAAGTGGG GGCTGGCCAG

TGCTGCTGAA GGAAGTAGCA GGACCGGAAC AGAAGGGTAA TCGTTGGACC TGGAGAACTT

GAATTTGAAT TTTAAGGTTG GTAACCTTAA AAAAGAGCAA TTTTAGATAC CTTTTGAAAT

TATTTGCAAG ATTTGTTTGG TATATGTGTT ATTCCAGGCA AAGGGACCAG AAAAGTAAAA

AATACTTACT GAACAGTTAC TGCATGCCTG GCACTGTAAC ACCCTGTTTA ATTCTCACGG

CAACCCTATA GAGTAGGTGT CATCATCCCC ATCTTACAGA TGAGGATATG AGGTGCAGCT

AGATTAAGCA GTTTGCCTCA GGTTACACCA ACTGGTTAAC GTAGAGCTAG GATTTGAACC

CGGATGGGCT GATCCCAGAG CTCATGCTTT AAATCGCTAG ACTGGTGCTC ACAGAAGACT

GGGACCGAAA AAAATTAATA AAAAAAATAA GGAGCCCCCT GGGCTAGCAA ATTAGGAGTT

GTTCAGACAG ATGTGAAAAG GAAAGCAAGG CAGAGGGAAA GTCACTGTAC AGAAGAGAGA

GACCCATGAC AGCAGAGACA GTGAGCTGGT AAAGTGGCTG GCGATCTAGC CCCTGAAAAT

ACCTCCAGAG AGGCAGGCTC ACGCCTGTAA TCCCAGCACT TTGGGAGGCC GAGGTGGGCA

GATCACCTGA GGTCAGGAGT TTGAGACCAG CCTGGCCAAT GGCGAAATCC CGTCTCTACT

AAAAATACAA AAATTAGCCG AGCATGGTGA CAGGCACCTG TAATCCCAGC TGTTCAGTTG

GCTGAGTCAG GAGAATAGCC TGGATCCGGG AAGTGGAGGT TGTAGTAAGC CAAGATTGCG

CCACTGCATG CCAGCCTGGG CGACAGAGCA AGACTTTTCT TAAAACAAAC AAACAAAAAA

GAAAAAAGAA AAGGAAAGAA GAAAGAGACA AAGAAAGAAA GAGAGAAGGA AAGAAAGGAA

GGAAGGAAGA GAAGGAAGGA AGGAAAGAAA GAAAAGGAAA GAAAGAAAAA GAAAGAAGAA

AGAAAGGAAA GAAAAGAAAG AAAAAGAAAG AAAGAAAATA CCTCCAGAGA GCCAGGTCTC

TTAGGCCTTC TGAGAAACTC ACATCCCTTT TGATGAACAC AAATGCTTCA CACTCTCAAT

GTTATTGGTA ATCCAAGTTA TCAATATACC TAAATCACTT AGTACTGAAT CTGGCATATA

GTAATCACCT AATGAAGAGA TAAGAGTCAT GGAGTATTCT GAAGCAATTA GAATCAATAG

ACTCAATATA CACATGGCAA CAAAGTTGGA TCTTAAAAAC CGACCTGAGT GAAAAAGGAA

AGGGAAAGAT ACATAACACG GTACCATTAT GTAAATTGAT AATATATGCT TACACAATTT

GTAAGAACAC ATACAAATAG ATACATGTAT ATTAAATATA CTCGAACGGT TACCTATGGG

GTGGTGGCTG GAGTGGGGGT AAGTCCGTAA GCTGTAATGG AACCTAAACA AATACATGAA

ACGAGTAGGA ATCAGAAGGA GTAACAATAA AAATGTGCCA TGAACTGAGG AGTGTAAATT

AATCAACTCA CTGCATCTGA GGTTAAAAAT AGAAAGATGA TAATTGTTAT TCTTATTACT

CGTAGGTCTT CCACTTGCAC TCAGCTTTAC AATGTTGGAC TATCCTTCAG ATGGCACCCT

CCTTGCACTT GCTCAGGCAG GAGAGCTTTT TCCTCCAGCT TTCTAGGTGA TTTAATATAT

CAGGGAATAA GTATAAAAAA AGGCACGGTG CTCCCTGGGT AGCCTTTCTG GACTTCAGAG

CTAAATTGCA AAGTCAGTTT TACACATGTG ATTTCATCTA TGAAATTAGG GCAAGGTAGA

AAACTGGCAC AGAAAAAATG TGATTTATTA TGGTGTTACT ATCCCTTACA AGCGGAGTGT

CAGCTGCCTC TTTTTGTCCA CTGATTTAAG GCAAGATGAA CTGAAAGTGG CTATGATCAC

GTCTTCAAAA GCACACTCTG GCCCCTCGGC TGCAGGCGCC CTGCACATTC CCCAGCTGCG

TGTCCGGTGG TGACACAGTG CATAATTGTG GCGCCTTCCT GGTGCAAACT GTCTCACTTA

GCTCCGTCTT GCTGGCACAG CAGAAAGGAA GAAATCGAAA ATGTTTGGAT TTCAAAGGTA

ACAAGAAGCT GGAAAACAAC TACTGGCCGA GTCTGAGAGT TTCAGCGGAG ACTGGTGCAG

CCTTGTGTTT TTCCACTGAC AGCTGAAAAT GAGCCCAGCT TCAGTGAAGC TTGTTTCCTT

CCCTCCTCAA GGTTACCCAC AATTCTCAGT TCTCTCAGGA AAGCCAAAAA ATGAATTTGA

GGGTTTAGGA TTGTGGTTCT TTTATCTATT ACAGGATTGA TAATATGTTC CTCCACCAGA

TGTTCTGCTT GTAACAATAC TCACTTCCTG ACACTACTGC ATATGCAGGA GTGTTACTAC

CAAGGTAAAC ACAGAATTGG CTGCCCAATT CCAAATCCCT GAACTGAGTG AGAGAAATCA

GAATTATAAT AGGGGATTCA ACAGAGCTGG CTACGGATGT GCCAGTGGTC AGATACTTTG

CTCATCATAC GCAGGTGCTG CTGCTCTAGC AACTGCTCAC TGCTTCATTT CCTGCCTTGG

TCTTTAAATA CTGCTTTTCT CAGCTCAATT GGCTTTCTTC CCTCTGGCAG TCACGTTTCT

TTGGGTCAAA CAGCAAATGA TTCTTTAGAA TCACCTGGTA CTCAAAGGAG CTACAAGACA

TTGGGCATCC ACTTCCACTC TCTTGGAAAA ACAATTTTAT GGAAGCCAAG GTTGCCATAG

TGCCTCTTGA GGTTGTTTGC TCAGCCAAGG CCCAAGCTTT GTGCTTCAAA CATGAAATTA

GAGAGCTTCA GAACAAGATC CACATTTTCA ATGGCCTCAC CCAACTGGAT AAAAGAACAA

TTGCCATATC TCAATGACCA CCTTTTTCAG GTGGGATGGT AGATGCTGGA ATGGGTCACA

GCATTGCCCA ACCAAACTTT GCAAAAAAGG CTGGAAGCTC TGACTGGGGA CCCTAAATAT

GCAAAAGTTG ATAGGCTCTT CATGCAGAAT ATGAACCCCG TGTATGGATA TAGCTAAAGG

GTTGGCCTTT ATGTTTCTAT TCCTTCACAA ACCTGGTAGA ATAGATATGC TTGTTTCCCT

TTAAAAAATG TCAACAATTG CATTTATGAT GCTGTGTATA GTAACTCACA GATCATGCTC

CATGAAAATG CTTCAGAACC CAATATAAGG AGATTTTTTA GCCATGTGTG ACAAAAGAGA

GGCCATTTCA GTGTTGAAAT TGTTCAGAGA AGTATTTGAT TATGTTTTCT CAGATCTTTT

TATTTTTATT TTTTTTGAAA CAGAGTCTCA CTTTGTCACC CAGGCTGGAG TACAGTGGCT

GTGGTCTCGG CTCACTGCAA CCTCTGCCTC CCAGGTTCAA GCGATTCTCC TGTCAGCTTC

CCGAATAGCT GGGATTACAG GCGCATGCAC CACCATGCCT AATTTTTGTA TTTTTAGTAG

AGACAGAGTT TCGCCATGTT GACCAGGCTT GCCTTGAACT CCTGACTTCA GGTGATCCAC

CCACCTCAGC CTCCCAAAGC ACTGGGATTA CAGGCATGAG CCACCGTGCC CAGCCTGTTT

TCTCAGATCC TGTATTTGTT TCTGAAGCCT TCATTTCTAT CTTCTTATTC ATTTTGGAAG

TAGTACACCT AAGTAAGGTT TTTAACAATC AAATATCTTT GGAAAATTCC CTGGTTCCTT

TCTTATTCCT ACAAAAATAT GTTCAGTATA GCTGATGTTA TGTTTCTTTC AAATTATTCA

TTTCTCTATC TCAGAATTTA TCTCATGCCT AATTGTTATT GAATAGTCTT CACTTCTTGT

CATCCAGTTT CTGGTCTCTT ATTTCACTCT AAGTCTAAGT GGCTATTAGA ATAAAGAGCT

TGTAACAGAT TCTTTCTCCA ATATGTCTTA TCTTTTGACT GCATGCCAGT GACAAACTGT

TAACTGTTTT GATTCTTCAT AACATTCCAC AGAACATGCT GACTCCTCTC TTCCTGAAAG

CAATGCCCAA GCACAGCATT GTTAGATAGT ATGTACGCAA CAGGGACATG GGTGCATAGC

AAAAACTAGA AGGAAGGAGG ACCTTCCTTA GCAATGGGTG ATATGGTCCC TGGACTTAGA

CTCCAAAGGG TCGTGAGGTG AAACACACAT CGTCCATACC CAGGAAGCAC ACAGGTGGGA

TGGAAGAGCT GTGCCTAATG AAACTTCATC CACGTGGAGG TGGAGGAGGC TGCAGCTGCA

AGAACTCAGA GCTGCCTTAC CCAGACCAGG GACCAGGGAG GGCTTTCTGG AGGAAACAGC

CTCTGAACTG CCAGCTGATA GAGGAGCTCT ACCTCAACTC TTCTGGTTCC CCAGGGCTGC

TTTTCCACGT CCATTTATTG GCACTGAAGT TTGAATACCT TCAGGGGCCC GAAAGCCTGC

CAGGTCCTCT TCTCTGCAGA GCAATCACAC CAACCTGCAA AGGGCTAGGA AAGGGCTGTC

ATCATCTCCT ACTCAGAAAC TGGTTCACTG GAAGGACTCA GGGGCCACTG AATACATCCT

GGCAGCTTTC ACAAGAAGGG CTTCTGACTC AAGGATGTTT CCATCTTTGC CAGGTCGCCT

TTTCTCCTTC TCTTAGAGTT TGGAGGACGC AAATGTGCTG AGAAGTCAAC CTTTCCTGCA

AGGTGAGACA CAAGGGCCTT TCCCAGCAGA AAGAAGAGAG CAAATGGAAG GTCCTTCTTC

CTCCAGTAGA GGATGGACTC TGTCTGGCAG CCACCCAACA GGAAAAGCAC AATGCATGCC

TGCCTGCTTC CCTCCCTCCC TCCGTTTCTC CCTCCCTCCC TCCTTCCTCC CTTCCATTCT

```
CTTCCCTTCC CCTCCCTTCC CTTCCCCTCC CTTCCCTTCC CCTCCCCTCC CCTTCCCTTC
TCCCTCTCCT TCCCTTCCTC TTCCCTTCCT TCCTCTTCCC TTCCTTTCCC CTCCCCTTCC
TTTCCCTTCC TCCCTCCCTT CCTCCCTTCT TTCCTTCCCT TCTTTCCTTC CTCATTTCCT
CCCTTCCTTC CTTCCTTCCT TCCTTTCTTC CTACTTTCCT ACCTTTAGGG CTCTGTGTCT
TTGGAGTCCA TTCTGATTAT GCTGTAATGT CTGCCCCTTC CTCTTCTCTG TCAAAAAATG
AAAGACATGG AAGCCACTTG CCTTTTACTG AATTAAAAAT TAGTAAAAGA GCTAAAAATT
AATGGTTAAA AATGTACGCA TAAATTATGC AGTATACTAA CCAATGAAAA GATACACTTC
TCTTAATTAA AAGCTGACAG GGAGGGAAAC AAGAAAAGAG AAACACAAAA CAATAATCTA
AATGACCTAT TAGTTGGAAG AACAACATCA GAGAAAATAG ATACTGTGTA TAGTCATGTG
TATGTCTATG GAATAACATT TGTAGAGAAA TCTGGACTGA TCCTTTCTGA GTAAAGAGAG
CTGTGGGTAC AATTAAGGGG AGATTGAAAG GAATCCAAAA GCATAGCAGA TGCTGTGCCT
```

CACTGGAATG GTTGCCGATC TCCTCCAAAC TATGAAGTGT TTGAGGCTCA ACTTTAATAT

AATTAAGATA CAAAGACAGA ATGAGAGAAA GAGAGAAGGG AGCTCACTGG AAGAACACTC

AAGATTCCTT ACTACTCATT CTCTAAAATT ACAATTGTTC TAGATGGAAA AGAAAAAAAG

CTTCTCTGTT AAAAAAGGAG CTTGTGCTAT AGGAGGTTTA AAATATACTT CTGACCCATC

TCCAACATTC TAAATCCTTC CCAGAAAAGT ATGCCAATCC CAAGAAATAT TCAATCAAAT

TGCTGGAAAG AAAAATACAA AATATTAAAA TGTATTAGGA AGCGACAGTA ATTAAATCAG

AACTGGAGCA GGAATAGACC AGCAGATCAA TGAGACAGAC ATCAAGTCCC GGAATGTGGA

CTTGCAAATG CATTAAGTAA TATGATATGC AATAAAGGTG GCACAGTGAA CCAATGGGAA

AAAAATTAAT CTTATAATAA TTGATATTGC AATAATTGTC TAGTAATTGG GGGAAGAAAT

AAGCTTATTC CTTATCTCAT TTCTTTTTTT CTTTTTGAGA CAGAGTCTCA CTCTGGTAGC

CCAGGCTGGA GTGCAGCGAT GCGATCTCTG CCCACTGCAA CCTTGCTCTC CCGGGCTCAG

GCGATTCTCC CACCTCAGCC TCCCGAGCAG CTGAACTACA GGCGTGTGCC ACCACTCCCG

GCAATTTTTT TTTCCATTTT TAGTAAAAAT GGGGTTTCAC CATGTTGCCT GGGCTGGTCT

TGAACTCCTG GGCTCAGGCA ATCCACCCGC CTTGGCCTCC CAAAGTGCTA GCATTACAGG

CATGAGCCAC CGCGCCTGGC AGCTCATTTC TTAGACTAAA TAAATTGGAG ATGGCTAAAA

GATTTCTATG TAGGCCAACT ATGTTTTTAA AAAGTTTTTT TTTTAAGGAT ATCTGCTGGA

ACCAATCATG CCACCAACCA AAGATGCAAG ACTATAAAAC ATACCCAGTT TTTCAAAGCA

TTTAAAAATT ATTCTAAAAA TATTTTTTCT CCAGAAATTT TGCATTGATT CCCTGAAGAA

GCATTAATAT GGGACCTGAC TTATAAAATG ATGAACTCAA TCTCCCCACT CAAGGTAGGA

GTCTCTCAGA TTTAAAAAAT AAGCATCCTA GTCCTCTTGT CCCTGTAAAA GTTAACCCTT

ACACCTGAAA CACCAGGAGA CTGGCGGTTG TTTGCATAGG GGTTACAATT AAAGTTGAGC

TACCTCTGAC ATCTATTAAC ACCAAAATTA GTAAACTATG CATGTATGGA GACTTTTATG

ATTGAACTTG TTTATTGAGT CAAGAGATAT AGTTTACAAT GAAAATTTGG GGCATATCAA

AATGACCTTG GCTTAGCTTA GCATTTGCTG ATGTTAACTA TTTTCTTCAT TGGGCTGATT

TTAGTTGCTT AGGAAAAATA CAAACACACA CACTTTAAAA TTATATTAAA ATCCCGTCCT

AAACCTCAGA GTCCAGAACC GCATCCTAAC ACTGGTCATG CATAATATGT TTAAATTTTT

GTGCTTTAAA AACTACAAAT AAGGAATGTA TTAATAGTTC CACAATCAAT GGTCAGTTAG

CCGAGGGAAG ATTAGCATAG TTAAAGACTT AAAATGGCTT TACAACATAT ATCAAAAGGA

CAAAATAAGG GGAACAGAGT CTAGAAATGA GGAAACTGGG ACACAGGCAA AAAAAAAAAA

TGAGAACTGG GACATGAATA ACGCAAGGGA TAAGACTAAT ACACAAAACA CCCCAAATAA

ATAGCCAGCA TTTGCTGAGC TCTTACTGTG AGCCTGTTCT AAGCACTTTA CATATATTAA

CTCATTTCAT CCTCAAGGAA CCATCTGAGG CAGGCACTGT TATCATCTCC ATTTTACAGA

TAAGGAATAG ACCCAGAGAG GCTGAGCAAC TGGGCCTATT CCACAGCTAC TATGGTGGAG

ATGAGATTTA AATCTAATCA TTGGCTCCAG AGCCCATGCA CCCAATGGCT GCACTAAGTG

AATGCATGCG CTATCAACGT TGCCAAAAGT GGGCCACAGC TCGGATCTGC GTTTTCCAGT

AGCCAAAGCA GAGAGTGTGA TCAGACCTCA CTTTAATAAG CAAGTCTCAA GCCAGAGAGA

GGTGGTATCA GGCAGCAAAC AGGCTGCTAG TCGAAATCCC ACTTCTTCTC TGAGTGGTCC

ATACAGTTTT ACTCTACTTG CTTACAGAAT GAAAATAGCT GGAGTTCAGG TGCGCTTTCA

ATGCCCTGTT GTCAGGATTG GGCTTTTCAA GTTTATTTTT TGTTGTTGTT TTTAATAGAC

TGTACTTTTT AGAAAATTTT TAGATTTACA GAAAGATTGA GAGGATAGTA CAGAGAGTTC

CCGTATACCT CACACCCAGT TTCTGCAATT ATTAACCTCT TACATTCATG CGGTACATTT

GTTACAATTA ATGAGCCAGG GCCGGCCGGG CACAGTGGTT CAGGCCCCTA ATCCCAGCAC

TTTGGGAGGC AGAGGCAAGC GAATCACTTG AGGTCAGGAG TTCGAGACTA GCCTGACCAA

CATGGTAAAC CCTTTCTGTA CTAAAAATAC AAAAAATTAG CCAGGCATGG TGCTGGTTGC

CTGTATTCCC AGATACTCAG GAGGCTGAGG CACAAGAATT GCTTGAACCA GGGAGGCGGA

GGTTGCAGTA AGCCGAGATC GTGCCACTGC ACTCCAGCCT GGGCAACAGA GCGAGACTCC

ATCAAAAAAA AAAAAAAAAA AAAAAGAAGG AAGGAAGGAA GGAAAATTAA TGAGCCAATA

TTGAGACATT ATTATTACTA AAGTCCATGC TTTATGCAGA TTTTCTTAGT TTTTACCTGC

TGTCATTTTT CAGTTCCAGG AATGCATTCA GGATGCCATA CCACATTTAG TTCTCATATC

TGCTTAGGCT CCTCTTGGCT AGACTGAGTT TTAATCTACT TTCTGCAGAG CCTGAGAACT

TTAGCATAAT TTCCTTGGAA ATTACAGCTC AATATTTTCA AGCACTTATA CAAACAGCCT

AATGTTACGT TGGCCCATAA CAGTGTTTCA AGGTAATAAA CTTCTTTGTT TTCTGTGCCG

ATTGAAAGAA CTGCTGCTTA GCCTCCTGCC AGATGATGAA CTGGGTACAC ACGAGCATTT

TTCCAGGTAA AGCATATTTC GTGCGACTTC TTAAGCTGCA GCCTTATATG CAATAATTGT

CCATTTACAA GACTTATGTT CGAATTTCAG GCACTCTGTT TTCACTAACC ATATCCTTCA

ACTTTGATAA GTACTGCTTT AATCAACTCA GAAAATTTAA CTTGACTAAT TTTTTTTCAC

CATCAGTTTT TTTTCTGTTG ACTCTTTCTC CTTTTTCTGT TTGCCCAGAA ACATGCTCAG

GATTCTCTCA GGCTTTAAAA AATGAAAAAA TGTTTCCTGC AATCTAGTTA CTCCTTGATT

CTCTTGTTCT GTTTATCGCT GGAATTCTTG AAAGCTTGGT GTATTAGTCT TTTTTCATGC

TGCTGATAAA GATATACCTG AGACTGGATA ATTTATAAAG AAAAAGAGGT TTAATGGACT

CACAGTTCCA CGTGGCTGAG GAAGCCTCAC AATCATGGTG GAAGGCAAAA GGCATGTCTT

ACATGGCAGC AGACAAGAGA GAATGAGAAC CAAGGGATTT CCCCTTATAA AACCATCAGA

TCTTGTGAGA CTTATTCACT ACCACAAGAA CAATATGGGG TAAACCGCCC CCATGATTCA

ATTATCTCCC ACCGGGGCCC TCCCACAACA CGTGGGAATT ATGGGAGCTA CAATTCAAGA

TGACATTTGG GTGGGGACAT GGCCAAACCA TATCACCTGG CCTATAGCAT TATTTCCATT

TCTTCCCCAT CCTTTTATTC CTCAAACCGG TACAACCAGA CCTCTTTTTT TTTTTTTCTA

CCTGAAACTG CTCTTTTGAG GGTAGCTGAT AAGTCCAAAA TACTGTCACC TTTTCTCAAT

TCCGTTCCTT CTTATGCCTT TGGAGCAATT GACTGTGTTG GTTGCCCCCT CCTTTAAAGT

GTCTCTCACT TGGTTTTATG ACTAATGATG ATTTTCTTTT TCCTCTCTAA ACATTCCGCT

ATCTTTTTAG CTTCCCTTCC CCCTCCCATC CCCTAAATGT CCTTGTTTCC CAGAATCTGC

CTCACCTCTT TGACTTCTCT ATGCCCTGTC ATTCACTCAT GGGTCTTTAT TACATTATTG

CATCTGTGTC AATAACTCTG GTCTTTCTGT TAAGTTCCAG TCTCCCATTT TCAAATGTCC

CCAGACATTT CCAATTGAGT ATCTCTCCAA TGTATTTAAC CTGCTAAATA TCTAACACAT

AATCTTTCCC ATCAAATCGT TTCCTCTTAA GCTTTTCGTT ATTTCCTATT AGACTCCTGC

ACTTCTCCCA GGAGCCCAGA CTTAAAACCT TGAATTTCTC ACCATAACCT CTCTTTTGTC

TCCCATAATC AATTAGTAGC AAGTGTTATC AATGATTACT TGACAATATC TTTTTCTATT

TCCCTCCCTG CTATGATCAT TCATCTAGCA AGAAGAGTTG GCCCTTTGTA TCTGTGGTTT

CTGCATCCCT GGATTCAACC AACTGTAGAT GGAAAATATT TGAAGAAAAA AGCGTCTATA
CTGAGTATGA AAAAATTTTA TTTCTTGTCA TTATTCCCTA AACAATACAG TATAACAACT
ACAGCATTTA CACTGTAGCG TATAGATCTT ATAATCTAGA AATGATTTCA AGTACACCAT
TATATATAAG GGACTTGAGC ATCTGTGAAG TTTGGTATTT GTGGGGCATA CTGGGACCAA
TTCCCCCATG GATACAGAGG GACAACTATA TTTACTCAGT GCTTACTAAA TACCAGTTGG
CCAATGTGTT TTTCTTTTTC TGTTTTCCTG TCTTTAGTTT GCCCCTTGCC AATTAATTCA
ATAGTGCTGC CAATGCCAGG TGTACCTTCA GAATATTCTA TTCTAATTTT GTCATCTCCA
AGCTTAAAAA TATTTAATGG GCCAGGCGCA GTGGCTCACA CTTGTAATCC CAGCATTTTG
GGAGGCCAAG GGGGGGTGTA TCACTTGAGG TCAGGAGTTC CAGACCAGCC TGGCCAACAT
GGCGAAACCC TGTCTCTACA AAAAAGTATA AAAGTTAACC AGGTGCTGGA GCATTTGCCT
GTGGTCCCAG CTACTCAGGA GGCTGAGGCA GGAAAATCAC TTTAATCTGG GAGGTGGAGT

TTGCAGTGAG CCAAGATCTC TCCACTGCAC TCCAGCCTGG GTGACACAGC AAGACTCTAT

CTCAAAACAA CAATAACAAC AACAACGAAA AACATTTAAT GGCTGCACCT TGCCTGTGAA

AAATGCATTT CTTGGCCAGA TGTGGTGGCT CAAACCTGTA ATCCCAACAC TTTGGGAAGC

TAAGGCCAGG AGTTCGAGAC GAGCTGGGAT ATATAGGAAG ACACAATCTC TACAAAAAAA

AATCCACAAA ATTAGTCAGG CTTATTGTTC ATGCCTGTAG TCCCAGGTAC TCAGGAGGCT

GAGGCAGGAT TCCTCAAGCC CAGGAGTTCA AGGCTTCCGT GAGCTATGAT GGCACAACTG

CACTCCATCT TGGGTGACAG AGCAAGGTCC TATCTCTGGA GAAAAAAAAA AAAAGAAGGC

ATTTCTTAGG AGAGTTCTTC TCTGTAGAGT CCTAAGGGTT CCATGGAACT CCTTAAAAGC

ATCAGAGTAT GTGAGTGCAA TGGGAGGAAG CATTTAGCCA GAGCAGTTGT GCTCCCATTG

CATATTAATT TTTAAAAAAC AAAGCTATAA AAAAAAGTTG AAAACTACTA CGTTAGCATC

AGCCTGACAT TTAATGGCCT CGTAAATCAA ACCTTAATTG ACTTTTTAGC CAGTTATGCT

ACTAGCCAAC TACAGACAAC ACACTTTTTA ACCAAATTAG ACTAATAGTT GTCATCAGTG

GAAATCAAGT TTGCCATTCT TCCATGCCTT TGCTCACACC ATTACCTTTT CTGGAATGTC

CTGTACTCAT CTTCCTGTGT TGAACTCTAT ACCCAACTTT AAAAACCTAG CTCAAAGTTC

AACACTTCCA TTCCATTTCA AAAAGAGCTT TCCTCTTCCT TAAAGTTTAA GAACTCATTT

TCATGAATCT TTTTGGCATT TATTGCACAC ATGCTTGCTT TGTGTTATTT GTGTTCAGCC

TCATATGCCC CCAAGGTGTT TTAGACTCCT TAACGGCAAA AATGATGCTC TAAACACCTT

TCTATCTTTC ATAGTGTCTT AGTCTGTTTG TGTTGCTATA AAGGAATACC TGAGGCTGGG

GAATTTATTT AAAAAAGAGG TTTATTTGGC TCACAGTTCT GCAGCTATAT AAGAAGCATA

GTGTCAGCAT CTGCTTCAGG TGAGGGCTTC AGGAAGTTTC CACCCATGGT AGAAGGCAAA

GGGGAGCAGG CATCACATAT CAAGAGAGGA GGAAAAAAAG GAAGGAAGAA AGGAGGGTGC

CATTCTCTTT CAACAATCAG TTCTTGTGGG AACTAATGGG ACAAGAGGCT GGGCACGGTG

GCTCATGCCT GTAATCCCAG CCCTTTGGGA GACCAAGGTG GGTGGATCAC CTGAAGTCAG

AAGCCTGAGA CCAGCCTGGC CAATGTGGTG AAACTCCGTC TCTACTAAAA ATACAAAAAT

TAGCTGGGCC TGGTGGCGTG TACCTGTAGT CCCAGATACT CAGGAGGCTG AGGTAGGATA

ATCACTTGAA CCCGGAAGAC AGAGGTTGCA GTGAGCTTGT GCCACTGCAC TCCAGCCGGG

GCAACAGAGT GAGACGGTCT CAAAAAATTT TAAAAACTTT AAAAATAATA GAGCAAGAAA

GCACCAAGTT ATTCAGGAGG GATCCACCCC CAATGACTCA AATACCTCCC ACCAGGCCTC

ACTTCCAACA CTGGGGATCA ATTTCCGTAT GAGATTTGGA GGAGACAAAT ATCCAAACTA

TATCACATAG TAATGAACAT AGTACCTTAT CTATAGAAAG CAATGGCTAG ACAACTGTTG

AATGGCTAAC CAAATCTGCT TTCCTATGGT CTCGCTCTAG AGGGGGTCAG TATGAGTTTC

TGTCAAAAGG AGAAAAAAAA ATGTATAGTC AGTTTTGTGT GTGTGTGTGT TCATGTAAAA

GAGATCAAGA GAAAAGAACA AGAGAAATCA TGAAAAGGAG GGGGAATATA AGAATAATAC

ATAGAAAAAA GCAAATTATC TTGTTTATCA GTAATACCCA AGGGGGTAGA AATGGTAAGT

AATAATCCTT CTTCACTTTG TCTGTAGTTC ACTTTTTTGC ACCTTTATTT TGATGAATTC

ACATCGAAGA CATTAACTCA TTAAGGCTTC CAATATTTTT GGAGATAAGA AGGGCTGCTA

TGCTCTTTAT AGATGGAAAA CTTGGGTCAT TAATAACTCA AACAAGGACA TAACAAAGAA

ATGGAGCATA AACTGCCAGG TCCTGACTGT AGATTTGGAT TCCCAGTTGG TGTCTTGTCA

CCCTTTGTTA CTCTTCCTAA AGTTATGATC TTTTCTTGTG CATAGGAAAT TCATAGTGAT

TTCCCATCAC CCTTGGGATT ATCATAGCTC CTTTAAGGTC CCCTCTATGC ACTCAATAAC

ATCAACAGTA AGTGTTCTTC GAGCACTTAC TGAGTGTATA TCATTGTGTT CTCACGCAGC

ACCCACAGAT CTCACCAAGA ACCTAGCTGA AGCCTGTAGA ATGAATAGGT AAGTACTGCC

ATGCCAATCT GGAGTACTCA AGCGATGCAA ATGATTCCTT TAATTGTACT TTTGCAGGCT

TGTCAGTTTT GCTCATGGAG AAGTGGCTAC TGCATCCATG TTATATCTAT GTAATGTTGG

ACTGCGAAGC ATCACTTGAC TTTTTCCAAG CAGAAATTAC AGCTGATGAC AAGCTGCTGC

TGAGAAAATG GATATTTTTC TGAATTCAGT TCTACGTGGA AACAGCTGAC TAGTTTCCAT

TGCTGTAAGA ATGGCTCTTT TGCTCTTGGT TGATTTTGAG TAATGGCTTT ACTTCTGTAG

AAAGGAGATT TCATTTGAAG TCCACTCAGG GATTTGGTTC AACAAACTGG AGTACAGGTT

TCAGAAAATA TCTCTTTAAT CCTCCAATAA TAAATTTTCT CATCTATAAT TCCTGGAACA

CTTCATCCTT TGCAGCCGAG CATATAGATA GATTTGTTGC TCACTGTGTT CTGATTGCCA

CTTTGACCTG CTTTTTCAAC TTAGGTTACA AATAGAACAG AATCTCTCTG ATTTTTCTCA

TTAATTGTTT GAATTCCCAC TTTTCCTCAT TAGCAAGAAG TCCAGTATCT TCCTGAGAAC

TTCCTTTTCT CAATCTAGGA ACTTACTTGG TCCATAAGGT AACAGTCTTA TTTCTGACTA

TCAAGGAGAG AAATAACAGG AGCCATTATC ATCTTCATGG TGTCACTTTT GAAAACTGGT

CCTCTGTAGA TCTTCAGATT CTTGCGTTAG TCCATTCAGC TGCTATAACA AAATTGCATA

GACAGCATGG CTTATAAATA ACAGAAATGT ATTTCTGACA GTTCTGAAGG CTAGAAAGTC

AAAGATTAAG ACACTGGCTG ATTTGGTGTC TGGCGAAGGC CCATTTGCTC ATAGATGGAC

GATGACCTTT CACTCTGTCT GCACATGGCA GAAGGGCAAG AGAGCTCTCT GGGTCTTTTT

TATAAGGGCA CTAATCTCAT TTTTGAGGAC CCTGCCCCCA TGACTTAATC ACCTCCCAAA

GGCACTGTCT CCCAATACCA TCACCTTGAG GGTTAGGATT TCAACATATG ATTTTGGGGG

GACAGAAACA CGCAGTCCAT CTCGCTTGTC CACTCCATGG TGGTATTCTT GCTGGATCAG

TTTCCTCCTT GGGGTGCATT TGTGTTCCAT GTCTAACTTG CAAGTTATAG CAGGCCCGAT

AGCAAAGTAT TCCAATGTTG GTATGCAGAG GCATTGAATA ATCAGAATGA ACCCACGCCA

TAAACAACTG GTAGAGCTGC AGAGAGTACC AGCTGATTAT GAGCCCTGGG TAACAGTGGT

TTTTAGTTCC TATGTCCGTC AGCCCTTTTC TCCCATAGTA GCCCCACTGT GTTGAAGTGG

CTGAATCGAC AGAAGCTTCC AGCTTGGGCC ACATGCTCAT GGAACCAATT CTCCTTATGA

GCCGTACAAG AGCTGGGTTG CCATTCTGGA TACCCTCTTT TTTCAAGAGA TTTTATTTCA

AGGATATTTT TTCTTTTATC AACTACAGGG ATTATTTAGA ATCTTAGGGC AGTGGTGCCC

AACCTTTTTG GCCCCAGGGA CAGGTTTTGT GGGAGACAGT TTTTCCATGG ACCAGTGTCA

GGGGGCTGGG AGGCATGGTT TTGGGATGAG TCAAGTACAT TACGTTTGTT GTATACTTTA

TTTCTATTAT TATTATATTG TAATATATAA TGAAATAATT ACACAACTCA CCATAATGTA

GGAATCAGTG GGGAGCCCTA AGTTTGTTTT CCTGCAACTA GACAGTCCCA TCTGGGGGCA

ATGGGAGATA GTGACAGATC ATCAAGCATT AGATTCTCAT AAGGAGTGCT CAGCCTAGAT

CCCCGGCATG TGCAGTTCAC AATAGGATTT GCTCACCTAT GAGAATCTAA TGCCACTGCT

GATCTGACAG GAGGTGGAGC TCGGGCAGTA ATGCGAGGGT TGGGGAGCAG CTGTCAATAT

AGATGAAGCT TTGCTCGCTC GCCTGCCACT CACCTCCTGC TGTGTGGTCC ACTTCCTAAC

AGGTCACAGA CTGGTACTGG TCCATGGCCA GGGAGTTGGG GACCCTGTCT TAGGGAGTAG

GGGTGGAGTT CCCTTCACTT CTAGAAGGCC CTGGATTAGT ATCCCAGAGC TGTCATTACA
GAGTATCACA AACCAGGTGG CTAAAAACAG ACATGAATTC TCTCTTATTT TTGATGGCTT
GGAAGTCCAA AGTCAAGGTG CTGCCAGGGC CATGCTCCCT CTGAAATGTG TAGGGGAGAA
TCCTTCCTTC CTCTTTCTAG CTTCTGGTGG TTTGCTGGCA ATCACTGGCA TCGCTTGGCT
TGCAGCACTT CAACATCTGC CTTTACTGTC TCATAGTGTT CTCCCCTCAT GTCTCCAGGT
CTCTCTGTCT CTCTTCTTTG TATAAGGAAA CTAGTCATAT TGGATTAAGG GCCAACCCTA
CTCTAGTATG ACCTCATCTT AAGGTCACAT GCAATGACTA TTCCAGATAA GGTCACATTC
TGAAGAACTG GGAGTTAGGA CTTCATATCT TTTGAAGGAA CACAGTTCAA CCAATAACAG
CCCCTGTACT GTTTTACAAA TAGGTATTCC TCTCCTTCCC AAAGTTCTTC ATAGCAGAGA
CAACTTGTAC CAAAAGGCAA AATACCTTAT TATGTAACCT TAACCTAGGA TCATAGATCC
CTACTGTCTG GTGCTTTATA AGCACAGAAC CACCGGGAAA TCATTATTAA GACAAGGAAA

GGCCAAGTGC AGTGGCTCAT GCCTGTAATC CCAGCACTTT GGGAAATTGA GGCGAGTGGA
TCAACCTGAA GTCAAGAGTT TGAGACCAAA CTGACCAGCA TGACAGAACC CCATCTCTAC
TAAAAATACA AAAATTAGTT GGGCATGGTG GCATGTGCCT GTAATCCCAG CTACTCAAAA
GACTGAGGCA GGAAAATCAC TTGAACCGAG GATGCCAAGA TAGCAGTGAG CCAATATCGT
GCCACTGCAC TCCAGTCTGG ATGATAGAGC AAGATCCTGT CTCAAAAAAT TAATAAATAA
ATAAAAAGAC AAGGAAAGCC TTTTCCAAGG AGACCCTTCT GCTTTGCTAG TTCAGAGAAC
TTCTCTTTTG GAGAAAACAA ACACCCAGTC CATTAGCAGC AACGTCAGGG ATTGAATTCT
TAGGGCAGCA GGCTGGGCAC AGTGGCTCAT GCCTGTAATC CCAGTACTTT GGGAGGCTGA
GATGGGTGGA TCACTTGACA TCAGGTGTTC GAGACCAGCC TGGCCAACAT GGTGAAAACT
CATCTCTACA AAAAATATGA AAAAAAAAAA AAAAAAAAAA GCTGGGTGTG TTGGCTTATG
CCTGTAGTCT CAGCTACCTG GGAGGCTGAA GCAGGAGAAT CACTTGAACC CGGGAGTTGG

AGGTTGCAGT GAGCTGAGAT TGCCCTACTG TACTCCAACC TGGGTGACAG AGAGAGACTC

CATCTCAAAA AAATAAAGAA TTCTTCGGGC AGCAGTCTTT CCTCCACCTC ATAGACCATG

GAGGTGAGCC AGCTCTGACA AACCATGAGA ACAATGGCAG AGACATACCT GTAACGTAAC

TGACTGGGGC AAAGACAAAG GTGAGGAAAA TGACAAGTTT GAGGAACTAT GAGACCAGGC

AGTGGGGAAC ACCACTAGCA GAAATGATGG AAGTTCTCAA GAATAACAAC AGAGAAATAG

ACCATGGCCA GAGTCTAGAA CCCTCCAGGG AAAGGAGATG GGCTCCAGAG GCAGAAGAGG

ACGTTGAAGG GAATGGGGAG TGGGTGAAAT ATATAGACGA TGGGGACCAC CCAAGAGCAG

TCGCTATTGC AAAACTGAGG AGAAGGAGAG TCTGGAGGGG GTGGTGGGAA GCTGGGTCTC

CTAAGGAGGT TTTGACAAAA GCAGTCATGG AGCGGGCTTA GAAATCACAG TTGGGGACAG

GGTAAAGTTC CTCGGGATAT AGAGGATGAG ATTAGAAGAG GTTCCAACTA GGGTAGTGTG

GAGAAAAGCA CTATTGACCC AAAAAGGAAG GAGAATGTGG GTGGAAGTGG CAGAGAAAGA

GGGGTTTGAG CAGAGAGTGG TGATTTTTCT AATGCAGAGT TGTGGGAGGT GGAGTGCAGG

GAGCCAGGCT GGGTGGCTGT GCTGATGTGA TTAAGCACTT ACTGACTGCC AGGCAATGGG

CTAAGTACCT GAGATGCTTT GTCTGTTATC CCTCCCGAAA CCCCTCTGAG CAGGTGCAGT

TATTATTCTC ACTTCACAGA TAAGGAAATT GAGGCACAGA GAATTGAGTA ACTTACCCAA

GGTGACATAG CTCATATATG GTAAAGCAGG CTTTGAACTC AGTCTAGCTC CCGAACCTAA

GCTTGTAACT ACTATGCTTT TCCCAAAAAA AGGGGGCTGG CACAAAAAGA GCTGAGGGGG

CTGGGCATGG TGGCTCATGC CTGTAATCCC AGCACTTCGG GAGACTGAGG CAGGTGGTTC

ACCAGAGTTC AGGAGTTCGA GACCAGCCTG GTCAACATGG TGAAGCCCTG TCTCTACTAA

AAATACAAAA ATTAGCTGGG TGTGGTGGTG TGCACCTGTA GTCCCAGCTA CTTTGGGAGG

CTGAGGCAGG AGAATCGCTT GAACCCCAGA GGCGGATGTT GTAGTGAGCC AAGATCATGC

CACTGGACTC CAGCCTGGGT GACAGAGTGA GACTCCATCC AAAAAAAAGA AGAGCTGAGG

TGATGGCCAC CATCAGCATC AGCCTGGAAG TTATAGCAGG ATGCTAAGTT TCTCTAAAGC

TGTCTTTCTT AGGACTTGAA AAAGATAACT TGGGTTTGTA TCCCATCTCT GCCATTAGTA

GTTTACTGGC TTTGGATAAA TTACTTAGCC TTACTGAACC AACTTTGGAT TTTTATAGAG

ATACTGTAAT GAAAGGAATA AGGTATCAGT CTTAGCAGAG CATCCAGAGT GTTCCTATTA

AAACCTAAAT CATATCCTGT CATTGCTGTG CCCCAAACCA TTCAATGGCT TCCCAACTCA

AAGTTAAAAA CTCATCTTTC CAGTGGCCTG CAAGAGCCTA TGCTATCCGG TGTCTGACCT

CATCTGTTGT TCCTTTCTCC CTCCCTTTCT TGGCTCCAGA CGCACTCTGG TCTCCTTGCT

GTTCCTTGAA TACACCAGGC ACACTCTCTT CGCCTGAAAC ACTTTACCCC AGATATCTTA

GCTTACTCTC TGCCTCCCTC AATTCATTGA TGAAATGTCT CAGTGAAGTC TTCTCTCTCT

CCTCTGTAAA AGTATACTCT CTGTTCCCCT TCTTTACTGT TCTAGCTACT ATTGCTGTGT

AACAAATCAC TCCCCAAATT TAATGAGTGA AAACATCAGC CATCATCTTA TTTCTCACGG

TTTCTGAGGG TCAGGAATTC TGGAAGGGCT CAGCTGGGAG GTTCTGGCTC TATAATCTCT

TATGCAGTGA GAGTCAGATG CTGGCTAAAA CTGAAACAAA GCAGGGTTCT AGTAGCTGAG

GGCTGGCTGG GTCTCTCAGA TATAGTTCAG ATCTCCTCCA GGGGGTCTCT CCACGTGGGC

TAGTCTGAAC TTCCTCACAG CATGGTGGCC TCAGGGCAGT GGACTCTGCA TAGTGGCTGA

AGGCTTCGCA GCTGAGTATT CCAGCAAGCA AAGTGGGAGC TGTATTGCCT CATATGACCC

AACCTTGGAA TCCACACAGC ATCACTTCCG TGTATTCTAC GGGTTGAAAA GTCACAAAAA

CCAACCAGTT TCAAGGAGAA GGAACAGAGA TCACATTTCT CAATTGGAGA AGGGTCAAAG

TCACATTGTA ATCAGAGCCT ATGGGATACG AAGTATTGCG GTCAGGTATG AAAAATTTGA

TTTGCTGCAT CTGCTTTACT TTCTCCACAG CGTTCATGAT CTGCTTCTCA CATGATATTG

ACTTACGTCA TTTCTGCGTT TCCTGTCTTC CACACTAAAA TGTCAGCCTG TTTTGTTCAC

TGCTGTATCC CCAGAGCCTA GCACGGAGCC CAGCATGTAG TGGTATCCAA TAAATACTTG

TTGCATGAAT GAATTCTGTC TTTTAATCCT AGCTATAGGT TTCTAAGTTA AATATTACTA

TAATCATCTT ACAGACGAGG GAAATGAGGC TCAAGAAGAT TTGGTAACTT ATGCGGGATC

ACTCAGCCAC ATAATGGAAG AGACAGCATT GAAGTACACA TGCTTGCTCT GTCTGCTCTT

CCAAGCTGCT CATCACACAG CTGCACCTCT GAGGACTTCC CTCCCCAGTC CACCTCCACC

CTTACCCAGA GACACACATG GCCACAATCC ACTAGCAGAC CAAAATTCAA TTTTTCCCCA

GTTGGTTGCA CTCAAGCTGA GAGCAAAGCA ATTGCACTTT AAATCCCCTT ACAGCAGATA

TTTCAGAGCA TGTTCGGAAG AACCCATCAC ACTTGGCTTT TAGATCTTAT TTCTGGTTTG

TTACAAAAAC ACAATTAAAT GAAAGGTTAG GTAGCTTTTG AATGGCCAGC TCAAAGTTTT

GGCTTATTTT TGCCTTGCTG TCTTTATAGG CATTTTACCA ATATTTATCA CTATTTCCCT

TAGGGAACCC TTAGATCTGT GATATTTGAA ATAATAAAGC CTCTCCATTG GCCCTTTAAA

AGGTTTGTGG TAAAACCACA CCATTAACAT TCACAGTTCC TTATTTATGA GGCCTGATTG

```
CACTTATTTC CATATTTCTC ACTGTTTCTC CGATGAGGAT TTCACATAAT AGTGTTTGAA
GGCTAAAGAC TTCAAAGCAG ATTCTTTACT ATTTTTATCT TGAAAAATAT TCAATATTTG
TGTAATTAAA GTGAAGTCTT CCTAGAGAAA ATGACAACTC AAATAATCTT AAATGTACCT
CCAAGAAAAA AGCTGTCAAA GTGACATTTA GTAATAGAGT CACATTCTCT AAGGCCTTTG
CTTCTCCTTC TGATTCTTAT CATCTTTGAA GGTTATGTCA TGGGCTGACT TCAAATCAAC
TTTTAAAATT ATTATGGCCT TCTTTAAATG TGAGTTCTGA AGGTGAGGGG CTTTATCTTT
CTTTTGCTCC AGATTTTTTT TACCGCGTCA TTACCAAGCA TCTTAAAACA AAACCTAAAA
ACAAAAATCT TCCTTGACCT GGTTTTTCCC ACTAGCTAAC ATCCTATTTT TATCTTTCCC
CTTTGCACTA AAGGTTTTTA AACGGATCTT TATACCCTCT GTCTCCATTT TCTCATCTGC
TAACTTATAT GGCAAAGATT ACCACTGCCT TTCAACATAA TTGGCCAATC TACAGAAAGT
TTTCAAGTTC TCTTTTTAAT TGACCACCTC CTGCCTACCT CCCCACCTTT GACATCTTGC
```

```
TTCTCACTTG GCACCTTACC CAGTGTTCAA GATTCCCTCC TTTAGGATGT CTTCAGAGCA
GCTACACAGT TGGTACTATA ATTTATACAT CCTTGTACAC AGGGCTTGCT GGGATATTGA
TGGAGAGAAG GAGGAAACTG GAAGTAGTTC AGGCCAGAGC TAGGGAAATT GACCCATCTC
CAGGTCTCAG GTCTGCAAGG GGAGCTCACA GCTTAACACA TGGAGTCTAG AAACTTGTGC
TGGACCTTGA CCAACACCAG CCCATGGAGT CCAATACAGT GCTCAATAGG GATTTCCAGG
AAATTGCTAT ATTTATTCAA AGAGAACTTA CCAAGTGTCA GCTACGTGTT GGGCATTGTG
CTAGGCACAG GGACCACAAA GATAAGACAT TGTAGCTTTC CTTAAGTTGC TCACTGAGTA
AATAGAGAGA CAGAAAGGTA AACAGGTAAG TGCAAAAATA CATACAATTC AGCAATAGTG
TTCATAGTGG CTATGGAGAG AACGCTCACT AACTTTGTTT AAACAGTTGT TCTTTCAAGG
ATTTGACATG GATTTGATTG GAAAAGCATG ATACCATTTT TTGCAATTAA ACACAGGAAT
ACATAAATAA AATGCATCAG TATTTTTTAC AAATAGCTAC TAAGAGCTAC TAGAAAACCT
```

GGGAATTCTT AAAACCTTAC CATGCTACTT GCTCTAAAAT ATTTTATTTT ATGTTATTTT

GTACATTTCT TTACCTACAC AAACACCACT GTTTTCTTCA TTTCTTAGTC TATTTAAACC

TCACACCCTT TCAGCATCTC TTAATTATTT ACTACCATCT GTTAGTTCTC CTGTCCTGAA

TGAAACAAAA ATGGCAGAAT GTAAAACGAG GGCGAACAGA TTTTTGACAG GAAGTATTCA

GAGGTAGAAG GAAATAGTCA AGACACATAT GATAAACGAA AACAATAATA ACTTTATACA

TAACAACTTA TAGACACATT TAAAAAGTTT AAGATCTCAA GAGCTATGTC TGAATAGATA

GGAGTAAAAA CTCTATTAAG TAATTAGGAA AATAACAAGA ACAGTGAATT TCTTAATGAA

TGGCATGTAA TCAAAACTGT ACTTATCGTC TAATTCATAA TCTTGAATGT TTTTATTTTA

TTTATTTATT TTTTTATTTT TTGAGACAGA GTCTTGCTCT GTCACCCAGG CTAGAGTACA

GTGGCGTGAT CTCAGCTCAC TGCAACCTCC ACCTCCCAGG TTCAAGCGAT TCTGCTGCCT

CAGCCTCCTG AGTAGCTGGG ATTACAGAGG CCTGCCACTG CACCCGGCTA ATTTCTGTAT

TTTTAGTAGA GATGGGGTTT CACCATCTTG GCCAGGCTGG TCTTGAACTC CTGACCTCAT

GATCCACCAG CCTTGGCCTC CCAAAGTGCT GGGATTACAG GCGTGAGCCA CCACGCCTGG

TCGAATGTCT TTATTATTTG AAGAGACAAC ATGGGCCTTA AATCTGTCTT CTATTTGACA

GACTTTGATG GAGTCAAATC CCAATGCTGC CACTTACTGA ACGGCCTTAA ATGACTTAGT

CTCTCTCAGC TGTCTTTCTG CATATGTAAG GTGGAATAAT GATGGCTTTC AAGGAGGAAT

AAACCTATGA AAAGTGTTGA GGATAGTGTT TGATATGAAA TAAGGATTTC AACAAGTAGT

AGCTGCTATT GAAGATTTAA GAGTTATTTA TTACAACTAT TTAATAAAAT TTTAAAAACT

AATACACTTA AATTATTAAA GAGCTTTGAA ATGGGCCAGG CGCAGTAGCT CCTGCCTGTA

ATCCCAACAC TTTGGGAGGC CAAGGTGGGC GGATCACCTG AGGTCAGGAG TTTAAGACCA

GCCTGGCCAA CATGGTGAAA CCCTGTCTCT ACTAAAAACG CAAAAATTAG CCAGGTGTGG

TGGCATGCAC CTGTAGTCCC AACTACTCAG GAGGTTGAGG GAGGAGAATT GCTTGAACCT

AGGAGGTGGA GGTTGCAGTA ACCCGAGATG TCACTGCACT CCAGCCTGGC AACAGAGCAA

GACTCCATAA AGACAACAAA AGCTTTGAAA TTGTGTAAAT GAGTTGTACC TATCTTCATT

TAAGAAATTC ATCTTTGTTC ATTTATTTTT ACTTGACATG AGAGCTTCCA GCAATTTTTA

ATTAAGCCCT CACAGATTTT ATGTCACTGG CTATGTGATA AACAAATTAT TTGCTAAAAT

AATATTCTTG CTTCTTTTTT AAGGAATTGT CTCCCTAGAA ACGGTTTGTA CCAAACAATA

CACTGACTTT ACACAAAATC AGATCTGATT GGCAACAGTT GCAGATGTTT TCAAAAGATT

TTCATTTGAG AAGGGGCCCA TTTGGGTTAT TTAGATTCTA AGAACTGAAA CTGCTTTGTT

CTGTTTTTCT GGCTTCTGGG AGAGGAGGAG ACATGAATTC AGTTAGCACC TTGGTATTTT

CTTTATCCTT CATTTCAATA CAGAAGATGC TTCATATGCA CAGTGGTGTC AGGTCACATC

AAAAGAAAGA GAAACAGTTT CTTGGTTTTT AATTTTCAAC CGGAAAGGAA AGGCACCCAT

TTTGTTCCGC TCTAATTAGC CAGTGCATGA CTTAGAGAGC AGGCAGATGC TTTGAAGGCG

TGGTAACACA GGTCTTCATT AATCTCCACG CAGGACTTGC ACTTCTACTA TGCCTAGGCT
GAAGAAAATG GCTCAGGAAG ATGAACAATC TCACAGAGCC CTAACTAACT GAAGCCAGGT
GTTATAAAGC ACAAGTCAAG AGGGTGAGAA ACTAACGTTC TTGAAATCTC CCACTTCTTT
CTACGTCAGA AGAGCCAAGC TGATTATTTT AGTTGGAATT TAGAAATTTT TAAAAATTAT
TCTAAAGTCA TGAACAAGCC TAATTATAAA GATAGTTGCT GTGAAGGTGC TGAAATAACT
CGATTTTACC AACCCCCTCT TCTGGAGGAA GCCATAATGG AATCCTGTAC AATGTTCACT
CTACCAACGA ACTCTTGTTT TTCTAATGAG GAAACAGAGG CCCACAGTAT TAAACTATCT
TAACCAATAC AAAATGACTA GTGCTCTGGT CCTTTTATTA AGCACTAAAA TTTTGATCCA
ATAATAAATC TGTCCATTAG AAGGAGTTTC CCTAATGTAC TGGTTCTAAC TTGTTCCCTT
CAAGGGGCCA GTGTCCCGTA CACATAGCTA AATGGGACTT CTCTTCAACT ACCATTACCC
AGAGGGCAGA ACCTAAAATG CTGTGAATGA CATTCTGCTG TTCACATCTC AGCAGCA

GTGTTGCATT TGAGCTTCTG CAGGGCCACC CAGGACCTAT ATCTGCTCAG ATGTTTAACT

CATCTAATTC AGTGAACACT TCATTCTAGT TAACTGAACA TCTACTTTGT ACAAGGCACT

ACAGCGGTTC AGAGATGAAT AAAATCATGA GATTCCACTG TCTCCTATAA ACCATCACTT

TGGGAAATTT TAGAAATGTG GGTAAGCTCC AGGGCTTCCT GCAGCGTAGA AGTCACAAAC

TCAAATGCCT GCAGAGGCCC AGCTGACAAC ATAAGTAAAT GATTCTGGCT GGGCGGAAAA

CAATTACGGG TGGGTGGGTT TCCAGCTGGG GAGTGCACGC CTGTGTTAAA GGACAGCTGC

TACTCATTTC CAGCCAACTG TGTTCCCATG TAGAACTGCG GCCCAGTGTA GCCAGTACCG

AAGATTTCTC AGAAAAAGCC GGAGATCTCA ATGTTAGTGT AAAATCTCTC AAATTTCCAA

GAGGATTATA TGGGGCAAAG GTTCTCAGAT CAGTTTGCAG TCTCTTACTT AGCCCATGTG

CAGAGCAGTC GTAGAGGGTA GCATGCAGTG TCCTACATAA TAATTCTTTT TTATTTTATT

TTATGCCTTC CTCCTTCCTG TCTCTCTTTA ACCTTTCTTC TTCCCTCAGG CTGGCTTCTT

CCCTCAGCCT CGTCCGACCC CAGCCTGGGT TCAATGAACA TTCGGTAAAG GAACACGGAA

TGTCAAGCGC ATTAGAGACA ACCTTGAGAC ACATTCCTCT TGCGGTAAGC ACTTCACTGT

AGATTTTTAA TTTTAAACAA GACAATGTTT ACGACTTGCT TCTTTCAGGG AAGAGCGATA

TCAATTTTAG TGAACACTTC AAGGCTGAGA TACGCTAGGA GAGTCGTGTG GTGTTGCACA

GCAAAGAATT CCACTTTGAA GCGAGTGGGA AAAAAAGCAT CAAATGCCAC ATGTAACTCA

CCGCCTGAAG GGTTACATTG GTATGAAACC TGGGTTTAAA AAGGGACCGA ATAGACTAGC

CATTAAAAGA CCTGCGTACA ACCTCTCTCT CTCTCTTTGA GAGATAATGT ATCTGGACAA

TAAACATGAA CAGAGTGGAG TCTATCCTGT TTAAAACATT GCCTACTGTA CAGGCACCAG

GAGCTGAAGG GTCAGAATAT TAGCAGTGGG AGCTTGATTA GAGTTGATGA GAGATGGGTA

GTAGGAGGAA AGAGTGAGAT AGAGGAAGAG GACATGGGGG TTACCCATAA GTGGAGAGTA

GAAAAGTAGA ATCAGCTGGC CATCAAAGGG CGTGGGACTG AGGAACAGTA TGGCATGTAT

TAAATATACT AAGCGCTGAC ATTGGAGGAG AACTAGGAAG TTAAATGAAA TCAATAGGGG
ATGATGGAGA ATAGTTAGGT GTGCAGGGAT TAGGGTTATG ATAGAAATAC ATGTGAATAC
ATGCAGTATT GTCCTGGAAA ATGGTTAACA GTTGGTTCTC CTGGGGGGTG AGGGGAAGCC
CTGATTTGTA ATATTTGCCT ATTTCTGTGG TGCAAATACT CCCACCATGA CCAGTTTCAA
GCTATGAATG TTGAAGTCAC AGAAAGCAGG TTGGGAGGAG ATGCGCACAT TTGTTCCCCG
GCAAGGTGGA AGGTAAGGAA GGTGAAATCA ACAAGGTCAA AGAAAACTCA AGATTTCGAG
GTGCCTCAGG TCTGAGGGGC AATGAAGTCT AGGAATGGCT GTGCTGAGGT AGCTGAAATA
GAAGTGACTG CAGAGGTCAT GAAGCTGAAG AGGTGAAAAC AGAAATTAGA AAGGCAAACC
CCCACCGCCC AACCCCCACC CCTGCAGCCA GTTTCTGAGG GTGACAATAG AGGAAAGGGT
GGAGATGGAG TTCAGGTCCA GAAGCCATAG AAGCGAGTGT GACATTGTGC TCAAGGTCAG
CACATGTCAG TGTGGGGTGT CACATGCTGT TGTGAACCAT CATTTATCAC CAATTATGGA

AGACCTCCTA TGGGCATCTT GCCATATGCA TTATAAAGAT GTGTAAGAAG ACATTTCCCT
CCACTTGGTG AGGAGAATTA GGGCTGTACA CAGATACTGT AGAGTGCCAT GTGCCTGGTA
CAGATAAGGT GTGTTAGAGG TTAAAAGATG AGGCTCTTAA TATTAATGAT AGATCCCACT
TACCTGAGTC TGACTTACAA TGTGCCTAGC ATTAAGTGTT TTACCTGCAT TCCCTTTGAC
GTTCAGAACA ACCCATTTTA CAGATAGGGA AATTGGGTCA GAAAGTTTCA GTAACTTATC
CAAGGTCAAC ACAATTGGCA AGTGCCAGAG CTGAGCCAGG AACTGAGGTC CTTCTAACAC
CAAACAGCTT GTCTCCCCAA TCACTGTGCT ATTTTCCTCC CCCAGAAGAT AATACTCTGA
TGGAAATGAA GGATAGTGTA ATAGGAGATT CGGTGTTCCT TTTTTTAAAA AAAATTCAGC
TTGCATATTC CTAAAGAGTC AATTCATGTT TAAAAAAAAT TTCCCTTGTG CTTGCATGTG
ACATGTATTT TTAGGATCTG CTGTTAGCAA GTGTATTTTT GTGTGATTGA GTGGGAGAGT
GGGAAAAGTT TTGCAGAGCT GTTGAAGCCA GAATGCAGGG GGGCTGCGCA GCAGAGACTG

```
TAAAATCTCT GCCATCTCAG GTCTTGGAAC AAGCACAAAG AGATGTGTTC TCGATTTATT
ATTCTATGTA CATCCCCAGA TGAATGACTA GTTAAAGGTA TTGTTAAAGC ATTTTAAATG
ACCCACTTCC AGCAGCGAAC AAAATCACTT GCTGTGCCAA GCCAACTGGC ATTTCTGAGA
TGATAAAACC ACAAAGTGAG GAAAACGTTA AAACTGCTAA AGCAAAAATG ATACACAATA
ATGGAGAAGG AGAAAAATTG AGCTTTATTG TCTGCCTAGG CAGATGGCTG ACCACTAGGT
GGGCCTCGGC GTCACGTCCA GGGTAATTGG TTGCTGGGGT GTTTCTGGCG AGGAAGATTC
ACGCTTCAGC TCGGTCCACA AGATCCTGGC TCATTCTTTC CTAGATTCCA TTTTCTGCCT
CCTCTCCATG ACTGGGTCTG ATGGTTGATC CAAACGGGCA ATTGAAATCA GAAGGTTACC
TTTACCTTAA AATGCTTTTC TGGAAATAAA AGGACATGAA AAGTAACTAA GGACCGGATT
TCCTAGCCGT CTTTCTCTCC TGCATGCGCA ATTTATCCCC AGATATAAAA TTGCCTGCTT
TGATAATTAT ACCCTCTAAA TGAGGGGCAA GTGGCTAATT ATGCCCACAT GTGGCCGATT
```

GCACTCCCCA TTAGCCAATT ATGTGCTCAA TTATTTGTGC ACATGAATAA TTGCACTCAT

GGAAAATAGC GCCCTCCTTT CAAATCCTCG TGCTTGGAGT GGCTGATGGA GTAATTGTCA

CACTGGAAAT GCACTTGGTG GGGAGGGAAA GAGTATCAGA TACCAGGAAA CGCATAAGTG

ACCAGAGCTC GCAGATGTTC ACTGCCACAA ATGGCCTTAG GAGCCAGAGA GAGCGGGAAG

GACCACAGGA TGGAACGGGC CAGCCTGTGA GTTAGGAAGC CTGCTTCTGA AGTTGCCTGG

GCAGCTCATG TGCGGTGACC TTGGGCAAGT CATTAACTTT CCTTCAGGTC TAACTGGTTC

TGCATACACA ATGAGGATGG TAATAACGCC CAATTCCCAT CACTATCGTG GGATGGATCA

GACTATTTAA AAGGATTTAC AATCTGCTTG GGTAAAAGCT TTACATAAAT ATGAGGCATT

ATCATGTCGC TTGGTACATC TCCAATTATG AAGGAAGGGT AATGACCCTC CACAGCAATG

CAGGACTCCT GGTTTGGAGG GAGGGAAAGT TTGAGAAGGA CAGGAAGCTT GTTGCCCCAG

CACTGATGTT TCTACTGAGG TACCAGAAAA TGTCATGTGG TCATACAGAA TTCATTTATT

CATTCAACAA ACATCTGTCA ATTGTTACAC TGTCCTGAGA ATTTGGAAAA ATGATGAAAG

ACTCAGTCCT GCCTTAGGAG GTCACTGGCA CATTGGCCCG GGCCCCTGTT TTGGGCCTTT

TACTCTGACC TGTGCTGATT TGCAAATAGT GGGAAATTTT ATCTCAAGTC TATGAAATCT

GGCATGCATT TTCACGGTTT GATTGCCAGG TACATTCGAT GGCAATGAGT CTTATAATGT

TTGGTTACCT TCATTTACCT AAGAACTGTG GTTGTTGCTG TGGTTGTTGT TTTTGTTGTT

TTTGAGACGG AGTCTTGCTC TGTCATCCAG GCTGGAGTGC AGTGGCATGA TCTCCGGTCA

CTGCAAACTC CACCTCCCAG GTTCAAGCGA TTCTCATGCC TCAGCCCCCT CAGTAGCTGG

ATTACAGGCG CGCACCACCA TGCCCGGCTA ATTTTTGTAT TTTTTGTTCG GGACACAGAT

TTCACATGTT GGCCAGGCTG GTCTCGAACT CCTGATCTCT GGTGATCCGC CTGCCTCGGC

CTCCCAAAGT GCTGTGATTA CAGGCGTGAG CCACTGTGCC CAGCCAGAAC TGTGGTTTTA

ATGACAATGC TAAAAAGTGG TATATGTCAC AGTGTCGGGT GGGGCTAAGA GGCACATTGC

TGCAGTGATC CATCATTCAT TTCCCACCAT TCTCGCCTGG ATTAGCGCAG CAGCTCCCAG

AGAGGCACCT CACTTTGACC TTCTTCCTCA AAGACATTCT CTGTGACCTG CCTGGCCCTT

ATTACCTCTC TAGCTTTGCC ACTTCCCTAT GTCTCCATCT CCCCTCTCAC ACGTAGTAGA

AAGAGACTCT ACCTCATGGA GTAAGGAGAG GCTTCACAGA GGCAGGATTG CTATTAGTCT

TCAAAGATGA GGTATTTGCT AAATGAATGA GACAAAGGGA TTGGGGCCAC ATTACAGGGA

AATTGAGGTA TGTAATAGCC TGGTGCAGGT TAAGAGTGTG GACTCTGAAA CCAGACTCAG

CCTGGAATTG AATCCTGGCT GTGTGATGTT GGGCCAGTGA CTTAACCTCT CTGTGCTTTT

ATTCACTCTT CTATAAAATG GGGATTATAA TAAACCTACC TTATAAGGTT ATTATAACAG

TCAGTAAATA TAAAAATAGA AGTTTTTGGA TGATGACTAT CACATCAGTA AACACTTGTT

TGCCATTATT TTTATTACTT GACTAAAAAT ATACCAAAAA GACCATCCAA GAAAACCCTT

TAAGCTGCTA GTGCAGAAAG ATTCCCCTTG TGTTTGTGTG CTGGGGGGTC AGTGGTGCCT

GTGGCCCACT GGAGAGGAGA CAGCTATGGC TGGAGTGATT CTCAAACTTC AGAATGTCTA

AAATCATCAC ATGGACAACT TATTAAGGAA AGCAAATGCC TGGGCTCCAT CCTCAGAGAG

TCTCATTCAC TGGGTCAGGA TAGAGCCCAG GAATCTTTAC CTTAAAGAAC CATCCCACCT

CCCACCTCAT ATGATCCTTA TGCAGGTGAT CTGGGGCCCA CACTTTGAGA AATAGACTCA

GGTCAAAGTG GCTCTAACTG CATCTCATTT CTTACCTGGC ATATCTAATA GTAGAGAAGA

AGACAATGCT AAGATTTTTG TTGGAGATCT TTTGCTGGGA TTGCTGCTTC ATTCATTCAC

TCATTTATTT ATTTATTTAT TTATTTTGAA ACAGAGTCTC ACTTTGTCAC CCAGGCTGGA

GGGCAGTGGC ACAATCTGAG CTCACTGCAG CCTCAGGCTC CTGGGTTCAA TCGATTCTCT

TGCCTCAGCC TCCCGAGTAG CTGGGATTAC AGTCATGCAC CACCACGCCC AACTAATTCT

TGTATTTTTA GTAGTGACAG CGTTTCACCA TGTTAGCTAG ACTGGTCTCG AACTCCTGAC

ATCAGGTAAT CTGCCTGCCT CGGCCTCTCA AAATTAGTAG CTGCAATTAC ACGTGTGAGC

TGCCGTGCCT GGCCTGCTGT TTCTTTTAGT TGGGCCTCTT CTGTAATAGA GTGTGAGAAT

TCTGACTTGC TGCAACAGTC TGCTTTGAAG CAGGGCTGTG TTTACACTGG TCAGATGTGG

AATTGTGGGG CACACTTAGC AGCTTCCTTC TCTAATTTTT CTGTATTTTC AGGAGAACAA

TTTTAAAAAA TTTAATAAAA ATGCCTTAAA AATTAACATT ATTATAAGAT GAATCCCATT

TTTCTAATCT TGTAAATTAA AAACAATCAT AAGCATATGA GCACCTGCAC TTAGGGAATC

AAGGTTGGCA AAGCTAAACA CTTCCAGCTC TAGGTGATTC GCGGCAATAC AAATGGAGCT

GGACTTTGGC CACAGTGCAA AAATATTGAT CTGTTGTTAG ATGCTCTGAA GTTTCCAGAA

AGAATTGGTT CTGCCTGCTG TGCTTCAGTG CTTAAGGGAA GTGGTTCCTC AAAATGTTAG

TTTTTAAGCC CAGCTTTCTT AAATAGGAAG ATTCTAATAG TAGCAAAAAT ATAAACTGCT

TCTAGGTTTA AAAAGGACCC AGCACACAAT GGTTATCACA CACCTTTCTC CTCAGGTGAT

GAGTGGATGA GTGGCCTGGT GTATTTCATA ACATCTCCCA GGTCCAAATG CTAAAGCAAT

TGCTGAAAAG ATACCATGTG TACCGGAACC TTGCAGAGGT ATTTTGTTGG CATAAAAAGA

AATATTGATC ATCTATAGTA AAAATGGTTC TACTTTAATA CTACTGAGAA AAGATTTTCT

TTTCCCAGAT CTACATCCTG AATCTTCATG AAGACAAGAT CCCCTAAACT TCCACTAACA

CCATAATGTG TGCTGTCCTT TGTAATGTAG TCCACAGATC TCATAAACTG TCAGAAATAG

CAGAGATTGT AAGGTCATCC ACTTCCCCTG TAAGGCCTGC GTCCCTCACT TACATCCCTA

ATAACGTCCT CTAACCTCTG CTGGAGGGCA GATTTAGCTG CCAGCTGGGA AGAGCTCTGC

CCTAGTCAAC ATTTTTATCT GTGGCTTTCA GATGAGAACA CTGGATGCTT ATCTGAAAAA

AGCTCCTCAG GCTGGAGGGA GGGATTGGCT CTAACAAGAT GCAATGTGAT AAGAATAAAA

GCGAAGCCAA ACTCTAGGCC CAAAGGCTCT AGCAACACAC TTTTGAGAAC CTTGGAGACG

AGTTTTGGCT GATGCGAGCT TCTCCGCCTG CTAAAGTAGC CCATTCCATT TGGACGGCTC

TAGAGGCTGG CATGTTCTTC TCCACGTTGT GTTAATGTAC TCCAGTTTCT TCCTGCCATG

AACTGGCATG CCCTGGCTCC TCCTACCTTC CCCACTTTAA GTCTTCCCTC CCTCCTTCTG

ACCTTCCCAT TCCAGCCACA CTGGCCTTTT GTCTGGTCCT AACAAACCAT GCCTTTCCTG

CCTCCAAGCC CTACACCTGC TATCCATCCC TCTGTCTGAG AGACACTCCC ACCCCTTCAC

AAAGCCTGTT TCTCATCCTT CCAGTTCAGA TGTCTTCTCA GCTTGCCTCA ACTGACCTCT

TTCAGCTATT CTCACTCTTT GTACTCTGTT CATTTCCTTC CTGGCAGTCA CCATAATTTA

TCTTTATTTG AATCAATTTC TTAGTTGTAT TATTTAGTTA TTTGCACACT CTGTCTCTCT

GTGCCTTTCT TATTCACTGC AGGCTTTCTT ATGTAAGTAA TTTATTTACT TAAATTTTTA

AAAATAATTT CAACTTTTGG CCGGGCACAG TGGCTCACGC CTGTAATCCC AGCACTTTGG

GAGGCCGAGG TGGGTAGATC AGCTGAGGTC AGGAGTTCGA GACCAGCCTG GCCAACATGG

TGAAATCCCA TCTCTATTTA AAATACAAAA ACTAGCCGGG CGTGGTGGTA TGCACCTGTA

ATCCCAGCTA CTCGGGAGGT TGAGGGAGGA GAATCACTTG AACCGGGGAG GTGGAGGTTG

CAGTGAGCTG AGATCACGCC ATTGCACTCC AGCCTGGGGC ACGAGAGTGA GACTTCATCT

CAAAAAAACA AAAAACAAAA AACCCCTGCT TTTCAGAGGG GCTGAACTAA TTTACATTCT

CACCAATAGT GTATAAGCAT TCCCCTTTCT CTACAGCCTC ACTAGCATTT ACTTTTTTAA

AAAACTTTTT AATAATAGCC ATTCTGACTG GTATGAGATG GTATCTCCTT GTGGTTTTCA

CTTGCAATTC TCTGATGATT AGTGATATTG AGCATTGTTT TATGTTTGTT GGCTGTTCGT

ATGTCTTCTT TTGAGAAGTG TCTTTTCATA TATTCTGCCC ATTTTTTGAA TGGAGTTGTT

TTGTGCTTGT TGAATTAAGT TCCTTATAGA TTCTAGATAT TAGACTTTTG TTGGATGCAT

AGTTTGTGAA TATTTTCTCC CATCCTATAG TTCTGTTTAC TCTGTTGATA GTTCCTGTTT

TGTTATGTTT TGTTTTTTTG CTGTACAGAA GCTGTTTAAT CTAATTGGTC CCACTTGTCA

ATTTTTGTTT TTGTTGCAAT GGCTTTTGAA TTTTAATAAT AAATTCTTTC CTAAGGCTGA

TGCCCAGAAC AGCATTTTCT AGGTTTTCTT CTAGGATTCT TATAGTTCAA AGTCTTATAT

TTAAGCTTTT AATCCACCTC AAGTTAATTT TTATATATAG TGAAATGCAG GGGTCCTGTT

TCATTCTTTT GCATGTGGCC AGCCAGCAAT CCCAGAACCA TTTATTGAAT AAGGAATCTT

TTCCTCATTG CTTATTTTGT CAACTTTGTC AAAGATCGGA TGACTGTAGG AGTGTGGCTT

TTTCTGGGTT ATCTACTCTG TTACATTGGT CTATGTGTCT GTTTTTGTAT CAGTATCATG

CTGTTTTTGT TACTATGGTC TCATAACATA GTTTAAAGTT GGATAATGTT ATGCCTCTGC

TTTGCTGTTT TTGCTTAAGA TTGCTTTGGC TATTGAGGCT CTTTTTTCAC TTCATATGAA

TTTTAGAATA GTTTTTTCTA ATTCTTTGAA AAATGACCTT GGCAGTTTGA TAGGAATAGC

ATTGAATCTA TAGATTGCTT TGGGCAGTAT GCTATTTTAA TGATATTGAT TCTTCCTATC

CATGAGCATG GAATATTTTT CCATTTGTTT GTGTCATCTA CTATTTCCTT TAGCAATGTT

TTTTAGTTTT CCTTGTAGAG ATCCTCCTAG GTATTTCATT TTTTATGTGA CTATTTTAAA

TGGGATTGCA TTCTTCATGT GGCTCTCAGC TTGAATGTTA TTGGTGTATA GAAATGCTAC

AGAGTTTTGT ACACTGATTC TGTATCCTGA AACCTTACTG AAGTCATTTA TCAGTTCTAG

GAGCCTTTGG CAAAGTCTGT AGTGTTTTCT AGGTATAGAA TCATATCATT AGCAAAGAAA

GATAGTTTGA CTTCTTCTTT TCCTATTTGA ATGCCTTTTA TTTCTTTCCC TTGTCTGATT

GCTCTTCCAG TACTACGTTG AATAGGAGTG CTGAGAGTGA GCATCCTTGT CTTGTTCCAC

CTCTCAGGGG AAATGGTTCC AGCTTTTGCC CATTCAATAT GATGTTGGCC ATGGGTTTGT

CACAGATGGC TCTTATTATT TTGAGGTGTA TTCCTTTGAT GCCTAGTTTG TCAAAGGCCT

TTATCATGAA GGGATGTTGG ATTTTATTGA AAGCTTTTTC TGGGTCTTAT TTGGTGAATT

GCATTTATTG AATTGTGCAT GTTGAGCCAA ACTTCCATCC CAGGGATTAA ACCTACTTAA

TCATGGTGTT AACTTTTTGA TGTGCTGCTG GATTTGGTTT GCTAATTTTT TTTTTTTTTT

TAAGATGGAG TCTCGCTCTG TCGCGCAGGC TGGAGTGCAG TGGTGTGATC TTGGCTCACT

GCAAGCTCCA CCTCCCGAGT TCATGCCATT CTCCTGCCTC AGCCTCCCGA GTAGCTGGGA

CTACAGGCAC CCGCTACCAT ACCCAGCTAA TTTTTGTATT TTTTAGTAGA GACAGGATTT

CACCATGTTA GCCAGGATGG TCTTGATCTC CTGACCTCGT GATCTGCCTG CCTCAGCCTC

CCAAAGTGGC TAGTATTTTT TTAATTACTA TTTTTTCTCA CCCTTGCTGC CATCTTATGA

TTTTCTAGTA TTTTGTTGAA GATTTTTGCA TCTATTTTCA TCAGGGATAT TGGCCTGTAA

TTTTCTTTTT TCATTTCATC TTTACCACAT TTTTGTATCA GGTTCATACT GGCTTCATAG

AATGAGTTCA GGAATGGTCC CTCCTCCTCG AATTTTCTCT GTAGAATTAG TACCAGCTCT

TTGTGTGTCT GGGAGAAGTT GTATGCCAAT AATTTAAATG CAGTTAATAT TTACTGGACA

ATTTCCTCCA GATAATTGTA TATGATTTTT GGTCCACCCT GAGTTGATAC ATGTATTTTA

ATTGTATCAT GGTATGAAAA GAGCAAGAGT TATTTGGTCA CCTAGTCTTG CCTATAGATG

TTGCCTAATG ATTCAAAGTA GATATTTTGG GAGCCTTAAC AGGTGCCGTG GACTAGGCAG

TTTTGTTTTT TTTTTTTTTT GAGGGACAGA GTCTCGTTAT GCTGCGCAGG GCTGGAGTGC

AGGGGCATGA TGTAGGATCA ATGCAACATC CGCCTCGTGG GTTCAGAGCA ATTATACTGC

ATCAGCCTCC CCAGTAGCTG GGACTACAGG CTCACGCCAC CACGCCTGGC TAATTTTTGT

ATTTTTAGTA GAGATGGGGT TTCACCATAT TGGCCAGGCT GGTGTTGAAC TCGTGGCCTC

ATGATCCACC CGCCTCGGCT CCCAATGTGC TGGGCTTACA GGCGTGAGCC ACCGCACCCG

GAGATTAGGC AATTTTATAT TCCCAAATAT CCAACTCTTC TGACCCGCTT TCTCAGCCTG

GGTGTATCAG GCACAAGGCC TGTTCAGATT ATGTGGTCTC TGAAGATATG GCTCTCCAGG

GTTGACAATG TGGATAAGGA TTCACCTGGT TTAGGATTTA CACATTCGCC TTGAATGTCT

GTTGCACCAA GTAGACAGTC CATCCCAACT TGGCCATTTG GTCAGAGCTG TAAGGAGACA

AGGAGGTGGG CAGCCGCTGC TGTGAACTGC TTGGACAAAG ACTGCCAAAT AGCTATCAGA

CAGTGTTAAC AACAGCTGAT TTAGGTTTGA AGGGGGCAGT CTCTTGGGCC ACTTACTATG

CTGCATCATC CTCTTTGGAA AATGCTCTTC AGGTAACTGC CTAACAGACT GAGAAAATAA

AATGCTCACA GAGAAAAAAG ACCCGGAAAG TCTGACTTCT CAGAGCTCAG TGTTTAGGTG

CAGAACTGGA TTGTGAAAGG ATTTTTAAAT TTTTTATATT CATTGCAGGG AACATTCATT

TATTCCATCC TTCTCCACTC CCACCTGTCT GTCGTTGTCT TTGTCTCTGT CTCCCCACCT

CTCTCTCTAG ACACACACAC GCACACACAC ACACACACAC ACACACACAC ACACACACAC

ACACACACAC ACACACACAC ACACACACAC CCCTATTCAT TGCCAACAGT AATAGAGTTG

CTTCTTTACT TCTTGGAGAG AAAAGCCTCA ATCTGAGGAA GCTGTGCTGA CTAGCCTTGC

TCTTAATCAT GGAGACAATG CTTTATGCCT TTATCTTTGC ACAGCTGAAA GCCATGGCAG

AAGCAGTCCT CTAAACGAAA TAAAATAGAA AGGTTCCTGC TAAGCCCTGG CAAATGCAGC

CTTCTATCCC TCCCCCAACA CTCACAGCTT CTGAGCAAGA TGTTGCTGCC TTCCAGGAGC

TGGGTGATGG GCAATAATGA GCAGAGCCAC GTGAAGGAAA GATGGGTGAA GAAATGTGTG

TGGAGTCATG CTGGCTGCAC TGACCATGAA ACAAAGGATC TACCCCTCTA GTAACTGCCC

TACTCCTTTG GTAACTGTTC TGAAATTATA ACTTGCCAGA AGTTCAGAAG GACCTAGTGC

AGGTATTAGA GGAAATTCGT AAGATTGAGC CATTTATTCC TGCACAGATA CATAATAATG

GACACGGGCC ATGGTGGCCA GCATTCTTGC TCTTGACAAT GGTGAAGGGA AGGGTTGTAG

GTCATGGCTA TGCTCTCAGA ATTATAATGG AAAGAAACAG CTCCTGAGTG TTTACTATGA

GCCAAGGGCT GTGCTAAACA CTTTACCATA TGATGACATC TTTTTCTCAC AGGTATCAAA

AAACAATAGG ACATACCGGA TAGCTACAAT CTTTGGGCCC CTGCAAACAC AATAATGTGT

ATTCTCTTCT TCAAATCCTA CATATTGCTA CAAACTGTAT CCCTGAGGCA TATTCATTGT

AAAATAAAAA CATATAAAGT ACTACTTTTG TTTTTTGAGA TGGAGTCTCG CTCTGTCACC

CAGACTGGAG TGCAATAGCA TGATCGTGGC TCACTGCAAC CCCCTGCTCC TGGGCTCAAG

TGATTCTCCT GACTCAGCCT CTCAAGTAGC TGGGATTACA GGCGCACGCC CCCATGCCTG

GCTAATTTTT GTACTTTTAA TAGAGACCAG GTTTCACCAT GTTGGCCAGG CTGGTCTCAA

ACTCCTGACC TCAAGTGATC CACCTGCCTC GGCCTTCCAA AGTGCTGGCA TTACAGCTGT

GAGCCACTGC ACCCGGCCCA TATAAAGTAC TACTAATGTA ACAGGGTGCT AGTCCAGACA

GTGACCACAC GTGGTGTTCA TTGAAGGCTG GACTAACAAC TCCAGCCTCT CCGCCATCAC

AGAGTGATGA CTGCCTTCCC TGAAGCAAAG CTTCTGGTTC AAGGAAAGGC CAGTAAGTGA

CTGCTCTTTG TTGTATACAT GTTAGATGAT CAGGCCTCAA GAAAAGTATA AAGAGATCTT

TGTGCTCTCT GGGACTCAAA AAGCTGCACT CTTTGGGGGA AGGATAGCCA GGTAAAAGTG

GCCCAGGTAA AGAGGGCCTG GTACACCTGG TTCTGCAAGA TGGTAGACAC AAAAATGAGA

GCTACATTTG GAGCTTATGT GCCCCTAACT CTGTACATAA CCTGCAAGAT CTAATTACTA

ACAACTGGAA TCTTGGAAAC ACCTGTAGTA CATCCTTGGC TAAGGTTAGC CCCAACAGAG

AGGGCTCTCC TCTTACAGAG AACCATTACA TTTGTGCCTT CATCCTAGAG TAGAAAAGGC

ATGATCAGAC TACTAAAAAG ACATCAGGAA AGGGCCTGTG ACATCTGAGG GAAGTGGTTG

CCCTCTCTGG GATGTTGGTT CGGGAAGAGG GGCATGGAGG AGTGCCTGCT TTAGATGGTC

ATTCAGGAAC CCAGGCTGAT AGTGAGAGGT GAAGCCAGTT GGGCTTCTGG GCTAGGGGGG

ACTTGGAGAA CTTTTGTGTC TAGCTAAAGG ATTGTAAATG CACCAATCAG CACTCTGTAA

AATGGACCAA TCAGCAGGAT GTGGGCAGGG CCAAATAAGG GAATAAAAGC TGGCCACCAG

AGCCAGCAGT GGCAAACTGC TCAGGTCCCC TTCCACGCTG TGGAAGCTTT GTTCTTTTGC

TCTTCACAAT AAATCTTGCT GCTGCTCACT CTTTGGGTCT GCACTATCTT TATGAGCTGT

AACACTCACC GTGAGGGTCT GTGGCTTCAT TCCTGAAGTC AGTGAGACCA CAAACCCACT

GGGAGGAACA AACAACTCTG GACACGCCAA CTTTAAGAGC TGTAACATTC ACTGCGAAGG

TCTGCGGCTT CACCTCTGAA GTCAGCGAGA CTATGAACCC ACTGGAAGGA AGAAACTCCA

GACACATCTG AACATCTGAA GGAAGAAACT CCAGACACAC CATCTTTAAG AGCTGTAACA

CTCACTGCAA GGGTCTGCGG CTTCATTCTT GAAGTCAGCA AGACCAAGAA CCCACTGGAA

GGAAACAATT CCGGACACAT TTTGGTGACC CAGATGGGAC TATCACCAAG TGGTGAGTAC

CATCAACCCC TTTCACTTGT TATTCTGTCC TATTTTTCCT TAGAATTCGG GGGCTAAATA

TTGGGCACCT GTCAGCCAGT TAAAAGCGAC TAGCATGGCT GCCAGACTTA AGAAACTAAA

GACACGGGTG TCAGACTTTC TGGGAAAGGG CTCTCTAATA ACCCCCAACT CTTTGGAGTT

GGGAGCGTTG GTTTGCCTGG AACCAGCTTC CACATTTCCT GTACTTCTGG GCTGAGACGA

GGGTCAACAT AGAGGAAAGC CATTCAGCTC TGGGGTCCCG ACAGCAAGTT GGTTGACCCT

GTGGCCATGA TCACAACTCT CGAAGTCATG TTGCCCAAGC GAGACTCACC CATCTATCCT

ATCTATCCTG ACTCTTGCTT CCTGGGTCCT AATGCCTGGA AGACAAAACT TCCTCTTGTC

TCTGTTCTCC AAGGCTAGTC CCACTTCTAA AAACCACTCC CTGTCTCTGG TGCTTTTCTA

GTTTCTCCTA TAAGAATGAT TTCTAGTATA AACTCCAGGA CTCTATTCTC TTCTTTAGGC

ACCCGGGCTC ACCAATCAGA AAGCCATAAT TTTTGCCCAA AGCCCCATCT TAGGGGGGAC

TATCTGGAAT TTTAGGATCC CTCCTCAGAC AAGCAGGCCT AACAAAAGCT ATTCCTGAAG

CTAGGATATG GGGAGCCTCA GAAATGATAT CCTTCCTATT CAAGTGAGGA CAAAAGGCAT

CACTCTTCCA ATTCTGGAGA TCCCTTCCCT CCCTCAGGGT ATGGCCCTCC ACTTCACTTT

TGGGGCATAA CGTCTTTATA GGACACGGGT AAAGTCCCAA TACTAACAGG AGAATGTTTA

GGACTCTAAC AGGTTTTCAA GAATGTGTCG GTAAGGGCCA CTAAATCCGA TTTTTCTCGG

TCCTCTTTGT GGTCTAGGAG GACAGGTAAG GGTGCAGGTT TTCAATAATG TGTTGGTAAG

GGCCACTAAA TCTGACATTC CTTGGTCCTC CTTGTGGTCT AGGAGGAAAA CTAGTGTTTC

TGCTGCTGCA TCAGTGAGCG CAACTATTCC AATCAACAGG GTCCAGGGAC CATTGTGGGT

TCTTGGGCAA GAGGTGTTTC TGCTGCTGCA TTGGTGGGCT CAACTATTCC AATCAGCAGG

GTCCAGTGAC CTTTGCGGGT TCTTGGGTCG GGGGGTGGGG GGAACAAACA GACCAAAACT

GGGGGCAGTT TTGTCTTTCA GATGGGAAAC ACTCAGGCAC CAACAGGCTC ACCCTTGAAA

TGTATCCTAA GCCATTGGGA CTAATTTGAC CCGCAAACCC TGAAAAAGAG TGGCTCATTT

TATTCTGCAC TATGGCCTGG TCCCAATATT CTCTCTCTGA TGGGGAAAAA TGGCCACCTG

AAGGAAGTAT AAATTACAAT ACTATCCTGC AGCTTGACCT TTTCTGTAAG AAGGAAAGCA

AATGGAGTGA AATACCTTAT GTCCAAACTT TCTTTTCATT AAAGGAAAAT CCACAACTAT

GCAAAACTTA CAATTCACAT CCCACAAGAA GAACTCTCAC TTACCCCCAT ATCCTAGCTT

CCCTATAGCT CCCCTTCCTA TTAATGATAA GCCTCCTCTA TCTCCCCACC CAGAAGGAAA

CAAGCAAAGA AATCTCCAAA GGACCACAAA AACCCCTGGG CTATCGGTTA TGTCCCCTTC

AAGCTGTAGC GGGGGAGGGG AATTTGGCCC AACCCAGGTA CATGTCCCCT TCTCCCTCTC

TGATTTAAAG CAGATCAAGG CAGACCAGGG GAAGCTTTCA GATGATCCTG ATAGGTATAC

AGATGTCCTA CAGGGTCTAG GGCAAACCTT CAATCTCACT TGGAGAGATG TCATGCTATT

GTTAGATCAA ACCCTGGCCT TTAATTTAAA GAATGTGGCT TTAGCCACAG CCCGAGAGTT

TGGAGATACC TGGTATCTTA GTCAAGTAAA TGATAGAATG ACAGCTGGGG AAAGGGACAA
AGTCTCTCCC GGTCAGCAAG CCATCCCTAG TGTGGATCCC CACTGGGACC TAGACTCAGA
TCATTGGGAC TGGAGTCGCA AACATCTGTT GACCTGTGTT CTAGAAAGAC TAAGGAGAAT
TAGGAAAGAG CCTATGAATT ATTCAATGAT GTCCACCATA ACTCAGGAAA AGGAAGAAAG
TCTTGCCTTC CTTGAGTGGC TACAGGAGCC TTAAGAAAAT ACACTCCCCT GTCACCCAAC
TCACTCAAGG GTTAATTGAT TCTAAAAGAT ATGTTTATTA CTCAATCAGC TGCAGATATC
AGGAGAAAGC TCCCAAAAGC AAGCCCTTGG CCCTGAACAA AATTTGGAGG CATTATTAAA
CCTGGCAACC TTGGTGTTCT ATAATAGGGG CCAAGAGGAG CAGGCCAAAA TGGAAAAGCG
AGATAAGAGA AAGGCCACAG CCTTAGTCAT GGCCCTCAGA CAAACAAACC TTGGTGGTTC
AGAGAGGACA GAAAATGGAG CAGGCCAATC ACCCAGTAGG GCTTGTTGTC AGTGTGGTTT
GCAAGGACAG TTTAAAAAAG ATTGTCCTAT GAGAAACAAG CTGCCCCCTC ACCCATGTCC

ACTATCGCTG AAGCAATCAC TGGAAGCCAC ACTGCCCCAA AGGACAAAGA TTATCTGGGC

CAGAAGCCCC CAAGCAGATG ATCCAACCAC AGGACTGAGG TGCTCAGGGT TAGCGCCAGC

TCATGTCATC ACCTCACTGA GCCCTGGGTA CATTTAACCA TTGAGGGCCA GGAAATTGAC

TTCTACTGGA CACTGGTGCG GCTTTCTCAG TGTTAACCTC CTGTCCTGGA CAGCTGTCCT

CAAGGTCTGT TACCATCCGA GGAATCCTGG GACAGCCTAT ATCCAGGTAT TTCTCCCACC

TCCTCAGTTG TAACTGGGAG ACTTTGCTAC AGATAGTAAG TATGCTTACC TAATCCTACA

TGCCCATGCT GCGATATGGA AAGAAAGGGA ATTCCTAACT TCTGGGTGAA CCCCCATTAA

ATATCACAAG GAAACTATGG AGTTATTGCA CACAGTGCAA AAACCCAAGG AGGTGGCGGT

CTTACATTGC CGAAGCCATC AAAAGGGGAA GGAGAGGGGA GAACTGCAGC ATAAGTGGCT

GGCAGAGGCA GGGAAAGACA AGCAGAAAGG AAAGAGAGAA AGAGCAGAAA GTGAGAGAGA

AAGAGAGATA GGAAGTGATA GCAAAGAGGG AGTCAGAAAG AAAAGAGAGA GGAGAGAGAG

AGGGGGAAAG ACAGAGAGAG ACAGAGGAAG AGACAGAGAG ACAGAAAGAG AGAAGCAAAG

AGAGGAAGAG ACAAAGAAGG AGTCAAAGAG AGGGAAAGAG AAGTAGTAAA GAAAAAACAG

TGTACCCTAT TCCTTTAAAA GCCAGGTTAA ATTTAAAACC TATAATTGAT AATTGAAGGC

CTTTTCTGTT AACCCTATAA TACTCCCAAT ACCACCTTGT TGTTCAGTGT TAAACAAGGG

TTATTAGCCC AAAAGCCACT GAGGCCACTG ACAACCCGTA GCCTTCTTAT CCAAAATCCT

TAACACAGCA GGTTTCCTAA CAGGGATCTA ATCTTAGGTC GACCAGACTG GAGAACTGCC

TTCAGGACAG GATGATAGAT GGTTCCTCCC AGGTGATTAA GGAAAAAGAC ACAATGGGTA

TTCAGTAAGT GATAAGGAAA CTCTTATAGA AGCAGAGTTA GGAAAATTGC GAAATAAGTG

GTCTGCTCAA ACGTTGAAGC TGTTTGCTGT TTGCACTCAG CTAAACCTTA AAGTACTTAC

AGAATCAGGA AGGAGCCATC TATACCAATT CTAAGTTAAT ATGGACTGAA CGAGGTTTTA

TTAATAGCAA AGAAAATTAA AATCTCAAAC TTACGAGGTT TTCAAGTAAA GTAAAGTTTG

GTAAAAGTTA ACAGCGTAAC ATGTATTATC CTAGTACCAC ACATTCTCTC AAAGGATTTG

CTCAGACAGT TTGCAAAAAA GAACGAAATC TGTCCTTACT CTACAATCCC AAATAGACTT

TTGGCAGCAG TGACTCTCCA AAACCGCTGA GGCCTAGACT CTCATGTTGA GAAAGGAAGA

TTCTGCACTT CTTAGGGGTA GAGTGTTGTT TTTATACTAA CCAGTCAGGG ATAGTATGAG

ATACCACCCA GTGTTTACAG GAAAAGGCTT CTGAAATCAG ACAATGCCTT TCAAACTCTT

ATACCAACCT CTGGAGTTGG GCGACATGGC TTCTCCCCTT TCTAGGTCCT GTGACAGCCA

TCTTGCTAAT AGTCGCATTT GGGCCCTGTA TTTTTAACCT CTTGGTCAAA TTTGTTTCCT

CTAGGATCGA GGCCATCAAG CTACAGATGA TCTTACAAAT GTAACCCCAA ATGAGCTCAA

CTAACAACTT CTGCTGAGGA CCCCTGGACC GACCCGCTGG CCCTTTCAAT GGCCTAAAGA

GCTCCCCTCT GGAGGACACT ACCACTGCAG GGCCCCTTCT TCACCCCTAT CCAGCAGGAA

GTAGCTACAG CGGTCATCGC CAAATCCCAA CAGCAGCTGG GGTGTCCTGT TTGGAGGGGG

GATTGAGAGG TGAAGCCAGC TGGGCTTCTG GGTCAGGTGG GGACTTGGAG AACTTTTGTG

TCTAGCTAAA GGATTGTAAA TGCACCAATC AGCACTCTGT GTCTAGCTAA AGGATTGTAA

ATGCACCAAT CAGCACTCTG TAAAATGGAC CAATCAGCAG GATGTGGGCG GGGTCAAATA

AGGGAGTAAA AACTGGCCAC CCGAGCCAGC AGTGGCAACC CACTCGGGTC CCCTTCCACA

CTGTGGAAGC TTTGTTCTTT TGCTCTTCAC AATAAATCTT GCTGCTGCTC ATTCTTTGTG

TCCACACTAC CTTTATGAGC TGTAACACTC ACTGCGAGGG TCTGTGGCTT CATTCCTGAA

GTCAACAGAC CACGAACCCA CTGGAAGGAA CAAAGAACTC CCGATGTGCT GCCTTTAAGA

GCTGTAACAC TCACTGCGAA GCTCTGCAGC TTCACTCCTG AAGTCAGTGA GACCACAAAC

CCACCAGAAG GAAGAAACTC TGGACACACC TGAATATCTG AAGGAACAAA CTCCAGACAC

ACCATCTTTC AGAGCTGTAA CACTCACCGC AAGGGTCTGT GGCTTCATTC TTGAAGTCAG

CAAGACCAAG AACCCACCGG AAGGAACAAA TTCCAGACAC AGTAGGAAAT CTGTATTTTT

GATCTGTGGC TTCCAGGGTT ACTCCAGTCA TTGAAGTCTC CATTGCAGCC TTAAGGAAAC
AGAGAATGGT TTGGAGGAGC ACATGTGGGA ATTGTTATGG ACCAGGCTTG AGATGCACAT
AGGGCATTTC TGATCAAACC TAGCTGGAAG CAGGGCCAGG AAATATAATC TAAGGAAGAC
AGTTTTTGTA GACAGTAGTA GTCTTTGCAT CTGAGACATG TAGATTATCA AGCAATTAAT
TAGAAAAAAT ATAGCCAGGT GCGATGGCTC ATGCCTGTAA TCCCAGCACT TTGGGAGGCC
AAGGGGTGTG GATCACGAGG TCAGGCGTTC GAGACCAGCC TGGCCAACAT GGTGAAACCC
CGTCTCTACT AAAAATACAA AAATTAGCCT GGTGTGGTGG CACGCATCTG TAATCCCAGT
ACTCAGGAGG CTGAGGCAGG GGAATCTCTT GAACTTGGGA GGCAGAGGTT GCAGTGAGCC
AAGATCACAC CACAGCACTC CATCCTGGGT GACAGAGCGA GACTCTGTCT CAAAAAAAAA
AAAAAAAAAA GGAAAGGAAA ATATAATCAA GAATATTGAC AGGTAACATT TATTCAACAC
TTACTATGCA CCAGGCAATA CACTAAGTGT TTTACATGGA TTAACTCATT TAATCTTAAC

AATAGCCCTA TGAAGTCAGT GCTGTTATTA TCTCCACTTT ATAGATAAGG AAACTGAAGT
ACAGAAAGGT CAAGTAGAGA AATGGCCATG CTTGCATTCT CAGTTTTTGA AGCAACTGTT
ACAGGAATCT GGTGTGAGAA ATGCTCTAAC AAGATGTGAG TCAGGGGTTG GGAGGTACTG
AGTCTGAGTT GGGCAGTTGG GGATGGAAGG ATGGATGAAG AACAGCTTGA CAGAGAAGCT
GACACTTGGC AACTCTGTGG GACCTTGAAG GGTTAGAGGG ACTTCACCAA AGAAACTGGT
GGTCAGGGAT ACGGGAGGGT CACGGCAAGG AGGGAAAGGA AACTGTACCA CAGCAGAGAG
TCTGAAGCTA CTACAGTGTA GTTCAGCGTA TAAAGAATAA TTATTTTAAG GTAAACTTAT
AACCTCATGC AAATATAAAA TGAACACGTG TCAAAGATCT TATTTAATTT ATTAATTAAT
GAGGGAACCT GTAAGATGTT ACAGCCAGTT CAAAGGATAA TTCAAATAAA TCCATGCACA
TATGTAGGCA ATAAGGAATG CTGAAATGAA TTTAAAAGTA GATGTAAACT GATTTATCCA
CAGAGAAATA ATCAGTTGCA TTTCACATAA CAAAATTCAG TTGCTTTTCT ACAGAAGGAA

TTGTTTGCAT CATTACCAAT TTTTCTACAA CTAACAGAAT TATAAAATAA CTCAAACACA

ATGAAAGGCA GATATAACCC ACAATGGTAT GATAGATACA ATATCCACAT CCAGGATGTT

TTTTTCTCAT TTCAAAGTCT TTCACAAGTT TTCCTGATAA GGGAGTGTCA ATAATACTGT

ATGGCAGGCA ATAAGACTGG ATGGATGGTT GGGGCCAGGT TTTAAGGGGT AATAAATGCC

ATGTAAAGGT ATGTGCATAC TGTGCAACAT GTCGGGGAAT CTCAAATTAT TGGTAGAGTA

TGTAAGAAAC ACTTGTGGAG CTTGTTAATA AATTCAAATT CCCAGACCCA ACTCCTCAAG

GGTCTAATAC AGTAGGTTTG GAGTAAAGCC TGAAAATCTG CAATTGTGCA AAAAAAAAAA

CCCAGGTGAT TCTGATACAC TTTGAGAAGC ACTGGTGGAA CTAATAGTCA CTGAACGTTT

TTGAGCAGGG GAGAAACCTG AGGACGTCTA TGTTGCAGCA GTGGAAACTT GATTAGAAGT

AGGAGAAGAT GCATGGTCTT AAAAGAATGC AAAATGATGG CTAATATTTG AGTGCTTATG

ATGGGCCAGG GGCTGTGCTA GGCGCGTGGC ACACATTCAA TACGATGGAA GCCTGTACCA

GTCAGTATTA GTGGGGTATC TTTAAGAGTG ACCAGAATTA AGGGGGGTTT TCACCAAAGC

CTGAGGACTG AGCCTCCTCA TCCTAAATTC AGACACAATG CTGTACCTAT GCATTTGCCT

CCAGGCTGTT CCTGGGCCTC CAGGGACTGG CCCAGGCTCC TGATAAATAG GGACTCCCAA

CAACATAAAG CCTGGATTTT GGAACTTCCT GAATGTTACT CAGGCTTTCT AGTAACTGTG

GAGATCTGAA TAATAACACA ATTCTAAGTT CCCCTACTCA TAAAGCTGCT CATCATTTAG

ATGGGGTAAA GCACCTGAAA TACAATGAGC ATCACTATTT TCATTCATCC ATGAAATGAA

CATTCCGGGG AGATCAGTAA GTTGATGTAT CACCCTTGAA CAGGGCAAAA TGAATACTCA

CCAGGAATAT GTGGTATTTT AAAAAGAAGG CAAAGGGAAG AATAGTGGGG ATGGGGCAAA

AACTTTAAAT AGATTCCCCC AATCATATAT GGCAATTGAA GATAATTAAA TTATCATTTT

AATTGAGTAA GTACTCATAG AGCCCTCACT ATTTGAAAAT GAACTGCCTC CTAATTGTTA

TTGTGCAAAT GTGATACATT AAACTTAAGC TATTTTAATA AAACATCCAT TTTCGGAAGC

TGTAGTAGGT TCTCCCAGGT CAGATTTGAT AAGCCATAAA GAACAAATGC CAACTCCTAT

TTTTCTATGG TGCTGGGAAA TAAGAGAGAA ATGTGTAATT CAAAGCAATC ATTTAATTTT

ATCCAATAGC TTGATTCTCC TCTCTCTTCT AGCCTTTTAG CTAAGCTGTT ACCAAGTAAC

CACACTAGTT GGCTTGAGTC TTACCACTGT TTCCCTGACC CCACAGTGGA GAGACTGCAT

CTGTTAAAGA GCAGTTATGT AACCATGGCT ATGCTGAGCT GGGATTCCCA AGGCTTAGGT

TCTTTCTGTG AATGACCTTC ACCAAGACAC CTGAGGTCTG TGTGGAACCA CAGGCTTGTC

ATCTCTAAGG CAGAGTTGAT AATTCCATCT GTTTCTTGAG CCCACACTGA GAAAAAGATT

ACATGACTGC AGTTATTTGA ATGCCTCATG GAAAGACGTC TTATAAATAT TATAATTAAT

GTTATCATTA AGTAATGCTT CAATGCAGAT CTTCCAAGTA TAAATATCAG CTGAGTAAGA

AGTCAATCTT CCCTGAAGCA AAATTGAAAT TTGTAAATGC GATTTCTGGG AGCTTATTTT

GTAATACATG ATTCCAGAGT GTCCATAACA CACACAATTG TCTTTTTTCC CCTACATGGG

CTATTTACAA CAAAATTGGA CTTATAATGT TTATTTCCAG GGATGACTAG AACTTTAATA

ACAAACCTTG GGCCAGGCAT AGTGGCTCAT GCCTATAATC ACAGCACTTC GGGAGGCTGA

GGCTGGTTAG ATTACTTGAG GCCAGGAGTT TGAGAACAGC CTGGCCAACA TGGCAAAACC

CTGTCTCTAC TAAAAATACA AAAATTAGCC GGGTGTGGTG GCGCATGCCA GTAATCCCAG

TTACTAGGTA GGCTGAGGTA CGACAATCGC TGGAACCTGG GAGGCGGAGG TTGCAGTGAG

CTGAGATTGC ACTACTGCAC TCCAGCCTGG GTGACAGAGA AAGACTCTGT CTCAAAAAAA

AAAAAAAAAT AATAATAATA ATAATAAACC CTGATGAAAG GTTTCTAAAA TGTTTTCATC

TAATGGTTTT CTTGACAATT AAATTTTCTA TATAATGTCA GTTCATAAAA AAACTGAGAA

CGACCACATG TCATATCGAC TGCTTAAAAG AAAATACGTA TATTTACAAA CATATACACA

ATACTGTCTT TTGTCTGGTT AGTTTAGAGG TTAGATAAAC TGCAGTATGT TGTAGTGGAC

AGATCATAGA ACTAGGAGTC AGGATGTCTG GATTCCTAGG AAGCAATGAA TAGGTTGCAC

GGTGCAGCTC AAGGTTATTC AAAGTGTGGT GCCCAGACCA GCATCATGAG TATCCTCAGG
GAGCTTGTTA GAACTGCAGA TCCTTTAACT CATTGAATCA GAATCCCTAG GTGTGGGGCC
CTGAAATCTG TATTTTAGCA GGCTCTCTGG GATTGTGATG TGCCTTAGAG TTTGACAACC
ACTGGGTAGC TGATCCTGAC TTAGACTTAT CAGGCATGTG ATCTTGAACA AGTCACATAA
TCTCACTGAG TTCAGTTTTC TTATGTTTAA AATAGGCCCA ATAATATCTA TTTCACATGG
ATTGCTTTGA GGATTAGGCA AGAGATCTGT AACAGACACT GTAGAACAGT GTCTCTGGTC
TACAGCTGAC CTTCCATAAA TGGTAGTTGC CTTGATTCTC TGCTCTGCCA CATAATAGCT
GGTTAACTAT GAGCAAGTAA TTTAGTTCTT CTCAGTTTAG TTTCTTCCCC TGTAAAAGAA
GGAAAATAAC TGTTATACTC CATTTCTGAA TTGCTATAAA AGTCATTTAA TTATGGGCAT
TGAAGCTCTT TGTTCACTGT ATAAGGACTG TACATCTAAG GGATTAATGA GACCAGGCTT
ATGATTTTAA GCATGGAGTA AATAGTAACA CTGACTCTGT TCTATGAACC ACATGGAAAC

TCTAAAGAAT ATGCACATTT GAAACACAGG TATCATCTGG GGAAGGTGAT CTGCTCACCC
AAACCAGTTC ATGAACATCA ATCTCCAGTG GCGTGCTGGA GCTAGCTGTA CCAGCTCATG
AGGGCCAATT GTTTCATTTT TAGGAATTTT GTTTGCTGGT TAAAAATAGT CATTATTTAA
AATTAAATTA TGTAAACAAT AATATTAGAT AAAATAAGTT AAAATAAAAA CAAAGGAACT
AATTATCCCC AAACTCTTCC CCACCTAATT ATTTTACTAT CTGTGCCTTG GGATTATTTA
CATTGATTTT ATCCATATGG TGACAATACT ATTCATATAT AAATGGTGTG CTTCTCTTCA
TAACTCTACA TAGCCTGATG TCAGGCTAGT AGCTTGAAAT TGGCCACAGT GGGAGTGTGA
GCATTTGTAC CATGAGGCTT GGCCAAGGCT ACAAATCCAG ACTTTTGTTT TTCCCTCCTG
GAGAGCTGTC TGTTAAAAAT TTACCAACAC ACCACTGGTC TTACCTTTGT TAATTTACCA
CAGTCCAGGT TCTGACCTAG ACTTAGAAAC CTGGATTTGT CAGCAAGCTG AGGATAGAGC
CATTATTTCT AAGAAGGACT CACATTACCC AAGTGCAAAG CCTGATATAT ACCTTCAGAA

TATCAATTTA TTAATTTACA GTGAAGAAAG CCACCCCAGG GCATTCCCCA GGGGAAGGCA

AAAAGAGCTA GTTGCACATT TTGAATGTTT GATGACATTA GGGTAAGGTG ACACAGAATA

TCCATTTCCA CAACTGAGAT ACCTGCTGCC TTAAGGAAGG GACAGGCAAG TCCTTGGGCA

GGACCTTAGA TTGTCACTGT CCATCTTGCT GTAGGACTCT CCTTTCCAGG CATGACGATG

GCCAACTCTG TCCTCCTACC CTACTGATGG GATTATCTTT TCTTGACACA TGGCAATGCC

TCCAATCAGA GGCTGGTAGC TATTTTTAAT CTTCAGGGCA GTATTTTTCA AAGGGAAGTT

CATGGACCAT ATGCATCTGT ATCATTTAGA TGTATATTAA AAATGCTTAG TCTTCCCCAG

TTATACTAGA TCAGAATCTC TGTTGGTGGG GCCCACGAAT CGGTATTTTC AACAAATCAC

TAGGTAATTT CTGTATATAC TATAGTGTGA AGACCACTGC TTGAAGGTTT CTTTGCATAT

CTCCACTAAA TATAAAAAAT ATTGACTTCT AGATTTAACT CCCAAAGCAC TTGCATTTTT

AAGTTTCTGG GGGCATTATA TTGTGGTACC CCTATACCAC TCACACTCTA GTCAGGAGGT

ATATTATGGA CTGAATGTTT GTGTCCCTCC AAAACTCATA TGTTGAAGTC TTAGCTTCCA

ATGTGATAGT ATTAGGAGAT GGTGCCTTCT GGAGGTAAAA TCAAGCCCTC ATGAATGGGA

TTAGTGCCTT TAGAAAGAGA GCTCGTCACT GTCTTTCCAT CAATTGAAGA TGCAGTGAGA

AGCTGGTAGT CTTGCATCTG GAAGAGGGCC CTCACACAAC CTGATCATGC TGGCACCTGG

TCTCAGACTT TCTGCCTCCA GAACTATGAG ATGATAAATT TCTGTTGTTC ATACCCCACC

CAGGCTACAA TATTAGGTTG CTGCAAAGTA TTTGTGATTT TTGCCTTTAC TTTTCAGGGC

AAAAACTGCA ATTACTTTTG TGCCAACCTA ATATTTTGTT ATAGCAGCCC GAACTAAGGC

AAGGGAGACT ACATCAGACA GTGTAGCTAT GTAAGTACAA ATGTATCCCT GTTGAAGGAA

AACTAAGTTC TAACCCTGAC TTCAGGCCAG TAGCCACCTT TTCAATCTCT TTCATGAAGG

GACCATTATC ATTATCACTG GTGGCAAAAA TAGAGCACGA GAATGGAATT TGCTTTTCTG

TGAAATCTCA GTGTATACAG ATGAAGAGCA AGGGTTTGCT TTCATCTCTA AGAAGCAAAA

GTGAGTACGG ACTGGCACAT TATCAGAGAA AGAATCATTC TAGCTCGGTG GGTCTTAACC

AGGAGTGAAT TTGACTCCAG GGAACAGTTG GCAATGTCTG GAGACGTTTT TATTTGTTAT

AGCTGGGGGA TGAGTGGGTG GGTTGCTACT GGCATCTAGT GGGTGGAGAC CAGAGATGCT

GTTAAACATC CCGCAAAGCA CAGGACAGTC CCCGACAACA AAGAATTATC TGGCCCCAAA

TATCAATAGT GCCAAAGTTG AGAAACCTCA TTCTAGCTTC CTTTTCCCTT CTACGTTCTA

ATCAACTGTT GTTCTTTCAG CATTAGGATT CATCCAGCAG TCTCTTTCCC CAGCAATTTG

TTGAAATTTT TTTAAAAATG GACTCATTTT AGTGTCACAA GAAAAAAATA CATTCACAGG

AAAGGATGGG TCATTTTGTT TAATGATGTT TTGCCTTTCA CATAGCAAAA GCTTAATAAA

GTATTTTTAA ATAAAATGGT GAATAGATCA AAACATTAAT TTCACATGTG TTTTAATAAA

TAACAGGAAG ATGGCTATAT TATATAAATT GTTCTTGTAT ATGTCTTGAG TGGATCATCA

AACACAAACG TATCTACATG CCTTTTCTTG TGAATAGATC TAATAATAAC GCTCTTCTAA

AAACAAATTA AATGGATATT ATTTGCTGAG AATGTAATGC TTGTGTGAAT AGAAGCCAGC
CCTGAATCCA AGCCCCCAGA TCTATTTAAA GAATTTGAAG AATGTCAGAA AAGCACGTGG
CTTCAAGGTT AATGTGTAAG ACTCACAGAA ACTTGAAAAA TCACTATGAC TAAAAAGAAA
GTATGAGCTC CCTGCATGCC TGTAAATTGG AATGACAGCC AAAACCAGTT AATTATAAAA
ACAGCTAATT TAACAGGTTT TCAAATTTGT TTCTTTCTCC AAGTAGCATA TAGTCAATAA
TCCTTAAAGA GAAAGCAAAG AAGGGGAAGC ACTGAACCAA ATTTGCTTTT TTGTACCTGC
TCAGCTCAAA TGCAGAGTTC TCTACCTGGA AATTGACTGC TTCCATAGTT TGATAGCCAC
AGAGAGATGG GAACAGAAGG AGAGGTATAA TCCCAGACTT GATTCAGCTA TAGAGAATGA
CAATAGTGTC AGAGGCCTTC CAACCAGAGC GACTCCATCT TGAATACGGG CTGGGTAAAA
CAGGGCTGAG ACCTACTGGG CTGCATTCCC AGGAGGCTAA GCATTCTAAG TCACAGGATG
AGACAGGAGG TCAGCACAAG ACCTTGCTGA TAAAACAGGT TGTAATAAAG AAGCCAGCCA

AAACCCACCA AAACCAAGAT GGCCATGAGA GTTATCTGTG GTTGGTCTCA CTGCTCATTG

TATGCTAATT ATAATGTATT AGCATGTTAA AAGACACTCC CACCAGTGCT ATGACAGTTT

ACAGGTACAT TGGCAACTTC CGGAAGTTAC CCTCTATGGT CTAAAAAGGG GAGGAACCCT

CACCTCCCAG AATTGCCCAC CCCTTTCCTG GAAAACTTGT GAATAATTCA CCCTTGTTCA

GCATATAATC AAGAAGTAAC TGTAAGTATC CTTAGGCCAG AAGCTCAGGC CACTGCTCTG

AATGTGGAAT AGCCATTCTT TTATCCTTTA CTTTCTTAAT AAACTTGCTT TCACTTTACT

GTATGGACCC CTGTGAATTC TTTCTTGCAA GAGATCCAAA AACTCTCTCT TGGGGTCTGG

ATCAGGACCT CTTCCCAGTA ACAATAGTAG TAAGGGGTCG GGGAAACTGG ACAAAGGAGT

TTAAGAAGCC TTAGATAAAG GGTCCTCATC ATTGTCATAA CATAAAATCA TGGACTCCTA

GAATTTTATA GCTGATAGGA TTAGAAATTT CAAAATTCAA TTTCATTAAT TTTCATCTGC

GAAAACAGAT GGCCAGAGAG GCCAAACAAT TTGTTAAGGA GCACTGAGGC GATGGAACAC

CACACTGGAC CGCAAACCTC CTAGCAGAGT ATACAAGGCC TTTGATCTCC TCAGTCAGAA

TGAACTAGAG CTTTCCAGGG GTACCCTTTC TGACTGTTTA GCATGTTTGC CAGTCTGACT

AATTTTGAAG TTGCTTAAAT ATCTGTCATT TCCACTGTAT CATAATCTCC TCATTCATCT

TCAATCTCCA ATGCCTTGAA CTCAGTAAAT GTTAGTTGAA CAAAAGTAAA TTGAACCCAG

AATTTCTGAT CATAATCTGG AGCACTTTAA AATTGTCAGC TTACTGGGAA ACGGGATAAC

ATGTGATTTG TCTTTGATTT TTTTTTTCTC ATATGCTTTT TCCACCTATA GATGCTACAC

GAATGTTTTT AAAATCTGAT ATAAAAATTA AAATTAAAAA ATTAAAAAAA GAAAATTTGA

TACAATGCTA CATTTAGAGT GTTGTGATTA GATTCCTTAA GTGTATCATG GTGATCTCTA

CATCACGTGG TGATCAAATT GCTTTGGGTT TTAACACATA ACTGACAAAG GCTTGGGGAC

ATGTAAGATC CCAAATACAT TTTTATTGAT TTTTTTTTCT TGTTTGTCCT CTTTTAAATA

ACTTTTTTTT GTTATAAGAA TAATTCATGT TCAGTGGAGA AACCATAGAA AATAGTGACA

AAA AAA

FIG. 6A(104)

AAA — AAA

AGTGAAGGAA TAAATTTAAA ATGACCCATA ATTGTACCAT ACATTCTGAT TTTTTAAACG

CTGAACAAAT TAGCCTTGGG TAAGTACCAG GAATAGAGTG CAGCATTGAA AGTTAAAGTT

TGGGGAAGGA TAGCTGACTT AAGAAATTAT CTAGTTAGAC ATTTTTTGGA TGGGGTAATT

TTGCAGATGA CATTAGTGAG AGAAAGGACT TGCCACTCTC ACACAGCTAG TAGGGGTGTG

GGAGGATATT GGAACCAAGT TTCAAGTCTT CAGTGAAGAA TCAAGGGAGA AGTTCTAAAA

CCTAACAATA TCCCTCTGGA TGGACATTTA TTTTATTACT ACAATAAGCC ACACGGTGAG

TCATAAGGAG CATTTCATTC TTCTAATATG TCTCTACTGT ATTTAGAATC TGATAAAGCC

CTATTAGAAT TCATCTCTTT AAGAATAAAA GAAGCTGAGG AACTAAAGAG AGGGTTGGAA

TAATCCACTA ATTATATCCG TTAAGCTTCA GTTACGCTAA TAAGGAATAT CACATGACTG

TGGTGTGTGC TTGTTCTGAA CAGTAAAGTA CATGAGGAAA GATAAGATTC AGGGCTGAAA

TGTCCTTCAG CATATGTAGG TAGTGGTGAT GAAAGTCATT AAAAGAAAAA TTGATTGAGG

BBB — BBB

FIG. 6A(105)

BBB ——— BBB

TATTTTAGTA AACAAAAGAA CTCACCACTT ACCCATCAGG AAGTGTATTG TTAATGCAGT

GCTGTTCAGC CTTCTGGAAG AAAAGGTTTC TTCATGCTTC TCTCTTTAGC CTAATTCTTA

TCCTGTCACT TTTCAGGCAA AATTAAAAAA AAAAAAAGAT TGAAAACGAT GCTCCTATTT

TATTTGCTTC AAAAGAAACA GGCTGTTGCA TTGTGCTTGG AACAGTTTAC TCTTGGCCTT

GATGTAAGTG TGAAAGGAAG CCCATGTAAT TGACTAGGCA GTATCTGAAG AAGCAGGAAA

TACAGTGTTA AGAAAATGAA CAGGCATGAA AACCATGGCT ATTTGATAAA AGTAAATAAT

TTCTGCAGTT CACATGTTCT CAGCATATTT TCTTTGATAC TGACTTGCTT AATATGACAA

TAGCAGAACC ATGGTAGCTT GTAGGCATTA CTTTTCTTTT AATTTCTTTT ACATTTTGAA

TTTACCAGCA CTCACATTTG TATTACTTTT GGGTTATACT GAGGATCTAT AACTTATAGA

TCAAATACCT GACATATATA TGCATTCTCT GAAGTCTTAG GGCAGAACTA GAACATTCTT

GTGAACATCA GTATAAGATA TTAAAATGGA AGTTTTGCCT AAGACTGAAG ACAATAAAAA

CCC ——— CCC

FIG. 6A(106)

CCC ——— CCC

TATCATAGTC TGAAATGAAT GCCAGCACAC CATACAGGAT TTAAATATCT ATACATATAT

ATGTGTGTGT ATTATATATA TTTAATATAT ATCTGTGTGG GATAGGAAGA GGTAGGGGGA

AATCAGTTTT ACAATTATTA AGTATTTCAC CCTTGACAAG AGTATATATA TTGGAAATCA

GTTGGAGAGT ATTTTCAAAG ATAAATGTTA GTGTGCTATG AATGAATCCA CCCCTACCAC

CACTGAGGCA GGGTAGGAGA GGCCTGTGCT CCTCAAGCAT AGTTGGAAAA GGACCTCAAC

AAGACCACTT CAAGAGTCTA ATGTGTGGAG ACTGTTGCTT AGGGAGACCT TATGGTCTAG

CTTCTGACTC ACAGCTAAGT CAGGGAGACA GGTTGGCTGC TCTGATCGTG GAGTCCAAAA

GATGGCCTGC ACTGAAAAGC CTCATGAGTG TTGACTTAGG GCTAGTCTAA GAGGTCCCTG

GAAGAAGAAA CACTCAGTAG GAGAGAAGCT GGAGGTACCT TCAGTGCTGA ATTGGAACTA

GATTCATTCC CCCGTGGAGC AAATTACATA GGAAAGATGC CCAGTGATGG AGAGTGGGGG

TGTCTCTAAC AATTACCCAC CCACTGCCCC CACCCTAAGA AAAAGAAAAT CACATACAAC

DDD ——— DDD

FIG. 6A(107)

DDD —————————————————— DDD

CAGTCAGCTG TAAACATATG CCGAGCCTAG TAAACTCAGA TACTAAGTTA CCAGGGTACC

TGGCAAGTAA GAACATTCCT GATTCCCTTC CTCTCTTCTC TTTGCCCTCC AACCTTAGTG

GCTAGCAAGA TGGGGAGAGG AGGAGAAGCT GTAAGTGGGG AAAAAAGAGC AGCTTTCTCT

CCTTTTCAGC TGCTGGATTC TCCCTCATCA TAGGCCTGAG CTGGGGAATC AGGAAGAAGG

ATTCTTTTTA AAACTGAAGT AACGTTATCA TTTAATTTTA AAACATTTTA AATTTTGACA

ATGTTGAGAT TAGATATACT AATTATTAAA CTAAGATTAT GTTTTGCAGC TTGAAGTGAT

AAGAAAAACT CTTATCTAAG AGCATCCAGG AAAGTCGGGG GTTTCCTGAA CATCCTTTTA

AATCCTTTGG AAGTCAGCTT TCAGAGAGGA TTTAAAGTGT AGACTGGGCC TTCAGAAACT

TGGTTAATGT AGGGGTTTCC TATGCAGACT TGGGGACTAT ACCTTGTGTG GAAGAGAGAA

AATAAGATTA TCTTACATTT TTCCCATTCC TTTTTCAAAA AGAAAGCTCA GCTAGCATGA

AAGTTAAATT CAAAACGTAA TGGGTATTAT TTGCATATTC AAATCTAGTG CATATCATGT

EEE —————————————————— EEE

FIG. 6A(108)

EEE —— EEE

```
AAGTACTGAA TTATGGTATT CATTATTTCA AATGACAAGC TGGATTTTTT TTTCTTTCGA
ATTTCACAAA TTAATTTTCC TTGGAACCTT TTGGTTTGGG CTTTAAGAGT TTAGGCTTTC
ATCACAAAGA GAGGACAGCC TTGAAGATTA AAGTGTGTGG CTCTTCTCAA GATGTTCTTA
GTCCAGCAAA GGATTCTATG CATATTTGGG CTTCCTTCTG TCTCATAACC TGTATTTCTT
GATATTCTAT TTATATTCTG TAAGATTTTT TTTTTAAAGG AAAAATTCTT CCATGGTTGA
AGGACATGTC AAAAATAGAG GATACAGTTT TATATCAAAG GAAGTTTCAT GATATGACTG
TAGAAGCTCA TTTGACTTAA GACACATCAT TTCCTCATGG AAGTGTTAAA CAGATCTGTA
CAATAAGGTT GGCAATCTTT GTGTAAAACA GTTTTTTTTC TCCTGCTCTA AAGAAAGTGT
ATATTTCAAA ATGTGAATGT CAGCAGTCAG AAAATAGTAT TTTTTTAACT TCGTTTTCAA
AGTCCTCAAA AACCTGTACC TAATCATGAA TTTTTTTTCC CACAGATTGT TTCTTCTTCT
CCCTCCCAGA AACTTTGAAG TTTTTCTACA TGACACCAGG ACCTATGTCT TTTTTTAATT
```

FFF —— FFF

FIG. 6A(109)

FFF —— FFF

ACACAGAAAT GAAAGAAAAA AAGTGTGTTG TATCGTTAAC CAAATATATG AAATCTTTAA

GCTGTATTTT TATTTTTAAC TTTGTTTTGC AAAGAGGCCA TTCCCTTTGG TTAAATAATT

TGTTATTCAC AGTTTCCTTG TCCTCATATT ATCAAGGGGA AAATTGTAGA AATTTTAAAG

GAAGCTCTAG GCAATGTTTT CATCCCTGAA TCTTTGGAGA GTTATAAAAA CAAACAGATT

ACTGAACCTG TAAGAGAACC AATCGTGAAG TCATTACATC TAAGCATAAG CAAAATCTCC

TCTTGGATCA TTAAGTTATA GAAGAAAAGA AAGCCTGCAC TTTGAAATTT AGATAAAGCT

TGGTAACTTG TAAGTCAAAC ACGTAAAATT TTACAATTCA GGAATATCGA TAGCAGTTGA

GTTTAATAGA CTTCTCACAT TCCAAATTTA AAGCTTCCTT CTCTGTGCTA ATAGAGATAC

AATAGCAGTA GGCGTTTAAG AAGAATGAAT CAACAATTTA AAACTATAAT GTGTTTTTTA

TTCATCTCCC TTATTCACAT ATATTTGTTT TGTTTTGAGA AGGAGTTCTG CTCTGTCGCC

CAGGCAGGAG TGCTGTGGCA CGATCTCAGC TCACCGCAAC CTCTGCCTCC CGGGTTCAAG

GGG —— GGG

FIG. 6A(110)

GGG ——— GGG

CGATTCTCTT GCCTCAGCCT CCTGAGTAGC TGCGATTACA GGCGTGCGCC AGCAACCCCG

GCTAATTTTT GTATTTTTAG TAGAGACAGG GTTTCACCAC GTTGGACATC TTGGTCTCGA

ACCCCTGATC TCAAGTGATC AGCCCGCCTC GGCCTCCCAA AGTGCTGGGA TTACAGGCGT

GAGCCATCAC TTCTGGCCCT TATTCGCATA CAATTTAAAA ATCATCACAG AAGGTTTGAA

AGAAGGAAGG GGCAGAAAAT TACCTACTTT TCCTCTCCCC AGCGATCTCC TTCAAATCTG

TGCCTTTTCC TCAGGCCCAG GCCTCAATTT ACTGAGCAGT CACACCTCAC AGAGGGAGGT

CTGGGCAATC CACTCTTGGT CACAGGAAAG CCATTGACCC TCCCACTTCC TCTCCTCCAC

CTTGTTCTCA ACTCTTGACT TTGGGCTTTG TTTCTGTTCA AGTCCTAGAA CTGGTTTCTT

TTATCAGGTT AAGTGATTAG TTCTCTTTCC CTCTAGTTGC TCTCACTCCC TGACTCTTGC

CTTCTGTAAC AACTGGAGAC AACTCTTTCA AAACCAGCTC CAAGCCCCAG ACTTCTCTCT

GGGCTTTAGT TCGTAAGGCA GGTGCCCTAC TGAGTGAGCC TAGATCAGAC AGAAACATAG

HHH ——— HHH

FIG. 6A(111)

HHH ——— HHH

CTGTTGGCAA GGATTTAGGT GAATTTCCTT CCATTGTTTT TCTAATACCT TTTTTTTTTT

TTTGTAAATA TAACCATGCA CCTACACACA TATTTGAATA TCCTGCCTTT TTATTTAAAA

TGACATGATA GGTCCGGGAG TGGTGGCTCA TGCCTGTAAT CCCAGCACTT TGGGAGGCCG

AGGTGGGCAG ATCACCTGAG GTCAGGAGTT CGAGACCAGC CTGGCCAACA TGGTGAAACT

CCATCTCTAC TAAAAATCAA AAATTAGCCG GGCATGGTGG CAGGCTCCCA GCTACTCAGG

AGGCTGAGAT GTGAAAATCG CTTGAACCCG GGAGGTAGAG GTTGCAGTGA GCTGAGATCT

TGCCATTGCA TTCCAGCCTG GGCAATAAGA GCGAAACTCC ATCTCAAAAA AAAAAAAAAA

AAAAAGACAG GATAAACATT CTAGATAGTC TCTATAATGG TCATGATTAA GACAATAAAA

TAGTCTGAAA TTGTCAATAT ATATTAATAA TAATTTATTT GGCCATTCTG CCAAGTAGCA

GACACCTGTC ATTCTGCCCA CTCAGCACCT CTCTTTCTTT TAGGGAAATG CTACCCACTC

TTTGCATGGG TTCTGGATGG AACTGTTGAT CACAGTGTTT TCACTCCCCA TTTTGCCTCA

III ——— III

FIG. 6A(112)

III

CCAGAGGTAG ACAGAAGACC CAAGCCAGGC CAGTTACACA CAATCTTCAG ATAATTACCG

TATTGATCAC AGTATCACCC CACTCAAGGC TTGGTTGGAG ATGAGCAGAA GAGACTAAAG

CTGGGTCATT TTAATTAACA CCTGTACCCC AAAGAAAGAC TGTCAATGAG GCTTTTATAC

CGACACTCCT GGTTTCCATT CTTCCTGATG CCATTCATTT GACGAACTAC CCAATCTTTC

CAACAGTGTC TTTGGAAGAA AGATAGTCAG AAAAGAAGAT AGAGTTGTTT TCTGTTCTTT

GCAACCAAGG AACTCTAAAT GATAGACTTG TTGCTAGGCA CTTTGGTTAT TTTTATTATC

TTGAATACTT CTGTGATATA CTTCTTTGTG CATGCCTGTT TGTACGGATG TAGCTTTTTA

TATATTTTAT ATAATTTCTC AGAAGTGGAA TTACTTAGTC AAAAGGTATG AACATTTTCT

GATTCTTAAT ATAAATTGTG CAAATGCTTT TTAAGAAGAT TATACCAGTT TACATTTTGT

GTTATATATA ACAGAAAGTA CTACTGAAAA ATATTACAAA AATTGTCTCT CTGTTCAGGA

GGACTTGTAA TAGATGATAA AGTACTTGAA ATAGGAACAT AGAGCATTTT CAGTTTAAAA

JJJ

FIG. 6A(113)

JJJ

TAATTTCATT GGGTTATTTA CGGAATCCTT AGAATTATGG CCAGACATTT ATAGATGATC

TGTACCAAAC CTAGTTGGTT ACATAAATTG CTTATTCAAC TGGCTTAAAT CTATAATAGA

AAGATGACAC TTACTGAATG TTTAATATAC ACTTTGTCAG GGGCTTTGTA TTATTCTATG

ACATCTTCAA AATGACCCTA CTTTCCTATT TTATAAGTAA GGACAGGAAG GCTTCAAGAA

CATGACTAAT TTTCCCAAGG GCTGTACCAA AGCCAGAACC CAAATCTATA AGGCTTTTAA

ACCTGCATTC TAAAACTGCA TCTCGGCCAT CTTATTCCTA CAGAACTTAA GGTTAGAAAG

CCAGATTGGA GTCCCAATTT CACCACTTAG TAACCAGACA AACTTGAGGA ATTCACTCAA

CGTCTTTGAA TCTCCATTTC CTAATCTTTA AAACTAAAAC AATAATACTG GCCCTACCTA

TTTCCTAAAA TTTCGTGAGG CACATAGAGC TAGTGTGGTA GAGTGCTGTA CAGATGTCAA

GTGTTAGCGT GAATTACTTA GATCCCTGAA CACCATGGAT GAATGTGTCT GACTGCTATT

AGAGGTCATA AAGAATATTG GGGCCAGGTA CATTGGCTTA TTCCTATAAT GCCAGCACTT

KKK

FIG. 6A(114)

KKK — KKK

TGGGAGCCTG AGACAGGAGG ATCACTCGAG GCCACAATTT CAAGACCGGC CTGGGCAACA

TAGTGAGACC CCTTCTCTAC AAAAAAAAAA AAGCAGCCAC GTGTAGTGGC ACACACCTGT

AGTCCCACAT ACTCAGGAGG GTGATTTGGG AGGATAACTT TAGTCCAGGA GTTTCAAGGT

GCAGTGAGCT GTGATTGCAC CACTGTACTC TAACCTGGAC AGCAGAGTGA GACCCTGTCT

CTAAAAAAAA AGAAAAAAAA AATAATAATA ATAAAGAATA ATGGGCCTTG GGATACCCAC

TCCTCTCTTT CTGCTCTGAG TTGTGAAGCA GTTGAGTTAC ATATGCATGT CCAATGGATG

AGGTTGAAAA TATCAACTGG ATTGGAATGT GGCTTACTTG CGTGGCCACA ATGAGCTTCG

TAACACTTCC TGACAGGGTG AGAAGACAAA CTTCCTCACC CAGTCACTGG CAGAGCTGGA

CACTCTGTGT CTCTCCCACA GAACAACCTC TTACTGCATG GAGGTGGATG AAAAAGTCAA

CCGAGAACAG GCTACTCCAA AAAGCAGAGC ACCAAAGGCA CCAGCTGGTC AGGTCCCCCT

TCCTAAGTAA ACAATCACGT AATTCATTCG GGACAAAGCC AGAGAGGTGG TGTGGAGAAA

LLL — LLL

FIG. 6A(115)

LLL —— LLL

GAGAGGGCAG TTTCCTCCCA AGTTTTTCCT GGAATTCTTT ATGGGAATAT GAGGTTTAGG

GGAATAAGAC TTCCCTTTAA CAGTGAAGAA TCCCCAGCTC TATTGGTAAT AGGAAATCGC

TTACAAGGAT CATGGGGAGT ATTTCCTCAG CTCGTTCTGC CTCCTACTTG GCTGAGTGGA

ATGGAACCAT CTGTGGCTGC TGCATATGAT ATTGTCAACT TTGTCATTCC ACACCCACTC

CTTGACGCCC TACCATGTGG TCATAAGACT CCCTTTAAAG TGTTCCTTTA AAAAACAAAA

TGTGTTTTGT TTCTATAAAA TACAGCTCAA TGTCAGAACC CTTGTCTTGT TTGCTCTCTG

ATGTAACCCT TTCACAATGT TTGGGCAGCT TATTCTCTCT ATTTCCCTGT AGGGTCCCAT

CCAGGCCAAA GTGAGTGCCA GCCTCATTTG GGCAGCACAT GCCCTGTGGA AGGGCAGGAA

GAGACGAAAG CTAATTGTAA CTTTGTGATT AGCTGTCATG GATGCCTGGT CCTGTCAATA

GCGCTCAATA AAGCCAGAAG GCCAAGCGTT CGCTTCTGCA TACTGATTGC TGAGTCAGAT

TTCTCAGTGC AGAAGGGCTT TCTAGGCAGT CAATTTTAGA ATATTAGTCT TGGTTCTTAA

MMM —— MMM

FIG. 6A(116)

MMM ——— MMM

GTGGTTAAAA TCCCTAGCTG GTCTTTAATC TGAGCCTGGA GAATTTAGTT AGGGCTGACA

TTCTGCTGTG ATATTTTTGC CCTCAATATA TATGTCTTTC CTCCATCTCT TAGATCCCTG

AATCATAGAG ATATATATGT TATATAATCA ACTGTCTCCA GTCTCTAAGA GTGATAAGTA

CACATTGTGT CAGGTTGAGG GGACAGGAGA ACTTTCAAAA GCCTTTCTTG CCCCTTTTTC

CTTCTCACTG CCTCCCACTA AGTCCAGCCA CTTATTATTC AGCTGACACT ATCATCATGA

CCATGAGTCT TTTGGGGCTA CCCTGGTTCG GATCCTTTTG GAGGTTTGTT GCTTAACTCT

GTCTTCAGTC CTATGGAGCT GCTTTTTCAA TAAGTTTCTA TTTTGGCTAA AGTTGGCCAG

AATCTCCTTG TAACCAAAGA ACAAATAAAA TACCAGCTTG CAATGTTCTA TGTTGCTTCC

ACCAAACTTA TGCAGCACTT CCTATCTAAT CCACCTACTA GTCTTTTTTT TTTTTATTTT

TTTGGAGACG GAGTCTCGCT CTGTTGCTCA GGATGGAGTG CAATGGTGCA ATCTCGGCTC

ACTGCAACCT CTGCCTCCCG GGTTCAAGCA ATTCCCCGGC CTCAGCCTCC TGAGTAGCTG

NNN ——— NNN

FIG. 6A(117)

NNN NNN

GGACTACAGG TGCATGCCAC CACGTCCGGC TAATTTTTGT ATTTTAGGAG AGAGAGGGTT

TCACCATGTT GCCCAGGCTG GTCACGAACT CCTGAGCTCA GGCAATCCGC CCTCCTCGGG

CTCCCAAAGT GCTGGGATTA CAGGAGTGAG CCACCTCACC TGGCCCCGAC CTACTAGTCT

TTAGTGTTTG CTTCCTTCTA TTGGGTAATT GTCTGTTTAT ATGCATGTCT TGTTTCCTCA

AATAAAATGT GGTCTTCTCA AGGGTATTGG CCCATGTTCT ATCCATCTGT AGATATCACA

GCACCTAGCA GTGTCTTTCA CAGAGGAAGT ACACAACTGG CATTATTGAT TCATTGCTCC

ATTTTTTCCT TCTTTATCCC CAGCATTTCT CAATAATTTC AAACATCTCC ATTGGAGTAC

CGGAGAAAGC AGGTAGCTTT ACTTGCAGCT ATGTTTCTAT CCCCATAGTA ACTAAAAGAG

GACCCAGAGA AACATGTTTA AATGCTGTCC TGTTATCAGG ACCTCAGCCT TCTGATGCTC

CGTGGCTTGG GGGTTAATGC TTGATCATTT CCTCCCCAAC CTACACTGTG TACCTATGCT

AGTCTCTTCA TGAGGACTAA GCCCCATAGT AAAAGGGCTA GATAAATAGA AAATCATTTT

OOO OOO

FIG. 6A(18)

OOO — OOO

ATGTAATTAT AAGAATGAGA ATACTGAGTA TTACTGGTGT TTGTTTAGGA TAAGCACATC
TTTATTTGTA TGAGAAAAAG AAAAAGAGAG TGAAAAATAT ATTAACGTGC ATATAGTTCA
GGACCATGGA TTGCAAGTGA CAGAAACTCA ATTCAAACCA ACGTAAGTCA AAAGGAAAAT
ATATTGGCTC ATGTAACCTT CTCACAGAGA GGGCAGGATG GAAGGGGCTT TGGGAACAAG
AGAATTGTTC TCAAATTCTA GGAATACTAG GATTAGTCCA GGATGGGTCA CCTTCCTGTC
CCTGAGGTGG TGGTAGCGAT GGTAGAGTCT TATGGGAGGA AAGAGTGCAT GTTAGGATGA

PPP — PPP

FIG. 6A(119)

PPP —— PPP

AGGTAGGGCT AAGCAAACAA GGGCAAGGGC CACTATATCA TGCTAAAAAT GGTTTTTTTT

GATGTCTTCC TTAATTTCAC AAATGCTTCC AACAAAGTAG CACACAGGAA AAAGAACATA

GGGACTCTAC TGGTGGGTGC TTTTATCTTA AGCCTTGTAC TTGCTTTTCA CAGCTTACTC

ACTGCTTGTA CCTGAGGCCA TATGCCCTGT AAAAGCTTCT GCAGGGTTTC TACTAAGCTG

GGTTCCTTAT ATGGCTCTCT CCCATTTCTG TTGCCTCACT CTAGTGATCT TTCTCTTTTC

QQQ —— QQQ

FIG. 6A(120)

QQQ —— QQQ

CTCACCTCTG GGACTGGTGG CTGTTTGTAT GGACTGCCTT AGCTTTGCTT TGGGTTTTTT

CCTGGGGACA ATGTCTTCAG ATTATCCTAG ACCAAATAAA CTACAGCCAC TGGGCCAGGC

TCTTCCTCCT CCAACTGGAC CATGTTCCCA GGGCTCTTCA CCTTAGTTTA GGTCAAGCAT

TCTTGGCAAA AGAAAGGCCT AGTTAACAAT AGACATTCTA GCAATTGATT CTTTTTGACA

TGTTGTAAGA TCTATTCACA TTTTGTAATT AAAGCATTCC CCTATGGAAA CCAACACGAA

CTAAGCTGCT CCTGGAATGC AGGGTGGCCT CCTCAATACA GGATGTTCTA GAGAGCTGTA

RRR —— RRR

FIG. 6A(121)

RRR —— RRR

TTTTGGGCAC TTAACTATTC TCCACTACTT AGGGCACAGC ACTGAAATTA ACACCACTAA

GTTTGTCATG TCCATGTAGT TAGTCTCAGG CAGTGCAGCC TCAGGAGTGG AACTGACCTC

TTATGTGTGT CCAGCCTTTC TTCCTTCAGA AGTCAGCTGT GTTTTCTGCT GACTCTCCAT

AGGAACATCA GTCCTGAATC CTCAGACCAC CATCTGGAGT AGTAAGTGCT CCTGACAGTC

CTAGAAGTTG TCTACCGCTG GATCTCCAAA GCGTGTGACA CACCGTGAGA GAGAAATGAG

SSS —— SSS

FIG. 6A(122)

SSS —— SSS

AAAGCTGGGC TCTTCAGGTA AATCTTGCTT TTTCACAAGC CCCCTAATTT TACTGCATAA

TTATTTTGAA TTCACTGATA ATTTCTACAA TTTTCCCATA AGTCATCTAC ACACAATACC

CTCTCATGCA ACACTTGGCT TTGCTAATAC ATATCTATTA TGAGAGCTGT GCTTCTTAAG

CGTAAATGTT TTATATGCAC TAAGGCTCTT GGCTTACATA TAAAAGGGGT ATTGAGCAAT

GTGATACAGA AGTCTTTTCT CCACAGGTCT CATATGTAAA GAATTCATTA GATTGGCTGA

AATAGACTGA TCTGTCCATT TCTCTGCTCA CTTATCATAA GGAAGTCATT AGCTAAGGAA

CAAAAACTAC AATCTATGTA ATTAGAAGAA CAAGCTGGTT TTGCTCAATA TAAAAATAAG

AAAAAGAAAC CATGTGAAAG TCAAAATATT TGTTTAATCA GGTCATTGAG AATCTATTAA

AAAGTATTTG AATTCTTTAT GATGAGAACT ATCTTGACTC AAGTGGACAG TGGTGAGCTT

TTTGGCCTGT GGTCCCTACG TAGAAAGGAG GCTTTGTCAT AAAGTCTTAT ATGGTACAGG

TGCCAAGTTA AGTGCCCAAG CTTGCTCTTA AAAGCATACT GGATTTTGTT TTAGACTTTT

TTT —— TTT

FIG. 6A(123)

TTT ——— TTT

AGTGAACTGA AGGGAATAAA CAAATCCCTC TGGGAGAACT TCTCCTCCAT CCTTGGTGAA

GTCATTCTGC CAGAATTC

FIG. 6A(124)

Procedure used to retrofit YAC 3 and YAC 5.

MCS = T7, EcoRI, BglII, NotI, XmaIII, SstII, SalI, NruI, NheI, BstBI, ClaI

T7, EcoRI, BglII, NotI, XmaIII, SstII, SalI, NruI, NheI, BstBI, ClaI

T7, EcoRI, BglII, NotI, XmaIII, SstII, SalI, NruI, NheI, BstBI, ClaI

Specific TAR of HC-region from mar (del) 10

1. Co-Transformation into YPH857
2. Select for $HIS^+$ colonies
3. Screen for HC-region by PCR
4. Prepare high-MW DNA
5. Digest with I-SceI to expose hTELs
6. Transfect HT1080 cells
7. Select for $G418^R$
8. Analyze by PFGE and FISH Cloning in Yeast as YAC/HAC NC-Contig (80225 bp)

TGGTTGATTTGTNNATAAGGAAGTTTGGAATCAATCCCGGAAGGAATTTTTTTTTAAAAAATTTTTTG
GAAGGGTTTGGTAWTAAAAAARCCAATTTGGGTTTTTAAAAATAGGAATTTTATGGGAAAAAATTTTCC
CTTTTTTTTTTTTTAAGTTTAGATGTTATGTTTCCTTATACTTAAAGTGGGTGTCTTATAGGCAGCAT
ATATCTGGGTCTTGATGTATTATTTAATCTGATAATCTCAACCTTTTTGTTGGAGTGTTTAGGCCATTT
ACATTTAGTGTAATTATAGACATGGTTTGATTTGCTATACCATCTTTTCATTTGTTTTATATGTGAGCC
ATCTTTTCATTGTTCTTTTTTCATCTTTGACCATTTTCTTTAGTACTGAATACTTTTTTTGTATTTCAT
TATATCTATTGGCTTTTTAGTTATACCTCTTAAAATTTTTTTTTCTGTTTTATGTAGGATTTATAATAT
ACATCTTTAACTTATCACAGATTACCTTCAAATAGTATTTTACCAGCTCAAGTGTAATGTAGAAACCTT
ACAAGAGTATATTTTCATTTCTGTCTCCTAATTTTTATGCTATTGTCTATAATACATTAGGTTTGTTGT
TGTTTGTTTTTACCTTATTGCTGTTGGCTGGGGTCAGCAAACATTTTCTGTAAAGGGCTAGATAGTACA
GGCATACCTTGGAGATACTGTGGGTTTGGTTCCATACCACCACAATAATACAAATATGCAAGAAGTGGA
TATCACAATAAAGTGAGTCACACAAGTCTTTTGGCTTCCCAGTGCATATAAAAGTTTTGCTTATACTAC
ACTGTAGTCTGTTCAGTGTGCAATAGTGTTATGTCTAAAAAAACACATACCTTAATTTTAAAATGCTTT
ATTACTAAAAAATGCTAACAATCATTTGAGCATTCAGTGAGTTGTAATCTTTTTGCTGGTGGAAGGTCT
TTTCTTATTGATGACTGATCGGGGGTCAGGTGCTGAAGCTTAGGGTGGCTGTGGCAGTTTCTTAAAACA
ACAGTGAAGATTGCAATATCAGTTGACTCTTCCTTTCATGAAAGATTTCTCTCTAGTGTGTGATGCTTT
TTGATAGCATTTTATGCACAGTAGAACTTCTTTGAAAATTGGAGTCAATCCTCTCAAACCCTGCTCTGC
TTTAACAACCTAAGTTAATATAATATTCTGAATCCATTGTTGTCATTTCAACAATTTTCACAGTGTCTT
CACCAGGAGTAGATTCCATCTCATTTCCTGAGATGGAATCTTTGCTCATCCATAAGAAGAAATTCCTCA
TCTGTTCAAGTTTTATCATGAGATTGCAGCAATACAGTCATGTCTTCAGGCCTCACTTCACTTTTAATT
CCAGTTCTCTTGCTGTTTCTACCACATCTGTGGTTCCTTCCTCCATTGAAGTCTTGAACCTCTCCAAGT
CATCCATGAGGGCTGGAATCGACTTCTTCCAAATTCCTGTTAATATTTATATTTTGACCTCCCATGAAT
CATGAATGTTCTTAATGGCACCTGGAATGGTGAATCCTTTCCAAAAGGTTTTCAATTTACTTAGTCCAG
ATCCATCCATCCAGAGGATCCACTTTCAATGCCAGTTATAGCCTTATGGAATGTATTTCTTCAATAATA
AGGCTTGAAAGTTGAAATTACTCCTTGATCCATTTTCTGCAAAATAGATGTTGTGTTAGCAGGCATGAA
AGCAACATTAATCTTTTTGTACATGTCCATCAGAGCTCTTGGGTGACCAGGTATATTGCCAGTGAGCAG
TAATACTTTGAAAGGAATTATTTTTCTTAGCAGTAGGTCTCAACAATGGGCTTAAAATATTTGGTCCAC
CATTCTGTAAACTGATGTGCTGTCATCTAAACTTTGTAGTTTCATTTATAGAGCACAGGCAGAGTAGAT
GTAGCATAATTCTTAAGGGACTTAGGATTTTCAGAATGGTAAATGAACATTGGCATCAATTTAAATCAC
TAGCTGTATTAGCCCCCAACAAGAGAGTCAGCCTATTTTTTGAAGCTTTGAAGCCAAGCGTCGACTTCT

CCTCCCTGGTTACAAAAGTCCTAAATGGCATCTTCTTCCAATATAAGGCTGTTTTATCTACATTGAAAA
TCTGTTGTTTAGTGTAGCCACCTTCATCAATGATACTATCTAAATCTCTTGGATAACTTGTGCAGCTTC
TACATCAGCATTTGCTACTTCACCTTGTACTCTTATGTAATGGAGTGGCATCTTTCCTCGTACCTCATG
AACCAACCTCTGCTAGCTTCCAACTTTTCTTCTGTAGTTTCCTCGCCTCTCTCAGCCTTCATAGACTTG
AGGATAGTTAGAGACTTGCTTTGGATTAGATTTTGGCTTCAGGAAATGTTGTGGCTGGTTTGATCTTCT
ATCCAGACCACTAAAACTTTATCCATATCAGCAATAAGGCTGTTTTGCTTTCTTATTATTTGTGTGTTC
ACTGGAGTAGCACTTTTAATTTGCTTCAAGATATATTTCTTTGCATTCACAACTTGGCTGACTGGTGCA
AGAGGCCTAGCTTTCAGACTATCTTGGCTTTTGACATGCCTTCCTCACTAAGCTTAATCATTTCTAGCT
TTTGATTTAAAATGAGAGATGTAGGCCAGGCACAGTGGCAGGCACAGTGGCATATGCCTGTAATTCCAA
CACATTAAGAGGCCAAGGTGGGAGGATTGCTTGAACCCAGGAGGTGGAGGTTGTAGAGATCACACCACT
GCATTCCGTCCTGGATGACAGAGCAAGACCCTTTCTCAAAATAAAATGAGAGGTGTGCTTCTTCTTTTT
GTTTGAGCCCATAGAAGCCATAGTATGATTTTTAATTGGCCTAATTTCAATACTGTTGTGTCTCAGAGA
ATAGGGAGGTCTGAAGAGAGGGAGAGAGGTGGGGGAATGGCTGGTCAGTGGAGCAGTCAGAACACACAT
AACACTAATAAATTGTTTGCTGTCTTATATGGATGTGGTTTGTGATGCCCCCAAACAATTACAATAGTT
ACAGCAAATATCACTGATCACAGATCACCATAACAGATATAAGAATCATGGAAAAGTTTGAAATATTTT
GAGAATTAGCAAAGTGTGACACAGAGAAACAAAGTGAGCACATGCTGTTGGAAAAAATTGGTGTTGATA
GACTTGCTCCATGTAAGTTTGCCATACGCCTTCAATTTATAAAAAACACAATATCTAGGAAGTTCAATA
AAGTGAAGTGCAATAAGATGAAGTATGCCTGTAAATATTTCAGGCTTTCCAGACCATAGGGTTTCTGTT
GCAACTGCTCACCTCTGCCATTATAGCATGAAAGCAGCTATAGAAAATATACATAAATGAGGCCTGTAA
TCCCAACACTTTGGGAGCCCAAGGTGGATGGATCACTTGAGGTCAGGAATTCGAGACCAGCTTGGCCAA
CATGGCAAAACCCCGTCTCTACTAAAAATACAAAAATGAGCCAGGACTACGCATGCCTGTAGTCCCAGC
TACTTGGGAGGCTGAGGCAGGAGAATCTCTTGAACCCGGGAAGGGGAGGTTACAGTGAGCCAAGATTGT
GCCACTGCACTCCAGCCTGGGCAACAGAGTGAGACTGTCTCACAAAAAAAAAAAAAAGGAAAAGAAAATA
CACATAAATGAATGTATGTGGCTGTGTACCAGTATATCCTCATGCTCTAGCTTGCCAACCCTTGCTTTA
CACTGTCAGTTACCTTCTAAAGAGATTAAAAATCATAACAATATCTATTACGTTTATTCACATCCTAGT
GTCATTTCTTCCTTATGTAGAATCAAATTTCATTCTGGTATCATATTTCTTCTTTCTAAATAATTTCCT
TTAATATTTTTTATAGCACAGGTCTAATAGCAATGCATTATGCAATTCATTGCTATTAGACCTGTGCTA
TAAAATAGCAATGAATTATGTCAGTTTTTATTTGTCTGAAAAAGTTTTTTGTTTTTGAAATATACTTTT
GCTGGGTATATAAATCCATGTTGCATAACTTCTCTTTTCTTCAGCACTTTAATGAAGTCACTCAGTTAT
CTTCTGGCTTGTATAGTTTCTCTGGCTGCCTTCAAGATTTTTTCATTGTCTTTAATTTTTAGCAGTTTG
ATGTGTCTAGGAGTGATTTTCTTTGTATTTATCCTTTTGGGGGCCTCTTAATTTCTTTGATCCTTTTTT
TCTTTTTTTTTTTTTTTAAACCATTTTGGGTCTTTCCCCCCATTTGGGGTGAAAAAAAAAAAAAAAATAA

AATCATAGTTTAAAAAACTAATTTTGGAAAATTTTCAGCTATCATTTCTTCAAATATTTATCCTACTCT
ATGCTCCCCTCCTCCCCTTTCCTTCTGTGACTCAAATTACAGGTATATTTAACCATTTTATTTGTTCAC
GGCACTTGGATGCTCTGCTTTCTTATTTTTTGTCTTTCATTTTGGATAATTTCTACTGACCTATCTTCA
AGTTCACTGATTCTTTTCTCAGTCATGTCTAGTGTGCTCAACGCCTGTTGAAGAAATCCTTTGTCTTTA
ATATCATGTTTTTTATTTCTAGCATTTTCATGTAACTCTTTGTTCTGGTTTCCATCTCTCTACTCACTT
TTTTTTTTTTTTTTTTTTTTTTTTTTTTTTTTTAGACAGAGTCTCGCTCTGTCACCCAGGCTGGAGTG
TAGTGGCGCGATCTCGGCTCACTGCAACTTCCGTCCCCTGGGTTCAAGTGATTCTCCTGCCTCATCCTC
CCGAATAGTTGGAATTACAGGTGCCCACCACCGTGGCTGGCTAATTTTTGTATTTTTTTAGTGGAAACA
GGGTTTCACCATGTTGGCCAGGCTGGTCTTGAATTCCTGACCTCAGGTGATCCACCTGCCTCAGCCTCC
CCAATTGCTGAAATTACTGGCATGAGGCACTGCACCCAGCTCTGCTGACATTTTTTATCTTTTGCTGCA
TTTTGTCTACCTTTTCCATGAAATCCTTTAACATAGTAGTCATAATTACTTTCAATTCCTTGTCTGACA
GTTCTGACATTCAAGTCTAGGTCTGTTAATACTTTGTGAATCTGTTAACAGCTTTTTTTCATTCTTGTC
TGTGTGTTTTGTATTTCTTGATTGTATGCCAAATATTGCCTGTAAAATAAACTTAGATAAGTCATACTT
CTATCCAGAAATAGCACATTTTTTGTGTCCAGTCATTATGTGGAGGAGTTGGGGCAGTCTATCAGTGGC
TGAACTAGTTTGGATTTGTTGATGCTATACTTAGAATGCACCAGACTTCCATTCACTGCAAGAGTGGGC
TGCTGCGCTTTGTGATTCATGTGAGGCCTGAATTGTGGAAGGGTTTTTCCTTAGTGTGTCCCTCCATGC
TCAGATTTCAGCAAGTCTTCATATCTGTGCCACAGAAGGAATCTGACCCATGCTCTTTTTGACCTCCCC
AAGTGATCAACTGTTGCTTGTTATAGCTTGTCATGGAGTAAGAGGGTGTTTTTTTAGTTTTCATCCTCC
AGCCTTGGTCTTGGGCCCTGAGCTCCTAGACTCCAGGAGTGGATGGAATCCAGTGATTTCTCAGTAATT
CAGCCCCTTCTCCAGTAGTGGCAGATCTCTGCTTTGTATCAGTGCAAGATCCTGGGCTGAGCTCATTTT
CTGCCCTTCCTCGAGTGGCAGACAGCTCTTGCTTTCACCCTTCTACCAAAGGCAGTGCATCTTTTCTTG
GGCCTCTCCCCATTGAACTTATGACTTTCACATAAGAGAAGGGCTCATGTATCAGAGAATTCTGTGACT
TTGTGCCACATACAGAGTCTCTCAGTTCTCTTGCCCTGCCCCAGTCTTTTTTGTGAGCACCTAGTAGAG
ACCCTTGGAGAAGAGCAAGGAAGCGAGTATGGACTTCTTTTGTGTCTGTCGATTGCTTTGTTTCTCAAC
TGCTACTCTTGGACTTTAAGAATTCATTAAAATTTCAGCTGTTTTCTTTTTTTCTTTCGTTTTTCTTTT
TTTTTTTTTTTTTTTTTAGATGGAGTCTTGCTCTGTTGCCCAGGCTGGAGTGCAGTGGTGTGATCTTGG
CTTGCTGCAACCTCCGCCTCCCGGGTTCAAGCGATTCTCCTGCCTCAGCCTCCCAAGTAGTTGGGATTA
CAGGTGCCCACCACCACACCTGGCTAATTTTTGTATTTTTAGTAGACACAGGGTTTCACCATTTTGGTC
AGGCTTGTCTCAAACTCCTGACCTCATGATCTGCCCGCCTCAGCCTCCCAAAGTGCTGGGATTACAGGC
ATGAGCCACCGCGCCAGGCCTCAGCTGTTCTCTTTTTACCTGCTGGGATGGCTAGTTTTCTGTGTCAAC
TTGACTGGGCCATGGATGTCCAGATATGTAATTAAACAGTATTTCTGGGTGTTTCTGTGAGGGTGTCT

TCAGAAGAGATTTGCATTTGAATTGGTGAACTAAGTAAAGCAGAGGGCCCTGTCTAGTAGGGGTAGGCA
TCATCCAGTCTGTTGAGGACTTGAATAGAACAAAAGGCAGGGGAAGGTTGGAATTGCCCCCTCTCTGCT
TGAGCTGAGACATCTATCCTGCCCTTGGCACTCCTGGTTCTCAGGGGTTCAGACCTGGATTCCTGGTCT
CCACCTTGCCCATGGCAGACTGTGGGACTTCTCAGCCTCCTATCTAATTAATAAATTTTTTTTACACA
CACACACACACACACACACACACACACACACACACACACACACACCCTATGTATCCTTCTGTTTTTCTGCA
GAACCATATTTAATACACCTGCTTTTATGACGATTACCTATCGATTCTGTATTCTGCCAAAACTGAAAA
CAGTTCATTTTTCCATCTCTTCTCAGAGAGGCTTGTCAGCCATTAGTTCTCTGATGGGCTCAAGAAGTT
ATGCAGTTTTTTTTTCTCACTGTTAGGATGGAATTGATATTCTGTTGAAACTTTCTATACCTAAGTGG
AAACTTGTTTTGAGGTTATTTTCTCTACTTACTTTTGCTGGAAATGGAACACTCTGTATCTAGTTAAGA
CACATAAACTGACTTGTGATACCATAATGTTGTGTTGAATTTTATATTCTTAGAAAATCATCTGTCAAG
GTGTTAACTAATGGCAAAGCATTTAATAAATCAGCATTCATGTATTCAGGTGCTCTGAATTATCTGACT
TTTAAATTCTTACTTTATAAATGAGAAAATTGGGGCATGGAAAAGTTAACTCTCCTAACCCCGAATTAT
TACATTATTAAGGACAGGACTTAGAGGCCAGATATCTTAAGTCATTAATATTCTTTGGCTCACAGAATT
GGCAGTATAACCTAAAGGTAATAACTAGGTGATTTTCTTTTATATCAATTAAATATGTCAGTTTTCAAA
TATTCATAAGTACCTACTGTGCAGGGAAAGAACATGCCATACAAAAGATGTAGTCCAGGCCTTTAAGAA
ACTTTCATTTAATGGGAACTCAAGAAGTGTACATATAAGGAGGGAAGTAGCAGTATGGTACAAGATAAT
ACATACATATCAGTGAATGATATTGCCAAAAAGTGCTATTGATAGAGCAATAATTCATTTCTGCAAACA
GCTGCTGATCTCCTACTGAAAACAGAGGAGGGAGAACAGGACGCCTCGTGGTCAGGATAGAAGAGAAAG
ACCTTGAGTTGAGCCTTGAACAGTATTTAATATTCAAAAGGTTAAGAGAGGAGAGCAATTGAGGAGGGG
AGAATAGTTCCAGCACAAATGATGGTGTACAAGATGAACACAGTCAGTAAAGAGCAGACTGGTCTGGAT
GGAGAGGAGGATTTGCATCATTTGGGATTACGTCATTTAGACCCTTGAAAGCCAGGATTGAGTAAAGCC
ACAGTGAAGCGACTGGCTCGTATGGAAGCTTTATTTTAAGAAGATTAATCTGGTAGTGACATGTGCCAA
AAACTGAATAGGTAGAAATGAGATGCAGAGAGCCCAGTTAGAACTAAGTCTGGTGCAGTAATGCAGGAT
TGAGGCAATAAACACCAAACTACAGTATCACCAGATAATGGATGTTTGAACGGACGGTTTAAAGGAAAA
TTGATGGTATTTGGTAATTTATTAGATAATCCAGGGCCATGGAATGAGAGGGGAAAATGACTAACCATA
GTCATCAAATGGTTTTTCTTAATGAATCTGAATTTTGGTGTAAGAGCAACATTTTCTTAGGCCTTGCCT
AGTTGGTACAGCTGACTATGATAATGACTGCTACCATGCTTGTTCCTCTTTTAGCAGCTGTGAGTCCCC
CACCAGCCAAACAATGAGCCTCTTGAAAAGGACGATGCCTTTTCACTTCTCTCCAAGTGCTTGGCAAAT
AGGAGGCCTTTTGAAGTTACTTTATAGTTAGGGGTTCCCAGTGAGTATTTGAAATATTAAGTCATGCCC
GTGGTTGACAGCATGGCCCTACTGCTCATCATCAGCTATTAACCTTAGGCAAGTTAATGAACTTTTCTA
AGCCCCAGTCTACTCATTTATAAAGTGGGATTATTAATAATGTCTACTTCATAAAATTATGAAGCCTGA

GTTAGGTCATTCAGATAGTGTTTAGTCTGATTCTTCGAACCTAGTAAACAGTCAGTAAACAGAAGCAAA
TGCCACATGCCTGATTTATATCCAAGGGGAGAAAGGTAAAAGTGAAATTTTCATGATTTATGGATTCAA
ATTATACATTTCAAAGATGCTTTATAAGCTATTGTTTTGGTAAGAAGAATTGAGCTGAAACAGAATTTT
CTGACAGCAGTGATTATTAAATGGTGAAATAGGCTATTGATGTCTTTAGAGGATATAGATGTTCACCTT
TTGCATATAAGTGCACAAAAATTCACTAAGTAGATATGTCTGTCTACACAGAGAGAGAGAGCGTGAGAG
CATTAAAGTTAGTAAACATCCCCCTCGCTTTTTTTTTTTGAGACAGGGTCTTACTCTGTTGCCTAGGC
TGGAGTGCAGTGGTGCAATCGTGGCTCACTGCAGTCTCAACATCCTGGGCTCAAGCGATCCTCTCGCTC
AGCCTCCTGAGTAGCTGAGGTGTGCACCACCACACCCGGCTAATTTTTAAATTTTTTTATTGTAAAGGT
GAGGTTTCACCATGTTGCCCAGGTCTCAAACTCCTGAGCTCAAGCAATCTGCTCACTTCAGCCTCCAAA
AATGCTGGGATTACAGGCGTGAGCCACCACGCCTGGCCAGTAAACCCCATTCATTTACATCATCTTACT
TGTCCCTCCAAAATCCTGCAAAGTAGGTAGGTTCTGTCTTTATTTGTTATTTAGGTGAAGAACTTGAAG
TGGTGTTGAGGAATAGGTGTTTTGCCAAGAGTCACGCAGCTGGAGTGGCAGAGCTGTATACTCTTCTGA
TTCCACCAACGCTGTTTACATCACATCTGGAGAAAAGTGCTCTGAGGCACAGATGTTTAGTGGGAGGGA
TGAGACACAGGCTGCAATGCCTAAAGATAATCGGGAATAAAAGCAGAAAACAAGACGTTTGTTTCTGTT
AAAATGAGACAGAAAATAAGGCGTTTGTTGTTTGGGATTGAGCACTTGGAGAAGTGGGGAGCGATTTGA
TTTGGGTGAGACTGCTCCTGGAATGCTGCATCTGGTTCTGGACTACTCATTACTAGGCTTATAGAAACT
AGCTGGAGGAGGTTCAAAGAAAAGCTCCAAAATGATTAGCGGGCTGACGGGATTGATTTATAAGAAATA
TTAAAAGAATTAAATGTGTATAGCTCAGCTAAGCAAAGATGAAAGAGACCAGCTAAATGTATACAAATA
TCTGAAACGTGCAAACTTTAAAAAGAGAGATTAATTATTTAACATGATACACGGGGGCACAATATGCAG
TCACAGGATGAAAATTTCAGCTGAGTATCTAGAAGAATTCCCCGATAGTGAATCTGTTAAGGCTGTCTG
TAGTGTGGCCTTTCCCTGGAGAGGCAATAGAAATTTCAAGTCTTACGATTTTAAAAGTTTCTTGGGAAC
TAGGTATTAGATGATGTTAGAGAATTATTATTAATTTGGTCAGGTATGATAATGGTATTGTAGTTCTAT
AAGAAAAATTGTATTTTTTAGAGTTACATACCCTGAAATATAAGCATAGAATATGATGTAGGAGATTTG
CTTTAAAATACCACAGTAAGGAAAGAAAGGAAGGAGGAAGAAAAGAAAGGAAGGGGAAGAAAGGGAAAA
AGAGGCAAAGAAGGAAGAGAAGGTAAGAGAAAGAAAAAGAATGAAGGAAGAAGGCTGGGCACTGTGGCT
CATGCCTATAATCCCAGCATTTAGGAGGCCAAGTTGGGAGGATCACTTAATTAAGCCCAGGAGTTCAAG
GCTGCAGTGAGCTGTGATTGCGCCACTGCACTCCAGCCTGGGTGGCAGAGTGAAGCCCTGTCTCTAAAA
AAAAAAAATAAGTTAAAAAGAAAGAAAAGGATAGATGAAGTATGGCAAGATGTTGGTAATGTTGAACCT
GAAGGAAGTTAATATGTGAGTTCACTTTCCTCTTCAGTCTTCTTTATGTATGTTTGCCAACTTTCATAA
TAAACAATTTAAATTATATTTTCCTGATCAAAACTTAGTAGCAGTATTAATCCCTGGGCTTCCTGACTA
GAACAGCCTCATTACCACATGGGCAGAGTTCTGGCCGACCAGGGACCACGTAGTGGTTCACCATCTTGC

TCTGGTAATGTGGTCTGGGCTGAAGGGCCCTTTCTAAGGTTGTAGATAGAAATCCAGGAAACTTGTTAG
AACTGCAGACCTATCAGGGTACCTGCAGGAGGTGAGTCTACTAAGGTGAAAAAGCAGAGGGCAGAGGTC
GTGATTAGCAGCTGACCGCCCCCTGCTTTTCTGTCCCTCATTCGTGGAAAATTGAGTGGAGCTCAATTT
TGAGTGGAGCTCTAAGTAGCTCCACTTGTAGACATTGAGTGGAGCTCTAAGTGTCTTCAGAATAGCAAA
ACACTAGTTTTCTTTTTCTTTTCTTTTTTTTTTTTGGGAGACAGAGTCTTGGTCTGTCCCCCAGGCTG
GAGTGCAATGGCACGATCTCCGCTCACTGAACTCTGCCTCCCGGGTTCAAGCGACTCTCCTGCCTCAGC
CTCCCGAGTAGCTGGGATTACAGGTGCCCACCACCACGCCCAGCTAATTTCCTATTTTTAGTAGAGAT
GAGGTTTCACCGTGTTGGCCAGGCTGGTCTCAAACTCCTGGCCTCAAGTGATCCGCCTGCCTTGGCCTC
CCAAAGTCCTGGGATTACAGGTGTGAGCCACCACACCCAGCTGCAAAACCCTATTTTTCTTGAATGGAG
AAACACTTTCCCCTTATTTATTGAGTTTGGGAAGCAAGAAGAGGGGTAATTCATTAAGTGAAAATTTCC
AAAATCCAGAAAACATCGATAAAGCAGCAGCTTAATTTTTTAAGGAAGAATTTTTTAAACTATCTTCT
TTTGAGCCTCTTTAGGAAGACCTCACGTCCTTGCCTTGAATGTTGAGAGTGGGAAATCCAGGGAGGTTT
TGGAATGCATGCCTTATGTCTGCTTTTTTGTTTGTTAGAGAAATATAAATATTTTATCTAGGTTTTGCT
GATGGCAGTCAAGCATGAACACAACCCACTGTTTGAGAAGCTGTAATTTCTGAATTTCTGCAGAGTGCA
CATCTAGGCCAGCAAATGGCAGTAAGAGTGAGGTGGATTTAGCTCAGTGTAAGGATGAACTCCAGAACC
ATCGGCTCTGACTGAAAGTGAAGCGGCAGCCGCGTTGTGGGAAAGCTGGCTGGAGTCTCTCTCATAAGC
AGGCATTCTTTTTCTCCAGCCCGTCACTGTGTTGGTTTGGGCCCACGGTAAGCCTCCTGGCCTCTAGGC
TGTAACCCCCACCATCCTCCTCTGCCTCGCCTCCAGAGTGATTGTTCTGAAGCACAACTGGATGTCATT
CCCCTTCCTGAACTCCTAGCACCTACAGGGACTCCATCCCTTGTGCCCCACATACCTCACACGTAGACA
TTCCTAATGAAGATTTGATTGAATTATTGTAAACTCAGTGCCTCCCACTCTTCTAGTTGCCTCTCTGCC
TGCCTTTGTACATTTATTTATTTATTTATTTATTTATTTATGAGACAGAGTCTTACTGTATCACC
CAGGCTGGAGTTTAGTGGCACCATCTCAGCTCACTGCAACCTCTACCTCCCAGACTCAAGCAATCCTCC
CACCTCAGCCTCCCGAGGAGCTGGGACCATAGGCACGTGCCACTATGCCCGGTTAATTTATTGTAATTT
TTGTAGAGATGGGGTTTCATCGTGTTGCCCAGGCTAGTCTTGAACTCCTGGACTCAGGCGATTCGCCCG
TCTCAGTCTCCCAAAGTGCTGGGATTATAGGCGTGAGCCACCATGCCCAGCCGCTAGCACTCATCTTAA
TCGTATATTTACTTATCTGGCTTTCCCACCAGACTGCGGGCTCTTCAAGAGTAAATGCCATGTTTTCAC
CTTTATTTCCCCAGTTTGTGGCACATTCTAGGCACTCGCCATCATGAAATAAACCTCTGGAGCTGTGAT
ATTACAAACGTGAAAAGATGACGAGCACTCAGCAACTTTCAGTGAGTAAACAAAGGCTTTCATTCAGCA
TGTATTTATTGACTGCCCTGATCTGGGCTGCTTCCTGTCTGTGGTTCAAGGAGAGCATAGTCTACAGAA
CCAGAGACCTGGCTACTCTGGAAGTTAGACTTAAGCCCACCCCGGTCCTTGAATGGGGAAATATTTCCC
TTCATTCCTGTGTTTTAGGGACAGAAAGATGAGTAATGCAGTGATACATGCTGGAAATGTTTATTCCAC

TACCCGAAGCTGCCTCTCAACTTAACAATCCATGAAAGAAACAAGATGGTATATAACTTTTTCTAATTT
GTGATGCCTTTGTTTATTTGTTTCCGGTTAAAAGAGGAGGTGGCATTGAATTGTTTGTTTGGTTTGGTT
TCTTCTTCAATAAGAAGCATCTTAATATAACTAGACTGGACATCTGTCCCATTTTCAAAAATTACAAGT
TTCGATCATTGCTAAATTGTACAGATCCCAATCTGTCTGCTCTGCATACATTTGCATTTATAAAAGCAG
AAGCAGACTAGCAGTCTTTCTAATGCAATCCCCCAAATGCATGAAGTATTAGATTGCTTCTCCCTATTG
GTTCATGCATTGCTAAAGGCTTAAAAGGATCATTGATTTAATTATTTAATGTGTACAGCAGGCTGAGC
TTCCTTTCTTTTTTAAGGGAAGAACCTTCAGGGGCATTGCTTTAGTTTTTAATGTTAAATCTCATTTT
TCTTTGAAAATAAGAAGTTAAAGCTGTATTCACACAAGCTCTCAAAGTGCCAGATTTTCATTGTGTTTT
TAAACCATCTAGGAAATGTTTGATTCTAATGAAACATTACTGCTGAAAATTGGGCTGAAATTGCTGGGC
TGAAAATATTGTTATAACTTCACATGATTCCAGTGTTGTATTATTATTTTTCTTTTCCTTTTTTTGAC
CCGATATAGATGAAGCGAAGAGACAAGGGAGCAATCCCATGTGTAATAAAAAAAGGCAGCCTGAATTGT
TGTTGCTGTTTTTGAAATTTAAGCTGGTTTTCAATTAAATTCAGTAAATGGTCCAGGACTATAAATGTT
GAACATTTTTTACCGTGTGATTTAAAATTTAGTTTTAATGTTTTTTTTTGGGTTTTTTTTTTTTTGAT
GGTTTACATTTTCCCCATGGAAAGCAGCTATGTCATGTCGGCATGATTCATCATGGTAACATCTCGGGT
TATTTTGGTTTGTGTTATGTTCAGAAAGCGGAATGCCAAAAATAAAGAGTGGTTTGTGATGTCTAGTGT
GTCTTCCTTTAACAAATCAAAGGCTTTTATTTAATCCACTTAATGGGACACTGCAGAAATTTAAAAAAT
GGAAGTCCCATCCACAGAAGGCAGGTACTATGATGTAAAAAGTTTAGGTGGGGGATTAATAGAGTGATC
ATATAATTTATGAGCTAAACCGGAGGCACTTTTTTTTTGAGATCGAGTCTCACTGTTGCCTAGGCTGG
AGTGCAGTGACGTGATCACAGCTCACTGCAACCTCCGCCTCCCGGGTTCAAGCGATTCTCATGCCTCAG
CCTCCTGAGTAGCTGGGACTATAGGCGCCCACCACCATGCCCAGCTAATTTTTGTGTTTTTTGTAGAGA
TGGGGTTTCACCATGTTGGCCAGGCTTGTCTCAAACTCCTGACCTCAGGTGATCCGCCCACCTCGACCT
CCTAAACTGCTGGGATTACAGGCGTAAGCCACCATGCCTGGCCCAGAGACACTTTTGAGAGTGAAGAGG
AAGCTGAGAATAATTCACTGATCTACAACTGGGACCATCCAGGGCAAGCCAGATGCCATTACCACTAGC
TAGAAAGCTTGCCAAGGTCTCATTTACCTTGGTATATAGCAAATTCTTCTTTGAATTCTGGAAATTCTG
GTAAGTCATTGAGGTAGCTCTGTGCCAAGGAGCAATATGGTAGAATTCTAATATTTCAGGCAGTACAAC
ACTTTCCTGCATTTGTAGCAGGTAAAGGGAGGTCAGGGCAGAAGACAAAACCACTGGGACTCGACAAAG
GGCATAAACGTCTAATGCACCTGATGTAGCTGATGGTAAATTGTTATCAGCTAAAGATCTTTCATAATA
AATAAACTTATCATTTGTAGGAGGGCACAGAAATCGTGGAAAGCTGGGATTCAGGTTGCCTGTGGCTTT
AATTCTGGAATCAGAAATATTAGTCAAGGATATCAGTCTATGAAGTAAGTTTTCAATGTTATATGCCAC
AAGATGCAGCTGTCCTATTTTCACTTCCAGTAWTTCCTTCTGAATTAATACACCTTAAAAATAGCTGCA
GCTTCTCAAATCTGTGAGAATCGTATGTGCTGCTTGCTACTCTTTCTTTTTCCCGAAGGCCTCTTTGAG
GTCTTTCAAGAACTCAATTCAATTCAGCAACAATTAGGGGGTCTAAGGTATACAGACGCTGTGCAAGAT

GCTCCTGAGACACAAAGAGGAGGTCAAGCCCCTGCCTTCAGGCACCTCTCTATAATATAGGAGGAGAAA
GAGAAGAAACACCAATACACATAGGTAGGTGCCATTAAAAGGGTGCATACATTAAAGCCAGGTGGTAGG
TGTAAGAAGATTTGTAACATGAGAATTTTCTGCATGTTTGAAATATCTTATAATTTTTAAAAATTAAAA
TGGGAGATACATATATATGTATTTATGTATGTATATATGTATGTACATATACACACATATATACATAAA
TATATACATAAATATGTATATATGTGTATATAGACATAAATATGTATATATGTGTATATATACATAAAT
ATGTATATATGTGTATATAGACATAAATATGTATATATGTGTGTATAGACATAAATATGTATATATGTG
TATATAGACATAAATATGTATATGTGTATATAGACATAAATATGTATATATGTGTATATAGACATAAAT
ATGTATATATGTGTATATAGACATAAATATGTATATATGTGTATATAGACATAAATATGTATATATATG
TATATAGACATAAATATGTATATATGTGTATATAGACATAAATATGTATATATGTGTATATAGACATAA
ATATGTATATATGTGTATATAGACATAAATATGTATATATGTGTATATAGACATAAATATGTATATATG
TGTATATAGACATAGATATGTATATATGTGTGTATATAGACATAAATATGTATATATGTGTGTACATAT
ACACACATATATACATACATAAACATTCTGCATTATACCATTCACTTTGTAACCCATCTTCCCTAAAAA
CTGTCTCATAAAGAGTCTTCTTTTCCCTGTACCTATGCAATGGTAAGTAGCAAAACACACATTCTTTTG
GGTCCCCATAACATTCCCTGTAGTTTGCCCTTAACAGTCTTTGATGTGAAATTTACTGTTTCTGTCTTA
ACCTTGCCTGTCTCGCGTACATGGAGTTTTGGCTCCTGGCTCCTAGTCTGCATCTTCACCCCATCCCTT
GCCCAAAGAATCTGGTTATGTGACCACTGCTCATCTTTTCTGCTGTCACAACTCCAGTCCAAGCCACAA
ACCTCTCTCTCCTGGATCCTGCGGGGAGTTCCTTTCTCTCCCTGCATGAGTCTATTCTCCGCACAACTG
GCAGAGGTAAGTGAGACTGCGGAAGAGGCAAGTTTGCAAGTCCAGAGGAAATGAAGACTCTGCTTGTGC
ACATGCTGGGTTTGACGGGTGCTGGATATCCGATGGATGGCCCTTAAGGTGAGCTCAAGGCTTAAGGGA
GAGATAGGGGCTGATGATCTGAGATTCATCAGTGTGTGGCTGATGTTTAAACCCAGGGGACAGGATAAG
AAGGTTATTCCAGGGAGAGCGTAGATAAAGAAGCTAAATGGCTTCTGGGTCCTTAGTCATTCAAAATCG
GACCTCTGAGGCAGGAGGAAAGCCCAGAAAGAGTAGATTCCTGGGACTCACGGGATAAAGACTTTCAAA
AAGTGGGGGCTGGCCAGTGCTGCTGAAGGAAGTAGCAGGACCGGAACAGAAGGGTAATCGTTGGACCTG
GAGAACTTGAATTTGAATTTTAAGGTTGGTAACCTTAAAAAAGAGCAATTTTAGATACCTTTTGAAATT
ATTTGCAAGATTTGTTTGGTATATGTGTTATTCCAGGCAAAGGGACCAGAAAAGTAAAAAATACTTACT
GAACAGTTACTGCATGCCTGGCACTGTAACACCCTGTTTAATTCTCACGGCAACCCTATAGAGTAGGTG
TCATCATCCCCATCTTACAGATGAGGATATGAGGTGCAGCTAGATTAAGCAGTTTGCCTCAGGTTACAC
CAACTGGTTAACGTAGAGCTAGGATTTGAACCCGGATGGGCTGATCCCAGAGCTCATGCTTTAAATCGC
TAGACTGGTGCTCACAGAAGACTGGGACCGAAAAAAATTAATAAAAAAAATAAGGAGCCCCCTGGGCTA
GCAAATTAGGAGTTGTTCAGACAGATGTGAAAAGGAAAGCAAGGCAGAGGGAAAGTCACTGTACAGAAG
AGAGAGACCCATGACAGCAGAGACAGTGAGCTGGTAAAGTGGCTGGCGATCTAGCCCCTGAAAATACCT

CCAGAGAGGCAGGCTCACGCCTGTAATCCCAGCACTTTGGGAGGCCGAGGTGGGCAGATCACCTGAGGT
CAGGAGTTTGAGACCAGCCTGGCCAATGGCGAAATCCCGTCTCTACTAAAAATACAAAAATTAGCCGAG
CATGGTGACAGGCACCTGTAATCCCAGCTGTTCAGTTGGCTGAGTCAGGAGAATAGCCTGGATCCGGGA
AGTGGAGGTTGTAGTAAGCCAAGATTGCGCCACTGCATGCCAGCCTGGGCGACAGAGCAAGACTTTTCT
TAAAACAAACAAACAAAAAAGAAAAAAGAAAAGGAAAGAAGAAAGAGACAAAGAAAGAAAGAGAGAAGG
AAAGAAAGGAAGGAAGGAAGAGAAGGAAGGAAGGAAAGAAAGAAAAGGAAAGAAAGAAAAAGAAAGAAG
AAAGAAAGGAAAGAAAAGAAAGAAAAAGAAAGAAAGAAAATACCTCCAGAGAGCCAGGTCTCTTAGGCC
TTCTGAGAAACTCACATCCCTTTTGATGAACACAAATGCTTCACACTCTCAATGTTATTGGTAATCCAA
GTTATCAATATACCTAAATCACTTAGTACTGAATCTGGCATATAGTAATCACCTAATGAAGAGATAAGA
GTCATGGAGTATTCTGAAGCAATTAGAATCAATAGACTCAATATACACATGGCAACAAAGTTGGATCTT
AAAAACCGACCTGAGTGAAAAAGGAAAGGGAAAGATACATAACACGGTACCATTATGTAAATTGATAAT
ATATGCTTACACAATTTGTAAGAACACATACAAATAGATACATGTATATTAAACATACTCGAACGGTTA
CCCTATGGGGTGGTGGCTGGAGTGGGGGTAAGTCCGTAAGCTGTAATGGAACCTAAACAAATACATGAA.
ACGAGTAGGAATCAGAAGGAGTAACAATAAAAATGTGCCATGAACTGAGGAGTGTAAATTAATCAACTC
ACTGCATCTGAGGTTAAAAATAGAAAGATGATAATTGTTATTCTTATTACTCCTAGGTCTTCCACTTGC
ACTCAGCTTTACAATGTTGGACTATCCTTCAGATGGCACCCTCCTTGCACTTGCTCAGGCAGGAGAGCT
TTTTCCTCCAGCTTTCTAGGTGATTTAATATATCAGGGAATAAGTATAAAAAAAGGCACGGTGCTCCCT
GGGTAGCCTTTCTGGACTTCAGAGCTAAATTGCAAAGTCAGTTTTACACATGTGATTTCATCTATGAAA
TTAGGGCAAGGTATAAAACTGGCACAGAAAAAATGTGATTTATTATGGTGTTACTATCCCTTACAAGCG
GAGTGTCAGCTGCCTCTTTTTGTCCACTGATTTAAGGCAAGATGAACTGAAAGTGGCTATGATCACGTC
TTCAAAAGCACACTCTGGCCCCTCGGCTGCAGGCGCCCTGCACATTCCCCAGCTGCGTGTCCGGTGGTG
ACACAGTGCATAATTGTGGCGCCTTCCTGGTGCAAACTGTCTCACTTAGCTCCGTCTTGCTGGCACAGC
AGAAAGGAAGAAATCGAAAATGTTTGGATTTCAAAGGTAACAAGAAGCTGGAAAACAACTACTGGCCGA
GTCTGAGAGTTTCAGCGGAGACTGGTGCAGCCTTGTGTTTTTCCACTGACAGCTGAAAATGAGCCCAGC
TTCAGTGAAGCTTGTTTCCTTCCCTCCTCAAGGTTACCCACAATTCTCAGTTCTCTCAGGAAAGCCAAA
AAATGAATTTGAGGGTTTAGGATTGTGGTTCTTTTATCTATTACAGGATTGATAATATGTTCCTCCACC
AGATGTTCTGCTTGTAACAATACTCACTTCCTGACACTACTGCATATGCAGGAGTGTCACTACCAAGGT
AAACACAGAATTGGCTGCCCAATTCCAAATCCCTGAACTGAGTGAGAGAAATCAGAATTATAATAGGGG
ATTCAACAGAGCTGGCTACGGATGTGCCAGTGGTCAGATACTTTGCTCATCATACGCAGGTGCTGCTGC
TCTAGCAACTGCTCACTGCTTCATTTCCTGCCTTGGTCTTTAAATACTGCTTTTCTCAGCTCAATTGGC
TTTCTTCCCTCTGGCAGTCACGTTTCTTTGGGTCAAACAGCAAATGATTCTTTAGAATCACCTGGTACT
CAAAGGAGCTACAAGACATTGGGCATCCACTTCCACTCTCTTGGAAAAACAATTTTATGGAAGCCAAGG

TTGCCATAGTGCCTCTTGAGGTTGTTTGCTCAGCCAAGGCCCAAGCTTTGTGCTTCAAACATGAAATTA
GAGAGCTTCAGAACAAGATCCACATTTTCAATGGCCTCACCCAACTGGATAAAAGAACAATTGCCATAT
CTCAATGACCACCTTTTCTCAGGTGGGATGGTAGATGCTGGAATGGGTCACAGCATTGCCCAACCAAAC
TTTGCAAAAAAGGCTGGAAGCTCTGACTGGGGACCCTAAATATGCAAAAGTTAATAGGCTCTTCATGCA
GAATATGAACCCCGTGTATGGATATAGCTAAAGGGTTGGCCTTTATGTTTCTATTCCTTCACAAACCTG
GTAGAATAGATATGCTTGTTTCCCTTTAAAAAATGTCAACAATTGCATTTATGATGCTGTGTATAGTAA
CTCACAGATCATGCTCCATGAAAATGCTTCAGAACCCAATATAAGGAGATTTTTTAGCCATGTGTGACA
AAAGAGAGGCCATTTCAGTGTTGAAATTGTTCAGAGAAGTATTTGATTATGTTTTCTCAGATCTTTTTA
TTTTTATTTTTTTTGAAACAGAGTCTCACTTTGTCACCCAGGCTGGAGTACAGTGGCTGTGGTCTCGGC
TCACTGCAACCTCTGCCTCCCAGGTTCAAGCGATTCTCCTGTCAGCTTCCCGAATAGCTGGGATTACAG
GCGCATGCACCACCATGCCTAATTTTTGTATTTTTAGTAGAGACAGAGTTTCGCCATGTTGACCAGGCT
TGCCTTGAACTCCTGACTTCAGGTGATCCACCCACCTCAGCCTCCCAAAGCACTGGGATTACAGGCATG
AGCCACCGTGCCCAGCCTGTTTTCTCAGATCCTGTATTTTGTTTCTGAAGCCTTCATTTCTATCTTCTT
ATTCATTTTGGAAGTAGTACACCTAAGTAAGGTTTTTAACAATCAAATATCTTTGGAAAATTCCCTGGT
TCCTTTCTTATTCCTACAAAAATATGTTCAGTATAGCTGATGTTATGTTTCTTTCAAATTATTCATTTC
TCTATCTCAGAATTTATCTCATGCCTAATTGTTATTGAATAGTCTTCACTTCTTGTCATCCAGTTTCTG
GTCTCTTATTTCACTCTAAGTCTAATTGGCTATTAGAATAAAGAGCTTGTAACAGATTCTTTCTCCAAT
ATGTCTTATCTTTTGACTGCATGCCAGTGACAAACTGTTAACTGTTTTGATTCTTCATAACATTCCACA
GAACATGCTGACTCCTCTCTTCCTGAAAGCAATGCCCAAGCACAGCATTGTTAGATAGTATGTACGCAA
CAGGGACATGGGTGCATAGCAAAAACTAGAAGGAAGGAGGACCTTCCTTAGCAATGGGTGATATGGTCC
CTGGACTTAGACTCCAAAGGGTCGTGAGGTGAAACACACATCGTCCATACCCAGGAAGCACACAGGTGG
GATGGAAGAGCTGTGCCTAATGAAACTTCATCCACGTGGAGGTGGAGGAGGCTGCAGCTGCAAGAACTC
AGAGCTGCCTTACCCAGACCAGGGACCAGGGAGGGCTTTCTGGAGGAAACAGCCTCTGAACTGCCAGCT
GATAGAGGAGCTCTACCTCAACTCTTCTGGTTCCCCAGGGCTGCTTTTCCACGTCCATTTATTGGCACT
GAAGTTTGAATACCTTCAGGGGCCCGAAAGCCTGCCAGGTCCTCTTCTCTGCAGAGCAATCACACCAAC
CTGCAAAGGGCTAGGAAAGGGCTGTCATCATCTCCTACTCAGAAACTGGTTCACTGGAAGGACTCAGGG
GCCACTGAATACATCCTGGCAGCTTTCACAAGAAGGGCTTCTGACTCAAGGATGTTTCCATCTTTGCCA
GGTCGCCTTTTCTCCTTCTCTTAGAGTTTGGAGGACGCAAATGTGCTGAGAAGTCAACCTTTCCTGCAA
GGTGAGACACAAGGGCCTTTCCCAGCAGAAAGAAGAGAGCAAATGGAAGGTCCTTCTTCCTCCAGTAGA
GGATGGACTCTGTCTGGCAGCCACCCAACAGGAAAAGCACAATGCATGCCTGCCTGCTTCCCTCCCTCC
CTCCGTTTCTCCCTCCCTCCCTCCTTCCTCCCTTCCATTCTCTTCCCTTCCCCTCCCTTCCCTTCCCCT

CCCTTCCCTTCCCCTCCCCTCCCCTTCCCTTCTCCCTCTCCTTCCCTTCCTCTTCCCTTCCTTCCTCTT
CCCTTCCTTTCCCCTCCCCTTCCTTTCCCTTCCTCCCTCCCTTCCTCCCTTCTTTCCTTCCCTTCTTTC
CTTCCTCATTTCCTCCCTTCCTTCCTTCCTTCCTTCCTTTCTTCCTACTTTCCTACCTTTAGGGCTCTG
TGTCTTTGGAGTCCATTCTGATTATGCTGTAATGTCTGCCCCTTCCTCTTCTCTGTCAAAAAATGAAAG
ACATGGAAGCCACTTGCCTTTTACTGAATTAAAAATTAGTAAAAGAGCTAAAAATTAATGGTTAAAAAT
GTACGCATAAATTATGCAGTATACTAACCAATGAAAAGATACACTTCTCTTAATTAAAAGCTGACAGGG
AGGGAAACAAGAAAAGAGAAACACAAAACAATAATCTAAATGACCTATTAGTTGGAAGAACAACATCAG
AGAAAATAGATACTGTGTATAGTCATGTGTATGTCTATGGAATAACATTTGTAGAGAAATCTGGACTGA
TCCTTTCTGAGTAAAGAGAGCTGTGGGTACAATTAAGGGGAGATTGAAAGGAATCCAAAAGCATAGCAG
ATGCTGTGCCTCACTGGAATGGTTGCCGATCTCCTCCAAACTATGAAGTGTTTGAGGCTCAACTTTAAT
ATAATTAAGATACAAAGACAGAATGAGAGAAAGAGAGAAGGGAGCTCACTGGAAGAACACTCAAGATTC
CTTACTACTCATTCTCTAAAATTACAATTGTTCTAGATGGAAAAGAAAAAAAGCTTCTCTGTTAAAAAA
GGAGCTTGTGCTATAGGAGGTTTAAAATATACTTCTGACCCATCTCCAACATTCTAAATCCTTCCCAGA
AAAGTATGCCAATCCCAAGAAATATTCAATCAAATTGCTGGAAAGAAAAATACAAAATATTAAAATGTA
TTAGGAAGCGACAGTAATTAAATCAGAACTGGAGCAGGAATAGACCAGCAGATCAATGAGACAGACATC
AAGTCCCGGAATGTGGACTTGCAAATGCATTAAGTAATATGATATGCAATAAAGGTGGCACAGTGAACC
AATGGGAAAAAAATTAATCTTATAATAATTGATATTGCAATAATTGTCTAGTAATTGGGGGAAGAAATA
AGCTTATTCCTTATCTCATTTCTTTTTTTCTTTTTGAGACAGAGTCTCACTCTGGTAGCCCAGGCTGGA
GTGCAGCGATGCGATCTCTGCCCACTGCAACCTTGCTCTCCCGGGCTCAGGCGATTCTCCCACCTCAGC
CTCCCGAGCAGCTGAACTACAGGCGTGTGCCACCACTCCCGGCAATTTTTTTTTCCATTTTTAGTAGAA
ATGGGGTTTCACCATGTTGCCTGGGCTGGTCTTGAACTCCTGGGCTCAGGCAATCCACCCGCCTTGGCC
TCCCAAAGTGCTAGCATTACAGGCATGAGCCACCGCGCCTGGCAGCTCATTTTTTAGACTAAATAAATT
GGAGATGGCTAAAAGATTTTTATGTAGGCCAACTATGTTTTAAAAAGTTTTTTTTTTAAGGATATCT
GCTGGAACCAATCATGCCACCAACCAAAGATGCAAGACTATAAAACATACCCAGTTTTCAAAGCATTT
AAAAATTATTCTAAAAATATTTTTTCTCCAGAAATTTTGCATTGATTCCCTGAAGAAGCATTAATATGG
GACCTGACTTATAAAATGATGAACTCAATCTCCCCACTCAAGGTAGGAGTCTCTCAGATTTAAAAAAATA
AGCATCCTAGTCCTCTTGTCCCTGTAAAAGTTAACCCTTACACCTGAAACACCAGGAGACTGGCGGTTG
TTTGCATAGGGGTTACAATTAAAGTTGAGCTACCTCTGACATCTATTAACACCAAAATTAGTAAACTAT
GCATGTATGGAGACTTTTATGATTGAACTTGTTTATTGAGTCAAGAGATATAGTTTACAATGAAAATTT
GGGGCATATCAAAATGACCTTGGCTTAGCTTAGCATTTGCTGATGTTAACTATTTTCTTCATTGGGCTG
ATTTTAGTTGCTTAGGAAAAATACAAACACACACACTTTAAAATTATATTAAAATCCCGTCCTAAACCT
CAGAGTCCAGAACCGCATCCTAACACTGGTCATGCATAATATGTTTAAATTTTTGTGCTTTAAAAACTA

CAAATAAGGAATGTATTAATAGTTCCACAATCAATGGTCAGTTAGCCGAGGGAAGATTAGCATAGTTAA
AGACTTAAAATGGCTTAACAACATATATCAAAAGGACAAAATAAGGGGAACAGAGTCTAGAAATGAGGA
AACTGGGACACAGGCAAAAAAAAAAAAATGAGAACTGGGACATGAATAACGCAAGGATAAGACTAATAC
ACAAAACACCCCAAATAAATAGCCAGCATTTGCTGAGCTCTTACTGTGAGCCTGTTCTAAGCACTTTAC
ATATATTAACTCATTTCATCCTCAAGGAACCATCTGAGGCAGGCACTGTTATCATCTCCATTTTACAGA
TAAGGAATAGACCCAGAGAGGCTGAGCAACTGGGCCTATTCCACAGCTACTATGGTGGAGATGAGATTT
AAATCTAATCATTGGCTCCAGAGCCCATGCACCCAATGGCTGCACTAAGTGAATGCATGCGCTATCAAC
GTTGCCAAAAGTGGGCCACAGCTCGGATCTGCGTTTTCCAGTAGCCAAAGCAGAGAGTGTGATCAGACC
TCACTTTAATAAGCAAGTCTCAAGCCAGAGAGAGGTGGTATCAGGCAGCAAACAGGCTGCTAGTCGAAA
TCCCACTTCTTCTCTGAGTGGTCCATACAGTTTTACTCTACTTGCTTACAGAATGAAAATAGCTGGAGT
TCAGGTGCGCTTTCAATGCCCTGTTGTCAGGATTGGGCTTTTCAAGTTTATTTTTTGTTGTTGTTTTTA
ATAGACTGTACTTTTTAGAAAATTTTTAGATTTACAGAAAGATTGAGAGGATAGTACAGAGAGTTCCCG
TATACCTCACACCCAGTTTCTGCAATTATTAACCTCTTACATTCATGCGGTACATTTGTTACAATTAAT
GAGCCAGGGCCGGCCGGGCACAGTGGTTCAGGCCCCTAATCCCAGCACTTTGGGAGGCAGAGGCAAGCG
AATCACTTGAGGTCAGGAGTTCGAGACTAGCCTGACCAACATGGTAAACCCTTTCTGTACTAAAAATAC
AAAAAATTAGCCAGGCATGGTGCTGGTTGCCTGTATTCCCAGATACTCAGGAGGCTGAGGCACAAGAAT
TGCTTGAACCAGGGAGGCGGAGGTTGCAGTAAGCCGAGATCGTGCCACTGCACTCCAGCCTGGGCAACA
GAGCGAGACTCCATCTCAAAAAAAAAAAAAAAAAAAAAGAAGGAAGGAAGGAAAATTAATGAGCCA
ATATTGAGACATTATTATTACTAAAGTCCATGCTTTATGCAGATTTTCTTAGTTTTTACCTGCTGTCAT
TTTTCAGTTCCAGGAATGCATTCAGGATGCCATACCACATTTAGTTCTCATATCTGCTTAGGCTCCTCT
TGGCTAGACTGAGTTTTAATCTACTTTCTGCAGAGCCTGAGAACTTTAGCATAATTTCCTTGAAATTAC
AGCTCAATATTTTCAAGCACTTATACAAACAGCCTAATGTTACGTTGGCCCATAACAGTGTTTCAAGGT
AATAAACTTCTTTGTTTTCTGTGCCGATTGAAAGAACTGCTGCTTAGCCTCCTGCCAGATGATGAACTG
GGTACACACGAGCATTTTTCCAGGTAAAGCATATTTCGTGCGACTTCTTAAGCTGCAGCCTTATATGCA
ATAATTGTCCATTTACAAGACTTATGTTCGAATTTCAGGCACTCTGTTTTCACTAACCATATCTTCAAC
TTTGATAAGTACTGCTTTAATCACTCAGAAAATTTAACTTGACTAATTTTTTTCACCATCAGTTTTTT
TTCTGTTGACTCTTTCTCCTTTTTCTGTTTGCCCAGAAACATGCTCAGGATTCTCTCAGGCTTTAAAAA
ATGAAAAAATGTTTCCTGCAATCTAGTTACTCCTTGATTCTCTTGTTCTGTTTATCGCTGGAATTCTTG
AAAGCTTGGTGTATTAGTCTTTTTTCATGCTGCTGATAAAGATATACCTGAGACTGGATAATTTATAAA
GAAAAAGAGGTTTAATGGACTCACAGTTCCACGTGGCTGAGGAAGCCTCACAATCATGGTGGAAGGCAA
AAGGCATGTCTTACATGGCAGCAGACAAGAGAGAATGAGAACCAAGGGATTTCCCCTTATAAAACCATC

AGATCTTGTGAGACTTATTCACTACCACAAGAACAATATGGGGTAAACCGCCCCCATGATTCAATTATC
TCCCACCGGGGCCCTCCCACAACACGTGGGAATTATGGGAGCTACAATTCAAGATGACATTTGGGTGGG
GACATGGCCAAACCATATCACCTGGCCTATAGCATTATTTCCATTTCTTCCCCATCCTTTTATTCCTCA
AACCGGTACAACCAGACCTCTTTTTTTTTTTTCTACCTGAAACTGCTCTTTTGAGGGTAGCTGATAAG
TCCAAAATACTGTCACCTTTTCTCAATTCCGTTCCTTCTTATGCCTTTGGAGCAATTGACTGTGTTGGT
TGCCCCCTCCTTTAAAGTGTCTCTCACTTGGTTTTTATGACTAATGATCATGATTTTCTTTTTCCTCTC
TAAACATTCCGCTATCTTTTTAGCTTCCCTTCCCCCTCCCATCCCCTAAATGTCCTTGTTTCCCAGAAT
CTGCCTCACCTCTTTGACTTCTCTATGCCCTGTCATTCACTCATGGGTCTTTATTACATTATTGCATCT
GTGTCAATAACTCTGGTCTTTCTCTTAAGTTCCAGTCTCCCATTTTCAAATGTCCCCAGACATTTCCAA
TTGAGTATCTCTCCAATGTATTTAACCTGCTAAATATCTAACACATAATCTTTCCCATCAAATCGTTTC
CTCTTAAGCTTTTCTTATTTCCTATTAGTACTCCTGCACTTCTCCCAGGAGCCCAGACTTAAAACCTTG
AATTTCTCACCATAACCTCTCTTTTGTCTCCCATAATCAATTAGTAGCAAGTGTTATCAATGATTACTT
GACAATATCTTTTTCTATTTCCCTCCCTGCTATGATCATTCATCTAGCAAGAAGAGTTGGCCCTTTGTA
TCTGTGGTTTCTGCATCCCTGGATTCAACCAACTGTAGATGGAAAATATTTGAAGAAAAAAGCGTCTAT
ACTGAGTATGAAAAAATTTTATTTCTTGTCATTATTCCCTAAACAATACAGTATAACAACTACAGCATT
TACACTGTAGCGTATAGATCTTATAATCTAGAAATGATTTCAAGTACACCATTATATATAAGGGACTTG
AGCATCTGTGAAGTTTGGTATTTGTGGGGCATACTGGGACCAATTCCCCCATGGATACAGAGGGACAAC
TATATTTACTCAGTGCTTACTAAATACCAGTTGGCCAATGTGTTTTTCTTTTTCTGTTTTCCTGTCTTT
AGTTTGCCCCTTGCCAATTAATTCAATAGTGCTGCCAATGCCAGGTGTACCTTCAGAATATTCTATTCT
AATTTTGTCATCTCCAAGCTTAAAAATATTTAATGGGCCAGGCGCAGTGGCTCACACTTGTAATCCCAG
CATTTTGGGAGGCCAAGGGGGGGTGTATCACTTGAGGTCAGGAGTTCCAGACCAGCCTGGCCAACATGG
CGAAACCCTGTCTCTACAAAAAAGTATAAAAGTTAACCAGGTGCTGGAGCATTTGCCTGTGGTCCCAGC
TACTCACGAGGCTGAGGCAAGAGAATCGCTTTAATCTGGGAGGTGGAGTTTGCAGTGAGCCAAGATCTC
TCCACTGCACTCCAGCCTGGGTGACACAGCAAGACTCTATCTCAAAACAACAATAACAACAACAACGAA
AAACATTTAATGGCTGCACCTTGCCTGTGAAAAATGCATTTCTTGGCCAGATGTGGTGGCTCAAACCTG
TAATCCCAACACTTTGGGAAGCTAAGGCCAGGAGTTCGAGACGAGCTGGGATATATAGGAAGACACAAT
CTCTACAAAAAAAAATCCACAAAATTAGTCAGGCTTAGTGTTCATGCCTGTAGTCCCAGGTACTCAGGA
GGCTGAGGCAGGATTCCTCAAGCCCAGGAGTTCAAGGCTTCCGTGAGCTATGATGGCACAACTGCACTC
CATCTTGGGTGACAGAGCAAGGTCCTATCTCTGGAGAAAAAAAAAAAAGAAGGCATTTCTTAGGAGAGT
TCTTCTCTGTAGAGTCCTAAGGGTTCCATGGAACTCCTTAAAAGCATCAGAGTATGTGAGTGCAATGGG
AGGAAGCATTTAGCCAGAGCAGTTGTGCTCCCATTGCATATTAATTTTAAAAAACAAAGCTATAAAAA
AAAGTTGAAAACTACTACGTTAGCATCAGCCTGACATTTAATGGCCTCGTAAATCAAACCTTAATTGAC

TTTTTAGCCAGTTATGCTACTAGCCAACTACAGACAACACACTTTTTAACCAAATTAGACTAATAGTTG
TCATCAGTGGAAATCAAGTTTGCCATTCTTCCATGCCTTTGCTCACACCATTACCTTTTCTGGAATGTC
CTGTACTCATCTTCCTGTGTTGAACTCTATACCCAACTTTAAAAACCTAGCTCAAAGTTCAACACTTCC
ATTCCATTTCAAAAAGAGCTTTCCTCTTCCTTAAAGTTTAAGAACTCATTTTCATGAATCTTTTTGGCA
TTTATTGCACACATGCTTGCTTTGTGTTATTTGTGTTCATGCCTCATATGCCCCCAAGGTGTTTTAGAC
TCCTTAACGGCAAAAATGATGCTCTAAACACCTTTCTATCTTTCATAGTGTCTTAGTCTGTTTGTGTTG
CTATAAAGGAATACCTGAGGCTGGGGAATTTATTTAAAAAAGAGGTTTATTTGGCTCACAGTTCTGCAG
CTATATAAGAAGCATAGTGTCAGCATCTGCTTCAGGTGAGGGCTTCAGGAAGTTTCCACCCATGGTAGA
AGGCAAAGGGGAGCAGGCATCACATATCAAGAGAGGAGGAAAAAAAGGAAGGAAGAAAGGAGGGTGCCA
TTCTCTTTCAACAATCAGTTCTTGTGGGAACTAATGGGACAAGAGGCTGGGCACGGTGGCTCATGCCTG
TAATCCCAGCCCTTTGGGAGACCAAGGTGGGTGGATCACCAGAAGTCAGAAGCCTGAGACCAGCCTGGC
CAATGTGGTGAAACTCCGTCTCTACTAAAGATACATAAATTAGATCTAGCTGGGCCTGGTGGCGTGTAC
CTGTAGTCCCAGATACTCAGGAGGCTGAGGTAGGATAATCACTTGAACCCGGAAGACAGAGGTTGCAGT
GAGCTTGTGCCACTGCACTCCAGCCGGGGCAACAGAGTGAGACGGTCTCAAAAAATTTTAAAAACTTTA
AAAATAATAGAGCAAGAAAGCACCAAGTTATTCAGGAGGGATCCACCCCCAATGACTCAAATACCTCCC
ACCAGGCCTCACTTCCAACACTGGGGATCAATTTCCGTATGAGATTTGGAGGAGACAAATATCCAAACT
ATATCACATAGTAATGAACATAGTACCTTATCTATAGAAAGCAATGGCTAGACAACTGTTGAATGGCTA
ACCAAATCTGCTTTCCTATGGTCTCGCTCTAGAGGGGGTCAGTATGAGTTTCTGTCAAAAGGAGAAAAA
AAAATGTATAGTCAGTTTTGTGTGTGTGTGTGTTCATGTAAAAGAGATCAAGAGAAAAGAACAAGAGAA
ATCATGAAAAGGAGGGGGAATATAAGAATAATACATAGAAAAAAGCAAATTATCTTGTTTATCAGTAAT
ACCCAAGGGGGTAGAAATGGTAAGTAATAATCCTTCTTCACTTTGTCTGTAGTTCACTTTTTTGCACCT
TTATTTTGATGAATTCACATCGAAGACATTAACTCATTAAGGCTTCCAATATTTTTGGAGATAAGAAGG
GCTGCTATGCTCTTTATAGATGGAAAACTTGGGTCATTAATAACTCAAACAAGGACATAACAAAGAAAT
GGAGCATAAACTGCCAGGTCCTGACTGTAGATTTGGATTCCCAGTTGGTGTCTTGTCACCCTTTGTTAC
TCTTCCTAAAGTTATGATCTTTTCTTGTGCATAGGAAATTCATAGTGATTTCCCATCACCCTTGGGATT
ATCATAGCTCCTTTAAGGTCCCCTCTATGCACTCAATAACATCAACAGTAAGTGTTCTTCGAGCACTTA
CTGAGTGTATATCATTGTGTTCTCACGCAGCACCCACAGATCTCACCAAGAACCTAGCTGAAGCCTGTA
GAATGAATAGGTAAGTACTGCCATGCCAATCTGGAGTACTCAAGCGATGCAAATGATTCCTTTAATTGT
ACTTTTGCAGGCTTGTCAGTTTTGCTCATGGAGAAGTGGCTACTGCATCCATGTTATATCTATGTAATG
TTGGACTGCGAAGCATCACTTGACTTTTTCCAAGCAGAAATTACAGCTGATGACAAGCTGCTGCTGAGA
AAATGGATATTTTTCTGAATTCAGTTCTACGTGGAAACAGCTGACTAGTTTCCATTGCTGTAAGATGGC
TCTTTTGCTCTTGGTTGATTTTGAGTAATGGCTTTACTTCTGTAGAAAGGAGATTTCATTTGAAGTCCA

CTCAGGGATTTGGTTCAACAAACTGGAGTACAGGTTTCAGAAAATATCTCTTTAATCCTCCAATAATAA
ATTTTCTCATCTATAATTCCTGGAACACTTCATCCTTTGCAGCCGAGCATATAGATAGATTTGTTGCTC
ACTGTGTTCTGATTGCCACTTTGACCTGCTTTTTCAACTTAGGTTACAAATAGAACAGAATCTCTCTGA
TTTTTCTCATTAATTGTTTGAATTCCCACTTTTCCTCATTAGCAAGAAGTCCAGTATCTTCCTGAGAAC
TTCCTTTTCTCAATCTAGGAACTTACTTGGTCCATAAGGTAACAGTCTTATTTCTGACTATCAAGGAGA
GAAATAACAGGAGCCATTATCATCTTCATGGTGTCACTTTTGAAAACTGGTCCTCTGTAGATCTTCAGA
TTCTTGCGTTAGTCCATTCAGCTGCTATAACAAAATTGCATAGACAGCATGGCTTATAAATAACAGAAA
TGTATTTCTGACAGTTCTGAAGGCTAGAAAGTCAAAGATTAAGACACTGGCTGATTTGGTGTCTGGCGA
AGGCCCATTTGCTCATAGATGGACGATGACCTTTCACTCTGTCTGCACATGGCAGAAGGGCAAGAGAGC
TCTCTGGGTCTTTTTTATAAGGGCACTAATCTCATTTTTGAGGACCCTGCCCCCATGACTTAATCACCT
CCCAAAGGCACTGTCTCCCAATACCATCACCTTGAGGGTTAGGATTTCAACATATGATTTTGGGGGAC
AGAAACACGCAGTCCATCTCGCTTGTCCACTCCATGGTGGTATTCTTGCTGGATCAGTTTCCTCCTTGG
GGTGCATTTGTGTTCCATGTCTAACTTGCAAGTTATAGCAGGCCCGATAGCAAAGTATTCCAATGTTGG
TATGCAGAGGCATTGAATAATCAGAATGAACCCACGCCATAAACAACTGGTAGAGCTGCAGAGAGTACC
AGCTGATTATGAGCCCTGGGTAACAGTGGTTTTTAGTTCCTATGTCCGTCAGCCCTTTTCTCCCATAGT
AGCCCCACTGTGTTGAAGTGGCTGAATCGACAGAAGCTTCCAGCTTGGGCCACATGCTCATGGAACCAA
TTCTCCTTATGAGCCGTACAAGAGCTGGGTTGCCATTCTGGATACCCTCTTTCTTCAAGAGATTTTATT
TCAAGGATATTTTTTCTTTTATCAACTACAGGGATTATTTAGAATCTTAGGGCAGTGGTGCCCAACCTT
TTTGGCCCCAGGGACAGGTTTTGTGGGAGACAATTTTTCCATGGACCAGTGTCAGGGGGCTGGGAGGCA
TGGTTTTGGGATGAGTCAAGTACATTACGTTTGTTGTATACTTTATTTCTATTATTATTATATTGTAAT
ATATAATGAAATAATTACACAACTCACCATAATGTAGGAATCAGTGGGGAGCCCTAAGTTTGTTTTCCT
GCAACTAGACAGTCCCATCTGGGGGCAATGGGAGATAGTGACAGATCATCAAGCATTAGATTCTCATAA
GGAGTGCTCAGCCTAGATCCCCGGCATGTGCAGTTCACAATAGGATTTGCTCACCTATGAGAATCTAAT
GCCACTGCTGATCTGACAGGAGGTGGAGCTCGGGCAGTAATGCGAGGGTTGGGGAGCAGCTGTCAATAT
AGATGAAGCTTTGCTCGCTCGCCTGCCACTCACCTCCTGCTGTGTGGTCCACTTCCTAACAGGTCACAG
ACTGGTACTGGTCCATGGCCAGGGAGTTGGGACCCTGTCTTAGGGAGTAGGGGTGGAGTTCCCTTCACT
TCTAGAAGGCCCTGGATTAGTATCCCAGAGCTGTCATTACAGAGTATCACAAACCAGGTGGCTAAAAAC
AGACATGAATTCTCTCTTATTTTTGATGGCTTGGAAGTCCAAAGTCAAGGTGCTGCCAGGGCCATGCTC
CCTCTGAAATGTGTAGGGGAGAATCCTTCCTTCCTCTTTCTAGCTTCTGGTGGTTTGCTGGCAATCACT
GGCATCGCTTGGCTTGCAGCACTTCAACATCTGCCTTTACTGTCTCATAGTGTTCTCCCCTCATGTCTC
CAGGTCTCTCTGTCTCTCTTCTTTGTATAAGGAAACTAGTCATATTGGATTAAGGGCCAACCCTACTCT
AGTATGACCTCATCTTAAGGTCACATGCAATGACTATTCCAGATAAGGTCACATTCTGAAGAACTGGGA

GTTAGGACTTCATATCTTTTGAAGGAACACAGTTCAACCAATAACAGCCCCTGTACTGTTTTACAAATA
GGTATTCCTCTCCTTCCCAAAGTTCTTCATAGCAGAGACAACTTGTACCAAAAGGCAAAATACCTTATT
ATGTAACCTTAACCTAGGATCATAGATCCCTACTTGTCTGGTGCTTTTATAAGCCACAGAACCACCCGG
GAAATCATTATTAAGACAAGGAAAGGCCAAGTGCAGTGGTTCATGCCTGTAATCCCAGCACTTTGGGAA
ATTGAGGCGAGTGGATCACCTGAAGTCAAGAGTTTGAGACCAAACTGACCAGCATGACAGAACCCCATC
TTTACTAAAAATACAAAAATTAGTTGGGCATGGTGGCATGTGCCTGTAATCCCAGCTACTCAAAAGACT
GAGGCAGGAAAATCACTTGAACCGAGGATGCCAAGATAGCAGTGAGCCAATATCGTGCCACTGCACTCC
AGTCTGGATGATAGAGCAAGATCCTGTCTCAAAAAATTAATAAATAAATAAAAAGACAAGGAAAGCCTT
TTCCAAGGAGACCCTTCTGCTTTGCTAGTTCAGAGAACTTCTCTTTGGAGAAAACAAACACCCAGTCCA
TTAGCAGCAACGTCAGGGATTGAATTCTTAGGGCAGCAGGCTGGGCACAGTGGCTCATGCCTGTAATCC
CAGTACTTTGGGAGGCTGAGATGGGTGGATCACTTGACATCAGGTGTTCGAGACCAGCCTGGCCAACAT
GGTGAAAACTCATCTCTACAAAAAATATGAAAAAAAAAAAAAAGCTGGGTGTGTTGGCTTATGCCTGTA
GTCTCAGCTACCTGGGAGGCTGAAGCAGGAGAATCACTTGAACCCGGGAGTTGGAGGTTGCAGTGAGCT
GAGATTGCCCTACTGTACTCCAACCTGGGTGACAGAGAGAGACTCCATCTCAAAAAAATAAAGAATTCT
TCGGGCAGCAGTCTTTCCTCCACCTCATAGACCATGGAGGTGAGCCAGCTCTGACAAACCATGAGAACA
ATGGCAGAGACATACCTGTAACGTAACTGACTGGGGCAAAGACAAAGGTGAGGAAAATGACAAGTTTGA
GGAACTATGAGACCAGGCAGTGGGGAACACCACTAGCAGAAATGATGGAAGTTCTCAAGAATAACAACA
GAGAAATAGACCATGGCCAGAGTCTAGAACCCTCCAGGGAAAGGAGATGGGCTCCAGAGGCAGAAGAGG
ACGTTGAAGGGAATGGGGAGTGGGTGAAATATATAGACGATGGGGACCACCCAAGAGCAGTCGCTATTG
CAAAACTGAGGAGAAGGAGAGTCTGGAGGGGGTGGTGGGAAGCTGGGTCTCCTAAGGAGGTTTTGACAA
AAGCAGTCATGGAGCGGGCTTAGAAATCACAGTTGGGGACAGGGTAAAGTTCCTCGGGATATAGAGGAT
GAGATTAGAAGAGGTTCCAACTAGGGTAGTGTGGAGAAAAGCACTATTGACCCAAAAAGGAAGGAGAAT
GTGGGTGGAAGTGGCAGAGAAAGAGGGGTTTGAGCAGAGAGTGGTGATTTTTCTAATGCAGAGTTGTGG
GAGGTGGAGTGCAGGGAGCCAGGCTGGGTGGCTGTGCTGATGTGATTAAGCACTTACTGACTGCCAGGC
AATGGGCTAAGTACCTGAGATGCTTTGTCTGTTATCCCTCCCGAAACCCCTCTGAGCAGGTGCAGTTAT
TATTCTCACTTCACAGATAAGGAAATTGAGGCACAGAGAATTGAGTAACTTACCCAAGGTGACATAGCT
CATATATGGTAAAGCAGGCTTTGAACTCAGTCTAGCTCCCGAACCTAAGCTTGTAACTACTATGCTTTT
CCCAAAAAAAAGGGGGCTGGCACAAAAAGAGCTGAGGGGGGCTGGGCATGGTGGCTCATGCCTGTAATCC
CAGCACTTCGGGAGACTGAGGCAGGTGGTTCACCAGAGGTCAGGAGTTCGAGACCAGCCTGGTCAACAT
GGTGAAGCCCTGTCTCTACTAAAAATACAAAAATTAGCTGGGTGTGGTGGTGTGCACCTGTAGTCCCAG
CTACTTTGGGAGGCTGAGGCAGGAGAATCGCTTGAACCCCAGAGGCGGATGTTGTAGTGAGCCAAGATC

ATGCCACTGGACTCCAGCCTGGGTGACAGAGTGAGACTCCATCCAAAAAAAAGAAGAGCTGAGGTGATG
GCCACCATCAGCATCAGCCTGGAAGTTATAGCAGGATGCTAAGTTTCTCTAAAGCTGTCTTTCTTAGGA
CTTGAAAAAGATAACTTGGGTTTGTATCCCATCTCTGCCATTAGTAGTTTACTGGCTTTGGATAAATTA
CTTAGCCTTACTGAACCAACTTTGGATTTTTATAGAGATACTGTAATGAAAGGAATAAGGTATCAGTCT
TAGCAGAGCATCCAGAGTGTTCCTATTAAAACCTAAATCATATCCTGTCATTGCTCTGCCCCAAACCAT
TCAATGGCTTCCCAACTCAAAGTTAAAAACTCATCTTTCCAGTGGCCTGCAAGAGCCTATGCTATCCGG
TGTCTGACCTCATCTGTTGTTCCTTTCTCCCTCCCTTTCTTGGCTCCAGACGCACTCTGGTCTCCTTGC
TGTTCCTTGAATACACCAGGCACACTCTTTTCACCTGAAACACTTTACCCCAGATATCTTAGCTTACTC
TCTGCCTCCCTCAATTCATTGATGAAATGTCTCAGTGAAGTCTTCTCTCTCTCCTCTGTAAAAGTATAC
TCTCTGTTCCCCTTCTTTACTGTTCTAGCTACTATTGCTGTGTAACAAATCACTCCCCAAATTTAATGA
GTGAAAACATCAGCCATCATCTTATTTCTCACGGTTTCTGAGGGTCAGGAATTCTGGAAGGGCTCAGCT
GGGAGGTTCTGGCTCTATAATCTCTTATGCAGTGAGAGTCAGATGCTGGCTAAAACTGAAACAAAGCAG
GGTTCTAGTAGCTGAGGGCTGGCTGGGTCTCTCAGATATAGTTCAGATCTCCTCCAGGGGGTCTCTCCA
CGTGGGCTAGTCTGAACTTCCTCACAGCATGGTGGCCTCAGGGCAGTGGACTCTGCATAGTGGCTGAAG
GCTTCGCAGCTGAGTATTCCAGCAAGCAAAGTGGGAGCTGTATTGCCTCATATGACCCAACCTTGGAAT
CCACACAGCATCACTTCCGTGTATTCTACGGGTTGAAAAGTCACAAAAACCAACCAGTTTCAAGGAGAA
GGAACAGAGATCACATTTCTCAATTGGAGAAGGGTCAAAGTCACATTGTAATCAGAGCCTATGGGATAC
GAAGTATTGCGGTCAGGTATGAAAAATTTGATTTGCTGCATCTGCTTTACTTTCTCCACAGCGTTCATG
ATCTGCTTCTCACATGATATTGACTTACGTCATTTCTGCATTTCCTGTCTTCCACACTAAAATGTCAGC
CTGTTTTGTTCACTGCTGTATCCCCAGAGCCTAGCACGGAGCCCAGCATGTAGTGGTATCCAATAAATA
CTTGTTGCATGAATGAATTCTGTCTTTTAATCCTAGCTATAGGTTTCTAAGTTAAATATTACTATAATC
ATCTTACAGACGAGGGAAATGAGGCTCAAGAAGATTTGGTAACTTATGCGGGATCACTCAGCCACATAA
TGGAAGAGACAGCATTGAAGTACACATGCTTGCTCTGTCTGCTCTTCCAAGCTGCTCATCACACAGCTG
CACCTCTGAGGACTTCCCTCCCCAGTCCACCTCCACCCTTACCCAGAGACACACATGGCCACAATCCAC
TAGCAGACCAAAATTCAATTTTTCCCCAGTTGGTTGCACTCAAGCTGAGAGCAAAGCAATTGCACTTTA
AATCCCCTTACAGCAGATATTTCAGAGCATGTTCGGAAGAACCCATCACACTTGGCTTTTAGATCTTAT
TTCTGGTTTGTTACAAAAACACAATTAAATGAAAGGTTAGGTAGCTTTTGAATGGCCAGCTCAAAGTTT
TGGCTTATTTTTGCCTTGCTGTCTTTATAGGCATTTTACCAATATTTATCACTATTTCCCTTAGGGAAC
CCTTAGATCTGTGATATTTGAAATAATAAAGCCTCTCCATTGGCCCTTTAAAAGGTTTGTGGTAAAACC
ACACCATTAACATTCACAGTTCCTTATTTATGAGGCCTGATTGCACTTATTTCCATATTTCTCACTGTT
TCTCCGATGAGGATTTCACATAATAGTGTTTGAAGGCTAAAGACTTCAAAGCAGATTCTTTACTATTTT
TATCTTGAAAAATATTCAATATTTGTGTAATTAAAGTGAAGTCTTCCTAGAGAAAATGACAACTCAAAT

AATCTTAAATGTACCTCCAAGAAAAAAGCTGTCAAAGTGACATTTAGTAGTAGAGTCACATTCTCTAAG
GCCTTTGCTTCTCCTTCTGAGTTCTTATCATCTTTGAAGGTTATGTCATGGCTGACTTCAAATCACTTT
TAAAATTATTATGGCCTTCTTTAAATGTGAGTTCTGAAGGTGAGGGGCTTTATCTTTCTTTTGCTCCAG
ATTTTTTCTACCGCGTCATTACCAAGCATCTTAAAACAAAACCTAAAAACAAAAATCTTCCTTGACCTG
GTTTTTCCCACTAGCTAACATCCTATTTTTATCTTTCCCTTTGCACTAAAGGTTTTTAAACGGATCTTT
ATACCCTCTGTCTCCATTTTCTCATCTGCTAACTTATATGGCAAAGATTACCACTGCCTTTCAACATAA
TTGGCCAATCTACAGAAAGTTTTCAAGTTCTCTTTTTAATTGACCACCTCCTGCCTACCTCCCCACCTT
TGACATCTTGCTTCTCACTTGGCACCTTACCCAGTGTTCAAGATTCCCTCCTTTAGGATGTCTTCAGAG
CAGCTACACAGTTGGTACTATAATTTATACATCCTTGTACACAGGGCTTGCTGGGATATTGATGGAGAG
AAGGAGGAAACTGGAAGTAGTTCAGGCCAGAGCTAGGGAAATTGACCCATCTCCAGGTCTCAGGTCTGC
AAGGGGAGCTCACAGCTTAACACATGGAGTCTAGAAACTTGTGCTGGACCTTGACCAACACCAGCCCAT
GGAGTCCAATACAGTGCTCAATAGGGATTTCCAGGAAATTGCTATATTTATTCAAAGAGAACTTACCAA
GTGTCAGCTACGTGTTGGGCATTGTGTTAGGCACAGGGACCACAAAGATAAGACATTGTAGCTTTCCTT
AAGTTGCTCACTGAGTAAATAGAGAGACAGAAAGGTAAACAGGTAAGTGCAAAAATACATACAATTCTG
CAATAGTGTTCATAGTGGCTATGGAGAGAACGCTCACTAACTTTGTTTAAACAGTTGTTCTTTCAAGGA
TTTGACATGGATTTGATTGGAAAAGCATGATACCATTTTTTGCAATTAAACACAGGAATACATAAATAA
AATGCATCAGTATTTTTTACAAATAGCTACTAAGAGCTACTAGAAAACCTGGGAATTCTTAAAACCTTA
CCATGCTACTTGCTCTAAAATATTTTATTTTATGTTATTTTGTACATTTCTTTACCTACACAAACACCA
CTGTTTTCTTCATTTCTTAGTCTATTTAAACCTCACACCCTTTCAGCATCTCTTAATTATTTACTACCA
TCTGTTAGTTCTCCTGTCCTGAATGAAACAAAAATGGCAGAATGTAAAACGAGGGCGAACAGATTTTTG
ACAGGAAGTATTCAGAGGTAGAAGGAAATAGTCAAGACACATATGATAAACGAAAACAATAATAACTTT
ATACATAACAACTTATAGACACATTTAAAAAGTTTAAGATCTCAAGAGCTATGTCTGAATAGATAGAAG
TAAAAACTCTATTAAGTAATTAGGAAAATAACAAGAACAGTGAATTTCTTAATGAATGGCATGTAATCA
AAACTGTACTTATCGTCTAATTCATAATCTTGAATGTTTTTATTTTATTTATTTATTTTTTTATTTTTT
GAGACAGAGTCTTGCTCTGTCACCCAGGCTAGAGTACAGTGGCGTGATCTCAGCTCACTGCAACCTCCA
CCTCCCAGGTTCAAGCGATTCTGCTGCCTCAGCCTCCTGAGTAGCTGGGATTACAGAGGCCTGCCACTG
CACCCGGCTAATTTCTGTATTTTTAGTAGAGATGGGGTTTCACCATCTTGGCCAGGCTGGTCTTGAACT
CCTGACCTCATGATCCACCAGCCTTGGCCTCCCAAAGTGCTGGGATTACAGGCGTGAGCCACCACGCCT
GGTCGAATGTTTTTATTATTTGAAGAGACAACATGGGCCTTAAATCTGTCTTCTATTTGACAGACTTTG
ATGGAGTCAAATCCCAATGCTGCCACTTACTGAACGGCCTTAAATGACTTAGTCTCTCTCAGCTGTCTT
TCTGCATATGTAAGGTGGAATAATGATGGCTTCAAGGAGGAATAAACCTATGAAAAGTGTTGAGGATAG

TGTCTGATATGAAATAAGGATTCAACAAGTAGTAGCTGCTATTGAAGATTTAAGAGTTATTTATTACAA
CTATTTAATAAAATTTTAAAAACTAATACACTTAAATTATTAAAGAGCTTTGAAATGGGCCAGGCGCAG
TAGCTCCTGCCTGTAATCCCAACACTTTGGGAGGCCAAGGTGGGCGGATCACCTGAGGTCAGGAGTTTA
AGACCAGCCTGGCCAACATGGTGAAACCCTGTCTCTACTAAAAACGCAAAAATTAGCCAGGTGTGGTGG
CATGCACCTGTAGTCCCAACTACTCAGGAGGTTGAGGGAGGAGAATTGCTTGAACCTAGGAGCTGGAGG
TTGCAGTGACCCGAGATGTCACTGCACTCCAGCCTGGCAACAGAGCAAGACTCCATAAAGACAACAAAA
GCTTTGAAATTGTGTAAATGAGTTGTACCTATCTTCATTTAAGAAATTCATCTTTGTTCATCTATTTTT
ACTTGACATGAGAGCTTCCAGCAATTTTTAATTAAGCCCTCACAGATTTTATGTCACTGGCTATGTGAT
AAACAAATTATTTGCTAAAATAATATTCTTGCTTCTTTTTTAAGGAATTGTCTCCCTAGAAACGGTTTG
TACCAAACAATACACTGACTTTACACAAAATCAGATCTGATTGGCAACAGTTGCAGATGTTTTCAAAGG
ATTTTCATTTGAGAAGGGGCCCATTTGGGTTATTTAGATTCTAAGAACTGAAACTGCTTTGTTCTGTTT
TTCTGGCTTCTGGGAGAGGAGGAGACATGAATTCAGTTAGCACCTTGGTATTTTCTTTATCCTTCATTT
CAATACAGAAGATGCTTCATATGCACAGTGGTGTCAGGTCACATCAAAAGAAAGAGAAACAGTTTCTTG
GTTTTTAATTTTCAACCGGAAAGGAAAGGCACCCATTTTGTTCCGCTCTAATTAGCCAGTGCATGACTT
AGAGAGCAGGCAGATGCTTTGAAGGCGTGGTAACACAGGTCTTCATTAATCTCCACGCAGGACTTGCAC
TTCTACTATGCCTAGGCTGAAGAAAATGGCTCAGGAAGATGAACAATCTCACAGAGCCCTAACTAACTG
AAGCCAGGTGTTATAAAGCACAAGTCAAGAGGGTGAGAAACTAACGTTCTTGAAATCTCCCACTTCTTT
CTACGTCAGAAGAGCCAAGCTGATTATTTTAGTTGGAATTTAGAAATTTTTAAAAATTATTCTAAAGTC
ATGAACAAGCCTAATTATAAAGATAGTTGCTGTGAAGGTGCTGAAATAACTCGATTTTACCAACCCCCT
CTTCTGGAGGAAGCCAGAATGGAATCCTGTAGAATGTTCACTCTACCAACGAACTCTTGTTTTTCTAAT
GAGGAAACAGAGGCCCACAGTAGTAAACTATCTTAACCAAGACAAAATGACTAGTGCTCTGGTCCTTTT
ATTAAGCACTAAAATTTTGATCCAATAATAAATCTGTCCAGTAGAAGGAGTTTCCCTAATGTACTGGTT
CTAACTTGTTCCCTTCAAGGGGCCAGTGTCCCGTACACATAGCTAAATGGGACTTCTCTTCAACTACCA
TTACCCAGAGGGCAGAACCTAAAATGCTGTGAATGACATTCTGCTGTTCACATCTCAGCAGCAGTGTTG
CATTTGAGCTTCTGCAGGGCCACCCAGGACCTATATCTGCTCAGATGTTTAACTCATCTAATTCAGTGA
ACACTTCATTCTAGTTAACTGAACATCTACTTTGTACAAGGCACTACAGCGGTTCAGAGATGAATAAAA
TCATGAGATTCCACTGTCTCCTATAAACCATCACTTTGGGAAATTTTAGAAATGTGGGTAAGCTCCAGG
GCTTCCTGCAGCGTAGAAGTCACAAACTCAAATGCCTGCAGAGGCCCAGCTGACAACATAAGTAAATGA
TTCTGGCTGGGCGGAAAACAATTACGGGTGGGTGGGTTTCCAGCTGGGGAGTGCACGCCTGTGTTAAAG
GACAGCTGCTACTCATTTCCAGCCAACTGTGTTCCCATGTAGAACTGCGGCCCAGTGTAGCCAGTACCG
AAGATTTCTCAGAAAAAGCCGGAGATCTCAATGTTAGTGTAAAATCTCTCAAATTTCCAAGAGGATTAT

ATGGGGCAAAGGTTCTCAGATCAGTTTGCAGTCTCTTACTTAGCCCATGTGCAGAGCAGTCGTAGAGGG
TAGCATGCAGTGTCCTACATAATAATTCTTTTTTATTTTATTTTATGCCTTCCTCCTTCCTGTCTCTCT
TTAACCTTTCTTCTTCCCTCAGGCTGGCTTCTTCCCTCAGCCTCGTCCGACCCCAGCCTGGGTTCAATG
AACATTCGGTAAAGGAACACGGAATGTCAAGCGCATTAGAGACAACCTTGAGACACATTCCTCTTGCGG
TAAGCACTTCACTGTAGATTTTTAATTTTAAACAAGACAATGTTTACGACTTGCTTCTTTCAGGGAAGA
GCGATATCAATTTTAGTGAACACTTCAAGGCTGAGATACGCTAGGAGAGTCGTGTGGTGTTGCACAGCA
AAGAATTCCACTTTGAAGCGAGTGGGAAAAAAAGCATCAAATGCCACATGTAACTCACCGCCTGAAGGG
TTACATTGGTATGAAACCTGGGTTTAAAAAGGGACCGAATAGACTAGCCATTAAAAGACCTGCGTACAA
CCTCTCTCTCTCTCTTTGAGAGATAATGTATCTGGACAATAAACATGAACAGAGTGGAGTCTATCCTGT
TTAAAACATTGCCTACTGTACAGGCACCAGGAGCTGAAGGGTCAGAATATTAGCAGTGGGAGCTTGATT
AGAAGTTGATGAGAGATGGGTAGTAGGAGGAAAGAGTGAGATAGAGGAAGAGGACATGGGGGTTACCCG
TAAGTGGAGAGTAGAAAAGTAGAATCAGCTGGCCATCAAAGGGCGTGGGACTGAGGAACAGTATGGCAT
GTATTAAATATACTAAGCGCTGACATTGGAGGAGAACTAGGAAGGTAAATGAAATCAATAGGGGATGAT
GGAGAATAGTTAGGTGTGCAGGGATTAGGGTTATGATAGAAATACATGTGAATACATGCAGTATTGTCC
TGGAAAATGGTTAACAGTTGGTTCTCCTGGGGGGTGAGGGGAAGCCCTGATTTGTAATATTTGCCTATT
TCTGTGGTGCAAATACTCCCACCATGACCAGTTTCAAGCTATGAATGTGAATCACAAAAGCAGGTTGGG
AGGAGATGCGCACATTTGTTCCCCGGCAAGGTGGAAGGTAAGGAAGGTGAAATCAACAAGGTCAAAGAA
AACTCAAGATTTCGAGGTGCCTCAGGTCTGAGGGGCAATGAAGTCTAGGAATGGCTGTGCTGAGGTAGC
TGAAATAGAAGTGACTGCAGAGGTCATGAAGCTGAAGAGGTGAAAACAGAAATTAGAAAGGCAAACCCC
CACCGCCCAACCCCCACCCCTGCAGCCAGTTTCTGAGGGTGACAATAGAGGAAAGGGTGGAGATGGAGT
TCAGGTCCAGAAGCCATAGAAGCGAGTGTGACATTGTGCTCAAGGTCAGCACATGTCAGTGTGGGGTGT
CACATGCTGTTGTGAACCATCATTTATCACCAATTATGGAAGACCTCCTATGGGCATCTTGCCATATGC
ATTATAAAGATGTGTAAGAAGACATTTCCCTCCACTTGGTGAGGAGAATTAGGGCTGTACACAGATACT
GTAGAGTGCCATGTGCCTGGTACAGATAAGGTGTGTTAGAGGTTAAAAGATGAGGCTCTTAATATTAAT
GATAGATCCCACTTACCTGAGTCTGACTTACAATGTGCCTAGCATTAAGTGTTTTACCTGCATTCCCTT
TGACCTTCAGAACAACCCATTTTACAGATAGGGAAATTGGGTCAGAAAGTTTCAGTAACTTATCCAAGG
TCACACAATTGGCAAGTGCCAGAGCTGAGCCAGGAACTGAGGTCCTTCTAACACCAAACAGCTTGTCTC
CCCAATCACTGTGCTATTTTCCCTCCCCCAGAAGATAATACTCTGATGGAAATGAAGGATAGTGTAATA
GGAGATTCGGTGTTCCTTTTTTTAAAAAAAATTCAGCTTGCATATTCCTAAAGAGTCAATTCATGTTTA
AAAAAAATTTCCCTTGTGCTTGCATGTGACATGTATTTTTAGGATCTGCTGTTAGCAAGTGTATTTTTG
TGTGATTGAGTGGGAGAGTGGGAAAAGTTTTGCAGAGCTGTTGAAGCCAGAATGCAGGGGGGCTGCGCA

GCAGAGACTGTAAAATCTCTGCCATCTCAGGTCTTGGAACAAGCACAAAGAGATGTGTTCTCGATTTAT
TATTCTATGTACATCCCCAGATGAATGACTAGTTAAAGGTATTGTTAAAGCATTTTAAATGACCCACTT
CCAGCAGCGAACAAAATCACTTGCTGTGCCAAGCCAACTGGCATTTCTGAGATGATAAAACCACAAAGT
GAGGAAAACGTTAAAACTGCTAAAGCAAAAATGATACACAATAATGGAGAAGGAGAAAAATTGAGCTTT
ATTGTCTGCCTAGGCAGATGGCTGACCACTAGGTGGGCTCGGCGTCACGTCCAGGGTAATTGGTTGCTG
GGGTGTTTCTGGCGAGGAAGATTCACGCTTCAGCTCGGTCCACAAGATCCTGGCTCATTCTTTCCTAGA
TTCCATTTTCTGCCTCCTCTCCATGACTGGGTCTGATGGTTGATCCAAACGGGCAATTGAAATCAGAAG
GTTACCTTTACCTTAAAATGCTTTTCTGGAAATAAAAGGACATGAAAAGTAACTAAGGACCGGATTTCC
TAGCCGTCTTTCTCTCCTGCATGCGCAATTTATCCCCAGATATAAAATTGCCTGCTTTGATAATTATAC
CCTCTAAATGAGGGGCAAGTGGCTAATTATGCCCACATGTGGCCGATTGCACTCCCCATTAGCCAATTA
TGTGCTCAATTATTTGTGCACATGAATAATTGCACTCATGGAAAATAGCGGCCCTCCTTTCAAATCCTC
GTGCTTGGAGTGGCTGATGGAGTAATTGTCACACTGGAAATGCACTTGGTGGGGAGGGAAAGAGTATCA
GATACCAGGAAACGCATAAGTGACCAGAGCTCGCAGATGTTCACTGCCACAAATGGCCTTAGGAGCCAG
AGAGAGCGGGAAGGACCACAGGATGGAACGGGCCAGCCTGTGAGTTAGGAAGCCTGCTTCTGAAGTTGC
CTGGGCAGCTCATGTGCGGTGACCTTGGGCAAGTCATTAACTTTCCTTCAGGTCTAACTGGTTCTGCAT
ACACAATGAGGATGGTAATAACGCCCAATTCCCATCACTATCGTGGGATGGATCAGACTATTTAAAAGG
ATTTACAATCTGCTTGGGTAAAAGCTTTACATAAATATGAGGCATTATCATGTCGCTTGGTACATCTCC
AATTATGAAGGAAGGGTAATGACCCTCCACAGCAATGCAGGACTCCTGGTTTGGAGGGAGGGAAAGTTT
GAGAAGGACAGGAAGCTTGTTGCCCCAGCACTGATGTTTCTACTGAGGTACCAGAAAATGTCATGTGGT
CATACAGAATTCATTTATTCATTCAACAAACATCTGTCAATTGTTACACTGTCCTGAGAATTTGGAAAA
ATGATGAAAGACTCAGTCCTGCCTTAGGAGGTCACTGGCACATTGGCCCGGGCCCCTGTTTTGGGCCTT
TTACTCTGACCTGTGCTGATTTGCAAATAGTGGGAAATTTTATCTCAAGTCTAGGAAATCTGGCATGCA
TTTTCACGGTTTGATTGCCAGGTACATTCGATGGCAATGAGTCTTATAATGTTTGGTTACCTTCATTTA
CCTAAAAACTGTGGTTGTTGCTGTGGTTGTTGTTTTTGTTGTTTTTGAGACGGAGTCTTGCTCTGTCAT
CCAGGCTGGAGTGCAGTGGCATGATCTCCGGTCACTGCAAACTCCACCTCCCAGGTTCAAGCGATTCTC
ATGCCTCAGCCCCCTCAGTAGCTGGATTACAGGCGCGCACCACCATGCCCGGCTAATTTTTGTATTTTT
AGTGGAGACAGAGTTTCACCATGTTTGGCCAGGCTGGTCTCGAACTCCTGATCTCTGGTGATCCGCCTG
CCTCGGCCTCCCAAAGTGCTGTGATTACAGGCGTGAGCCACTGTGCCCAGCCAGAACTGTGGTTTTAAT
GACAATGCTAAAAAGTGGTATATGTCACAGTGTCGGGTGGGGCTAAGAGGCACATTGCTGCAGTGATCC
ATCATTCATTTCCCACCATTCTCGCCTGGATTAGCGCAGCAGCTCCCAGAGAGGCACCTCACTTTGACC
TTCTTCCTCAAAGACATTCTCTGTGACCTGCCTGGCCCTTATTACCTCTCTAGCTTTGCCACTTCCCTA
TGTCTCCATCTCCCCTCTCACACGTAGTAAGAAAGAGACTCTACCTCCATGGAAGTTAAGGAGAGGTTT

```
CACAGAGGCAGGATTGCTTATTAGTCTTCAAAGATGAGGTATTTGCTAAATGAATGAGACAAAGGATT
GGGGCCACATTACAGGAAATTGAGGTATGTAATAGCCTGGTGCAGGTTAAGAGTGTGGACTCTGAAACC
AGACTCAGCCTGGAATTGAATCCTGGCTGTGTGATGTTGGGCCAGTGACTTAACCTCTCTGTGCTTTTA
TTCACTCTTCTATAAAATGGGGATTATAATAAACCTACCTTATAAGGTTATTATAAGAGTCAGTAAATA
TAAAAATAGAAGTTTTTGGATGATGACTAGCACAGAGTAAACACTTGTTTGCCATTATTTTTATTACTT
GACTAAAAATATACCAAAAAGACCATCCAAGAAAAGCCTTTAAGCTGCTAGTGCAGAAAGATTCCCCTT
GTGTTTGTGTGCTGGGGGGTCAGTGGTGCCTGTGGCCCACTGGAGAGGAGACAGCTATGGCTGGAGTGA
TTCTCAAACTTCAGAATGTCTAAAATCATCACATGGACAACTTATTAAGGAAAGCAAATGCCTGGGCTC
CATCCTCAGAGAGTCTCATTCACTGGGTCAGGATAGAGCCCAGGAATCTTTACCTTAAAGAACCATCCC
ACCTCCCACCTCATATGATCCTTATGCAGGTGATCTGGGGGCCCACACTTTGAGAAATAGACTCAGGTC
AAAGTGGGCTCTAACTGCATCTCATTTCTTACCTGGCATATCTAATAGTAGAGAAGAAGACAATGCTAA
GATTTTTGTTGGAGATCTTTTGCTGGGATTGCKGSTGTCAYYCAKTCAYTCATTTAYYTAWWTAWKTAK
TYAWTKTGAAACAGAGTCWCAYTTTGTCACCCRGGMWGGAGGGCAGTGGCACAATCTGAGCTCACTGCA
GCCTCAGGCTCCTGGGTTCAATCGATTCTCTTGCCTCAGCCTCCCGAGTAGCTGGGATTACAGTCATGC
ACCACCACGCCCAACTAATTCTTGTATTTTTAGTAGTGACAGCGTTTCACCATGTTAGCTAGACTGGTC
TCGAACTCCTGACATCAGGTAATCTGCCTGCCTCGGCCTCTCAAAATTAGTAGCTGCAATTACACGTGT
GAGCTGCCGTGCCTGGCCTGCTGTTTCTTTTAGTTGGGCCTCTTCTGTAATAGAGTGTGAGAATTCTGA
CTTGCTGCAACAGTCTGCTTTGAAGCAGGGCTGTGTTTACACTGGTCAGATGTGGAATTGTGGGGCACA
CTTAGCAGCTTCCTTCTCTAATTTTTCTGTATTTTCAGGAGAACAATTTTAAAAAATTTAATAAAAATG
CCTTAAAAATTAACATTATTATAAGATGAATCCCATTTTTCTAATCTTGTAAATTAAAAACAATCATAA
GCATATGAGCACCTGCACTTAGGGAATCAAGGTGGCAAAGCTAAACACTTCCAGCTCTAGGTGATTCGC
GGCAATACAAATGGAGCTGGACTTTGGCCACAGTGCAAAAATATTGATCTGTTGTTAGATGCTCTGAAG
TTTCCACAAAGAATTGGTTCTGCCTGCTGTGCTTCAGTGCTTAAGGGAAGTGGTTCCTCAAAATGTTAG
TTTTTAAGCCCAGCTTTCTTAAATAGGAAGATTCTAATAGTAGCAAAAATATAAACTGCTTCTAGGTTT
AAAAAGGACCAGCACACAATGGTTATCACACACCTTTCTCCTCAGGTGATGAGTGGATGAGTGGCCTGG
TGTATTTCATAACATCTCCCAGGGTCCAAATGCTAAAGCAATTGCTGAAAAGATACCATGTGTACCGGA
ACCTTGCAGAGGTATTTTGTTGGCATAAAAAGAAATATTGATCATCTATAGTAAAAATGGTTCTACTTT
AATACTACTGAGAAAAGATTTTCTTTTCCCAGATCTACATCCTGAATCTTCATGAAGACAAGATCCCCT
AAACTTCCACTAACACCATAATGTGTGCTGTCCTTTGTAATGTAGTCCACAGATCTCATAAACTGTCAG
AAATAGCAGAGATTGTAAGGTCATCCACTTCCCCTGTAAGGCCTGCGTCCCTCACTTACATCCCTAATA
ACGTCCTCTAACCTCTGCTGGAGGGCAGATTTAGCTGCCAGCTGGGAAGAGCTCTGCCCTAGTCAACAT
```

TTTTATCTGTGGCTTTCAGATGAGAACACTGGATGCTTATCTGAAAAAAGCTCCTCAGGCTGGAGGGAG
GGATTGGCTCTAACAAGATGCAATGTGATAAGAATAAAAGCGAAGCCAAACTCTAGGCCCAAAGGCTCT
AGCAACACACTTTTGAGAACCTTGGAGACGAGTTTTGGCTGATGCGAGCTTCTCCGCCTGCTAAAGTAG
CCCATTCCATTTGGACGGCTCTAGAGGCTGGCATGTTCTTCTCCACGTTGTGTTAATGTACTCCAGTTT
CTTCCTGCCATGAACTGGCATGCCCTGGCTCCTCCTACCTTCCCCACTTTAAGTCTTCCCTCCCTCCTT
CTGACCTTCCCATTCCAGCCACACTGGCCTTTTGTCTGGTCCTAACAAACCATGCCTTTCCTGCCTCCA
AGCCCTACACCTGCTATCCATCCCTCTGTCTGAGAGACACTCCCACCCCTTCACAAAGCCTGTTTCTCA
TCCTTCCAGTTCAGATGTCTTCTCAGCTTGCCTCAACTGACCTCTTTCAGCTATTCTCACTCTTTGTAC
TCTGTTCATTTCCTTCCTGGCAGTCACCATAATTTATCTTTATTTGAATCAATTTCTTAGTTGTATTAT
TTAGTTATTTGCACACTCTGTCTCTCTGTGCCTTTCTTATTCACTGCAGGCTTTCTTATGTAAGTAATT
TATTTACTTAAATTTTTAAAAATAATTTCAACTTTTGGCCGGGCACAGTGGCTCACGCCTGTAATCCCA
GCACTTTGGGAGGCCGAGGTGGGTAGATCAGCTGAGGTCAGGAGTTCGAGACCAGCCTGGCCAACATGG
TGAAATCCCATCTCTATTTAAAATACAAAAACTAGCCGGGCGTGGTGGTATGCACCTGTAATCCCAGCT
ACTCGGGAGGTTGAGGGAGGAGAATCACTTGAACCGGGGAGGTGGAGGTTGCAGTGAGCTGAGATCACG
CCATTGCACTCCAGCCTGGGGCACGAGAGTGAGACTTCATCTCAAAAAAACAAAAAACAAAAAACCCCT
GCTTTTCAGAGGGGCTGAACTAATTTACATTCTCACCAATAGTGTATAAGCATTCCCCTTTCTCTACAG
CCTCACTAGCATTTACTTTTTAAAAAACTTTTAATAATAGCCATTCTGACTGGTATGAGATGGTATC
TCCTTGTGGTTTTCACTTGCAATTCTCTGATGATTAGTGATATTGAGCATTGTTTTATGTTTGTTGGCT
GTTCGTATGTCTTCTTTTGAGAAGTGTCTTTTCATATATTCTGCCCATTTTTTGAATGGAGTTGTTTTG
TGCTTGTTGAATTAAGTTCCTTATAGATTCTAGATATTAGACTTTTGTTGGATGCATAGTTTGTGAATA
TTTTCTCCCATCCTATAGTTCTGTTTACTCTGTTGATAGTTCCTGTTTTGTTATGTTTTGTTTTTTTGC
TGTACAGAAGCTGTTTAATCTAATTGGTCCCACTTGTCAATTTTTGTTTTTGTTGCAATGGCTTTTGAA
TTTTAATAATAAATTCTTTCCTAAGGCTGATGCCCAGAACAGCATTTTCTAGGTTTTCTTCTAGGATTC
TTATAGTTCAAAGTCTTATATTTAAGCTTTTAATCCACCTCAAGTTAATTTTTATATATAGTGAAATGC
AGGGGTCCTGTTTCATTCTTTTGCATGTGGCCAGCCAGCAATCCCAGAACCATTTATTGAATAAGGAAT
CTTTTCCTCATTGCTTATTTTGTCAACTTTGTCAAAGATCGGATGACTGTAGGAGTGTGGCTTTTTCTG
GGTTATCTACTCTGTTACATTGGTCTATGTGTCTGTTTTTGTATCAGTATCATGCTGTTTTTGTTACTA
TGGTCTCATAACATAGTTTAAAGTTGGATAATGTTATGCCTCTGCTTTGCTGTTTTTGCTTAAGATTGC
TTTGGCTATTGAGGCTCTTTTTTCACTTCATATGAATTTTAGAATAGTTTTTTCTAATTCTTTGAAAAA
TGACCTTGGCAGTTTGATAGGAATAGCATTGAATCTATAGATTGCTTTGGGCAGTATGCTATTTTAATG
ATATTGATTCTTCCTATCCATGAGCATGGAATATTTTTCCATTTGTTTGTGTCATCTACTATTTCCTTT

AGCAATGTTTTTTAGTTTTCCTTGTAGAGATCCTCCTAGGTATTTCATTTTTTATGTGACTATTTTAAA
TGGGATTGCATTCTTCATGTGGCTCTCAGCTTGAATGTTATTGGTGTATAGAAATGCTACAGAGTTTTG
TACACTGATTCTGTATCCTGAAACCTTACTGAAGTCATTTATCAGTTCTAGGAGCCTTTGGCAAAGTCT
GTAGTGTTTTCTAGGTATAGAATCATATCATTAGCAAAGAAAGATAGTTTGACTTCTTCTTTTCCTATT
TGAATGCCTTTTATTTCTTTCCCTTGTCTGATTGCTCTTCCAGTACTACGTTGAATAGGAGTGCTGAGA
GTGAGCATCCTTGTCTTGTTCCACCTCTCAAGGGAAATGGTTCCAGCTTTTGCCCATTCAATATGATGT
TGGCCATGGGTTTGTCACAGATGGCTCTTATTATTTTGAGGTGTATTCCTTTGATGCCTAGTTTGTCAA
AGGCCTTTATCATGAAGGGATGTTGGATTTTATTGAAAGCTTTTTCTGGGTCTTATTTGGTGAATTGCA
TTTATTGAATTGTGCATGTTGAGCCAAACTTCCATCCCAGGGATTAAACCTACTTAATCATGGTGTTAA
CTTTTTGATGTGCTGCTGGATTTGGTTTGCTAATTTTTTTTTTTTTTTTAAAATGGATTCTCCCTCTGT
CCCCCAGGCTGGATTGCAGTGGTGTGATCTTGGCTCACTGCAAGCTCCACCTCCCGATTTCATGCCATT
CTCCTGCCTCAGCCTCCCGATTAGCTGGGACTACAGGCACCCGCTACCATACCCAGCTAATTTTTGTAT
TTTTTAGTAAAAACAGGATTTCACCATGTTAGCCAGGATGGTCTTGATCTCCTGACCTCGTGATCTGCC
TGCCTCAGCCTCCCAAAGTGGCTAGTATTTTTTTAATTACTATTTTTTCTCACCCTTGCTGCCATCTTA
TGATTTTCTAGTATTTTGTTGAAGATTTTTGCATCTATTTTCATCAGGGATATTGGCCTGTAATTTTCT
TTTTTCATTTCATCTTTACCACATTTTTGTATCAGGTTCATACTGGCTTCATAGAATGAGTTCAGGAAT
GGTCCCTCCTCCTCGAATTTTCTCTGTAGAATTAGTACCAGCTCTTTGTGTGTCTGGGAGAAGTTGTAT
GCCAATAATTTAAATGCAGTTAATATTTACTGGACAATTTCCTCCAGATAATTGTATATGATTTTTGGT
CCACCCTGAGTTGATACATGTATTTTAATTGTATCATGGTATGAAAAGAGCAAGAGTATTTGGTCACCT
AGTCTTGCCTATAGATGTGCCTAATGATTCAAAGTAGATATTTTGGGAGCCTAACAGGTGCCGTGACTA
GGCAGTTTTGTTTTTTTTTTTTTTTGAGACAGAGTCTCGTTATGCTGCCCAGGCTGGAGTGCAGTGGCA
TGATCTCGGCTCACTGCAACATCCGCCTCCTGGGTTCAAGCAATTATACTGCCTCAGCCTCCCCAGTAG
CTGGGACTACAGGCTCACGCCACCACGCCTGGCTAATTTTTGTATTTTTAGTAGAGATGGGGTTTCACC
ATATTGGCCAGGCTGGTGTTGAACTCCTGGCCTCATGATCCACCCGCCTCGGCCTCCCAATGTGCTGGG
CTTACAGGCGTGAGCCACCGCACCCGGAGATTAGGCAATTTTATATTCCCAAATATCCAACTCTTCTGA
CCCGCTTTCTCAGCCTGGGTGTATCAGGCACAAGGCCTGTTCAGATTATGTGGTCTCTGAAGATATGGC
TCTCCAGGGTTGACAATGTGGATAAGGATTCACCTGGTTTAGGATTTACACATTCGCCTTGAATGTCTG
TTGCATCAAGTAGACAGTCCATCCCAACTTGGCCATTTGGTCAGAGCTGTAAGGAGACAAGGAGGTGGG
CAGCCGCTGCTGTGAACTGCTTGGACAAAGACTGCCAAATAGCTATCAGACAGTGTTAACAACAGCTGA
TTTAGGTTTGAAGGGGGCAGTCTCTTGGGCCACTTACTATGCTGCATCATCCTCTTTGGAAAATGCTCT
TCAGGTAACTGCCTAACAGACTGAGAAAATAAAATGCTCACAGAGAAAAAAGACCCGGAAAGTCTGACT

TCTCAGAGCTCAGTGTTTAGGTGCAGAACTGGATTGTGAAAGGATTTTTAAATTTTTATATTCATTGC
AGGGAACATTCATTTATTCCATCCTTCTCCACTCCCACCTGTCTGTCGTTGTCTTTGTCTCTGTCTCCC
CACCTCTCTCTCTAGACACACACACACACACACACACACACACACACACACACACACACACACACAC
ACACACACACACACACACACACACACCCCTATTCATTGCCAACAGTAATAGAGTTGCTTCTTTACTTCTTG
GAGAGAAAAGCCTCAATCTGAGGAAGCTGTGCTGACTAGCCTTGCTCTTAATCATGGAGACAATGCTTT
ATGCCTTTATCTTTGCACAGCTGAAAGCCATGGCAGAAGCAGTCCTCTAAACGAAATAAAATAGAAAGG
TTCCTGCTAAGCCCTGGCAAATGCAGCCTTCTATCCCTCCCCCAACACTCACAGCTTCTGAGCAAGATG
TAGCTGCCTTCCAGGAGGCTGGGTGATGGGCAATAATGAGCAGAGCCACGTGAAGGAAAGATGGGTGAA
GAAATGTGTGTGGAGGTCATGCTGGCTGCACTGACCATGAAACAAAGGATCTACCCCTCTAGTAACTGC
CCTACTCCTTTGGTAACTGTTCTGAAATTATAACTTGCCAGAAGTTCAGAAGGACCTAGTGCAGGTATT
AGAGGAAATTCGTAAGATTGAGCCATTTATTCCTGCACAGATACATAATAATGGACACGGGCCATGGTG
GCCAGCATTCTTGCTCTTGACAATGGTGAAGGGAAGGGTTGTAGGTCATGGCTATGCTCTCAGAATTAT
AATGGAAAGAAACAGCTCCTGAGTGTTTACTATGAGCCAAGGGCTGTGCTAAACACTTTACCATATGAT
GACATCTTTTTCTCACAGGTATCAAAAAACAATAGGACATACCGGATAGCTACAATCTTTGGGCCCCTG
CAAACACAATAATGTGTATTCTCTTCTTCAAATCCTACATATTGCTACAAACTGTATCCCTGAGGCATA
TTCATTGTAAAATAAAAACATATAAAGTACTACTTTTGTTTTTTGAGATGGAGTCTCGCTCTGTCACCC
AGACTGGAGTGCAATAGCATGATCGTGGCTCACTGCAACCCCCTGCTCCTGGGCTCAAGTGATTCTCCT
GACTCAGCCTCTCAAGTAGCTGGGATTACAGGCGCACGCCCCCATGCCTGGCTAATTTTTGTACTTTTA
ATAGAGACCAGGTTTCACCATGTTGGCCAGGCTGGTCTCAAACTCCTGACCTCAAGTGATCCACCTGCC
TCGGCCTTCCAAAGTGCTGGCATTACAGATGTGAGCCACTGCACCCGGCCCATATAAAGTACTACTAAT
GTAACAGGGTGCTAGTCCAGACAGTGACCACACGTGGTGTTCATTGAAGGCTGGACTAACAACTCCAGC
CTCTCCGCCATCACAGAGTGATGACTGCCTTCCCTGAAGCAAAGCTTCTGGTTCAAGGAAAGGCCAGTA
AGTGACTGCTCTTTGTTGTATACATGTTAGATGATCAGGCCTCAAGAAAAGTATAAAGAGATCTTTGTG
CTCTCTGGGACTCAAAAAGCTGCACTCTTTGGGGGAAGGATAGCCAGGTAAAAGTGGCCCAGGTAAAGA
GGGCCTGGTACACCTGGTTCTGCAAGATGGTAGACACAAAAATGAGAGCCACATTTGGAGCTTATGTGC
CCCTAACTCTGTACATAACCTGCAAGATCTAATTACTAACAACTGGAATCTTGGAAACACCTGTAGTAC
ATCCTTGGCTAAGGTTAGCCCCAACAGAGAGGGCTCTCCTCTTACAGAGAACCATTACATTTGTGCCTT
CATCCTAGAGTAGAAAAGGCATGATCAGACTACTAAAAAGACATCAGGAAAGGGCCTGTGACATCTGAG
GGAAGTGGTTGCCCTCTCTGGGATGTTGGTTCGGGAAGAGGGGCATGGAGGAGTGCCTGCTTTAGATGG
TCATTCAGGAACCCAGGCTGATAGTGAGAGGTGAAGCCAGCTGGGCTTCTGGGCTAGGGGGGACTTGGA
GAACTTTTGTGTCTAGCTAAAGGATTGTAAATGCACCAATCAGCACTCTGTAAAATGGACCAATCAGCA
CTCTGTAAAATGGACCAATCAGCAGGATGTGGGCAGGGCCAAATAAGGGAATAAAAGCTGGCCACCAGA

GCCAGCAGTGGCAAACTGCTCAGGTCCCCTTCCACGCTGTGGAAGCTTTGTTCTTTTGCTCTTCACAAT
AAATCTTGCTGCTGCTCACTCTTTGGGTCTGCACTATCTTTATGAGCTGTAACACTCACCGTGAGGGTC
TGTGGCTTCATTCCTGAAGTCAGTGAGACCACAAACCCACTGGGAGGAACAAACAACTCTGGACACGCC
AACTTTAAGAGCTGTAACATTCACTGCGAAGGTCTGCGGCTTCACCTCTGAAGTCAGCGAGACTATGAA
CCCACTGGAAGGAAGAAACTCCAGACACATCTGAACATCTGAAGGAAGAAACTCCAGACACACCATCTT
TAAGAGCTGTAACACTCACTGCAAGGGTCTGCGGCTTCATTYTTGAAGTCAGCAAGACCAAGAACCCAC
TGGAAGGAAACAATTCCGGACACATTTTGGTGACCCAGATGGGACTATCACCAAGTGGTGAGTACCATC
AACCCCTTTCACTTGTTATTCTGTCCTATTTTTCCTTAGAATTCGGGGGCTAAATATTGGGCACCTGTC
AGCCAGTTAAAAGCGACTAGCATGGCTGCCAGACTTAAGAGACTAAAGACACGGGTGTCAGACTTTCTG
GGAAAGGGCTCTCTAATAACCCCCAACTCTTTGGAGTTGGGAGCGTTGGTTTGCCTGGAACCAGCTTCC
ACATTTCCTGTACTTCTGGGCTGAGACGAGGGTCAACAGAGAGGAAAGCCATTCAGCTCTGGGGTCCCG
ACAGCAAGTTGGTTGACCCTGTGGCCATGAACAGAACTCTCGAAGTCATGTTGCCCAAGCGAGACTCAC
CCATCTATCCTATCTATCCTGACTCTTGCTTCCTGGGTCCTAATGCCTGGAAGACAAAACTTCCTCTTG
TCTCTGTTCTCCAAGGCTAGTCCCACTTCTAAAAACCACTCCCTGTCTCTGGTGCTTTTCTAGTTTCTC
CTATAAGAATGATTTCTAGTATAAACTCCAGGACTCTATTCTCTTCTTTAGGCACCCGGGCTCACCAAT
CAGAAAGCCATAATTTTTGCCCAAAGCCCCATCTTAGGGGGGACTATCTGGAATTTTAGGATCCCTCCT
CAGACAAGCAGGCCTAACAAAAGCTATTCCTGAAGCTAGGATATGGGGAGCCTCAGAAATGATATCCTT
CCTATTCAAGTGAGGACAAAAGGCATCACTCTTCCAATTCTGGAAATCCCTTCCCTCCCTCAGGGTATG
GCCCTCCACTTCACTTTTGGGGCATAACGTCTTTATAGGACACGGGTAAAGTCCCAATGCTAACAGGAG
AATGTTTAGGACTCTAACAGGTTTTCAAGAATGTGTCGGTAAGGGCCACTAAATCCGATTTTTCTCAGT
CCTCTTTGTGGTCTAGGAGGACAGGTAAGGGTGCAGGTTTTCAAAAATGTGTTGGTAAGGGCCACTAAA
TCTGACATTCCTTGGTCCTCCTTGTGGTCTAGGAGGAAAACTAGTGTTTCTGCTGCTGCATCAGTGAGC
GCAACTATTCCAATCAACAGGGTCCAGGGACCATTGTGGGTTCTTGGGCAAGAGGTGTTTCTGCTGCTG
CATTGGTGGGCTCAACTATTCCAATCAGCAGGGTCCAGTGACCTTTGCGGGTTCTTGGGTCGGGGGGTG
GGGGGAACAAACAGACCAAAACTGGGGGCAGTTTTGTCTTTCAGATGGGAAACACTCAGGCACCAACAG
GCTCACCCTTGAAATGTATCCTAAGCCATTGGGACTAATTTGACCCGCAAACCCTGAAAAAGAGTGGCT
CATTTTATTCTGCACTATGGCCTGGTCCCAATATTCTCTCTCTGATGGGGAAAAATGGCCACCTGAAGG
AAGTATAAATTACAATACTATCCTGCAGCTTGACCTTTTCTGTAAGAAGGAAAGCAAATGGAGTGAAAT
ACCTTATGTCCAAACTTTCTTTTCATTAAAGGAAAATCCACAACTATGCAAAACTTACAATTCACATCC
CACAAGAGGACCTCTCAGCTTACCCCCATATCATAGCTTCCCTATAGCTCCCCTTCCTATTAATGATAA
GCCTCCTTAATCTCCCCCACCCAGAAGGAAACAAGCAAAGAAATCTCCAAAGGACCACAAAAACCCCTG

GGCTATCGGTTATGTCCCCTTCAAGCTGTAGCGGGGAGGGGAATTTGGCCCAACCCAGGTACATGTCC
CCTTCTCCCTCTCTGATTTAAAGCAGATCAAGGCAGACCAGGGGAAGCTTTCAGATGATCCTGATAGGT
ATACAGATGTCCTACAGGGTCTAGGGCAAACCTTCAATCTCACTTGGAGAGATGTCATGCTATTGTTAG
ATCAAACCCTGGCCTTTAATTTAAAGAATGTGGCTTTAGCCACAGCCCGAGAGTTTGGAGATACCTGGT
ATCTTAGTCAAGTAAATGATAGAATGACAGCTGGGGAAAGGGACAAAGTCTCTCCCGGTCAGCAAGCCA
TCCCTAGTGTGGATCCCCACTGGGACCTAGACTCAGATCATTGGGACTGGAGTCGCAAACATCTGTTGA
CCTGTGTTCTAGAAAGACTAAGGAGAATTAGGAAAGAGCCTATGAATTATTCAATGATGTCCACCATAA
CTCAGGAAAAGGAAGAAAGTCTTGCCTTCCCTTGAGTGGCTACAGGGAGGCCTTAAGGAAAATATAACT
CCCCTGTCACCCAACTCACTTCAAGGGTTAATTGATTCTAAAAGATATGTTTATTACTCAATCAGCTGC
AGATATCAGGAGAAAGCTCCAAAAGCAAGCCCTTGGCCCTGAACAAAATCTGGAGGCATTATTAAACCT
GGCAACCTTGGTGTTCTATAATAGGGGCCAAGAGGAGCAGGCCAAAATGGAAAAGCGAGATAAGAGAAA
GGCCACAGCCTTAGTCATGGCCCTCAGACAAACAAACCTTGGTGGTTCAGAGAGGACAGAAAATGGAGC
AGGCCAATCACCCAGTAGGGCTTGTTGTCAGTGTGGTTTGCAAGGACAGTTTAAAAAAGATTGTCCTAT
GAGAAACAAGCTGCCCCCTCACCCATGTCCACTATGCTGAAGCAATCACTGGAAGCCACACTGCCCCAA
AGGACAAAGATTATCTGGGCCAGAAGCCCCCAAGCAGATGATCCAACCACAGGACTGAGGGTGCTCAGG
GTTAGCGCCAGCTCATGTCATCACCCTCACTGAGCCCTGGGTACATTTAACCATTGAGGGCCAGGAAAT
TGACTTCCTACTGGACACTGGTGCGGCTTTCTCAGTGTTAACCTCCTGTCCTGGACAGCTGTCCTCAAG
GTCTGTTACCATCCGAGGAATCCTGGGACAGCCTATATCCAGGTATTTCTCCCACCTCCTCAGTTGTAA
CTGGGAGACTTTGCTACAGATAGTAAGTATGCTTACCTAATCCTACATGCCCATGCTGCGATATGGAAA
GAAAGGGAATTCCTAACTTCTGGGTGAACCCCCATTAAATATCACAAGGAAACTATGGAGTTATTGCAC
ACAGTGCAAAAACCCAAGGAGGTGGCGGTCTTACATTGCCGAAGCCATCAAAAGGGGAAGGAGAGGGGA
GAACTGCAGCATAAGTGGCTGGCAGAGGCAGGGAAAGACAAGCAGAAAGGAAAGAGAGAAAGAGCAGAA
AGTGAGAGAGAAAGAGAGATAGGAAGTGATAGCAAAGAGGGAGTCCGAAAGAAAAGAGAGAGGAGAGAG
AGAGGGGGAAAGACAGAGAGAGACAGAGGAAGAGACAGAGAGACAGAAAGAGAGAAGCAAAGAGAGGAA
GAGACAAAGAAGGAGTCAAAGAGAGGGAAAGAGAAGTAGTAAAGAAAAAACAGTGTACCCTATTCCTTT
AAAAGCCAGGTTAAATTTAAAACCTATAATTGATAATTGAAGGCCTTTTCTGTAACCCTATAATACTCC
AATACCACCTTGTTGTCAGTGTAAACAAGGGTATAGCCCAAAAGCACTGAGGCCACTGACAACCCGTAG
CCTTCTTATCAAAAATCCTTAACACAGCAGGTTTCCTAACAGGGAATCTAAATCTTAAGGTCGGACCAG
ACATAGGAGGAACTGCCTTCAGGACAGGATGATAGATGGTTCCTCCCAGGTGATTAAGGAAAAAGACAC
AATGGGTATTCAGTAAGTGATAAGGAAACTCTTATAGAAGCAGAGTTAGGAAAATTGCCTAATAAGTGG
TCTGCTCAAACGTTGAAGCTGTTTGCTGTTTGCACTCAGCTAAACCTTAAAGTACTTACAGAATCAGGA
AGGAGCCATCTATACCAATTCTAAGTTAATATGGACTGAACGAGGTTTTATTAATAGCAAAGAAAATTA

AAATCTCAAACTTACAAGGTTTTCAACTAAAGTAAAGTTTGCTAAAAGTTAACAGCGTAACATGTATTA
TCCTACTACCTCACACTCTCTCAAAGGATTTCTCAGACAGTTTGCAAAAAAGAACGAAATCTGTCCTTA
CTCTACAATCCCAAATAGACTCTTTGGCAGCAGTGACTCTCCAAAACCGCTGAGGCCTAGACTCTCTTA
CTGCTGAGAAAGGAAGATTCTGCACTTCTTAGGGGTAGAGTGTTGTTTTTATACTAACCAGTCAGGGAT
AATATGAGATACCACCCAGTGTTTACAGGAAAAGGCTTCTGAAATCAGACAATGCCTTTCAAACTCTTA
TACCAACCTCTGGAGTTGGGCGACATGGCTTCTCCCCTTTCTAGGTCCTGTGACAGCCATCTTGCTAAT
AGTCGCATTTGGGCCCTGTATTTTTAACCTCTTGGTCAAATTTGTTTCCTCTAGGATCGAGGCCATCAA
GCTACAGATGATCTTACAAATGTAACCCCAAATGAGCTCAACTAACAACTTCTGCTGAGGACCCCTGGA
CCGACCCGCTGGCCCTTTCAATGGCCTAAAGAGCTCCCCTCTGGAGGACACTACCACTGCAGGGCCCCT
TCTTCACCCCTATCCAGCAGGAAGTAGCTACAGCGGTCATCGCCAAATCCCAACAGCAGCTGGGGTGTC
CTGTTTGGAGGGGGGATTGAGAGGTGAAGCCAGCTGGGCTTCTGGGTCAGGTGGGGACTTGGAGAACTT
TTGTGTCTAGCTAAAGGATTGTAAATGCACCAATCAGCACTCTGTGTCTAGCTAAAGGATTGTAAATGC
ACCAATCAGCACTCTGTAAAATGGACCAATCAGCAGGATGTGGGCGGGGTCAAATAAGGGAGTAAAAAC
TGGCCACCCGAGCCAGCAGTGGCAACCCACTCGGGTCCCCTTCCACACTGTGGAAGCTTTGTTCTTTTG
CTCTTCACAATAAATCTTGCTGCTGCTCATTCTTTGTGTCCACACTACCTTTATGAGCTGTAACACTCA
CTGCGAGGGTCTGTGGCTTCATTCCTGAAGTCAACAGACCACGAACCCACTGGAAGGAACAAAGAACTC
CCGATGTGCTGCCTTTAAGAGCTGTAACACTCACTGCGAAGCTCTGCAGCTTCACTCCTGAAGTCAGTG
AGACCACAAACCCACCAGAAGGAAGAAACTCTGGACACACCTGAATATCTGAAGGAACAAACTCCAGAC
ACACCATCTTTCAGAGCTGTAACACTCACCGCAAGGGTCTGTGGCTTCATTCTTGAAGTCAGCAAGACC
AAGAACCCACCGGAAGGAACAAATTCCAGACACAGTAGGAAATCTGTATTTTTGATCTGTGGCTTCCAG
GGTTACTCCAGTCATTGAAGTCTCCATTGCAGCCTTAAGGAAACAGAGAATGGTTTGGAGGAGCACATG
TGGGAATTGTTATGGACCAGGCTTGAGATGCACATAGGGCATTTCTGATCAAACCTAGCTGGAAGCAGG
GCCAGGAAATATAATCTAAGGAAGACAGTTTTTGTAGACAGTAGTAGTCTTTGCATCTGAGACATGTAG
ATTATCAAGCAATTAATTAGAAAAAATATAGCCAGGTGCGATGGCTCATGCCTGTAATCCCAGCACTTT
GGGAGGCCAAGGGGTGTGGATCACAAGGTCAGGCGTTCGAGACCAGCCTGGCCAACATGGTGAAACCCC
GTCTCTACTAAAAATACAAAAATTAGCCTGGTGTGGTGGCACGCATCTGTAATCCCAGTACTCAGGAGG
CTGAGGCAGGGGAATCTCTTGAACTTGGGAGGCAGAGGTTGCAGTGAGCCAAGATCACACCACAGCACT
CCATCCTGGGTGACAGAGCGAGACTCTGTCTCAAAAAAAAAAAAAAAAAAAAGGAAAGGAAAATATAATC
AAGAATATTGACAGGTAACATTTATTCAACACTTACTATGCACCAGGCAATACACTAAGTGTTTTACAT
GGATTAACTCATTTAATCTTAACAATAGCCCTATGAAGTCAGTGCTGTTATTATCTCCACTTTATAGAT
AAGGAAACTGAAGTACAGAAAGGTCAAGTAGAGAAATGGCCATGCTTGCATTCTCAGTTTTTGAAGCAA

CTGTTACAGGAATCTGGTGTGAGAAATGCTCTAACAAGATGTGAGTCAGGGGTTGGGAGGTACTGAGTC
TGAGTTGGGCAGTTGGGGATGGAAGGATGGATGAAGAACAGCTTGACAGAGAAGCTGACACTTGGCAAC
TCTGTGGGACCTTGAAGGGTTAGAGGGACTTCACCAAAGAAACTGGTGGTCAGGGAAACGGGAGGGTCA
CGGCAAGGAGGGAAAGGAAACTGTACCACAGCAGAGAGTCTGAAGCTACTACAGTGTAGTTCAGCGTAT
AAAGAATAATTATTTTAAGGTAAACTTATAACCTCATGCAAATATAAAATGAACACGTGTCAAAGATCT
TATTTAATTTATTAATTAATGAGGGAACCTGTAAGATGTTACAGCCAGTTCAAAGGATAATTCAAATAA
ATCCATGCACATATGTAGGCAATAAGGAATGCTGAAATGAATTTAAAAGTAGATGTAAACTGATTTATC
CACAGAGAAATAATCAGTTGCATTTCACATAACAAAATTCAGTTGCTTTTCTACAGAAGGAATTGTTTG
CATCATTACCAATTTTTCTACAACTAACAGAATTATAAAATAACTCAAACACAATGAAAGGCAGATATA
ACCCACAATGGTATGATAGATACAATATCCACATCCAGGATGTTTTTTTCTCATTTCAAAGTCTTTCAC
AAGTTTTCCTGATAAGGGAGTGTCAATAATACTGTATGGCAGGCAATAAGACTGGATGGATGGTTGGGG
CCAGGTTTTAAGGGGTAATAAATGCCATGTAAAGGTATGTGCATACTGTGCAACATGTCGGGGGAATCT
CAAATTATTGGTAGAGTATGTAGGAAACACTTGTGGGAGCTTGTTAATAAATTCAAATTCCCAGACCCA
ACTCCTCAAGGGGTCTAATACAGTAGGTTTGGAGTAAAGCCTGAAAATCTGCAATTGTGCAAAAAAAAA
ACCCAGGTGATTCTGATACACTTTGAGAAGCACTGGTGGAACTAATAGTCACTGAACGTTTTTGAGCAG
GGGAGAAACCTGAGGACGTCTATGTTGCAGCAGTGGAAACTTGATTAGAAGTAGGAGAAGATGCATGGT
CTTAAAAGAATGCAAAATGATGGCTAATATTTGAGTGCTTATGATGGGCCAGGGGCTGTGCTAGGCGCG
TGGCACACATTCAATACGATGGAAGCCTGTACCAGTCAGTATTAGTGGGGTATCTTTAAGAGTGACCAG
AATTAAGGGGGGTTTCACCAAAGCCTGAGGACTGAGCCTCCTCATCCTAAATTCAGACACAATGCTGT
ACCTATGCATTTGCCTCCAGGCTGTTCCTGGGCCTCCAGGGACTGGCCCAGGCTCCTGATAAATAGGGA
CTCCCAACAACATAAAGCCTGGATTTTGGAACTTCCTGAATGTTACTCAGGCTTTCTAGTAACTGTGGA
GATCTGAATAATAACACAATTCTAAGTTCCCCTACTCATAAAGCTGCTCATCATTTAGATGGGGTAAAG
CACCTGAAATACAATGAGCATCACTATTTTCATTCATCCATGAAATGAACATTCCGGGGAGATCAGTAA
GTTGATGTATCACCCTTGAACAGGGCAAAATGAATACTCACCAGGAATATGTGGTATTTTAAAAAGAAG
GCAAAGGGAAGAATAGTGGGGATGGGGCAAAAACTTTAAATAGATTCCCCCAATCATATATGGCAATTG
AAGATAATTAAATTATCATTTTAATTGAGTAAGTACTCATAGAGCCCTCACTATTTGAAAATGAACTGC
CTCCTAATTGTTATTGTGCAAATGTGATACATTAAACTTAAGCTATTTTAATAAAACATCCATTTTCGG
AAGCTGTAGTAGGTTCTCCCAGGTCAGATTTGATAAGCCATAAAGAACAAATGCCAACTCCTATTTTTC
TATGGTGCTGGGAAATAAGAGAGAAATGTGTAATTCAAAGCAATCATTTAATTTTATCCAATAGCTTGA
TTCTCCTCTCTCTTCTAGCCTTTTAGCTAAGCTGTTACCAAGTAACCACACTAGTTGGCTTGAGTCTTA
CCACTGTTTCCCTGACCCCACAGTGGAGAGACTGCATCTGTTAAAGAGCAGTTATGTAACCATGGCTAT

GCTGAGCTGGGATTCCCAAGGCTTAGGTTCTTTCTGTGAATGACCTTCACCAAGACACCTGAGGTCTGT
GTGGAACCACAGGCTTGTCATCTCTAAGGCAGAGTTGATAATTCCATCTGTTTCTTGAGCCCACACTGA
GAAAAAGATTACATGACTGCAGTTATTTGAATGCCTCATGGAAAGACGTCTTATAAATATTATAATTAA
TGTTATCATTAAGTAATGCTTCAATGCAGATCTTCCAAGTATAAATATCAGCTGAGTAAGAAGTCAATC
TTCCCTGAAGCAAAATTGAAATTTGTAAATGCGATTTCTGGGAGCTTATTTTGTAATACATGATTCCAG
AGTGTCCATAACACACACAATTGTCTTTTTCCCCTACATGGGCTATTTACAACAAAATTGGACTTATA
ATGTTTATTTCCAGGGATGACTAGAACTTTAATAACAAACCTTGGGCCAGGCATAGTGGCTCATGCCTA
TAATCACAGCACTTCGGGAGGCTGAGGCTGGTAGATTACTTGAGGCCAGGAGTTTGAGAACAGCCTGGC
CAACATGGCAAAACCCTGTCTCTACTAAAAATATAAAAATTAGCCGGGTGTGGTGGCGCATGCCAGTAA
TCCCAGTTACTAAGTAGGCTGAGGTACGACAATCGCTGGAACCTGGGAGGCGGAGGTTGCAGTGAGCTG
AGATTGCACTACTGCACTCCAGCCTGGGTGACAGAGAAAGACTCTGTCTCAAAAAAAAAAAAAAAAAT
AATAATAATAATAAACCCTGATGAAAGGTTTCTAAAATGTTTCATCTAATGGTTTTCTTGACAATTAA
ATTTTCTATATAATGTCAGTTCATAAAAAAACTGAGAACGACCACATGTCATATCGACTGCTTAAAAGA
AAATACGTATATTTACAAACATATACACGATACTGTCTTTTGTCTGGTTAGTTTAGAGGTTAGATAAAC
TGCAGTATGTTGTAGTGGACAGATCATAGAACTAGGAGTCAGGATGTCTGGATTCCTAGGAAGCAATGA
ATAGGTTGCACGGTGCAGACCAGCATCATGAGTATCCTCAGGGAGCTTGTTAGAACTGCAGATCCTTTA
ACTCATTGAATCAGAATCCCTAGGTGTGGGGCCCTGAAATCTGTATTTTAGCAGGCTCTCTGGGATTGT
GATGTGCCTTAGAGTTTGACAACCACTGGGTAGCTGATCCTGACTTAGACTTATCAGGCATGTGATCTT
GAACAAGTCACATAATCTCACTGAGTTCAGTTTTCTTATGCTTAAAATAGGCCCAATAATATCTATTTC
ACATGGACTGCTTTGAGGATTAGGCAAGAGATCTGTAACAGACACTGTAGAACAGTGTCTCTGGTCTAC
AGCTGACCTTCCATAAATGGTAGTTGCCTTGATCTCTGCTCTGCCACATAATAGCTGGTTAACTATGAG
CAAGTAATTTAGTTCTTCTCAGTTTAGTTTCTTCACCTGTAAAAGAAGGAAAATAACTGTTATACTCAA
TTTCTGAAGTGGCTATAAAAATCAGTTTAAATTATGGGCATTGAAGCTCTTTGTACACTGTATAAGGAC
TGTACATCTAAGGGATTAATGAGACCAGGCTTATGATTTTAAGCATGGAGTAAATAGTAACACTGACTC
TGTTCTATGAACCACATGGAAACTCTAAAGAATATGCACATTTGAAACACAGGTATCATCTGGGGAAGG
TGATCTGCTCACCCAAACCAGTTCATGAACATCAATCTCCAGTGGCGTGCTGGAGCTAGCTGTACCAGC
TCATGAGGGCCAATTGTTTCATTTTTAGGAATTTTGTTTGCTGGTTAAAAATAGTCATTATTTAAAATT
AAATTATGTAAACAATAATATTAGATAAAATAAGTTAAAATAAAAACAAAGGAACTAATTATCCCCAAA
CTCTTCCCCACCTAATTATTTTACTATCTGTGCCTTGGGATTATTTACATTGATTTTATCCATATGGTG
ACAATACTATTCATATATAAATGGTGTGCTTCTCTTCATAACTCTACATAGCCTGATGTCAGGCTAGTA

GCTTGAAATTGGCCACAGTGGGAGTGTGAGCATTTGTACCATGAGGCTTGGCCAAGGCTACAAATCCAG
ACTTTTGTTTTTCCCTCCTGGAGAGCTGTCTGTTAAAAATTTACCAACACACCACTGGTCTTACCTTTG
TTAATTTACCACAGTCCAGGTTCTGACCTAGACTTAGAAACCTGGATTTGTCAGCAAGCTGAGGATAGA
GCCATTATTTTTAAGAAGGACTCACATTACCCAAGTGCAAAGCCTGATATATACCTTCAGAATATCAAT
TTATTAATTTACAGTGAAGAAAGCCACCCCAGGGCATTCCCCAGGGGAAGGCAAAAAGAGCTAGTTGCA
CATTTTGAATGTTTGATGACATTAGGGTAAGGTGACACAGAATATCCATTTCCACAACTGAGATACCTG
CTGCCTTAAGGAAGGGACAGGCAAGTCCTTGGGCAGGACCTTAGATTGTCACTGTCCATCTTGCTCTAG
GACTCTCCTTTCCAGGCATGACGATGGCCAACTCTGTCCTCCTACCCTACTGATGGGATTATCTTTTCT
TGACACATGGCAATGCCTCCAATCAGAGGCTGGTAGCTATTTTTAATCTTCAGGGCAGTATTTTTCAAA
GGGAAGTTCATGGACCATATGCATCTGTATCATTTAGATGTATATTAAAAATGCTTAGTCTTCCCCAGT
TATACTAGATCAGAATCTCTGTTGGTGGGGCCCACGAATCGGTATTTTCAACAAATCACTAGGTAATTT
CTGTATATACTATAGTGTGAAGACCACTGCTTGAAGGTTTCTTTGCATATCTCCACTAAATATAAAAAA
TATTGACTTCTAGATTTAACTCCCAAAGCACTTGCATTTTTAAGTTTCTGGGGGCATTATATTGTGGTA
CCCCTATACCACTCACACTCTAGTCAGGAGGTATATTATGGACTGAATGTTTGTGTCCCTCCAAAACTC
ATATGTTGAAGTCTTAGCTTCCAATGTGATAGTATTAGGAGATGGTGCCTTCTGGAGGTAAAATCAAGC
CCTCATGAATGGGATTAGTGCCTTTAGAAAGAGAGCTCCGTCACTGTCTTTCCATCAATTGAAGATGCA
GTGAGAAGCTGGTAGTCTTGCATCTGGAAGAGGGCCCTCACACAACCTGATCATGCTGGCACCTGGTCT
CAGACTTTCTGCCTCCAGAACTATGAGATGATAAATTTCTGTTGTTCATACCCCACCCAGGCTACAATA
TTAGGTTGCTGCAAAGTATTTGTGATTTTTGCCTTTACTTTTCAGGGCAAAAACTGCAATTACTTTTGT
GCCAACCTAATATTTTGTTATAGCAGCCCGAACTAAGGCAAGGGAGACTACATCAGACAGTGTAGCTAT
GTAAGTACAAATGTATCCCTGTTGAGGAAAACTAAGTTCTAACCCTGACTTCAGGCCAGTAGCCACCTT
TTCAATCTCTTTCATGAAGGGACCATTATCATTATCACTGGTGGCAAAAATAGAGGCACGAGAATGGAA
TTTGCTTTTCTGTGAAATCTCAGTGTATACAGATTGAAGAGCAAGGGTTTGCTTTCATCTCTAAGAAGC
AAAAGTGAGTACGGACTGGCACATTATCAGAGAAAGAATCATTCTAGCTCGGTGGGTCTTAACCAGGAG
TGAATTTGACTCCAGGGAACAGTTGGCAATGTCTGGAGACGTTTTTATTTGTTATAGCTGGGGGATGAG
TGGGTGGGTTGCTACTGGCATCTAGTGGGTGGAGACCAGAGATGCTGTTAAACATCCCGCAAAGCACAG
GACAGTCCCCGACAACAAAGAATTATCTGGCCCCAAATATCAATAGTGCCAAAGTTGAGAAACCTCATT
CTAGCTTCCTTTTCCCTTCTACGTTCTAATCAACTGTTGTTCTTTCAGCATTAGGATTCATCCAGCAGT
CTCTTTCCCCAGCAATTTGTTGAAATTTTTTAAAAATGGACTCATTTAGTGTCACAAGAAAAAAATA
CATTCACAGGAAAGGATGGGTCATTTTGTTTAATGATGTTTTGCCTTTCACATAGCAAAAGCTTAATAA
AGTATTTTTAAATAAAATGGTGAATAGATCAAAACATTAATTTCACATGTGTTTTAATAAATAACAGGA
AGATGGCTATATTATATAAATTGTTCTTGTATATGTCTTGAGTGGATCATCAAACACAAACGTATCTAC

ATGCCTTTTCTTGTGAATAGATCTAATAATAACGCTCTTCTAAAAACAAATTAAATGGATATTATTTGC
TGAGAATGTAATGCTTGTGTGAATAGAAGCCAGCCCTGAATCCAAGCCCCCAGATCTATTTAAAGAATT
TGAAGAATGTCAGAAAAGCACGTGGCTTCAAGGTTAATGTGTAAGACTCACAGAAACTTGAAAAATCAC
TATGACTAAAAAGAAAGTATGAGCTCCCTGCATGCCTGTAAATTGGAATGACAGCCAAAACCAGTTAAT
TATAAAAACAGCTAATTTAACAGGTTTTCAAATTTGTTTCTTTCTCCAAGTAGCATATAGTCAATAATC
CTTAAAGAGAAAGCAAAGAAGGGGAAGCACTGAACCAAATTTGCTTTTTTGTACCTGCTCAGCTCAAAT
GCAGAGTTCTCTACCTGGAAATTGACTGCTTCCATAGTTTGATAGCCACAGAGAGATGGGAACAGAAGG
AGAGGTATAATCCCAGACTTGATTCAGCTATAGAGAATGACAATAGTGTCAGAGGCCTTCCAACCAGAG
CGACTCCATCTTGAATACGGGCTGGGTAAAACAGGGCTGAGACCTACTGGGCTGCATTCCCAGGAGGCT
AAGCATTCTAAGTCACAGGATGAGACAGGAGGTCAGCACAAGACCTTGCTGATAAAACAGGTTGTAATA
AAGAAGCCAGCCAAAACCCACCAAAACCAAGATGGCCATGAGAGTTATCTGTGGTTGGTCTCACTGCTC
ATTGTATGCTAATTATAATGTATTAGCATGTTAAAAGACACTCCCACCAGTGCTATGACAGTTTACAGG
TACATTGGCAACTTCCGGAAGTTACCCTCTATGGTCTAAAAAGGGGAGGAACCCTCACCTCCCAGAATT
GCCCACCCCTTTCCTGGAAAACTTGTGAATAATTCACCCTTGTTCAGCATATAATCAAGAAGTAACTGT
AAGTATCCTTAGGCCAGAAGCTCAGGCCACTGCTCTGAATGTGGAATAGCCATTCTTTTATCCTTTACT
TTCTTAATAAACTTGCTTTCACTTTACTGTATGGACTCCCTGTGAATTCTTTCTTGCAAGAGATCCAAG
AACTCTCTCTTGGGGTCTGGATCAGGACCTCTTTCCAGTAACAATAGTAGTAAGGGGTCAGGGAGACTG
GACAAAGGAGTTTAAGAAGCCTTAGATAAAGGGTCCTCATCATTGTCATAACATAAAATCATGGACTCC
TAGAATTTTATAGCTGATAGGATTAGAAATTTCAAAATTCAATTTCATTAATTTTCATCTGCGAAAACA
GATGGCCAGAGAGGCCAAACAATTTGTTAAGGAGCACTGAGGGCAGACCACACTGGAACGCAAACCTCT
TAGCAGAGTATACAAGGCCTTTGATCTCCTCAGTCAGAATGAACTAGAGCTTTCCAGGGTACCCTTTCT
GACTGTTTAGCATGTTTGCCAGTCTGACTAATTTTGAAGTTGCTTAAATATCTGTCATTTCCACTGTAT
CATAATCTCCTCATTCATCTTCAATCTCCAATGCCTTGAACTCAGTAAATGTTAGTTGAACAAAAGTAA
ATTGAACCCAGAATTTCTGATCATAATCTGGAGCACTTTAAAATTGTCAGCTTACTGGGAAACGGGATA
ACATGTGATTTGTCTTTGATTTTTTTTTCTCATATGCTTTTTCCACCTATAGATGCTACACGAATGTT
TTTAAAATCTGATATAAAAATTAAAATTAAAAAATTAAAAAAAGAAAATTTGATACAATGCTACATTTA
GAGTGTTGTGATTAGATTCCTTAAGTGTATCATGGTGATCTCTACATCACGTGGTGATCAAATTGCTTT
GGGTTTTAACACATAACTGACAAAGGCTTGGGGACATGTAAGATCCCAAATACATTTTTATTGATTTTT
TTTTCTTGTTTGTCCTCTTTTAAATAACTTTTTTTTGTTATAAGAATAATTCATGTTCAGTGGAGAAAC
CATAGAAAATAGTGACAAGTGAAGGAATAAATTTAAAATGACCCATAATTGTACCATACATTCTGATTT
TTTAAACGCTGAACAAATTAGCCTTGGGTAAGTACCAGGAATAGAGTGCAGCATTGAAAGTTAAAGTTT
GGGGAAGGATAGCTGACTTAAGAAATTATCTAGTTAGACATTTTTTGGATGGGGTACACTGTTGRGAAG

GGCGATCGGTGCGGGCTTATTCGSTATAACGCCAGCTGGCGAAAGGGGGATGTGCTGCAAGGCGATTAA
GTTGGGTAACGCCAGGGTTTTCCCAGTCAACGACGTTGTAAAACGACGGCCAGTGAATTGTAATACGAC
TCACTATAGGGCGAAATGGGCCCGACGTCGCATGCTCCCGGCCGCCATGACCGCGGGATTATGTCTCTA
CTGTATTTAGAATCTGATAAAGCCCCTATTAGAATTCATCTCTTTAAGAATAAAAGAAGCTGAGGAACT
AAAGAGAGGGTTGGAATAATCCACTAATTATATCCGTTAAGCTTCAGTTACGCTAATAAGGAATATCAC
ATGACTGTGGTGTGTGCTTGTTCTGAACAGTAAAGTACATGAGGAAAGATAAGATTCAGGGCTGAAATG
TCCTTCAGCATATGTAGGTAGTGGTGATGAAAGTCATTAAAAGAAAAATTGATTGAGGTATTTTAGTAA
ACAAAAGAACTCACCACTTACCCATCAGGAAGTGTATTGTTAATGCAGTGCTGTTCAGCCTTCTGGAAG
AAAAGGTTTCTTCATGCTTCTCTCTTTAGCCTAATTCTTATCCTGTCACTTTTCAGGCAAAATTAAAAA
AAAAAAAAGATTGAAAACGATGCTCCTATTTTATTTGCTTCAAAAGAAACAGGCTGTTGCATTGTGCTT
GGAACAGTTTACTCTTGGCCTTGATGTAAGTGTGAAAGGAAGCCCATGTAATTGACTAGGCAGTATCTG
AAGAAGCAGGAAATACAGTGTTAAGAAAATGAACAGGCATGAAAACCATGGCTATTTGATAAAAGTAAA
TAATTTCTGCAGTTCACATGTTCTCAGCATATTTTCTTTGATACTGACTTGCTTAATATGACAATAGCA
GAACCATGGTAGCTTGTAGGCATTACTTTTCTTTTAATTTCTTTTACATTTTGAATTTACCAGCACTCA
CATTTGTATTACTTTTGGGTTATACTGAGGATCTATAACTTATAGATCAAATACCTGACATATATATGC
ATTCTCTGAAGTCTTAGGGCAGAACTAGAACATTCTTGTGAACATCAGTATAAGATATTAAAATGGAAG
TTTTGCCTAAGACTGAAGACAATAAAAATATCATAGTCTGAAATGAATGCCAGCACACCATACAGGATT
TAAATATCTATACATATATATGTGTGTGTATTATATATATTTAATATATATCTGTGTGGGATAGGAAGA
GGTAGGGGGAAATCAGTTTTACAATTATTAAGTATTTCACCCTTGACAAGAGTATATATATTGGAAATC
AGTTGGAGAGTATTTTCAAAGATAAATGTTAGTGTGCTATGAATGAATCCACCCCTACCACCACTGAGG
CAGGGTAGGAGAGGCCTGTGCTCCTCAAGCATAGTTGGAAAAGGACCTCAACAAGACCACTTCAAGAGT
CTAATGTGTGGAGACTGTTGCTTAGGGAGACCTTATGGTCTAGCTTCTGACTCACAGCTAAGTCAGGGA
GACAGGTTGGCTGCTCTGATCGTGGAGTCCAAAAGATGGCCTGCACTGAAAAGCCTCATGAGTGTTGAC
TTAGGGCTAGTCTAAGAGGTCCCTGGAAGAAGAAACACTCAGTAGGAGAGAAGCTGGAGGTACCTTCAG
TGCTGAATTGGAACCTAGATTCATTCCCCCGTGGAGCAAATTACATAGGAAAGATGCCCAGTGATGGAG
AGTGGGGGTGTCTCTAACAATTACCCACCCACCTGCCCCCACCCCTAAGAAAAAGAAAATCACATACAA
CCAGTCAGCTGTAAACATATGCCGAGCCTAGTAAACTCAGATACTAAGTTACCAGGGTACCTGGCAAGT
AAGAACATTCCTGATTCCCTTCCCTCCTCTTCCTCTTTGCCCTCCAACCTTAGTGGCTAGCAAGATGGG
GAGAGGAGGAGAAGCTGTAAGTGGGGAAAAAAGAGCAGCTTTCTCTCCTTTTCAGCTGCTGGATTCTCC
CTCATCATAGGCCTGAGCTGGGGAATCAGGAAGAAGGATTCTTTTTAAAACTGAAGTAACGTTATCATT
TAATTTTAAAACATTTTAAATTTTGACAATGTTGAGATTAGATATACTAATTATTAAACTAAGATTATG
TTTTGCAGCTTGAAGTGATAAGAAAAACCTCTTATCTAAGAGCATCCAGGAAAGTCGGGGGTTTCCTGA

ACATCCTTTTAAATCCTTTGGAAGTCAGCTTTCAGAGAGGATTTAAAGTGTAGACTGGGCCTTCAGAAA
CTTGGTTAATGTAGGGGTTTCCTATGCAGACTTGGGGACTATACCTTGTGTGGAAGAGAGAAAATAAGA
TTATCTTACATTTTTCCCATTCCTTTTTCAAAAAGAAAGCTCAGCTAGCATGAAAGTTAAATTCAAAAC
GTAATGGGTATTATTTGCATATTCAAATCTAGTGCATATCATGTAAGTACTGAATTATGGTATTCATTA
TTTCAAATGACAAGCTGGATTTTTTTTTCTTTCGAATTTCACAAATTAATTTTCCTTGGAACCTTTTGG
TTTGGGCTTTAAGAGTTTAGGCTTTCATCACAAAGAGAGGACAGCCTTGAAGATTAAAGTGTGTGGCTC
TTCTCAAGATGTTCTTAGTCCAGCAAAGGATTCTATGCATATTTGGGCTTCCTTCTGTCTCATAACCTG
TATTTCTTGATATTCTATTTATATTCTGTAAGATTTTTTTTTAAAGGAAAAATTCTTCCATGGTTGAA
GGACATGTCAAAAATAGAGGATACAGTTTTATATCAAAGGAAGTTTCATGATATGACTGTAGAAGCTCA
TTTGACTTAAGACACATCATTTCCTCATGGAAGTGTTAAACAGATCTGTACAATAAGGTTGGCAATCTT
TGTGTAAAACAGTTTTTTTCTCCTGCTCTAAAGAAAGTGTATATTTCAAAATGTGAATGTCAGCAGTC
AGAAAATAGTATTTTTTTAACTTCGTTTTCAAAGTCCTCAAAAACCTGTACCTAATCATGAATTTTTTT
TCCCACAGATTGTTTCTTCTTCTCCCTCCCAGAAACTTTGAAGTTTTTCTACATGACACCAGGACCTAT
GTCTTTTTTTAATTACACAGAAATGAAAGAAAAAAAGTGTGTTGTATCGTTAACCAAATATATGAAATC
TTTAAGCTGTATTTTTATTTTTAACTTTGTTTTGCAAAGAGGCCATTCCCTTTGGTTAAATAATTTGTT
ATTCACAGTTTCCTTGTCCTCATATTATCAAGGGGAAAATTGTAGAAATTTTAAAGGAAGCTCTAGGCA
ATGTTTTCATCCCTGAATCTTTGGAGAGTTATAAAAACAAACAGATTACTGAACCTGTAAGAGAACCAA
TCGTGAAGTCATTACATCTAAGCATAAGCAAAATCTCCTCTTGGATCATTAAGTTATAGAAGAAAAGAA
AGCCTGCACTTTGAAATTTAAATAAAGCTTGGTAACTTGTAAGTCAAACACGTAAAATTTTACAATTCA
GGAATATCGATAGCAGTTGAGTTTAATAGACTTCTCACATTCCAAATTTAAAGCTTCCTTCTCTGTGCT
AATAGAGATACAATAGCAGTAGGCGTTTAAGAAGAATGAATCAACAATTTAAAACTATAATGTGTTTTT
TATTCATCTCCCTTATTCACATATATTTGTTTTGTTTTGAGAAGGAGTTCTGCTCTGTCGCCCAGGCAG
GAGTGCTGTGGCACGATCTCAGCTCACCGCAACCTCTGCCTCCCGGGTTCAAGCGATTCTCTTGCCTCA
GCCTCCTGAGTAGCTGGGAGCCTGCCACCATGCCCGGCTAATTTTTGATTTTTAGTAGAGATGGAGTTT
CACCATGTTGGCCAGGCTGGTCTCGAACTCCTGACCTCAGGTGATCTGCCCACCTCGGCCTCCCAAAGT
GCTGGGATTACAGGCGTGAGCCATCACTTCTGGCCCTTATTCGCATACAATTTAAAAATCATCACAGAA
GGTTTGAAAGAAGGAAGGGGCAGAAAATTACCTACTTTTCCTCTCCCCAGCGATCTCCTTCAAATCTGT
GCCTTTTCCTCAGGCCCAGGCCTCAATTTACTGAGCAGTCACACCTCACAGAGGGAGGTCTGGGCAATC
CACTCTTGGTCACAGGAAAGCCATTGACCCTCCCACTTCCTCTCCTCCACCTTGTTCTCAACTCTTGAC
TTTGGGCTTTGTTTCTGTTCAAGTCCTAGGAACTGGTTTCTTTTATCAGGTTAAGTGATTAGTTCTCTT
TCCCTCTAGTTGCTCTCACTCCCTGACTCTTGCCTTCTGTAACAACTGGAGACAACTCTTTCAAAACCA
GCTCCAAGCCCCAGACTTCTCTCTGGGCTTTAGTTCGTAAGGCAGGTGCCCTACTGAGTGAGCCTAGAT

CAGACAGAAACATAGCTGTTGGCAATGATTTAGGTGAATTTCCTTCCATTGTTTTTCTAATACCTTCTT
TTTTTTGTAAATATAACCATGCACATACACACATATTTGAATATCCTGCCTTTTTATTTAAAATGACAA
TAGGTCCGGGAGTGGTGGCTCATGCCTGTAATCCCAGCACTTTGGGAGGCCGAGGTGGGCAATCACCTG
AGGTCAGGAGTTCGAGACCAGCCTGGCCAACATGGTGAAACTCCATCTCTACTAAAAATCAAAAATTAG
CCGGGCATGGTGGCAGGCTCCCAGCTACTCAGGAGGCTGAGATGTGAAAATCGCTTGAACCCGGGAGGT
AGAGGTTGCAGTGAGCTGAGATCTTGCCATTGCACTCCAACCTGGGCAATAAGAGCGAAACTCCATCTC
ATGGAAAAAAAAAAAAAAAAAGACAGGATAAACATTCTAGATAGTCTCTATAATGGTCATGATTAAGACA
ATAAAATAGTCTGAAATTGTCAATATATATTAATAATAATTTATTTGGCCATTCTGCCAAGTAGCAGAC
ACCTGTCATTCTGCCCACTCAGCACCTCTCTTTCTTTTAGGGAAATGCTACCCACTCTTTGCATGGGTT
CTGGATGGAACTGTTGATCACAGTGTTTTCACTCCCCATTTTGCCTCACCAGAGGTAGACAGAAGACCC
AAGCCAGGCCAGTTACACACAATCTTCAGATAATTACCGTATTGATCACAGTATCACCCCACTCAAGGC
TTGGTTGGAGATGAGCAGAAGAGACTAAAGCTGGGTCATTTTAATTAACACCTGTACCCCAAAGAAAGA
CTGTCAATGAGGCTTTTATACCGACACTCCTGGTTTCCATTCTTCCTGATGCCATTCATTTGACGAACT
ACCCAATCTTTCCAACAGTGTCTTTGGAAGAAAGATAGTCAGAAAAGAAGATAGAGTTGTTTTCTGTTC
TTTGCAACCAAGGAACTCTAAATGATAGACTTGTTGCTAGGCACTTTGGTTATTTTTATTATCTTGAAT
ACTTCTGTGATATACTTCTTTGTGCATGCCTGTTTGTACGGATGTAGCTTTTTATATATTTTATATAAT
TTCTCAGAAGTGGAATTACTTAGTCAAAAGGTATGAACATTTTTCTGATTCTTAATATAAATTGTGCAA
ATGCTTTTTAAGAGGATTATACCAGTTTACATTTTGTGTTATATATAACAGAAAGTACTACTGAAAAAA
TATTACAAAAATTTGTCTCTCTGTTCAGGAGGACCTTGTAATAGATGATAAAGTACTTGAAATAGGAAC
ATAGAGCATTTTCAGTTTAAAATAATTTCATTGGGTTATTTACGGAATCCTTAGAATTATGGCCAGACA
TTTATAGATGATCTGTACCAAACCTAGGTTGGTTACATAAATTGCTTATTCAACTGGCTTAAATCTATA
ATAGAAAGATGACACTTACTGAATGTTTAATATACACTTTGTCAGGGGCTTTGTATTATTCTATGACAT
CTTCAAAATGACCCTACTTTCCTATTTTATAAGTAAGGACAGGAAGGCTTCAAGAACATGACTAATTTT
CCCAAGGGCTGTACCAAAGCCAGAACCCAAATCTATAAGGCTTTTAAACCTGCATTCTAAAACTGCATC
TCGGCCATCTTATTCCTACAGAACTTAAGGTTAGAAAGCCAGATTGGAGTCCCAATTTCACCACTTAGT
AACCAGACAAACTTGAGGAATTCACTCAACGTCTTTGAATCTCCATTTCCTAATCTTTAAAACTAAAAC
AATAATACTGGCCCTACCTATTTCCTAAAATTTCGTGAGGCACATAAAAATAGTGTGGAAAATTGCTGT
ACAAATGTCAATTGTTACCGTGATTACTTAAATCCCTGAACACCATGGATGAATGTCTCTGACTGCTAT
TAAAGGTCATAAAAAATATTGGGGCCAGGTACATTGGCTTATCCCTATAATGCCAGCACTTTGGGAGCC
TGAGACAGGAGGATCACTCGAGGCCACGAGTTCAAGACCGGCCTGGGCAACATAGTGAGACCCCTTCTC
TACAAAAAAAAAAGCAGCCACGTGTAGTGGCACACACCTGTAGTCCCACATACTCAGGAGGGTGAGTTG
GGAGGATAACTTTAGTCCAGGAGTTTCAAGGTGCAGTGAGCTGTGATTGCACCACTGTACTCTAACCTG

GACAGCAGAGTGAGACCCTGTCTCTAAAAAAAAAGAAAAAAAAATAATAATAATAAAGAATAATGGGGC
CTTGGGATACCCACTCCTCTCTTTCTGCTCTGAGTTGTGAAGCAGTTGAGTTACATATGCATGTCCAAT
GGATGAGGTTGAAAATATCAACTGGATTGGAATGTGGCTTACTTGCGTGGCCACAATGAGCTTCGTAAC
ACTTCCTGACAGGGTGAGAAGACAAACTTCCTCACCCAGTCACTGGCAGAGCTGGACACTCTGTGTCTC
TCCCACAGAACAACCTCTTACTGCATGGAGGTGGATGAAAAAGTCAACCGAGAACAGGCTACTCCAAAA
AGCAGAGCACCAAAGGCACCAGCTGGTCAGGTCCCCCTTCCTAAGTAAACAATCACGTAATTCATTCGG
GACAAAGCCAGAGAGGTGGTGTGGAGAAAGAGAGGGCAGTTTCCTCCCAAGTTTTTCCTGGAATTCTTT
ATGGGAATATGAGGTTTAGGGGAATAAGACTTCCCTTTAACAGTGAAGAATCCCCAGCTCTATTGGTAA
TAGGAAATCGCTTACAAGGATCATGGGGAGTATTTCCTCAGCTCGTTCTGCCTCCTACTTGGCTGAGTG
GAATGGAACCATCTGTGGCTGCTGCATATGATATTGTCAACTTTGTCATTCCACACCCACTCCTTGACG
CCCTACCATGTGGTCATAAGACTCCCTTTAAAGTGTTCCTTTAAAAAACAAAATGTGTTTTGTTTCTAT
AAAATACAGCTCAATGTCAGAACCCTTGTCTTGTTTGCTCTCTGATGTAACCCTTTCACAATGTTTGGG
CAGCTTATTCTCTCTATTTCCCTGTAGGGTCCCATCCAGGCCAAAGTGAGTGCCAGCCTCATTTGGGCA
GCAGATGCCCTGTGGAAGGGCAGGAGGAGACGAGAGCTAATTGTAACTTTGTGATTAGCTGTCATGGAT
GCCTGGTCCTGTCAATAGCGCTCAATAAAGCCAGAAGGCCAAGCGTTCGCTTCTGCATACTGATTGCTG
AGTCAGATTTCTCAGTGCAGAAGGGCTTTCTAGGCAGTCAATTTAGAATATTAGTCTTGGTTCTTAAG
TGGTTAAAATCCCTAGCTGGTCTTTAATCTGAGCCTGGAGAATTTAGTTATGGCTGACATTCTGCTGTG
ATATTTTTGCCCTCAATATATATGTCTTTCCTCCATCTCTTAGATCCCTGAATCATAGAGATATATATG
TTCCCGGCGCCATGGGCGCGGGATTTCTCTAAGAGTGATAAGTACACATTGTGTCAGGTTGAGGGGACA
GGAGAACTTTCAAAAGCCTTTCTTGCCCCTTTTTCCTTCTCACTGCCTCCCACTAAGTCCAGCCACTTA
TTATTCAGCTGACACTATCATCATGACCATGAGGTCTTTTGGGGCTACCCTGGTTCGGATCCTTCTGGA
GGTTTGTTGCTTAACTCTGTCTTCAGTCCTATGAGCTGCTTTTTCAATAAGTTTCTATTTTGGCTAAAG
TTGGCCAGAATCTCCTTGTAACCAAAGAACAAATAAAATACCAGCTTGCAATGTTCTATGTTGCTTCCA
CCAAACTTATGCAGCACTTCCTATCTAATCCACCTACTAGTCTTTTTTTTTTTATTTTTTTGAGACG
GAGTCTCGCTCTGTTGCTCAGGATGGAGTGCAATGGTGCAATCTCGGCTCACTGCAACCTCTGCCTCCC
GGGTTCAAGCAATTCCCCGGCCTCAGCCTCCTGAGTAGCTGGGACTACAGGTGCATGCCACCACGTCCG
GCTAATTTTTGTATTTTAGGAGAGAGAGGGTTTCACCATGTTGCCCAGGCTGGTCACGAACTCCTGAGC
TCAGGCAATCCGCCCTCCTCGGGCTCCCAAAGTGCTGGGATTACAGGAGTGAGCCACCTCACCTGGCCC
CGACCTACTAGTCTTTAGTGTTTGCTTCCTTCTATTGGGTAATTGTCTGTTTATATGCATGTCTTGTTT
CCTCAAATAAAATGTGGTCTTCTCAAGGGTATTGGCCCATGTTCTATCCATCTGTAGATATCACAGCAC
CTAGCAGTGTCTTTCACAGAGGAAGTACACAACTGGCATTATTGATTCATTGCTCCATTTTTTCCTTCT
TTATCCCCAGCATTTCTCAATAATTTCAAACATCTCCATTGGAGTACCGGAGAAAGCAGGTAGCTTTAC

TTGCAGCTATGTTTCTATCCCCATAGTAACTAAAAGAGGACCCAGAGAAACATGTTTAAATGCTGTCCT
GTTATCAGGACCTCAGCCTTCTGATGCTCCGTGGCTTGGGGGTTATTGCTTGATCATCTCCTCCCCAAC
CTACACTGTGTACCTATGCTAGTCTCTTCATGAGGACTAAGCCCCATAGTAAAAGGGCTAGATAAATAG
AAAATCATTTTATGTAATTATAAGAATGAGAATACTGAGTATTCTGGTGTTTGTTTAGGATAAGCACAT
CTTTATTTGTATGAGAAAAAGAAAAAGAGAGTGAAAAATATATTAACGTGCATATTGTTCAGAACCCTT
GGATTGCAAGTGACAGAAACTCAATTCAAACCAACGTAAGTCAAAAGGAAAATATATTGGCTCATGTAA
CCTTCTCACAGAGAGGGCAGGATGGAAGGGGCTTTGGGAACAAGAGAATTGTTCTCAAATTCTAGGAAT
ACTAGGATTAGTCCAGGATGGGTCACCTTCCTGTCCCTGAGGTGGTGGTAGCGATGGTAGAGTCTTATG
GGAGGAAAGAGTGCATGTTAGGATGAAGGTAGGGCTAAGCAAACAAGGGCAAGGGCCACTATATCATGC
TAAAAATGGTTTTTTTTGATGTCTTCCTTAATTTCACAAATGCTTCCAACAAAGTAGCACACAGGAAAA
AGAACATAGGGACTCTACTGGTGGGTGCTTTTATCTTAAGCCTTGTACTTGCTTTTCACAGCTTACTCA
CTGCTTGTACCTGAGGCCATATGCCCTGTAAAAGCTTCTGCAGGGTTTCTACTAAGCTGGGTTCCTTAT
ATGGCTCTCTCCCATTTCTGTTGCCTCACTCTAGTGATCTTTCTCTTTTCCTCACCTCTGGGACTGGTG
GCTGTTTGTATGGACTGCCTTAGCTTTGCTTTGGGTTTTTCCTGGGGACAATGTCTTCAGATTATCCT
AGACCAAATAAACTACAGCCACTGGGCCAGGCTCTTCCTCCTCCAACTGGACCATGTTCCCAGGGCTCT
TCACCTTAGTTTAGGTCAAGCATTCTTGGCAAAAGAAAGGCCTAGTTAACAATAGACATTCTAGCAATT
GATTCTTTTTGACATGTTGTAAGATCTATTCACATTTTGTAATTAAAGCATTCCCCTATGGAAACCAAC
ACGAACTAAGCTGCTCCTGGAATGCAGGGTGGCCTCCTCAATACAGGATGTTCTAGAGAGCTGTATTTT
GGGCACTTAACTATTCTCCACTACTTAGGGCACAGCACTGAAATTAACACCACTAAGTTTGTCATGTCC
ATGTAGTTAGTCTCAGGCAGTGCAGCCTCAGGAGTGGAACTGACCTCTTATGTGTGTCCAGCCTTTCTT
CCTTCAGAAGTCAGCTGTGTTTTCTGCTGACTCTCCATAGGAACATCAGTCCTGAATCCTCAGACCACC
ATCTGGAGTAGTAAGTGCTCCTGACAGTCCTAGAAGTTGTCTACCGCTGGATCTCCAAAGCGTGTGACA
CACCGTGAGAGAGAAATGAGAAAGCTGGGCTCTTCAGGTAAATCTTGCTTTTTCACAAGCCCCCTAATT
TTACTGCATAATTATTTTGAATTCACTGATAATTTCTACAATTTTCCCATAAGTCATCTACACACAATA
CCCTCTCATGCAACACTTGGCTTTGCTAATACATATCTATTATGAGAGCTGTGCTTCTTAAGCGTAAAT
GTTTTATATGCACTAAGGCTCTTGGCTTACATATAAAAGGGGTATTGAGCAATGTGATACAGAAGTCTT
TTCTCCACAGGTCTCATATGTAAAGAATTCATTAGATTGGCTGAAATAGACTGATCTGTCCATTTCTCT
GCTCACTTATCATAAGGAAGTCATTAGCTAAGGAACAAAAACTACAATCTATGTAATTAGAAGAACAAG
CTGGTTTTGCTCAATATAAAAATAAGAAAAAGAAACCATGTGAAAGTCAAAATATTTGTTTAATCAGGT
CATTGAGAATCTATTAAAAAGTATTTGAATTCTTTATGATGAGAACTATCTTGACTCAAGTGGACAGTG
GTGAGCTTTTTGGCCTGTGGTCCCTACGTAGAAAGGAGGCTTTGTCATAAAGTCTTATATGGTACAGGT
GCCAAGTTAAGTGCCCAAGCTTGCTCTTAAAAGCATACTGGATTTTG

FIG. 16A(37)

BAC-F2 sequence contigs

Contig 1 (5596 bp)

TATGGACATATTGTCGTTAGAACGCGGCTACAATTAATACATAACCTTATGTATCATACACATACGATT
TAGGTGACACTATAGAACCAGATCTGATATCGAATGAATTCTTTCTTGCAAGAGATCCAAGAACTCTCT
CTTGGGGTCTGGATCAGGACCTCTTTCCAGTAACAATAGTAGTAAGGGGTCAGGGAGACTGGACAAAGG
AGTTTAAGAAGCCTTAGATAAAGGGTCCTCATCATTGTCATAACATAAAATCATGGACTCCTAGAATTT
TATAGCTGATAGGATTAGAAATTTCAAAATTCAATTTCATTAATTTTCATCTGCGAAAACAGATGGCCA
GAGAGGCCAAACAATTTGTTAAGGAGCACTGAGGGCAGACCACACTGGAACGCAAACCTCTTAGCAGAG
TATACAAGGCCTTTGATCTCCTCAGTCAGAATGAACTAGAGCTTTCCAGGGTACCCTTTCTGACTGTTT
AGCATGTTTGCCAGTCTGACTAATTTTGAAGTTGCTTAAATATCTGTCATTTCCACTGTATCATAATCT
CCTCATTCATCTTCAATCTCCAATGCCTTGAACTCAGTAAATGTTARTTGAACAAAAGTAAATTGAACC
CAGAATTTCTGATCATAATCTGGAGCACTTTAAAATTGTCAGCTTACTGGGAAACGGGATAACATGTGA
TTTGTCTTTGATTTTTTTTTCTCATATGCTTTTTCCACCTATAGATGCTACACGAATGTTTTTAAAAT
CTGATATAAAAATTAAAATTAAAAAATTAAAAAAAGAAAATTTGATACAATGCTACATTTAGAGTGTTG
TGATTAGATTCCTTAAGTGTATCATGGTGATCTCTACATCACGTGGTGATCAAATTGCTTTGGGTTTTA
ACACATAACTGACAAAGGCTTGGGGACATGTAAGATCCCAAATACATTTTTATTGATTTTTTTTTCTKG
TTTGTCCTCTTTTAAATAACTTTTTTTGTTATAAGAATAATTCATGTTCAGTGGAGAAACCATAGAAA
ATAGTGACAAGTGAAGGAATAAATTTAAAATGACCCATAATTGTACCATACATTCTGATTTTTTAAACG
CTGAACAAATTAGCCTTGGGTAAGTACCAGGAATAGAGTGCAGCATTGAAAGTTAAAGTTTGGGGAAGG
ATAGCTGACTTAAGAAATTATCTAGTTAGACATTTTTTGGATGGGGTAATTTTGCAGATGACATTAGTG
AGAGAAAGGACTTGCCACTCTCACACAGCTAGTAGGGGTGTGGGAGGATATTGGAACCAAGTTTCAAGT
CTTCAGTGAAGAATCAAGGGAGAAGTTCTAAAACCTAACAATATCCCTCTGGATGGACATTTATTTTAT
TACTACAATAAGCCACACGGTGAGTCATAAGGAGCATTTCATTCTTCTAATATGTCTCTACTGTATTTA
GAATCTGATAAAGCCCCTATTAGAATTCATCTCTTTAAGAATAAAAGAAGCTGAGGAACTAAAGAGAGG
GTTGGAATAATCCACTAATTATATCCGTTAAGCTTCAGTTACGCTAATAAGGAATATCACATGACTGTG
GTGTGTGCTTGTTCTGAACAGTAAAGTACATGAGGAAAGATAAGATTCAGGGCTGAAATGTCCTTCAGC
ATATGTAGGTAGTGGTGATGAAAGTCATTAAAAGAAAAATTGATTGAGGTATTTTAGTAAACAAAAGAA
CTCACCACTTACCCATCAGGAAGTGTATTGTTAATGCAGTGCTGTTCAGCCTTCTGGAAGAAAAGGTTT

CTTCATGCTTCTCTCTTTAGCCTAATTCTTATCCTGTCACTTTTCAGGCAAAATTAAAAAAAAAAAAAG
ATTGAAAACGATGCTCCTATTTTATTTGCTTCAAAAGAAACAGGCTGTTGCATTGTGCTTGGAACAGTT
TACTCTTGGCCTTGATGTAAGTGTGAAAGGAAGCCCATGTAATTGACTAGGCAGTATCTGAAGAAGCAG
GAAATACAGTGTTAAGAAAATGAACAGGCATGAAAACCATGGCTATTTGATAAAAGTAAATAATTTCTG
CAGTTCACATGTTCTCAGCATATTTTCTTTGATACTGACTTGCTTAATATGACAATAGCAGAACCATGG
TAGCTTGTAGGCATTACTTTTCTTTTAATTTCTTTTACATTTTGAATTTACCAGCACTCACATTTGTAT
TACTTTTGGGTTATACTGAGGATCTATAACTTATAGATCAAATACCTGACATATATATGCATTCTCTGA
AGTCTTAGGGCAGAACTAGAACATTCTTGTGAACATCAGTATAAGATATTAAAATGGAAGTTTTGCCTA
AGACTGAAGACAATAAAAATATCATAGTCTGAAATGAATGCCAGCACACCATACAGGATTTAAATATCT
ATACATATATATGTGTGTGTATTATATATATTTAATATATATCTGTGTGGGATAGGAAGAGGTAGGGGG
AAATCAGTTTTACAATTATTAAGTATTTCACCCTTGACAAGAGTATATATATTGGAAATCAGTTGGAGA
GTATTTTCAAAGATAAATGTTAGTGTGCTATGAATGAATCCACCCCTACCACCACTGAGGCAGGGTAGG
AGAGGCCTGTGCTCCTCAAGCATAGTTGGAAAAGGACCTCAACAAGACCACTTCAAGAGTCTAATGTGT
GGAGACTGTTGCTTAGGGAGACCTTATGGTCTAGCTTCTGACTCACAGCTAAGTCAGGGAGACAGGTTG
GCTGCTCTGATCGTGGAGTCCAAAAGATGGCCTGCACTGAAAAGCCTCATGAGTGTTGACTTAGGGCTA
GTCTAAGAGGTCCCTGGAAGAAGAAACACTCAGTAGGAGAGAAGCTGGAGGTACCTTCAGTGCTGAATT
GGAACCTAGATTCATTCCCCCGTGGAGCAAATTACATAGGAAAGATGCCCAGTGATGGAGAGTGGGGGT
GTCTCTAACAATTACCCACCCACCTGCCCCCACCCCTAAGAAAAAGAAAATCACATACAACCAGTCAGC
TGTAAACATATGCCGAGCCTAGTAAACTCAGATACTAAGTTACCAGGGTACCTGGCAAGTAAGAACATT
CCTGATTCCCTTCCCTCCTCTTCCTCTTTGCCCTCCAACCTTAGTGGCTAGCAAGATGGGGAGAGGAGG
AGAAGCTGTAAGTGGGGAAAAAAGAGCAGCTTTCTCTCCTTTTCAGCTGCTGGATTCTCCCTCATCATA
GGCCTGAGCTGGGGAATCAGGAAGAAGGATTCTTTTTAAAACTGAAGTAACGTTATCATTTAATTTTAA
AACATTTTAAATTTTGACAATGTTGAGATTAGATATACTAATTATTAAACTAAGATTATGTTTTGCAGC
TTGAAGTGATAAGAAAAACCTCTTATCTAAGAGCATCCAGGAAAGTCGGGGGTTTCCTGAACATCCTTT
TAAATCCTTTGGAAGTCAGCTTTCAGAGAGGATTTAAAGTGTAGACTGGGCCTTCAGAAACTTGGTTAA
TGTAGGGGTTTCCTATGCAGACTTGGGGACTATACCTTGTGTGGAAGAGAGAAAATAAGATTATCTTAC
ATTTTTCCCATTCCTTTTTCAAAAAGAAAGCTCAGCTAGCATGAAAGTTAAATTCAAAACGTAATGGGT
ATTATTTGCATATTCAAATCTAGTGCATATCATGTAAGTACTGAATTATGGTATTCATTATTTCAAATG
ACAAGCTGGATTTTTTTTCTTTCGAATTTCACAAATTAATTTTCCTTGGAACCTTTTGGTTTGGGCTT
TAAGAGTTTAGGCTTTCATCACAAAGAGAGGACAGCCTTGAAGATTAAAGTGTGTGGCTCTTCTCAAGA
TGTTCTTAGTCCAGCAAAGGATTCTATGCATATTTGGGCTTCCTTCTGTCTCATAACCTGTATTTCTTG

ATATTCTATTTATATTCTGTAAGATTTTTTTTTAAAGGAAAAATTCTTCCATGGTTGAAGGACATGTC
AAAAATAGAGGATACAGTTTTATATCAAAGGAAGTTTCATGATATGACTGTAGAAGCTCATTTGACTTA
AGACACATCATTTCCTCATGGAAGTGTTAAACAGATCTGTACAATAAGGTTGGCAATCTTTGTGTAAAA
CAGTTTTTTTTCTCCTGCTCTAAAGAAAGTGTATATTTCAAAATGTGAATGTCAGCAGTCAGAAAATAG
TATTTTTTTAACTTCGTTTCAAAGTCCTCAAAAACCTGTACCTAATCATGAATTTTTTTCCCACAGA
TTGTTTCTTCTTCTCCCTCCCAGAAACTTTGAAGTTTTCTACATGACACCAGGACCTATGTCTTTTTT
TAATTACACAGAAATGAAAGAAAAAAAGTGTGTTGTATCGTTAACCAAATATATGAAATCTTTAAGCTG
TATTTTTATTTTTAACTTTGTTTTGCAAAGAGGCCATTCCCTTTGGTTAAATAATTTGTTATTCACAGT
TTCCTTGTCCTCATATTATCAAGGGGAAAATTGTAGAAATTTTAAAGGAAGCTCTAGGCAATGTTTTCA
TCCCTGAATCTTTGGAGAGTTATAAAAACAAACAGATTACTGAACCTGTAAGAGAACCAATCGTGAAGT
CATTACATCTAAGCATAAGCAAAATCTCCTCTTGGATCATTAAGTTATAGAAGAAAAGAAAGCCTGCAC
TTTGAAATTTAAATAAAGCTTGGTAACTTGTAAGTCAAACACGTAAAATTTTACAATTCAGGAATATCG
ATAGCAGTTGAGTTTAATAGACTTCTCACATTCCAAATTTAAAGCTTCCTTCTCTGTGCTAATAGAGAT
ACAATAGCAGTAGGCGTTTAAGAAGAATGAATCAACAATTTAAAACTATAATGTGTTTTTTATTCATCT
CCCTTATTCACATATATTTGTTTTGTTTTGAGAAGGAGTTCTGCTCTGTCGCCCAGGCAGGAGTGCTGT
GGCACGATCTCAGCTCACCGCAACCTCTGCCTCCCGGGTTCAAGCGATTCTCTTGCCTCAGCCTCCTGA
GTAGCTGCGATTACAGGCGTGCGCCAGCAACCCCGGCTAATTTTTGTATTTTTAGTAGAGACAGGGTTT
CACCACGTTGGCCAGGTTGGTCTCGAACCCCTGATCTCAAGTGATCAGCCCGCCTCGGCCTCCCAAAGT
GCTGGGATTACAGGCGTGAGCCATCACTTCTGGCCCTTATTCGCATACAATTTAAAAATCATCACAGAA
GGTTTGAAAGAAGGAAGGGGCAGAAAATTACCTACTTTTCCTCTCCCCAGCGATCTCCTTCAAATCTGT
GCCTTTTCCTCAGGCCCAGGCCTCAATTTACTGAGCAGTCACACCTCACAGAGGGAGGTCTGGGCAATC
CACTCTTGGTCACAGGAAAGCCATTGACCCTCCCACTTCCTCTCCTCCACCTTGTTCTCAACTCTTGAC
TTTGGGCTTTGTTTCTGTTCAAGTCCTAGGAACTGGTTTCTTTTATCAGGTTAAGTGATTAGTTCTCTT
TCCCTCTAGTTGCTCTCACTCCCTGACTCGGGGGATCCACTAGTTCTAGAGCGGCCGCCACCGCGTGGA
CTCACAG

Contig 2 (18457 bp)
GAGGGCGGGAACCCCCTTTCCAAAAAAAAAGAAACAAAGACAGGATAAACATTCTAGATAGTCTCTATA
ATGGTCATGATTAAGACAATAAAATAGTCTGAAATTGTCAATATATATTAATAATAATTTATTTGGCCA
TTCTGCCAAGTAGCAGACACCTGTCATTCTGCCCACTCAGCACCTCTCTTTCTTTTAGGGAAATGCTAC
CCACTCTTTGCATGGGTTCTGGATGGAACTGTTGATCACAGTGTTTTCACTCCCCATTTTGCCTCACCA

GAGGTAGACAGAAGACCCAAGCCAGGCCAGTTACACACAATCTTCAGATAATTACCGTATTGATCACAG
TATCACCCCACTCAAGGCTTGGTTGGAGATGAGCAGAAGAGACTAAAGCTGGGTCATTTAATTAACAC
CTGTACCCCAAAGAAAGACTGTCAATGAGGCTTTTATACCGACACTCCTGGTTTCCATTCTTCCTGATG
CCATTCATTTGACGAACTACCCAATCTTTCCAACAGTGTCTTTGGAAGAAAGATAGTCAGAAAAGAAGA
TAGAGTTGTTTTCTGTTCTTTGCAACCAAGGAACTCTAAATGATAGACTTGTTGCTAGGCACTTTGGTT
ATTTTTATTATCTTGAATACTTCTGTGATATACTTCTTTGTGCATGCCTGTTTGTACGGATGTAGCTTT
TTATATATTTTATATAATTTCTCAGAAGTGGAATTACTTAGTCAAAAGGTATGAACATTTTTCTGATTC
TTAATATAAATTGTGCAAATGCTTTTTAAGAGGATTATACCAGTTTACATTTTGTGTTATATATAACAG
AAAGTACTACTGAAAAAATATTACAAAAATTTGTCTCTCTGTTCAGGAGGACCTTGTAATAGATGATAA
AGTACTTGAAATAGGAACATAGAGCATTTTCAGTTTAAAATAATTTCATTGGGTTATTTACGGAATCCT
TAGAATTATGGCCAGACATTTATAGATGATCTGTACCAAACCTAGGTTGGTTACATAAATTGCTTATTC
AACTGGCTTAAATCTATAATAGAAAGATGACACTTACTGAATGTTTAATATACACTTTGTCAGGGGCTT
TGTATTATTCTATGACATCTTCAAAATGACCCTACTTTCCTATTTTATAAGTAAGGACAGGAAGGCTTC
AAGAACATGACTAATTTTCCCAAGGGCTGTACCAAAGCCAGAACCCAAATCTATAAGGCTTTTAAACCT
GCATTCTAAAACTGCATCTCGGCCATCTTATTCCTACAGAACTTAAGGTTAGAAAGCCAGATTGGAGTC
CCAATTTCACCACTTAGTAACCAGACAAACTTGAGGAATTCACTCAACGTCTTTGAATCTTCATTTTCT
AATCTTTAAAACTAAAACAATAATACTTGCTCTACCTATGTCCTAAGATTTCGTGAGGCACATAGAGAT
AGTGTGGAAGAGTGCTGTACAGATGTCAAGTGTTAGCGTGATTACTTAGATCCCTGAACACCATGGATG
AATGTCTCTGACTGCTATTAGAGGTCATAAAGAATATTGGGGCCAGGTACATTGGCTTATTCCTATAAT
GCCAGCACTTTGGGAGCCTGAGACAGGAGGATCACTCGAGGCCACGAGTTCAAGACCGGCCTGGGCAAC
ATAGTGAGACCCCTTCTCTACAAAAAAAAAAGCAGCCACGTGTAGTGGCACACACCTGTAGTCCCACAT
ACTCAGGAGGGTGAGTTGGGAGGATAACTTTAGTCCAGGAGTTTCAAGGTGCAGTGAGCTGTGATTGCA
CCACTGTACTCTAACCTGGACAGCAGAGTGAGACCCTGTCTCTAAAAAAAAAGAAAAAAAAATAATAAT
AATAAAGAATAATGGGGCCTTGGGATACCCACTCCTCTCTTTCTGCTCTGAGTTGTGAAGCAGTTGAGT
TACATATGCATGTCCAATGGATGAGGTTGAAAATATCAACTGGATTGGAATGTGGCTTACTTGCGTGGC
CACAATGAGCTTCGTAACACTTCCTGACAGGGTGAGAAGACAAACTTCCTCACCCAGTCACTGGCAGAG
CTGGACACTCTGTGTCTCTCCCACAGAACAACCTCTTACTGCATGGAGGTGGATGAAAAAGTCAACCGA
GAACAGGCTACTCCAAAAAGCAGAGCACCAAAGGCACCAGCTGGTCAGGTCCCCCTTCCTAAGTAAACA
ATCACGTAATTCATTCGGGACAAAGCCAGAGAGGTGGTGTGGAGAAAGAGAGGGCAGTTTCCTCCCAAG
TTTTTCCTGGAATTCTTTATGGGAATATGAGGTTTAGGGGAATAAGACTTCCCTTTAACAGTGAAGAAT
CCCCAGCTCTATTGGTAATAGGAAATCGCTTACAAGGATCATGGGGAGTATTTCCTCAGCTCGTTCTGC

CTCCTACTTGGCTGAGTGGAATGGAACCATCTGTGGCTGCTGCATATGATATTGTCAACTTTGTCATTC
CACACCCACTCCTTGACGCCCTACCATGTGGTCATAAGACTCCCTTTAAAGTGTTCCTTTAAAAAACAA
AATGTGTTTTGTTTCTATAAAATACAGCTCAATGTCAGAACCCTTGTCTTGTTTGCTCTCTGATGTAAC
CCTTTCACAATGTTTGGGCAGCTTATTCTCTCTATTTCCCTGTAGGGTCCCATCCAGGCCAAAGTGAGT
GCCAGCCTCATTTGGGCAGCAGATGCCCTGTGGAAGGGCAGGAGGAGACGAGAGCTAATTGTAACTTTG
TGATTAGCTGTCATGGATGCCTGGTCCTGTCAATAGCGCTCAATAAAGCCAGAAGGCCAAGCGTTCGCT
TCTGCATACTGATTGCTGAGTCAGATTTCTCAGTGCAGAAGGGCTTTCTAGGCAGTCAATTTTAGAATA
TTAGTCTTGGTTCTTAAGTGGTTAAAATCCCTAGCTGGTCTTTAATCTGAGCCTGGAGAATTTAGTTAT
GGCTGACATTCTGCTGTGATATTTTTGCCCTCAATATATATGTCTTTCCTCCATCTCTTAGATCCCTGA
ATCATAGAGATATATATGTTATATAATCAACTGTCTCCAGTCTCTAAGAGTGATAAGTACACATTGTGT
CAGGTTGAGGGGACAGGAGAACTTTCAAAAGCCTTTCTTGCCCCTTTTTCCTTCTCACTGCCTCCCACT
AAGTCCAGCCACTTATTATTCAGCTGACACTATCATCATGACCATGAGGTCTTTTGGGGCTACCCTGGT
TCGGATCCTTCTGGAGGTTTGTTGCTTAACTCTGTCTTCAGTCCTATGAGCTGCTTTTTCAATAAGTTT
CTATTTTGGCTAAAGTTGGCCAGAATCTCCTTGTAACCAAAGAACAAATAAAATACCAGCTTGCAATGT
TCTATGTTGCTTCCACCAAACTTATGCAGCACTTCCTATCTAATCCACCTACTAGTCTTTTTTTTTTTT
ATTTTTTTGAGACGGAGTCTCGCTCTGTTGCTCAGGATGGAGTGCAATGGTGCAATCTCGGCTCACTG
CAACCTCTGCCTCCCGGGTTCAAGCAATTCCCCGGCCTCAGCCTCCTGAGTAGCTGGGACTACAGGTGC
ATGCCACCACGTCCGGCTAATTTTTGTATTTTAGGAGAGAGAGGGTTTCACCATGTTGCCCAGGCTGGT
CACGAACTCCTGAGCTCAGGCAATCCGCCCTCCTCGGGCTCCCAAAGTGCTGGGATTACAGGAGTGAGC
CACCTCACCTGGCCCCGACCTACTAGTCTTTAGTGTTTGCTTCCTTCTATTGGGTAATTGTCTGTTTAT
ATGCATGTCTTGTTTCCTCAAATAAAATGTGGTCTTCTCAAGGGTATTGGCCCATGTTCTATCCATCTG
TAGATATCACAGCACCTAGCAGTGTCTTTCACAGAGGAAGTACACAACTGGCATTATTGATTCATTGCT
CCATTTTTTCCTTCTTTATCCCCAGCATTTCTCAATAATTTCAAACATCTCCATTGGAGTACCGGAGAA
AGCAGGTAGCTTTACTTGCAGCTATGTTTCTATCCCCATAGTAACTAAAAGAGGACCCAGAGAAACATG
TTTAAATGCTGTCCTGTTATCAGGACCTCAGCCTTCTGATGCTCCGTGGCTTGGGGGTTATTGCTTGAT
CATCTCCTCCCCAACCTACACTGTGTACCTATGCTAGTCTCTTCATGAGGACTAAGCCCCATAGTAAAA
GGGCTAGATAAATAGAAAATCATTTTATGTAATTATAAGAATGAGAATACTGAGTATTCTGGTGTTTGT
TTAGGATAAGCACATCTTTATTTGTATGAGAAAAAGAAAAAGAGAGTGAAAAATATATTAACGTGCATA
TTGTTCAGAACCCTTGGATTGCAAGTGACAGAAACTCAATTCAAACCAACGTAAGTCAAAAGGAAAATA
TATTGGCTCATGTAACCTTCTCACAGAGAGGGCAGGATGGAAGGGGCTTTGGGAACAAGAGAATTGTTC
TCAAATTCTAGGAATACTAGGATTAGTCCAGGATGGGTCACCTTCCTGTCCCTGAGGTGGTGGTAGCGA
TGGTAGAGTCTTATGGGAGGAAAGAGTGCATGTTAGGATGAAGGTAGGGCTAAGCAAACAAGGGCAAGG

GCCACTATATCATGCTAAAAATGGTTTTTTTGATGTCTTCCTTAATTTCACAAATGCTTCCAACAAAG
TAGCACACAGGAAAAAGAACATAGGGACTCTACTGGTGGGTGCTTTATCTTAAGCCTTGTACTTGCTT
TTCACAGCTTACTCACTGCTTGTACCTGAGGCCATATGCCCTGTAAAAGCTTCTGCAGGGTTTCTACTA
AGCTGGGTTCCTTATATGGCTCTCTCCCATTTCTGTTGCCTCACTCTAGTGATCTTTCTCTTTTCCTCA
CCTCTGGGACTGGTGGCTGTTTGTATGGACTGCCTTAGCTTTGCTTTGGGTTTTTTCCTGGGGACAATG
TCTTCAGATTATCCTAGACCAAATAAACTACAGCCACTGGGCCAGGCTCTTCCTCCTCCAACTGGAGCA
TGTTCCCAGGGCTCTTCACCTTAGTTTAGGTCAAGCATTCTTGGCAAAAGAAAGGCCTAGTTAACAATA
GACATTCTAGCAATTGATTCTTTTTGACATGTTGTAAGATCTATTCACATTTTGTAATTAAAGCATTCC
CCTATGGAAACCAACACGAACTAAGCTGCTCCTGGAATGCAGGGTGGCCTCCTCAATACAGGATGTTCT
AGAGAGCTGTATTTTGGGCACTTAACTATTCTCCACTACTTAGGGCACAGCACTGAAATTAACACCACT
AAGTTTGTCATGTCCATGTAGTTAGTCTCAGGCAGTGCAGCCTCAGGAGTGGAACTGACCTCTTATGTG
TGTCCAGCCTTTCTTCCTTCAGAAGTCAGCTGTGTTTTCTGCTGACTCTCCATAGGAACATCAGTCCTG
AATCCTCAGACCACCATCTGGAGTAGTAAGTGCTCCTGACAGTCCTAGAAGTTGTCTACCGCTGGATCT
CCAAAGCGTGTGACACACCGTGAGAGAGAAATGAGAAAGCTGGGCTCTTCAGGTAAATCTTGCTTTTTC
ACAAGCCCCCTAATTTTACTGCATAATTATTTTGAATTCACTGATAATTTCTACAATTTTCCCATAAGT
CATCTACACACAATACCCTCTCATGCAACACTTGGCTTTGCTAATACATATCTATTATGAGAGCTGTGC
TTCTTAAGCGTAAATGTTTTATATGCACTAAGGCTCTTGGCTTACATATAAAAGGGGTATTGAGCAATG
TGATACAGAAGTCTTTTCTCCACAGGTCTCATATGTAAAGAATTCATTAGATTGGCTGAAATAGACTGA
TCTGTCCATTTCTCTGCTCACTTATCATAAGGAAGTCATTAGCTAAGGAACAAAAACTACAATCTATGT
AATTAGAAGAACAAGCTGGTTTTGCTCAATATAAAAATAAGAAAAAGAAACCATGTGAAAGTCAAAATA
TTTGTTTAATCAGGTCATTGAGAATCTATTA:AAAAGTATTTGAATTCTTTATGATGAGAACTATCTTG
ACTCAAGTGGACAGTGGTGAGCTTTTTGGCCTGTGGTCCCTACGTAGAAAGGAGGCTTTGTCATAAAGT
CTTATATGGTACAGGTGCCAAGTTAAGTGCCCAAGCTTGMTCTTAAAAGCATACTGGATTTTGTTTTAG
ACTTTTAGTGAACTGAAGGGAATAAACAAATCCCTCTGGGAGAACTTCTCCTCCATCCTTGGTGAAGTC
ATTCTGCCAGAATTCTATCTGGTAGTTACCTTCTCCGATTCATTAAATGTTGTCCCATGGTCCGACATG
GGTAATTTTTCTCTCATTTGTGATTAGTTCCACTACAAGGAATTAAATATTCAACTTCTTGCCTTCTGG
GATATACTCAGCCTTATCACAGAGCTCCTCCAGGGAAGGAACTTAGATTCTTTGAAGAACTTCCCTGCT
CTTACCCAAACCGATTCAGTTGTTAATTCTGTCCACCTTGCTCCATTTTCAGTGCAGGAGAAAAAGCAT
TTGTGGCAAGTCTGACCTTACAAAGGCTCGTTAATGCTCAATAACTGTGAGGACCTGCTATAAGTCATG
CCTTTTAAGAAAAAATACACACATGCACACACTCACGACAAGACTGCAACACAACTGTGATGGCAGCTT
GCATATTGAACCAGCTGTTCCCTAAAACATTTGATTCGGCATCCTTTGTAGACAGTAAATGCAAAAGA

CTTAGGTTGGAAAAGTGCATTAGGTTTTGATTAACGATTGGATGAGGGCCAGTTAAATTTTTAAATCTG
AATGAGCTTGCTGACTCAGGAGCCTTAGCAGCATAATGGACAGACAGTCCTCAAAGCTTTCATTAAAAG
GGTTTCTGGTAACTGATGTCTARAGAAATGAGTTGAAATACAATTCACTGAACCACTCAGCTTTCATCT
AAAACAGAATATGTAATCTCAAAGAACTCAACTGGTCTCTTGAAATATTCAGGTAAAATTAAATGTAAA
GAAGCTAGAGCTTAAATATTTTGAGGAAAGGAAGCCTCCTGTAGCTTTGTGACTATATCACTTTATCCT
TTTGAATGCCGTATTTAATTATGTTAATTGCATTTTAAGTATAGCTGGAGTCACCGATCTGCTGAAAAC
AAACTCTASAATGGTTTGTGGGAGGTGCTCAGGATGTATCAGAGACTGATTTGATTTGCATTTTATTTT
TAACTTTAGTTCCTCTCTGAACTCTGCCTTCTCATGTTTGTTTTTTWTGTTGTTGTTGCTTAATACAGT
CATGTGCCACCTAATGACAGGGATATGTTCTGAGAAATGCATTATTAGGTGATTTTGCCATTGTGCAAA
CATCACAGTGTACTTACACAAACCTAGATGGCATAGCCTACTACACACGTCTGCTATATGGTAGAGCCT
ATTGCTTCCAGACTACAAACCTGTATAGCATGTTACTGTACTAACTACTGTAGGCAGTTGTAACACTGG
TATTTGTGTATCTAAACCTATCTAAACATAGAAAAGGTACAATAAAAATACAGTATTATAATCTTATGG
GACCACTGCTATATATGCAGTCCATCATTGACTGAAACATTATGTGGTGCATGACTATAATAGGATCAA
ACTATGCCTTTGCAGAAATCCCCCTGGAAAGCCTCTGAAACTACCCTGATCTTAGAGGCAGTTTTATAA
ATCACGGCCAATGATTCTCAGCCTTTGGGTTGTGCCAGAGATGTGTCCGCTCTCCTTTTGCAATGACCC
TAGAGGTAAAGGTGCTCTTTCTTCTTCTGCTTCTCATGAAAAAATGTAAATGTTGTATTTTAGCTTCTT
TTCCCAGTCTAGTAATATCTTGTTAAATTTACAAGATTGTAGCGGTGCCTCCAAAAGGGGATAGCAATA
GTTACTTTGAAAATGGGTGAGTTCTTTGCAACCATCTCTGAGTTGAACAGTTCTTGTATAATCTGTCTT
CCCAGTTAGGCTGTGAGCCGCCTGAAGGCAGCAAGTGTATCTTTCACTCTTCTCTGATCTCCTCAGCCA
CTCTTCTGCCCCACAATTCCAAAAATCAGTTACCAAGCCATTGTAATTCCTTTTCTGAAATGTGTAGTA
GACTCCTTTTAGGGTATTTGCCCAGTTCACAAAGACCCCTGCCCTCTTTGGAAATCTGTCCTTGCAGCC
ATATATGGTTTTTGTTTGTTTGTTTGTTTGAGACAGAGTTTCACTCTGTCGCCCAGGCTGGAGTGCAGT
GGTGCGATCTCGGCTCACTGCAAGCTCCCCCTCCCGGGTTCACGCCATTCTCCTGCCTCAGCCTCCCAA
GTAGCTGGGACTACAGGCGCCTGCCACCATACCCAGTTAATTTTTTGTATTTTTAGTAGAGACGGGCT
TTCACCATGTTAGCCAGGATGGTCTCGATCTCCTGACCTCGTGATCTGCCCGCTTTGGCCTCCCAAAGT
GCTGGGATTACAGGCGTGAGCCACTGCACCCGGCAGCCATATATGTTCTATATGACTCTTTCTGAGACA
ATAGCTGATTAGAACAGTGATTAGAACTGTGATTTCTGAGACAATAGCTGATTTCTGAGACAATAGCTG
ATTAGAACAGTTGCCACGAGCTGGACCAATCATATTAATATTCTCTATCTCTCTCTTTTGCTCTCGAAA
TCTCAAATTGAGATTCAGAAACAGCTATGTAGTCTCTGTTTGTGGCTAGAACTGTAACATATGAACCCA
GAGCTAGAGAGATGCAATATTCTATCAAGCAGAGAGAGAAGCAGAGGAAGCCGGTCGGCACAGACGGAA
TGCAGTAGCACACAGAGAGAAGCAGACACTCGGAGATGTCTGACACCTTTCTGCTTAGATTCCAGTCAG
TTCAGAGGCCCAGACGCATTCCTGTCTGGAAGCATTCTGATCCTGTTTTGTAAATCAACAATAAATCCC

TTGCCACCCTCTTTGCGTGTTAGCTTAAGTTGTCTTGCTCTTAAAAATCTAAAGAGTTCTAAATGATAT
GAAATGTCTGTTATACAGAAAGTAGAATGACAATTGCCAGGGGCTGAGAGGAGAGGGAAATGGAAAATT
GCTCAATGGTTATAGTTTAGCTTTGCAAGAGGAAAAAGTTGTGGATATTGGTGGCACAACAATGCGAA
TATACTTACCACTACTGAGCTCTATGCTTAGATACGGTTAAGATGGTAAATTTTATGTTATGTATATTT
TATCGCTGTTTTTAAAAAAGTTTAAAATAGCCTGTTGTAGTCAGCTTCCTTGTCTTCCTTACTACTGCA
GCCATATTCAGGTCTCCATGGCCCAAGGTATGGACAACTGTAGTCACCAAACTGGTCTCCCCACTTCCA
CCCCTTGGAATTTGGTCCCCAGCAATCTACCCTACATGCATGGAGCAATCAATATTACCCATAAAGCAC
TAACGCTGTGCTGTACTCCAAAATGCAAACCTTCATGGTGTCCCATTGAATTCAGGATCAAGTTCATAC
TCCCCAGCTTGTCATACAGGACCCAGTGATCCTTTCCAACCTTCTGACCTACTGATTCCCAGTAGGAAG
CAAACCCTAGCAAGACTGGTCTGCCTCATCCCAGAACAGTACTTACTCATGCTGTTTCCTTGCCATGAT
TACCTTCCTTCTCCTCACCACATCTTATCTTTCTTTCACTTGATCTTAGTCCAAATGCCGAGAAGCAAT
CTTATCTTACTTTCAAAGCCCAGGTTCAGACCCATCAATTCTATAAAACATTTCTGACCACACTAGTCC
TCCATGGACATTTATTTGAATTGAACTTCTTAGCATTTAAATATACACAGTTTCTTATTCATCTGTCTT
GTTCTTCTGCTAGTTTATAAATTGCTTGATTATAGAACATGAGCTTGATAATCTTTGATTTTTCCTGGA
TACTGTGTTCTTGCTAGGCTGTTAATAATGCTTGTTGAATGAAATGAGAAATGAAGAACGGCTGCTTTA
CCAGTTTGTCTCTTCTGCCAACTTTTTACATGGATTTTACACGTCAACTTTTTTACACAATGATTAAA
TATACCTAATTTGATCATCCCAACAACACTAGTAAATATATATGATCATTATCCTCATACTACAGATGA
GGAAACACAGGCACACATCGTTTGTTTGTTTTTTTTTTTGAGACGGAGTCTTGCTCTGTTGCCCAGGCT
GGAGTACAGTAGCACGATCTTGGCTCACTGCAACCTCTGCTCCTGGGTTCAGGCCATTYTCCTGCYTCA
GCCTCCCGAGTAGCTGGGACTACAGGCATGTGCCACAATGCCTGGCTAATTTTTGTACTTTCAGTAGAG
ATGGGGTTTCACTATGTTGGCCAGGCTGATCTCGAACTCCTGACCTGATGATCTGCCTGCTTCGGACTC
CCAAAGTGCTGGGATTACAAGCATGAACCACTGTGCTGGGCCAAGCACACATAGTTAAATAACTTGCAA
AAAAAAAAAAATCGTATCTATTTGTAGGAGGCAGAGTCGTGATTCTGAGCTGAATCTATTTGGCTCCTA
AGCTTATGCTTTTTCTACAGTATCACCACATATCCCATACTCTATTGTTATTGTTGGCTTTATTGCCTG
TTTTTCCTGTGAATTTTAACCTTCCCAAAAGCAGGAATCTTATCTCAGTATATCACAGAGAATCACTAA
GTATCTATAGAGGAAAGGAAGGAGAGAAGGAAAGAAGAAAAGGAAGAAGGAAAGGAGGGAAGAAAGGAA
GAAGGAAAGGAGGGAAGAAAGGAAGGAAGGAAGGAGGGAAGGCAAGAGGGCAGGAAGACAGAAAAGAAG
GAAGGAAGAAGGAAGGAAGGGAGGGAGGAAGGAAAGAAGGGAGGGAGGGAGGAACGGATAGGAGGGCAG
AAACTCTGGAAAGGAGCTTGTCTTACTCCTAAGCTTGGTAAAGATCAGTCTTGCAAGGGGCTTGACTAG
AAAACACTGGCTTATCTCACTGAACCATATTCCCAATGTCATTGACTCCTTTCCCCTGGGGAGTAATTC
AACCATGTGTTCACTGTATGGATCAGAGTTGATGATGAATATTCTCTTGCCTCAGTCTCTTTTGGCCAG

AGTTCCTTGGCTTCCAGCCTGCTCCTTGCTTGTTTTGAACGAATAATATATGACTTTCCTTCTTAACTG
GCAAATGCTGAACTGTGGCCTCTCTTAACCCTCAAGTCTCCCGATAAAAAGCAAAATATTAGATTCGCT
GACCAGCGCTACTCCTTACCCCGGCTGATTTCACATGAAGAGCTATATATGGGGTGGTAACATAGGTTT
AAGGATGGATGTGCATATAACTCCTGGATACCGTTCCTGAAAATATACTATTGGGGATTATTTCTTTGG
TTGAAGAGTCCCTTCACTACCACATGTCAGTCCCCTTACCTATAAAATGGGAACCTTAGGGTTGTTATA
AGGATTAAATGAGTTAATGTGTATAATGTGCTTAGCACAGTACCTGCCACTCAATGCTATTATTGTTGT
TGTTGTTATTATTATTGGTAGTAGTAGTAGCAGTAGTTGTTGTATGAAGATGCATGATTTCCTGGGAAA
GGTAGCACATTAAGGCAGGATCAGTCATGAGTTACCTCAAGCAGATTAATTTACTAGCCCTTTCATGCT
ATTTCCCAAAGGGATGGTTTATCAAGTTGAGGAAGATGTAGATGTGATTTATGATGGATTTGAGGTTAG
TACTGTGTATCCAGGTTGTGTGTGAGAAGACAAGAAGGAACTGAGGGCACAGCTGTACTTAGGAAGAAC
TCTGGTTTGCAAGGTACATAAGCTAATTCAGACGAGTTTAAACCATAGGAGATTTTGTTACAAAGGCAC
TAGGTAACTGCAGGGACCAGGGAGCAGGGTGTCCACTCTCATTCCAGATTCTTTTGAATTCTGTATATT
TTATTCTCTTTCCACAAACAGACTTTCTATCCACGGTGGTGATGATAACCAATAACATTTCCTTCAGTC
TCACCCTTGTAGCTCTGTGACCAAAAATGCAAAGCTGCTGCTTCTCCAGCTTCAAAATTTAATAAGAAT
CACAGGGCAGAACATTTATTGGCTAGGCCTGAGTTGCATGTCTAACCTTGGAGAACTCACTTTGAATAG
GGGAATTCAGAACTAGGATTGGTGGCTCCACAAATCTCACAAAAATGGAGCAAARTAGGAACTCATCAA
ACAGAAATCAATAGATCTCCACTGGCTTTATAGTACGTGGTTCTGGGAATCCAGATATTCAGAGCCTAG
GTGAACCTGAACATTTCCCTTTAGGCAGATGGAAATCCACGTTCTTCTAGCTAAAATTTTTCCATTCTC
TTTGAGGGGAGTTTCCATGGAGAGGCTAGCTTTGTGGGAGAGAGTGGGAARAAACAACTCATGCTGTTT
TTCATTGGGGACCATTCTTATTGCTACTTTAGTCCAGTCCTGCCCACGGATCACACATTATTCCTTACT
CTTGTTGCTTCTGGGCTTTTTCTTTTTCCTTTGCATGCTGCTTATATTCCCTTCCCTAAAAGCTACTCT
ATTAAGAGGGAGATTAGGCAAGTAGGCTGGTTTGATTATGTGCTGGTTTAACCCATAATCACATACCTC
AAAAAGAAAATGTCAGACACACTATAATAGCTCCAGATACAAAACATGAAGTACGAAGACCTCTTCAGA
AAACTGCAGGCTTGCTACTCACCCACAGACAAATAGAGCTGATTCTATTAGAACAGTGAGGAAAGAACA
CAGTAAAGAATGGCATTTAAGATCAATTGTGGCAATGTCTAATTTTGTCTGGGAAGACCATGGCAGTGA
GGGATGCAAAGGGATGACATCAAGTTTTCAGAACAGTGCCTATATGTTTAGGACGAAGAGTTAAATAAT
GAGAGAAAACAAATGCAATACAATTTCATTGGCTACCTGGTTAGACCTAGCATGAACTGTGTCTGTGAT
GGTGCTATTAATTTGTGATGGAGACATTGGATATTGTCTTTCCCTATTTGGTAAGAGCTTGATTCAGGT
AGAGAGAAACAATAATTATTTTACAGTGTACAAAGCACTTTCTTATACGATATATTATTTTCATCCTCC
CAACTAGTTTGATAGGCAGTAATATTATTCCCATTTCACAGAGGGGGAAACCTGGGTTAGGGCCCAGGA

ACTTGGCTGGTGAGTTTGGAAAGCTTGAATAGCAATGATTATAATCTTGGTGCACAGAAGCAGCCAGTG
AAATTCTGAAATGCATATTTCTGTTCTCTACTTCCAGAGGGTCTGATTGAGTTAGCTTGGGGAAGGGCC
TAAGAAATGGAATCTTTTTTATTCACACCAGGTGATTTTGAAGCATGGGGTCTACTGAGTATGCTTATG
AAACATTAACTTTAGGTCCTAGGCACTGGCTTAGTTGACTGTGAGAAACTGAAGCACAAAATTGTGTGA
CCAAGTTCTTTCTGAGCCTCAGTTTCCTCACCTGAAAAATGAATGATGATGATAAAAATAACTAGGCTC
CATGCCAAGTGATTTACATATTTCCCCTCAAATCATCTTTCTTACAAACCTAGGAGTTCGGAGGCATTG
TTGTTCCTATGCTATGGGACTCAAACCCAAATCATTTCTACTCACTCTTCCTTTCATAATTGTCAGGAA
GATTAGACATAGAAAGTATCTAGCACATATTCCTGATGTTGAAGGAATAGCAGCAGCTGTTATAACTAC
TACTAAAACTGACAATACTGACCATACAGCCACCACTAAAATGYTGGGGTTGAATTCAGATAATCTCTA
AGGTTCTTCCCAGCTCCACCATACCCTGATTTCAGCATTTCAAATATATGCTGTATTTGTGGGGGGGT
TCCTAGAAAGAGTGTGGCAGTAACTGAACTCAACTATACAAAAGACCGAATTCTTCCTTTAGTTGGAGA
TTTATTGATTTTTGTAAGTGAGTTTATAGACAAAAACGAGGAAGATACAGAGAAAAAAGAGAAGAATTA
CTGTGCTTTGATAGTAGGGCTATGGGTGATTATTTTATTTTTAAAATTTTATTTTTTATACATTAATGT
GGTTTCTATAACAAACACAAATTTAGAATAAAAGTAAGATATTTCTCTTGTGCTTCCAATTTACCATAT
ACTTCTTAAATGTATTTGTATCATAATCATCAGCTGTAAGTTTACTATTAAAAAAAATCAACAAAAGAA
CAATATCAGAGCTAAAGGACTTCAGGCCTGATGAACCTAAGTCTAGTTTCTGTGCTCACTAGCCTTGGC
TTATCCCAAAATATTAAAAGTAAAATATGATCCAATCTGCATCTCTTGCACATGTCATGTTTTGTAAAT
AGAAAGTTCTTGGAACAATCTGTAACATCGTTGAAGTACTTCATTCAATTCTTGGGCATTAAATTTTAT
CTTCTGTTCCTGCCTCATATCATTAAACAGTACCTTCACCTACATTGCAGTCAACTATGGAGGACTAAT
GCTCTATTTTTTTTATGTTGAACATGAAGCATAAACATGTACAGCTCTGAACCTGAGTTTTCCTTGCTT
TAGAAATAAGAGGTGTTGATGAAAGAGGAAATCCCTGAGACTCTGTAAACCTWACCTGCAGGTATGAGA
ATACAATCTGTGTTTWATTTATKGTATTCTTWAGCAAAATTATAGTAAAATTAGTATTTTTCTTTTCAT
TTGCTCTCGAATTATCCTTTAGTAACAGAGTGAACTTGTATGTCCATATTTTGGGTTTAAAGAACATGG
TTACTGTAGCAAAGAAGGGGCTAGCCCATGTATTAAGGTCCTGGATTATACTGTTGCTCACAGGAGAGC
ATGGGTTTGAAGATGAGGCTGCATAGTAAAGTAGGTAAAAGTTTGGACCTTGGGGCCAAACTGCCTAAG
CTCAAATCATGGTCCTGCCAGTACTCTCTGTTCGACCTTTAGCAAGTTACTTAATCCTTGTAGACCTCT
GATTTGGTCTCTTCAAAATAGGGATAGCAATAATGCCTGTCTTATAGAGACATTGTGAGGATTCAATGA
ATTGATATTTGTAGAAGAATATTGAGTTGGTTTTGCTAGAAGATATTAAGTGCGCAGTCTTTCTAAAAT
AACTAAATGCTACAAAAAGCAAAATAGCCATTCTGCAAAGAGCAGTGATTGAAGCAGGAAAAATGCCTG
CCTTCATAAAGCTTACATTATAAGGAGAGAAAAATAAGCAAAACAAACTACGTGGTATATATGTAAAAT
AAAAATAAAGAGGGGGAAGCATGGGGTGGGGCAGATATTGCAGTTATAAATAGAATGGTCATTGGAGGC

TTTATTGAAAAGGGGACATTTGAGCAAAGTCTTCAAGGGGGTATGGAAGTGAGCCATGTGAGTATTTTG
GTGTAGGGAAGGAAAAACATCCTTCTACCCTCTTAGGTTTGGTGGCTAACCTAAGAATTAAAACAACAT
AGATTAACAAGAGAAAAGCATGCACATTTATTTAATGTTTTTATGTATACATGGGAGTCCTCAGAGAAA
AATGAAGACCCAAAGAAGACTTTATGCCCCAAAGCTTATATACATTTTTTACACAAAGAATGATAAACT
GTGGAGATGTGACAAGACAAAAGGCCTTGGGCTAGAAGCAGTAAATTGTGGGAGTAAGGGATATACAGG
CGAAACTAGTGGAAAATGAGGATGATTTTAGTTTTTTTTACAGGTCCATTTCGATGATAACTCCAGTC
ATCTCTGGTGATACTATTCTTCTCTTCCTGGCACAAGGAGGGCACCTTTCTCATGGGAAATTTTATGAC
CTGCTTTTTGGTAGAAAGGGGAAGTCTGAGAGCTCTTCCTGCCCCTAGTGTTTCTCAAGCGCCTTCAGC
TCAAAATAATCATTATGCCAAAGTGGCATATTTTGAGGTGGCATGTTCTGAGCCATTTCATGGGGTAAG
GATATTCCAGGCTGAAGGAACTGGGAATGCAAAGGCCCTTAGACAGGAACATGCCTGGTATATTCAAGA
GACATCTGGGAAGCCAAGGTAATGAATGACAGCAGAGCATGAGGGTGTGGGTGGCAGGAGATGAGGAGA
TGGTACAGGAGGCACAAATCAGGCAGCATGTTATTGATCACCGGCAGAGCTCCAGGTTTCATTCCATTC
TGAGTGACATGAACGGCCATCAAAGGTGTTTGAGTAGAGGAGTGACTGTGTTTAGAATGGACTGCAGGG
GAATAAGGGTAGAAGCGGGAAGACCAGTTAGAAACTGTTAGAGATGATAGTGGCTTAGACCTGAGTGAC
AGCAGTAGAATAGGTAAGAGATGGATTATGAGTGTGTCTGGCTGATTCACTCTTATATCCCCTATGCTA
AGGCATCATGCTTGGCACATAGTAGGGACTCAATAAATACTTGCAGAGCGAATGAATAAATGGGAGTTC
AACTTGGGTAAGGCAACTTCTCTAAGGCTCTGTTTCCTCATCTCTAAAATGAGGGTAAGAAAAATATTA
ATAGATCTACCTCCAACGGTTATTGTGGAGATTAAATGAGGTCATTCCCATGCATTGCTTAGCATAGTA
ACTGAAACATAAGATAGGGCTAAGATGTATACATACACATAAATATAAAGCATTTTTGCAAGAGTTTAC
CTTTGGAGACATGGAGGAAGGTAGACTTTTATTCTTCATTTTATGAACTAAAAGCAAAAGAAGAAAACA
AGTGTTGAAATTATGAGTCATTTTCAAGTTCTTTTTGTACTTTTCACTACCATTTGGAATTTTCCTATA
ATGAATATGCGAGGCAAAGACAGAAATGAAAGGATAAGATCACTCAGAATTTCAGGTTTTTATAAAGCA
TCAGAAATGTAAGACTTTTTTCTGCTACTGCATGGCCCATTTCTCTGACTCTTTGAATGTGGGTATTAT
TCTCATCTTTCTCCCTCCTCTTCTCTTTTTGGTTAAAAGTAAAGAGAGCTTTTGAAGCTATTATGGAAC
AAGAACAACAGCCTAGTTCATCCTCACATTTTGGAGCCTCTTATTCCTTCCAAAGAACAAACACATCTA
TTTAGTGGCTAAGAGTCTCTTGAGCTGAAACCATTCATCACCATAACTACATTCAAACTGTCTGAGGTA
TACATTATAACTAAGAAAATGGGGTTCCTCATTGGAATTTACAAACTAAATATTCAAAGAAGGGTTCTG
ATGCTTTTAAAATAGGGGCGCCACCAAAAGGTAAAGTAAGACATGTGGTTGAAGACACAGGAAAGGGCA
GAGGTCACCAGAAAAGTTGGTTGTCACGCCTGATCTTAGGGCCTCATAAAGAAATAATTATGGCAGAAT
GAGCCCTAAGAAGCAAGCACTTTAGCATGGCTCTCCCTGGACAAAGTGGAGAGGCCCTTCCACCCTAAC
TTATCCTATTGTCCTGGTCTTCAGTCTTTCCTGTCTGTTTGCCTTTCCTGGTGTTAATATACTTGTTCC
TAAGGTTTTCACCCTGCTGACTTTAGCTCTTCTTGCTAAGATTCCTGGCTGTACATTAGAAAACTCCT

GAGCAACTAAACACAAAAAAATATTTGGCAGGGGGATAGGGGGTGCTTCTAGGCCCTAACTAAGACCTG
TTAAATTAGAGTCTCTTTCGGGTGGCTCCTGGGCATTGGGGTTTTTTGTCCTTTTTTTTTTTTTTT
AAATCTAAAGCTTCCCAGTTGATTCCAATATGTAGCCAGAATTGAGACCAGAAAGCTGTTAATACCCAA
GTAGTATACTAATATTAATAATGATCATAATAGATTAATAACTAACATTGAATGAACTTTAAATGTGTT
AGCTGATTTAATTCTCAATGACTCTGAGGCAGTTACTATTATTATTAATGTACCCCTTCTACAGATGAA
GAATTCAAGATACCAAAAATCTACATAATTTGGCAAACAAGTAAATGCTAAAGTTGGAATTCAAACACA
GGTAGTTTAGTGTCCGAGCCCACACTCTTCACCACCACACTGGTGGATTGCCCACCTGCAATGTTAAAA
ATCGCAGAGGATAGTGATGATACTGCAGACACACTGCCTGCATTTTATCTCCTCCTTGTTAGGCTGAGC
CATTCATACCTCAGTGGTCCACACCTTAAAGGCAGGATATAAAGGTAAATATATGTACCTTCTCTGATA
TGAACTAGAGACTCCATCCCTTCTTTTTAAGTAATGTAAATGATTAACCAGCTTTCTGTTATTCCTTTC
AGAATCTCATTCATAGAATAAATTCCTGGCATAAATTAGTATCATAAGTTTTCTATTATTGCTCATTAA
TCAGTATGTGATGTAAGATCAAGCAGTAAGAGTTCCCCCCAACCCCAAAGAATGGTCTTTCTGTTTGTG
ACAAATTATTCTTGGCAATGTAATTAGCCAGTTGGGTTATTGAGGGGGATCCACTAGTTCTAGAGCGGC
CGCCACCGCGGTGGACTAGAT

Contig 3 (11811 bp)
CCTGTTAAAGTTTACCTTGTATCTTAAAACTTGCCCTAACCGGATTAATTTTCTGGCCAAATAGGGAGG
CTGAATGAAAGTTTCACATAAACCTTAGATACTCCTAATTAACTGTTTTTTATGTCTGTTTTTCTAGGA
CACATGTTCAAAGAGCATAATTAACTTTTTAAAAGAAGCTAGTAAGTACTGAAATAGTTTTTTAAGTTT
TTTCTACAAGAATAGAGGAAGAAAGGAAACATGGAATTCTGAAGGGCTACTTAGCAAGCTGCTTATGGC
ATAATCTGGGGTGGGGGTGCATAGTAAAGGATTTGCATTTTACTGAGACCGATACATGTCAAGGGAATG
GTATTTAAAATTAGTGATATGTGTTGATTTTTCAAGGACTATAGCCCATCAACTACAATAGGCTCCAAA
AAATTCTGGTGAAATTAGCTTCTTGGAGCCTTCCAGTTTACCTACTATGTTATTCCCACTATAAAATAT
TCTCAACTTTTGGGGTTTTAGCCACTTAAGTTTTTTATTTTCTCTAATGTCTCTAGTATCTGCTTTAGT
TTCCTGTCAATGCTAGACTCTGTGGTTCAGCAGTTCATCCATTCTCTTCCCAGTACTCAACCTCGTTGC
TTATAGTTTCATTACATTCATCTAGCAAAACCTTAATTCTGTATGTTTGCCATACCATTAGTGCTTAGA
GCATTTTTTCAGAAAAGAATCCTGGAAAAATGGATCTTATCTCACCTGGGCCCTCAGGACTGCTGGGCT
GCCTGGTGTCAGCACTTCCCGCCATTTTCTATAGCACCAGTATTATTCTTAATACTTTAAAAAACCACC
AGGCACGGTGGCTCACGCCTGGAATCCCAGCACTTTGGGAGGCCAAGGTGGGCGGATCACAAGGTCAGG
AGATCAAGACCATCCTGGCTAACACGGTGAAACCCTGTCTGTACTAAAAATAGAAAAAAATTAGCTGGG
CGTGGTGGCATGCACCTGTAGTCCCAGCTGCTGGGGAGGCTGAGGCAGGAGAATGGCGTGAACCCGGGA

GGCGGAGCTTGCAGTGAGCCGAGATTGCACCACTGCACTCCAGCCTGGGTGACAGAGCGAGACTCCGTC
TCAAAAAAAAAAAGTAAATAAAAATAAAAAACCATATCCCACTATCTCCCCCTTCTCTCTTTGCCTGTG
ATCTTGCTGCATACTTATGGGAAATCTTTAAGATGTCAGATTTCAGTTCTCTCACTTTTCTACAACTT
CTCCCACTTTTGCCTTTCTTATGTACCTTCCCTTCCTTCCCATCTGATTCCTTATCAGTATTTACACAT
GATTAGTTCTTGCCTAACCTAATAGACCCTTTCTTGAGTGCAAATCAGTGGCTATTTTTGCTAGGGTAT
AAAAATTACCTATCTAATCACCTTGACAAAGTTACCCTGTTATTTCCAATAACTTACTTCCTATGGATT
CTTGTAGATTTTCTTTTTTTTTTTTTAATTTTTTTATTTTCAGATGTTTTCTCGCTTTGTCACCATGC
CTGGCCTAAATTCTCGTAGGTTTTCTATGTAAACAATCAGATTTTCTGCAAGTATTAGTCTCCTTTCTA
ATTGTTATAATTTTAATTTCTTTTTCTTTTTAAAATTTTTCGTAGAGACAAGGTTTTGCTATGTTGTCC
AGCCTGGTCTTGAACTCCTGGGCTCAAGCAATCCTCCCATCTCAGCCTCCCAAAGTGCCATTACAGTGG
CATGAGCCACTGTGCCTGGCCAAATTTCTTTTCTTGTTGCGAAGGCAGACTTTTCATACAATACTGAAT
AGAAGTGATAGTAGATTACTTTATTTCTGATTTTCAAAGGAATGCTTTCCGTTTCTCTCTGTTGAAGAT
AATTGCGTATTGTTTTTTTTTTTAAATAGTAACTTTTATCAGGTTAAGGAAGGTTTCTTCTATTTCTAT
TTAAAAGGATTTTTTAAAATCTTGAATTCATATGTTTTTATCTAATGCATTTTCTACATCAGTTGAAAT
GGTTGTATGAACTCTTTTAATATGGGTGAATTATATTTATAGATTTTATGTTAAAATATCCTTGTATAT
CTTGGATAAACTCAACTGGATCATGATTTATCTTTTTTATATGCTAGATTCAATTTGTTGATACTTTGT
TATGATTTTTGAATATATATTATTGTGTAAAAGTGAGCCTGTGATTTTCTTTCTTGTAATGTTTCTGTC
CAGTTTTGGTGCCTGGTTTTGCTCTCTCCTTAGAATGAGCTGGGAACTAGTCACTCTTGTTTTCTCACC
TATAATAGCATCTGGGTCCAGTGTTTTTTATGTGGACAAATTTGAACTTGTGGTCAACCTCTTTAATT
GTAAGAATATTCAGGTCTTTTGTTCTTCCTGGGCTAGTTTTTTATTCTTTTTCTAGAGATTCGTTCATT
TTTCTTAGTTTTATTTGCCTATAATTGTGGATAATCTGTTTTTTATCTGCTACTTCTGTAATTATTTCC
ACATTTGATTTATAATATTAACTTGTGGCCAGGCGTCGTGGCTCACACCTGTAATCCCAGCACTTTGG
GAGGCCGAGGCGGGCGGATCACGAGGTCAAGAGATCGAGACCATCCTGGCCCATGGTGAAACCCCGTCT
CTACTAAAAATACAAAGAAAAAAATTAGCCGGGCGTGGTGGCAGGCACCTGTAGTCCCAGCTACTCAGA
AGGCTGAGGCAGGAGAATGGCGTGAACCCAGGAGGCGGAGGTTGCAGTGAGCCGAGATCGCACCACTGC
ACTCCAGCCTGGGCGACAGAGCGAGACTCCATCTCAAAAAAAAAAAAAAATTTACTTGTGTCTTCTCTTT
TTACCTGTTTGTTAATTTATCAAATAACTACTTTTGGCTTTGTTTCATTTTTATTATACAATAAAATGA
AATTCTTTTCATTGTATTTCTTTTCATTGATTATTCCTATAATTCTTAAACAACTTTATAATTGATGTA
ACAATAACCTGTACACATTTAAAGTGTAAAATTTATTACATTTTGATCCATGTATATAGCAGGGAAATA
TCACCACAACAAGAGTGTGAACATATAATCTCTCCCCAAAGTTTTCTTGTGTCTTTTATAATCACTGCC
TCTTGCCCCTGCCCACTCCCTCATCCTTAAGCAACCATTGGTCTGTTTTCTGCCACTATAGATTAGATT
GTATTTTCTAGAGTTTATACAAGTGAAATCATGTAGTATAGTATTAACCATGTGTTTGTTTGTTTGTT

TGTTTCTTTCTTTCTTTCTTTTTTTTTAGACGGAGTCTCGCTTTGTCACCCAGGCTAAAGTGCAGTGG
GGCGATCTCGGCTTACTGCCAGCTCCGACTCCGGGGTTCACACCATTCTCCTACCTCTGCCTCCCGAGT
AGCTGGGACTCCAGGCGTGCCCGCCACCACGCCCAGCTAGTTTTTGTATTTTTAGTAGAGACGGGGTTT
CACCATGTTAGCCAGGATGGTCTCGATCTCCTGACCTCGTGATCCGCCCACCTCAGCCTCCCAAAGCGC
TGGGATTACAGGCAGGAGCCACTGCGCCCAGCAACTATGTGTTTCTGATCCTTTGTCAGGGCTAGCCAA
TTCCTAGAGACAGTGAATAACTCACTCATAATCTAGCTGCCTCCTTTATGTCGCTCTCATAGGACTTTG
ACACCTCTCTGCTACAATCCACCTGCCCTGTTCATTTCAAGATCAGGTACCAGGAAACTCGGGACATCC
CTATGCTGCAGAACTCACTGAAATTATTCAAACTAGCCAGTCCTAAACATGCTTACCCTGCCTTGCCCA
TTCCTTCCGCTGAAACCACATAAAGGCTCTTGCCCATGTTTTCATCCCATTCCATTGACCTCCTTACTG
ACCCTAGCTAGTGCTTCCTCATGTGGCCCCTGCATGGCATGGTGTGCACCTTCCTCTTCGGAACTGCGA
GTAACTGTCTTGTCAGCGGCAATCATCTTGTGATCTGTTGGCCTCATCATATTTGAATAACAATAAAAT
CTGTTTTAAGGCTGGGCGCGGTGGCTCATGCCTGTAATCCCAGCACTTTGGGAGGCCAAGGCAGGCGGA
TCACGAGGTCAAGAGATTGAGGTGAAACCCCCTCTCTACTAAAAGTAGAAAAATTAGCTGGGCATGGTG
GTGCGTGCCTGTAATCCCAGCTACTCAGGAGACTGAGGCAGGGAATCTCTTGAACCCAGGAGGCAGAGG
TTGCGGTGAGCCAAGATTGCACCACGGCACTCCAGCCTGGTGACAGAGCGAGACTCCATCTCAAAAAAA
GAAAAAAAAAAAACTGTCAAATGATACTCCAAAATGGTTGTACCATTTTATATTTGCAACAACAATGTC
TGAGGGTACTGATTGCTCCATATCCTTGACAGCACTTGGTATAGCTGATCTTTTAATTTTAGTCACTTT
AGTGGGCATATACTGGTATTTTATGTTTTACTTTTTATTTTCCTAATGATTAATAGTTTGCAGCATCTT
TCATGTGCTTATTTCCCTTTCATATATCTTCTTTGATAAAAATATCTGTTCAAATATTTTGCCCATTAT
TTTGTTGGAATACTTATTTTCTTACTGTTGAGCTTTGAGAGTTCTTTATATATCTGGATACCAATCCTT
TGTCAGATATATTTTTTGCAAAATTTTTTCCCAGCCTGTGATTTAGTTTGTTATTCTCATGTCTTTTAA
AAAAAATTGTAGTTAAAATATACACATAATACAAAATTTAACATTTTAACTCTTTGTAAGTATACAGTT
TTGTGGTATTAAGCATAGTCACATTGTTGTGCAACCATCACCGCCATCCATCTCTGGAACTTTTTCATC
CTCCCTGACTGAAATTCTGTACCCATTTAAACACTAACTTCTCATTCCCCCTTACTCCAGCCCCTGGCA
ACCATCGTTCTGTTTTCCTTCTCTATGAGTTTGACTGCTCTAAGTACTTCATATAAGTGGAGTCATACA
ATATTTTCATTTTGTGACTGGCTTATTAGTATAATGTCTTCAAGTTTCATCCATGTGGTAGCATGTGTC
AGAATTTCCTTCCTTTTTAAGGCTAACATTCCATCCTATGTATATACCACATTTTATCCATTCATCTGT
TGATGGACATTTAAGTTGCTTCCTCCTTTTGGCTATTGTGAATAATGCTGCTGTGAATGTTGTTGTATA
AATATCTGTTCGAGTTCCTGCTTTCAATTCTTTTGAGTATGTTCCCAAAAGTAGAATTGCTGGGTCATA
TGTTAATACTGTATTTAGTTTTTTGAGGAATTGCCATACTGATTTCTATAGTAGTGGTACCATTTACAT
TCCAACCAGCAGTGTTCAGGGTTCCAATTTGTTAACATTCTTGCCAACCCTTGTTGTTTTCTGGATTTT

TTTTATTTTGGGGTTTTTTATTTTATTTATTTATTTTTTTTTTGAGGCAGAGTCTCACTCTGTCACCCA
GGCTGAAGTGTAGTGGCGCAATCTCGGCTCACTGCAACCTCTGCCCCCCGGGTTCAAGCGATTCTCCTG
CCTCAGCCTCCGAGTAGCTGGGACTACAGGCGCGCGTTACCACGCCTGGCTAATTTTTTGTATTTTTAG
TAGAGGTGGGGTTTCACTGTGTTAATCAGGATGGTCTCGATCTCCGGACCTTGTGATTCACCCGCCTCA
GCCTCCCGAAGTGCTGGGATTACAGGCGTGAGCACTATGCCTGGCCATTTTTTATTTTTAAACAATAGC
CATCCTAATGGGTATGAAATAGGTTTTTTGGTGTTTTGTTTTTTTTTTTTTGAGACAGAATCTTGCTGTG
TTGCCCTGGCTGGAGTTTAGTGACGTGATCTCGGCTCACCTCAACCTCCGTCTCCTGGGTTCAAGCACT
TCTCCTGCCTCAGACTTCCAAGTGGCTGGGACTACAGGCGCCCGCCACCACACCCAGCTAGTTTTTGTA
TTTTTAGTAGAGATGGGGTTTCACTGTGTTGGCCAGGCTGGTCCACGATCCATCCACCTTGGCCTCCCA
AAGTGTTGGGATTACAGGGGTGAGCCACCATGCACAGCCAGGGTTTTGTTTTGTTTTGTTTTTACTATT
TTTTTTTTTTTTTAGAGACAAGCTGTCTCCCAAGCTGTAGTGCAGTGGCACCATTCGTATCTCACTGTA
ACCTCAAAATCCTGGACCCAAGCAATCCTCCTGCCTCAGCCTTCCATGTAGCTACCTCTACAGGGAATT
GCCCCCATACCCCGGGAAATTTTTTTTTTTTTTTTTTTGAGAGTTTTGCTCTTGTTGCCCAGGCTGG
AGTGCAATGGCATGATCTTGGCTCACTGCAACCTCCTCTTCCTGGGTTCAAGTGATTTTCCTGCCTCAG
CCTCCTGAGTAGCTGGGATTACAGGCGCCCGCCACCACGCCTGGCTAATTTTTTGTATTTTTAGTAGAG
ATGGGGTTTCACCATGTTGGCCAGGCTGGGCTCGAACTCCTGACCTCAGGTGATCCACCCACCTTGACC
TCCCAAAGGGCTGGGATTACAGGCGTGCGCCACCACACCTGGCCCCCAGCTAACTTTTAAATGTATTTT
GTAGAGATGAGGTCTCACTGTGTTGGCCAGGCTGGTCTTGAACTTCTGAGCTCAAGTCATTCTCCCACC
TCGGCCTCCCAAAGTGCTGGGATTACAGGCATGAGCCACCACACCTGGCCCCTTTGCCCATTTTAAAAA
TTAGGTTGTTTTTGTTGTTGTTGAGTTGTAGGAGCTCTTTGTATATTCTGCATTTCGGTTCCTTATTGG
ATATGTGATTGGCATACATTTTTTCCCATCCATGGATTGCTTTTTCATTCTGTTATAGTATCCTTGATT
CACAGAAGTTTTTAATATTGATGAGGTCCTGCTTAGTCTGTGTTTTGTTTTGTTGCTTGTGCTTTTGGT
GTTATATCCAAGAAATTTTTGCCAAATCCAAAGTCATGAAGCTTTGCCCTCTGTTTCCTTCTGAGTTTT
ATAGTTTTAGGACTTAAATTTAGGTTTTCGACCCATTTTTAGTTAATTTTTGCAAGTGGTATAAGGGAG
GGGTCCAGCGTTATTGTTTCACGTGTAGATATACAGTTTTCTGAGTACCATTTGATGAAAAGGCTGTCC
ATTGAATTGCTTTTGCAACTTTTATTTGGGCATATTTATGTGAGTCTGTTACTGGTTCTATATTTTACT
CCATTGATCTATGTGTCTATTCCTCTGCTAATACTGTCTTAAATATGGTAGCTATATAGTAAGCCTTAA
CACTGAGTAGATAGATTTCTCCCCTTTTTTTGTTCTTTTTCAAAATTGTCACTGGTTTGTTTTTATTTT
TTACTTTATGCAGATAATCTGTACTATACTTTGGTTTCATGTATCAAGTAGTTTGTTCCAAGTTGTGCT
TTAAGCAGAACAAATAAATTTTCATATTGTTCTTTGTGTTAATCTGCAATATAAACCTATACCAAATTC
TATTTTGTGTATTTGTTTATTGTAGTAATCTGACTGACTCTTTTGCCTCCAGACTCATCTCTTTCAAGG
TCCCCAACTGAATCTTGTTTTAGGTGGAACTTAGAAGCAGTAGAAGTTAAGAATCTATTTCACAGCCTT

AGTAGTCTAGTTTCATTCTCTATATAATGTTGTCTATGCAAGTGAGCTGCTCTCCAGTGCCTTAGTTTC
ACTAATGTTGGGGAAGGTCTCTTCTCTTGTTTTGGACTTCTCTATCACATTGCCTTTCTCAAGAGAAGA
CATATAATGAAAGTTGATATCTGGTGTTCTAGGACTTCTTCAGAAGCTTGCCAGTTTTTCAAGCTGATT
TCTCTCACTGGCAACTCTTCAGAGTGCTGTTCCTACTCCACCCTCCCCTGGTGGTATGTATCAGTTTTC
TACTCATCAGCACCCACCTACTCCTGCCTACTGTGTTTCTCAGATGTCTGCTGCCTGGCTAGCTCATTG
CTGCTTTTGTCACTCATAGAGCTGTCTTCTTCCCTTTTTTTGGCTTTCTGCCTGACTTCCAGGGCAGCT
GCTCTGTCATTGCCTGTCTGCCATTCTGTCTTTTTTCCCCCTACCCCCCACAGATACAACATCTACTCT
AATACCACACATTCTCCATGTTCAAACTAACCTCATCACTTTCCCCACCACATTCCCCAAAACTGGTCA
TCCTCCAGCTTATAGCATTGCAGTTCACTGAAGTTAGACATCTGGGCCTTGCTTACCTCCAACATCTCA
TTAGCCTTCGATTCTACCCCTATAAATCCTCTTCTCAGTCTCCTTTAGATATTCCTGCCCTGCTGTGAG
ATCCATCTGGTTTATTGGCTAGATTACTTCAGAAAGCTTCAGTCAGTGACCCTCCTTACTTCAAACCCC
ACCAGTTGATCCTTCACTCTGCCATCAGTCATTGCTTCTAAAATCTAAATTGTTCCATTTAACCTTGCT
GTGATAAAACCTTTGGTAGTTCTTCAGTGTGTTCAGTGGTAAGTTAAAACTTTCACTGTAATGTACAGG
CCCCTTCATGATATGATCGCTGCCTCCTCGAGCCTCATTGTGTGCATTTCCCCGCCCCACCCTTTCCTC
ACCCACCCTAGTCTTTCATGTCTGCCATTTTTACATTCATTTAGCAGATATTTATTGAAGCCCCCTGTG
ATGTCCTTACCTAGGTCTTTCTTGTTGCCAGGACCAGACAGGCTTTTTCAAGCTTCCAAGTCATCTCAG
TTTGAAAGACTATGTCTGACCCTTGTCTTGGCCAATTACTCTTTATCCTTCCAAGTTCAATGATTGTCC
CACTGCACTCCAACCAGAGTGAGAGAGCAAGACCCTGTCTCAGTAAATAAAAATAAATAAATAAATAAA
TAAATAAATAAATAAATCAGCCATAATTTATTTAATCATGTCTCTCTCCCCCATTGATAGACGTTAAGG
GTATTTCCAGTATTCTTCTCTTGAAAACAATGCTACATTGAATAACCTTGTACATGGGTCACTTTGAAA
GTATGGATATGTATCCGTGGAATAAGTTTCCAGAAGTGGAATTGTGTCAGAGGGGTTGTGCATTTGTAA
TTCTGATGAATATTTATAGATTATATGAGAGTACCTGTTTACTCAAACTCTTGCCAATGCAGCATTATC
AAAGTTTTTTATGTTCGCCAGTGTGATAGATTAAAAAATGGTATCTCAGCCAGGCGCAGTGGCTCACGC
CTGTAATCCCAGCACTTTGGGAGGCTGAGGCGGGCAGATCACGGGGTCAGGAGATCGAGACCATCCTGG
CCAACACAGTGAAACCCTGTCTCTACTAAAAATACAAAAAATTATCCAGGCGTGGTGGCGGGCACCTGT
AGTCCCAGCTACTCGGAAGGCTGAGGCAGGAGAATGGCATGAACCTGGGAGGCGGAGCTTGCACTGAGC
CGAGATCGCGCCACAACATTCGAGCCTGGGCGACAGAGCGAGACTCCGTCTCAAATAATAAAAAAAAAA
GATGGTATCTCAGCATTGATTTCTTTGATCATCAGTGAGGTTGAGCATCTTTTCATAGATTTAAGAGAA
CTGTATGGTTTTTTGTGAGTTATGTTTCATATCGTTTACCCATTTTACTTTTAGGCTGGAAGCAGCTGT
TTTAGTGGAATGGTGGAACAAGAAGCCAGATTGCCATGGAGAGACAACTCTTTCTAGAGATTTGGCTAT
GAAGCAGAGTAGAGACAATGATAGCTGAAGGATTGATGTAGATGCAAAGAAATTTTTCATCTTCTTTGA

AAACTTAATTGTGTTAAAAACTGGTATGAAAGGGAGGGGTTAAAGCTAGAGATGGTGGTAGAAAAAAAT
GCAGGGTTCCTAAAGGACTGAGATTCCTGGATGGAATTTCAGGGAAGGGGAAAATTTCTGGATATAGTG
ACTGGGGAGTTAAGGGTGTCTAGTCCAATGGCTTTTATTTTCTTGGAAGGGTAGGCAAGGCCAACAGCC
ACATGTGTGGGAGGAGATGGTTAGAGGGGAGAGGAGGTTTGAAGGCACCGCTATGGAGAATTGGAGAGA
GCTAAGGAAAGACAGAAAGACTGCAGAAAGTGCTTAGGGTTCCACTGAAGCGGAAATAGTGATTTGTAG
TGATACAACCCTTATGAGTTATTTGATTTTTTTTTTTTTTTAAGCAGCATCTGGCAGTCCAAGTATAGG
GCTGACAGTTTGGGATTTTTCTTTCCATGTTGGTGTAAAAGAAGAACAGTGTAGTGAAGGAAGTTAGGA
CAAAAGAATGATTGAACTGACACCAAGTTTTCTTGATTTGGTAGAAAAGGAAATAAAGATAGAGCAGAG
ATATTGAAAAGAATTAGAGAGGGGTTCAAGAGACTGAAGGCCTGGGTGAGGTCAGAGAGCAGGTGTGGT
AGACATAACAGAGAGAACTACAAGGATAGAAAGTGTGGTTGGAGAGTGGGAAGGCAAGATTTATTCAGT
ATGGGGGCTTTTCTGGGTGATGACAGCATCTGGAGTACAGCCATTGTCGTGAGTGGCCCAAGTGTAGCA
GAGATAAAGCGTTGTTGGAGTGAAGGAAGTCAAGGAACTGAGAGGCTGGCCTAGATGGGGATTTTGGTT
GTCATCCATGAGGATATTGAAGTCATCCAGGAGAATAGCAGGCCTGGGGGACAGGAAGGAAACTGAGCC
ACTTACAGTGTCTTCAGTGATAGGAAAGCACAGGGCAAAAAGCTTTCAAGAACAGGGACTGTTAAGCCG
GGTACAGTGGCTCACACCTATAATCCTAGCATTTTGGGAGGCCAAGGCGGGTGGATCACTTGAGGTCAG
GAGTTCAAGACCAGCCTGGCCAACATGGTGAAACCCCATCTCTACTAAAAATACAAAAATTAGCCAGGC
ATGGTGGCACGCGCCTGTAATCCCAGCTACTTGGGAGGCTGAGGCAGGAGAATTGCTTGAACCTAGGAG
GCGGAGGTGGCAGTGAGCCTAGATCGCGCCCTTGGCTGCGATCCAGACTTCACTCCAGCCTGGGTGACA
GAGCAAGACTCTGTCTCAAAAAAAAAAAAGAAAATCAGACTCTTAATATTTGTAAAGAAGTAGTCCTTG
AGCTACTACTTAAGTCTAGAAAGAGTTGATATTCTTGTTTTAAGAGTGTTAGGGCACTTTGGGAGGCTG
AGGCAGGTGGATCACTTGAGCCCAGGAGTTCCAGACCAGCCTGAGCAATATGGGGAAACCTTGTCTCTA
CTAAAAATACAAAAATTAACCAGGCATGTGGTACGTACCTGTAGTCCCAGCCACTTGGGACGCTGAGGT
GGGAGGATCACCTGAGCCCAGGAAATGGAGGTTGCAGTGAGCCAAGATTGCGTGACTGTACTCTAGCCT
GGGCAACAGAGCAAGACTCTGTCTCAAAAAAAAAAAAGGCGGGATTATCATAGTGCCATTATTATTAT
GAGTTTATGATGGCTTTCTCTAAGCACCTTTTACATTCGGCATTTATTCAGTACCTATTAAGCATCAAG
GAGTCCAGAAAAAATTTTATATATAAATATATATAAAATATGTAAATATATATATGCATATGCTTCCCT
ATCTCAGGAAGGAAATATGTGAACATCAGGAACCGAAGTCTACTCAGTTACATGCCATTGGATATATCA
CACAAAGTGCTGAGGGAACTCAGAAGGCTCATTATATCTGGGGAGTGGGAAGGAGGCACAGAGATGTGC
TTTGGGAAGTTTAAATTAAAATAGCAAATGGGGAAAATGAAGACACACCAGACAGGGCACAAGCAAAGA
GACATGAAAGAGTAAGTCATGTGTTTGAGGATCTGGGGATCCACTAGTTCTAGAGCGGCCGCCACCGCG
TAGCAGTTACGG

Contig 4 (1241 bp)

TCGTGATGCGGTATTTTCTCCTTACGCATCTGTGCGGTATTTCACACCGCATAGATCCGTCGAGTTCAA
GAGAAAAAAAAAGAAAAAGCAAAAAGAAAAAAGGAAAGCGCGCCTCGTTCAGAATGACACGTATAGAAT
GATGCATTACCTTGTCATCTTCAGTATCATACTGTTCGTATACATACTTACTGACATTCATAGGTATAC
ATATATACACATGTATATATATCGTATGCTGCAGCTTTAAATAATCGGTGTCACTACATAAGAACACCT
TTGGTGGAGGGAACATCGTTGGTACCATTGGGCGAGGTGGCTTCTCTTATGGCAACCGCAAGAGCCTTG
AACGCACTCTCACTACGGTGATGATCATTCTTGCCTCGCAGACAATCAACGTGGAGGGTAATTCTGCTA
GCCTCTGCAAAGCTTTCAAGAAAATGCGGGATCATCTCGCAAGAGAGATCTCCTACTTTCTCCCTTTGC
AAACCAAGTTCGACAACTGCGTACGGCCTGTTCGAAAGATCTACCACCGCTCTGGAAAGTGCCTCATCC
AAAGGCGCAAATCCTGATCCAAACCTTTTTACTCCACGCACGGCCCCTAGGGCCTCTTTAAAAGCTTGA
CCGAGAGCAATCCCGCAGTCTTCAGTGGTGTGATGGTCGTCTATGTGTAAGTCACCAATGCACTCAACG
ATTAGCGACCAGCCGGAATGCTTGGCCAGAGCATGTATCATATGGTCCAGAAACCCTATACCTGTGTGG
ACGTTAATCACTTGCGATTGTGTGGCCTGTTCTGCTACTGCTTCTGCCTCTTTTTCTGGGAAGATCGAG
TGCTCTATCGCTAGGGGACCACCCTTTAAAGAGATCGCAATCTGAATCTTGGTTTCATTTGTAATACGC
TTTACTAGGGCTTTCTGCTCTGTCATCTTTGCCTTCGTTTATCTTGCCTGCTCATTTTTTAGTATATTC
TTCGAAGAAATCACATTACTTTATATAATGTATAATTCATTATGTGATAATGCCAATCGCTAAGAAAAA
AAAAGAGTCATCCGCTAGGTGGAAAAAAAAAAATGAAAATCATTACCGAGGCATAAAAAAATATAGAGT
GTACTAGAGGAGGCCAAGAGTAATAGAAAAAGAAAATTGCGGGAAAGGACTGTGTTATGACTTCCCTGA
CTAATGCCGTGTTCAAACGATACCTGGCAGTGACTCCTAGCGCTCACCAAGCTCTTAAAACGGGAATT

Contig 5 (1701 bp)

ATAAAAAACAGTTAATTAGGAGTATCTAGGTTATGTGAAGCATTCATCACCYYCCTAYTGRCAGAAAWT
WTCGWTAGGCAAATTTTATATTWTAAGTAACTTTAACATGAACACTTCTTAAACTTTGGCTCATAATTT
CACAAAAATTAGGCTGCAAGTCACCATATTCATCAGATACTGGCAGACACTAACTTCTGCGGCTATGAC
ACCAAGCAATACTGAAATCTCTTATCTTTCCAGGGGGGTTGTTCATGTATTCAGTGTTTGCAAAGAGTT
CCTGCTGAGCTAAACACAGTCCACTGTGCACTCTACGAAAGAGTCCATGAGACAAGCATGGGGGAGGGT
AGGAAGTTTAATACTTTCACAATGCCTGTGGAGACGCTGGCAGTGATGAAAGCCTAGAAAACTCATGAA
AGGACCTTTTATGAGCAGGGTGAATGTAGAGCACAAAAGCAAAGTCAGATGACCCACTTAAAGCTTTGC
CTTTACTGATGAGAATTCATTCTCATTCCAGATTAGTCTCTCTCTAGAAAAAGCAAACCTTATATAAGA
GTTGGAAAATTAAGATACAGGAAGTATAATTCTACTAAATTCCAGTTTTTCCTTCTCAAATATCAGCCT
AAGTCCTAAGGTCTGTGGCCAAAGACAGAAAATACAAGGCGCTGAGAAATATGCTATTTATCTTGGTGT

AACAATCTCTGACTGTTGGGGTTTGAGGAAATTTAAGCTCTACAATCCATAGATCAGACCAGAAGTTTA
GGGTAGTAATATTATGAGAGGAAATAGTTTCTTTCTGGAACTTATATAAAGCAAATAACTGGTAAACCT
GATTTGCAAGGTAATGACAGTCCAAGTTCCTTCAAAGCAGAGAACCACTTATTTGCTCATTCATTCAAC
TAAGTTCCTTGTCTTGTGCCAGGCTGGAGAGAGAAAGCAGCTCCTGTCCTCAAGGAGCTCACATCTCAG
GCATCTTCTCACCCTCCTTTCTCATGTTAACCAAAACATTTCAGGTTCATCAATGAAACTCTTCATCCA
GGAGGCAGATAAAATGGCTTCTCTTCATTTTGATTCATTTACTCTTTCTTTTATTTATTTTATTATTAT
TATTTTTTTTTTTTCTGAGAAGGAGTCTCGCTCTGTTGCCCAGGCTGGAGTGCAGTGGCGTGATCTCGG
CTCACTGCAACCTCTGCCTCCCGGGTTCAAGCGATTCTCCTGCCTCAGCCTCCCAAGTAGCTGGGATTA
CAGGCATGCGCCACCACGCCCGGCTAATTTTTGTAATTTTAGTAGAGATGGGGTTTCACCATGTTGGTC
AGGCTGGTGTCAAACTCCTGACCTTGTGATCCGCCTGCCTCAGCCTCCCAAAGTGCTGGGATTACAGGT
GTGAGCCACCATGCCCGGCCTACTCTTTCTTTTAAACAGAGAAATAAGATGGAATATTTTTATCCCATC
TTTTCTTCTGTAATTAAAAAAGGAATACGAAGAAACTTGACATAGTCTCTCTCCTCATGTGCTCTCTTA
CTTCCCATCCCAATTCCATGTTTGCTCTCTTTTTCCTCTCTCCTTCTGTTTTGTTGTGAATGAAGAATT
AGGTAACTAGTCCAAAACTACAGAGCTACACCTGGAGCCTAGATTCACTGGTAGCAAATCACTAATTTT
CTGAAGGTAAATGGGAGAAAATGGGGGTGGGGGGAAACTCATTAA

Contig 6 (1293 bp)

GGAGATAATAAGTATACACTATGTGTGAAGGGGGTGTCTCTATTGTTGTTGTGGCGATTAGGTGAGTAA
TTTTACACCTGGTTGTGAATAAAGTCCGAGATTGGGGGACTCACGCTTTGTAGAGTCTCCCAGGACAAT
GGGTTTTGCCCCCGTGCCCAATTAATAGTTAAAGGTTGGGGGCTTTTCGATTCCCTTATTCCAACTGGA
TAGGGCTCTTGAAATGCCCCCAAAAAAGGTTGACCCTTTCCCCACACGTCAAAGAGGGAATTCTCCCGC
TAGACTACCCTTGAACCTGAAGTGCAGTCCCTACAGGGTATTCTAGCTTGTTAGCATCCCCCACTGTGA
ATCAATCCCTTAAAATAAACCTATATAAGATGTATGTAATAGAGGACTAATCTTTAATATAATAAGCAT
ATATTTAATATAATTTCGGTACTACCCCCTTATCTGGGGGGGGGGTGGGGGGATATGTTCCAAGACTCC
CAGTAGATGCCTGAAACCACAGATGGTACTGAACCCTACGTAAACTGTATTTCATTCCTATACATGCAG
GCTATGTGTTGTAATCTGTAGGGTAACCACTAAAAGAACAGGGTCTATAACTTGGCAAGAGGGAAAAAA
GCTAGGATAGTAAAAAAGTCTATCAATCCAAAAAGCAAGAAAAAAGAGAAAAAGGAACATGCTGGCATA
TTATTATAAGTATTGTATTTTATTATTAGTTATTGTTAATTTTTTACTGTGCCTAATTTATAAATTAAA
CTTTATCACAGCTATGTATGTATAGGAAAATATATATCTGTGGTTTTAGGCATCCACTGGGGGTCTTGG
AATATAATGCTTCCCCCAGATAAGAAGGTACTACTGTAATTATATTATATGTCATATTAAGTATACATT
AATTCTACTAGGTAGTAGCCACATTATATATTAATTATATTAAATATATATCATATAGAATTATTTTAA

GGAATTGACTCATAATAGAAGAGGCTGGCAGGCTGGAGATTCAGGGAGGAGTTGCATTTCAAGTGCAAA
GGCAGACTGCCAGAGAATTCCCTCTTGCTTGGGGGAGGTCAGCCTTTTGTTCTATTCAAATCTTTGAGG
AAAATAGAAAGCAAAGAATATATTAACTATATTAAACAAACTAAATGTTCCAATTAAAATACAAAAATT
ATAAAGCCTAATAATAAAAGCCCTCAATTATATGCTGTTTAAAAGAGACATTTTTAAGCTTAAGGATAT
AGAAAAGTTGAACATACAAGCATGGAATAAAATAAGCATGCAAAATACTAG

Contig 7 (3140 bp)

CTCGGAGTCCACCGCGGTGGCGGCCGCTCTAGAACTAGTGGATCCCCCGAAAATAAAAGAATGGAATAA
AATAAGCCATGAAAATACTAGTATAACACTGATGTCAAAATCTGACAAAGCACACAAAAAAGAAAATAA
CTTTAACTGCAAAATCTTAAAATCCTAGCAAAGAAAAAGCAGCATATGTTATAATTATACCACAACCTG
ATCAAGTAAGGCTTACTTCAAAAATTTAACCATGGTCCATTATTGGAAAACATATTAATAAAAATCCTC
ACAAAAATAATTCAAAATATAAAAAGCCATATGATAAGCCTGATGAATGCTGGTTTACAGAACTGGTTT
TCTTTAAAAAGGCAATCATTGGGGAAATAACCCGCTTACTCAGTATTTACTATGTGCTAGGCCCTGTTC
CTTCTACTAGAAATAGTGAACAAATTCTAACAGAATCCCTATCTTCATGAAGCTTACAGTCTAGTAGCA
GAAAACTGACATTAAACAAATCACCTCACAGACAAATAGGAGAAGTGATGGAAAAGAGAATTATAGGAC
TCTAAGAGCCTATAGAAGAAGAAAATTTGACCTAGTCAGGGAGCTCAGCCAAGGCCTCCCTAAGGCACT
GATTCCTGAGCTGACAAGTAGAAGATGAACAGGAATCAGGGAGGCATTAAGGAGGGCAGGGAACTCCAT
GCCAGTCCGTAACCTCAGAAAGGGCAGGAGCAGGGTCTGAAAGAAGCCACCGTGTCTGAAGTATAAAGA
GTAAGGGGGAGCAGGTGCCAGGAAGCTGGAGATGTATACAGGGTAGGGCCACACAAGGGTGATTTTTCT
TTGTCCCATAAGCATTAAGAAGCCTTTGAAGAACAGAAGCATGACAGTGACCTCCCTGCCCTGCATTTT
GGAATGAACACTTCATTTAGCTGGGTGTAGAGAATATAGCACTGGATGTGGACAGTCCAGTTAGAAGTT
ACTGGTGGAGACACAAAAGTGTTACAAGGAAGGAGATATTCAGGAAGTAAACTGCACAGGGTGTGATAA
TAGATTTGCTCTTGGGGTGACAGGGAGTGCTGAATGCTACTCCTCTTTGGTTTCTGATTTACCTAACAG
ATGCCATCCAGTAAGTCAGATAACAGAGGAAAAGAGACAAGGCGTAGTGGCTCATGCCTGTAATCCCAG
CACTTTGGGAGGCCGAGGCAGGTGGATCATTTGAGGTGAGGAGTTCGAGACCAGCCTGGCCCCTCTGCT
GGTCTTGATTGAAGTCATTCATGCAACTGTAATCATCTAATGGTTCATCTGGGACTGAGATTGTCTCAA
GCACATGTCTGGCAGTTGGTGTCACTTGTTGATTGGGCCTCTCTCTTAACGTAAGGAAGTGAGCCAAAG
CTTCTCACATTATGACAGCAGTGTTCCCATAGAGCCAAATGACAGCTGTAAGTTCTCTTGAGGTATCAA
CTTGGAAGACACACCATTACTTCTGCATTTTATTGGTTTAAGCAAGTCACAGGGCCAACTCAAATTAAA
GGAATGGAGAAATAAACTTCACCTGTTGATAGGAGTGGCAGTGTCTCACTGTAAAAGGCATGTGTACAA
GGATGGGATTTTACGTAGCCATCTTTGCAAACAGTCTACCACAGTGTCTTTTTTCCTTTCGAGTGCTTA

AAAAAATTGTTTTTAAATAATTATTTGGTTTTCAGAAATTTCACTATTGTGTATCTAGACACAGATTTC
CTTTTTATTTATCTGTTTGGGGGGTGTTTAGGGCTTCTTGGATCTGTGGTTTGATGTTTTTCCTCAGTT
TTGGAGAATTTTCAGCCTTCGTCTGTTCTTCGAATATTTCTTCTGTTCCATTTCTCCCTTTCCGCTTTT
CTGAAACTGAAATTACATGTAGGTTAGATCATTTCATTGTATCCTTTATACCTCTTACCTTCTCTTTGG
TATTTTTTTATAAATCTTTTTGCTTCTCTCTGCTTCATTCTAGATACTTCCTTTTGACCTATTTACCAG
CTCACTAATTCTCTCTTCAGGTATATTTTACCTGTTCTTAAATTTATCCATTAAGATCTTTTTTTCAGA
TCTGCTATTACATTTTTATACCATTCTTGACTAAAATTCTTAATGCTACAGGACTGTTCTTCTTGTCTG
TTTCTTACTGATTCTCATGTTGCCTTTTTATGGACTAGACACTGTAGTTTTAAAATTATTTATAGAAAT
GACCTGAGACCTATGATATATTTTTCAAGAGAGGATTTACGTTTGTTTCTAGCTTTGCCTAGGAGTCTT
CAATCATTTTAATTCAGTTTCAGGGACTGATTTGCTTTTAAGCAGGGCTGTAGTCCCTACAGGGGTGGT
CAACTTCATTTCACTACCTAATATACCTATTATGTGTGGAGTACTTTGCTAGATGTTGGGTAGGTCTTG
TGAGCAGAGCAGACCTCTCTTTGGTCTGTATGGAGCACGGAGCTTGATTATAATTGGCAGGTGTGTGTG
TGTGTGTGTGTGTGTGTGTAAATAAATAAATATTTATTTATTTATTTATTATAGGCCGGGTACAGTG
GCTTACACCTGTAATCCCAGCACTTTATGAAGTCAAGGCAGGTGGATCACTTGAGGTCAGGAGTTTGAG
GCCAGCCTTGCCAACATGGTGAAACCCTGTCTCTTCTGAAAATACAAAAATTAGCCAGACGTGGTGGCA
GGTGCCTGTAATCCCAGCTACTCGAGAGGCTGCGGCATGACAGTCACTCAAGCCCGGGAGGTAGAGGTT
GCAGTGAGCTGAGATTGTGCCACTGTAATCCAGCCTGGGTGACAGAGTGAGACTCCATCTCAATATATA
TATGCGTGTGTGTATATATATATATCTATATCTTTAAGATAGATATATTTATATAGCTAAGTAATTAAT
AAATATATTAAGTTCTATGAAAGCAATGAGTAGGCTGCTATGGTTGTGAATATTTGGACTACACAGGGG
ATAAGAATGGGTCTACCATAATTAGCAGGGACAGGTTTTGTTTAAGCCAAAAACTAAGAGGGCTTAGAA
CAGAAACCGCCAGGCAGAAGCAGTTACCAGTGTGAAGACTAGATGACAACCAAAGGGGGATCCACTAGT
TCTAGAGCGGCCGCCACCGCAGGTGGAGCTCGCAG

Contig 8 (18073 bp)

AGCGCGTGCGCCGCTCTAGAACTAGTGGATCCCCCGAGGAGTGAGGAGGACCTCAACCCTACTTCCTGA
AATGGAGCTCTGAGATGTTGGAGTAGAAATTTGGAAACCAGAGAGAGAAGTAAGGGTAGTGTTGTTGCA
ACATGCATTGTATATGGGGGGTCGGGAAGTCACAGGAGTTTGCCTCAAAGTCTTTCTCGGAGACGGATG
AGGTTTTCACTGTGATTTTCCTGGTCGTGGTCTATGGATATAGTACCTGTTAGTGACATGGATCTTCTT
AACTTCTGATGTGTCTTTTCCTCCCTAGTGTACGCATACCAATTCTCTCCACAGCTTCCATCACCATGC
ATTTGTTCTTTTCCCTTGTTCTTGTATTACCTTTCTGGAAAGGAATTTTTATTGTAGGCTAATTGTTAC
TCCCACCAGTATTTAACCACTGGATATTTCATATGATTGATCTCTTCTGATTTGGAAAATAAAAATGTA

ATCTCATTATATTCATTTGATTAGTGGGGACAGTCAACACTTCTTTGTGTATTTTCTTAGCTGTTCGTT
TTTCTCGTCTGTAAATTATCTGTTTAGGTCCTTCAGATTTTCAAAATTGGACTGTTATGTTTTCAGTA
TTGTTATGAGTTCTTGTTTCAATTATTTATGACAGTTCATTTTCTTTTTTAAAATAGACTTTTTTTTTC
TTAGAGAAATAAGAAAAAATAAAAATTAAAATAGACTTTGTGTTTTAGAGAGTTTCAGGTTCACAGCAA
AATTGATCAAAAAGTATGGAGAGTTCCGGCCAGGCGCGGTGGCTCACACCTGTAATCCCAGCACTTTGG
AAGGCCAAGGTGGGCAGATCACAAGGTCAGGAGTTTAAGACCAGCCTGGCCAATATGATGAAACCCCAT
GTCTACTAACAATACACAAATTAGCTGGGTGTGGTGGTGCACACCTGTAACTGTACCTACTCAGGAGGC
TGAGGCAGAAGAATCTCTTGAACCTGGGAGGTGGAGGTTACAGTGAGCCACAGTCATGCCCCTGCACTC
CAGCCTGGGCAACAGAGTGAGACTCCGTCCTAAAAAAAGAAAGAAAGAAAATATAGAGCATTCCTAAAT
ACCACCTGTCCCCAACACCTGCACAGCCTCCTCATTATCCACATCCTACACCACTGTGGTACCTTTGTT
GCAATTGATGGACCAACATTGACTCCTCATTATCACCCAAGCTTTGGTGTTGTACATTCTGTAGATTTG
GACAAATGTATAATGACATGTGTCTACCATTGTAGTATCATACAGAAGAATTTGACTGCCCTGACAGTC
CTCTGCTCCACCTGCTTACTCCTCTCTCCCTTTTCCTAACTGCACAACCACTGATTTTTTTTTTTTTTT
TTTGAGAGGGGGTCTCACTCTGTCCCCCAGGCCGGAGTGCAGTGGGGCCATTTGGGGTCACTGAAAGCT
CCACCTCCGGGGTTAATGCAATTCTCCGGCCTCAGCCTCCCGGGTAACTGGGATTAAAGGGGCCCGCCA
CCAAATCGGGGTAATTTTTGGAATTTGAAGTAAAAAGGGGGTTTCCCCATTTTAGCCAGGATGGTCTCG
ATCTCCTGACCTCGTGATCCGCCCACCTCGGCCTCCCAAAGCTGGGATTACAGGCATGAGCCACCACGC
CCTACCTTTTTTTAAAAAACAAGGTCTTGCTCTGTCACCCAGGCCTGAGTGCAGTGATGATCACTCCT
CACTGAAGCGTCGACCTCCCAGGCTCAAGTGATCCTCCCACCTCAGCCTCCTAAATAGCTGAGACTACA
CACACACACCACCATGCCCAGCTAAGTTTTGTATTTTTTATAGAAATGTGGTCTTGCTGTGTTGTCCAG
GCTGGTCTTGAACTCCTGAGTTCAAGCAATTTGCCTGCCTTGGCCTCTCAAGGTGTTGGGATTACAGGC
ATGAGTCACCGCACCTGGCCTTTTTTATTTTCTTTTTTTTTTTTTAACCAGTGATCTTTTACTGTCTCC
ATGGTTTTTCACATTGGCTTCTGTCACTTAGTAATATATGTTTAAGTTTCTTCTACGTATTTTCATGTT
TTTAGCTTATTTCTTTTTAGCAGTGAGTAATATTTCATTGTCTGGATGTGCCATCACTTATTTATCCAT
TCGCCTGCTGAAGGATATCTTGATTGCTCCCAGTCGTGGCAATTATAAATAAAGTTGCTGTAAACATCC
ATGTGCAGGTTTTTTTTAAGTGGCATAAGTTTTCATCTCATTTGGTTAAATACCAAGGAGCACAATTGC
TGGATCATATGGTAAGAGCTTATTTATTTTTTTGAGAGACTACCAAGCTGCCTTCCAAAGTGGATGTAC
CATTTTGCATTCCCACCAGCAGTGAATGAGAGTTCCTGCTGCTCCATATTCTTACAAACATGTAGTATT
GTCAAATGTTTTGGATTTTAAAACCAAAATCCATTTTCATAGATGTGTAGTGGTATCCCGTTTTAATTT
GCAATTACCTAATGACTTGATGTTCTGTGTCTTTTCAGATGCTTATTTGCCGTACTGTTTATCTTCTTT
GGTGAGGTGTCTATTCAGGTCTTTTGCCCATTTTTAATCTGGTTGTTATTTTTCTTGTTGAGTTTAAGA

ATTCTCTGTCCTTTGTCAGATCTATCTTTTGCAAATATTTTCTCCTAGTCTGTGGCTTATCCTCTGATT
CTCTTGGCATTGTCTTTCACAGAGTAGACATTTTATATTTAATGAAGTCCAGACTATCAATTATGTTC
TCATGGATCATGCCTTTGATGTTATATCTAAAAAGTTCTCGCCATACCCAAAGTCATCTAGATTTTCTC
CTGTTATCTTCTTGGCATTTTATAGTCTTATGATTGATATTTAGGTCTATGATTCATTTTTAGTTAAAT
TTTTGTGAAAGATAATAAGGTCTGATATGGATTAATTTTTCTATATGTAGCTGTCCCGTTCCAGTATCA
TTTGTTGAAAAGACTATCTTGCTCCATTTTATTGCCTTTGCTCCTTTGTCAGTTGACTATATTTATGTG
GGTCTGTTTATGATCTCTGTTCCGTTCCATTGATCTGTTTGCCTTTTCTTTTGCTAATACCACAGTCTT
AATTACCATAGCTTTAAAGTAAGTCTTGAAGTCCAATAGCATTAATCTTTGACTCTTCTTTAATATTGA
GTTGCCCCTTCAGAATCTTAATGTCTCTCCATGTAAACTTTAGAATCAGCATTTTTATATTCACAAAAT
AACTTGCTGAGATTATGATTGAGATTGCATTGAATCTATAGGCTTATTTGGGAATAACTGACATCTTGA
CAATATTGAGTCTTCCTGTCCATAAACATTATTTATGATGGGCTTCTTCTTTATGTTTAGGAGCTTTTG
TTTTTTCTGTCAGATATTCCACTTCTACCTTTATGATTTCTTAATTGCCTTTTATGCTTAGAAAGTTTT
TCCTCATCCTGAGCTCACATATTCATTTATTTTCTTTTAAAATGTGTTTTCAAGCATTTAATTTTTAAA
CCTATGTGGAATTTATTTTGGTATATGGAATGAGGTGGTGGTCTAACTCCCTCCTCTCAAATATGTAGT
TATTTTTCCCAAAACCATTTTCTATTAATTTATCAAGAATAGACATGTATACATATACATATATAATAG
TCAGCCTTCCACTTGTTGTTTGACCCTTGTGAAGGAAATTGTATGAGTTTCCAATTTTGGATTAGGCTC
AGGTAGTAATTGAGCTGGGTTCTGCCAGAGATCCATGTTAATTCACTATCCAAACAGAGTTATAAAATG
TAAGTTTTATGAAAATCTAACAGTATATCACTGGTTTAATGATCACAGCCTAGGAAGAATGGGGAAATT
GTCAAAATCTTCTGTGGATGCACCTGAAGGCCACTGCTGAACCCATTTCCCTGCTAGGCACGGCTGCTG
GTACCAGGGGCAAACTCCTGGAGTATATATGAACCACCTACATCTCCTTCTCTTCCCCCCCTACCCTTG
AGATTTTCATGTGTCCCTTAAGGATGTGTGTCCTACTTCCCTTGGAGAGTCACTACCACATTGAACACT
TTAGACTGTGAGTCCTGTGAAGATGGGGCTCATGAGTGTATTGCTCCCCAGTTGTTTCTCTAGCACTAG
CTCAGTATAGGGCATAAAAATCTGAATGGATGAACAAACCACTATTACTGGTGGGGACATGCTACTATC
TTACATGGTTCGAGGTGGAATAAAGGTTGAGAACAGCTATATAATGTGTTCCTTGAAGGGCAGCAGTAC
ATCAGTGCAATCAGCCTACCTTCTCCATACTTCTCACTCTGAAAACTGTAAAGCTGCACCTAGCAATCA
ACTTGGGAGCTTTAAAAGGGACTGCTCCCTAGCTCTCACCCACAAAGCTGTAGTCTAGCACAGGTGACT
TTTTTAAAAAAGTTTTTTGGTCCAGATGTGATGACTCACGCCTGTAATCCCAGCACTTCGGGAGGCTGA
GGCTGGGAGGTCACCTGGGGTCAGGAGTTTGAGACCAGCGTGACCAACATGGAGAAACCCCATCTCTAC
TAAAAATTTGCCGGGCATGGTGGCACATGCCTCTAATCTCAGCTACTCGGGAGGCTGAGGCAGGAGAAT
TGCTTGAACCCGGGAGGCGGAGGTTGCCGTGAGCCAAGATCACACCATTGCACTCCAGCCCGGGCGACA
GTGCAAGACTCCGTCTCAAAAAAAAATAAAAAAGGAGTCCTATTAAGACTTATTTTTACAGGTTGGATA

TCTCTAATCCCAAAATCTGAAATGCTCCAAAATTTGAAACTTTTTGAGCGCAGACATGATGCTCAAAAA
AATGCTCACTGGGACATTTTGGATTTCAAAATTTGGATTAGGGACTAGGTGTGGGAGCTCACACCTGTA
ATCATAGCACTTTGGGAAGTTGAAGCAAGAGGATCAGTTGAACCCAAGAGTTTGAGAGCAGCCTAGACA
ACATAGTGAGACGCCGTCTCTACAGAAAATTTTAAAAATTAGCCAGGCATCGTAGTACATGCCTATAGT
CCCAGCTACTCAGGAGGCTGAGACAGAAGGATCACTTGAGTCCAGGAGGTAGAGGCTGCACTGAGCTAT
GATCATAACCACTGTCTCCATCCTGGGCAACAGAGCAAGACCCTATCTCTTAAAAAAAATCTGAAACAC
TGCTAGTCCTCAAGATAAGGGATAGTCAGTCTTTATAAAGACTCAATTAGTTATTGGATATCTGAGGAA
GCATGCATATCAGGCTCCCAAAAGATCATTGGTTTAGGCACACATTTTAATAGCTTGGAAATCCAGAAT
ACTCTTCTGGTGACCAGCTCAGACATAGTCCTGATAATATAGGACCTCATCTAACATGACTCCCTATTT
TCCAGATAAGCATGGATTCCTGGTTCATTCTTGTTCTGCTCGGCAGTGGTCTGATATGTGTCAGTGCCA
ACAATGCTACCACAGGTAAATTGTCATTTGATAAGGCTGCTATTTGAAATGAAATTTTGCTTTCACATT
TAATGAGCCACATTTGAAAACCGAGATGGTATTTGAAGAAAGGAATATAAAAATTTTATTCAAAGTGAT
GGTAAAATAGGTGTCTTCAGAAATCTTGGAATTGAATGCTCAGCATTGTTTTTCATACATACATAACTG
CTTTAAATAAATCAAAGAGATTATGTGTTCTTTCCTGAAAAGTAAAATAAATTGTTGACATTTACAACT
CTATATATGGTTTCTGAGGAACTAAGTGAAGAATCTTGTGTCTTTCTCCCTTAAACCGTAGTCCTTTGG
AGGAGGTAGGAAAGGTCCAGCATGAGATAAAAACGTAGGGGGTGGGTGGTGTTGAGGGGGATTGGTCTT
TGCTTGGTCTCCATATGTTTGAGAGTTTATTAAGGCTTGCTGCTTTGTGTCTCACAGCTTTTTAGCCTC
ACATTCTTCATGTGCTATTTCCTTGTTTTTTGGTGTTTGTAGTTGCACCTTCTGTAGGAATTACAAGAT
TAATTAACTCATCAACGGCAGAACCAGTTAAAGAAGAGGCCAAAACTTCAAATCCAACTTCTTCACTAA
CTTCTCTTTCTGTGGCACCAACATTCAGCCCAAATATAACTCTGGGACCCACCTATTTAACCACTGTCA
ATTCTTCAGACTCTGACAATGGGACCACAAGAACAGCAAGCACCAATTCTATAGGCATTACAATTTCAC
CAAATGGAACGTGGCTTCCAGATAACCAGTTCACGGATGCCAGAACAGAACCCTGGGAGGGGAATTCCA
GCACCGCAGCAACCACTCCAGAAACTTTCCCTCCTTCAGGTACTAGAGATGATTCTGTTTGTTCTTTTG
CTCTTTGAGTTTAGTCTTCCTTTTATTATCTTGTTTGTGTTTTCTAGCCTTAAAATTTCTTCAAATAAG
TAAAATTGCTCAAGTGAAGTAATGAAACCTGTATGTGGAATTTTTGGGTTAGCATGAGTGAAGAGGAAA
GAAGAAAGATTCTGGAGAATATCTTTCTGCTAGGTGGGATCCTGGTTAGATTGAGAGGACTTAAATGTG
TTTAAAGGTAGAGAAGAAGGCTTAAAAAGACAAGAGAAATAGAGGAGCTCATTGACGATGCAAGAGACT
GAAGATGAAAAGATACAGAGAATGAGTAATAAGATTAGGTTTGGAAAGGGAGGGATCCGTGGAGACCAT
GGAAAGGAGAATGGGTATTGATGTCCATGACAGTTAGATGTGAGATACAGAGAATGAGTAATAAGATTA
GGTTTGGAAAGGGAGGGATCCATGGAGACCATGGAAAGGAGAATGGACATTGATGTCCATGACAGTTAG
ATATGGAGTGGCAGGCCAGTGGCCAGGGGTGGCATCAGGCTCTGGGAAATGGTTACATTGCAGTGCCAG

TTGTTCAGGGCCTCAGGTTGAAGCAGTAGTCCCAAGGAGAAAATCAGAGACGTGGATCTGAGACCAGGG
CAGGTAAGACAAGTTTCTGACCTCTTTGAACCTTAGGTACCTTGTCTGTAAAAGAGGATTAGAGATACC
CTCAAAGGGCTTCTATGAGGAGTAAAGGAAATAATCATTACCTGATTGCTATGTAACTGTCATCCCTTT
TCTAGCAAAAATCACTCTTTCCTCTTCTGTGTTCCCAGTTAGATGGTGAGTGCCCCTAAGCAGAATCAC
ATCTCGCTCATGTGGAACATTCAGGAACTGTTTGCTCAGTTGATTCTCATTTGTTACTACAGATGATAT
CTTTTACTGCGCCTTATAACTCAGACCCTTCACCTGCCAGCTTTTCCCCATATTTTCTACCGTAAAGAC
AAGACAGCATTTGCAGTTAAGAGCACAGTCTTCAGTGCCACACTGAGTTTGAATCCCAGCTCTTCCATA
AACCAGCCATGTTTATGGCATAGCTGGCTTACTTTATCTCTCTACCTCGGTTTGTTCATCTGTGAAACA
AGAATGAGTGATAGTAATAGTTCTTACCTCATAGAGGAGATATTAGGATTAAACAAGTTAATATGGGTA
AAGCACTTATAAAGGTGCCTACACATGGTAAGCACTATTTTTAAGTGTGAGCTGTTAGTATTGTTGTGG
TTATTGCTCTGATAGTTACCAGTAAAATATATGAAGGTACCTTTAATGCAGATGGCATCCCACTATTCT
TGATGAGATAGGGGACTGCAGACAAATAATGTCTGATACTTGCTTTGTGCTTTAGAGTTAATGTAGTTT
TGTCATAGTTATTACTGTGTGCTAGGCATCGTACTAAGAGTTTTCTAGAATAATCCTATGAATTAAGTT
CTATTTTATGTTTTATAGGTGAAAGTATTTTACAATGATGAAACCATAATTTGTGGAATGTTTTTCAGT
GTACAGGTCATGACACAATTCATGAAATCACTTTAGCAGGCCACCACTAGTTGTTTGTTTTGTTTTATT
TTAATGGATGATCCAGTTCCATGTTTATTCTTTTAATGTTACATACAATTTTTTGAAATTTTAGTAACA
ACATAAAATGTTGGGTTGTGGCCATTGCTTAGGGAGAAAGGCAGGATAACTTGTACAAACTGTATGAGT
GAATGGAAAAGGTGGAGACTGTAACACAGGCCTGACTGACTGAACAGCCCATGTTCTATTGTGTACTGT
CTTTCATTTAACAGTTCTGTGACATGACCATGGATAATCATCTCCTTTTAACAGATGCTTGATTTCAGA
CTGTATATAGAGGTTAAATGATTTGTTTTAGATCTCAAGGCTGACAAATTAGGCCTATTTCTCACTTTT
GCGGTCTTTCCACTCTGCTTGTAGGGAACTTAGTTTTCCATAAACTGACTTAGGTCCAAATTGTGCCAC
AGCTAAGAATCTAGTTATTGTACATTTAACACAGTTCACGTCATAGGAGGCTGAGACTATGTTTCTCTA
GTGGCGTTTATTCAAGATGAGTAAAACACAAGAAACCATTATCGCACATGGGAATTTCATAGTCTTAAA
CCCCACATCCCACTTATCACCACCATTTACCAGTCCTCCTGTAACAGTTACAATTTTTTATTAAATCAG
TATTTGATGTATATTATTGTAATTATGAAATATTCATTGCTGAGCTATAAGTATAAATGGATTGTTTTT
CTTGTACAGTTTTTTTTCTGGATTTAATACTTACCTTATTTTTTGTTTATTTAGTTTTCTATTTAGTCA
GGCCAGGCACACTGGCTAACACCTGTAATCCCAGCACTTTGGGAGGCCAAGGTGGACAGATCACTTGAG
CTCAAGAGTTTGAGACCAGCCTGGGGAACATGGTGAAACCCCATCTCTACAAAAAATACAAAAATTAGC
TGGGCATGGGTGCATGTGCTTGTAGTCCCAGCTACTCAGGAGCCTGAGGTGGGAGGATTGCTTAAGCCC
AGGAGGTTGAGGCTGCAGTGAGCTGTGTTCATACCACTGCACTCCAGCCTGGGTGACAAAGCGAGACCA
TGTCTCAAAAAAGTTATTGCTACTCAATTCTTACCATGCTCTCCAGAGCCTCTCAAAACAGCTTTCTAC

AAAGTGAGATCTGTTAGATAATCTATTTCTTTTTACCTCTAGAAATTCCTCCTGAGCCCTCCATTGTC
TTATTCCAGTCTAGGCTTGTCGATCTCTAGGGCTACTACACAGATACATCAGCCTGAGATTTCCCTTCT
CTGTCATTCTGGGAATTCCCCTTGCTGCTGCTTCCTGACTTCCATATTGTCTTCCTTTTTGTCTTCTCA
TCATTCGGTAGATTCCTGAGAAAAGGGGTCCATGGGAGGCAAATTGCATCCTTACATATCTAAAAATAT
CTTTAGGGCTGTGCATAGAATTTGAGGAATATTTTTCCCCCAGAATTTTTAAAGTAATGCCCTAACTGA
CACCTGTTTACCAGGTTTGGAGGATTTTACTGCTATCTTAATCCCTAATTGTTTGTATGCTTTCTAGGA
TCTTCTCTTTATCATCAGTATCCTGAAATTTCACAGAGATGTATCTTGATGTGGGTCTTTTTCGTTCAT
TATTATGGATACTTAATAGGCCCTTTAGAGCCTTGATCTTGCATTTCTGAAAATTTTCTCCCATTTCTT
TGAAACCTTCTCCCCCTCTTCCTTTTTTTTTTTTCTCAAATTCTTAATATTTGGATATTGGATGTATCC
TGAATTAATTCTTTAATCTTTAAAATTTTTCCTTTCTGTTGATCTTTGCTTTGAGTCTTTTTCTCCTTT
TAAAAATAAACAAAGGCCAGCTAGGCACAGTGGCTTATATCTGTAATTCCAGCACTTTGGGAGGCTGAA
GCAGGAGGATCGCTTAAGCCCGGGAGTTTGAGACCAGCCTAAGCATCGCAGCAAAACCTCATCTCTACA
AATGATTTAGAAATTAGCAGGGCCTAATGGCTCATGCCTGTGGTCCCAGCTACTCAGGGCTGAGGCAGG
AGGATTACTTGAGGCCTGGCAGTTGAGGCTGCTGCAGTGAGCTGTGATCGCACCACCGTACTCCAGTCT
GGGCAACAGAGGGAGACCTCATCTCAAAAATAAATAGGCCTGGTGTGGTGGCTCACTCCTGTAATCCCA
GCACTTTGGGAGGCCAAGGCAGGTGGATCACTTGAAGCCAGGAGCTCAAGACCAGCCTAGCCGACATGG
CAAAACCCTCTGTCTACCTACTAAAAATAAAAAAATTAGTCAAACGTGTTGGCATATACTTGTAATCCC
AGCTACTTGGGAGGCTGAGACATGAGAATTGCTTGAACCTGGGAGGTGGAGGTTGCAGTGAGTCAAGTC
CCTGCACTATAGCCTGGGGAACAGAGTGAGACCCGAGACTCTATCTCAAAAAAAAAAAATCAGTGACAA
GTAAAAAGGTAGAATACCTTTTTTTTTTTCTTTGAGACAGTCTCACCCTGTCGCCCAGTCTGGAGTGCA
ATGGCGCAGTCTCGGCATACTGCAAACTCTGCCTTCAGGGTTCAAACAATTCTCCTGCCTCAGCCTCCT
GAGTAGCTGGGATTACACATGCCCACGACCACACCCAGCTTTTTTTGTATTTTTAGTAGAGACAGGTT
TCACCATGTTGGCCATGCTGGTCTCGAACTCCTGACCTCATGATCCACCTGCCCCGGCCTCCCAAAGTG
CTGGTATTACAGGCGTGAGCCACTGCGCCCAGCCTAGAATACCTTTTAAAAATAAATAAATAGGCCGGG
CGCGGCGGCTCATGCCTGTAATCCCAGCACTTTGGGAGGCTGAGGCGGGCAGATCACGAGGTCAGGAGA
TCAAGACCCTCCTGGCTAACATGGTGAACCCCATCTCTACTAAAAAATACAAAAAAAAATTAGCTGGGC
GTGGTGGCAGGTGCCTGTAGTCCCAGCTACTCTGGAGGCTGAGGCAGGAGAATGGCGTGAACCCAGGAG
GTGGAGCTTGCAGTGAGCCGAGATTGCGCCACTACACTCCAGCCTGGGCAACAGAGCAAGACTCTCTCT
CTAAATAAATAATAAATAAATAAATAAATAAATAAATAACTCCTTTTACAAAAGCATATATATTCATTT
TTTCCATTTATAATATAAATAATAGATATGCTGAGTTGATTTCTGCATATTGCTTTTTCAGTTACCCTA
TCATACTTGCTCTTTGTTTTAGTAAAGAGCTGCTGTATTGAAGGATATACCTTAATCTCTTTATCCAGT

TTCCCCATCAGTGGACACTAAGATTGTTTTCAGAGTACTCTTATAAACAATACAGTTTGTCATTTCAGA
CACATATGAGAATATTAGCAGGATGAATTATTTTAAGTCTGCATTTATAAATTTATGGATATTGCCACA
TTTACCTCTGCTAGGAAGTCTATTCCTATTAACAATATGTCAAAGTGCCTATTTTTCTAAACTCTCTTC
AGTGTGGTGAATTGTTAAACTTGGGGATCTCTGCCAATCTGACAGGTGAAAAATAACATCTCAGTGTAA
GTTTAATTTGCATTTTGCTGAGATTGAGCAATTTTGTGTAATTTAAAAGATCATTTATTTTTCTGAGCA
TTCTCTGTTGATATTCTTTACCCATTTTTATTAGAGTGTCAAGGTTTTCCTGACTCGTTTGTAGATGTT
CTTTGTACGTTTGGGAAATGAGTCCTTTGCCTATGGTAAAACTGCAAATGTTGTTCCCTAGGTGGTCAT
CTAGATTTTCTGCATTGCAGAAGATATCATTAGCTATTTTTAATTTTTTTAATTTAAATATTTCTCAGT
TTAGGTTTTCTAGGAATTGGGTCATATCTAGGAAGGCTTTCCTTACTCCAAGATTATAAAAATAATTTT
CTTCTGGACTTCTATGGTTTCGTGTGTGTGTGTGTGTGTGTGTACACGCACTTAAGTCTGTCTCGAATT
TATTCTGATGCAGAGTGAGCTATGGATCTGTTTTTCCCCAAATATCTAACTTGTCCCAATACCCCTTAA
TAATTTATTTTTCCTCATTGATTTGAAATGCCACCTATCTTATATATTGAATTCAGATATTTATTTACC
TCTTCATATGTATTTGAGTATTTGGGAACATTCATTTTATTTTCTATTAATCTTTTTCTCTGTCCATGT
GCAAAGCCTCACTGTCTCAATAATTGTAACTTTGTAAAGTATTTAATATCCAGTAAAATGAGTCATTCC
TTGTTAATTTTATTTTTCAGAATTTTGTTAGCAATTCTTATTATAAACATTAGAATTAACTTGTCTAGC
AGGAAAAAAAGTTTGTATTGATCATGTTAAATACGTAGATTAACAGAGAAAATGGCATCTTACAGATGT
TGAGTCTAACTATCCAAGAATGCAATATATTCCATTTTCTGAAGTCTTTTTTTTTAAATCTTCTGTTT
TTGTAATTATAAATGGAGCATTTTCTTCCATCAGATCTTCTAACTGGCTGCTGTTGGGGATATGAAGGC
TACTGATTTTTGTAGAGACATTTTGTACTGGCCACCTTAAACTCTCTTAGTATTGGAAGTAATTTTCTT
CATTAATTTTTATGGCTTCAAGTCATCTCATCTGCATATATCTTCCAAATTTTTAGAACTTTCTTTTTC
TTCTGTTTAATCGCATTGATGAATACCTCCAGAACAAAGTTAAGCAGCTGGTAAATGCAGACAGCATTC
TCTTGTATCTGACACTAAGGAGGACACTTTCAGTGGTTTTCATTATACGTGGTACTGACTCTTGAGTT
GAGATAAACATATTTTATTGTGTTCAGGATTTAATGAGCGTTTATGTTAGGAATGGGTGTTAAATTTTG
CCAGTTGCCTGTTCAGGATCAATGAGAAAGATCTGAATGATTTTTTTTCTCTTTTGGTCTGTTTCTATG
GTGGATTCTATTCCTAGGTTTGTTTGTTTGTTTGTTTATTTTGAGATGGAGTCTGTTACCAGGCTGGAG
TGCAGTGGCGCCATCTCAGCTCACTGCAACCTCCACCTCGCGGGTTCAAGTGATTCCCCTGCCTCAGCC
TCCGAGTAGCTGGGACTACAGGCACGCACCACCATGCCCGGCTAATTTTTTGTATTTTAGTAGAGACGT
GGTTTCACCATGTTGGCCAACCTGGTCTCGAACTCCTGACCCCATGATCCTGCCTCAGCCTCCCAAAGT
GCTGGGATTATAGGTGTGAGCCACTGCGCCCTGCCAGTTTTTATTTATTCATTTTTTAGAGACAGGGTC
TTGCTCTGAATTAATTCTTTAATCTTCTTAATTTTTCTTTTCTGTTGACCTTTGCTTTGCTTTAAGTCT
TTTCCTTTGAGTCATCCAGGCTGAAGTACAGTGGCACGATCATGGCTCACTGTAACCTTGAACTCCCAG

ACTTAAGCAAACCCCACCTCAGACTTCTGAGTAGCTAAGGACTATAGGCGCATGTCACCACGCCCAGCT
AATTTTTAAATTTTCTCAGAAACAGGGACTCACTGTGTTGCCCAGACTGGTCATGAACTCCTGGCCTCA
AGCAGTCCTCAGCCTTAGCCTTCCAAAGCACTGGGATTATAGGCATGAGCCAAGGCCGCCCAAACATAT
TGTATCGTTCCTGTAACAAGCTGTTGCAGTCTATTTGATATTATTTCTTATTTTTTCATTTAGAATTT
TCTCTGTCTAGATATTCTCAAATTATCTCTAAATGAGATTGATCTATGTTTTTCCTTTGTGTGTGTATT
CTTTTTGATAAGTTTTAGTTTTTAGTGTTTTGTTTTGCTACATGGAAAGGATTTGAAAGTTTACACTAA
AAAATATGCTTTTTTTTTTTAAGACAGGCTTTTTCACTGTTGCCTAGTGCTGGAGTGCAGTGGCATGAT
CTCGGCTCATTGCGGCCTGCACCTCCTGGGCTCAGGTGATCCTCTCACCTCAGCCTCCCAAGTAGCTGG
GATTACAGGTGTGTTCCACCATGCCCAGCTAATTTTTTGTATTTTTTTGTAGAGATGGGGTTTCGCCAT
GTTGCCCAGGCTGGTCTTGAACTCCTGGGCTCACATGATTCTCCTGTCTTAGCCTCCCAAAGTGCTAGG
ATTACAGGTGTGAGCCACCACATCTGGCCATTTCATTCATGTTTTCAAATGTATTTGAATGAGGAAAAG
TTCTCCCTTGTGATTATTTATTATAATAGCCTACAGAGCTATTAATTTTTAAATTTTGTTTACTTTATG
TCTCCTTTTTTTTTTTGTTTAGGCTGAATAACCATTTATTTCATAGGTTTATTGCCTTTTTTCTTCCAA
AGAACTTGCTATTGTGCATTTATAGTCCTTTTATGTTTACGTTTCTATTTCATTGATTTTAACTTTCT
ACCTTCTTTAGATTTATTTTGTTCTTTTTCTATCTTCTTGAATTGAGTGTGCTTTAATTGCATTCTTTC
CAGTTAATTAACATATTTAGTGCTGTGAATTTTGAACAAGCACAGCTTTAGCCACATCCCATAGGTGTT
TCTATAGGCAGTTGTATTAGGATGCGCTATAAGCTGCTCTGACAAAGATACCAAAATTCAGTGACTTAA
ATAAGACCAAAGTGTCTTTCTCTCCCCAGTTACATTCCAGAGGTAGACAGGGCCTTCGTCTCAGTAGGG
ACCAAATTCCTTTCCTCTTGTGGCCCTGCCATCCTAACAATATTGCCCTTATCTGTTTGGTTAGAGATA
GTTCTCACCATTGGGTTCTAGTTCCAACCACTGCGAAGGACAAACAAAGGGAATAGGGGCCATTTCTCT
TCCAAAAGATGTGACCTGGAAGTTACTCACATTGCTTTAGCTCACATCCCGTTGGCTAGAATTCATCAC
ATGACCACACCTAGCACAAAGGAGTCTCAAATATAGTCTGCCAGGAGAGCTTGGTGCTCAGCTAAAAAA
CAAAGGTTCTGTATCAAGGCAAGAAGAGAAAGAGACTGATCTGAGGGGAGGAGAGTTGGCAGGTTCTGT
CACAAAACTTCTCGTCATTGTTATTTTAAGGTATTTTTCCATTTTGGGTTTTTTGTTTGTCTGATTTT
TTTTTTTTTTTTGAGATGGAGTCTCGCTCTGTTGCCCAGGCTGGAGTGCAGTGGCGTGATCTCTGCTC
ACCGCAAGCTCTGCCTCCTGGTTCACGCCATTCTCCTGCCTCAGCCTCCCAAGTAGCTGGGACTACAGG
CGTACACCACCACGCCTGGCTAATTTTTTTTTGTATTTTTATTAGAGACAGGGTTTCACTGTGTTACC
CAGGATGGTCTCATTCTCCTGACTTTGTGATCTGCCCACTTCGGCCTCCCAAAGTGTTAGGATTACAGG
CGTGAGCCACCGCGCCCGGCCGTCTGTTTGATTTTTGAGATGGAATCTCACTCTGCCCCCCTTCTGGAG
TACAGTGGTGTGATCTTGGGTCACTGCAACCTCTACCCTCCCAGGTTTAAGCAATTCTTGTGCCTCAGC
CTCCCAAAGTGCTGGGATTAAAGACGTGAGCCACTGTGCCCAGCCCATTTTGGTTTTGATTTTTTTTT

TCTTTGAAATAGAGTCTCGCTCTGTTACCTAGGCTGGAGTACAGTGGCATGATCTCGGCTCACTGCAAC
CTCCCCCTCCTGGGTTCAAGTGATTCTCGTGCCTCAGCCTCCCAAGTAGCTGGGATTATAGGCACCCAC
CACCACGCCCAGCTAATTTGTTTTGTATTTTTAGTAGAGACGGGGTTTACCATGTTGGCCAGGCTGGT
CTCGAACTCCTGACCTCAGGTGATCCACTGCACCCGGCCTCATTTTGGTTTTGATTTTTATTTTCAAAT
GTTTTCTTACTTTGTCAATTTCTAATTTTATTGCATTGGGACAAAAGAATATTGTACTCTTTCTACTGT
TGGGGTTTATAAGGGCTGTGGATATTTCACTCGCCTTTGAAAAGAAGGTTTTCTCTGTTAGTCTGTAGA
GTTTGGTATGTACCAATTAGATTTTATTACTTATCATTTTGGTCTTTTGTATCCTTACTTAATTTTGTC
CTCTTGAATTTTAATGGAGCAAAAGACATAAAGTCCTCTAATAACATGCGTTCTGTTTGCATTCTCATA
CTTTTTATGAATATTGATGCTGCACTATTTGTGTACCCAGGGAGAAGGCCAGACCACTGTCCAAAGTTT
AGTGAATCTGGGCAGCCTTGTTTCCCAGTTGTTGGAGGATGCCTCATGGAGGAAAGCATTCCTAATCCT
GGAGCTTGTTTTGTTGTACTCTAATTGAATTGTAATGTGTTTCTTTAACCTGAATGAATGTTTCTATTT
TTTACTTATTACACAGGTAATTCTGACTCGAAGGACAGAAGAGGTGAGCTGCTCACCTTATATCTGTTG
TTCCTTTTACACAGTGTACAGTATTCATTTATTTCCTCTGCTCACAGTCTGTGGTAACCGTGTGCATCT
GTGGCTGTGTTGTTTGTTTACTTTCCCTTAAGTTATTTCCATGTTAATCTCATGGAGAAGAGCAATAGA
AACAAGTACTGTATTCAGTATGTTTTTAATATAGACTATGGATTCTAACAGCTATGATGTATTTTAAC
AAGTAACAAAATATATCTTACTTTGACATGTCACTTTGTTAACATTACTTTTTGGTGATATTAGGTCAT
AATTTCTATACCATTAGTTACTTCTGATTTCTAGGCCACAGTTCCCTTTAAATATTCTTTGTGTTGTTT
TTCCCCTAGTGTATAAAATGTCAACCCTTTGTGGCTTTATATGGATTTTATGGATTTTCAGCCCTTAAA
TGTAAAGTCTCTATGGCCTGAGATGTTGTGTCTGTGGTTTAAGCTGGACTGCTGAGTCCCTGGTCACTA
GAGAGTAGGGGGACATGGGTACTTGTCTGCAGAAGTGTGGCACATTTTGCCTAGAATGACAGTAAGGCT
GCTATCAAAGAGCATGAGAGAAAGAGAAAGAGATCATCTAACATTCTAAGAAGTGATTATTACATTTGA
GTTTTAAAAATGTTACTATTCGAAGCAGTGTTTTTATCATAATTTTCTATTTTATCAAATCAGACTTGA
GTTTTTTTTCTGATTCTGTTATTTAACCATACACAATTTTCCCTGTGTAATTAAGTAATGGAACACTTG
GAGGCATATGAAGTCCCACTAAGTAGGGAGCATTTGAGTCAGAAAAGTGGGTACTCTCTTCCTTTATGT
GATGTCCATCTGCCATTGTATTTGGTAAGGAATAGTGAGGTGTTACCATACTGTGTACAGATTTCCCTC
ACTTTTCCACCTCTCACTTTCCTAAACTTGGGAACTAAACATTGGATTAATACAGTGTCTTTGCTGTTC
AGATTCACTTGCCAGATTTTATCAAATGTAGACTTAAATAGGTTTTATTGTGATAGATATTTACTTGCT
CCCTAAAACTGCTCTCTTAACCAGCCTTACAATAAAGTCAAAAGTCAAAGTGGTAGGCTTCAAGATGAA
ACATAAGATCTGTTGACTCCTTCCTCTATTTAGTATATATTTTCATAATATTCAGCCTTTTCTTGCCCC
AGATATCATATCTATTTTACCTACCCAATATTTAAGTAGTTTCCATGTTGTGATTAAGAAAACAAAATT
ACCATAATTACCTAGATTATTGCTAATTGTGACATATGTAAAGTCTATTAATGTAATAAATCTCCTTTC

TTAAGTCAAAAAATAATTTTGTGTAATTCCAAACAGGAAACTGAAAAGGCATAGGTATTCTCAGCAGTC
TCTAAAGTCCCAAAATCTAATGGCAATTTTACCAGAGCAGATCTTTAGAAGTATTGCTATAAATTTGGA
TATCCCATTCTAATTTTAAGCCAAATGCTTTTTGAGAAATAAGCCAGCTGTTTGGAAATGCTTGTATTA
TAATCGGTTTGATAAGCAGTTATGTCTTATGCAGATGAATTAGGGGCTACCTGTTTTTATGCACTGGTC
TTTGGGGTGCTTTTGAACAGTAGTGTCTGATGTTTTAATTGTCAAAGCAAAAAGAAATGAGAGGGAGGG
CAACTTTTCTTCCTCTTCTGAATTCCAGGAAACTGGTTATTTTCTCATGCCATATGATTTTAAAATATA
TTCCCAGCCAGGTGCAGTGGGTCACGCTTGTAATCCCAGATTTTTGGGATGCCAAGCGGGGGGA

Contig 9 (7505 bp)

TCCGAGCTCCACGCGGTGGCGGCCGCTCTAGAACTAGTGGATCCCTCTGGTGGCCCATTGAGAATCAAA
ACTTGCAGTGAGTGACTCTATAAAATGGAAAATTGAATCAAGTCTGAAAATGATCCACATAGTTCTACA
GCAGGGCTGGACACCGTGGTCAGGACCTCAATATATTCTGCTTCCACAGAATTCAGACAGTTCAGAGTT
TGGTGAATTAACCTCAAAGGCAGCAAGATATCTGTCCCGGGAGTCAGCAGGTAAGCATAGCAGAAATGG
CTGGAGCAGCGGGAGCCTGCTTTCCTTCTGTTGGCTGCTAGCGTCCACTCCATTATAGCTCCTGATGGA
AGATTTCTACAGAGTGATGCCTCAGAATCTTCCTTATACCTTTCTTCCATGATCCTTGCACCTCTTTTT
CTAGATTTGCCCACATTCTTATGTGCAAGTAACTAGATATACATTATCAGACAAGCTAGCAGACCTGCA
TATATCCACTTCCCTACTTTTCCTATAATTTCTTCACCTGAACCTCTATCATTCTTCTCTTTCTGTGTT
GACTCTGGTGTTAACCTTGCAGGCAAGTTGAGCGTGGGTTTGGTGTCACAGTGAAGGACTAAGGGAATA
GTTAGCCTTCTATTTATTAACAAATCTTCCCTTTGATGTCTGGATCAGTGTCTCTCTAATAGGAATTAT
TGGCATGTTAAGGCAAAGAACATATGCTTATTGAGTGCTGACTGATTGGGGTTAATACTAATTTGATAC
TATTAAGGTGTGGGGCCCAGGAATGCCAAAATTCTACCTCAATGTAGAGCCACCATTCCCCTTGAGGTA
ACCTAGGTGGGATAGATATACGTGTAAGGGCTAATGGAAGATAGGGAATCAAAGTATCACTTTATTTTT
TATTTTTATTTTTTATTTAATTTTTTTGAGATGGAGTCTTGCTCTGTTGCTAGGCTGTAGCGCAGTGGC
ACAATGAAAGTATCACTTTATTATTATCTGAGCTTGTGCCCTAAACTTCACTGCAGAATATGCTGGTAA
AATGGACTGGATTACAGGATTTAGAGGCAAGGTCCACAGGTCAGGATAAGAGGTAAAGAGGGAAATCTT
TCTCTCTTCCTAAGCCCAAACCCTCCATGACAATTGAGATTAAAAAAAAAAAATAAACTGATGAGAGAA
TCCAAGCACAGTTGATCAAAGAGGAAAGAGAAATGATGATGTTTCCCTCTTTCTTTTTCATGAGAAAGT
GGCTCTCTTATTGATCGGCTACTTGATTAGAGAAACAGTGGGGGAAAGAACTGCCATATCCACATGTGC
AATTTTTTAAAACACACAGTGATTCTGAACACTAGTATAAATTCCCAGTCAGTGTTCTGGCCATCTGAC
TACTCAGGTTATAATACCTAATTTTTACAAGGGAGTTGGGAAGTGTGCCAAACCTGTAGAAGTCTATAT
CTACTGTATTCAGATTTTATATGCATTATTTTATATAACCTTTTGACCTCTCTCCTCTATCATCACTTG

AGTGATTTCATCCAGCGTCATCATTTAACATATTTTAAATAACTCTATATACTGATAATTCCCAAATTT
ATATCTCCATCCCCGATTGTTCTCCTAACCTCCAGCCTCTAATATCCAACTGCCTACTCAAGCCTCAGC
AATGGTGAGCGCCCCTGCCCCAGCCTCGCTGCTGCCTTGCAGCTCGATCTCAGACTGCTGTGCTGGCAA
TGAGCGAGGCTCCGTGGGCGTGGGACCTTCCGAGCCAGGCGCAGGATATAATCTCCTGGTGTGCTGTTT
GCTAAGACCGTTGGAAAAGCACAGTATTAGGGTGGGAGTGACCCAATTTTCCAGGTGTCGTCTGTCACA
GCTTTGCTTGGCTACGAAAGGGAATTCGCTGACCCCTTGCACTTCCTGGGTGAGGCAATGCCTCGCCCT
GCTTCGGCTCATGCTCAGTGCGCTGCACCCACTGTCCTGCACCCAGTGTCCGACGAGCCCCAGTGGGAT
GAACCCGGTACCTCAGTTGGAAATACAGAAATCACCCGTCTTCTGTGTCCCTCATGCTGGGAGCTGTAG
ACTGGAGCTGTTCCTATTTGGCCATCTTGGAACTGCCTTGCATTCAGTTTTTAATATCCAACTGCCTAT
ACGATATCTTCACTTGGATTTTGAATAGGCATATCAAACTTGTCATGTTCAAAAGTGAGGTTCTAATCT
TCCCTCCCAAACCTGCTTCTCCCATGGCTTTCCCCATCTCAGTAAATAGGAATTTCATCCTTCCAATTG
CTCATGCCAAAAATTTGGGAGTTATCCTTGACTCTTCTCTTTCTCACACCCCACATTCAATCCATCACC
ACATTCTGATGCCTCTATCTTCAAGATATACTTAGACTTTCACCACTTTTCTTCACTCTGCAATTACCA
CTTTGGTCCAAGCCACTGTTATCTCTTTCTTGGATTATTGTAATAGCTTCCTAATAATTTGTCCCCTTT
CTTCCACCTTTGTTTCCCCTACAGTATAATCTTAACGAAGCAGCCAGAATGGTTGCCTACAAACCTTTA
AAATGGTAAGCCAGAACATGTAGGTATATTCAAAACCTTCCAATGGCTTGTCATGGAACTAAAAGTCTC
TACATTGGCCTATAAGACCCTATGTCATCTACCCCTAGTCTCCTCCTTTCTAACTTCATCTCCTGCTAT
GCTGTCCTTCAACTCACTCTGCTCCAGGTGCTCTGGCCTCCTCAAACACACCACACACACTTGCAGCTC
ACAGTCTTGGCACTTGCTGTTCTTCTCCTCTAGGACCTTCTTCCTCCAACTGTCTGGTTCACCCACCCC
TTCCTTCTGGATTTCTGCTCTGATGTCATTTTATCAGTGGGCACTTCCCAATTTCTCTATTTAAGACCA
CAATTCCAGGCCAGGGTGGTGGTTCATGCCTGTAATCCCAGCACTTTGGGAAGCCGAGGTGGGCAGATC
ATGAGGTCAAGAATTCGAGACCAGCTTGGCCAACATGGTGAAACCCCATCTCTACTAAAAATACAAAAA
AAATTAGCCAGGTGTGGTGGCACATGCCTGTAATCTCAGCTACTTAGGAGGCTGAGGCAGGAGAATCGC
TTGAACCTGGGGGGCAGAGGTTGTAGTGAGCCGAGATTGCGCCACTGCACTTCAGCCTGGGCAATAGAG
CGAGACTCTGTCTCAAAAAAAAAAAAAAATTTGCTGTTATTTCCTATACTATTTTTGTAAGGCAAGGAC
CTTATTATTTTCCTTGATAATACCTCTCACACTTTATAATTACATATTTGACTTTGTTGATTAATGAAT
ATCCCTCCTTTATAGCATAAATTCCACAAGAGCAAGGATTACATGTCTGCTTCATTCTCACTGTACACC
TAAAACCTAGCACAGGGTCTCACACATAACAGGCACAAAACAAACAATGGATTACGTTGAGCCAAAGAA
CAAAAAAAAATAGTAATTTATCACTAAATGTCTTTGTTAAATTCCAACAACAGGGGGCAGTATATCAGG
TATTATAAGAAAGTAATTAGGCACATCCCAGCACTTTGGGAGGCCGAGGCGGGTGGATCACAAGGTCAG
GAGTTCAAGACCAGCCTGGCCAATATGGTGAAACCCCGTCTCTGCTAAAAATACAAAATTAGCGGGTGT

GGTGGCACACCCCTCTGGTCCCAGCTACTCAGGAGGCTGAGGCAGGAGAATCGCTTGTACCCAGGAGGC
GGAGGTTTCAGTGAGCCAAGATCGTGCCACTGCACTCCAGCCTGGGTGACGGAGCGAGACTCTGCCTCA
AAAAAAAAAAAAAAAAGAAGAAGAAGAAAGTAATTAGGCACCTTTGGCTTAAGACACTGGGCTAAATCC
ATGAATTTACTTCATCTTCCCCCAAAGCACACTGACATGGTAGAAGAAATATAAAAATACTAATGAATC
AACAGCATATCTGAAAGGCAGCAAACGGTGGCATATGTAGATCAGAATCTTTGAGAGATTTCTGGAAGA
CAAAACAGACCAGACTCGATGTCCAAGAGATCAAACAGAGCCAAAGAGCCTCCAGCTGAAAACTAAGTA
CTAGTTCTACCAGTTTGGGCCTGGAAACACCTCAAGCTCAGAGGGAATTGGGACTGGGGTTGAAAGTGG
ACCTTGAGGTACCAGGATGGTACTTAAGCAAAGGCCTGCCAACCCAGCACCAGTACACCCACAGCCCAA
ATGACAAGCGGGGCTTCCCATCTAGACTCAGCTGGAAAAACAGTGCTCTACACAGAGTAGAGAGTTTGT
CACAGAGACTGGTAAGGGCTTCTTTTTTACAAAACATATGCTGCATATATATTTTCTCAACGTCACACT
AATGACATTTTGGGCTATACAATTCTCTGTTATGTGGGTCTGTCATGTGCACTGTAGGACATTTAACAA
TATCCCTAGCCTCTAATTATTAGATGTCTGTAGCAAATTCCCAATTTTGATGACCAAAAGTATCTCCAA
GCATTGCTAAATGCCTTTGTGGGGGAAATAGCCCCCAGTAAGGAACCACTGGTCTATACTCACGCCATT
CTAACTGAATTCTTTTAAGGCAAATCCGAGACCTAGCATTTCAAATGCAATTACTTAGGTATGTATCAC
CAAGAGATCAAGATTCTTAACATAAACATAATACTATTATCCAATTTAAAAAGTAACACTAATTCCTTA
GTATCATCTAATATTATTCAGTTACTGCTTGAATTTCCCTGAGTGTCTCATAAATGCTTTTTTTTTGTT
TTGGTTAGAATTGACACCAGAGCAGGTCTACACTGCATATGATTGTTAAGTATATTGGGTCCACAGAAG
GTCTCCTGGGGCCTGCAGACAGAAAAAAACCATAGTAGTGCCCAAGCTAATTCTAGGCAACCACAAGAG
AGGAAAGGAAAAAGAAAACGGCAGCTCGCCTAGAGGATAACTGCACCCTGCCCCGATTTTCCTGAGCCA
TCACTGAACCCCTTCCTGGTTTAGGACGTATGTCCATGTTTGTCTTCTGAAGGGATGAAGGGACACCTA
TTGTGAGCACAGTCTAAGCCACTCAATGGTCCAGGGCATAGCTCAAACAGAGCAACAGTAGCCCTGGGA
AATGGAGGTGACAAAAGAAACAGAATAAATCTTTCAAAATATACTGCAATTTGTGCAACAGGATGCCAT
ATTGATTTAAAAAAATTTTTTTCTTAAATTTTTTGTAGAGATGGGGGGAGGGGGTCTTGTTGTTGCCC
AGGCTGGTCTTGAACTCTTGGTCTCAAGTGATCTTCTTGCCTTGGCCTCCCAAAATGCTATGATTATGT
GCGTGAGCCACTGCTGCATTGCGTTTTTTTTTCTTTTCTCGAGACGGAGTCTCACTCCGTCACCCAGGC
TGAAGTGCACTGGCGTGATCTTGGTTCACTGCAACGGCCTCCTGGTTCGAGCGATCCTCACACCTTAGC
CTCCCTAGTAGCTGGAACTGCAGGCCTGGCTAAGTTTTGTATTTTTAGTAGAGACAGGGTTTCACTATG
TTGGCCAGCCTGGTCTTGAACTCCTGACCTCAGGTGATCAGCCTGCCTCAGCCTCCCAAAGTGCTGGGA
TTATAGGTGTGAGCCACTGTGCCCAGCCTACATTGATATTTTTTAAAAGCCACTATTTAAAAAGGAGTA
ATCTGAGTAGTAAGAAGGAGTTCTTTAAAAACTGGCCGGGCATGGTGGCTCACGCCTGTAATCCCAACA
CTTTGGGAGGCCGAGGCAGGCAGATCACCTGAGGTTGGTAGTTTAAGAGCAGCCTGACCAACATAGAGA

AACCCCATCTCTACTAAAAATACAAAATTAGCCAGGTGTGGTGGCACATGCCTGTAATCCCAGCTACTC
TGGGGGCTGAGGCAGGAGAATCGTTTGAACCTGGAAGGCAGAGGTTGCGGTGAACCGAGATCGTGCCAT
TGCACACCAGCTTGGGCAACAAGAGCAAAACTCCGTCTCAAAACAAAACAAAACAAAAATGAAAACAAA
CAAAAAAACACCAACATGATTAGGAGGGAAAAAATCTAGATAGAAAGGCTTAACAGGGCCGGGCACGGT
GGCTCATGCCTGTAAGCCCAACACTTTGGGAGGCCAGGGTGGGAGGACTGCTTGAGGCCAGGAGTTTGA
GACCAGCCTGGGCAACTTAGCGAGACTCTGGTAGTCTGTCTCTACCAAACAAACAAACAAACACCTGAT
TAGCTGGGCATGGTGGCATATGCCTATAGTCCCAGCTACCCGGGAGGCTGAGGCTGGAGGATCGCTTGA
GTCCCAGAGGTCAAGGCTGCAGTGAGCTGTGATCAGGCCACTGCACTCCAGCCTGGGCGACAGAGCATG
AGTCTGCCCCAGCCCTGCCTCCAAAAAAAGAAAGGCTAAATAGGAGAACTGATATAACTGAAAACCAAA
TTAGTTGTGTGAAAGAGCAACTGTCCTGGAAGCTCCCAGAACACAGAGCAATAAGAGATGAAAAATATG
ACAGCATAGAAAAGAAAGGAACTGGATAGGTCCAGGAGATCCAATACCTGTGCAACAGGAGAGTCCAAA
GAAGAAACCAGTAAGAAGGGAGAGAAGTAATACAAGAAAGTTCCTGAGTTATCAGGCCAAAAGAAATAA
TCTAGTTTGTGGAGTAATATTGACAAAAAAATCTTTACACCTAGATGTATTCTGAAAAAATTCTTAAAT
TCTAATTGAAATCAACCAACGAACCACAGGCCAGCCTTAGAAAACCATTTCCAGGGCATGGGGTTTTAG
GGTCTGACAGACCTGAAGTTCAAATTCCTACTATCCTAACTTACTAGTAGTGTGATAATCTCTTAGAAC
AATGTATGAAATGGAAGCATAATAGCACCCTCCACCTTTTAGAGTTAATGGGAGATCTAAAAGAGGTAA
CATTTGCAAAGTGTCTGACATGAAGGGAAGAGATTGGCTTTGGCATCCACAAGTTCACACACTAGCAGA
GAACCTCAGTCCAGCTTCCTACGCTCAGGCAGTTCTTTGCCTAGAAGAGGGGTCGGCAAACTATAGCCC
AAATTTAGCCCACTGCCTGTTTTTGTAAATAAAATGCTATCAGAACATGGCCATGTTCATTCATTTACA
TACCATCTATGGCTGCTTTTACATTACAAAGGCAGAGCTGAGTAGATGAGACAGAGACAGTATGGTTAC
AAACCGAAACTGTTTCAACCCCAACTTCATTCCAGCAAAGTTTTACTTTCTAGATTCAGGCCAGGGAGC
AAGCATGAAAATGAAAACCACTAAAATGGTGTCCCGGGACAACAGATACCTACTTGCTATAACTTCTTT
CCTTGAAAACAAAGGGCCATATTAATTGAAGGGCTCACCTCTAAACAGGTGAGTGACTTAAGGACTTCA
GACACACACTGGTCAACTACAAACTAGTCAGTAAAGGAATAGCCATAGTCCTATAGCCCCAGTTCCTAT
GGCCCAGGGGGATCCACTAGTTCTAGAGCGGCCGCCACCGCGGTGGACTCCAG

Contig 15 (529 bp)
GCTGAGGTGCATCGCGGTGGCGGACGCTCTAGAACTAGTGGATCCCCAAACAAAACCTGTCCCTGCTAA
TGATGGTAGACCCAATCAGATCCCCGGAGAAGCCGAAATACGGAAACCATATCAGCATACGCATGGCAT
ACATAGAACCCCATACATGGATTGCTTACTCAGCCAGATATAGAAATCTATCTTCACGATAGAGATATA
TATATATAGACACACTGCATATACAGATGTGAGATGGAGGCTCACTCTGCCACCCGTGCTGGATCTACA
GTGGCACAAGCTCAGTCCACAGTCACGTCGATCTGCCGGGCGTGACCGACTGAGATGCAGCGGCCTCGG
GCGTAGCTGTGAGTACACGCACCAGTCATCGCGACTGGCTGCAAGTGGTATAAGCGGAGGGACAGGGT
TACAGCATGACGGCTAGGCAGGCCGCAAACTGAGGACCACAAGAGTGCCACGCTGCCCGAACGCATGCA
GTGGCGAGATTACATGGGGCAGCCACTAGAGCCGCCGTATCAGAAA Contig 33 (635 bp)
TACCACGCGGTAGCGCCGCTCTAGAACTAGTGGATCGGGTAATCCAGCACTTTGGGAGGCCAAGGAGGG
CAGATCACCTGAAGTCAGGAGTTTGAGACCAGCCTGGCCAACATGGTGAAACTCCATCTCTACTAAAAT
TACAAAAATTAGCCGGGCGTGGTGGCGCATGCCTGTAATCCCAGCTACTCGAGAGGCTGCGGCATGACA
GTCACTCAAGCCCGGGAGGTAGAGGTTGCAGTGAGCTGAGATTGTGCCACTGCACTCCAGCCTGGGTGG
CAGAGTGAGACCCTGTCTAAAAAAAAAAAAAAAAAAAGGCCCATTAGGGGACCCAAACGGTTCCCCAGC
TTTGTTGGATTTCCCCAAATTTGGGGCCAATTTTTGGAGGGTTGTCCCTTAAAAATTTAAATTTGGGGG
TTTTTTTCCAGGCGCCCATTAGAAATGGGTTCCGAAAATTTTTGGCCAAAAAAATTTGGTTTAACCGC
GGACCAAAATCCTAAGGTTTAACTTTTTCCTAAACCTTTTAGAATTTAAAGTTTCCGGGGTTTCTCAGG
AGGGGGTAACCCTTCACCCCAATATAACTCGGAAACCCCCCTTTTTTAGGAAAAGGGGAATTAGTGGTG
CTTTCCGGGCCAAA Contig 39 (938 bp)
CCCAGGGACCAAGCGAGTGCGACCGCTCTAGAACTAGTGGATCCCCCTTGAAGACTATATTTCTTTTCA
TCACGTGCTATAAAAATAATTATAATTTAAATTTTTTAATATAAATATATAAATTAAAAATAGAAAGTA
AAAAAAGAAATTAAAGAAAAAAATAGTTTTTGGTTTCCGAAGATGTATAATAGGTTGAAAGTTAGAAATT
ATTATTATAATAGCAAAAAAAATTTAAAGTTAGAAATTAGAATTTAAGGCTCTACACACGTTTACGATG
ATATTGGACGAACGACACGATTAGACAGTTGTAGGTTGTGTGTTGTGATGTTTTTGAGTGATTTGTAGT
GTTTAACCTTGTGGTTTGGAAAGGTNGTATGAGTATTAATCTCGGGCTTATTGGGAGGTTTATGTGCAA
TGCATTTTGTGGTTTTTTTATAATGTTGTGTTTAGGGTTAAAACCTGTTGTGTATATTGTGTTGGTTTG
TTGCTTGTTTGTACATTGGTATGATGCCTNTTTTGCTTATGGGTTNGGTGTTTGGTTTTGGTTGTGTTT
TTTGTGGTGTGTTGTTTGATAGTTTTAGCGGTTGTTTTTGGGTTGTTGTTTTATGTTGTGGTGGTGTTT

FIG. 16B(34)

NUCLEIC ACID MOLECULES COMPRISING A NEOCENTROMERE

FIELD OF THE INVENTION

The present invention is directed generally to an isolated nucleic acid molecule encompassing a neocentromere or a functional derivative thereof or a latent, synthetic or hybrid form thereof and its use inter alia in developing a range of eukaryotic artificial chromosomes including mammalian (e.g. human) and non-mammalian artificial chromosomes. Such artificial chromosomes are useful in a range of genetic therapies.

BACKGROUND OF THE INVENTION

Bibliographic details of the publications referred to by author in this specification are collected at the end of the description.

The rapidly increasing sophistication of recombinant DNA technology is greatly facilitating research and development in the medical and allied health fields. A particularly important area is in mammalian including human genetics and the molecular mechanisms behind some genetic abnormalities. Progress in research in this area has been hampered by the lack of a cloned nucleic acid molecule encompassing a human centromere. The identification and cloning of a human centromere will promote the development of techniques for introducing genes into eukaryotic cells and in particular mammalian including human cells and will be an important asset to gene therapy and the development of a range of genetic diagnostic tests.

The centromere is an essential structure for sister chromatid cohesion and proper chromosomal segregation during mitotic and meiotic cell divisions. The centromere of the budding yeast *Saccharomyces cerevisiae* has been extensively studied and shown to be contained within a relatively short DNA segment of 125 bp that is organized into an 3-bp (CDEI) and 26-bp (CDEIII) domain, separated by a 78- to 87-bp, highly AT-rich, middle (CDEII) domain (Clarke and Carbon, 1985). The centromere of the fission yeast *Schizosaccharomyces pombe* is considerably larger, ranging from 40 to 100 kb, and consists of a central core DNA element of 4 to 7 kb flanked on both sides by inverted repeat units (Steiner et al., 1993). Recently, the functional DNA components of a higher eukaryotic centromere have been characterized in a minichromosome from *Drosophila melanogaster* and shown to consist of a 220-kb essential core DNA flanked by 200 kb of highly repeated sequences on one side (Murphy and Karpen, 1995).

The mammalian centromere, like the centromeres of all higher eukaryotes studied to date, contains a great abundance of highly repetitive, heterochromatic DNA. For example, a typical human centromere contains 2 to 4 Mb of the 171-bp α-satellite repeat (Wevrick and Willard 1989, 1991; Trowell et al., 1993), plus a smaller and more variable quantity of a 5-bp satellite III DNA (Grady et al., 1992; Trowell et al., 1993). The role of these satellite sequences is presently unclear. Transfection of a cloned 17-kb uninterrupted α-satellite array into cultured simian cells (Haaf et al., 1992) or a 120-kb α-satellite-containing YAC into human and hamster cells (Larin et al., 1994) appear to confer centromere function at the sites of integration. Other workers have analyzed rearranged Y chromosomes (Tyler-Smith et al., 1993), or dissected the centromere of the human Y chromosome with cloned telomeric DNA (Brown et al., 1994) and suggested that 150 to 200 kb of α-satellite DNA plus ~300 kb of adjacent sequences are associated with human centromere function. In addition, a human X-derived minichromosome that retained 2.5 Mb of α-satellite array has been produced by telomere-associated chromosome fragmentation (Farr et al., 1995). In all these studies, it is not known whether non-α-satellite DNA sequences are embedded within the centromeric site and operate independently of, or in concert with, the α-satellite DNA.

In mammals, four constitutive centromere-binding proteins, CENP-A, CENP-B, CENP-C, and CENP-D, have been characterized to varying extents and implicated to have possible direct roles in centromere function. CENP-A a protein localized to the outer kinetochore domain, is a centromere-specific core histone that shows sequence homology to the histone H3 protein and may serve to differentiate the centromere from the rest of the chromosome at the most fundamental level of chromatin structure—the nucleosome (Sullivan et a., 1994). CENP-B, a protein which associates with the centromeric heterochromatin through its binding to the CENP-B box motif found in primate α-satellite and mouse minor satellite DNA, probably has a role in packaging centromeric heterochromatic DNA—a role which, however, may not be indispensable since the protein is undetectable on the Y chromosome (Pluta et al., 1990) and is found on the inactive centromeres of dicentric chromosomes (Earnshaw et al., 1989). CENP-C has been shown to be located at the inner kinetochore plate and is postulated to have an essential although yet undetermined centromere function, as seen, for example, from inhibition of mitotic progression following microinjection of anti-CENP-C antibodies into cells (Bernat et al., 1990; Tomkiel et al., 1994) and from its association with the active but not the inactive centromeres of dicentric chromosomes (Earnshaw et al., 1989; Page et al., 1995; Sullivan and Schwartz 1995). Finally, CENP-D (or RCC1) is a guanine exchange factor that appears to have a general cellular role that is neither specific nor clear for the centromere (Kingwell and Rattner 1987; Bischoff et al., 1990; Dasso, 1993). More recently, a new role for the mammalian centromere as a "marshalling station" for a host of "passenger proteins" (such as INCENPs, MCAK, CENP-E, CENP-F, 3F3/2 antigens, and cytoplasmic dynein), has been recognized (reviewed by Earnshaw and Mackay, 1994, and Pluta et al., 1995). These passenger proteins, whose appearance at the centromere is transient and tightly regulated by the cell cycle, provide vital functions that include motor movement of chromosomes, modulation of spindel dynamics, nuclear organization, intercellular bridge structure and function, sister chromatid cohesion and release, and cytokinesis. At present, except for CENP-B, none of the constitutive or passenger proteins have been demonstrated to bind mammalian centromere DNA directly.

In work leading up to the present invention, the inventors identified in a patient (hereinafter referred to as "BE") an unusual human marker chromosome, mardell 10, which is 100% stable in mitotic division both in patient BE and in established fibroblast and transformed lymphoblast cultures. In accordance with the present invention, a region of the mardel (10) chromosome has been cloned together with the corresponding region from a normal human subject. The nucleic acid molecules cloned contain no substantial α-satellite repeats yet are mitotically stable. The nucleic acid molecules encompass therefore, a new form of centromere referred to herein as a "neocentromere". The identification and cloning of a eukaryotic neocentromere without substantial α-satellite DNA repeat sequences now provides the means of generating a range of eukaryotic artificial chromosomes such as mammalian including human artificial chromosomes with uses in genetic therapy, transgenic plant and animal production and recombinant protein production. A range of diagnostic reagents is now also obtainable using the cloned neocentromere.

SUMMARY OF THE INVENTION

Sequence Identity Numbers (SEQ ID NOs.) for the nucleotide sequences referred to in the specification are defined following the bibliography.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

A fibroblast cell line 920158 carrying the mardel marker chromosome was deposited at the European Collection of Cell Cultures (ECACC), Centre for Applied Microbiology Research, Salisbury, Wiltshire, SP4 0JG, UK on May 1, 1997 under Accession No. 97051716. Bacterial artificial chromosomes (BACs) carrying portions of the mardel (10) chromosome have also been deposited at ECACC as follows:

BAC/E8-1: deposited on May 5, 1998 under Accession Number 980505016;

BAC/F2-14: deposited on May 5, 1998 under Accession Number 980505017.

A number of human fibrosarcoma cell lines carrying various neocentromeric constructs were deposited at ECACC as described hereafter by Accession Number with the date of deposit in parenthesises.

| | |
|---|---|
| HT-38 | 98050704 (7 May 1998) |
| HT-47 | 98050705 (7 May 1998) |
| HT-54 | 98050706 (7 May 1998) |
| HT-190 | 98050707 (7 May 1998) |
| HT-191 | 98050708 (7 May 1998). |

One aspect of the present invention provides an isolated nucleic acid molecule comprising a sequence of nucleotides derived from a eukaryotic chromosome and encompassing a neocentromere or a functional derivative synthetic or hybrid form thereof which nucleic acid molecule or its derivatives, synthetic forms or hybrid forms when introduced into a compatible cell is capable of replicating, acting as an extra-chromosomal element and segregating the cell division.

Another aspect of the present invention contemplates a nucleic acid molecule or its chemical equivalent having a tertiary structure which defines a human neocentromere or a functional derivative thereof or a latent, synthetic or hybrid form thereof or its mammalian or non-mammalian homologue.

Yet a further aspect of the present invention is directed to an isolated nucleic acid molecule comprising a sequence of nucleotides encompassing a neocentromere derived from a eukaryotic chromosome, which nucleic acid molecule when introduced into a compatible cell is a replicating, extra-chromosomal element which segregates with cell division.

Still another aspect of the present invention is directed to an isolated nucleic acid molecule having a sequence of nucleotides or their chemical equivalents which directs a conformation defining a human neocentromere or a functional derivative thereof or a latent; synthetic or hybrid form thereof or a mammalian or non-mammalian homologue thereof wherein the neocentromere associates with centromere binding proteins (CENP) -A and CENP-C or antibodies thereto and does not contain substantial α-satellite DNA repeat sequences.

A further aspect of the present invention is directed to an isolated nucleic acid molecule comprising a nucleotide sequence encompassing a neocentromere or a functional derivative, synthetic or hybrid form thereof which when said nucleic acid molecule is in linear form and co-introduced into a cell together with a telomeric sequence, is capable of replicating, remaining as an extra-chromosomal element and segregates with cell division.

Another aspect of the present invention provides an isolated nucleic acid molecule or a derivative, synthetic or hybrid form thereof comprising a sequence of nucleotides:

(i) which directs conformation defining a human neocentromere or a functional derivative thereof or a latent, synthetic or hybrid form thereof or its mammalian or non-mammalian homologue wherein said neocentromere is capable of associating with CENP-A and CENP-C;

(ii) which contains no substantial α-satellite DNA sequence repeat; and (iii) which is capable, when introduced into compatible cells, of replication, remaining extra-chromosomal and segregating with cell division.

Even yet another aspect of the present invention is directed to a genetic construct comprising an origin of replication for a eukaryotic cell and a nucleic acid molecule encompassing a human neocentromere or a functional derivative thereof or a latent, synthetic or hybrid form thereof or its mammalian or non-mammalian homologue flanked by telomeric nucleotide sequences functional in the cell in which the genetic construct is to replicate and wherein said genetic construct when introduced into a cell is a replicating, extra-chromosomal element which segregates with cell division.

Another aspect of the present invention is directed to a genetic construct in the form of a eukaryotic artificial chromosome such as a mammalian artificial chromosome (MAC), a human artificial chromosome (HAC) or comprising an origin of replication and a sequence of nucleotides which:

(i) directs a conformation defining a human neocentromere or a functional derivative thereof or a latent, synthetic or hybrid form thereof wherein said neocentromere is capable of associating with CENP-A and CENP-C or antibodies thereto; and (ii) contains no substantial α-satellite DNA repeat sequences;

said sequence of nucleotides flanked by eukaryotic (e.g. mammalian) telomeric sequences which are in turn flanked by yeast telomeric sequences wherein a unique enzyme site is located between the human and yeast telomeric nucleotide sequences such that upon contact with said enzyme, the yeast telomeric sequences are removed and the eukaryotic (e.g. mammalian) telomeric sequences are exposed.

Still another aspect of the present invention provides a genetic construct comprising an origin of replication and a first nucleic acid molecule defining a human neocentromere or a functional derivative thereof or latent, synthetic or hybrid form thereof, a second nucleic acid molecule encoding a peptide, polypeptide or protein, wherein said first and second nucleic acid molecules are flanked by a first set of eukaryotic (e.g. mammalian, such as human) telomeric sequences which are in turn flanked by a second set of eukaryotic (e.g. yeast) telomeric sequences wherein there are unique enzyme sites between the first and second telomeric sequences such that upon contact with a required enzyme, the second telomeric sequences are cleaved off to expose the first telomeric sequences.

BRIEF DESCRIPTION OF THE FIGURES

(FIG. 1A) Comparison of GTL banding patterns of mardel 10 and normal chromosome 10. The pair of open arrows indicate the two breakpoints on a normal chromosome 10 in generating the marker chromosome (Voullaire et al., 1993). The long and short arms of the marker chromosome are designated q' and p', respectively, to distinguish them from the q and p arms of the normal chromosome 10. Asterisk denotes the position of a cosmid 10pC38 that was used to "tag" the q'-arm of stretched marker chromosomes in the ANTI-CEN/FISH experiments. (FIG. 1B) A4-megabase YAC contig (#082) from 10q25.2 region that spans the marker centromere. The tilling path of YACs #0 to #23 and their corresponding CEPH library addresses are shown. (FIG. 1C) FISH mapping of selected YAC clones from contig #082 using normal fluorescence microscopy and standard metaphase chromosomes prepared from transformed lymphoblast cells of patient BE. The distribution of FISH signals (vertical axis) is shown as a percentage of the signals on one arm of the marker chromosome that is in excess of those found on the opposite arm of the chromosome. The total number of fluorescence signals scored for each of the YAC clones is indicated in brackets.

FIGS. 2A(1)–2C(*e*) are photographic representations showing ANTI-CEN/FISH analysis of the marker centromere. (FIGS. 2A(1)–2A(2)) Detection of α-satellite DNA using a mixture of α-satellite DNA probes (red signals) under low stringency conditions. Centromeres were counter-labelled with CREST#6 autoimmune antibody (pale blue dots; or white when superimposed on a red background). Chromosomes were prepared from transformed lymphoblast cells of patient BE. The right-hand panel represents green pseudo-coloring of DAPI images of chromosomes to provide a better definition of chromosome outline. Only the signal for the antibody, but not that for α-satellite, was seen on the marker centromere (arrowed). (FIGS. 2B(1)–2B(2)) Simultaneous labelling of stretched human metaphase chromosomes with CREST#6(red) and anti-CENP-C antibody, Am-C1 (pale blue), with the white color indicating full coincidence of the two antibody signals. (FIG. 2C(*c*)) Combined images of a and b, showing complete coincidence of Am-C1 and CREST#6 signals. (FIG. 2C(*d*)) FISH analysis of the same cell as a–c using the 10pC38 cosmid probe (pale blue dots and green arrows) to identify the marker chromosome. Some loss of ANTI-CEN signal, especially for the Am-C1 antibody was seen following FISH. (FIG. 2C(*e*)) Green pseudo-coloring of DAPI images. A colour photograph corresponding to this figure is available upon request.

FIGS. 3A(*a*1)–3B(2) are photographic representations showing ANTI-CEN/FISH analysis of cosmid clones on stretched (FIGS. 3A(*a*1)–3A(*f*2)) and superstretched (FIGS. 3B(1)–3B(2)) metaphase chromosomes. (FIGS. 3A(*a*1)–3A(*c*2)) Examples of cosmid signals (white arrows) localized to the q-region of the marker centromere. (FIGS. 3A(*d*1)–3A(*f*2)) Examples of cosmid signals (white arrows) localized to the p'-region of the marker centromere. Green arrows indicate positions of the 10pC38 cosmid DNA tag used to mark the q'-end of the marker chromosome. (FIGS. 3B(1)–3B(2)) Mapping of Y6C21 onto a superstretched metaphase chromosome. Not included is the 10pC38 q'-tag signal located further to the left of the chromosomal segment shown. ANTI-CEN signals are in red, FISH signals are in pale blue, and overlapping ANTI-CEN and FISH signals are in white. Each of the pictures is accompanied by DAPI images of chromosomes pseudo-coloured in green. A colour photograph corresponding to this figure is available upon request.

FIG. 4A, Relative positions of different cosmid and PAC clones within the YAC #082 contig, using YAC-3 as a reference. Cosmids are designated as YnCm, where 'n' denotes the YAC of origin and 'm' denotes the cosmid number. PACs 1–5 are five different PAC clones isolated from a human PAC library (Genome Systems Inc). "HC-contig" represents a group of overlapping cosmids that map tightly around the marker centromere in ANTI-CEN/FISH experiments. A genomic map corresponding to the depicted YAC region was derived from the DNA of patient BE and shown above the YAC map. S, SAlI; K, KspI; N, NotI; Sf, SfiI. FIG. 4B, Cumulative scoring of FISH signals in ANTI-CEN/FISH experiments for cosmids Y3C64, Y6C8, Y3C94, Y7C14, Y4C45, Y6C10, Y6C21, Y3C3, PAC5, Y13C1, Y13C8, and Y17C6. The distribution of FISH signals (vertical axis) is those found on the opposite arm of the chromosome. The total number of fluorescence signals scored for each of the cosmid clones is indicated in brackets. FIG. 4*c*, Restriction mapping of the 80-kb region covered by the eight overlapping cosmids of the HC-contig. These eight cosmids were derived from four different YACs (YAC-3, YAC-4, YAC-6, and YAC-7) and provided independent confirmation of the map. Furthermore, the map agreed fully with the restriction map of a 120 kb-insert PAC clone (PAC4) that spanned the entire HC-contig region. E, EcoRI; R, EcoRV; N, NotI.

FIGS. 6A(1)–6A(125), when joined at matchlines A—A through TTT—TTT, represent the full nucleotide sequence (SEQ ID NO:3) of the HC-contig DNA derived from normal human chromosome 10q 25.2 region.

(FIG. 11A) Structural map of the NC-contig region and flanking DNA. Arrows indicate the relative positions and directions of primers used in PCR analyses (Table 3). The restriction sites EcoRI, EcoRV, SrfI, and SftI and SftI are indicated by E, R, Sr and Sf, respectively. The position of the TAR "hook" CE-F2 is represented by the solid box. The hatched bar represents HC- or NC-contig. p' and q' refer to the short and long arms of mardel (10), respectively. (FIG. 11B) Circular TAR strategy using the vectors pVC39-Alu/C3-F2(+) and pVC39-Alu/C3-F2(−) for the direct cloning of the neocentromere DNA from mardel (10). The position of the Alu consensus sequence hook is represented by the white box. Crosses denote the sites of recombination between the TAR vector and the genomic DNA at the Alu and C3-F2 hooks during cloning. (FIG. 11C) Structural maps of the resulting circular YACs 5f-52-E8 and 5f-38-F2 containing the neocentromere DNA of the mardel (10) chromosome. The DNA flanking the NC-contig is represented by stippled bars. (FIG. 11D) Structural maps of BAC/E8-1 and BAC/F2–14. Nt represents NotI and URA-BAC-neo represents the retrofitting vector BRV1 (Larionov et al., 1997).

The method was as follows: (1) Co-transformation into YPH857; (2) Select $HIS^+$ colonies; (3) screen for HC-region by PCR; (4) Prepare high-MW DNA; (5) Digest with I-SceI to expose hTELS; (6) Transfect HT 1080 cells; (7) Select for $G418^R$; and (8) analyse by PFGE and FISH.

Figure 13:
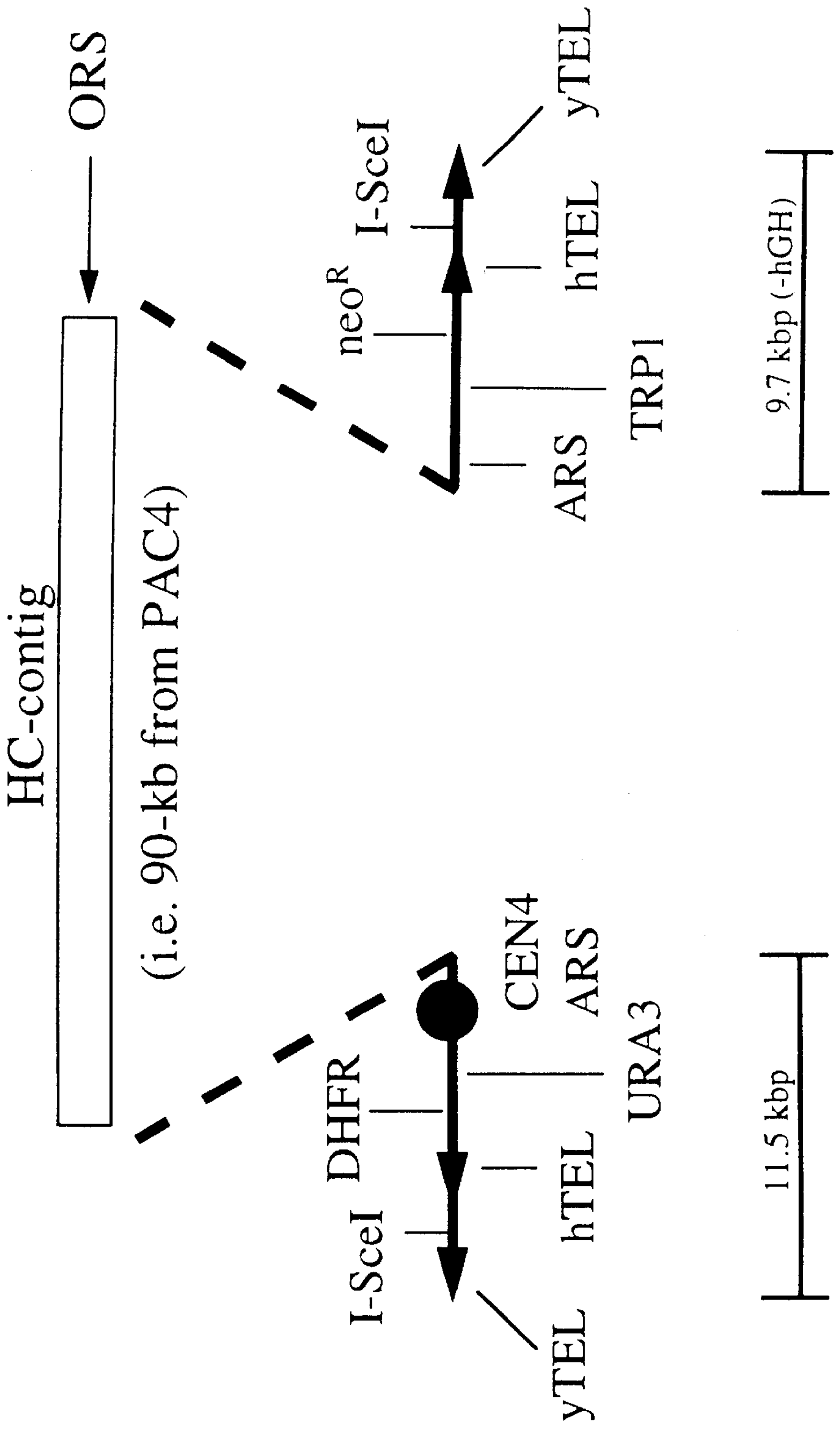

FIG. 13 is a diagrammatic representation showing cloning in yeast as YAC/HAC.

Figure 14:
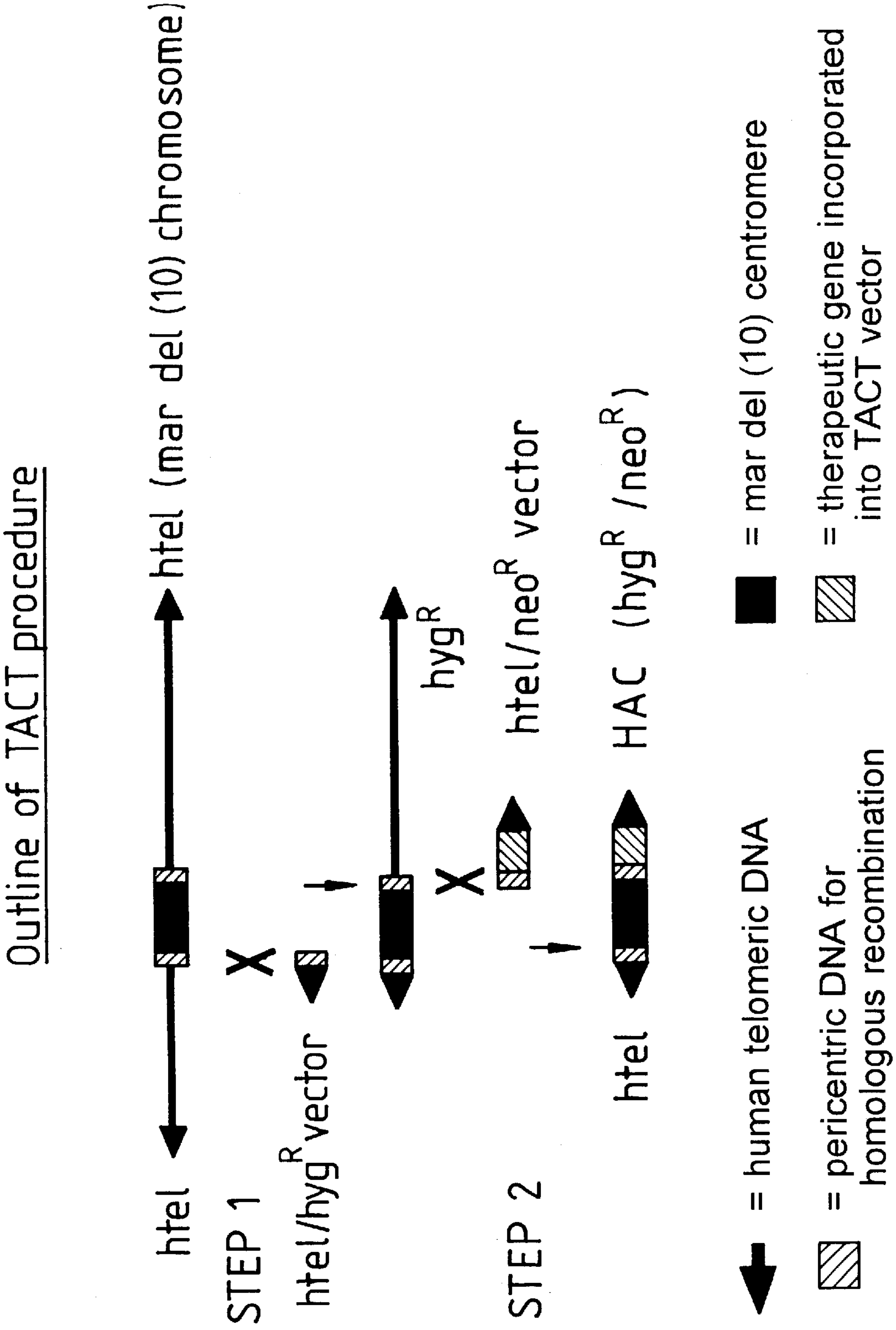

FIG. 14 is a diagrammatic representation outlining TACT procedure.

Figure 15A:
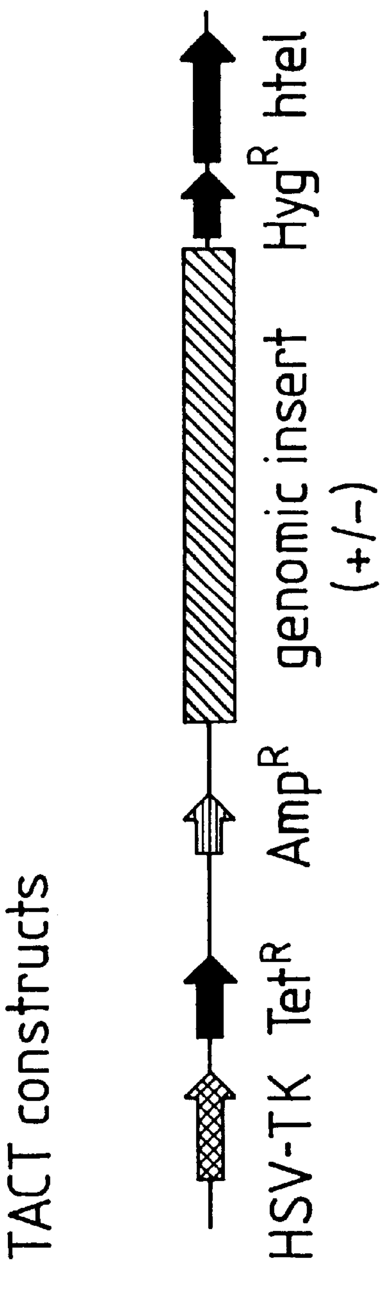
Figure 15B:
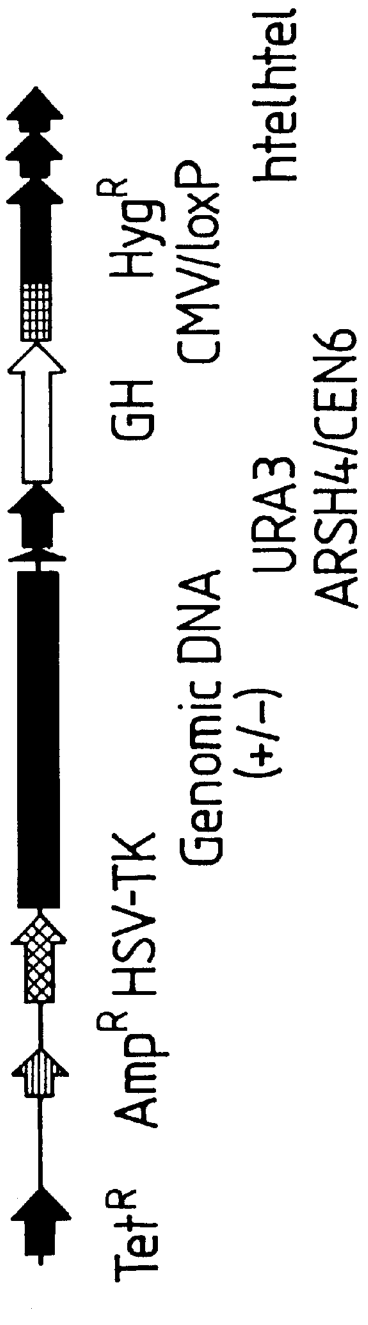

FIGS. 15A–15B are diagrammatic representations of TACT constructs.

FIGS. 16A(1)–16A(37), when joined at matchlines A—A through J'—J', depict the full nucleotide sequence (SEQ ID NO:4) of the NC-contig DNA derived from mardel (10) and corresponds to the HC-contig DNA region of the normal chromosome 10.

FIGS. 16B(1)–16B(34), when joined at matchlines A—A through G'—G', depict the partial nucleotide sequence of the BAC/F2–14 clone that is derived from a region immediately p' of the NC-contig DNA (see FIG. 11D) (SEQ ID NO:5–29).

SUMMARY OF SEQ ID NOs.

| SEQ ID NO. | DESCRIPTION |
|---|---|
| 1 | DNA primer |
| 2 | DNA primer |
| 3 | Nucleotide sequence of HC-contig |
| 4 | Nucleotide sequence of NC-contig |
| 5 | BAC-F2 contig 1 |
| 6 | BAC-F2 contig 2 |
| 7 | BAC-F2 contig 3 |
| 8 | BAC-F2 contig 4 |
| 9 | BAC-F2 contig 5 |
| 10 | BAC-F2 contig 6 |
| 11 | BAC-F2 contig 7 |
| 12 | BAC-F2 contig 8 |
| 13 | BAC-F2 contig 9 |
| 14 | BAC-F2 contig 15 |
| 15 | BAC-F2 contig 33 |
| 16 | BAC-F2 contig 39 |
| 17 | BAC-F2 contig 41 |
| 18 | BAC-F2 contig 42 |
| 19 | BAC-F2 contig 44 |
| 20 | BAC-F2 contig 47 |

-continued

| SEQ ID NO. | DESCRIPTION |
|---|---|
| 21 | BAC-F2 contig 47 fragment 1 |
| 22 | BAC-F2 contig 47 fragment 2 |
| 23 | BAC-F2 contig 47 fragment 3 |
| 24 | BAC-F2 contig 47 fragment 4 |
| 25 | BAC-F2 contig 47 fragment 5 |
| 26 | BAC-F2 contig 47 fragment 6 |
| 27 | BAC-F2 contig 47 fragment 7 |
| 28 | BAC-F2 contig 47 fragment 8 |
| 29 | BAC-F2 contig 47 fragment 9 |

ABBREVIATIONS USED IN THE SUBJECT SPECIFICATION

| | |
|---|---|
| mardel (10): | Marker chromosome from patient BE; comprises a rearrangement of chromosome 10. |
| HAC: | Human artificial chromosome |
| YAC: | Yeast artificial chromosome |
| MAC: | Bacterial artificial chromosome |
| PLAC: | Plant artificial chromosome |
| neocentromere: | A centromere containing no substantial α-satellite DNA |
| CENP: | Centromere binding protein |
| HC-contig: | Region of normal chromosome 10 comprising neocentromere |
| E8: | q' end/region of mardel (10) neocentromere |
| F2: | p' end/region of mardel (10) neocentromere |
| BE: | Patient from which mardel (10) identified |
| TAR: | Transformation-associated recombinant |
| PCR: | Polymerase chain reaction |
| Marker neocentromere: | neocentromere on mardel (10). |
| NC-contig | region of mardel (10) chromosome comprising neocentromere |

DETAILED DESCRIPTION OF PREFERRED EMBODIMENTS

The present invention is predicated in part on the identification and isolation of nucleic acid molecules exhibiting neocentromeric properties. In accordance with the present invention, a neocentromere is considered a centromere which does not contain substantial α-satellite DNA repeat sequences and, when activated, is capable of functioning as a centromere. The term "substantial" in this context means that the nucleic acid molecule does not contain detectable α-satellite by FISH analysis under medium stringency conditions. The neocentromere may contain a small number of highly diversed α-satellite DNA. In primates, α-satellite DNA is consider 171 bph in length. An nucleic acid molecule containing an activated neocentromere or a neocentromere otherwise functioning as a centromere facilitates in accordance with the present invention, the nucleic acid molecule replicating, remaining extra-chromosomal and segregating with cell division. Reference herein to "neocentromere" is taken to mean a centromere substantially devoid of α-satellite DNA repeat sequences.

Accordingly, one aspect of the present invention provides an isolated nucleic acid molecule comprising a sequence of nucleotides which defines an eukaryotic neocentromere.

More particularly the present invention provides an isolated nucleic acid molecule comprising a sequence of nucleotides derived from a eukaryotic chromosome and encompassing a neocentromere which nucleic acid molecule when introduced into a compatible cell is capable of replicating, acting as an extra-chromosomal element and segregating with cell division.

The present invention is exemplified herein by the identification and cloning of a human neocentromere. This is done, however, with the understanding that the present invention extends to all eukaryotic neocentromeres such as from mammalian, plant, aviary, insect, fungal, yeast and reptilian chromosomes. The most preferred neocentromere, however, is from human chromosomes and their mammalian homologues.

The present invention is predicated in part on the identification of an unusual chromosomal marker in a patient designated "BE". The chromosomal marker is referred to as "mardel (10)" and results from a rearrangement of human chromosome 10. The mardel (10) marker is mitotically stable and, in accordance with the present invention, contains a functional neocentromere at a location regarded as non-centromeric. The neocentromere at mardel (10) is located between q24 and q26 on chromosome 10 and more particularly around q25. Even more particularly, the neocentromere maps to q25.2 on chromosome 10. The present invention is exemplified by DNA cloned from the q24–q26 region of the mardel (10) chromosome as well as the corresponding region on normal human chromosome 10. These DNA molecules contain a functional neocentromere. The present invention extends, however, to any neocentromere or any chromosome in mammalian and non-mammalian animals as well as plants, yeasts and fungi.

For convenience, the DNA clones from the mardel (10) chromosomes as well as from normal human chromosome 10 are summarised in FIG. 11. The neocentromere located at or around 10q25 is located on a clone designated the "HC-contig". DNA clones from mardel (10) are referred to as "E8" or the "NC-contig" which extends from the long arm (q') of mardel (10) towards the short arm (p'). Clone F2 extends further p' from E8 (see FIG. 11). It is emphasised, however, that the present invention extends to any neocentromere on any human chromosome as well as neocentromeres on other mammalian and non-mammalian chromosomes including chromosomes from plants, insects, reptiles, yeast and fungi.

The present invention further contemplates a nucleic acid molecule or its chemical equivalent having a tertiary structure which defines a human neocentromere or a functional derivative thereof or a latent, synthetic or hybrid form thereof or its mammalian or non-mammalian homologue.

Even more particularly, the present invention is directed to an isolated nucleic acid molecule having a sequence of nucleotides or their chemical equivalents which directs a conformation defining a human neocentromere or a functional derivative thereof or a latent, synthetic or hybrid form thereof or its mammalian or non-mammalian homologue wherein the centromere associates with centromere binding proteins (CENP)-A and CENP-C or antibodies thereto.

Reference herein to "latent" in relation to a centromere includes reference to a centromere not normally functional but nevertheless activatable under certain conditions. A latent centromere may also be considered as a neocentromere provided it has no substantial α-satellite DNA repeat sequences.

The size of the neocentromere in accordance with the present invention may range from about 50 bp to about 1500 kbp, from about 70 bp to about 1000 kbp, from about 75 bp to about 800 kpb, from about 80 bp to about 500 kbp, from about 85 bp to about 200 kbp, from about 90 bp to about 100 kbp, from about 100 bp to about 1 kbp, about 120 bp to about 500 bp, about 180 bp to about 300 bp. In one particular embodiment, the centromere is approximately 60–100 kbp. In another embodiment, the centromere is about 80 kbp.

Figure 6A:
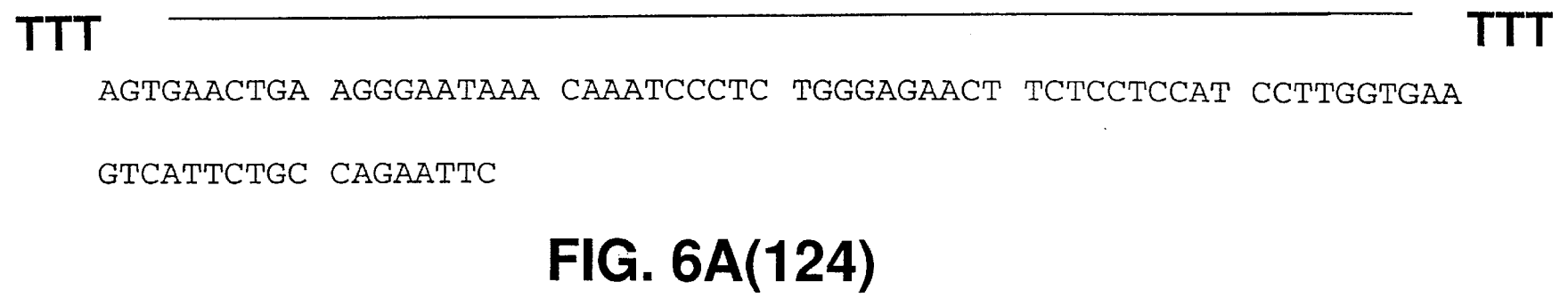

The nucleic acid molecule encompassing the HC-contig for human chromosome 10 of the present invention set forth in FIG. 6 (SEQ. ID NO: 3). The nucleic acid molecule encompassing the NC-contig (part of E8) form mardel (10) is set forth in FIG. 16A (SEQ ID NO: 4). The nucleic acid molecule encompassing F2 of mardel (10) is set forth in FIG. 16B as separate contigs (SEQ ID NOs: 5–29). The nucleic acid molecules have a tertiary structure and the neocentromere is a conformation of nucleotides within this tertiary structure. Accordingly, the neocentromere is not defined by a linear sequence of nucleotides although this aspect of the present invention is exemplified using the nucleotide sequence set forth in FIGS. 6, 16A and 16B, the subject invention extends to any sequence directing a conformation defining a centromere and hybridising to the sequence set forth in one or more of FIGS. 6, 16A and/or 16B under low stringency conditions at 42° C. and/or which comprises a nucleotide sequence having at least about 40% nucleotide similarity to one or more sequences set forth in FIGS. 6, 16A and/or 16B. Preferably, the percentage similarity is at lest about 50%, more preferably at least about 60%, still more preferably at least about 70%, even more preferably at least about 80–90% or above such as 95%, 97%, 98% and 99%.

Another embodiment of the present invention is directed to YAC3 and YAC5 encompassing the HC contig and flanking sequence as well as nucleotide sequences related to YAC3 and/or YAC5 at the homology, similarity or hybridization levels.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. These stringency conditions may be altered dependent on the source of DNA and other factors.

The term "similarity" as used herein includes exact identity between compared sequences at the nucleotide level. Where there is non-identity at the nucleotide level, "similarity" includes differences between sequences which nevertheless result in conformation defining a functional neocentromere.

The nucleic acid molecule of the present invention may comprise a naturally occurring nucleotide sequence from a healthy human subject or may comprise the nucleotide sequence from a human subject exhibiting one or more chromosomal-dependant conditions such as a subject carrying mardel 10 chromosome or a chromosome conferring an equivalent or similar condition or may carry one or more nucleotide substitutions, deletions and/or additions relative to the naturally or non-naturally occurring sequence. Such modifications are referred to herein as "derivatives" and include mutants, fragments, parts, homologues and analogues of the naturally occurring nucleotide sequence. Preferably, the derivatives of the present invention still define a functional neocentromere.

Reference herein to a "neocentromere" includes reference to a functional neocentromere or a functional derivative thereof meaning that it is capable of facilitating sister chromatid cohesion and chromosomal segregation during mitotic cell divisions and/or is capable of associating with CENP-A and/or CENP-C and/or is capable of interacting with anti-CENP-A antibodies or anti-CENP-C antibodies. Generally, and preferably, the neocentromere is incapable of interacting with CENP-B or anti-CEP-B antibodies. Alternatively, the neocentromere may be a latent centromere capable of activation by epigenetic mechanisms. The neocentromere may also be a hybrid of other human, mammalian, plant or yeast neocentromeres. Synthetic neocentromeres provided by, for example, polymeric techniques to arrive at the correct confromation are also contemplated by the present invention. All such forms and definitions of neocentromere are encompassed by use of this term.

Another aspect of the present invention provides an isolated nucleic acid molecule or chemical equivalent having the following characteristics:

(i) comprises a nucleotide sequence or chemical equivalent directing a conformation which defines a neocentromere or a functional derivative thereof or a latent, synthetic or hybrid form thereof or;

(ii) comprises a nucleotide sequence or chemical equivalent substantially as set forth in one or more of FIGS. 6, 16A and/or 16B or having at least about 40% similarity thereto or capable of hybridising thereto under low stringency conditions at 42° C.; and (iii) comprises a neocentromere capable of associating with CENP-A or CENP-C or antibodies thereto.

Preferably, the neocentromere is incapable of interacting with CENP-B or antibodies thereto.

In a particularly preferred embodiment, the centromere corresponds to a human genomic region which maps between q24 and q26 on chromosome 10, and in particular q25 on chromosome 10.

The nucleic acid molecule or its chemical equivalent of the present invention defining a conformational neocentromere or functional derivative thereof or latent, synthetic or hybrid form thereof is useful inter alia of the generation of artificial chromosomes such as human artificial chromosomes (HACs), mammalian artificial chromosomes (MACs), yeast artificial chromosomes (YACs) and plant artificial chromosomes (PLACs). HAC's are particularly useful since they are capable of accommodating large amounts of DNA and are capable of propagation in human cells. The HAC's are non-viral in origin and, hence, are more suitable for gene therapy by, for example, introducing therapeutic genes. Furthermore, the HACs remain extra-chromosomal and, hence, have no insertional/substitutional mutagenic potential. The essence of a HAC is the presence of a neocentromere or latent, synthetic or hybrid form thereof which enables stable segregation during cell division. The HAC also remains extra-chromosomal and, hence, is more suitable for gene therapy. Reference to "extra-chromosomal" means that it does not integrate into the main chromosome and, in effect, is episomal.

Accordingly, the present invention provides a genetic construct comprising an origin of replication for a eukaryotic cell and a nucleic acid molecule encompassing a eukaryotic neocentromere or a functional derivative thereof or a latent, synthetic, hybrid form thereof or its mammalian or non-mammalian homologue flanked by telomeric nucleotide sequences functional in the cell in which the genetic construct is to replicate and wherein said genetic construct when introduced into a cell is a replicating, extra-chromosomal element which segregates with cell division.

More particularly, the present invention further contemplates a genetic construct in the form of an artificial chromosome comprising an origin of replication for a mammalian, human, plant or yeast cell and a nucleic acid molecule encompassing a human neocentromere or a functional derivative thereof or a latent, synthetic or hybrid form thereof or its mammalian or non-mammalian homologue flanked by telomeric nucleotide sequences functional in the cell in which the artificial chromosome is to replicate.

Another embodiment provides a genetic construct in the form of an artificial chromosome comprising an origin of replication for a mammalian, human, plant or yeast cell and a nucleic acid molecule having a tertiary structure which defines a human neocentromere or a functional derivative thereof or a latent, synthetic or hybrid form thereof or its mammalian homologue flanked by telomeric sequences functional in the cell in which the artificial chromosome is to replicate.

Yet another embodiment is directed to a genetic construct in the form of an artificial chromosome comprising an origin of replication for a mammalian, human, plant or yeast cell and a nucleic acid molecule having a sequence of nucleotides which directs a conformation defining a human neocentromere wherein the centromere associates with CENP-A and/or CENP-C or antibodies thereto and does not contain substantial α-satellite DNA repeat sequences, said nucleic acid molecule flanked by telomeric nucleotide sequences functional in the cell which the artificial chromosome is to replicate.

Still yet another aspect of the present invention relates to a genetic construct in the form of an artificial chromosome comprising an origin of replication for a mammalian, human, plant or yeast cell and a nucleic acid molecule comprising a sequence of nucleotides which:

(i) directs a conformation which defines a neocentromere or a functional form thereof or a latent, synthetic or hybrid form thereof;

(ii) comprises a nucleotide sequence substantially as set forth in one or more of FIGS. 6, 16A and/or 16B or having at least about 40% similarity to the nucleotide sequences set forth in FIGS. 6, 16A and/or 16B or is capable of hybridising to one or more of these sequences under low stringency conditions at 42° C.;

wherein the neocentromere is capable of associating with CENP-A and/or CENP-C antibodies thereto and wherein said nucleic acid molecule is flanked by telomeric nucleotide sequences functional in the cell in which the artificial chromosome replicates.

In a preferred embodiment, the genetic construct is a HAC and comprises human telomeric sequences. In a particularly preferred embodiment, the HAC further comprises yeast artificial chromosome (YAC) arms and, hence, becomes a HAC/YAC shuttle vector capable of propagation in human and yeast cells. Preferably, the HAC/YAC contains a unique enzyme site between yeast telomeric sequences and human telomeric sequences such that upon contact with the particular enzyme, the yeast telomeric sequences are removed leaving the human telomeric sequences. Preferably, the unique enzyme site is a yeast specific enzyme site such as I-SceI.

According to this embodiment, there is provided a genetic construct defining a HAC/YAC comprising an origin of replication and a nucleic acid molecule encompassing a human neocentromere or a functional derivative thereof or a latent, synthetic or hybrid form thereof or a mammalian or non-mammalian homologue thereof, said nucleic acid molecule flanked by human telomeric sequences which are in turn flanked by yeast telomeric sequences wherein a unique enzyme site is located between the human and yeast telomeric nucleotide sequences such that upon contact with the enzyme, the yeast telomeric sequences are removed and the human telomeric sequences are exposed.

More particularly, the present invention is directed to a genetic construct defining a HAC/YAC comprising an origin of replication and a nucleic acid molecule encompassing a human centromere or a functional derivative thereof or a latent, synthetic or hybrid form thereof or a mammalian or non-mammalian homologue thereof wherein the neocentromere associates with CENP-A and/or -C or antibodies thereto and does not contain substantial α-satellite DNA sequences wherein said nucleic acid molecule is flanked by human telomeric sequences which are in turn flanked by yeast telomeric sequences wherein a unique enzyme site is located between the human and yeast telomeric nucleotide sequences such that upon contact with said enzyme, the yeast telomeric sequences are removed and the human telomeric sequences are exposed.

Even more particularly, the present invention is directed to a genetic construct in the form of a HAC/YAC comprising an origin of replication and a sequence of nucleotides which directs a conformation defining a human neocentromere or a functional derivative thereof or a latent, synthetic or hybrid form thereof or a mammalian or non-mammalian homologue thereof wherein said neocentromere is capable of associating with CENP-A and/or CENP-C or antibodies thereto, said sequence of nucleotides flanked by human telomeric sequences which are in turn flanked by yeast telomeric sequences wherein a unique enzyme site is located between the human and yeast telomeric nucleotide sequences such that upon contact with said enzyme, the yeast telomeric sequences are removed and the human telomeric sequences are exposed.

Preferably, the length of the nucleotide sequence is between about 30 kpb and 1500 kpb, and more preferably between 60 kbp and 1000 kpb.

In a particularly preferred embodiment, the unique enzyme site is a yeast specific enzyme site such as I-SceI.

The present invention extends to yeast cells and human cells carrying the genetic constructs of the present invention and to proteins produced therefrom.

The genetic constructs may also comprise marker genes and other unique restriction sites to facilitate insertion of adventitious DNA. Accordingly, the genetic constructs of the present invention may further comprise adventitious or heterologous DNA encoding a product of interest. Preferred products of interest include pharmaceutically useful genes such as genes encoding cytokines, receptors, growth regulators and the like. Endogenous genes may also be replaced by wild-type genes or modified genes.

The adventitious or heterologous DNA may also encode a molecule not synthesised in a sufficient amount in a particular subject and hence the increased copy number permits greater amounts of the molecule being synthesised.

Accordingly, the present invention contemplates a genetic construct comprising an origin of replication and a first nucleic acid molecule defining a human neocentromere or a functional derivative thereof or latent, synthetic or hybrid form thereof or a mammalian or non-mammalian homologue, a second nucleic acid molecule encoding a peptide, polypeptide or protein, wherein said first and second nucleic acid molecules are flanked by a first set of human telomeric sequences which are in turn flanked by a second set of yeast telomeric sequences wherein there are unique enzyme sites between the human and yeast telomeric sequences such that upon contact with said enzyme, the yeast telomeric sequences are cleaved off to expose the human telomeric sequences.

Reference herein to segregate preferably means mitotically stable segregation. Conveniently, stable segregation may be determined as the presence of an artificial chromosome in 40–60% of daughter cells after 4–6 months of continuous passage.

The present invention extends to other artificial chromosome analogues to the HACs and HAC/YACs described above such as MACs and PLACs.

Another aspect of the present invention relates to peptides, polypeptides and proteins which bind, interact or otherwise associate with the human neocentromere of the present invention or its mammalian and non-mammalian homologue. Preferably, the molecules are proteins, referred to as primary (1°) proteins. The 1° proteins bind to the neocentromere and secondary (2°) proteins bind to the 1° proteins before or after association with the neocentromere. The identification of the human neocentromere in accordance with the present invention provides a mechanism for assaying 1° proteins and 2° proteins which may be important for screening chromosomes in, for example, genetic disorders. This is particularly the use in Down's Syndrome which results from defective chromosome segregation.

The 1° proteins are readily detected by, for example, a gel shift assay. The nucleic acid molecule of the present invention defining the human neocentromere is digested, labelled and contacted with nuclear extract putatively containing the 1° proteins and resolved on a gel. When a 1° protein binds to a fragment carrying a binding portion of the neocentromere, the DNA fragment migrates in the gel at a slower rate due to the bound protein.

The present invention extends to purified 1° proteins capable of association with the subject centromere and to genetic sequences encoding same and to antibodies thereto.

The neocentromeres of the present invention are readily identified and characterised using, for example, human fibrosarcoma cell lines. For example, DNA suspect of carrying a neocentromere, is introduced into fibrosarcoma cells in a linear form, generally together with a telomeric sequence. The cells are then screened for the presence of replicating, extra-chromosomal and segregating elements, referred to as mini chromosomes.

The present invention further encompasses eukaryotic cells carrying replicating, extrachromosomal and segregation nucleic acid molecules. Preferably the eukaryotic cells are mammalian cells and most preferably human cells. The nucleic acid molecules according to this aspect of the present invention are preferably as herein described. Particularly preferred cells are HT-38, HT-47, HT-54, HT-190, HT-191, BAC/E8-1, and BAC/F2-14.

The present invention is further described by the following non-limiting Figures and Examples.

EXAMPLE 1

YAC and Cosmid Probes for FISH

YACs carrying specific STSs were identified (Moir et al., 1994) by PCR-based screening of YAC libraries prepared in pYAC4 vector at the Center for Genetics in Medicine at Washington University (Brownstein et al., 1989) and at the CEPH (Albertsen et al., 1990). Cosmid DNA inserts (35–40 kb) were ligated to SUPERCOS I vector (Stratagene) and packaged with GIGAPAK III GOLD extract (Stratagene) according to the manufacturer's instructions. YAC probes were prepared by Alu-PCR of total yeast genomic DNA using primers 5'-GGATTACAGG(C/T)(A/G)TGAGCCA-3' [SEQ ID NO:1] and 5'-(A/G)CCA(C/T)TGCACTGCAGCCTG-3' [SEQ ID NO:2] according to published method (Archidiacono et al., 1994). For probe labelling, 1 μg of the YAC PCR products or whole cosmid DNA isolated by CsCl centrifugation or Qiagen column was used. The DNA was labelled with Biotin-16-dUTP (Boehringer Mannheim) using a NICK translation kit (Boehinger Mannheim). A probe mix of 6–10μg/ml of biotinylated probe DNA, 300 μg/ml of COT-1 DNA (Boehringer Mannheim), 500 μg/ml of carrier salmon sperm DNA and, where indicated, 10 μg/ml of biotinylated 10pC38 tag DNA was ethanol precipitated, resuspended in a hybridization mix of 50% v/v formamide in 2×SSC and 10% w/v dextran sulphate, denatured at 95° C. for 5 min, preannealed for 30–60 min at 37° C. to suppress repetitive sequences, before adding to slides. FISH of α-satellite and satellite III probes was performed under low stringency as previously described (Voullaire et al., 1993).

EXAMPLE 2

Somatic Cell Hybrids and Other Cell Lines

Skin fibroblasts and transformed lymphoblast cell lines were established from patient BE (Voullaire et al., 1993) and from his normal parents. The presence of the mardel 10 chromosome in the patient cell lines was confirmed by FISH. In addition to these cell lines, two somatic cell hybrids were produced by fusing cultured fibroblast cells derived from patient BE with the Chinese hamster ovary cell line CHO-K1 using polyethylene glycol. Hybrid cells were selected in a proline-free medium for the glutamic oxaloacetic transminase-1 (GOT-1) gene located in 10q24–q25 region. One of the hybrid cell lines, designated BE2C1-18-1f, was shown to contain the normal chromosome 10 but not the marker chromosome, while another hybrid cell line, designated BE2C1-18-5F, contained the marker chromosome but not the normal chromosome 10 of patient BE. The presence or absence of these chromosomes was established by karyotyping and ANTI-CEN/FISH probing. In addition, PCR analysis of an STS (sequence tagged site) marker, AFM259xg5, which resided in YAC-3, confirmed the status of these chromosomes in the hybrids and excluded the presence of submicroscopic fragments of the marker centromere region within the genome of BE2C1-18-1f, or the presence of the corresponding region of normal chromosome 10 within the genome of BE2C1-18-5f. Use of this STS marker also demonstrated that the mardel 10 chromosome has originated from the patient's father.

EXAMPLE 3

Antisera

Antiserum CREST #6 was from a patient with calcinosis, Raynaud's phenomenon, esophageal dysmotility, sclerodactyly and telangiectasia (a constellation of symptoms commonly referred to as "CREST"; Moroi et al., 1981; Fritzler and Kinsella, 1980; Brenner et al., 1981). Western blot analysis of this antiserum indicated that the primary antigens detected were human CENP-A and CENP-B. A specific anti-CENP-C polyclonal antibody, designated Am-C1, was produced by the inventors by expressing a partial mouse CENP-C polypeptide (amino acid #41 to 345) as a GST-fusion product in *E. coli*, followed by gel purification of the product and its use as an antigen for antibody production in rabbit.

EXAMPLE 4

Preparation of Standard Metaphase Chromosomes for FISH analysis

Actively replicating transformed lymphoblasts were incubated at 37° C. for 17 h in the presence of 0.1M final concentration of thymidine before they were centrifuged at 2000 rpm for 10 min, washed with pre-warmed RPMI, and incubated for a further 5–6h. 15 min before harvesting, colcemid (10 μg/ml) was added. Cells were harvested according to standard cytogenetic techniques using 0.075 M KCl hypotonic solution for 15 min at 37° C., followed by three fixative washes in ice cold methanol/acetic acid 3:1, dropped onto clean glass slides, and stored dessicated at −20° C. until required.

EXAMPLE 5

Preparation of Mechanically Stretched Chromosomes for ANTI-CEN/FISH Mapping

Method-I

This is an adaptation of the method described by Page et al. (1995). Colcemid (10 μg/ml) was added to actively dividing transformed lymphoblasts for 2–3 h, before the cells were centrifuged at 1500 rpm for 10 min, washed in PBS, and resuspended in 0.075M KCl hypotonic solution for 10 min at RT at a concentration of approximately $5\times10^4$ cells/ml; the use of fewer cells here gave better stretching of the chromosomes. 200–300 μl of this suspension were then cytocentrifuged onto clean microscope slides using a CYTOSPIN 2 (Shandon) at 1000 rpm for 5 min at high acceleration. The slides were immediately removed, placed flat in a shallow dish and very gently flooded with KCM (Potassium Chromosome Medium: 120 mM KCl, 20 mM Nacl, 10 mM Tris-HCl, 0.5 mM $Na_2EDTA$, 0.1% v/v TRITON X-100) (Jeppesen et al., 1992). After 10 min at RT, immunofluorescence was performed without fixation (Earnshaw and Migeon, 1985; Earnshaw et al., 1989; Jeppesen et al., 1992; Jeppesen and Turner, 1993). KCM buffer was gently aspirated and 50 μl of CREST #6 serum [diluted 1:50 in 1×TEEN (1 mM Triethanolamine HCl, 0.2 mM $Na_2EDTA$, 25 mM NaCl), 0.1% v/v TRITON X-100, 0.1% w/v BSA] was added to the cell area of the slide and covered with a parafilm coverslip. The slides were incubated for 30 min at 37° C., then washed very gently by flooding in $1\times KB^-$ [10 mM Tris-HCl (pH 7.7), 0.15M NaCl, 0.1% w/v BSA), three rinses of 3 min each at RT. The primary antibody was detected with Texas Red-conjugated Affinipure Rabbit anti-Human IgG (H&L) (Jackson Laboratories) diluted 1:50 in 1×KB: 50 μl was added to each slide, covered with a parafilm coverslip, and incubated for 30 min at 37° C. The slides were again gently washed by flooding in $1\times KB^-$ for 2 min at RT, before they were fixed by flooding in 10% v/v formalin in KCM for 10 min at RT, followed by three rinses of 3 min each in distilled water. If FISH was not performed the slides were rinsed in PBS and mounted in DAP1 (0.25 μg/ml) in DABCO ANTIFADE mountant. [In experiments where CREST #6 and Am-Cl antisera were simultaneously used to label the centromere (FIGS. 2B and C), the above procedure was followed except for the addition of Am—Cl diluted 1:100 together with CREST #6, and the Am—Cl antibody was detected using 1:100 diluted Donkey anti-Rabbit DTAF (Jackson Laboratories)].

If FISH was to be performed on the slides, they were then given a second fix in 3:1 methanol/acetic acid for 15 min at RT. The slides were air dried for at least 5 min and either processed for FISH or stored at −20° C. for up to several days before continuing. For FISH, the slides were dehydrated at RT in 70%, 90%, 100% v/v ethanol (2 min each) and air dried. Chromosomal DNA was denatured in deionised 70% v/v formamide/2×SSC, pH 7.0 at 82° C. for 8 min followed by immediate dehydration in 70%, 90% and 100% v/v ethanol at −20° C. for 2 min each, then air dried for at least 10 min. (This high temperature of denaturation was critical to obtain maximum FISH signals). An amount of 15 μl of the prepared probe was added to each slide, covered with a 22 $mm^2$ coverslip, and sealed with rubber cement. Slides were hybridized overnight in a humid chamber at 37° C., then rinsed in 2×SSC at RT, followed by 3 washes of 0.1×SSC at 60° C. for 5 min each, rinsed again in 2×SSC, and immersed in a blocking agent of 5% non fat milk in 4×SSC for 10 min at RT. Probe hybridization was detected by incubation with FITC-conjugated avidin at 37° C. for 30 min, followed by three washes of 5 min each at RT in wash buffer (4×SSC, 0.05% v/v Tween-20). Signals were amplified by incubating with goat anti-avidin D antibodies for 20 min at 37° C., followed by three washes of 5 min each at RT in wash buffer, then with another layer of avidin-FITC for 30 min at 37° C., before the slides were washed in wash buffer, rinsed in PBS, and counter-stained with DAP1 (0.25 μg/ml) in DABCO mountant.

Method-II

The following method was modified from that of Haaf and Ward, (1994). Actively dividing lymphoblast cells were treated with 10 μg/ml colcemid for 2–3 h, washed in PBS and resuspended in a hyptotonic solution consisting of 10 mM Hepes (pH 7.3), 30 mM glycerol, 1.0 mM $CaCl_2$ and 0.8 mM $MgCl_2$, at a cell density of approx. $2.5\times10^2$/ml. After 10 min of hypotonic treatment at RT, 300 μl were cytocentrifuged (Shandon—CYTOSPIN 2) onto glass slides at 800 rpm for 4 min. The slides were immediately removed from the centrifuge, dried for 15 sec, fixed in methanol at −20° C. for 20–30 min, rinsed in acetone at −20° C. for a few sec, then washed in 3 rinses of PBS at RT. Immunofluorescence staining was done using CREST #6 at a dilution of 1:50 in PBS. After incubation at 37° C. for 30 min, the slides were washed three times in PBS for 2 min each. This primary antibody was then detected by a further incubation for 30 min at 37° C. with Texas Red-conjugated Rabbit anti-Human IgG diluted at 1:50 in PBS. The slides were fixed in 10% v/v formalin in KCM for 10 min at RT, then washed in 3 rinses of distilled water and drained. Before FISH was performed, slides were fixed in methanol/acetic acid 3:1 for 15 min at RT and air dried. Chromosomal DNA was denatured in 70% v/v deionised formamide (pH 7.0) in 2×SSC at 82° C. for 4–6 min. After dehydration in an ice cold ethanol series the slides were air dried, and used for FISH as described for Method I. Slides could be stored covered in foil at RT after methanol/acetic acid fix for up to several weeks before FISH.

Both methods I and II were used to obtain the results shown in FIGS. 2B, 2C, 3 and 4B.

EXAMPLE 6

Image Analysis

Hybridization signals for YAC mapping on standard metaphase preparations utilized a normal fluorescence microscope. Images for the ANTI-CEN/FISH experiments were analyzed on a Zeiss AXIOLAB fluorescence microscope equipped with a 100× objective and a cooled CCD camera (Photometrics Image Point) controlled by a POWER MAC computer. Gray scale images were captured separately using a LUDL filter wheel and controller for Texas Red, FITC and DAPI. These images were pseudocoloured and merged using IPLAB Spectrum software from Signal Analytics Corporation. A number of difficulties were commonly associated with the ANTI-CEN/FISH technique: (a) the deliberate "stretching" of the chromosomes, whilst increasing the resolution of mapping sometimes caused serious distortion to the chromosomes, often making them quite dysmorphic; (b) FISH treatment following the ANTI-CEN-labelling often significantly reduced the ANTI-CEN signals; (c) more highly stretched chromosomes (which would potentially give better mapping resolution) generally gave weaker ANTI-CEN signals; and (d) the ANTI-CEN signal on the mardel 10 centromere was usually weaker than those of the other human chromosomes. Thus, a cell would only be considered informative and used for scoring if both the p'- and q'-arms of the mardel 10 chromosome were discernible and separated by a discrete ANTI-CEN signal. In addition, FISH signals for both the test probe and the 10pC38 cosmid tag (used to identify the q'-arm of, and thus orientate, the marker chromosome) must be clearly present. Using these criteria, the overall frequency of informative cells was found to be approximately 1 in every 20–30 metaphases analyzed.

EXAMPLE 7

Restriction Analysis of Patient DNA

High-molecular weight genomic DNA was extracted from cultured fibroblast cell lines of patient BE and those of his parents and digested with different enzymes to generate restriction fragments ranging from <1 kb up to ~1 Mb. The digested DNA was resolved either on a standard agarose gel or by pulsed-field gel electrophoresis (PFGE) using a Bio-Rad CHEF-XA Mapper. For filter hybridization, 50–100 ng of whole cosmid or PAC DNA was labelled by random priming. The labelled probe was then added to 2 ml of hybridization buffer (0.5M $Na_3HPO_4$, 7% w/v SDS, 1% w/v BSA, 1 mM EDTA, pH. 7.0) containing 500 μg of human placental DNA (Sigma). The mixture was boiled for 5 min, then placed in a 65° C. water bath for preannealing of repetitive DNA for 90 min. The preannealed probe mix was then added to prehybridizing filters and hybridized overnight at 65° C. Post-hybridization washes were at a final stringency of 0.1×SSC, 0.1% w/v SDS at 68° C.

EXAMPLE 8

Identification of a YAC region spanning the marker centromere

Figures 1A, 1B:
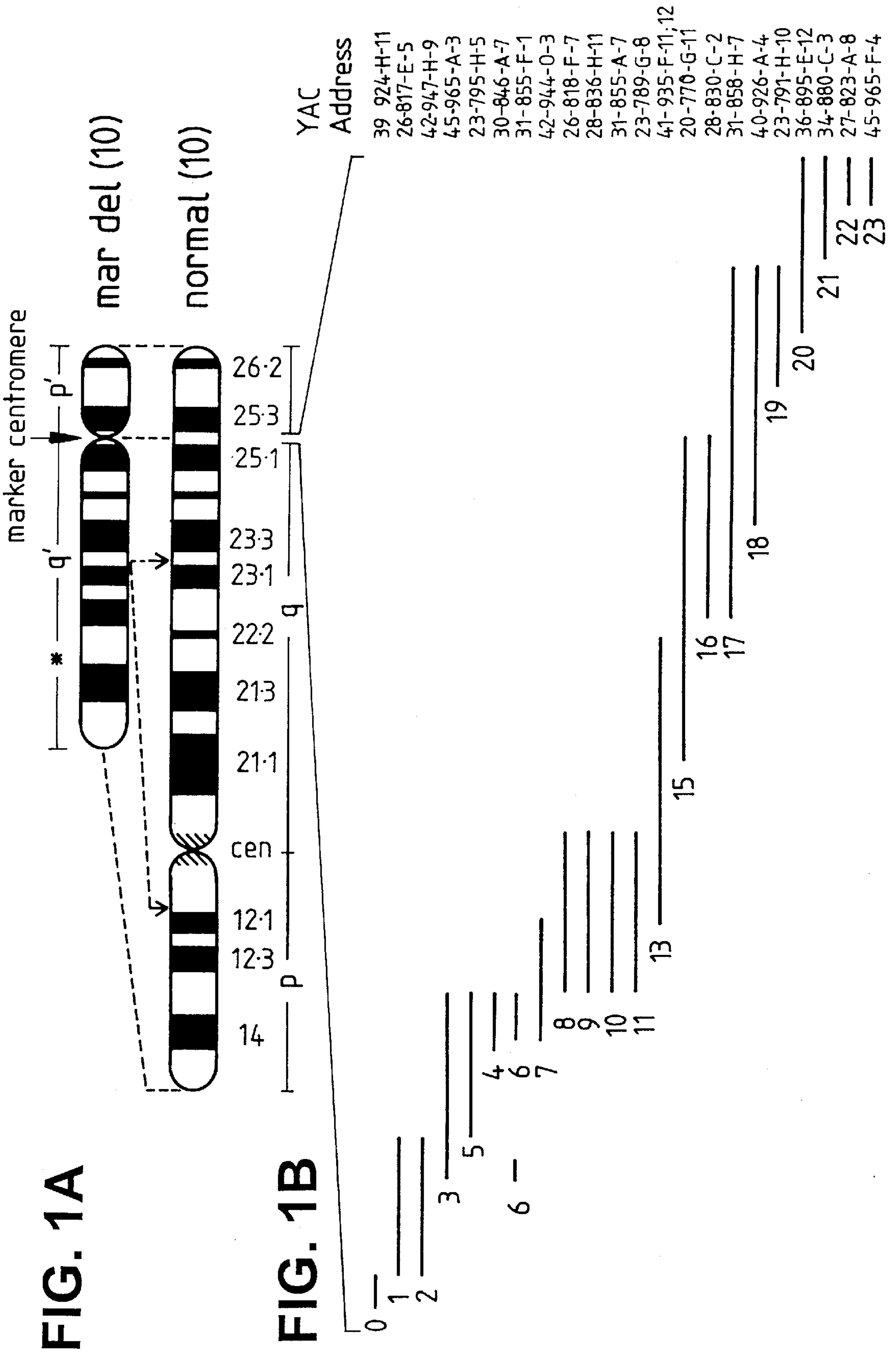
FIGS. 1A–1C are schematic representations showing identification of a YAC contig spanning the marker centromere region.
Figure 1C:
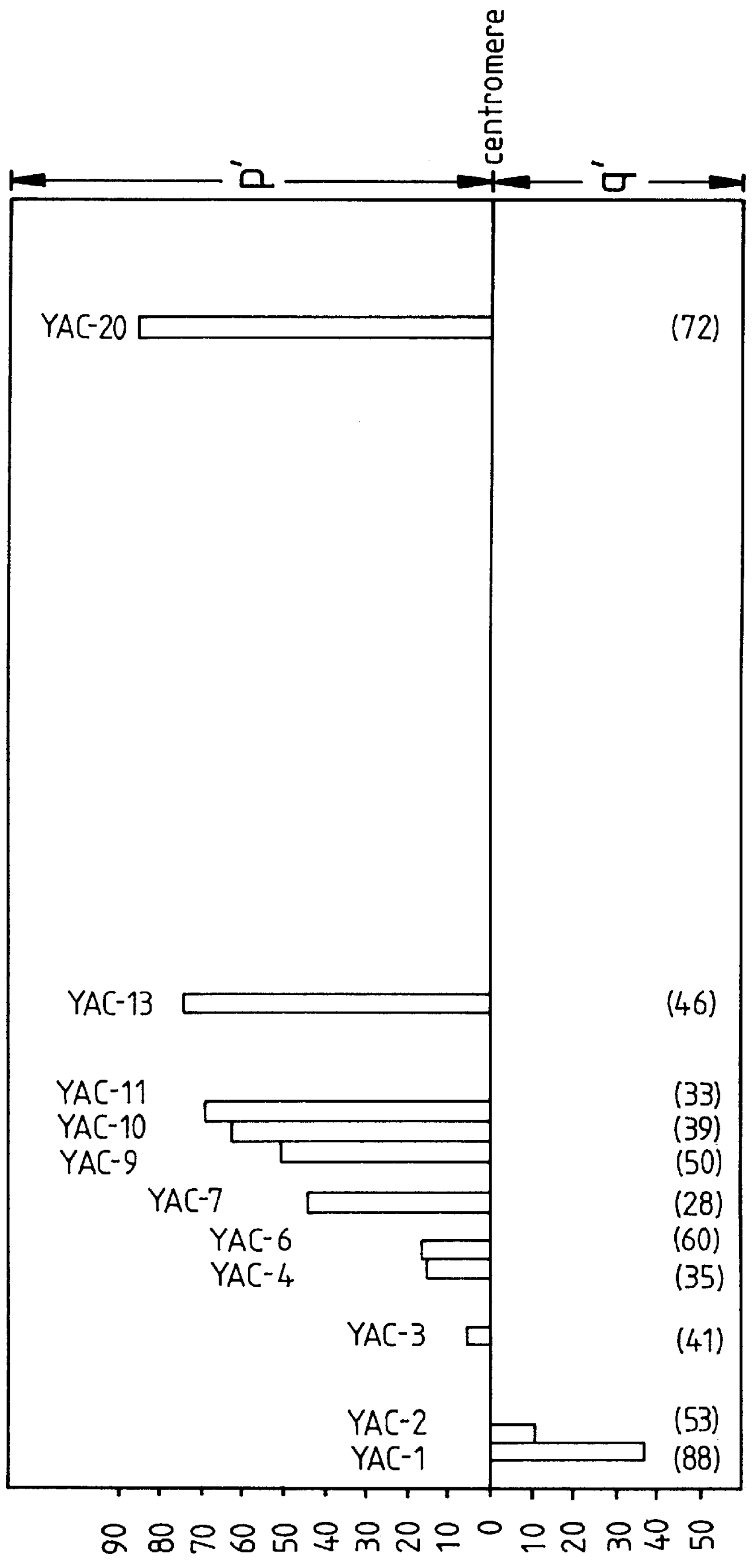

The initial search for DNA sequences spanning the centromere of the mardel 10 chromosome was based on fluorescence in situ hybridization (FISH) of existing cosmid and YAC clones (Moir et al., 1994; Zheng et al., 1994) that have been mapped to the q24–q26 region of the normal human chromosome 10 where the new marker centromere was formed (Voullaire et al., 1993) (FIG. 1A). This search led to the identification of a 4 megabase YAC contig (designated #082) that spanned the marker centromere region (FIG. 1B). FIG. 1C graphically presents the FISH mapping results with selected YACs from this contig. As can be seen, two of the YACs (YACs-1 and YAC-2) mapped to the q'-side of the marker centromere, whereas the remaining YACs mapped to the p'-side of the centromere. The low signal level observed for YAC-3 was due to a large proportion f this probe hybridising directly on the centromere itself. These results, therefore, provided evidence that YAC contig #082 spanned the marker centromere, and that the centromere region was likely to be within YAC-3, where the "cross-over" between the q' and p' signals occurred.

EXAMPLE 9

Development of Improved ANTI-CEN/FISH Methods for the Simultaneous Detection of Marker Centromere and Single-copy Cosmid DNA Probes Although normal fluorescence microscopy and FISH analysis of standard metaphase chromosomes were adequate for the initial identification of the YAC contig spanning the marker centromere, methods with significantly higher sensitivity and resolution were needed to allow further walking into the marker centromere DNA. Three requirements have to be satisfied by these methods: (a) the metaphase chromosomes have to be extended to offer much greater mapping resolution, (b) the centromeres have to be more precisely defined than that offered by a cytogenetic constriction, and (c) the methods should allow simultaneous visualization of both the centromere antibody and FISH signal. Two published methods were explored (designated here as ANTI-CEN/FISH methods) based on extending metaphase chromosomes by mechanical stretching and labelling of the neocentromere by autoimmune antibodies (Haaf and Ward, 1994; Page et al., 1995). Since these methods were originally established for the labelling of normal centromeres and for FISH analysis of highly repeated DNA, they were modified (see Example 4) to allow detection of the generally reduced ANTI-CEN signal of the subject marker neocentromere and the lower FISH signals resulting from the use of single-copy cosmid DNA probes.

With the improved detection methods, the status of α-satellite and satellite III DNA on the marker neocentromere was reassessed, since this was previously determined using standard microscopy and FISH (Voullaire et al., 1993). FIG. 2A shows the result of antibody labelling using CREST #6 and FISH using α-satellite DNA, and indicated the absence of detectable signal on the marker centromere. The same result was obtained when the experiments were repeated without ANTI-CEN-labelling, ruling out the possibility that the anti-centromere antibody might have obscured any weak FISH signals. Similar results were obtained with satellite III DNA. Since in separate reconstruction experiments, it was possible to demonstrate the sensitivity of the procedure in detecting a single-copy DNA probe of less than 1.5 kb, and making the reasonable assumption that the low-stringency hybridization conditions used for the α-satellite and satellite III DNA which, by virtue of the use of >100-fold excess of probes and the strong hybridisation of these probes to all the other centromeres, would have allowed the detection of any related sequences, it can be concluded that these satellite are absent.

EXAMPLE 10

Co-localization of CENP-C and CENP-A on the Marker neocentromere

Figure 2C:
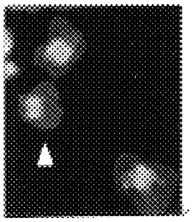
(FIGS. 2C(*a*)–2C(*e*)) Detection of CENP-C on the marker chromosome. Simultaneous labelling of the marker chromosome (arrowhead) with (FIG. 2C(*a*)) Am-C1 (pale blue) and (FIG. 2C(*b*)) CREST#6 (red).
Figure 2C:
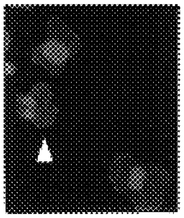
Figure 2C:
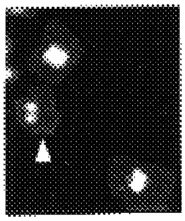
Figure 2C:
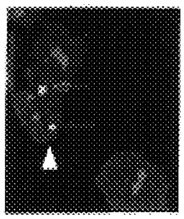
Figure 2C:
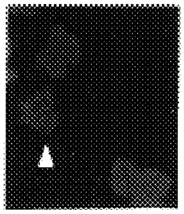

To test if CENP-C is present on the marker centromere, a specific rabbit polyclonal antibody was prepared against a recombinant product of mouse CENP-C. This antibody, designated Am—Cl, reacted strongly with the centromeres of rodent and human chromosomes. FIG. 2B shows results for the labelling of stretched human metaphase chromosomes using this antibody simultaneously with the CREST #6 autoimmune antibody. As can be seen, irrespective of the degree of chromosome stretching, the signals for the two antibodies coincided fully on all the centromeres. The localization of these two antibodies on the marker chromosome was further determined by employing the 10pC38 cosmid tag in an ANTI-CEN/FISH experiment to identify the marker chromosome. The results indicated that both the antibody signals were clearly present and again coincided completely on the marker centromere (FIG. 2C, a–e). Although CREST #6 was known to bind CENP-A and CENP-B, indirect evidence suggests that binding to the marker centromere presumably occurred via CENP-A since the presence of the marker centromere was previously demonstrated not to bind CENP-B (Voullaire et al., 1993). The above results, therefore, established the localization of CENP-C, and probably CENP-A, on the marker centromere.

EXAMPLE 11

Localization of the anti-centromere antibody-binding domain

Figure 4A:
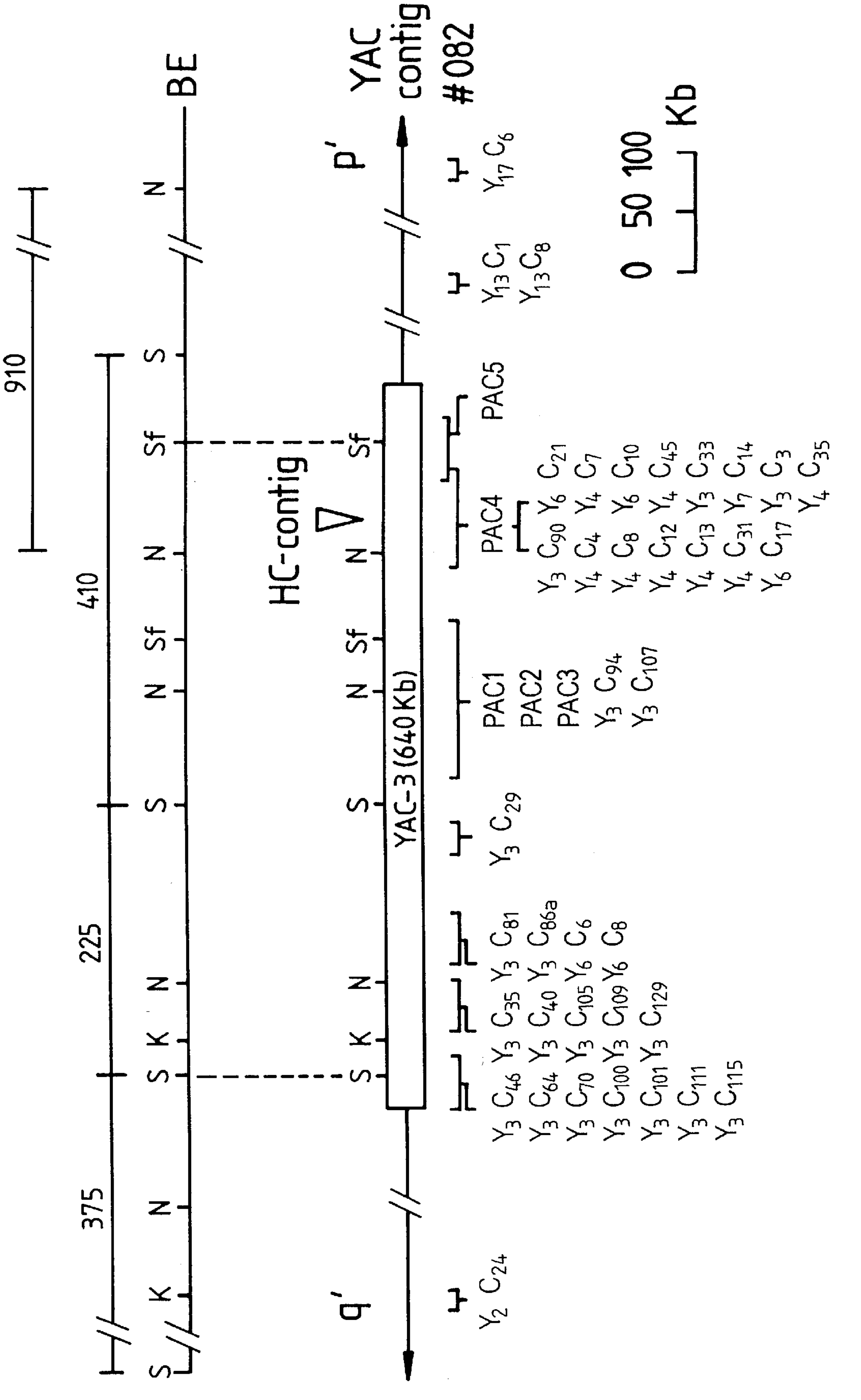
FIGS. 4A–4C Localization of the anti-centromere antibody-binding domain.
Figure 4B:
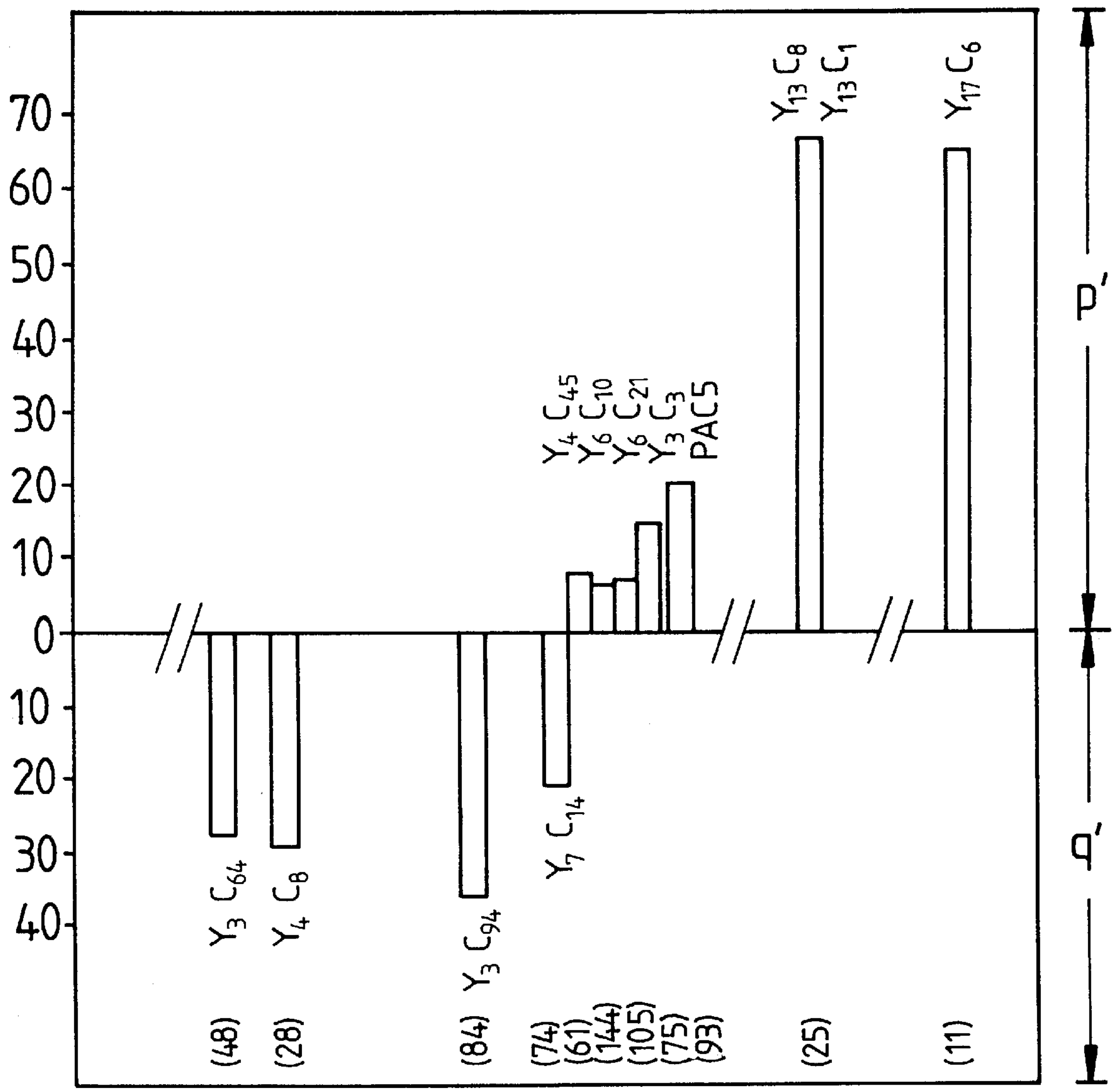
Figure 4C:
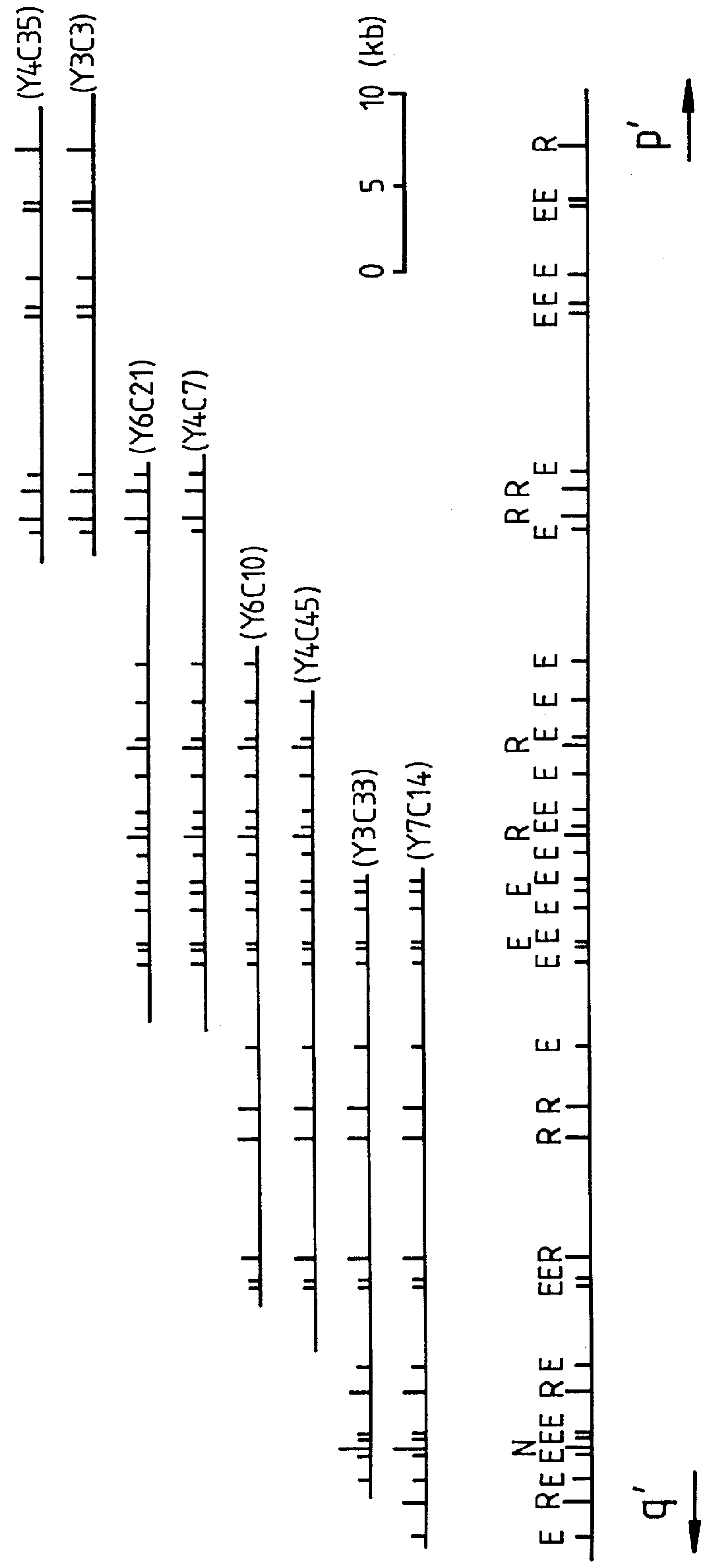

For further walking into the marker centromere region, cosmid libraries were prepared from total yeast genomic DNA containing YACs-2, -3, -4, -6, -7, -13, and -17. Cosmid clones containing human DNA inserts were isolated by hybridization with human COT-1 DNA using low stringency. All resulting cosmids were screened by standard FISH to confirm their localization to the expected marker centromere and normal chromosome 10 regions, and to eliminate clones that might have originated from other genomic sites due to chimeric YACs. Positive clones were then analyzed further with the ANTI-CEN/FISH methods, using CREST #6 to label the centromere. FIG. 3*a* (I and II) show examples of cosmid signals that mapped to the q'- and p'-side, respectively, of the marker centromere in the ANTI-CEN/FISH experiments. The cosmid tag (clone 10pC38) was used in these experiments to define the q' arm of the marker chromosome. For cosmid walking, we concentrated on clones derived from YAC-3 since FISH mapping of YAC contig #082 indicated that the marker centromere region was likely to be within this YAC. FIG. 4*a* shows a restriction map of the region covered by this and surrounding YACs and compares this map with a genomic map derived from patient BE. The relative positions of a series of cosmid clones (including five independent PACs) were also determined and placed on the YAC map. FIG. 4*b* presents the ANTI-CEN/FISH results obtained with a number of the cosmid clones and one of the PAC clones. Clones Y3C64, Y6C8, and Y3C94 localized preferentially to the q'-side, while Y13Cl+C8 and Y17C6 localized preferentially to the p'-side of the marker centromere, suggesting that the nucleus of the antibody-binding domain is situated between these two cosmid clusters. Within this central region a group of cosmid clones comprising the HC-contig (FIG. 4*a*) was found to map closely around the ANTI-CEN signal. FIG. 4*c* shows a restriction map for eight different overlapping clones from this HC-contig. The chromosomal positions of five of these overlapping clones were analyzed in detail using ANTI-CEN/FISH. FIG. 4*b* shows the cumulative results for more than 60 informative chromosomes for each of these five probes. The results indicated that Y7C14 mapped preferentially q'- of the antibody-binding domain, while the remaining four clones (Y4C45, Y6C10, Y6C21 and Y3C3) mapped preferentially to the p'-side. In addition, the results for PAC5 (a 75 kb-insert PAC clone that overlapped with the p'-end of PAC4 by approximately 5 kb; see FIG. 4*a*) provided further evidence for the emergence of the HC-contig region onto the p'-arm. Based on these results, we conclude that the eight contiguous cosmid clones within the HC-contig shown in FIG. 4*c*, which together constitute ~80 kbp of DNA, have defined the nucleus of the antibody-binding domain of the marker centromere.

From the above ANTI-CEN/FISH results, it was difficult to determine if the sequences of the HC-contig and its surrounding DNA, both originally derived from a normal individual, were part of the marker centromere DNA, or whether these sequences simply flanked a transposed centromere DNA with an unrelated nucleotide composition. However, supporting evidence from the ANTI-CEN/FISH experiments suggested that the DNA of the HC-contig region appeared to be a part of the marker centromere. This came from the mapping of Y6C10 and Y6C21 onto super-stretched chromosomes that were occasionally detected in the slide preparations. An example of such mapping is shown in FIG. 3*b* using Y6C21. As can be seen, whilst a significant portion of Y6C21 hybridized to the p'-side of the CREST signal on the highly extended chromosome, a substantial portion of the cosmid DNA also overlapped directly with the CREST signal. This suggests that at least part of the HC-contig region actually comprises the same DNA sequence as the marker centromere. This possibility was further investigated by detailed genomic mapping.

EXAMPLE 12

Figure 5A:
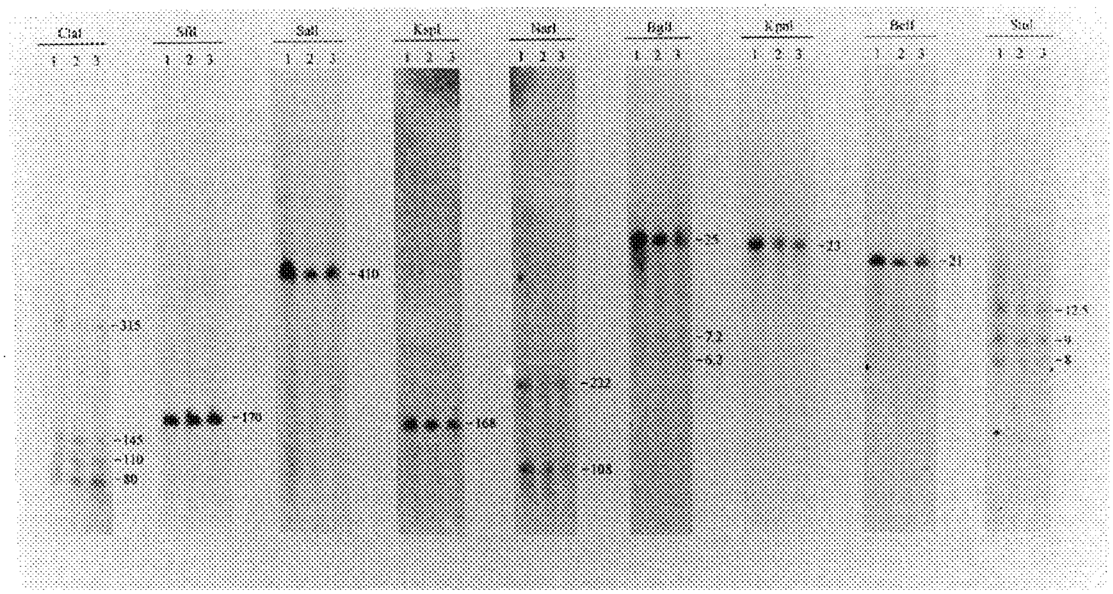
FIGS. 5A–5C are representations showing restriction analysis of genomic DNA of patient BE and those of his normal parents using Y6C10 as probe. DNA was resolved on a PFGE (FIG. 5A) or standard agarose gel (FIGS. 5B and 5C). Samples 1, 2 and 3 were fibroblast cultures of mother of BE, father of BE, and patient BE, respectively. Sample 4 was a somatic hybrid cell line BE2C1-18-5F containing the marker chromosome. Fragment sizes are in kilobases.
Figure 5B:
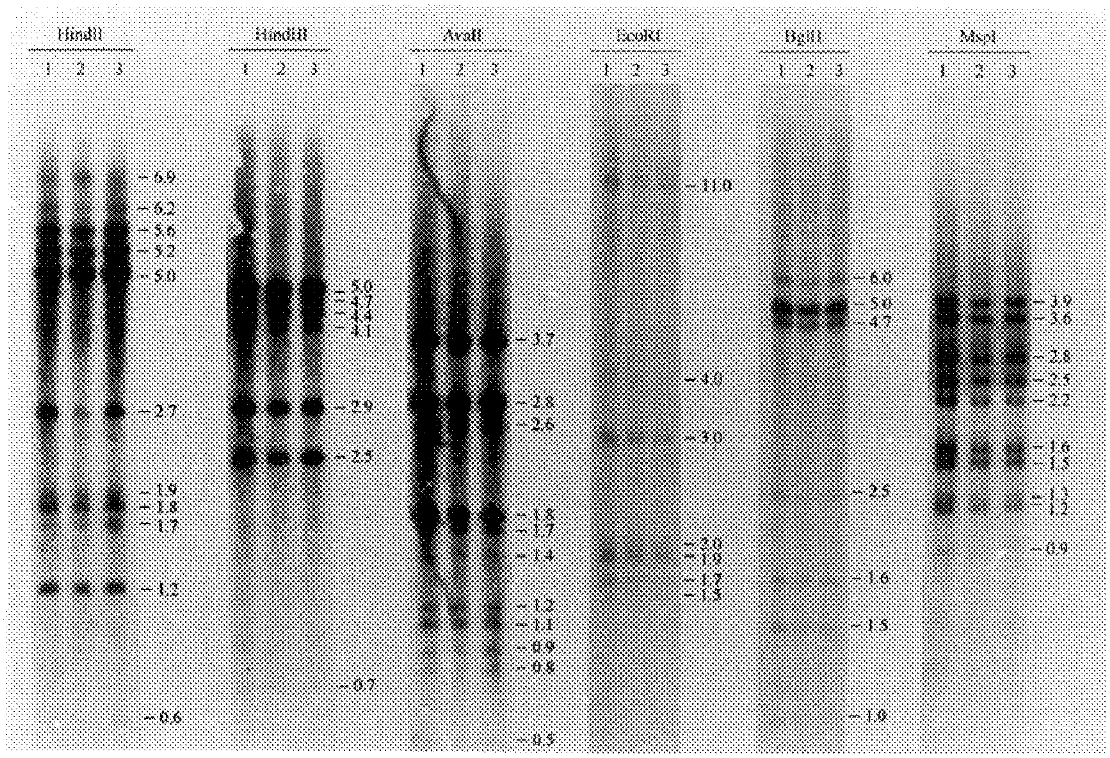
Figure 5C:
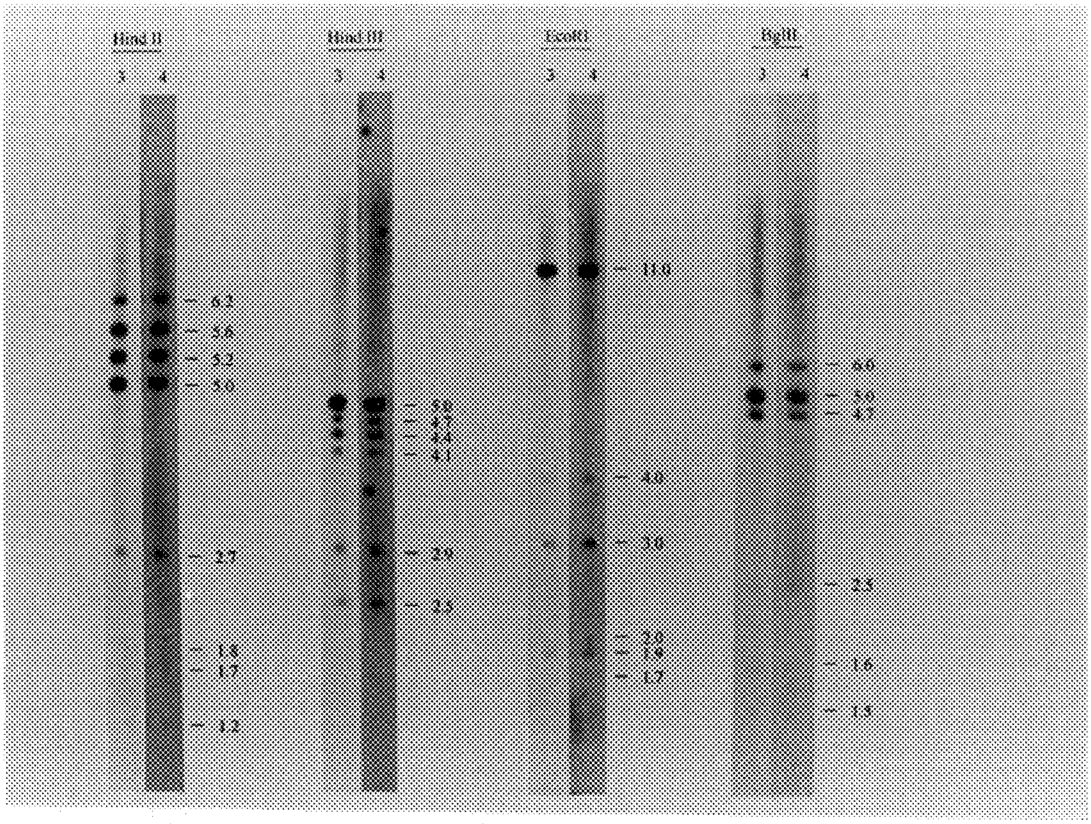

The Marker Centromere DNA has a Similar or Identical Sequence Organization as the HC-Contig The genomic organization of the HC-contig region was compared with that of the corresponding DNA region of the mardel (10) chromosome. Three overlapping cosmids (Y7C14, Y6C10, and Y4C7, the latter being essentially the same as Y6C21; FIG. 4C) from the HC-contig were used as probes to analyze the restriction patterns of genomic DNA prepared from patient BE and those of this karyotypically normal parents. FIG. 5 shows examples of the band patterns obtained with Y6C10, while Table 1 summarizes the results for all the enzymes tested with Y7C14, Y6C10 and Y4C7. The detection of a single and on PFGE gels with a number of the enzymes indicated that the cosmid DNA sequences were unique within the human genome (SfiI, SalI, KspI, KpnI and BclI in FIG. 5A; Table 1). The detection of a single on PFGE gels with a number of the enzymes (ClaI in FIG. 5A; Table 1) could be explained by differential methylation of different restriction sites found in this region (Nelson and McClelland, 1991); the reproducibility of these multiple band patterns ruled out incomplete digestion as a possible cause. The multiple bands detected with the more frequent cutting enzymes on a standard gel (FIG. 5B and Table 1) were a result of the presence of cleavage sites present within the probe DNA, since similarly digested cosmid DNA electrophoresed next to the genomic DNA yielded identical patterns for all the bands not containing cosmid vector sequences. In all, 37 enzymes were used to generate more than 160 different fragments for the three cosmid probes (Table 1). The results indicated that, except for a polymorphic fragment found in one of the parents, an identical banding pattern was present in the genomic DNA of patient BE and those of his parents. Furthermore, when the restriction patterns obtained for the genomic DNA of patient BE were compared with those of the smatic hybrid cell line BE2C1-18-5F, which contained the marker chromosome but not the normal chromosome 10, no detectable difference was seen between the two DNA preparations within the HC-contig region (FIG. 5C).

In addition to Y7C14, Y6C10and Y4C7, a host of other probes from within or surrounding the HC-contig have been tested, each with an average of 12 different information enzymes. These probes included PAC4 (which spanned the entire HC-coding region shown in FIG. 4C), Y3C64, Y3C109, Y6C6, Y6C8, Y3C94, PAC1, Y3C90, Y4C4, Y4C8, Y4C13, and Y3C33. The results again indicated identical restriction enzyme patterns between patient BE and normal DNA. Thus, through the analysis of a relatively large number of probes covering about 500 kb of YAC-3 around the HC-contig region, and the use of a high density of restriction enzymes that generated a range of fragments from <1 kb to −1 Mb, it was evident that the market centromere DNA and a substantial stretch of its adjoining regions showed no detectable difference against the corresponding genomic region of the normal chromosome 10.

Since a potential limitation of the above Southern blot analyses was that highly repeated sequences were not detected because of the preannealing step used in the hybridisation procedure, a different approach was employed to compare the DNA of the marker chromosome and that of the normal chromosome 10. In this approach, oligonucleotide primers from different regions of the HC-contig were used to prepare a series of PCR fragments from the BE2C1-18-5F and BE2C1-18-1F hybrid cell lines. Electrophoretic comparison of such fragments, which randomly covered approximately 40 kb of the HC-contig, indicated no detectable difference between the two chromosomes and provided independent support for the results obtained in the Southern blot analyses. Thus, it can be concluded that the sequence organization of the marker centromere region is similar, if not identical, to that found in the HC-contig region of the normal chromosome 10.

EXAMPLE 13

Implications for Centromere Study and Mammalian Artificial Chromosome Construction The mammalian centromere has been difficult to study due to the massive amount of repetitive DNA normally associated with it. By avoiding such repetitive DNA and analyzing the unusual centromere found in the present marker chromosome, the inventors have created a much more tractable system for centromere studies. The present analysis has already shed some light on the important question of DNA sequence versus conformational requirement of a centromere, and on the intriguing concepts of latent centromeres and epigenetic mechanisms. One urgent application of this DNA is to use it to identify the primary protein(s) which binds to the centromeric DNA. Another important application of the marker centromere DNA is in the construction of mammalian artificial chromosomes. Such artificial chromosomes offer a potentially powerful vehicle for the structural and functional analysis of chromosomes, for the genetic manipulation of plants and animals, and for the stable transmission of therapeutic genes in human gene therapy. The artificial chromosomes require a functional mammalian centromere, and the marker centromere DNA element of the present invention now provides a suitable centromere especially because of its relatively small size in the absence of α-satellite DNA and its cloning stability, as indicated by the cosmid, YAK and BAC clones of the HC-contig and NC-contig.

EXAMPLE 14

Sequence Analysis

FIGS. 6, 16A and 16B show partial nucleotide sequences for the HC-contig (SEQ ID NO: 3) NC-contig [SEQ ID NO: 4] and F2 (BAC/F2-14) [SEQ ID NO: 5–29] regions, respectively.

EXAMPLE 15

Human Artificial Chromosome (HAC)

The following are examples of the different approaches being used in the inventors' laboratory for the production of a HAC:

Retrofitting of HC-contig DNA from normal chromosome 10

This procedure aims to produce HACs of 100 kb to >1 Mb using the region of the normal chromosome 10 containing and surrounding the HC-contig DNA. The generation of a HAC by this approach will provide crucial proof that this normal DNA region can be reactivated to form a functional centromere.

Figure 7A:
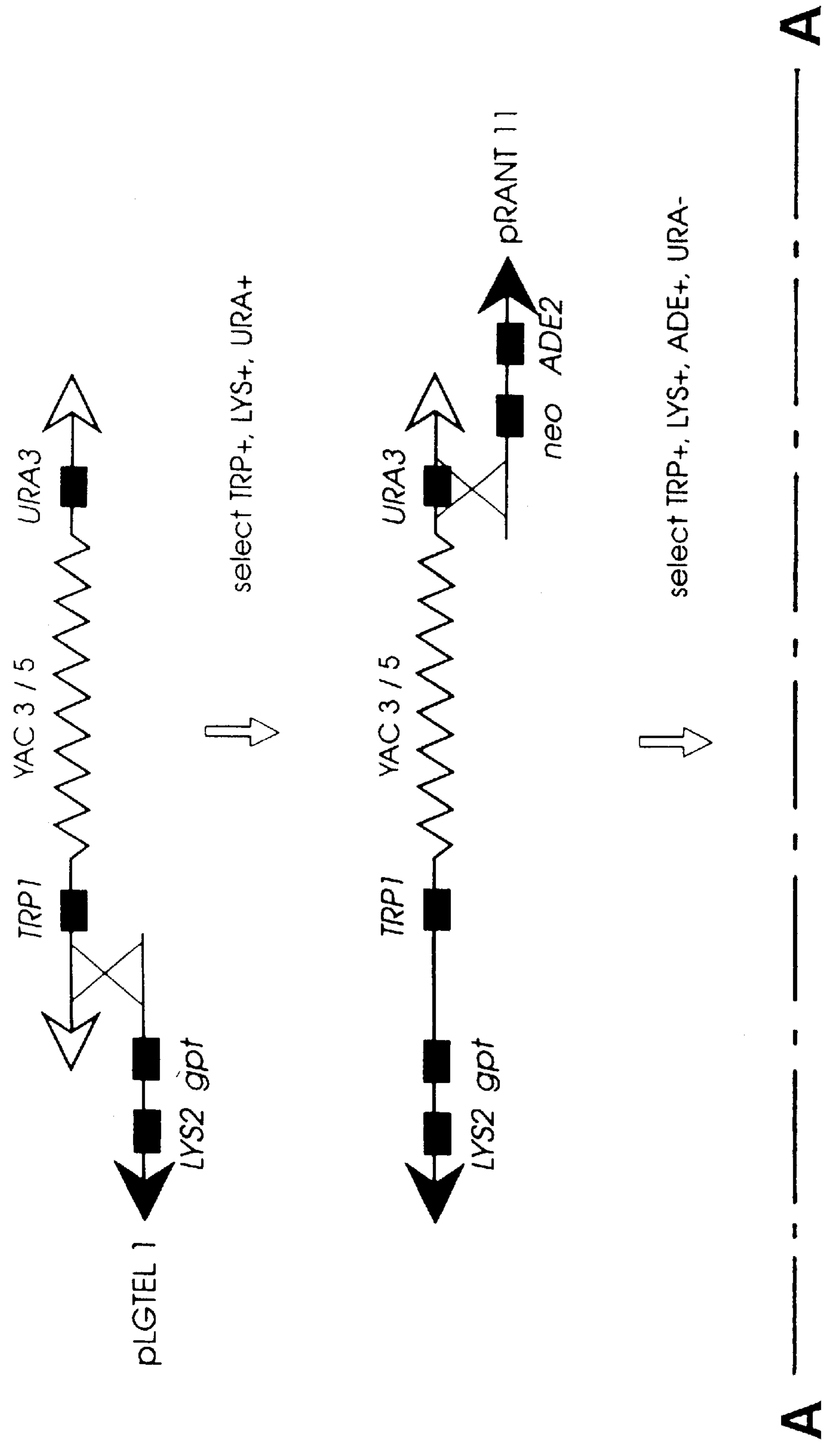
FIGS. 7A–7B, when joined at matchlines A—A, depict the method used to retrofit YAC3 and YAC5.
Figure 7B:
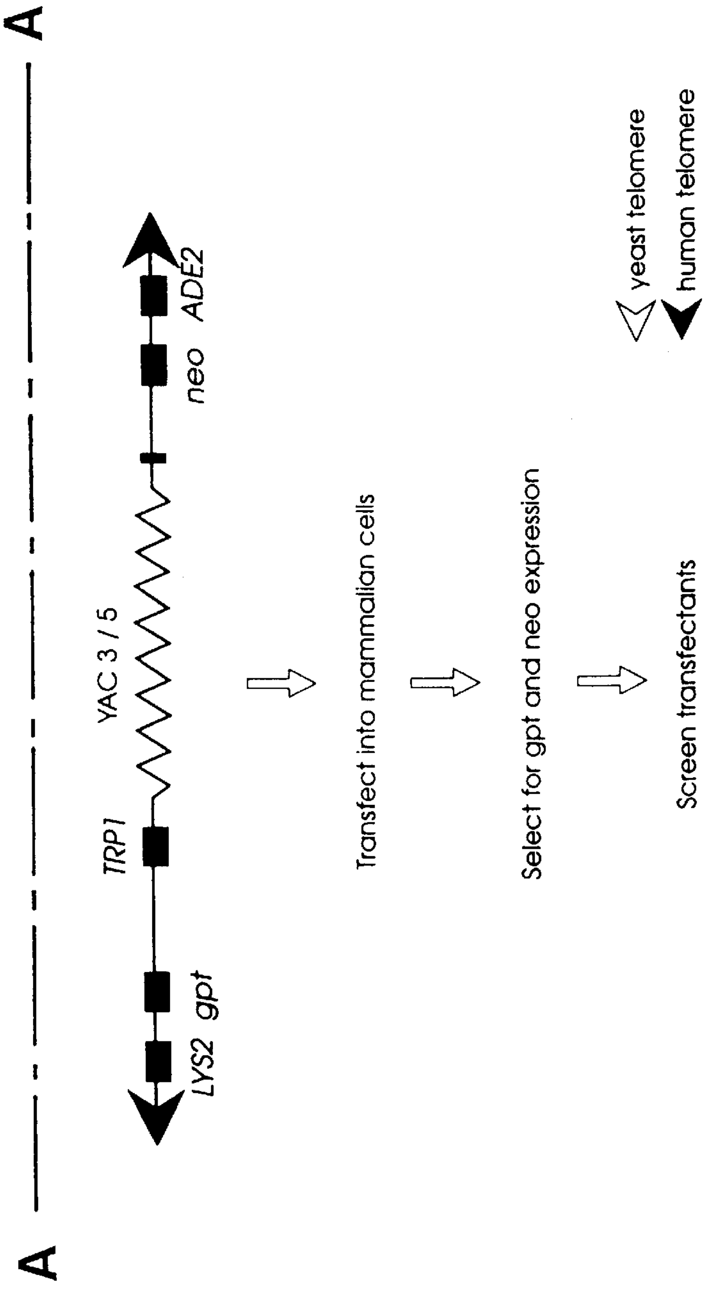

A retrofitting procedure suitable for introducing human telomeres to both ends of any YAC prepared in the pYAC4 vector in the yeast host strain AB1380 has been previously described (Larin et al., 1994; Taylor et al., 1994, 1996). YACs (in particular YAC-3 and YAC-5) spanning the normal HC-contig region are used for retrofitting by plasmid constructs designed to recombine with their pYAC4 vector arms (FIG. 7). The construct pLGTEL 1 is used to target the left arms of the YACs. This serves to add a LYS2 yeast selectable marker, gpt element for ultimate selection in mammalian and avian cell culture, and a human telomere. The right arm of the YACs are targeted by homologous recombination with pRANT 11 to produce a final construct where additional markers are introduced along with a second human telomere to cap the construct. Specifically, an ADE2 yeast marker is added and the URA3 gene of the YAC is disrupted, serving a useful role in negative selection of the construct. A neomycin (neo) resistance gene shown to function in mammalian and avian cells is also introduced. The finished constructs are transfected into different cultured cell lines, including HT1080 (of human sarcoma origin) (Larin et al., 1994; Rasheed et al., 1974), DT40 (a recombination-proficient chicken cell line) (Dicken et al., 1996), and BE2CI-18-5f (a human/hamster somatic hybrid cell line containing the mardel (10) chromosome but not the normal chromosome 10).

In vitro cloning HC-region into YAC/HAC vectors

The different vectors used for the cloning of the normal and mardel (10) centromeric DNA in the preparation of HACs are summarised in Table 2.

A number of different YAC cloning strategies are employed:

Conventional YAC cloning approach. FIGS. 8A–D show the different vectors used for cloning DNA as YACs by the conventional restriction/ligation methods. These YACs can then be shuttled into mammalian cells and tested for HAC function.

Figure 10:
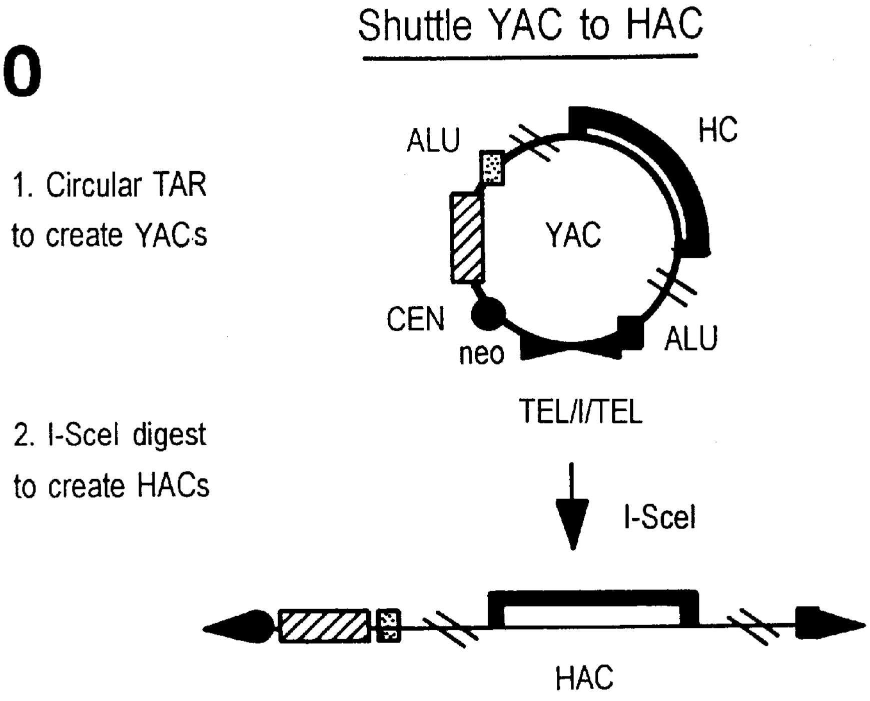
FIG. 10 is a diagrammatic representation showing modification of TAR vector.

ALU-ALU circular TAR cloning approach. Transformation-associated recombination (TAR) in the yeast *S. cerevisiae,* is a method for constructing linear and circular YACs from mammalian DNA (Larionov et al., 1996b). The recombination process is shown in FIG. 9. Briefly, the technique involves the use of a vector (pVC39-AAH2, FIG. 8E) lacking an autonomous replicating sequence (ARS) but containing a functional yeast centromere (e.g. CEN6) and selectable marker (e.g. HIS3), and two ALU DNA hooks to trap mammalian DNA by recombination at ALU sequences after co-transformation of linearized vector and high molecular weight DNA into yeast spheroplasts and followed by selection on medium lacking histidine. The key to the process is that the mammalian DNA provides an ARS (11-bp sequence found frequently in mammalian DNA) which allows the HIS*/CEN vector to replicate as a circular YAC. These YACs are very stable and range in size from 100 kb to greater than 600 kb (Larionov et al., 1996b).

pVC39-AAH2 vector is used to clone DNA from hybrid BE2CI-18-5f to make YACs with an average insert of 250 kb. This TAR vector is further modified to create pAAH-TCNa (FIG. 8G) so that it has the ability to shuttle between yeast and mammalian cells (as outlined in FIG. 10), including the potential to expose human telomeres (TEL) at each end of a cloned fragment using a unique restriction site I-SceI.

Semi-specific and specific circular TAR. A modified circular TAR method utilising two specific 5'C and 3'C DNA hooks (300–700 bp in size) may be used to clone a specific human DNA at a frequency of 3/1000 HIS* transformants. The inventors prepared the vectors pVC39-ALU/C3-F2 (+/–) and pTCN-TCS (Table 2) to perform semi-specific and specific TAR cloning, respectively.

The Semi-specific TAR methodology is a modification of a specific circular TAR strategy which permits the site directed isolation of target chromosomal DNA. Furthermore, in accordance with the present invention, the methodology described herein enables the site-specific cloning of target chromosomal DNA from total genomic DNA as a circular YAC at relatively high frequencies and without the need for the construction and extensive screen of complex libraries made from genomic DNA.

In a preferred embodiment of the present invention, the methodology employs a single specific DNA hook which flanks the mardel (10) chromosome and a less specific Alu-hook to trap the other side of the target DNA.

In initial experiments, a unique repeat DNA-free, 1.4 kb EcoRI fragment (designated C3-F2) was identified from the p' side of the 80-kb HC-contig (FIG. 11A) (du Sart et al., 1997). This fragment was subcloned into the centromere-based yeast circular TAR vector, pVC39-AAH2, by replacing the existing BLUR13 Alu (Larionov et al., 1996b) to create the pVC39-ALU/C3-F2 constructs. As the specific orientation of the C3-F2 sequence on the chromosome was not known, the fragment was cloned in two different orientations, for which the (+) orientation (FIG. 11B) was expected to trap the genomic region to the left of C3-F2, while the (–) orientation was expected to trap the region to the right. Both constructs were used in yeast transformation.

Figure 11A:
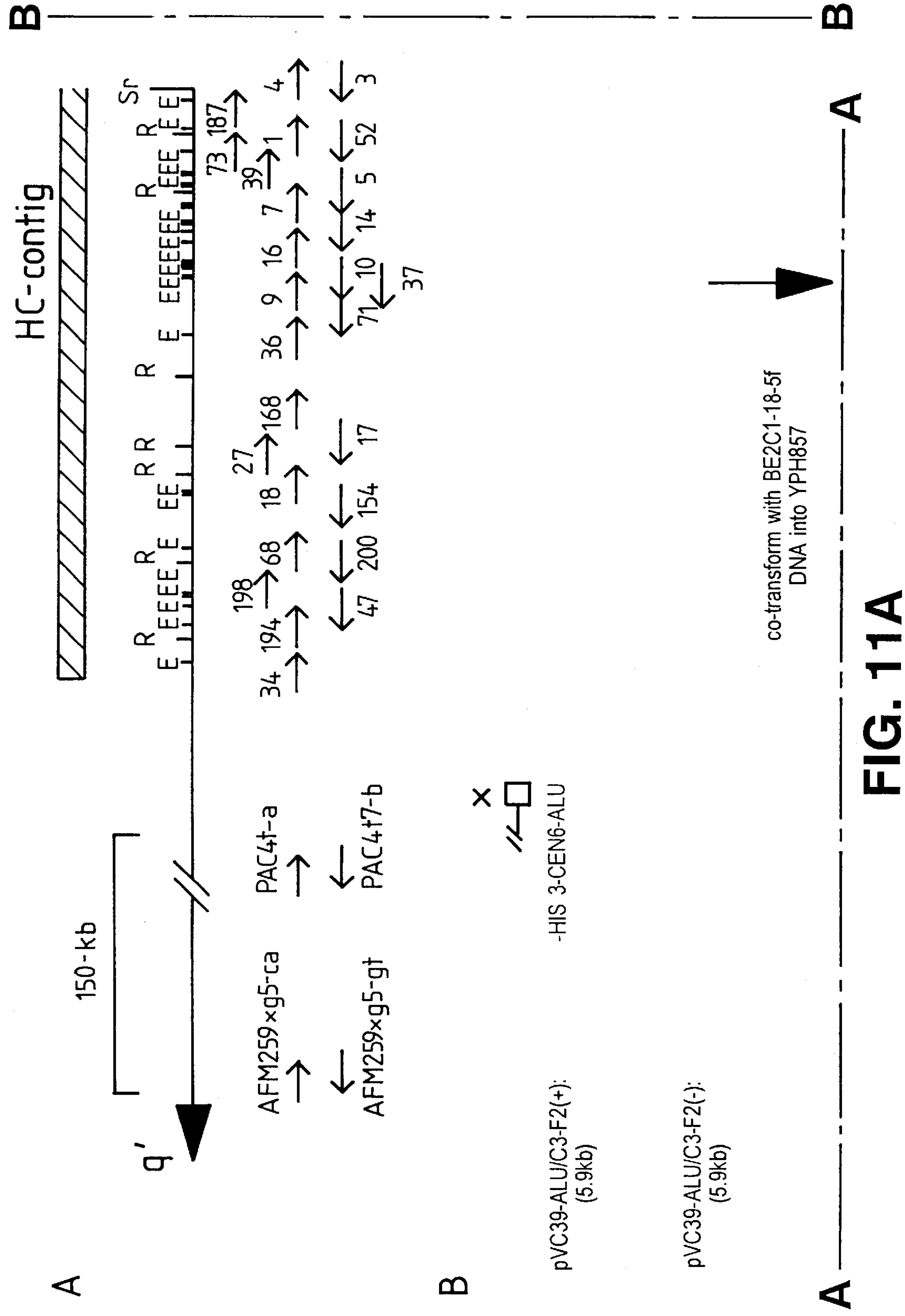
FIGS. 11A–11D, when joined at matchlines A—A through D—D, depict the cloning of 10q25 human neocentromere DNA from mardel (10) chromosome. This DNA is designated NC-contig DNA to distinguish it from the HC-contig derived from the corresponding region of the normal chromosome 10.
Figure 11B:
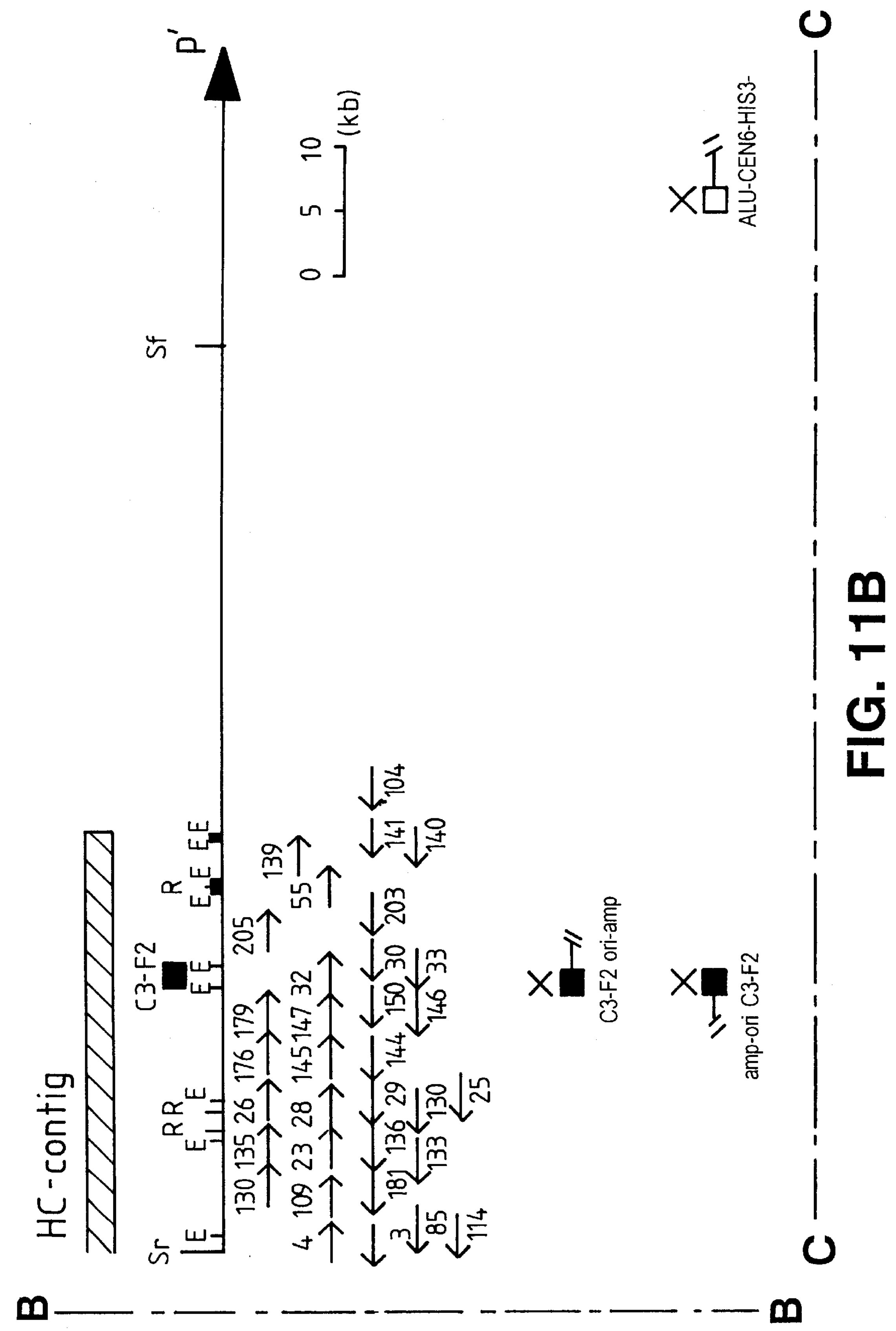
Figure 11C:
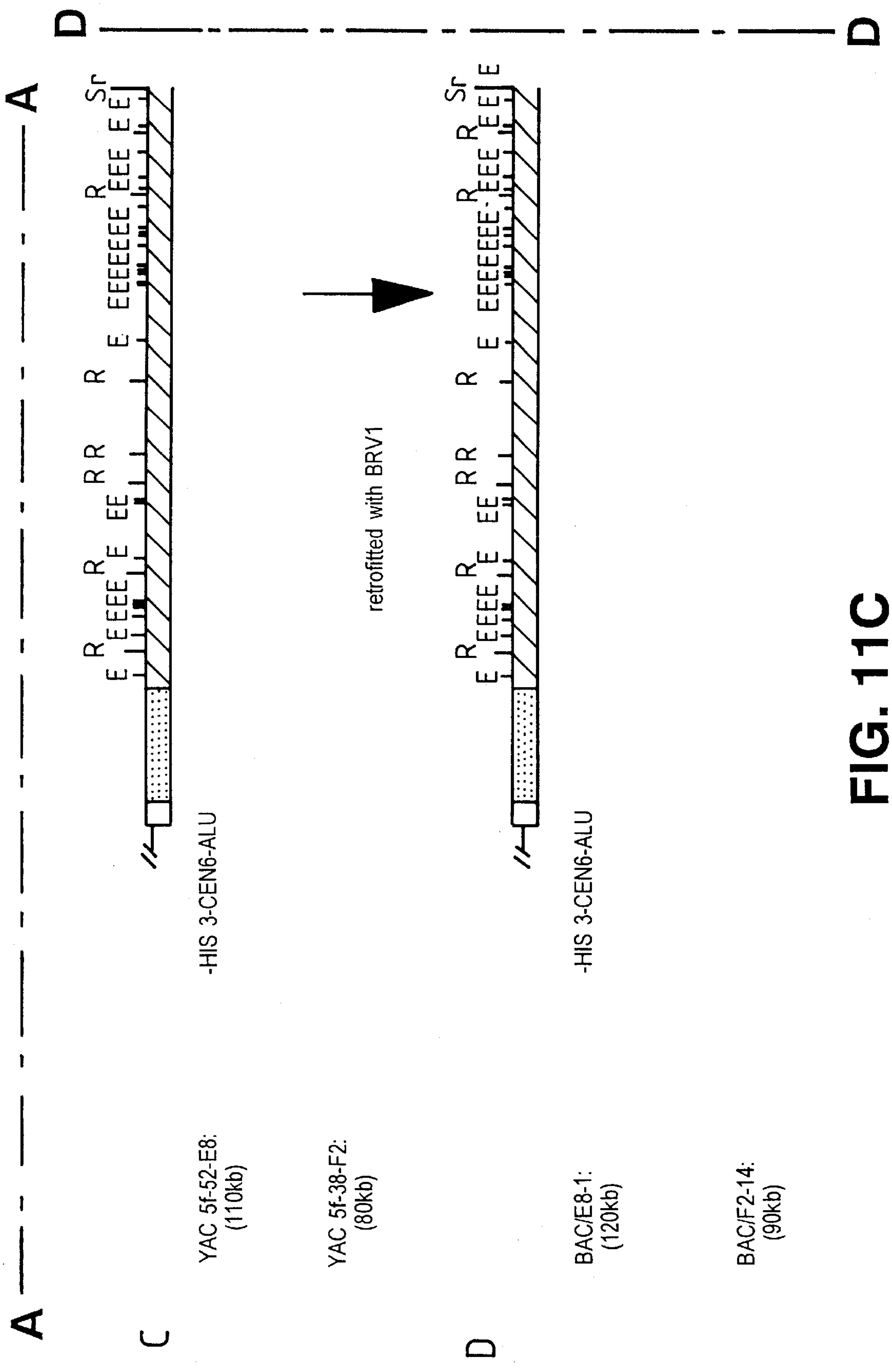

As a source of genomic DNA containing the neo-centromere, a somatic hybrid cell line, BE2C1- 18-5f (du Sart et al., 1997), containing the mardel 10 chromosome but no the normal human chromosome 10 was used, 5 $\mu$g of high-molecular-weight DNA from this cell line and 1 $\mu$g of pVC39-ALU/C3-F2(+) or pVC39-Alu/C3-F2(–) (linearized with SmaI to expose the 0.21-kb Alu and 1.4-kb C3-F2 hooks) were co-transformed into $10^9$ (previously prepared and stored frozen) spheroplasts of *S. cerevisiae* YPH857 which carries a HIS3 gene deletion, (Sikorski and Hieter, 1989) and grown on SD, without HIS medium, (Larionov et al., 1996a;b) to yield between 10 and 100 HIS* colonies. Control experiments in which YPH857 was transformed with vector alone did not produce any colonies, indicating that the C3-F2 fragment lacked ARS-like sequences. Twenty TAR experiments were performed and HIS* colonies were picked into 96-well trays containing YPD medium (supplemented with 50 $\mu$g/ml ampicillin and 15 $\mu$g/ml tetracycline), grown at 30° C. with aeration for 24 h and stored in 20% (v/v) glycerol at –70° C. Total yeast DNA was prepared in pools of 48 (Kwiatkowski jr et al., 1990) and screened by PCR with the primers norm 5 and norm 7 (Table 3) which are located 30-kb q' of C3-F2 (FIG. 11A). Two desired positive clones, designated 5f-52-E8 and 5f-38-F2, which contained the neo-centromere DNA derived from mardel 10 and mardel (10) and the DNA immediately p' of the neocentromeric DNA, respectively, were identified. For subsequent studies, these clones were grown on SD without HIS medium and single colonies were re-isolated for characterization.

Initially, the sequence nature and sizes of the 5f-52-E8 and 5f-38-F2 insert DNA were determined. High molecular-weight DNA was prepared in agarose blocks and digested with an enzyme (SrfI) that linearized with YAC (FIG. 11A). The linearized DNA, as well as uncut intact DNA, were resolved by pulsed-field gel electrophoresis (PFGE), transferred onto a nylon membrane and probed with radiolabelled PAC4, a P1-derived artificial chromosome clone containing a 120-kb insert that spans the entire HC-contig from normal chromosome 10, (du Sart et al., 1997) following preannealing with human placental DNA to suppress repetitive DNA. The intact 5f-52-E8 and 5f-38-F2 remained trapped in the electrophoretic wells and the linearized DNA migrated into the gel and demonstrated a size of approximately 110 kbp and 80 kbp, suggesting insert sizes of about 105 kbp and 75 kbp, respectively (given that the vector size is 5.9 kb).

Despite the use of a genomic DNA source previously shown by sequence-tag-site (STS) analysis to be free from normal chromosome 10 material, it is desirable to independently confirm the mardel (10)-origin of the 5f-52-E8 YAC clone. This was achieved using a set of primers (norm 17 and 18; FIG. 11A) that detected a variable-number-tandem repeat (VNTR) region within the HC-contig/neocentromere region. The results clearly indicated the presence of a 1.4-kb PCR product that was specific for the mardel (10) chromosome (Table 3).

PCR was used to further compare the 5f-52-E8 DNA with the previously cloned HC-contig sequence derived from normal chromosome 10. PCR products with sizes ranging between 0.2 and 15.9 kb were generated by standard PCR or with the Expand Long Template PCR system (Boehringer-Manneheim). Products greater than 1 kb were digested with frequent cutting enzymes, RsaI and BsiXI, and their fingerprints were compared by agarose gel electrophoresis. The results, shown in Table 3, indicated the absence of any detectable difference between the 5f-52-E8 DNA and those of the corresponding regions of the normal chromosome 10 (in somatic cell hybrid BE2C1-18-1f) and the neocentromere region of mardel (10) (in somatic cell hybrid BE2C1-18-5f). These results also demonstrated that the YAC 5f-52-E8 spanned at least 75 kb of the HC-contig region (FIG. 11C), consistent with the size determined by PFGE. Furthermore, the ability of all the internal primers to amplify DNA from 5f-52-E8 strongly suggested that the YAC was not chimeric. This result was confirmed by isolating DNA from four single-colony isolates of 5f-52-E8, digesting these with EcoRI and EcoRV, and probing with radiolabelled PC4. The hybridization patterns obtained with these enzymes were consistent with those established in the previous study (du Sart et al., 1997). Thus, this analysis, based on cloned DNA derived directly from mardel 10, has provided confirmation that the neocentromere DNA region is structurally identical to that of the corresponding HC-contig region of the normal chromosome 10 (du Sart et al., 1997).

Figure 11D:
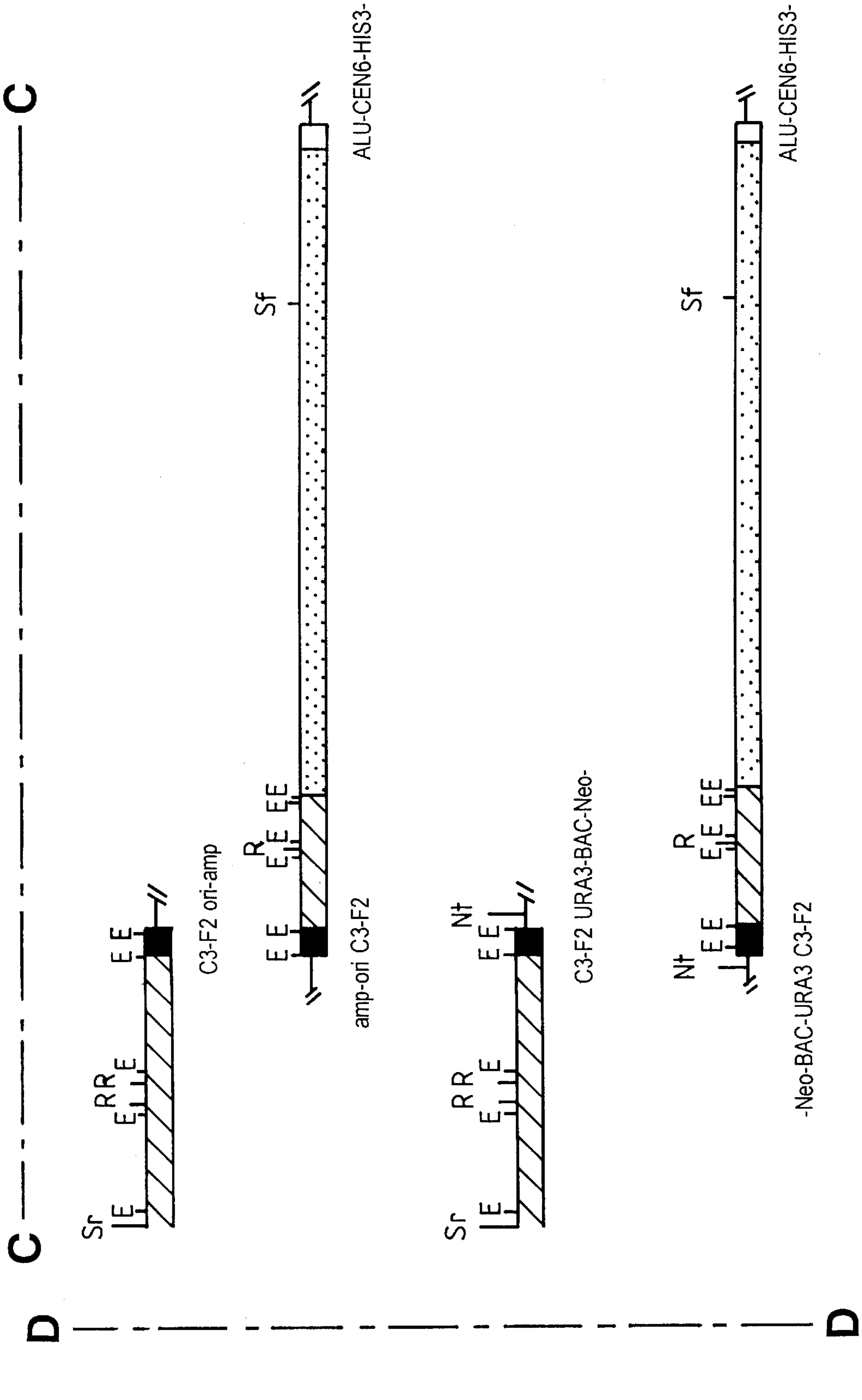

The circular YACs 5f-52-E8 and 5f-38-F2 were further retrofitted with the yeast-bacterial-mammalian cells shuttle vector BRV1 as previously described (Larionov et al., 1997). The resulting BAC clones were designated BAC/E8-1 and BAC/F2-14, respectively (FIG. 11D).

Figure 12:
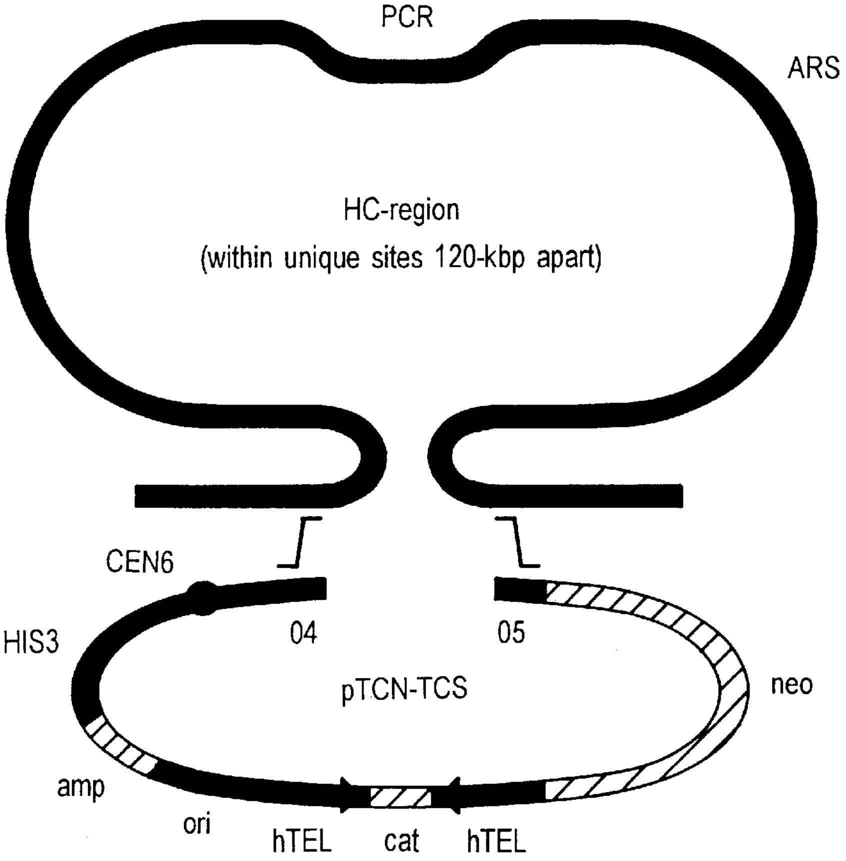
FIG. 12 is a diagrammatic representation specific TAR of HC-region from mardel 10.

The specific TAR strategy is outlined in FIG. 12 and uses unique fragments from the HC-contig region, such as the ends of PAC4 (a 120 kb-insert PAC clone containing the HC-region) to create the YAC/HAC shuttle vector pTCN-TCS. An example of a YAC/HAC construct containing the HC-contig region of normal chromosome 10 is shown in FIG. 13.

Completed constructs are transfected into different cultured mammalian or chicken cells (see above) by lipofection using Transfectam or DOSPER.

In vivo “cloning” of HC-region into HAC vectors

This strategy employs a technique known as Telomere Associated Chromosomal Truncation (TACT) (FIG. 14). The technique is based on the principle that cloned mammalian telomeric DNA when reintroduced into a mammalian cell can seed the formation of a new telomere at an intrachromosomal location. If the introduced telomeric DNA is target to a known site through homologous recombination, integration at that location and subsequent truncation of distal sequences on the original chromomosomal arm can result (Brown et al., 1994; Farr et al., 1995). This technique is employed in our own study to truncate the mardel 10 chromosome on either side of the HC-contig/core centromeric DNA element to produce in vivo a stable HAC of minimal size.

FIG. 15A shows an example of TACT-construct used in our study. Key features of this construct are: (a) Cloning of the pericentric human genomic DNA in both orientations (+/−). This is necessary since we do not know the chromosomal orientation of this DNA. This DNA is used to target the human telomeric sequences to locations on either side of the HC-coding region on mardel 10. Genomic DNA is derived from several different sources including Y2C24, Y3C64, Y3C109, Y3C94, Y13C12, Y13C15, Y17C6, Y17C8. The resulting truncation derivatives produced using these genomic DNAs will vary in size accordingly. (b) The termini contain 2.4 kilobases of tandem repeat human telomeric DNA (htel). This DNA has been shown previously to act as a substrate for mammalian telomerase to allow seeding of a complete telomere tens of kilobases in length. (c) The hygromycin (Hyg) resistance gene allows for positive selection of mammalian cell lines containing sequences integrated into the genome. This is the initial screening procedure. In addition, some constructs contain the neomycin phosphotransferase gene (Neo) rather than Hyg. (c) The Herpes simplex the thymidine kinase (TK) gene is used for negative selection against non homologous integration events into the genome. Those cell lines containing the TK gene can be selected against by adding the nucleoside analogue gancyclovir.

FIG. 15B shows another example of TACT-construct used in our study. In addition to the features of the linearised construct shown in FIG. 15A, specific additional features are: (a) The incorporation of tandem telomeric blocks (htel.htel) since others have shown these to have the highest seeding efficiency of new telomeres in mammalian cells. (b) The incorporation of yeast selectable marker (eg. URA3), DNA origin of replication (eg. ARS), and centromere (eg. CEN6), to allow transfer and maintenance of the resulting truncation derivatives into yeast. This should facilitate further characterisation and manipulation, such as the introduction of therapeutic genes for gene therapy purposes. (c) The relocation of the TK gene adjacent to the genomic DNA to increase the effectiveness of the negative selection system. (d) The human growth hormone (GH) gene has been included to allow proof of principle that human genes can be introduced into a HAC and expressed under the control of endogenous regulatory elements. This is essential for gene therapy applications of the resulting HAC. (e) A CMV promoter upstream of a P1 phage 1oxP site (CMV/1oxP) has been included to allow introduction of large human genes into a HAC in vivo. A plasmid containing a gene of interest, a second 1oxP site and a promoterless selectable marker gene is introduced into a mammalian cell line containing the HAC. Transient expression of CRE recombinase results in recombination between the two 1oxP sites within the cell, thereby integrating the introduced plasmid into the HAC and placing the selectable marker gene next to the CMV promoter to allow for marker selection.

For chromosomal truncation, the above TACT-constructs are transfected into a somatic cell hybrid line BE2CI-18-5f containing the mardel (10) chromosome. Positive selection is applied for Hygromycin or Geneticin resistance whereas negative selection is applied against the Thymidine Kinase Gene. Resulting colonies are further screened with distal p' and q' DNA fragments to ascertain the presence of absence of the two mardel 10 chromosome arms. In addition to the BE2CI-18-5f cell line, a human/chicken somatic cell hybrid line (derived from the recombination-proficient DT40 chicken cell line; Dieken et al., 1996) containing the mardel (10) chromosome will also be generated and used.

EXAMPLE 16

Analysis of HAC

Irrespective of which of the approaches described above is used, the presence of a new product in a mammalian cell line as an extrachromosomal, artificial chromosome, will be assessed by fluorescence in situ hybridisation (FISH) analysis, as well as tested by extracting high molecular weight DNA to determine independently existing chromosomal entity on pulsed field gel. The stability of the construct through successive cell division, both in the presence and absence of drug-resistance selection, will be determined. The presence of the construct, in all or a high percentage of the original transfected cells indicates stability. Demonstration of this stability indicates the successful creation of a HAC.

EXAMPLE 17

Production of HAC

This example describes the use of the neocentromere as a source of centromeric DNA in the "bottom-up" approach to produce HACs in human cell culture. Bacterial artificial chromosomes (BACs) containing cloned neocentromeric DNA and a selectable marker were co-transfected with human telomeric DNA into human HT1080 cells to yield independent HACs that were single-copy and stable in the absence of selection. The properties of these HACs, and their potential utility as a new, improved vector system for gene therapy are described.

Experimental Protocol

Preparation of DNA. Highly-purified BAC DNA was prepared using Qiagen columns according to the manufacturer's instructions. Prior to transfection, BACs were linearized with SgrAI in the presence of 2.5 mM spermidine and examined by pulsed-field gel electrophoresis. Human telomeric DNA was gel-purified as a 1.6-kb BamHI/BglII fragment from pSXneo270T2AG3 (Bianchi et al., 1997). High-molecular-weight genomic DNA was prepared from cultured cell lines using standard methods (du Sart et al., 1997).

Transfection of HT1080 cells. Transfection of human fibrosarcoma cell line HT1080 (Rasheed et al., 1974) was performed using the DOPSER liposomal transfection reagent (Boehringer-Mannheim). The day before transfection, 6-well trays (each well is 962 $mm^2$) were seeded with $3\times10^5$ HT1080 cells per well and grown at 37° C., 5% $CO_2$. Different combinations containing 1–2 $\mu$g of each BAC, 50 ng of telomeric DNA, 100 ng of each PAC-1, 4 and 5(du Sart et al., 1997) and 50 ng of human genomic DNA were prepared in 50 $\mu$l of HBS (20 mM HEPES, 150 mM NaCl) supplemented with 0.075 mM spermidine and 0.030 mM spermine. These DNA cocktails were mixed with 50 $\mu$l of 0.4 $\mu$g/$\mu$l DOPSER (diluted in HBS) and left at room temperature for 15 to 20 min. The HT1080 cells were washed with PBS (phosphate buffered saline) and 1 ml of serum-free DMEM (Dulbecco's modified Eagles medium) was placed in each well. The DNA-DOPSER mixture was then added dropwise with swirling and the cells were incubated for 6 h. 1 ml of DMEM and 20% v/v fetal calf serum (FCS) was then added and the cells left for 24 h at 37° C., 5% v/v $CO_2$. The cells were harvested and seeded into 48-well cluster trays (each well is 100 $mm^2$) containing DMEM-10% v/v FCS supplemented with Geneticin (G418, Gibco-BRL) at 250 $\mu$g/ml. The media was changed every 3 to 4 days. G418-resistant colonies normally appeared 10 to 14 days after transfection. These colonies were expanded into duplicate 6-well trays, where the cells of one tray were stored frozen in liquid $N_2$, and the remaining cells were analysed by fluorescence in situ hybridization (FISH).

Cell culture and mitotic stability. HT1080 cells were grown in DMEM supplemented with 10% v/v FCS, penicillin/streptomycin, and glutamine. The mitotic stability of HAC containing clones was determined by growth in 25 $cm^2$ flasks in the presence (200–250 $\mu$g/ml) or absence of G418 selection, and grown to confluency (3–4 days) and split 1/5 and 1/10, respectively. Aliquots of each culture were harvested fortnightly and analysed by FISH (20–50 metaphases) with BAC/E8 and/or BAC/F2 probes.

FISH, ANTI-CEN/FISH and PRINS/FISH. Fluorescence in situ hybridization (FISH) analysis of HT1080 clones was performed with BAC/E8, BAC/F2, and/or $\alpha$-satellite DNA probes. Hybridization using the BAC probes were performed under high stringency whereas the $\alpha$-satellite DNA probes were used in low stringency conditions (du Sart et al., 1997). ANTI-CEN/FISH analyses involved an initial immunofluorescence staining step using a CREST antibody or specific antibodies against CENP-B, CENP-C, or CENP-E, followed by FISH using the probes described above, essentially as previously described (du Sart et al., 1997).

Results

HAC construction strategy. The basic strategy involved the co-transfection of the 10q25.2 neocentromere DNA with human telomeric DNA into human cells. The neocentromere region is cloned as two, circular YACs in *Saccharomyces cerevisiae*. To facilitate handling and purification of the cloned DNA in large quantities, these YACs are retrofitted into BACs and maintained episomally in *E. coli* as circular molecules. One of the BAC clones, BAC/E8, is 120 kb in size and has an insert of 105 kb that encompassed 70 kb of the 80-kb core NC-DNA region (FIG. 16). The second BAC clone, BAC/F2, has an insert size of 75 kb that overlapped BAC/E8 by 1.4 kb, and contains ~10 kb of the core NC-DNA while extending ~65 kb into the '-side of the mardel (10) chromosome (FIG. 16). The BAC vector backbone further contains the neomycin-resistance (Neo®) gene to allow selection in mammalian cells. BAC/E8 and BAC/F2, used either on their own, in combination with each other or with additional DNA are used in the following transfection experiments.

Transfection of HT1080 cells. The human cell line HT1080 (Rasheed et al., 1974) is chosen for the transfection experiments because of its near-diploid karyotype, its high level of telomerase activity (Holt et al., 1997), and its demonstrated ability to form microchromosomes containing de novo centromeres from transfected arrays of α-satellite DNA and human telomeric DNA (Harrington et al., 1997; Ikeno et al., 1998). The resulting G418-resistant clones are analyzed by FISH and classified into different categories of events.

Transfected cell lines are designated HT-38, HT-47, HT-54, HT-190, and HT-191.

Those skilled in the art will appreciate that the invention described herein is susceptible to variation and modifications other than those specifically described. It is to be understood that the invention includes all such variations and modifications. The invention also includes all of the step, features, compositions and compounds referred to or indicated in this specification, individually or collectively, and any and all combinations of any two or more said steps or features.

TABLE 1

Restriction analysis of the genomic DNA of patient BE and those of his parents using three overlapping cosmids that span the marker centromere.

| | Y7C14 | Y6C10 | Y4C7 |
|---|---|---|---|
| NotI | n.a. | 910 | 910 |
| BssHII | n.a. | 815, 340 | n.a. |
| BsiWI | n.a. | 740 | 740 |
| SalI | 410 | 410 | 410, 540 |
| claI | 315, 145, 110, 80 | 315, 145, 110, 80 | 315, 145, 110, 80 |
| SnaBI | n.a. | 250, 148 | n.a. |
| NaeI | 240, 210, 155, 120 | 240, 210, 155, 120 | 240, 210, 155, 120 |
| NarI | 222, 108, 70 | 222, 108 | 222, 200, 108, 70 |
| EclXI | 180 | 180 | 180 |
| SfiI | 170 | 170 | 170 |
| KspI | 168 | 168 | 168 |
| AatII | 165, 146 | 165, 146 | 165, 146 |
| NheI | 38 | 38 | 38 |
| BstBI | n.a. | 35 | 35 |
| SmaI | n.a. | 90, 40, 22 | 90, 40, 22 |
| BglI | 25 | 25, 7.2, 6.2 | 25 |
| PacI | n.a. | 25 | n.a. |
| BamHI | 24, 19, 15 | 24, 22* | 24, 22* |
| KpnI | 23 | 23 | 23, 19 |
| BclI | 21 | 21 | 21 |
| PstI | 9.4, 5.9, 5.1, 4.2, 3.8, 3.3, 2.9, 2.4 | 9.4, 3.8, 2.9, 2.7, 2.4, 1.5, 1.1 | 9.4, 7.1, 4.2, 3.3, 2.9, 2.7, 1.9, 1.5, 1.1 |
| XbaI | 14 | 14, 10 | 10 |
| EaeI | n.a. | 15, 12, 8, 6 | n.a. |
| SphI | 16, 7.5 | 16 | 16,9 |
| PvuII | 14, 7.5 | 7.5, 6 | 7.5, 6 |
| HindII | 8.6, 6.9, 6.2, 2.7, 1.8, 1.2 | 6.9, 6.2, 5.6, 5.2, 5, 2.7, 1.9, 1.8, 1.7, 1.2, 0.6 | 6.2, 5.6, 5.2, 4.3, 2.9, 1.7, 1.2 |
| ApaI | 15, 8.5 | 15 | 15 |
| EcoRI | 11, 4.3, 3.9, 1.9, 1.5 | 11, 4, 3, 2, 1.9, 1.7, 1.5 | 10.2, 7.6, 3, 2, 1.9, 1.7, 1.5 |
| HpaII | 5.5, 4.3, 3.6, 1.6 | 6.9, 3.6, 2.8, 1.6, 1.2 | 3.6, 2.8, 2.5, 1.6, 1.2 |
| MspI | 3.9, 3.0, 2.8, 2.5, 2, 1.6 1.2 | 3.9, 3.6, 2.8, 2.5, 2.2, 1.6, 1.5, 1.3, 1.2, 0.9 | 3.6, 3.2, 2.8, 2.5, 2.2, 1.6, 1.5. 1.2. 1 |
| SspI | n.a. | 10 | n.a. |
| XhoII | 7.5 | n.a. | n.a. |
| DraI | 7.5 | 7.5 | 7.5 |
| BglII | 8.5, 6, 5, 4.7, 3.5, 2.5 | 6, 5, 4.7, 2.5, 1.6, 1.5, 1 | 7, 6, 5, 4.7, 2.5, 1.6, 1.5, 1.1, 1 |
| AvaII | 7.4, 3.7, 3.4, 2.8, 2.6, 1.8, 1.7, 1.4, 1.2, 1.1 | 3.7, 2.8, 2.6, 1.8, 1.7, 1.4, 1.2, 1.1, 0.9, 0.8, 0.5 | 4.3, 3.7, 2.8, 2.6, 1.8, 1.7, 1.4, 1.2 |
| StuI | 12.5, 8, 7.5 | 12.5, 9, 8.5 | 9, 8.5 |
| HindIII | 6.6, 5.4, 4.7, 4.4, 2.9, 2.5 | 5, 4.7, 4.4, 4.1, 2.9, 2.5, 0.7 | 5, 4.7, 4.1, 3.1, 2.5, 2.3, 1.9 |

n.a. = data not available. The values represent restriction fragment lengths in kilobases. Multiple values for an enzyme denote different bands detected by a cosmid probe on a gel lane. Since there were no detectable differences between the DNA of patient BE and those of his parents in any of the fragments (except for a BamHI polymorphic band found in one of the parents, indicated by an asterisk), only one set of values is shown for all three genomic DNA.

TABLE 2

Vectors for cloning centromeric regions from normal chromosome 10 or mardel (10) DNA into yeast artificial chromosomes (YACs). These YACs can be shuttled into mammalian cells to test for function as HACs.

Figure 8A:
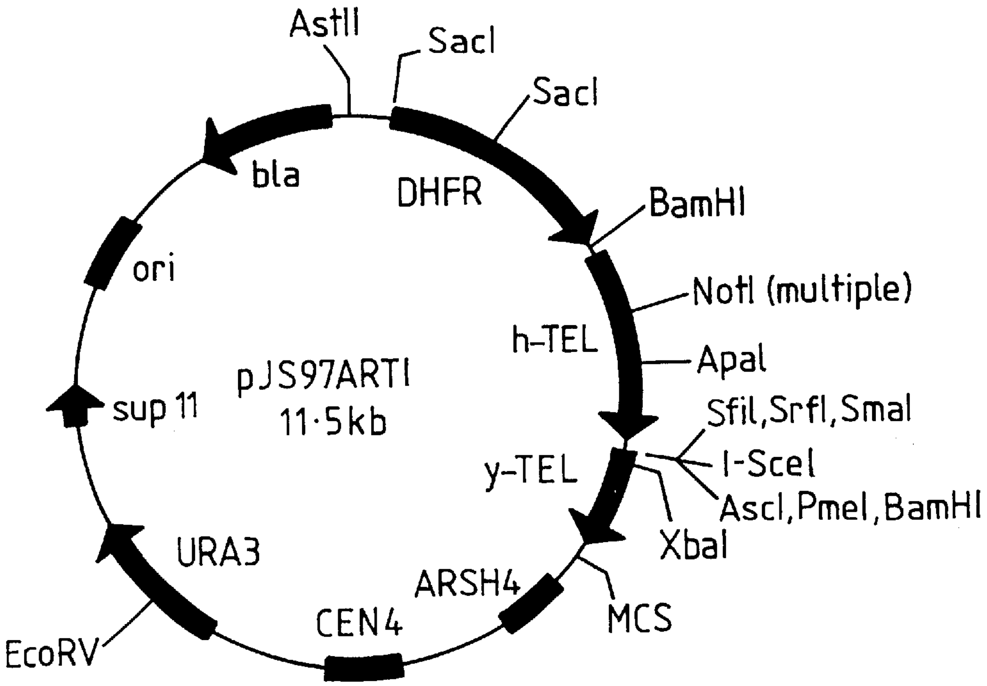
FIGS. 8A to J are diagrammatic representations of the different vectors used for cloning DNA as YACs by the conventional restriction/ligation methods.
Figure 8B:
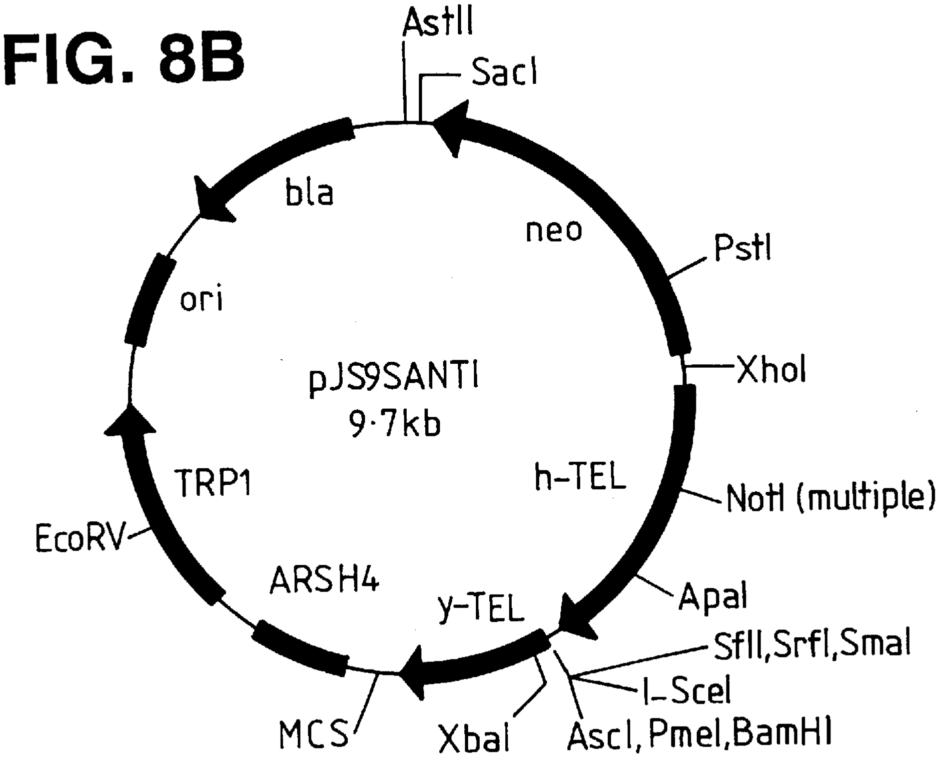
Figure 8C:
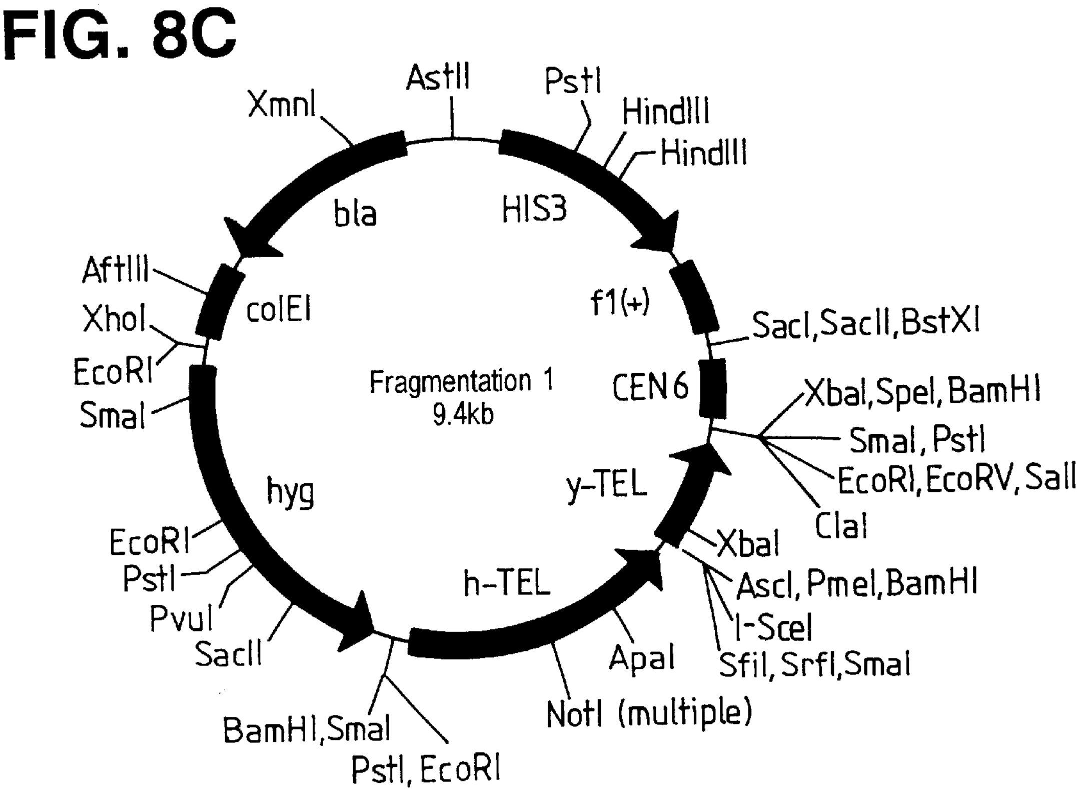
Figure 8D:
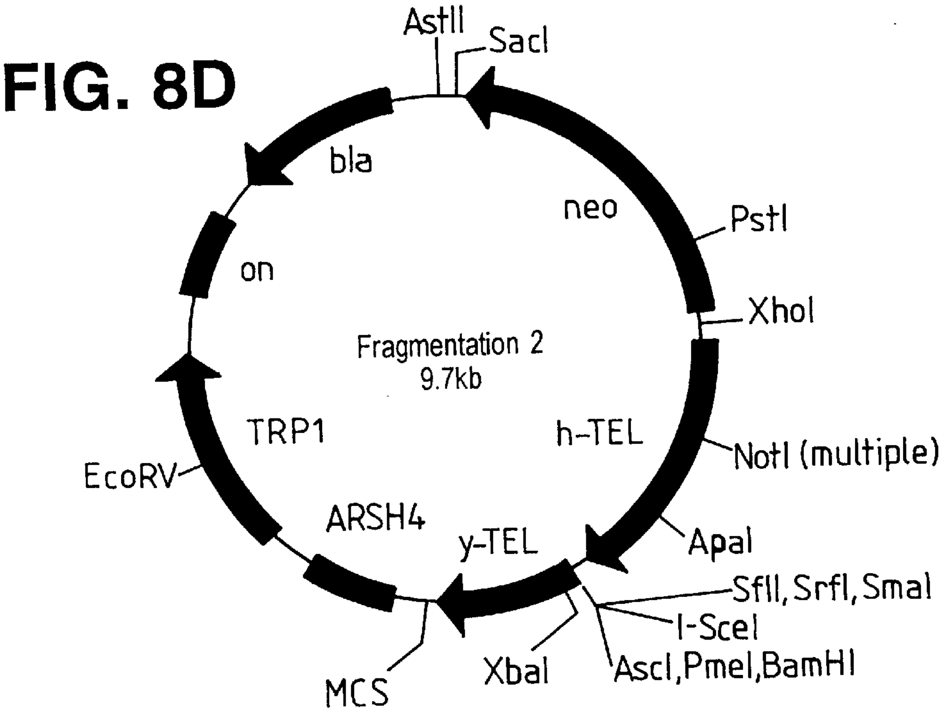
Figure 8E:
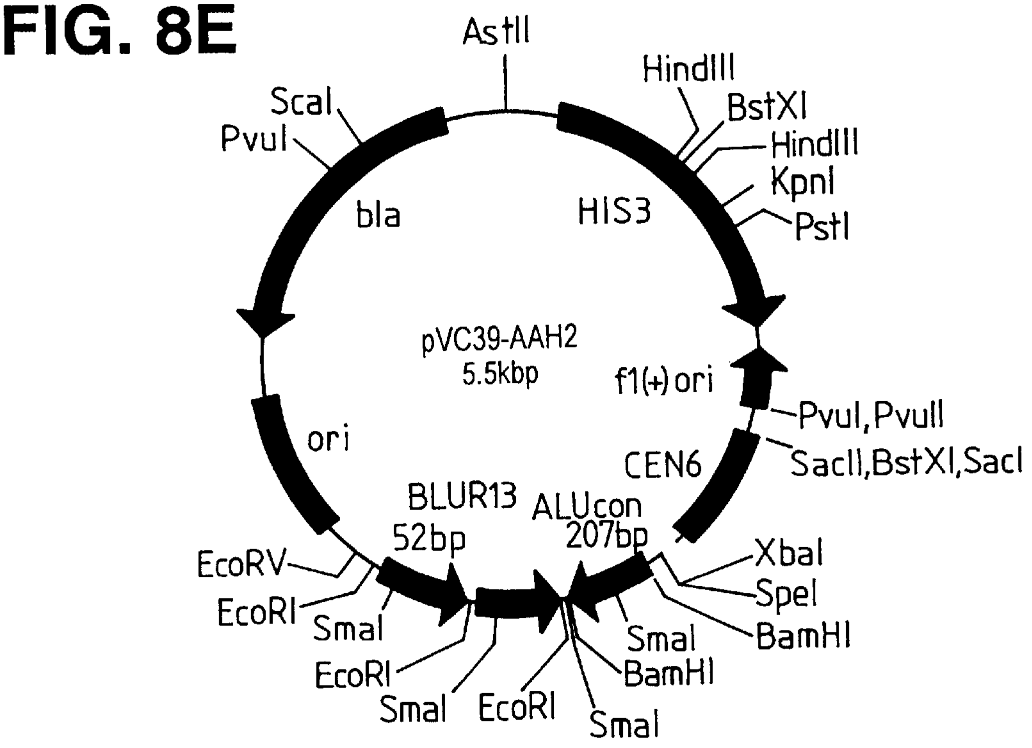
Figure 8F:
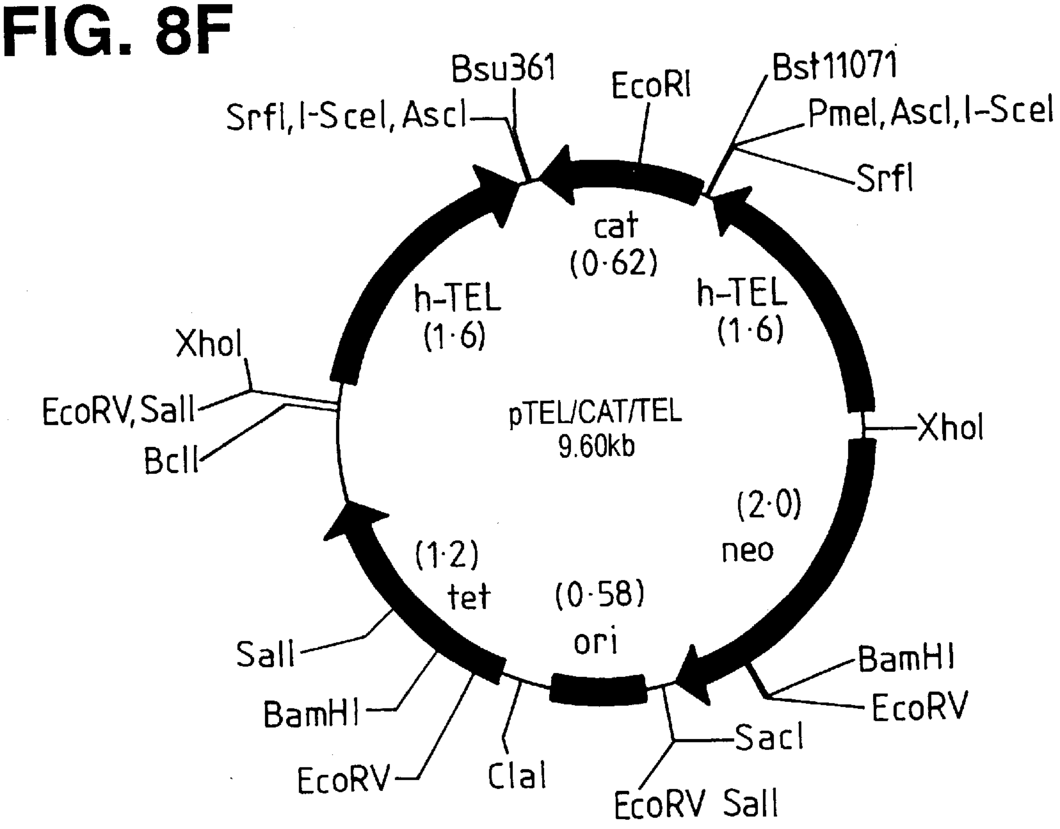
Figure 8G:
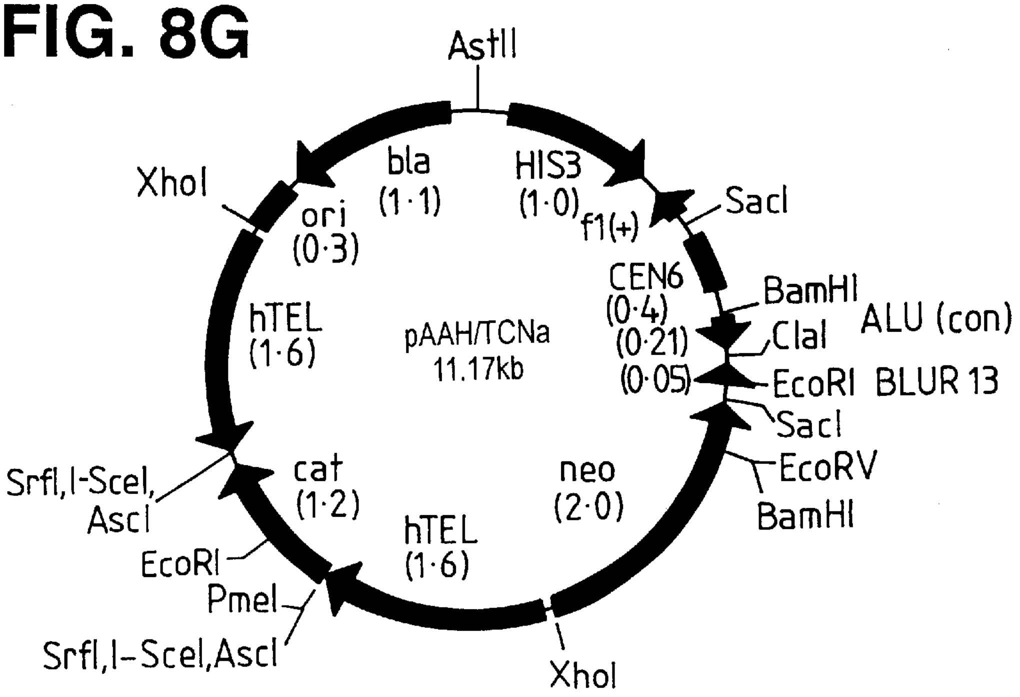
Figure 8H:
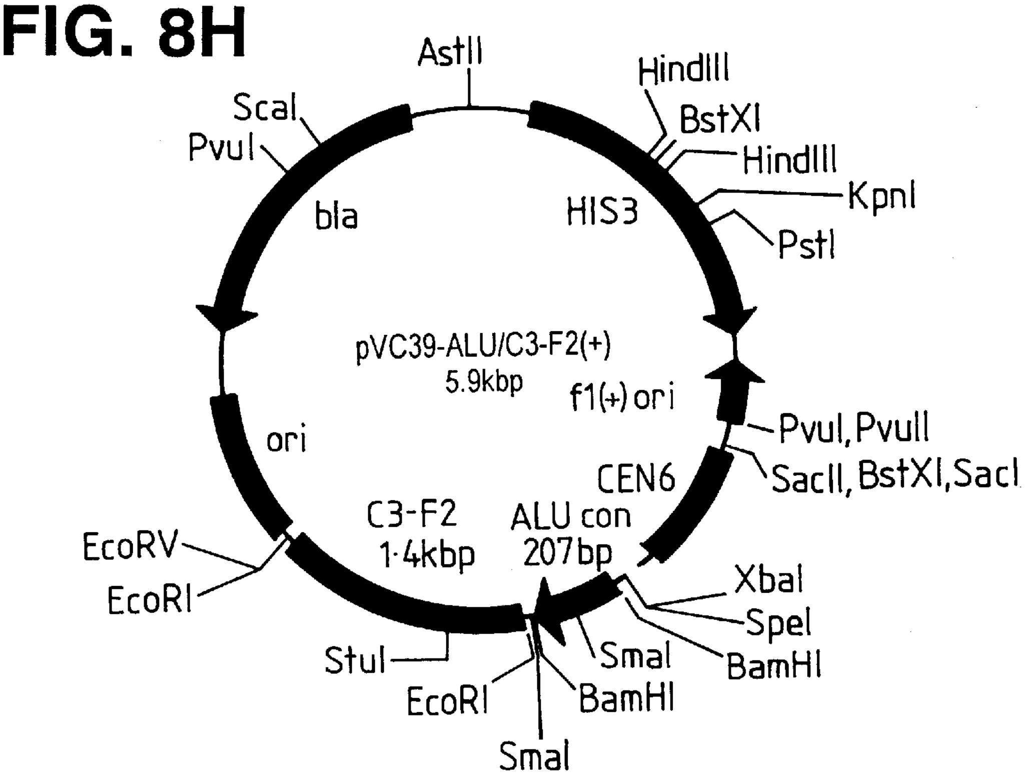
Figure 8I:
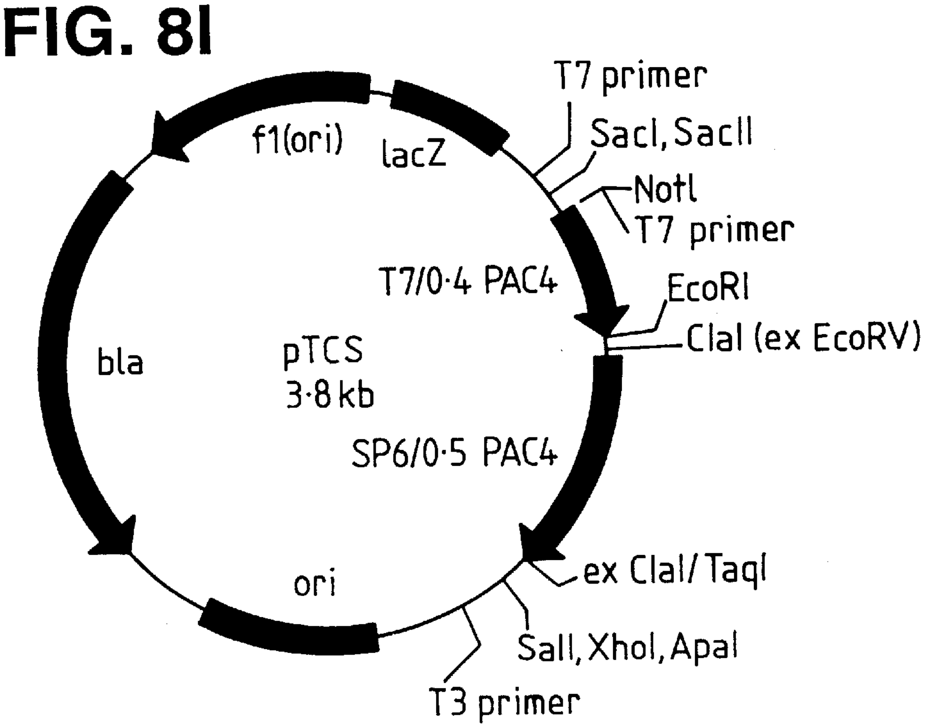
Figure 8J:
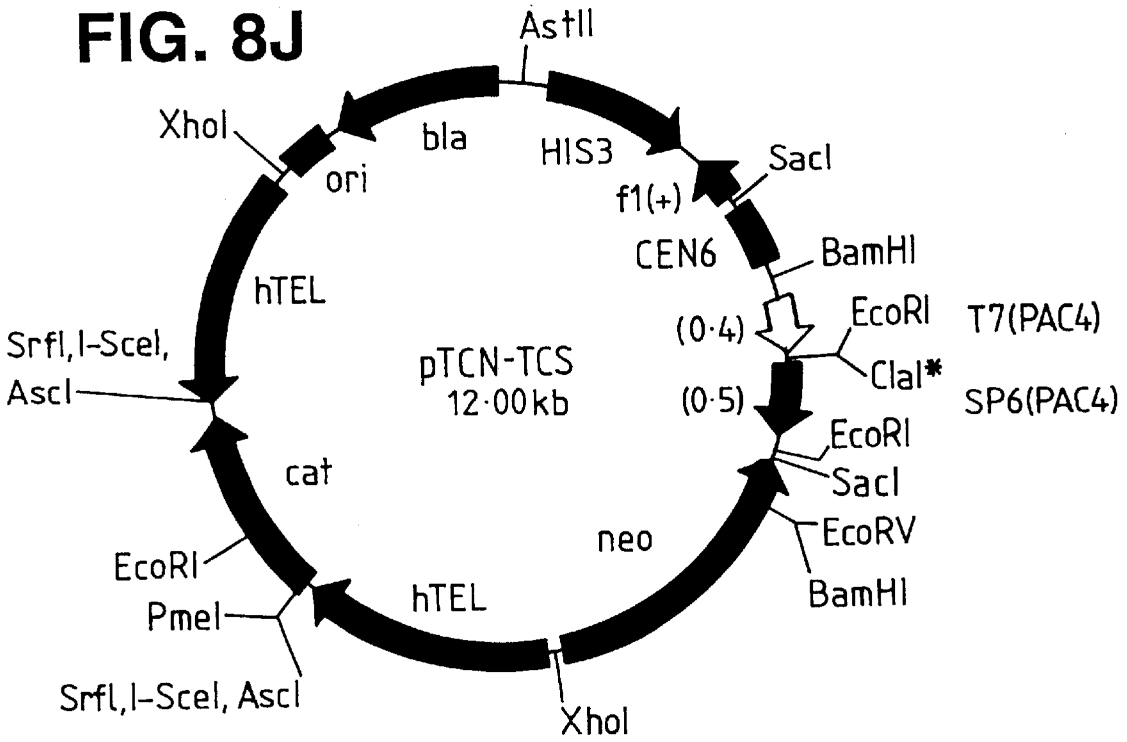
Figure 9:
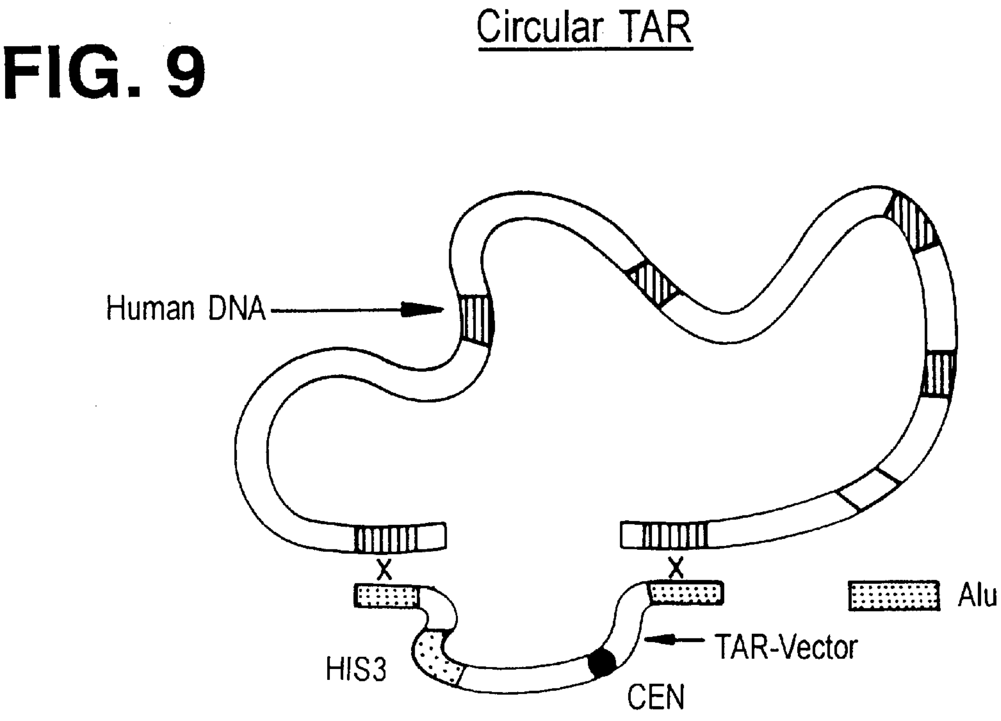
FIGS. 9 is a diagrammatic representation of circular TAR summarising the recombination process.

| Vector: | Key Feature(s) | Map |
|---|---|---|
| pJS97ARTi | hTEL/I-SceI/yTEL, DUFR | FIG. 8A |
| pJS98ANTi | hTEL/I-SceI/yTEL, neo | FIG. 8B |
| Fragmentation 1 | hTEL/I-SceI/yTEL, hyg | FIG. 8C |
| Fragmentation 2 (–/+ hGH) | hTEL/I-SceI/yTEL, neo, hGH | FIG. 8D |
| pVC39-AAH2 | ALU-ALU TAR vector | FIG. 8E |
| pTEL/CAT/TEL | hTEL/I-SceI/hTEL/neo | FIG. 8F |
| pAAH/TCNa | TAR vector with hTEL/I-SceI/hTEL/neo | FIG. 8G |
| pVC39-ALU/C3-F2(+/–) | ALU-specifc TAR vectors | FIG. 8H |
| pTCS | ends of PAC4 in pBS | FIG. 8I |
| pTCN-TCS | specific TAR vector hTEL/I-SceI/hTEL/neo | FIG. 8J |

TABLE 3

PCR analysis of YAC 5f-52-E8 clone and comparison with the HC-contig/neo-centromere region from normal chromosome 10 and mar del (10)

| | Genomic DNA used in PCR (product size in kb) | | |
|---|---|---|---|
| Primer-Pairs[a] | BE2Cl-18-1f[b] | BE2Cl-18-5f[b] | YAC 5f-52-E8 |
| norm: 141 + 55 | 1.80 | 1.80 | not present |
| norm: 32 + 30 | 0.90 | 0.90 | 0.90 |
| norm: 28 + 29 | 1.00 | 1.00 | 1.00 |
| norm: 1 + 3 | 2.90 | 2.90 | 2.90 |
| norm: 39 + 52 | 1.20 | 1.20 | 1.20 |
| norm: 5 + 7 | 023 | 0.23 | 0.23 |
| norm: 16 + 5 | 3.50 | 3.50 | 3.50 |
| norm: 9 + 14 | 0.90 | 0.90 | 0.90 |
| norm. 36 + 37 | 2.00 | 2.00 | 2.00 |
| norm: 168 + 71 | 4.00 | 4.00 | 4.00 |
| norm: 27 + 10 | 15.90 | 15.90 | 15.90 |
| norm: 18 + 17 (VNTR)[c] | 1.20 | 1.40 | 1.40 |
| norm: 68 + 17 | 8.00 | 8.00 | 8.00 |
| norm: 34 + 47 | 3.00 | 3.00 | 3.00 |
| PAC4t7: a + b | 0.30 | 0.30 | not present |
| AFM259xg5: ca + gt[c] | 0.21 | 0.19 | not present |

[a]Refer to FIG. 1a for the relative positions of each primer-pair.
[b]BE2Cl-18-1f and BE2Cl-18-5f are somatic hybrid cell lines containing the normal human chromosome 10 and mar del (10), respectively (2).
[c]The 'norm: 18 + 17' and 'AFM259xg5: ca and gt' primer sets allow distinction between the normal human chromosome 10 and mar del (10) by detecting a VNTR and a microsatellite, respectively.

BIBLIOGRAPHY

1. Albertsen, H., Abderrahim, H., Cann, H., J. D., Paslier, D. L., and Cohen, D. (1990). Construction and characterization of a yeast artificial chromosome library containing seven haploid human genome equivalents. *Proc. Natl. Acad. Sci. USA.* 87, 4256–4260.

2. Archidiacono, N., Antonacci, R., Forabosco, A., and Rocchi, M. (1994). Preparation of human chromosomal painting probes from somatic cell hybrids. In In Situ Hybridization Protocols. K. H. A. Choo, ed. (Totowa, N.J.: Humana Press), pp. 1–14.

3. Bernat, R. L., Borisy, G. G., Rothfield, N. F., and Earnshaw, W. C. (1990). Injection of anticentromere antibodies in terphase disrupts events required for chromosome movement in mitosis. *J. Cell. Biol.* 111, 1519–1533.

4. Bischoff, F., Maier, G. Tilz, G., and Ponstingl, H. (1990). A47-kDa human nuclear protein recognized by antikinetochore autoimmune sera is homologous with the protein encoded by RCCl, a gene implicated in onset of chromosome condensation , *Proc. Natl. Acad. Sci.* 87, 8617–8671.

5. Brenner, S., Pepper, D., Berns, M. W., Tan, E., and Brinkley, B. R. (1981). Kinetochore structure, duplication and distribution in mammalian cells: analysis by human autoantibodies from scleroderma patients. *J. Cell. Biol.* 91, 95–102.

6. Brown, K. E., Barnett, M. A., Burgtorf, C., Shaw, P., Buckle, V. J., and Brown, W. R. A. (1994). dissecting the centromere of the human Y chromosome with cloned telomeric DNA. *Hum. Mol. Gent.* 3, 1227–1237.

7. Brownstein, B., Silverman, G., Little, R., Burke, D., Korsmeyer, S., Schlessinger, D., and Olson, M. (1989). Isolation of single-copy human genes from a library of yeast artificial chromosome clones. *Science* 244, 1348–1351.

8. Clarke, L., and Carbon, J. (1985). The structure and function of yeast centromeres. *Annu. Rev. Genet.* 19, 29–56.

9. Dasso, M. (1993). RCC1 in the cell cycle: the regulator of chromosome condensation takes on new roles. *Trends Biochem. Sci.* 18, 96–101.

10. Dieken et al. (1996) *Nature Genetics* 12: 174–183.

11. du Sart, D., Cancilla, M. R., Earle, E., Mao, J., Saffery, R., Taintoon, K. M., Kalitsis, P., Martyn, J., Barry, A. D., and Choo, K. H. A. (1997). A functional neo-centromere formed through activation of a latent human centromere and consisting of non-alpha-satellit DNA. *Nature Genet.* 16, 144–153.

12. du Sart, D., Cancilla, M. R., Earle, E., Mao, J., Saffery, R., Tainton, K. M., Kalitsis, P., Martyn, J., Barry, A. E., and Choo, K. H. A. 1997. A functional neo-centromere formed through activation of a latent human centromere and consisting of non-alpha-satellite DNA. *Nature Genetics* 16:144–153.

13. Harrington, J. J., Van Bokkelen, G., Mays, R. W., Gustashaw, K, and Willard, H. F. 1997. Formation of de novo centromeres and construction of first-generation human artificial microchromosomes. *Nature Genetics* 15:345–355.

14. Holt, S. E., Aisner, D. L., Shay, J. W., and Wright, W. E. 1997. Lack of cell cycle regulation of telomerase activity in human cells. *Proc. Natl. Acad. Sci. USA* 94:10687–10693.

15. Ikeno, M., Grimes, B., Okazaki, T., Nakano, M., Saitoh, K., Hoshino, H., McGill, N. I., Cooke, H., and Masumoto, H. 1998. Construction of YAC-based mammalian artificial chromosomes. *Nature Biotechnology* 16:(in press).

16. Earnshaw, W., and MacKay, A. (1994). Role of nonhistone proteins in the chromosomal events of mitosis. *FASEB J.* 8, 947–956.

17. Earnshaw, W. C., and Migeon, B. R. (1985). Three related centromere proteins are absent from the inactive centromere of a stable isodicentric chromosome. *Chromosoma* 92, 290–296.

18. Earnshaw, W. C., Ratrie, H., and Stetten, G. (1989). Visualization of centromere proteins CENP-B and CENP-C on a stable dicentric chromosome in cytological spreads. *Chromosoma* 98, 1–12.

19. Parr, C., Bayne, R., Kipling, D., Mills, W., Critcher, R., and Cooke, H. (1995). Generation of a human X-derived minichromosome using telomere-associated chromosome fragmentation. *EMBO Journal* 14, 5444–5454.

20. Fritzler, M. J., and Kinsella, T. D. (1980). The CREST syndrome: a distinct serologic entity with anticentromere antibodies. *Am. J. Med.* 69, 520–526.

21. Grady, D., Ratliff, R., Robinson, D., McCanlies, E., Meyne, J., and Moyzis, R. (1992). Highly conserved repetitive DNA sequences are present at human centromeres. *Proc. Natl. Acad. Sci. USA* 89, 1695–9.

22. Haaf, T., and Ward, D. D. (1994). Structural analysis of α-satellite DNA and centromere proteins using extended chromatin and chromosomes. *Hum. Mol. Genet.* 3, 697–709.

23. Haaf, T., Warburton, P. E., and Willard, H. F. (1992). Integration of human α-satellite DNA into simian chromosomes: centromere protein binding and disruption of normal chromosome segregation. *Cell* 70, 681–696.

24. Jeppensen, P., Mitchell, A., Turner, B., and Perry, P. (1992). Antibodies to defined histone epitopes reveal variations in chromatin conformation and underacetylation of centric heterochromatin in human metaphase chromosomes. *Chromosoma* 101, 322–332.

25. Jeppensen, P., and Turner, B. M. (1993). The inactive X chromosome in female mammals is distinguished by a lack of histone H4 acetylation, a cytogentic marker for gene expression. *Cell* 74, 281–289.

26. Kingwell, B., and Rattner, J. (1987). Mammalian kinetochore/centromere composition: A 50 kDa antigen is present in the mammalian kinetochore/centromere. *Chromosoma* 95, 403–407.

27. Larin, Z., Fricker, M. D., and Tyler-Smith, C. (1994). De novo formation of several features of a centromere following introduction of a Y alpoid YAC into mammalian cells. *Hum. Mol. Genet.* 3, 689–695.

28. Larionov, V. et al. (1997) *Proc. Natl. Acad. Sci. USA* 94: 7384–7387.

29. Larionov, V., Kourpina, N., Graves, J., Chen, X. N., Korenberg, J. R., and Resnick, M. A. (1996b). Specific cloning of human DNA as yeast artificial chromosomes by transformation-associated recombination. *Proc. Nat. Acad. Sci. USA* 93, 491–496.

30. Larionov, V., Kouprina, N., Graves, J., and Resnick, M. A. (1996b). Highly selective isolation of human DNAs from rodent-human hybrid cells as circular yeast artificial chromosomes by transformation-associated recombination cloning. *Proc. Nat. Acad. Sci. USA* 93, 13925–13930.

31. Moir, D. T., Dorman, T. E., Day, J. C., Ma, N. S., Wang, M., and Mao, J. (1994). Toward a physical map of human chromosome 10: isolation of 183 YACs representing 80 loci and regional assignment of 94 YACs by fluorescence in situ hybridization. *Genomics* 22, 1–12.

32. Moroi, Y., Hartman, A. L., Nakane, P. K., and Tan, E. M. (1981). Distribution of kinetochore (centromere) antigen in mammalian cell nuclei. *J. Cell Biol.* 90, 254–259.

33. Moschonas, N. K., Spurr, N. K., and Mao, J. (1996). Report of the first international workshop on human chromosome 10 mapping 1995. *Cytogenet. Cell Genet.* 72: 99–112.

34. Murphy, T. D., and Karpen, G. H. (1995). Localization of centromere function in a *Drosophila minichromosome. Cell* 82, 599–609.

35. Nelson, M., and McClelland, M. (1991). Site-specific methylation: effect on DNA modification methyltransferases and restriction endonucleases. *Nucl. Acids Res.* 19: 2045–2071.

36. Page, S. L., Earnshaw, S. C., Choo, K. H. A., and Shaffer, L. G., (1995). Further evidence that CENP-C is a necessary component of active centromeres: studies of a dic(X;15) with simultaneous immunofluorescence and FISH. *Hum. Mol. Genet.* 4, 289–294.

37. Pluta, A. F., Cooke, C. A., and Earnshaw, W. C. (1990). Structure of the human centromere at metaphase. *Trends Biochem.* 15, 181–185.

38. Pluta, A. F., Mackay, A. M., Ainsztein, A. M., Goldberg, I. G., and Earnshaw, W. C. (1995). The centromere: hub of chromosomal activities. *Science* 270, 1591–1594.

39. Rasheed, S., Nelson-Rees, W. A., Toth, E. M., Arnstein, P., and Gardner, M. B. (1974) Characterisation of a newly derived human sarcoma line (HT1080). *Cancer* 33, 1027–1033.

40. Sikorski, R. S. and Hieter, P. (1989). A system of shuttle vectors and yeast host strains designed for efficient manipulation of DNA in *Saccharomyces cerevisiae. Genetic* 122, 19–27.

41. Steiner, N., Hahnenberger, K., and Clarke, L. (1993). Centromeres of the fission yeast *Schizosaccharomyces pombe* are highly variable genetic loci. *Mol. Cell. Biol.* 13, 4578–4587.

42. Sullivan, B. A. and Schwartz, S. (1995). Identification of centromeric antigens in dicentric Robertsonian translocations: CENP-C and CENP-E are necessary components of functional centromeres. *Hum. Mol. Genet.* 4, 2189–2197.

43. Sullivan, K. F., Hechenberger, M., and Masri, K. (1994). Human CENP-A contains a histone H3 related histone fold domain that is required for targeting to the centromere. *J. Cell Biol.* 127, 581–592.

44. Taylor, S. S., Larin, Z., and Tyler-Smith, C. (1994) Addition of functional human telomeres to YACs. *Human Mol Gent* 3, 1383–1386.

45. Taylor, S. S., Larin, Z., and Tyler-Smith, C. (1996) Analysis of extrachomosomal structures containing human centromeric alphoid satellite DNA sequence in mouse cells. *Chromosoma* 105, 70–81.

46. Tomkiel, J., Cooke, C. A., Saitoh, H., Bernat, R. L., and Earnshaw, W. C. (1994). CENP-C is required for maintaining proper kinetochore size and for a timely transition to anaphase. *J. Cell. Biol.* 125, 531–545.

47. Trowell, H. E., Nagy, A., Vissel, B., and Choo, K. H. A. (1993). Long-range analyses of the centromeric regions of human chromosomes 13, 14 and 21: identification of a narrow domain containing two key centromeric DNA elements. *Hum. Mol. Genet.* 2, 1639–1649.

48. Tyler-Smith, C., Oakey, R. J., Larin, Z., Fisher, R. B., Crocker, M., Affara, N. A., Ferguson-Smith, M. A., Muenke, M., Orsetta, Z., and Jobling, M. A. (1993). Localization of DNA sequences required for human centromere function through an analysis of rearranged Y chromosomes. *Nature Gent.* 5, 368–375.

49. Voullaire, L. E., Slater, H. R., Petrovic, V., and Choo, K. H. A. (1993). A functional marker centromere with no detectable alpha-satellite, satellite III, or CENP-B protein: activation of a latent centromere. *Am. J. Hum. Genet.* 52, 1153–1163.

50. Wevrick, R., and Willard, H. F. (1989). Long-range organization of tandem arrays of alpha-satellite DNA at the centromeres of human chromosomes: high-frequency array-length polymorphism and meiotic stability. *Proc. Natl. Acad. Sci. USA* 86, 9394–9398.

51. Wevrick, R., and Willard, H. F. (1991). Physical map of the centromeric region of human chromosome 7: relationship between two distinct alpha satellite arrays. *Nucl. Acids Res.* 19, 2295–2301.

52. Zheng, C., Ma, N. S., Dorman, T. E., Wang, M., Braunschweiger, K., Soares, L., Schuster, M. K., Rothschild, C. B., Bowden, D. W., Torrey, D., Keith, T. P., Moir, D. T., and Mao, J. (1994). Development of 124 sequence-tagged sites and cytogenetic localization of 217 cosmids for human chromosome 10. *Genomics* 22, 55–67.

What is claimed is:

1. An isolated nucleic acid molecule of at least 105 kilobases, wherein said nucleic acid molecule comprises a neocentromere from a human or non-human mammalian chromosome, and wherein said neocentromere has no detectable alpha satellite DNA as determined by fluorescent in situ hybridization (FISH).

2. An isolated nucleic acid molecule according to claim 1, wherein the chromosome is a human chromosome.

3. An isolated nucleic acid molecule according to claim 2, wherein the nucleic acid molecule associates with centromeric binding proteins (CENP)-A and -C.

4. An isolated nucleic acid molecule according to claim 3 wherein the chromosome is human chromosome 10.

5. An isolated nucleic acid molecule according to claim 4 wherein the nucleic acid molecule maps between q24 and q26 chromosome 10.

6. An isolated nucleic acid molecule according to claim 4 wherein the human chromosome 10 is a mardel (10) chromosome.

7. An isolated nucleic acid molecule according to claim 5 comprising a nucleotide sequence as set forth in SEQ ID NO: 3 or a nucleotide sequence having at least 40% similarity thereto or a nucleotide sequence capable of hybridising to SEQ ID NO: 3 or the complementary form thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

8. An isolated nucleic acid molecule according to claim 6 comprising a nucleotide sequence as set forth in SEQ ID NO: 4 or a nucleotide sequence having at least 40% similarity thereto or a nucleotide sequence capable of hybridising to SEQ ID NO: 4 or the complementary form thereof under low stringency conditions at 42° C., wherein said low stringency conditions comprise at least about 1% v/v to at least 15% v/v formamide and from at least about 1M to at least about 2M salt for hybridization, and at least 1M and to about 2M salt for washing conditions.

9. An isolated nucleic acid molecule according to claim 6 comprising a nucleotide sequence substantially as set forth in at least one of SEQ ID NOs: 5–29 or a nucleotide sequence having at least 40% similarity thereto or a nucleotide sequence capable of hybridising to at least one of SEQ ID NOs: 5–29 or the complementary forms thereof under low stringency conditions at 42° C., wherein said low stringency conditions comprise at least about 1% v/v to at least 15% v/v formamide and form at least about 1M to at least about 2M salt for hybridization, and at least about 1M and to about 2M salt for washing conditions.

10. An isolated nucleic acid molecule of at least 105 kilobases wherein said nucleic acid molecule comprises a neocentromere, wherein said neocentromere has no detectable alpha satellite DNA as determined by fluorescent in situ hybridization (FISH), and wherein a linear form of said nucleic acid molecule together with a telomeric sequence, replicates, remains as an extra-chromosomal element in a compatible eukayotic cell and segregates with cell division.

11. An isolated nucleic acid molecule according to claim 10, wherein said nucleic acid molecule associates with CENP-A and CENP-C.

12. An isolated nucleic acid molecule according to claim 10 or 11 wherein the mammalian chromosome is human chromosome 10.

13. An isolated nucleic acid molecule according to claim 12 wherein the human chromosome 10 is a mardel (10) chromosome.

14. An isolated nucleic acid molecule according to claim 12 comprising a nucleotide sequence as set forth in SEQ ID NO: 3 or a nucleotide sequence having at least 40% similarity thereto or a nucleotide sequence capable of hybridising to SEQ ID NO; 3 or the complementary form thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

15. An isolated nucleic acid molecule according to claim 12 wherein the nucleic acid molecule maps between q24 and q26 on chromosome 10.

16. An isolated nucleic acid molecule according to claim 15 comprising a nucleotide sequence as set forth in SEQ ID NO: 4 or a nucleotide sequence having at least 40% similarity thereto or a nucleotide sequence capable of hybridising to SEQ ID NO; 4 or the complementary form thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

17. An isolated nucleic acid molecule according to claim 15 comprising a nucleotide sequence substantially as set forth in at least one of SEQ ID NOs: 5–29 or a nucleotide sequence having at least 40% similarity thereto or a nucleotide sequence capable of hybridising to at least one of SEQ ID NOs: 5–29 or the complementary forms thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

18. A genetic construct comprising an origin of replication for a eukaryotic cell and a nucleic acid molecule, wherein said nucleic acid molecule comprises a neocentromere of at least 105 kilobases from a human or a non-human mammalian chromosome, and wherein said neocentromere has no detectable alpha satellite DNA as determined by fluorescent in situ hybridization (FISH).

19. A genetic construct according to claim 18 wherein the neocentromere is a human neocentromere.

20. A genetic construct according to claim 19 wherein the nucleic acid molecule associates with CENP-A and CENP-C.

21. A genetic construct according to claim 20 wherein the neocentromere is from human chromosome 10.

22. A genetic construct according to claim 21 wherein the neocentromere maps to a region between q24 and q26 on human chromosome 10.

23. A genetic construct according to claim 22 comprising a nucleotide sequence as set forth in SEQ ID NO: 3 or a nucleotide sequence having at least 40% similarity thereto or a nucleotide sequence capable of hybridising to SEQ ID NO: 3 or the complementary form thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

24. A genetic construct according to claim 21 wherein the human chromosome 10 is a mardel (10) chromosome.

25. A genetic construct according to claim 24 comprising a nucleotide sequence as set forth in SEQ ID NO: 4 or a nucleotide sequence having at least 40% similarity thereto or a nucleotide sequence capable of hybridising to SEQ ID NO: 4 or the complementary form thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

26. A genetic construct according to claim 24 comprising a nucleotide sequence substantially as set forth in at least one of SEQ ID NOs: 5–29 or a nucleotide sequence having at least 40% similarity thereto or a nucleotide sequence capable of hybridising to at least one of SEQ ID NOs: 5–29 or the complementary forms thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

27. An isolated nucleic acid molecule of about 105 to 1500 kilobases, wherein said nucleic acid molecule comprises a neocentromere from a human or non-human mammalian chromosome, and wherein said neocentromere has no detectable alpha satellite DNA as determined by fluorescent in situ hybridization (FISH).

28. An isolated nucleic acid molecule according to claim 27 wherein the nucleic acid molecule associates with centromeric binding proteins (CENP)-A and CENP-C.

29. An isolated nucleic acid molecule according to claim 27 or 28, wherein the chromosome is human chromosome 10.

30. An isolated nucleic acid molecule according to claim 29, wherein the nucleotide acid molecule maps between q24 and q26 on chromosome 10.

31. An isolated nucleic acid molecule according to claim 29, wherein the human chromosome 10 is a mardel (10) chromosome.

32. An isolated nucleic acid molecule according to claim 29, comprising a nucleotide sequence a set forth in SEQ ID NO: 3 or a nucleotide sequence having at least 40% similarity thereto or a nucleotide sequence capable of hybridising to SEQ ID NO: 3 or the complementary form thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

33. An isolated nucleic acid molecule according to claim 29, comprising a nucleotide sequence as set forth in SEQ ID NO; 4 or a nucleotide sequence having at least 40% similarity thereto or a nucleotide sequence capable of hybridising to SEQ ID NO: 4 or the complementary form thereof under low stringency conditions at 42° C., wherein said low stringency conditions comprise at least about 1% v/v to at least 15% formamide and from at least about 1M to at least about 2M salt for hybridization, and at least about 1M and to about 2M salt for washing conditions.

34. An isolated nucleic acid molecule according to claim 29, comprising a nucleotide sequence substantially as set forth in at least one of SEQ ID NOs: 5–29 or a nucleotide sequence having at least 40% similarity thereto or a nucleotide sequence capable of hybridising to at least one of SEQ ID NOs: 5–29 or the complementary forms thereof under low stringency conditions at 42° C., wherein said low stringency conditions comprise at least about 1% v/v to at least 15% v/v formamide and from at least about 1M to at least about 2M salt for hybridization, and at least about 1M and to about 2M salt for washing conditions.

* * * * *

SEQUENCE LISTING

```
<160> NUMBER OF SEQ ID NOS: 29

<210> SEQ ID NO 1
<211> LENGTH: 19
<212> TYPE: DNA
<213> ORGANISM: DNA primer

<400> SEQUENCE: 1

ggattacagg yrtgagcca                                                  19


<210> SEQ ID NO 2
<211> LENGTH: 19
<212> TYPE: DNA
<213> ORGANISM: DNA primer

<400> SEQUENCE: 2

rccaytgcac tgcagcctg                                                  19


<210> SEQ ID NO 3
<211> LENGTH: 80595
<212> TYPE: DNA
<213> ORGANISM: Nucleotide sequence of HC-contig

<400> SEQUENCE: 3

gaattctcct gcctcagcct cccaagtagc tgaggttaca ggtgccagcc accacgtcca     60

gctaattttt gtattttagt agagacgggg tttcaccgtg tttgccaggc tggtatcaaa    120

ctcctgacct caagtgatct gcctgcctca gcctcccaaa atgctaggat tacaggtgtg    180

agtcaccgca cccagccctt ctttcagttc tatcacctct ttttgctata tttgtatgag    240

agctttatta ttaggggcac atacatttaa aattgttatg tcttattgat agattgatct    300

gtcattatga atgtctgtat tcattccctg atagtatttc tttttctaaa tatttttctg    360

aatgtgtctg ctattaacat agccactctg gctttttaaa attagtattt ttatggtata    420

tatttttcct tttttttttt tttaagtttt agatgttatg tttccttata cttaaagtgg    480

gtgtcttata ggcagcatat atctgggtct tgatgtatta tttaatctga taatctcaac    540

ctttttgttg gagtgtttag gccatttaca tttagtgtaa ttatagacat ggtttgattt    600

gctataccat cttttcattt gttttatatg tgagccatct tttcattgtt ctttttttcat    660

ctttgaccat tttctttagt actgaatact ttttttgtat ttcattatat ctattggctt    720
```

-continued

```
tttagttata cctcttaaaa ttttttttc tgttttatgt aggatttata atatacatct    780
ttaacttatc acagattacc ttcaaatagt attttaccag ctcaagtgta atgtagaaac    840
cttacaagag tatattttca tttctgtctc ctaattttta tgctatgtct ataatacatt    900
aggtttgttg ttgtttgttt ttaccttatt gctgttggct ggggtcagca aacattttct    960
gtaaagggct agatagtaca ggcatacctt ggagatactg tgggtttggt tccataccac   1020
cacaataata caaatatgca agaagtggat atcacaataa agtgagtcac acaagtcttt   1080
tggcttccca gtgcatataa aagttttgct tatactacac tgtagtctgt taagtgtgca   1140
atagtgttat gtctaaaaaa acacatacct taattttaaa atgctttatt actaaaaaat   1200
gctaacaatc atttgagcat tcagtgagtt gtaatctttt tgctggtgga aggtcttttc   1260
ttattgatga ctgatcgggg gtcaggtgct gaagcttagg gtggctgtgg cagtttctta   1320
aaacaacagt gaagattgca atatcagttg actcttcctt tcatgaaaga tttctctcta   1380
gtgtgtgatg ctttttgata gcattttatg cacagtagaa cttctttgaa aattggatca   1440
atcctctcaa accctgctct gctttaacaa cctaagttaa tataatattc tgaatccatt   1500
gttgtcattt caacaatttt cacagtgtct tcaccaggag tagattccat ctcatttcct   1560
gagatggaat ctttgctcat ccataagaag aaattcctca tctgttcaag ttttatcatg   1620
agattgcagc aatacagtca tgtcttcagg cctcacttca cttttaattc cagttctctt   1680
gctgtttcta ccacatctgt ggttccttcc tccattgaag tcttgaacct ctccaagtca   1740
tccatgaggg ttggaatcga cttcttccaa attcctgtta atatttatat tttgacctcc   1800
catgaatcat gaatgttctt aatggcacct ggaatggtga atcctttcca aaaggttttc   1860
aatttactta gtccagatcc atccatccag aggatccact ttcaatgcca gttatagcct   1920
tatggaatgt atttcttcaa taataaggct tgaaagttga aattactcct tgatccattt   1980
tctgcaaaat agatgttgtg ttagcaggca tgaaagcaac attaatcttt ttgtacatgt   2040
ccatcagagc tcttgggtga ccaggtatat tgccagtgag cagtaatact ttgaaaggaa   2100
ttatttttct tagcagtagg tctcaacaat gggcttaaaa tatttggtcc accattctgt   2160
aaactgatgt gctgtcatct aaactttgta gtttcattta tagagcacag gcagagtaga   2220
tgtagcataa ttcttaaggg acttaggatt ttcagaatgg taaatgaaca ttggcatcaa   2280
tttaaatcac tagctgtatt agcccccaac aagagagtca gcctattttt tgaagctttg   2340
aagccaagcg tcgacttctc ctccctggtt acaaaagtcc taaatggcat cttcttccaa   2400
tataaggctg ttttatctac attgaaaatc tgttgtttag tgtagccacc ttcatcaatg   2460
atactatcta gatctcttgg ataacttgtg cagcttctac atcagcattt gctacttcac   2520
cttgtactct tatgtaatgg agtggcatct ttcctcgtac ctcatgaacc aacctctgct   2580
agcttccaac ttttcttctg tagtttcctc gcctctctca gccttcatag acttgaggat   2640
agttagagac ttgctttgga ttagattttg gcttcaggaa atgttgtggc tggtttgatc   2700
ttctatccag accactaaaa ctttatccat atcagcaata aggctgtttt gctttcttat   2760
tatttgtgtg ttcactggag tagcactttt aatttgcttc aagatatatt tctttgcatt   2820
cacaacttgg ctgactggtg caagaggcct agctttcaga ctatcttggc ttttgacatg   2880
ccttcctcac taagcttaat catttctagc ttttgattta aaatgagaga tgtaggccag   2940
gcacagtggc aggcacagtg gcatatgcct gtaattccaa cacattaaga ggccaaggtg   3000
ggaggattgc ttgaacccag gaggtggagg ttgtagagat cacaccactg cattccgtcc   3060
tggatgacag agcaagacct ttctcaaaat aaaatgagag gtgtgcttct tctttttgtt   3120
```

-continued

```
tgagcccata gaagccatag tatgattttt aattggccta atttcaatac tgttgtgtct   3180
cagagaatag ggaggtctga agagagggag agaggtgggg gaatggctgg tcagtggagc   3240
agtcagaaca cacataacac taataaattg tttgctgtct tatatggatg tggtttgtga   3300
tgcccccaaa caattacaat agttacagca aatatcactg atcacagatc accataacag   3360
atataagaat catggcaaag tttgaaatat tcttgagaat tagcaaagtg tgacacagag   3420
aaacaaagtg agcacatgcc gttggaaaaa attggtgttg atagacttgc tccatcgcaa   3480
gtttgccata cgccttcaat ttataaaaaa cacaatatct aggaagttca ataaagtgaa   3540
gtgcaataag atgaagtatg cctgtaaata tttcaggctt tccagaccat agggtttctg   3600
ttgcaactgc tcacctctgc cattatagca tgaaagcagc tatagaaaat atacataaat   3660
gaggcctgta atcccaacac tttgggagcc caaggtggat ggatcacttg aggtcaggaa   3720
ttcgagacca gcttggccaa catggcaaaa ccccgtctct actaaaaata caaaaatgag   3780
ccaggactac gcatgcctgt agtcccagct acttgggagg ctgaggcagg agaatctctt   3840
gaacccggga aggggaggtt acagtgagcc aagattgtgc cactgcactc cagcctgggc   3900
aacagagtga gactgtctca caaaaaaaaa aaaaggaaaa gaaaatacac ataaatgaat   3960
gtatgtggct gtgtaccagt atatcctcat gctctagctt gccaaccctt gctttacact   4020
gtcagttacc ttctaaagag attaaaaatc ataacaatat ctattacgtt tattcacatc   4080
ctagtgtcat ttcttcctta tgtagaatca aatttcattc tggtatcata tttcttcttt   4140
ctaaataatt tcctttaata ttttttatag cacaggtcta atagcaatgc attatgcaat   4200
tcattgctat tagacctgtg ctataaaata gcaatgaatt atgtcagttt ttatttgtct   4260
gaaaaagttt tttgtttttg aaatatactt ttgctgggta tataaatcca tgttgcataa   4320
cttctctttt cttcagcact ttaatgaagt cactcagtta tcttctggct tgtatagttt   4380
ctctggctgc cttcaagatt ttttcattgt ctttaatttt tagcagtttg atgtgtctag   4440
gagtgatttt ctttgtattt atccttttgg gggcctctta atttctttga tccttttttt   4500
cttttttttt ttttttaat cagttttggt ctgtctcctc aagtgggctg aaaaaaaaag   4560
aaaaataaaa tcatagttta aaaaactaat tttggaaaat tttcagctat catttcttca   4620
aatatttatc ctactctatg ctcccctcct cccctttcct tctgtgactc aaattacagg   4680
tatatttaac cattttattt gttcacggca cttggatgct ctgctttctt atttttttgtc   4740
tttcattttg gataatttct actgacctat cttcaagttc actgattctt ttctcagtca   4800
tatctagtgt gctcaacgcc tgttgaagaa atcctttgtc tttaatatca tgttttttat   4860
ttctagcatt ttcatgtaac tctttgttct ggtttccatc tctctactca cttttttttt   4920
tttttttttt ttttttgag acagagtctc gctctgtcac ccaggctgga gtgtagtggc   4980
gcgatctcgg ctcactgcaa cttccgtccc ctgggttcaa gtgattctcc tgcctcatcc   5040
tcccgagtag ttggaattac aggtgcccac caccgtggct ggctaatttt tgtatttttt   5100
tagtggaaac agggtttcac catgttggcc aggctggtct tgaattcctg acctcaggtg   5160
atccacctgc ctcagcctcc ccaattgctg aaattactgg catgaggcac tgcacccagc   5220
tctgctgaca ttttttatct tttgctgcat tttgtctacc ttttccatga aatcctttaa   5280
catagtagtc atagttactt tcaattcctt gtctgacagt tctgacattc aagtctaggt   5340
ctgttaatag ctttgtgagt ctgttaacag cttttttttca ttcttgtctg tgtgttttgt   5400
atttcttgat tgtatgccaa atattgcctg taaaataaac ttagataagt catacttcta   5460
```

-continued

```
tccagaaata ggcacatttt ttgtgtccag tcattagtgt ggagggaggt tggggcagtc   5520
tagtcagtgg ctgaactagg tttggatttg ttgatgctat acttagaatg caccagactt   5580
ccattcactg caagagtggg ctgctgcgct ttgtgattca tgtgaggcct gaattgtggg   5640
tttttcctta gtgtgtccct ccatgctcag atttcagcaa gtcttcatat ctgtgccaca   5700
gaaggaatct gacccatgct ctttttgacc tccccaagtg atcaactgtt gcttgttata   5760
gcttgtcatg gagtaagagg gtgttttttt agttttcatc ctccagcctt ggtcttgggc   5820
cctgagctcc tagactccag gagtggatgg aatccagtga tttctcagta attcagcccc   5880
ttctccagta gtggcagatc tctgctttgt atcagtgcaa gatcctgggc tgagctcatt   5940
ttctgccctt cctcgagtgg cagacagctc ttgctttcac ccttctacca aaggcagtgc   6000
atcttttctt gggcctctcc ccattgaact tatgactttc acataagaga agggctcatg   6060
tatcagagaa ttctgtgact ttgtgccaca tacagagtct ctcagttctc ttgccctgcc   6120
ccagtctttt ttgtgagcac ctagtagaga cccttggaga agagcaagga agcgagtatg   6180
gacttctttt gtgtctgtcg attgctttgt ttctcaactg ctactcttgg actttaagaa   6240
ttcattaaaa tttcagctgt tttcttttat tctttttgtt tttctttttt tttttttttt   6300
tttttagatg gagtcttgct ctgttgccca ggctggagtg cagtggtgtg atcttggctt   6360
gctgcaacct ccgcctcccg ggttcaagcg attctcctgc ctcagcctcc caagtagttg   6420
ggattacagg tgcccaccac cacacctggc taatttttgt atttttagta gacacagggt   6480
ttcaccattt tggtcaggct tgtctcaaac tcctgacctc atgatctgcc cgcctcagcc   6540
tcccaaagtg ctgggattac aggcatgagc caccgcgcca ggcctcagct gttctctttt   6600
tacctgctgg gatggctagt tttctgtgtc aacttgactg ggccatggga tgtccagata   6660
tgtaattaaa cagtatttct gggtgtttct gtgagggtgt cttcagaaga gatttgcatt   6720
tgaattggtg aactaagtaa agcagagggc cctgtctagt aggggtaggc atcatccagt   6780
ctgttgagga cttgaataga acaaaaggca ggggaaggtt ggaattgccc cctctctgct   6840
tgagctgaga catctatcct gcccttggca ctcctggttc tcaggggttc agacctggat   6900
tcctggtctc caccttgccc atggcagact gtgggacttc tcagcctcct atctaattaa   6960
taaatctctt catacacaca cacacacaca cacacacaca cacacacaca cacacacaca   7020
ccctatgtat ccttctgttt ctctgcagaa ccatatctaa tacacctgct tttatgacga   7080
ttacctatcg attctgtatt ctgccaaaac tgaaaacagt tcatttttcc atctcttctc   7140
agagaggctt gtcagccatt agttctctga tgggctcaag aagttatgca gttttttttt   7200
tctcactgtt aggatggaat tgatattctg ttgaaacttt ctatacctaa gtggaaactt   7260
gttttgaggt tattttctct acttactttt gctggaaatg gaacactctg tatctagtta   7320
agacacataa actgacttgt gataccataa tgttgtgttg aattttatat tcttagaaaa   7380
tcatctgtca aggtgttaac taatggcaaa gcatttaata aatcagcatt catgtattca   7440
ggtgctctga attatctgac ttttaaattc ttactttata aatgagaaaa ttggggcatg   7500
gaaaagttaa ctctcctaac cccgaattat tacattatta aggacaggac ttagaggcca   7560
gatatcttaa gtcattaata ttctttggct cacagaattg gcagtataac ctaaaggtaa   7620
taactaggtg attttctttt atatcaatta aatatgtcag ttttcaaata ttcataagta   7680
cctactgtgc agggaaagaa catgccatac aaaagatgta gtccaggcct ttaagaaact   7740
ttcatttaat gggaactcaa gaagtgtaca tataaggagg gaagtagcag tatggtacaa   7800
gataatacat acatatcagt gaatgatatt gccaaaaagt gctattgata gagaaataat   7860
```

-continued

```
tcatttctgc aaacagctgc tgatctccta ctgaaaacag aggagggaga acaggacgcc   7920
tcgtggtcag gatagaagag aaagaccttg agttgagcct tgaacagtat ttaatattca   7980
aaaggttaag agaggagagc aattgaggag gggagaatag ttccagcaca aatgatggtg   8040
tacaagatga acacagtcag taaagagcag actggtctgg atggagagga ggatttgcat   8100
catttgggat tacgtcattt agacccttga aagccaggat tgagtaaagc cacagtgaag   8160
cgactggctc gtatggaagc tttattttaa gaagattaat ctggtagtga catgtgccaa   8220
aaactgaata ggtagaaatg agatgcagag agcccagtta gaactaagtc tggtgcagta   8280
atgcaggatt gaggcaataa acaccaaact acagtatcac cagataatgg atgtttgaac   8340
ggacggttta aaggaaaatt gatggtattt ggtaatttat tagataatcc agggccatgg   8400
aatgagaggg gaaaatgact aaccatagtc atcaaatggt tttcttaat gaatctgaat    8460
tttggtgtaa gagcaacatt ttcttaggcc ttgcctagtt ggtacagctg actatgataa   8520
tgactgctac catgcttgtt cctcttttag cagctgtgag tcccccacca gccaaacaat   8580
gagcctcttg aaaaggacga tgccttttca cttctctcca agtgcttggc aaataggagg   8640
ccttttgaag ttactttata gttaggggtt cccagtgagt atttgaaata ttaagtcatg   8700
cccgtggttg acagcatggc cctactgctc atcatcagct attaacctta ggcaagttaa   8760
tgaacttttc taagccccag tctactcatt tataaagtgg gattattaat aatgtctact   8820
tcataaaatt atgaagcctg agttaggtca ttcagatagt gtttagtctg attcttcgaa   8880
cctagtaaac agtcagtaaa cagaagcaaa tgccacatgc ctgatttata tccaagggga   8940
gaaaggtaaa agtgaaattt tcatgattta tggattcaaa ttatacattt caaagatgct   9000
ttataagcta ttgttttggt aagaagaatt gagctgaaac agaattttct gacagcagtg   9060
attattaaat ggtgaaatag gctattgatg tctttagagg atatagatgt tcaccttttg   9120
catataagtg cacaaaaatt cactaagtag atatgtctgt ctacacagag agagagagcg   9180
tgagagcatt aaagttagta aacatccccc tcgctttttt ttttttgaga cagggtctta   9240
ctctgttgcc taggctggag tgcagtggtg caatcgtggc tcactgcagt ctcaacatcc   9300
tgggctcaag cgatcctctc gctcagcctc ctgagtagct gaggtgtgca ccaccacacc   9360
cggctaattt ttaaattttt ttattgtaaa ggtgaggttt caccatgttg cccaggtctc   9420
aaactcctga gctcaagcaa tctgctcact tcagcctcca aaaatgctgg gattacaggc   9480
gtgagccacc acgcctggcc agtaaacccc attcatttac atcatcttac ttgtccctcc   9540
aaaatcctgc aaagtaggta ggttctgtct ttatttgtta tttaggtgaa gaacttgaag   9600
tggtgttgag gaataggtgt tttgccaaga gtcacgcagc tggagtggca gagctgtata   9660
ctcttctgat tccaccaacg ctgtttacat cacatctgga gaaaagtgct ctgaggcaca   9720
gatgtttagt gggagggatg agacacaggc tgcaatgcct aaagataatc gggaataaaa   9780
gcagaaaaca agacgtttgt ttctgttaaa atgagacaga aaataaggcg tttgttgttt   9840
gggattgagc acttggagaa gtggggagcg atttgatttg ggtgagactg ctcctggaat   9900
gctgcatctg gttctggact actcattact aggcttatag aaactagctg gaggaggttc   9960
aaagaaaagc tccaaaatga ttagcgggct gacgggattg atttataaga aatattaaaa   10020
gaattaaatg tgtatagctc agctaagcaa agatgaaaga gaccagctaa atgtatacaa   10080
atatctgaaa cgtgcaaact ttaaaaagag agattaatta tttaacatga tacacggggg   10140
cacaatatgc agtcacagga tgaaaatttc agctgagtat ctagaagaat tccccgatag   10200
```

-continued

```
tgaatctgtt aaggctgtct gtagtgtggc ctttccctgg agaggcaata gaaatttcaa  10260
gtcttacgat tttaaaagtt tcttgggaac taggtattag atgatgttag agaattatta  10320
ttaatttggt caggtatgat aatggtattg tagttctata agaaaaattg tattttttag  10380
agttacatac cctgaaatat aagcatagaa tatgatgtag gagatttgct ttaaaatacc  10440
acagtaagga aagaaaggaa ggaggaagaa aagaaaggaa ggggaagaaa gggaaaaaga  10500
ggcaaagaag gaagagaagg taagagaaag aaaaagaatg aaggaagaag gctgggcact  10560
gtggctcatg cctataatcc cagcatttag gaggccaagt tgggaggatc acttaattaa  10620
gcccaggagt tcaaggctgc agtgagctgt gattgcgcca ctgcactcca gcctgggtgg  10680
cagagtgaag ccctgtctct aaaaaaaaaa aataagttaa aaagaaagaa aaggatagat  10740
gaagtatggc aagatgttgg taatgttgaa cctgaaggaa gttaatatgt gagttcactt  10800
tcctcttcag tcttctttat gtatgtttgc caactttcat aataaacaat ttaaattata  10860
ttttcctgat caaaacttag tagcagtatt aatccctggg cttcctgact agaacagcct  10920
cattaccaca tgggcagagt tctggccgac cagggaccac gtagtggttc accatcttgc  10980
tctggtaatg tggtctgggc tgaagggccc tttctaaggt tgtagataga aatccaggaa  11040
acttgttaga actgcagacc tatcagggta cctgcaggag gtgagtctac taaggtgaaa  11100
aagcagaggg cagaggtcgt gattagcagc tgaccgcccc ctgcttttct gtccctcatt  11160
cgtggaaaat tgagtggagc tcaattttga gtggagctct aagtagctcc acttgtagac  11220
attgagtgga gctctaagtg tcttcagaat agcaaaacac tagttttctt tttcttttct  11280
tttttttttt ttttggagac agagtcttgg tctgtcgccc aggctggagt gcaatggcac  11340
gatctccgct cactgaactc tgcctcccgg gttcaagcga ctctcctgcc tcagcctccc  11400
gagtagctgg gattacaggt gcccaccacc acgcccagct aattttccta tttttagtag  11460
agatgaggtt tcaccgtgtt ggccaggctg gtctcaaact cctggcctca agtgatccgc  11520
ctgccttggc ctcccaaagt cctgggatta caggtgtgag ccaccacacc cagctgcaaa  11580
accctatttt tcttgaatgg agaaacactt tccccttatt tattgagttt gggaagcaag  11640
aagaggggta attcattaag tgaaaatttc caaaatccag aaaacatcga taaagcagca  11700
gcttaatttt tttaaggaag aattttttaa actatcttct tttgagcctc tttaggaaga  11760
cctcacgtcc ttgccttgaa tgttgagagt gggaaatcca gggagttttg gaatgcatgc  11820
cttatgtctg cttttttgtt tgttagagaa atataaatat tttatctagg ttttgctgat  11880
ggcagtcaag catgaacaca acccactgtt tgagaagctg taatttctga atttctgcag  11940
agtgcacatc taggccagca aatggcagta agagtgaggt ggatttagct cagtgtaagg  12000
atgaactcca gaaccatcgg ctctgactga aagtgaagcg gcagccgcgt tgtgggaaag  12060
ctggctggag tctctctcat aagcaggcat tctttttctc cagcccgtca ctgtgttggt  12120
ttgggcccac ggtaagcctc ctggcctcta ggctgtaacc cccaccatcc tcctctgcct  12180
cgcctccaga gtgattgttc tgaagcacaa ctggatgtca ttccccttcc tgaactccta  12240
gcacctacag ggactccatc ccttgtgccc cacatacctc acacgtagac attcctaatg  12300
aagatttgat tgaattattg taaactcagt gcctcccact cttctagttg cctctctgcc  12360
tgcctttgta catttattta tttatttatt tatttattta tttatgagac agagtcttac  12420
tgtatcaccc aggctggagt ttagtggcac catctcagct cactgcaact tacctcccag  12480
atcaagcaat cctcccacct cagcctcccg aggagctggg accataggca cgtgccatat  12540
gcccggttaa tttattgtaa tttttgtaga gatggggttt catcgtgttg cccaggctag  12600
```

-continued

```
tcttgaactc ctggactcag gcgattcgcc cgtctcagtc tcccaaagtg ctgggattat  12660
aggcgtgagc caccatgccc agccgctagc actcatctta atcgtatatt tacttatctg  12720
gctttcccac cagactgcgg gctcttcaag agtaaatgcc atgttttcac ctttatttcc  12780
ccagtttgtg gcacattcta ggcactcgcc atcatgaaat aaacctctgg agctgtgata  12840
ttacaaacgt ggaaagatga cgagcactca gcaactttca gtgagtaaac aaaggctttc  12900
attcagcatg atttattgac tgcccaaatc tgggctgctt cctgtctgtg gttcaaggag  12960
agcatagtct acagaaccag agacctggct actctggaag ttagacttaa gcccaccccg  13020
gtccttgaat ggggaaatat ttcccttcat tcctgtgttt tagggacaga aagatgagta  13080
atgcagtgat acatgctgga aatgtttatt ccactacccg aagctgcctc tcaacttaac  13140
aatccatgaa agaaacaaga tggtatataa ctttttctaa tttgtgatgc ctttgtttat  13200
ttgtttccgg ttaaaagagg aggtggcatt gaattgtttg tttggtttgg tttcttcttc  13260
aataagaagc atcttaatat aactagactg gacatctgtc ccattttcaa aaattacaag  13320
tttcgatcat tgctaaattg tacagatccc aatctgtctg ctctgcatac atttgcattt  13380
ataaaagcag aagcagacta gcagtctttc taatgcaatc ccccaaatgc atgaagtatt  13440
agattgcttc tccctattgg ttcatgcatt gctaaaggct taaaaggatc attgatttta  13500
attatttaat gtgtacagca ggctgagctt cctttctttt ttaagggaag aaccttcagg  13560
ggcattgctt tagtttttta atgttaaatc tcatttttct ttgaaaataa gaagttaaag  13620
ctgtattcac acaagctctc aaagtgccag attttcattg tgtttttaaa ccatctagga  13680
aatgtttgat tctaatgaaa cattactgct gaaaattggg ctgaaattgc tgggctggaa  13740
atattgttat aacttcacat gattccagtg ttgtattatt attttttctt tttcttttt  13800
tgacccgata tagatgaagc gaagagacaa ggagcaatcc catgtgtaat agaaaaaggc  13860
agcctgaatt gttgttgctg tttttgaaat ttaagctggt tttcgattaa attcagtaaa  13920
tggtccagga ctataaatgt tgaacatttt ttaccgtgtg atttaaattt tagtcttatt  13980
gttttttttt tttttgatgg tttacatttt ccccatggga agcagctatg tcatgtcggc  14040
atgattcatc atggtaacat ctcgggttat tttggtttgt gttatgttca gaaagcggaa  14100
tgccaaaaat aaagagtggt ttgtgatgtc tagtgtgtct tcctttaaca aatcaaaggc  14160
ttttatttaa tccacttaat gggacactgc agaaatttaa aaaatggaag tcccatccac  14220
agaaggcagg tactatgatg taaaaagttt aggtggggga ttaatagagt gatcatataa  14280
tttatgagct aaaccggagg cacttttttt tttgagatcg agtctcactg ttgcctaggc  14340
tggagtgcag tgacgtgatc acagctcact gcaacctccg cctcccgggt tcaagcgatt  14400
ctcatgcctc agcctcctga gtagctggga ctataggcgc ccaccaccat gcccagctaa  14460
tttttgtgtt ttttgtagag atggggtttc accatgttgg ccaggcttgt ctcaaactcc  14520
tgacctcagg tgatccgccc acctcgacct cctaaactgc tgggattaca ggcgtaagcc  14580
accatgcctg gcccagagac acttttgaga gtgaagagga agctgagaat aattcactga  14640
tctacaactg ggaccatcca gggcaagcca gatgccatta ccactagcta gaaagcttgc  14700
caaggtctca tttaccttgg tatatagcaa attcttcttt tgaattctgg aaattctggt  14760
aagtcattga ggtagctctg tgccaaggag caatatggta gaattctaat atttcaggca  14820
gacaacactt tcctgcattt gtagcaggta aagggaggtc agggcagaag acaaaaccac  14880
tgggactcga caaagggcat aaacgtctaa tgcacctgat gtagctgatg gtaaattgtt  14940
```

-continued

```
atcagctaaa gatctttcat aataaataaa cttatcattt gtaggagggc acagaaatcg  15000
tggaaagctg ggattcaggt tgcctgtggc tttaattctg gaatcagaaa tattagtcaa  15060
ggatatcagt ctatgaagta agttttcaat gttatatgcc acaagatgca gctgtcctat  15120
tttcacttcc agtaattcct tctgaattaa tacaccttaa aaatagctgc agcttctcaa  15180
atctgtgaga atcgtatgtg ctgcttgcta cactttcttt ttcctgaagg ctctttgagg  15240
tctttcaaga actcaattca attcagcaac aattaggggg tctaaggtat acagacgctg  15300
tgcaagatgc tcctgagaca caaagaggag gtcaagcccc tgccttcagg cacctctcta  15360
taatatagga ggagaaagag aagaaacact aatacacata ggtaggtgcc attaaaaggg  15420
tacatacatt aaagccaggt ggtaggtgta agaagatttg taacatgaga attttctgca  15480
tgtttgaaat atcttataat ttttaaaaat taaaatggga gatacatata tatgtattta  15540
tgtatgtata tatgtatgta catatacaca catatataca taaatatata cataaatatg  15600
tatatatgtg tatatagaca taaatatgta tatatgtgta tatatacata aatatgtata  15660
tatgtgtata tagacataaa tatgtatata tgtgtatata gacataaata tgtatatatg  15720
tgtatataga cataaatatg tatatatgtg tatatagaca taaatatgta tatatgtgta  15780
tatagacata aatatgtata tatgtgtata tagacataaa tatgtatata tgtgtatata  15840
gacataaata tgtatatatg tgtatataga cataaatatg tatatatgtg tatatagaca  15900
taaatatgta tatatgtgta tatagacata aatatgtata tatgtgtata tagacataaa  15960
tatgtatata tgtgtatata gacataaata tgtatatatg tgtatataga cataaatatg  16020
tatatatgtt gtatatagac ataaatatgt atatatgtgt gtatataata atgtgtgtca  16080
tatacacaca tatatacata cataaacatt ctgcattata ccattcactt tgtaacccat  16140
cttccctaaa aactgtctca taaagagtct tcttttccct gtacctatgc aatggtaagt  16200
agcaaaacac acattctttt gggtccccat aacattccct gtagtttgcc cttaacagtc  16260
tttgatgtga aatttactgt ttctgtctta accttgcctg tctcgcgtac atggagtttt  16320
ggctcctggc tcctagtctg catcttcacc ccatcccttg cccaaagaat ctggttatgt  16380
gaccactgct catcttttct gctgccacaa ctccagtcca agccacaaac ctctctctcc  16440
tggactcctg cggggagttc ctttctctcc ctgcatgagt ctattctccg cacaactggc  16500
ataggtaagt gagactgcgg aagaggcaag tttgcaagtc cagaggaaat gaagactctg  16560
cttgtgcaca tgctgggttt gacgggtgct ggatatccga tggatggccc ttaaggtgag  16620
ctcaaggctt aagggagaga taggggctga tgatctgaga ttcatcagtg tgtggctgat  16680
gtttaaaccc aggggacagg ataagaaggt tattccaggg agagcgtaga taaagaagct  16740
aaatggcttc tgggtcctta gtcattcaaa atcggacctc tgaggcagga ggaaagccca  16800
gaaagagtag attcctggga ctcacgggat aaagactttc aaaaagtggg ggctggccag  16860
tgctgctgaa ggaagtagca ggaccggaac agaagggtaa tcgttggacc tggagaactt  16920
gaatttgaat tttaaggttg gtaaccttaa aaaagagcaa ttttagatac cttttgaaat  16980
tatttgcaag atttgtttgg tatatgtgtt attccaggca aagggaccag aaaagtaaaa  17040
aatacttact gaacagttac tgcatgcctg gcactgtaac accctgttta attctcacgg  17100
caaccctata gagtaggtgt catcatcccc atcttacaga tgaggatatg aggtgcagct  17160
agattaagca gtttgcctca ggttacacca actggttaac gtagagctag gatttgaacc  17220
cggatgggct gatcccagag ctcatgcttt aaatcgctag actggtgctc acagaagact  17280
gggaccgaaa aaaattaata aaaaaaataa ggagcccccct gggctagcaa attaggagtt  17340
```

-continued

```
gttcagacag atgtgaaaag gaaagcaagg cagagggaaa gtcactgtac agaagagaga  17400
gacccatgac agcagagaca gtgagctggt aaagtggctg gcgatctagc cctgaaaat  17460
acctccagag aggcaggctc acgcctgtaa tcccagcact ttgggaggcc gaggtgggca  17520
gatcacctga ggtcaggagt ttgagaccag cctggccaat ggcgaaatcc cgtctctact  17580
aaaaatacaa aaattagccg agcatggtga caggcacctg taatcccagc tgttcagttg  17640
gctgagtcag gagaatagcc tggatccggg aagtggaggt tgtagtaagc caagattgcg  17700
ccactgcatg ccagcctggg cgacagagca agacttttct taaaacaaac aaacaaaaaa  17760
gaaaaaagaa aaggaaagaa gaaagagaca aagaaagaaa gagagaagga aagaaaggaa  17820
ggaaggaaga gaaggaagga aggaaagaaa gaaaaggaaa gaaagaaaaa gaaagaagaa  17880
agaaaggaaa gaaaagaaag aaaaagaaag aaagaaaata cctccagaga gccaggtctc  17940
ttaggccttc tgagaaactc acatcccttt tgatgaacac aaatgcttca cactctcaat  18000
gttattggta atccaagtta tcaatatacc taaatcactt agtactgaat ctggcatata  18060
gtaatcacct aatgaagaga taagagtcat ggagtattct gaagcaatta gaatcaatag  18120
actcaatata cacatggcaa caaagttgga tcttaaaaac cgacctgagt gaaaaaggaa  18180
agggaaagat acataacacg gtaccattat gtaaattgat aatatatgct tacacaattt  18240
gtaagaacac atacaaatag atacatgtat attaaatata ctcgaacggt tacctatggg  18300
gtggtggctg gagtgggggt aagtccgtaa gctgtaatgg aacctaaaca aatacatgaa  18360
acgagtagga atcagaagga gtaacaataa aaatgtgcca tgaactgagg agtgtaaatt  18420
aatcaactca ctgcatctga ggttaaaaat agaaagatga taattgttat tcttattact  18480
cgtaggtctt ccacttgcac tcagctttac aatgttggac tatccttcag atggcaccct  18540
ccttgcactt gctcaggcag gagagctttt tcctccagct ttctaggtga tttaatatat  18600
cagggaataa gtataaaaaa aggcacggtg ctccctgggt agcctttctg gacttcagag  18660
ctaaattgca aagtcagttt tacacatgtg atttcatcta tgaaattagg gcaaggtaga  18720
aaactggcac agaaaaaatg tgatttatta tggtgttact atcccttaca agcggagtgt  18780
cagctgcctc tttttgtcca ctgatttaag gcaagatgaa ctgaaagtgg ctatgatcac  18840
gtcttcaaaa gcacactctg gcccctcggc tgcaggcgcc ctgcacattc cccagctgcg  18900
tgtccggtgg tgacacagtg cataattgtg gcgccttcct ggtgcaaact gtctcactta  18960
gctccgtctt gctggcacag cagaaaggaa gaaatcgaaa atgtttggat ttcaaaggta  19020
acaagaagct ggaaaacaac tactggccga gtctgagagt ttcagcggag actggtgcag  19080
ccttgtgttt ttccactgac agctgaaaat gagcccagct tcagtgaagc ttgtttcctt  19140
ccctcctcaa ggttacccac aattctcagt tctctcagga aagccaaaaa atgaatttga  19200
gggtttagga ttgtggttct tttatctatt acaggattga taatatgttc ctccaccaga  19260
tgttctgctt gtaacaatac tcacttcctg acactactgc atatgcagga gtgttactac  19320
caaggtaaac acagaattgg ctgcccaatt ccaaatccct gaactgagtg agagaaatca  19380
gaattataat aggggattca acagagctgg ctacggatgt gccagtggtc agatactttg  19440
ctcatcatac gcaggtgctg ctgctctagc aactgctcac tgcttcattt cctgccttgg  19500
tctttaaata ctgcttttct cagctcaatt ggctttcttc cctctggcag tcacgtttct  19560
ttgggtcaaa cagcaaatga ttctttagaa tcacctggta ctcaaaggag ctacaagaca  19620
ttgggcatcc acttccactc tcttggaaaa acaattttat ggaagccaag gttgccatag  19680
```

-continued

```
tgcctcttga ggttgtttgc tcagccaagg cccaagcttt gtgcttcaaa catgaaatta  19740
gagagcttca gaacaagatc cacattttca atggcctcac ccaactggat aaaagaacaa  19800
ttgccatatc tcaatgacca ccttttcag gtgggatggt agatgctgga atgggtcaca  19860
gcattgccca accaaacttt gcaaaaaagg ctggaagctc tgactgggga ccctaaatat  19920
gcaaaagttg ataggctctt catgcagaat atgaaccccg tgtatggata tagctaaagg  19980
gttggccttt atgtttctat tccttcacaa acctggtaga atagatatgc ttgtttccct  20040
ttaaaaaatg tcaacaattg catttatgat gctgtgtata gtaactcaca gatcatgctc  20100
catgaaaatg cttcagaacc caatataagg agatttttta gccatgtgtg acaaaagaga  20160
ggccatttca gtgttgaaat tgttcagaga agtatttgat tatgttttct cagatctttt  20220
tatttttatt ttttttgaaa cagagtctca ctttgtcacc caggctggag tacagtggct  20280
gtggtctcgg ctcactgcaa cctctgcctc ccaggttcaa gcgattctcc tgtcagcttc  20340
ccgaatagct gggattacag gcgcatgcac caccatgcct aatttttgta tttttagtag  20400
agacagagtt tcgccatgtt gaccaggctt gccttgaact cctgacttca ggtgatccac  20460
ccacctcagc ctcccaaagc actgggatta caggcatgag ccaccgtgcc cagcctgttt  20520
tctcagatcc tgtatttgtt tctgaagcct tcatttctat cttcttattc attttggaag  20580
tagtacacct aagtaaggtt tttaacaatc aaatatcttt ggaaaattcc ctggttcctt  20640
tcttattcct acaaaaatat gttcagtata gctgatgtta tgtttctttc aaattattca  20700
tttctctatc tcagaattta tctcatgcct aattgttatt gaatagtctt cacttcttgt  20760
catccagttt ctggtctctt atttcactct aagtctaagt ggctattaga ataaagagct  20820
tgtaacagat tctttctcca atatgtctta tcttttgact gcatgccagt gacaaactgt  20880
taactgtttt gattcttcat aacattccac agaacatgct gactcctctc ttcctgaaag  20940
caatgcccaa gcacagcatt gttagatagt atgtacgcaa cagggacatg ggtgcatagc  21000
aaaaactaga aggaaggagg accttcctta gcaatgggtg atatggtccc tggacttaga  21060
ctccaaaggg tcgtgaggtg aaacacacat cgtccatacc caggaagcac acaggtggga  21120
tggaagagct gtgcctaatg aaacttcatc cacgtggagg tggaggaggc tgcagctgca  21180
agaactcaga gctgccttac ccagaccagg gaccagggag ggctttctgg aggaaacagc  21240
ctctgaactg ccagctgata gaggagctct acctcaactc ttctggttcc ccagggctgc  21300
ttttccacgt ccatttattg gcactgaagt ttgaatacct tcaggggccc gaaagcctgc  21360
caggtcctct tctctgcaga gcaatcacac caacctgcaa agggctagga aagggctgtc  21420
atcatctcct actcagaaac tggttcactg gaaggactca ggggccactg aatacatcct  21480
ggcagctttc acaagaaggg cttctgactc aaggatgttt ccatctttgc caggtcgcct  21540
tttctccttc tcttagagtt tggaggacgc aaatgtgctg agaagtcaac ctttcctgca  21600
aggtgagaca caagggcctt tcccagcaga aagaagagag caaatggaag gtccttcttc  21660
ctccagtaga ggatggactc tgtctggcag ccacccaaca ggaaaagcac aatgcatgcc  21720
tgcctgcttc cctccctccc tccgtttctc cctccctccc tccttcctcc cttccattct  21780
cttcccttcc cctcccttcc cttcccctcc cttcccttcc cctcccctcc ccttcccttc  21840
tccctctcct tcccttcctc ttcccttcct tcctcttccc ttcctttccc ctccccttcc  21900
tttcccttcc tccctccctt cctcccttct ttccttccct tctttccttc ctcatttcct  21960
cccttccttc cttccttcct tcctttcttc ctactttcct acctttaggg ctctgtgtct  22020
ttggagtcca ttctgattat gctgtaatgt ctgccccttc ctcttctctg tcaaaaaatg  22080
```

-continued

```
aaagacatgg aagccacttg ccttttactg aattaaaaat tagtaaaaga gctaaaaatt  22140
aatggttaaa aatgtacgca taaattatgc agtatactaa ccaatgaaaa gatacacttc  22200
tcttaattaa aagctgacag ggagggaaac aagaaaagag aaacacaaaa caataatcta  22260
aatgacctat tagttggaag aacaacatca gagaaaatag atactgtgta tagtcatgtg  22320
tatgtctatg gaataacatt tgtagagaaa tctggactga tcctttctga gtaaagagag  22380
ctgtgggtac aattaagggg agattgaaag gaatccaaaa gcatagcaga tgctgtgcct  22440
cactggaatg gttgccgatc tcctccaaac tatgaagtgt ttgaggctca actttaatat  22500
aattaagata caaagacaga atgagagaaa gagagaaggg agctcactgg aagaacactc  22560
aagattcctt actactcatt ctctaaaatt acaattgttc tagatggaaa agaaaaaaag  22620
cttctctgtt aaaaaaggag cttgtgctat aggaggttta aaatatactt ctgacccatc  22680
tccaacattc taaatccttc ccagaaaagt atgccaatcc caagaaatat tcaatcaaat  22740
tgctggaaag aaaaatacaa aatattaaaa tgtattagga agcgacagta attaaatcag  22800
aactggagca ggaatagacc agcagatcaa tgagacagac atcaagtccc ggaatgtgga  22860
cttgcaaatg cattaagtaa tatgatatgc aataaaggtg gcacagtgaa ccaatgggaa  22920
aaaaattaat cttataataa ttgatattgc aataattgtc tagtaattgg gggaagaaat  22980
aagcttattc cttatctcat ttcttttttt ctttttgaga cagagtctca ctctggtagc  23040
ccaggctgga gtgcagcgat gcgatctctg cccactgcaa ccttgctctc ccgggctcag  23100
gcgattctcc cacctcagcc tcccgagcag ctgaactaca ggcgtgtgcc accactcccg  23160
gcaatttttt tttccatttt tagtaaaaat ggggtttcac catgttgcct gggctggtct  23220
tgaactcctg ggctcaggca atccacccgc cttggcctcc caaagtgcta gcattacagg  23280
catgagccac cgcgcctggc agctcatttc ttagactaaa taaattggag atggctaaaa  23340
gatttctatg taggccaact atgtttttaa aaagtttttt ttttaaggat atctgctgga  23400
accaatcatg ccaccaacca aagatgcaag actataaaac atacccagtt tttcaaagca  23460
tttaaaaatt attctaaaaa tatttttttct ccagaaattt tgcattgatt ccctgaagaa  23520
gcattaatat gggacctgac ttataaaatg atgaactcaa tctccccact caaggtagga  23580
gtctctcaga tttaaaaaat aagcatccta gtcctcttgt ccctgtaaaa gttaaccctt  23640
acacctgaaa caccaggaga ctggcggttg tttgcatagg ggttacaatt aaagttgagc  23700
tacctctgac atctattaac accaaaatta gtaaactatg catgtatgga gacttttatg  23760
attgaacttg tttattgagt caagagatat agtttacaat gaaaatttgg ggcatatcaa  23820
aatgaccttg gcttagctta gcatttgctg atgttaacta ttttcttcat tgggctgatt  23880
ttagttgctt aggaaaaata caaacacaca cactttaaaa ttatattaaa atcccgtcct  23940
aaacctcaga gtccagaacc gcatcctaac actggtcatg cataatatgt ttaaattttt  24000
gtgctttaaa aactacaaat aaggaatgta ttaatagttc cacaatcaat ggtcagttag  24060
ccgagggaag attagcatag ttaaagactt aaaatggctt tacaacatat atcaaaagga  24120
caaaataagg ggaacagagt ctagaaatga ggaaactggg acacaggcaa aaaaaaaaaa  24180
tgagaactgg gacatgaata acgcaaggga taagactaat acacaaaaca ccccaaataa  24240
atagccagca tttgctgagc tcttactgtg agcctgttct aagcacttta catatattaa  24300
ctcatttcat cctcaaggaa ccatctgagg caggcactgt tatcatctcc attttacaga  24360
taaggaatag acccagagag gctgagcaac tgggcctatt ccacagctac tatggtggag  24420
```

-continued

```
atgagattta aatctaatca ttggctccag agcccatgca cccaatggct gcactaagtg  24480
aatgcatgcg ctatcaacgt tgccaaaagt gggccacagc tcggatctgc gttttccagt  24540
agccaaagca gagagtgtga tcagacctca ctttaataag caagtctcaa gccagagaga  24600
ggtggtatca ggcagcaaac aggctgctag tcgaaatccc acttcttctc tgagtggtcc  24660
atacagtttt actctacttg cttacagaat gaaaatagct ggagttcagg tgcgctttca  24720
atgccctgtt gtcaggattg ggcttttcaa gtttattttt tgttgttgtt tttaatagac  24780
tgtacttttt agaaaatttt tagatttaca gaaagattga gaggatagta cagagagttc  24840
ccgtatacct cacacccagt ttctgcaatt attaacctct tacattcatg cggtacattt  24900
gttacaatta atgagccagg gccggccggg cacagtggtt caggccccta atcccagcac  24960
tttgggaggc agaggcaagc gaatcacttg aggtcaggag ttcgagacta gcctgaccaa  25020
catggtaaac cctttctgta ctaaaaatac aaaaaaattag ccaggcatgg tgctggttgc  25080
ctgtattccc agatactcag gaggctgagg cacaagaatt gcttgaacca gggaggcgga  25140
ggttgcagta agccgagatc gtgccactgc actccagcct gggcaacaga gcgagactcc  25200
atcaaaaaaa aaaaaaaaaa aaaaagaagg aaggaaggaa ggaaaattaa tgagccaata  25260
ttgagacatt attattacta aagtccatgc tttatgcaga ttttcttagt ttttacctgc  25320
tgtcattttt cagttccagg aatgcattca ggatgccata ccacatttag ttctcatatc  25380
tgcttaggct cctcttggct agactgagtt ttaatctact ttctgcagag cctgagaact  25440
ttagcataat ttccttggaa attacagctc aatattttca agcacttata caaacagcct  25500
aatgttacgt tggcccataa cagtgtttca aggtaataaa cttctttgtt ttctgtgccg  25560
attgaaagaa ctgctgctta gcctcctgcc agatgatgaa ctgggtacac acgagcattt  25620
ttccaggtaa agcatatttc gtgcgacttc ttaagctgca gccttatatg caataattgt  25680
ccatttacaa gacttatgtt cgaatttcag gcactctgtt ttcactaacc atatccttca  25740
actttgataa gtactgcttt aatcaactca gaaaatttaa cttgactaat tttttttcac  25800
catcagtttt ttttctgttg actctttctc ctttttctgt ttgcccagaa acatgctcag  25860
gattctctca ggctttaaaa aatgaaaaaa tgtttcctgc aatctagtta ctccttgatt  25920
ctcttgttct gtttatcgct ggaattcttg aaagcttggt gtattagtct tttttcatgc  25980
tgctgataaa gatatacctg agactggata atttataaag aaaaagaggt ttaatggact  26040
cacagttcca cgtggctgag gaagcctcac aatcatggtg gaaggcaaaa ggcatgtctt  26100
acatggcagc agacaagaga gaatgagaac caagggattt ccccttataa aaccatcaga  26160
tcttgtgaga cttattcact accacaagaa caatatgggg taaaccgccc ccatgattca  26220
attatctccc accggggccc tcccacaaca cgtgggaatt atgggagcta caattcaaga  26280
tgacatttgg gtggggacat ggccaaacca tatcacctgg cctatagcat tatttccatt  26340
tcttccccat ccttttattc ctcaaaccgg tacaaccaga cctctttttt tttttttcta  26400
cctgaaactg ctcttttgag ggtagctgat aagtccaaaa tactgtcacc ttttctcaat  26460
tccgttcctt cttatgcctt tggagcaatt gactgtgttg gttgccccct cctttaaagt  26520
gtctctcact tggttttatg actaatgatg attttctttt tcctctctaa acattccgct  26580
atctttttag cttcccttcc ccctcccatc ccctaaatgt ccttgtttcc cagaatctgc  26640
ctcacctctt tgacttctct atgccctgtc attcactcat gggtctttat tacattattg  26700
catctgtgtc aataactctg gtctttctgt taagttccag tctcccattt tcaaatgtcc  26760
ccagacattt ccaattgagt atctctccaa tgtatttaac ctgctaaata tctaacacat  26820
```

-continued

```
aatctttccc atcaaatcgt ttcctcttaa gcttttcgtt atttcctatt agactcctgc  26880
acttctccca ggagcccaga cttaaaacct tgaatttctc accataacct ctcttttgtc  26940
tcccataatc aattagtagc aagtgttatc aatgattact tgacaatatc tttttctatt  27000
tccctccctg ctatgatcat tcatctagca agaagagttg gccctttgta tctgtggttt  27060
ctgcatccct ggattcaacc aactgtagat ggaaaatatt tgaagaaaaa agcgtctata  27120
ctgagtatga aaaaatttta tttcttgtca ttattcccta aacaatacag tataacaact  27180
acagcattta cactgtagcg tatagatctt ataatctaga aatgatttca agtacaccat  27240
tatatataag ggacttgagc atctgtgaag tttggtattt gtggggcata ctgggaccaa  27300
ttcccccatg gatacagagg gacaactata tttactcagt gcttactaaa taccagttgg  27360
ccaatgtgtt tttctttttc tgttttcctg tctttagttt gccccttgcc aattaattca  27420
atagtgctgc caatgccagg tgtaccttca gaatattcta ttctaatttt gtcatctcca  27480
agcttaaaaa tatttaatgg gccaggcgca gtggctcaca cttgtaatcc cagcattttg  27540
ggaggccaag ggggggtgta tcacttgagg tcaggagttc cagaccagcc tggccaacat  27600
ggcgaaaccc tgtctctaca aaaaagtata aaagttaacc aggtgctgga gcatttgcct  27660
gtggtcccag ctactcagga ggctgaggca ggaaaatcac tttaatctgg gaggtggagt  27720
ttgcagtgag ccaagatctc tccactgcac tccagcctgg gtgacacagc aagactctat  27780
ctcaaaacaa caataacaac aacaacgaaa aacatttaat ggctgcacct tgcctgtgaa  27840
aaatgcattt cttggccaga tgtggtggct caaacctgta atcccaacac tttgggaagc  27900
taaggccagg agttcgagac gagctgggat atataggaag acacaatctc tacaaaaaaa  27960
aatccacaaa attagtcagg cttattgttc atgcctgtag tcccaggtac tcaggaggct  28020
gaggcaggat tcctcaagcc caggagttca aggcttccgt gagctatgat ggcacaactg  28080
cactccatct tgggtgacag agcaaggtcc tatctctgga gaaaaaaaaa aaaagaaggc  28140
atttcttagg agagttcttc tctgtagagt cctaagggtt ccatggaact ccttaaaagc  28200
atcagagtat gtgagtgcaa tgggaggaag catttagcca gagcagttgt gctcccattg  28260
catattaatt tttaaaaaac aaagctataa aaaaaagttg aaaactacta cgttagcatc  28320
agcctgacat ttaatggcct cgtaaatcaa accttaattg actttttagc cagttatgct  28380
actagccaac tacagacaac acacttttta accaaattag actaatagtt gtcatcagtg  28440
gaaatcaagt ttgccattct tccatgcctt tgctcacacc attacctttt ctggaatgtc  28500
ctgtactcat cttcctgtgt tgaactctat acccaacttt aaaaacctag ctcaaagttc  28560
aacacttcca ttccatttca aaaagagctt tcctcttcct taaagtttaa gaactcattt  28620
tcatgaatct ttttggcatt tattgcacac atgcttgctt tgtgttattt gtgttcagcc  28680
tcatatgccc ccaaggtgtt ttagactcct taacggcaaa aatgatgctc taaacacctt  28740
tctatctttc atagtgtctt agtctgtttg tgttgctata aaggaatacc tgaggctggg  28800
gaatttattt aaaaaagagg tttatttggc tcacagttct gcagctatat aagaagcata  28860
gtgtcagcat ctgcttcagg tgagggcttc aggaagtttc cacccatggt agaaggcaaa  28920
ggggagcagg catcacatat caagagagga ggaaaaaaag gaaggaagaa aggagggtgc  28980
cattctcttt caacaatcag ttcttgtggg aactaatggg acaagaggct gggcacggtg  29040
gctcatgcct gtaatcccag ccctttggga gaccaaggtg ggtggatcac ctgaagtcag  29100
aagcctgaga ccagcctggc caatgtggtg aaactccgtc tctactaaaa atacaaaaat  29160
```

-continued

```
tagctgggcc tggtggcgtg tacctgtagt cccagatact caggaggctg aggtaggata  29220
atcacttgaa cccggaagac agaggttgca gtgagcttgt gccactgcac tccagccggg  29280
gcaacagagt gagacggtct caaaaaattt taaaaacttt aaaaataata gagcaagaaa  29340
gcaccaagtt attcaggagg gatccacccc caatgactca aatacctccc accaggcctc  29400
acttccaaca ctggggatca atttccgtat gagatttgga ggagacaaat atccaaacta  29460
tatcacatag taatgaacat agtaccttat ctatagaaag caatggctag acaactgttg  29520
aatggctaac caaatctgct ttcctatggt ctcgctctag agggggtcag tatgagtttc  29580
tgtcaaaagg agaaaaaaaa atgtatagtc agttttgtgt gtgtgtgtgt tcatgtaaaa  29640
gagatcaaga gaaaagaaca agagaaatca tgaaaaggag ggggaatata agaataatac  29700
atagaaaaaa gcaaattatc ttgtttatca gtaataccca agggggtaga aatggtaagt  29760
aataatcctt cttcactttg tctgtagttc actttttgc acctttattt tgatgaattc  29820
acatcgaaga cattaactca ttaaggcttc caatattttt ggagataaga agggctgcta  29880
tgctctttat agatggaaaa cttgggtcat taataactca aacaaggaca taacaaagaa  29940
atggagcata aactgccagg tcctgactgt agatttggat tcccagttgg tgtcttgtca  30000
ccctttgtta ctcttcctaa agttatgatc ttttcttgtg cataggaaat tcatagtgat  30060
ttcccatcac ccttgggatt atcatagctc ctttaaggtc ccctctatgc actcaataac  30120
atcaacagta agtgttcttc gagcacttac tgagtgtata tcattgtgtt ctcacgcagc  30180
acccacagat ctcaccaaga acctagctga agcctgtaga atgaataggt aagtactgcc  30240
atgccaatct ggagtactca agcgatgcaa atgattcctt taattgtact tttgcaggct  30300
tgtcagtttt gctcatggag aagtggctac tgcatccatg ttatatctat gtaatgttgg  30360
actgcgaagc atcacttgac tttttccaag cagaaattac agctgatgac aagctgctgc  30420
tgagaaaatg gatatttttc tgaattcagt tctacgtgga aacagctgac tagtttccat  30480
tgctgtaaga atggctcttt tgctcttggt tgattttgag taatggcttt acttctgtag  30540
aaaggagatt tcatttgaag tccactcagg gatttggttc aacaaactgg agtacaggtt  30600
tcagaaaata tctctttaat cctccaataa taaattttct catctataat tcctggaaca  30660
cttcatcctt tgcagccgag catatagata gatttgttgc tcactgtgtt ctgattgcca  30720
ctttgacctg ctttttcaac ttaggttaca aatagaacag aatctctctg atttttctca  30780
ttaattgttt gaattcccac ttttcctcat tagcaagaag tccagtatct tcctgagaac  30840
ttccttttct caatctagga acttacttgg tccataaggt aacagtctta tttctgacta  30900
tcaaggagag aaataacagg agccattatc atcttcatgg tgtcactttt gaaaactggt  30960
cctctgtaga tcttcagatt cttgcgttag tccattcagc tgctataaca aaattgcata  31020
gacagcatgg cttataaata acagaaatgt atttctgaca gttctgaagg ctagaaagtc  31080
aaagattaag acactggctg atttggtgtc tggcgaaggc ccatttgctc atagatggac  31140
gatgaccttt cactctgtct gcacatggca gaagggcaag agagctctct gggtcttttt  31200
tataagggca ctaatctcat ttttgaggac cctgcccccca tgacttaatc acctcccaaa  31260
ggcactgtct cccaatacca tcaccttgag ggttaggatt tcaacatatg attttggggg  31320
gacagaaaca cgcagtccat ctcgcttgtc cactccatgg tggtattctt gctggatcag  31380
tttcctcctt ggggtgcatt tgtgttccat gtctaacttg caagttatag caggcccgat  31440
agcaaagtat tccaatgttg gtatgcagag gcattgaata atcagaatga acccacgcca  31500
taaacaactg gtagagctgc agagagtacc agctgattat gagccctggg taacagtggt  31560
```

-continued

```
ttttagttcc tatgtccgtc agccctttc tcccatagta gccccactgt gttgaagtgg  31620
ctgaatcgac agaagcttcc agcttgggcc acatgctcat ggaaccaatt ctccttatga  31680
gccgtacaag agctgggttg ccattctgga taccctcttt tttcaagaga ttttatttca  31740
aggatatttt ttcttttatc aactacaggg attatttaga atcttagggc agtggtgccc  31800
aacctttttg gccccaggga caggttttgt gggagacagt ttttccatgg accagtgtca  31860
gggggctggg aggcatggtt ttgggatgag tcaagtacat tacgtttgtt gtatacttta  31920
tttctattat tattatattg taatatataa tgaaataatt acacaactca ccataatgta  31980
ggaatcagtg gggagcccta agtttgtttt cctgcaacta gacagtccca tctgggggca  32040
atgggagata gtgacagatc atcaagcatt agattctcat aaggagtgct cagcctagat  32100
ccccggcatg tgcagttcac aataggattt gctcacctat gagaatctaa tgccactgct  32160
gatctgacag gaggtggagc tcgggcagta atgcgagggt tggggagcag ctgtcaatat  32220
agatgaagct ttgctcgctc gcctgccact cacctcctgc tgtgtggtcc acttcctaac  32280
aggtcacaga ctggtactgg tccatggcca gggagttggg gaccctgtct tagggagtag  32340
gggtggagtt cccttcactt ctagaaggcc ctggattagt atcccagagc tgtcattaca  32400
gagtatcaca aaccaggtgg ctaaaaacag acatgaattc tctcttattt ttgatggctt  32460
ggaagtccaa agtcaaggtg ctgccagggc catgctccct ctgaaatgtg taggggagaa  32520
tccttccttc ctctttctag cttctggtgg tttgctggca atcactggca tcgcttggct  32580
tgcagcactt caacatctgc ctttactgtc tcatagtgtt ctcccctcat gtctccaggt  32640
ctctctgtct ctcttctttg tataaggaaa ctagtcatat tggattaagg gccaacccta  32700
ctctagtatg acctcatctt aaggtcacat gcaatgacta ttccagataa ggtcacattc  32760
tgaagaactg ggagttagga cttcatatct tttgaaggaa cacagttcaa ccaataacag  32820
cccctgtact gttttacaaa taggtattcc tctccttccc aaagttcttc atagcagaga  32880
caacttgtac caaaaggcaa aataccttat tatgtaacct taacctagga tcatagatcc  32940
ctactgtctg gtgctttata agcacagaac caccgggaaa tcattattaa gacaaggaaa  33000
ggccaagtgc agtggctcat gcctgtaatc ccagcacttt gggaaattga ggcgagtgga  33060
tcaacctgaa gtcaagagtt tgagaccaaa ctgaccagca tgacagaacc ccatctctac  33120
taaaaataca aaaattagtt gggcatggtg gcatgtgcct gtaatcccag ctactcaaaa  33180
gactgaggca ggaaaatcac ttgaaccgag gatgccaaga tagcagtgag ccaatatcgt  33240
gccactgcac tccagtctgg atgatagagc aagatcctgt ctcaaaaaat taataaataa  33300
ataaaaagac aaggaaagcc ttttccaagg agacccttct gctttgctag ttcagagaac  33360
ttctcttttg gagaaaacaa acacccagtc cattagcagc aacgtcaggg attgaattct  33420
tagggcagca ggctgggcac agtggctcat gcctgtaatc ccagtacttt gggaggctga  33480
gatgggtgga tcacttgaca tcaggtgttc gagaccagcc tggccaacat ggtgaaaact  33540
catctctaca aaaaatatga aaaaaaaaaa aaaaaaaaaa gctgggtgtg ttggcttatg  33600
cctgtagtct cagctacctg ggaggctgaa gcaggagaat cacttgaacc cgggagttgg  33660
aggttgcagt gagctgagat tgccctactg tactccaacc tgggtgacag agagagactc  33720
catctcaaaa aaataaagaa ttcttcgggc agcagtcttt cctccacctc atagaccatg  33780
gaggtgagcc agctctgaca aaccatgaga acaatggcag agacatacct gtaacgtaac  33840
tgactggggc aaagacaaag gtgaggaaaa tgacaagttt gaggaactat gagaccaggc  33900
```

-continued

```
agtggggaac accactagca gaaatgatgg aagttctcaa gaataacaac agagaaatag  33960
accatggcca gagtctagaa ccctccaggg aaaggagatg ggctccagag gcagaagagg  34020
acgttgaagg gaatggggag tgggtgaaat atatagacga tggggaccac ccaagagcag  34080
tcgctattgc aaaactgagg agaaggagag tctggagggg gtggtgggaa gctgggtctc  34140
ctaaggaggt tttgacaaaa gcagtcatgg agcgggctta gaaatcacag ttggggacag  34200
ggtaaagttc ctcgggatat agaggatgag attagaagag gttccaacta gggtagtgtg  34260
gagaaaagca ctattgaccc aaaaaggaag gagaatgtgg gtggaagtgg cagagaaaga  34320
ggggtttgag cagagagtgg tgatttttct aatgcagagt tgtgggaggt ggagtgcagg  34380
gagccaggct gggtggctgt gctgatgtga ttaagcactt actgactgcc aggcaatggg  34440
ctaagtacct gagatgcttt gtctgttatc cctcccgaaa cccctctgag caggtgcagt  34500
tattattctc acttcacaga taaggaaatt gaggcacaga gaattgagta acttacccaa  34560
ggtgacatag ctcatatatg gtaaagcagg ctttgaactc agtctagctc ccgaacctaa  34620
gcttgtaact actatgcttt tcccaaaaaa agggggctgg cacaaaaaga gctgaggggg  34680
ctgggcatgg tggctcatgc ctgtaatccc agcacttcgg gagactgagg caggtggttc  34740
accagagttc aggagttcga gaccagcctg gtcaacatgg tgaagccctg tctctactaa  34800
aaatacaaaa attagctggg tgtggtggtg tgcacctgta gtcccagcta ctttgggagg  34860
ctgaggcagg agaatcgctt gaaccccaga ggcggatgtt gtagtgagcc aagatcatgc  34920
cactggactc cagcctgggt gacagagtga gactccatcc aaaaaaaaga agagctgagg  34980
tgatggccac catcagcatc agcctggaag ttatagcagg atgctaagtt tctctaaagc  35040
tgtctttctt aggacttgaa aaagataact tgggtttgta tcccatctct gccattagta  35100
gtttactggc tttggataaa ttacttagcc ttactgaacc aactttggat ttttatagag  35160
atactgtaat gaaaggaata aggtatcagt cttagcagag catccagagt gttcctatta  35220
aaacctaaat catatcctgt cattgctgtg ccccaaacca ttcaatggct tcccaactca  35280
aagttaaaaa ctcatctttc cagtggcctg caagagccta tgctatccgg tgtctgacct  35340
catctgttgt tcctttctcc ctccctttct tggctccaga cgcactctgg tctccttgct  35400
gttccttgaa tacaccaggc acactctctt cgcctgaaac actttacccc agatatctta  35460
gcttactctc tgcctccctc aattcattga tgaaatgtct cagtgaagtc ttctctctct  35520
cctctgtaaa agtatactct ctgttcccct tctttactgt tctagctact attgctgtgt  35580
aacaaatcac tccccaaatt taatgagtga aaacatcagc catcatctta tttctcacgg  35640
tttctgaggg tcaggaattc tggaagggct cagctgggag gttctggctc tataatctct  35700
tatgcagtga gagtcagatg ctggctaaaa ctgaaacaaa gcagggttct agtagctgag  35760
ggctggctgg gtctctcaga tatagttcag atctcctcca gggggtctct ccacgtgggc  35820
tagtctgaac ttcctcacag catggtggcc tcagggcagt ggactctgca tagtggctga  35880
aggcttcgca gctgagtatt ccagcaagca aagtgggagc tgtattgcct catatgaccc  35940
aaccttggaa tccacacagc atcacttccg tgtattctac gggttgaaaa gtcacaaaaa  36000
ccaaccagtt tcaaggagaa ggaacagaga tcacatttct caattggaga agggtcaaag  36060
tcacattgta atcagagcct atgggatacg aagtattgcg gtcaggtatg aaaaatttga  36120
tttgctgcat ctgctttact ttctccacag cgttcatgat ctgcttctca catgatattg  36180
acttacgtca tttctgcgtt tcctgtcttc cacactaaaa tgtcagcctg ttttgttcac  36240
tgctgtatcc ccagagccta gcacggagcc cagcatgtag tggtatccaa taaatacttg  36300
```

-continued

```
ttgcatgaat gaattctgtc ttttaatcct agctataggt ttctaagtta aatattacta  36360
taatcatctt acagacgagg gaaatgaggc tcaagaagat ttggtaactt atgcgggatc  36420
actcagccac ataatggaag agacagcatt gaagtacaca tgcttgctct gtctgctctt  36480
ccaagctgct catcacacag ctgcacctct gaggacttcc ctccccagtc cacctccacc  36540
cttacccaga gacacacatg gccacaatcc actagcagac caaaattcaa tttttcccca  36600
gttggttgca ctcaagctga gagcaaagca attgcacttt aaatcccctt acagcagata  36660
tttcagagca tgttcggaag aacccatcac acttggcttt tagatcttat ttctggtttg  36720
ttacaaaaac acaattaaat gaaaggttag gtagcttttg aatggccagc tcaaagtttt  36780
ggcttatttt tgccttgctg tctttatagg cattttacca atatttatca ctatttccct  36840
tagggaaccc ttagatctgt gatatttgaa ataataaagc ctctccattg gccctttaaa  36900
aggtttgtgg taaaaccaca ccattaacat tcacagttcc ttatttatga ggcctgattg  36960
cacttatttc catatttctc actgtttctc cgatgaggat ttcacataat agtgtttgaa  37020
ggctaaagac ttcaaagcag attctttact atttttatct tgaaaaatat tcaatatttg  37080
tgtaattaaa gtgaagtctt cctagagaaa atgacaactc aaataatctt aaatgtacct  37140
ccaagaaaaa agctgtcaaa gtgacattta gtaatagagt cacattctct aaggcctttg  37200
cttctccttc tgattcttat catctttgaa ggttatgtca tgggctgact tcaaatcaac  37260
ttttaaaatt attatggcct tctttaaatg tgagttctga aggtgagggg ctttatcttt  37320
cttttgctcc agattttttt taccgcgtca ttaccaagca tcttaaaaca aaacctaaaa  37380
acaaaaatct tccttgacct ggtttttccc actagctaac atcctatttt tatctttccc  37440
ctttgcacta aaggttttta aacggatctt tataccctct gtctccattt tctcatctgc  37500
taacttatat ggcaaagatt accactgcct ttcaacataa ttggccaatc tacagaaagt  37560
tttcaagttc tctttttaat tgaccacctc ctgcctacct ccccaccttt gacatcttgc  37620
ttctcacttg gcaccttacc cagtgttcaa gattccctcc tttaggatgt cttcagagca  37680
gctacacagt tggtactata atttatacat ccttgtacac agggcttgct gggatattga  37740
tggagagaag gaggaaactg gaagtagttc aggccagagc tagggaaatt gacccatctc  37800
caggtctcag gtctgcaagg ggagctcaca gcttaacaca tggagtctag aaacttgtgc  37860
tggaccttga ccaacaccag cccatggagt ccaatacagt gctcaatagg gatttccagg  37920
aaattgctat atttattcaa agagaactta ccaagtgtca gctacgtgtt gggcattgtg  37980
ctaggcacag ggaccacaaa gataagacat tgtagctttc cttaagttgc tcactgagta  38040
aatagagaga cagaaaggta aacaggtaag tgcaaaaata catacaattc agcaatagtg  38100
ttcatagtgg ctatggagag aacgctcact aactttgttt aaacagttgt tctttcaagg  38160
atttgacatg gatttgattg gaaaagcatg ataccatttt ttgcaattaa acacaggaat  38220
acataaataa aatgcatcag tattttttac aaatagctac taagagctac tagaaaacct  38280
gggaattctt aaaaccttac catgctactt gctctaaaat attttatttt atgttatttt  38340
gtacatttct ttacctacac aaacaccact gttttcttca tttcttagtc tatttaaacc  38400
tcacaccctt tcagcatctc ttaattattt actaccatct gttagttctc ctgtcctgaa  38460
tgaaacaaaa atggcagaat gtaaaacgag ggcgaacaga tttttgacag gaagtattca  38520
gaggtagaag gaaatagtca agacacatat gataaacgaa aacaataata actttataca  38580
taacaactta tagacacatt taaaaagttt aagatctcaa gagctatgtc tgaatagata  38640
```

-continued

```
ggagtaaaaa ctctattaag taattaggaa aataacaaga acagtgaatt tcttaatgaa  38700
tggcatgtaa tcaaaactgt acttatcgtc taattcataa tcttgaatgt ttttatttta  38760
tttatttatt tttttatttt ttgagacaga gtcttgctct gtcacccagg ctagagtaca  38820
gtggcgtgat ctcagctcac tgcaacctcc acctcccagg ttcaagcgat tctgctgcct  38880
cagcctcctg agtagctggg attacagagg cctgccactg cacccggcta atttctgtat  38940
ttttagtaga gatggggttt caccatcttg gccaggctgg tcttgaactc ctgacctcat  39000
gatccaccag ccttggcctc ccaaagtgct gggattacag gcgtgagcca ccacgcctgg  39060
tcgaatgtct ttattatttg aagagacaac atgggcctta aatctgtctt ctatttgaca  39120
gactttgatg gagtcaaatc ccaatgctgc cacttactga acggccttaa atgacttagt  39180
ctctctcagc tgtctttctg catatgtaag gtggaataat gatggctttc aaggaggaat  39240
aaacctatga aaagtgttga ggatagtgtt tgatatgaaa taaggatttc aacaagtagt  39300
agctgctatt gaagatttaa gagttattta ttacaactat ttaataaaat tttaaaaact  39360
aatacactta aattattaaa gagctttgaa atgggccagg cgcagtagct cctgcctgta  39420
atcccaacac tttgggaggc caaggtgggc ggatcacctg aggtcaggag tttaagacca  39480
gcctggccaa catggtgaaa ccctgtctct actaaaaacg caaaaattag ccaggtgtgg  39540
tggcatgcac ctgtagtccc aactactcag gaggttgagg gaggagaatt gcttgaacct  39600
aggaggtgga ggttgcagta acccgagatg tcactgcact ccagcctggc aacagagcaa  39660
gactccataa agacaacaaa agctttgaaa ttgtgtaaat gagttgtacc tatcttcatt  39720
taagaaattc atctttgttc atttattttt acttgacatg agagcttcca gcaattttta  39780
attaagccct cacagatttt atgtcactgg ctatgtgata aacaaattat ttgctaaaat  39840
aatattcttg cttctttttt aaggaattgt ctccctagaa acggtttgta ccaaacaata  39900
cactgacttt acacaaaatc agatctgatt ggcaacagtt gcagatgttt tcaaaagatt  39960
ttcatttgag aaggggccca tttgggttat ttagattcta agaactgaaa ctgctttgtt  40020
ctgtttttct ggcttctggg agaggaggag acatgaattc agttagcacc ttggtatttt  40080
ctttatcctt catttcaata cagaagatgc ttcatatgca cagtggtgtc aggtcacatc  40140
aaaagaaaga gaaacagttt cttggttttt aattttcaac cggaaaggaa aggcacccat  40200
tttgttccgc tctaattagc cagtgcatga cttagagagc aggcagatgc tttgaaggcg  40260
tggtaacaca ggtcttcatt aatctccacg caggacttgc acttctacta tgcctaggct  40320
gaagaaaatg gctcaggaag atgaacaatc tcacagagcc ctaactaact gaagccaggt  40380
gttataaagc acaagtcaag agggtgagaa actaacgttc ttgaaatctc ccacttcttt  40440
ctacgtcaga agagccaagc tgattatttt agttggaatt tagaaatttt taaaaattat  40500
tctaaagtca tgaacaagcc taattataaa gatagttgct gtgaaggtgc tgaaataact  40560
cgattttacc aaccccctct tctggaggaa gccataatgg aatcctgtac aatgttcact  40620
ctaccaacga actcttgttt ttctaatgag gaaacagagg cccacagtat taaactatct  40680
taaccaatac aaaatgacta gtgctctggt ccttttatta agcactaaaa ttttgatcca  40740
ataataaatc tgtccattag aaggagtttc cctaatgtac tggttctaac ttgttccctt  40800
caaggggcca gtgtcccgta cacatagcta aatgggactt ctcttcaact accattaccc  40860
agagggcaga acctaaaatg ctgtgaatga cattctgctg ttcacatctc agcagcagtg  40920
ttgcatttga gcttctgcag ggccacccag gacctatatc tgctcagatg tttaactcat  40980
ctaattcagt gaacacttca ttctagttaa ctgaacatct actttgtaca aggcactaca  41040
```

-continued

```
gcggttcaga gatgaataaa atcatgagat tccactgtct cctataaacc atcactttgg  41100
gaaattttag aaatgtgggt aagctccagg gcttcctgca gcgtagaagt cacaaactca  41160
aatgcctgca gaggcccagc tgacaacata agtaaatgat tctggctggg cggaaaacaa  41220
ttacgggtgg gtgggtttcc agctggggag tgcacgcctg tgttaaagga cagctgctac  41280
tcatttccag ccaactgtgt tcccatgtag aactgcggcc cagtgtagcc agtaccgaag  41340
atttctcaga aaaagccgga gatctcaatg ttagtgtaaa atctctcaaa tttccaagag  41400
gattatatgg ggcaaaggtt ctcagatcag tttgcagtct cttacttagc ccatgtgcag  41460
agcagtcgta gagggtagca tgcagtgtcc tacataataa ttctttttta ttttatttta  41520
tgccttcctc cttcctgtct ctctttaacc tttcttcttc cctcaggctg gcttcttccc  41580
tcagcctcgt ccgaccccag cctgggttca atgaacattc ggtaaaggaa cacggaatgt  41640
caagcgcatt agagacaacc ttgagacaca ttcctcttgc ggtaagcact tcactgtaga  41700
tttttaattt taaacaagac aatgtttacg acttgcttct ttcagggaag agcgatatca  41760
attttagtga acacttcaag gctgagatac gctaggagag tcgtgtggtg ttgcacagca  41820
aagaattcca ctttgaagcg agtgggaaaa aaagcatcaa atgccacatg taactcaccg  41880
cctgaagggt tacattggta tgaaacctgg gtttaaaaag ggaccgaata gactagccat  41940
taaaagacct gcgtacaacc tctctctctc tctttgagag ataatgtatc tggacaataa  42000
acatgaacag agtggagtct atcctgttta aaacattgcc tactgtacag gcaccaggag  42060
ctgaagggtc agaatattag cagtgggagc ttgattagag ttgatgagag atgggtagta  42120
ggaggaaaga gtgagataga ggaagaggac atgggggtta cccataagtg gagagtagaa  42180
aagtagaatc agctggccat caaagggcgt gggactgagg aacagtatgg catgtattaa  42240
atatactaag cgctgacatt ggaggagaac taggaagtta aatgaaatca ataggggatg  42300
atggagaata gttaggtgtg cagggattag ggttatgata gaaatacatg tgaatacatg  42360
cagtattgtc ctggaaaatg gttaacagtt ggttctcctg gggggtgagg ggaagccctg  42420
atttgtaata tttgcctatt tctgtggtgc aaatactccc accatgacca gtttcaagct  42480
atgaatgttg aagtcacaga aagcaggttg ggaggagatg cgcacatttg ttccccggca  42540
aggtggaagg taaggaaggt gaaatcaaca aggtcaaaga aaactcaaga tttcgaggtg  42600
cctcaggtct gaggggcaat gaagtctagg aatggctgtg ctgaggtagc tgaaatagaa  42660
gtgactgcag aggtcatgaa gctgaagagg tgaaaacaga aattagaaag gcaaaccccc  42720
accgcccaac ccccacccct gcagccagtt tctgagggtg acaatagagg aaagggtgga  42780
gatggagttc aggtccagaa gccatagaag cgagtgtgac attgtgctca aggtcagcac  42840
atgtcagtgt ggggtgtcac atgctgttgt gaaccatcat ttatcaccaa ttatggaaga  42900
cctcctatgg gcatcttgcc atatgcatta taaagatgtg taagaagaca tttccctcca  42960
cttggtgagg agaattaggg ctgtacacag atactgtaga gtgccatgtg cctggtacag  43020
ataaggtgtg ttagaggtta aaagatgagg ctcttaatat taatgataga tcccacttac  43080
ctgagtctga cttacaatgt gcctagcatt aagtgtttta cctgcattcc ctttgacgtt  43140
cagaacaacc cattttacag atagggaaat tgggtcagaa agtttcagta acttatccaa  43200
ggtcaacaca attggcaagt gccagagctg agccaggaac tgaggtcctt ctaacaccaa  43260
acagcttgtc tccccaatca ctgtgctatt ttcctccccc agaagataat actctgatgg  43320
aaatgaagga tagtgtaata ggagattcgg tgttcctttt tttaaaaaaa attcagcttg  43380
```

-continued

```
catattccta aagagtcaat tcatgtttaa aaaaaatttc ccttgtgctt gcatgtgaca  43440
tgtattttta ggatctgctg ttagcaagtg tatttttgtg tgattgagtg ggagagtggg  43500
aaaagttttg cagagctgtt gaagccagaa tgcagggggg ctgcgcagca gagactgtaa  43560
aatctctgcc atctcaggtc ttggaacaag cacaaagaga tgtgttctcg atttattatt  43620
ctatgtacat ccccagatga atgactagtt aaaggtattg ttaaagcatt ttaaatgacc  43680
cacttccagc agcgaacaaa atcacttgct gtgccaagcc aactggcatt tctgagatga  43740
taaaaccaca aagtgaggaa aacgttaaaa ctgctaaagc aaaaatgata cacaataatg  43800
gagaaggaga aaaattgagc tttattgtct gcctaggcag atggctgacc actaggtggg  43860
cctcggcgtc acgtccaggg taattggttg ctggggtgtt tctggcgagg aagattcacg  43920
cttcagctcg gtccacaaga tcctggctca ttctttccta gattccattt tctgcctcct  43980
ctccatgact gggtctgatg gttgatccaa acgggcaatt gaaatcagaa ggttaccttt  44040
accttaaaat gcttttctgg aaataaaagg acatgaaaag taactaagga ccggatttcc  44100
tagccgtctt tctctcctgc atgcgcaatt tatccccaga tataaaattg cctgctttga  44160
taattatacc ctctaaatga ggggcaagtg gctaattatg cccacatgtg gccgattgca  44220
ctccccatta gccaattatg tgctcaatta tttgtgcaca tgaataattg cactcatgga  44280
aaatagcgcc ctcctttcaa atcctcgtgc ttggagtggc tgatggagta attgtcacac  44340
tggaaatgca cttggtgggg agggaaagag tatcagatac caggaaacgc ataagtgacc  44400
agagctcgca gatgttcact gccacaaatg gccttaggag ccagagagag cgggaaggac  44460
cacaggatgg aacgggccag cctgtgagtt aggaagcctg cttctgaagt tgcctgggca  44520
gctcatgtgc ggtgaccttg ggcaagtcat taactttcct tcaggtctaa ctggttctgc  44580
atacacaatg aggatggtaa taacgcccaa ttcccatcac tatcgtggga tggatcagac  44640
tatttaaaag gatttacaat ctgcttgggt aaaagcttta cataaatatg aggcattatc  44700
atgtcgcttg gtacatctcc aattatgaag gaagggtaat gaccctccac agcaatgcag  44760
gactcctggt ttggagggag ggaaagtttg agaaggacag gaagcttgtt gccccagcac  44820
tgatgtttct actgaggtac cagaaaatgt catgtggtca tacagaattc atttattcat  44880
tcaacaaaca tctgtcaatt gttacactgt cctgagaatt tggaaaaatg atgaaagact  44940
cagtcctgcc ttaggaggtc actggcacat tggcccgggc ccctgttttg ggccttttac  45000
tctgacctgt gctgatttgc aaatagtggg aaattttatc tcaagtctat gaaatctggc  45060
atgcattttc acggtttgat tgccaggtac attcgatggc aatgagtctt ataatgtttg  45120
gttaccttca tttacctaag aactgtggtt gttgctgtgg ttgttgtttt tgttgttttt  45180
gagacggagt cttgctctgt catccaggct ggagtgcagt ggcatgatct ccggtcactg  45240
caaactccac ctcccaggtt caagcgattc tcatgcctca gccccctcag tagctggatt  45300
acaggcgcgc accaccatgc ccggctaatt tttgtatttt ttgttcggga cacagatttc  45360
acatgttggc caggctggtc tcgaactcct gatctctggt gatccgcctg cctcggcctc  45420
ccaaagtgct gtgattacag gcgtgagcca ctgtgcccag ccagaactgt ggttttaatg  45480
acaatgctaa aaagtggtat atgtcacagt gtcgggtggg gctaagaggc acattgctgc  45540
agtgatccat cattcatttc ccaccattct cgcctggatt agcgcagcag ctcccagaga  45600
ggcacctcac tttgaccttc ttcctcaaag acattctctg tgacctgcct ggcccttatt  45660
acctctctag ctttgccact tccctatgtc tccatctccc ctctcacacg tagtagaaag  45720
agactctacc tcatggagta aggagaggct tcacagaggc aggattgcta ttagtcttca  45780
```

-continued aagatgaggt atttgctaaa tgaatgagac aaagggattg gggccacatt acagggaaat 45840
tgaggtatgt aatagcctgg tgcaggttaa gagtgtggac tctgaaacca gactcagcct 45900
ggaattgaat cctggctgtg tgatgttggg ccagtgactt aacctctctg tgcttttatt 45960
cactcttcta taaaatgggg attataataa acctacctta taaggttatt ataacagtca 46020
gtaaatataa aaatagaagt ttttggatga tgactatcac atcagtaaac acttgtttgc 46080
cattattttt attacttgac taaaaatata ccaaaaagac catccaagaa aaccctttaa 46140
gctgctagtg cagaaagatt ccccttgtgt ttgtgtgctg gggggtcagt ggtgcctgtg 46200
gcccactgga gaggagacag ctatggctgg agtgattctc aaacttcaga atgtctaaaa 46260
tcatcacatg gacaacttat taaggaaagc aaatgcctgg gctccatcct cagagagtct 46320
cattcactgg gtcaggatag agcccaggaa tctttacctt aaagaaccat cccacctccc 46380
acctcatatg atccttatgc aggtgatctg gggcccacac tttgagaaat agactcaggt 46440
caaagtggct ctaactgcat ctcatttctt acctggcata tctaatagta gagaagaaga 46500
caatgctaag atttttgttg gagatctttt gctgggattg ctgcttcatt cattcactca 46560
tttatttatt tatttattta ttttgaaaca gagtctcact ttgtcaccca ggctggaggg 46620
cagtggcaca atctgagctc actgcagcct caggctcctg ggttcaatcg attctcttgc 46680
ctcagcctcc cgagtagctg ggattacagt catgcaccac cacgcccaac taattcttgt 46740
atttttagta gtgacagcgt ttcaccatgt tagctagact ggtctcgaac tcctgacatc 46800
aggtaatctg cctgcctcgg cctctcaaaa ttagtagctg caattacacg tgtgagctgc 46860
cgtgcctggc ctgctgtttc ttttagttgg gcctcttctg taatagagtg tgagaattct 46920
gacttgctgc aacagtctgc tttgaagcag ggctgtgttt acactggtca gatgtggaat 46980
tgtggggcac acttagcagc ttccttctct aatttttctg tattttcagg agaacaattt 47040
taaaaaattt aataaaaatg ccttaaaaat taacattatt ataagatgaa tcccattttt 47100
ctaatcttgt aaattaaaaa caatcataag catatgagca cctgcactta gggaatcaag 47160
gttggcaaag ctaaacactt ccagctctag gtgattcgcg gcaatacaaa tggagctgga 47220
ctttggccac agtgcaaaaa tattgatctg ttgttagatg ctctgaagtt tccagaaaga 47280
attggttctg cctgctgtgc ttcagtgctt aagggaagtg gttcctcaaa atgttagttt 47340
ttaagcccag ctttcttaaa taggaagatt ctaatagtag caaaaatata aactgcttct 47400
aggtttaaaa aggacccagc acacaatggt tatcacacac ctttctcctc aggtgatgag 47460
tggatgagtg gcctggtgta tttcataaca tctcccaggt ccaaatgcta aagcaattgc 47520
tgaaaagata ccatgtgtac cggaaccttg cagaggtatt ttgttggcat aaaaagaaat 47580
attgatcatc tatagtaaaa atggttctac tttaatacta ctgagaaaag attttctttt 47640
cccagatcta catcctgaat cttcatgaag acaagatccc ctaaacttcc actaacacca 47700
taatgtgtgc tgtcctttgt aatgtagtcc acagatctca taaactgtca gaaatagcag 47760
agattgtaag gtcatccact tcccctgtaa ggcctgcgtc cctcacttac atccctaata 47820
acgtcctcta acctctgctg gagggcagat ttagctgcca gctgggaaga gctctgccct 47880
agtcaacatt tttatctgtg gctttcagat gagaacactg gatgcttatc tgaaaaaagc 47940
tcctcaggct ggagggaggg attggctcta acaagatgca atgtgataag aataaaagcg 48000
aagccaaact ctaggcccaa aggctctagc aacacacttt tgagaacctt ggagacgagt 48060
tttggctgat gcgagcttct ccgcctgcta aagtagccca ttccatttgg acggctctag 48120

-continued

```
aggctggcat gttcttctcc acgttgtgtt aatgtactcc agtttcttcc tgccatgaac  48180
tggcatgccc tggctcctcc taccttcccc actttaagtc ttccctccct ccttctgacc  48240
ttcccattcc agccacactg gccttttgtc tggtcctaac aaaccatgcc tttcctgcct  48300
ccaagcccta cacctgctat ccatccctct gtctgagaga cactcccacc ccttcacaaa  48360
gcctgtttct catccttcca gttcagatgt cttctcagct tgcctcaact gacctctttc  48420
agctattctc actctttgta ctctgttcat ttccttcctg gcagtcacca taatttatct  48480
ttatttgaat caatttctta gttgtattat ttagttattt gcacactctg tctctctgtg  48540
cctttcttat tcactgcagg ctttcttatg taagtaattt atttacttaa atttttaaaa  48600
ataatttcaa cttttggccg ggcacagtgg ctcacgcctg taatcccagc actttgggag  48660
gccgaggtgg gtagatcagc tgaggtcagg agttcgagac cagcctggcc aacatggtga  48720
aatcccatct ctatttaaaa tacaaaaact agccgggcgt ggtggtatgc acctgtaatc  48780
ccagctactc gggaggttga gggaggagaa tcacttgaac cggggaggtg gaggttgcag  48840
tgagctgaga tcacgccatt gcactccagc ctggggcacg agagtgagac ttcatctcaa  48900
aaaaacaaaa aacaaaaaac ccctgctttt cagaggggct gaactaattt acattctcac  48960
caatagtgta taagcattcc cctttctcta cagcctcact agcatttact tttttaaaaa  49020
actttttaat aatagccatt ctgactggta tgagatggta tctccttgtg gttttcactt  49080
gcaattctct gatgattagt gatattgagc attgttttat gtttgttggc tgttcgtatg  49140
tcttcttttg agaagtgtct tttcatatat tctgcccatt ttttgaatgg agttgttttg  49200
tgcttgttga attaagttcc ttatagattc tagatattag acttttgttg gatgcatagt  49260
ttgtgaatat tttctcccat cctatagttc tgtttactct gttgatagtt cctgttttgt  49320
tatgttttgt ttttttgctg tacagaagct gtttaatcta attggtccca cttgtcaatt  49380
tttgtttttg ttgcaatggc ttttgaattt taataataaa ttctttccta aggctgatgc  49440
ccagaacagc attttctagg ttttcttcta ggattcttat agttcaaagt cttatattta  49500
agcttttaat ccacctcaag ttaattttta tatatagtga aatgcagggg tcctgtttca  49560
ttcttttgca tgtggccagc cagcaatccc agaaccattt attgaataag gaatcttttc  49620
ctcattgctt attttgtcaa ctttgtcaaa gatcggatga ctgtaggagt gtggcttttt  49680
ctgggttatc tactctgtta cattggtcta tgtgtctgtt tttgtatcag tatcatgctg  49740
tttttgttac tatggtctca taacatagtt taaagttgga taatgttatg cctctgcttt  49800
gctgtttttg cttaagattg ctttggctat tgaggctctt ttttcacttc atatgaattt  49860
tagaatagtt ttttctaatt ctttgaaaaa tgaccttggc agtttgatag gaatagcatt  49920
gaatctatag attgctttgg gcagtatgct attttaatga tattgattct tcctatccat  49980
gagcatggaa tatttttcca tttgtttgtg tcatctacta tttcctttag caatgttttt  50040
tagttttcct tgtagagatc ctcctaggta tttcattttt tatgtgacta ttttaaatgg  50100
gattgcattc ttcatgtggc tctcagcttg aatgttattg gtgtatagaa atgctacaga  50160
gttttgtaca ctgattctgt atcctgaaac cttactgaag tcatttatca gttctaggag  50220
cctttggcaa agtctgtagt gttttctagg tatagaatca tatcattagc aaagaaagat  50280
agtttgactt cttcttttcc tatttgaatg ccttttattt ctttcccttg tctgattgct  50340
cttccagtac tacgttgaat aggagtgctg agagtgagca tccttgtctt gttccacctc  50400
tcaggggaaa tggttccagc ttttgcccat tcaatatgat gttggccatg ggtttgtcac  50460
agatggctct tattattttg aggtgtattc ctttgatgcc tagtttgtca aaggccttta  50520
```

-continued tcatgaaggg atgttggatt ttattgaaag ctttttctgg gtcttatttg gtgaattgca 50580
tttattgaat tgtgcatgtt gagccaaact tccatcccag ggattaaacc tacttaatca 50640
tggtgttaac tttttgatgt gctgctggat ttggtttgct aatttttttt ttttttttaa 50700
gatggagtct cgctctgtcg cgcaggctgg agtgcagtgg tgtgatcttg gctcactgca 50760
agctccacct cccgagttca tgccattctc ctgcctcagc ctcccgagta gctgggacta 50820
caggcacccg ctaccatacc cagctaattt ttgtattttt tagtagagac aggatttcac 50880
catgttagcc aggatggtct tgatctcctg acctcgtgat ctgcctgcct cagcctccca 50940
aagtggctag tatttttta attactattt tttctcaccc ttgctgccat cttatgattt 51000
tctagtattt tgttgaagat ttttgcatct attttcatca gggatattgg cctgtaattt 51060
tctttttca tttcatcttt accacatttt tgtatcaggt tcatactggc ttcatagaat 51120
gagttcagga atggtccctc ctcctcgaat ttctctgta gaattagtac cagctctttg 51180
tgtgtctggg agaagttgta tgccaataat ttaaatgcag ttaatattta ctggacaatt 51240
tcctccagat aattgtatat gatttttggt ccaccctgag ttgatacatg tattttaatt 51300
gtatcatggt atgaaaagag caagagttat ttggtcacct agtcttgcct atagatgttg 51360
cctaatgatt caaagtagat attttgggag ccttaacagg tgccgtggac taggcagttt 51420
tgtttttttt tttttttgag ggacagagtc tcgttatgct gcgcagggct ggagtgcagg 51480
ggcatgatgt aggatcaatg caacatccgc ctcgtgggtt cagagcaatt atactgcatc 51540
agcctcccca gtagctggga ctacaggctc acgccaccac gcctggctaa tttttgtatt 51600
tttagtagag atggggtttc accatattgg ccaggctggt gttgaactcg tggcctcatg 51660
atccacccgc ctcggctccc aatgtgctgg gcttacaggc gtgagccacc gcacccggag 51720
attaggcaat tttatattcc caaatatcca actcttctga cccgctttct cagcctgggt 51780
gtatcaggca caaggcctgt tcagattatg tggtctctga agatatggct ctccagggtt 51840
gacaatgtgg ataaggattc acctggttta ggatttacac attcgccttg aatgtctgtt 51900
gcaccaagta gacagtccat cccaacttgg ccatttggtc agagctgtaa ggagacaagg 51960
aggtgggcag ccgctgctgt gaactgcttg gacaaagact gccaaatagc tatcagacag 52020
tgttaacaac agctgattta ggtttgaagg gggcagtctc ttgggccact tactatgctg 52080
catcatcctc tttggaaaat gctcttcagg taactgccta acagactgag aaaataaaat 52140
gctcacagag aaaaaagacc cggaaagtct gacttctcag agctcagtgt ttaggtgcag 52200
aactggattg tgaaaggatt tttaaatttt ttatattcat tgcagggaac attcatttat 52260
tccatccttc tccactccca cctgtctgtc gttgtctttg tctctgtctc cccacctctc 52320
tctctagaca cacacacgca cacacacaca cacacacaca cacacacaca cacacacaca 52380
cacacacaca cacacacaca cacacacccc tattcattgc caacagtaat agagttgctt 52440
ctttacttct tggagagaaa agcctcaatc tgaggaagct gtgctgacta gccttgctct 52500
taatcatgga gacaatgctt tatgccttta tctttgcaca gctgaaagcc atggcagaag 52560
cagtcctcta aacgaaataa aatagaaagg ttcctgctaa gccctggcaa atgcagcctt 52620
ctatccctcc cccaacactc acagcttctg agcaagatgt tgctgccttc caggagctgg 52680
gtgatgggca ataatgagca gagccacgtg aaggaaagat gggtgaagaa atgtgtgtgg 52740
agtcatgctg gctgcactga ccatgaaaca aaggatctac ccctctagta actgccctac 52800
tcctttggta actgttctga aattataact tgccagaagt tcagaaggac ctagtgcagg 52860

-continued

```
tattagagga aattcgtaag attgagccat ttattcctgc acagatacat aataatggac  52920
acgggccatg gtggccagca ttcttgctct tgacaatggt gaagggaagg gttgtaggtc  52980
atggctatgc tctcagaatt ataatggaaa gaaacagctc ctgagtgttt actatgagcc  53040
aagggctgtg ctaaacactt taccatatga tgacatcttt ttctcacagg tatcaaaaaa  53100
caataggaca taccggatag ctacaatctt tgggcccctg caaacacaat aatgtgtatt  53160
ctcttcttca aatcctacat attgctacaa actgtatccc tgaggcatat tcattgtaaa  53220
ataaaaacat ataaagtact acttttgttt tttgagatgg agtctcgctc tgtcacccag  53280
actggagtgc aatagcatga tcgtggctca ctgcaacccc ctgctcctgg gctcaagtga  53340
ttctcctgac tcagcctctc aagtagctgg gattacaggc gcacgccccc atgcctggct  53400
aatttttgta cttttaatag agaccaggtt tcaccatgtt ggccaggctg gtctcaaact  53460
cctgacctca agtgatccac ctgcctcggc cttccaaagt gctggcatta cagctgtgag  53520
ccactgcacc cggcccatat aaagtactac taatgtaaca gggtgctagt ccagacagtg  53580
accacacgtg gtgttcattg aaggctggac taacaactcc agcctctccg ccatcacaga  53640
gtgatgactg ccttccctga agcaaagctt ctggttcaag gaaaggccag taagtgactg  53700
ctctttgttg tatacatgtt agatgatcag gcctcaagaa aagtataaag agatctttgt  53760
gctctctggg actcaaaaag ctgcactctt tgggggaagg atagccaggt aaaagtggcc  53820
caggtaaaga gggcctggta cacctggttc tgcaagatgg tagacacaaa aatgagagct  53880
acatttggag cttatgtgcc cctaactctg tacataacct gcaagatcta attactaaca  53940
actggaatct tggaaacacc tgtagtacat ccttggctaa ggttagcccc aacagagagg  54000
gctctcctct tacagagaac cattacattt gtgccttcat cctagagtag aaaaggcatg  54060
atcagactac taaaaagaca tcaggaaagg gcctgtgaca tctgagggaa gtggttgccc  54120
tctctgggat gttggttcgg gaagaggggc atggaggagt gcctgcttta gatggtcatt  54180
caggaaccca ggctgatagt gagaggtgaa gccagttggg cttctgggct aggggggact  54240
tggagaactt ttgtgtctag ctaaaggatt gtaaatgcac caatcagcac tctgtaaaat  54300
ggaccaatca gcaggatgtg ggcagggcca aataagggaa taaaagctgg ccaccagagc  54360
cagcagtggc aaactgctca ggtccccttc cacgctgtgg aagctttgtt cttttgctct  54420
tcacaataaa tcttgctgct gctcactctt tgggtctgca ctatctttat gagctgtaac  54480
actcaccgtg agggtctgtg gcttcattcc tgaagtcagt gagaccacaa acccactggg  54540
aggaacaaac aactctggac acgccaactt taagagctgt aacattcact gcgaaggtct  54600
gcggcttcac ctctgaagtc agcgagacta tgaacccact ggaaggaaga aactccagac  54660
acatctgaac atctgaagga agaaactcca gacacaccat ctttaagagc tgtaacactc  54720
actgcaaggg tctgcggctt cattcttgaa gtcagcaaga ccaagaaccc actggaagga  54780
aacaattccg gacacatttt ggtgacccag atgggactat caccaagtgg tgagtaccat  54840
caaccccttt cacttgttat tctgtcctat ttttccttag aattcggggg ctaaatattg  54900
ggcacctgtc agccagttaa aagcgactag catggctgcc agacttaaga aactaaagac  54960
acgggtgtca gactttctgg gaaagggctc tctaataacc cccaactctt tggagttggg  55020
agcgttggtt tgcctggaac cagcttccac atttcctgta cttctgggct gagacgaggg  55080
tcaacataga ggaaagccat tcagctctgg ggtcccgaca gcaagttggt tgaccctgtg  55140
gccatgatca caactctcga agtcatgttg cccaagcgag actcacccat ctatcctatc  55200
tatcctgact cttgcttcct gggtcctaat gcctggaaga caaaacttcc tcttgtctct  55260
```

-continued gttctccaag gctagtccca cttctaaaaa ccactccctg tctctggtgc ttttctagtt 55320
tctcctataa gaatgatttc tagtataaac tccaggactc tattctcttc tttaggcacc 55380
cgggctcacc aatcagaaag ccataatttt tgcccaaagc cccatcttag gggggactat 55440
ctggaatttt aggatccctc ctcagacaag caggcctaac aaaagctatt cctgaagcta 55500
ggatatgggg agcctcagaa atgatatcct tcctattcaa gtgaggacaa aaggcatcac 55560
tcttccaatt ctggagatcc cttccctccc tcagggtatg gccctccact tcacttttgg 55620
ggcataacgt ctttatagga cacgggtaaa gtcccaatac taacaggaga atgtttagga 55680
ctctaacagg ttttcaagaa tgtgtcggta agggccacta aatccgattt ttctcggtcc 55740
tctttgtggt ctaggaggac aggtaagggt gcaggttttc aataatgtgt tggtaagggc 55800
cactaaatct gacattcctt ggtcctcctt gtggtctagg aggaaaacta gtgtttctgc 55860
tgctgcatca gtgagcgcaa ctattccaat caacagggtc cagggaccat tgtgggttct 55920
tgggcaagag gtgtttctgc tgctgcattg gtgggctcaa ctattccaat cagcagggtc 55980
cagtgacctt tgcgggttct tgggtcgggg ggtgggggga acaaacagac caaaactggg 56040
ggcagttttg tctttcagat gggaaacact caggcaccaa caggctcacc cttgaaatgt 56100
atcctaagcc attgggacta atttgacccg caaaccctga aaaagagtgg ctcattttat 56160
tctgcactat ggcctggtcc caatattctc tctctgatgg ggaaaaatgg ccacctgaag 56220
gaagtataaa ttacaatact atcctgcagc ttgacctttt ctgtaagaag gaaagcaaat 56280
ggagtgaaat accttatgtc caaactttct tttcattaaa ggaaaatcca caactatgca 56340
aaacttacaa ttcacatccc acaagaagaa ctctcactta cccccatatc ctagcttccc 56400
tatagctccc cttcctatta atgataagcc tcctctatct ccccacccag aaggaaacaa 56460
gcaaagaaat ctccaaagga ccacaaaaac ccctgggcta tcggttatgt cccccttcaag 56520
ctgtagcggg ggaggggaat ttggcccaac ccaggtacat gtccccttct ccctctctga 56580
tttaaagcag atcaaggcag accaggggaa gctttcagat gatcctgata ggtatacaga 56640
tgtcctacag ggtctagggc aaaccttcaa tctcacttgg agagatgtca tgctattgtt 56700
agatcaaacc ctggccttta atttaaagaa tgtggcttta gccacagccc gagagtttgg 56760
agatacctgg tatcttagtc aagtaaatga tagaatgaca gctggggaaa gggacaaagt 56820
ctctcccggt cagcaagcca tccctagtgt ggatccccac tgggacctag actcagatca 56880
ttgggactgg agtcgcaaac atctgttgac ctgtgttcta gaaagactaa ggagaattag 56940
gaaagagcct atgaattatt caatgatgtc caccataact caggaaaagg aagaaagtct 57000
tgccttcctt gagtggctac aggagcctta agaaaataca ctcccctgtc acccaactca 57060
ctcaagggtt aattgattct aaaagatatg tttattactc aatcagctgc agatatcagg 57120
agaaagctcc caaaagcaag cccttggccc tgaacaaaat ttggaggcat tattaaacct 57180
ggcaaccttg gtgttctata ataggggcca agaggagcag gccaaaatgg aaaagcgaga 57240
taagagaaag gccacagcct tagtcatggc cctcagacaa acaaaccttg gtggttcaga 57300
gaggacagaa aatggagcag gccaatcacc cagtagggct tgttgtcagt gtggtttgca 57360
aggacagttt aaaaaagatt gtcctatgag aaacaagctg ccccctcacc catgtccact 57420
atcgctgaag caatcactgg aagccacact gccccaaagg acaaagatta tctgggccag 57480
aagcccccaa gcagatgatc caaccacagg actgaggtgc tcagggttag cgccagctca 57540
tgtcatcacc tcactgagcc ctgggtacat ttaaccattg agggccagga aattgacttc 57600

-continued

```
tactggacac tggtgcggct ttctcagtgt taacctcctg tcctggacag ctgtcctcaa  57660
ggtctgttac catccgagga atcctgggac agcctatatc caggtatttc tcccacctcc  57720
tcagttgtaa ctgggagact ttgctacaga tagtaagtat gcttacctaa tcctacatgc  57780
ccatgctgcg atatggaaag aaagggaatt cctaacttct gggtgaaccc ccattaaata  57840
tcacaaggaa actatggagt tattgcacac agtgcaaaaa cccaaggagg tggcggtctt  57900
acattgccga agccatcaaa aggggaagga gaggggagaa ctgcagcata agtggctggc  57960
agaggcaggg aaagacaagc agaaaggaaa gagagaaaga gcagaaagtg agagagaaag  58020
agagatagga agtgatagca aagagggagt cagaaagaaa agagagagga gagagagagg  58080
gggaaagaca gagagagaca gaggaagaga cagagagaca gaaagagaga agcaaagaga  58140
ggaagagaca aagaaggagt caaagagagg gaaagagaag tagtaaagaa aaaacagtgt  58200
accctattcc tttaaaagcc aggttaaatt taaaacctat aattgataat tgaaggcctt  58260
ttctgttaac cctataatac tcccaatacc accttgttgt tcagtgttaa acaagggtta  58320
ttagcccaaa agccactgag gccactgaca acccgtagcc ttcttatcca aaatccttaa  58380
cacagcaggt ttcctaacag ggatctaatc ttaggtcgac cagactggag aactgccttc  58440
aggacaggat gatagatggt tcctcccagg tgattaagga aaaagacaca atgggtattc  58500
agtaagtgat aaggaaactc ttatagaagc agagttagga aaattgcgaa ataagtggtc  58560
tgctcaaacg ttgaagctgt ttgctgtttg cactcagcta aaccttaaag tacttacaga  58620
atcaggaagg agccatctat accaattcta agttaatatg gactgaacga ggttttatta  58680
atagcaaaga aaattaaaat ctcaaactta cgaggttttc aagtaaagta aagtttggta  58740
aaagttaaca gcgtaacatg tattatccta gtaccacaca ttctctcaaa ggatttgctc  58800
agacagtttg caaaaaagaa cgaaatctgt ccttactcta caatcccaaa tagacttttg  58860
gcagcagtga ctctccaaaa ccgctgaggc ctagactctc atgttgagaa aggaagattc  58920
tgcacttctt aggggtagag tgttgttttt atactaacca gtcagggata gtatgagata  58980
ccacccagtg tttacaggaa aaggcttctg aaatcagaca atgcctttca aactcttata  59040
ccaacctctg gagttgggcg acatggcttc tccccttttct aggtcctgtg acagccatct  59100
tgctaatagt cgcatttggg ccctgtattt ttaacctctt ggtcaaattt gtttcctcta  59160
ggatcgaggc catcaagcta cagatgatct tacaaatgta accccaaatg agctcaacta  59220
acaacttctg ctgaggaccc ctggaccgac ccgctggccc tttcaatggc ctaaagagct  59280
cccctctgga ggacactacc actgcagggc cccttcttca cccctatcca gcaggaagta  59340
gctacagcgg tcatcgccaa atcccaacag cagctggggt gtcctgtttg gagggggggat  59400
tgagaggtga agccagctgg gcttctgggt caggtgggga cttggagaac ttttgtgtct  59460
agctaaagga ttgtaaatgc accaatcagc actctgtgtc tagctaaagg attgtaaatg  59520
caccaatcag cactctgtaa aatggaccaa tcagcaggat gtgggcgggg tcaaataagg  59580
gagtaaaaac tggccacccg agccagcagt ggcaacccac tcgggtcccc ttccacactg  59640
tggaagcttt gttcttttgc tcttcacaat aaatcttgct gctgctcatt ctttgtgtcc  59700
acactacctt tatgagctgt aacactcact gcgagggtct gtggcttcat tcctgaagtc  59760
aacagaccac gaacccactg gaaggaacaa agaactcccg atgtgctgcc tttaagagct  59820
gtaacactca ctgcgaagct ctgcagcttc actcctgaag tcagtgagac cacaaaccca  59880
ccagaaggaa gaaactctgg acacacctga atatctgaag gaacaaactc cagacacacc  59940
atctttcaga gctgtaacac tcaccgcaag ggtctgtggc ttcattcttg aagtcagcaa  60000
```

-continued

```
gaccaagaac ccaccggaag gaacaaattc cagacacagt aggaaatctg tatttttgat  60060
ctgtggcttc cagggttact ccagtcattg aagtctccat tgcagcctta aggaaacaga  60120
gaatggtttg gaggagcaca tgtgggaatt gttatggacc aggcttgaga tgcacatagg  60180
gcatttctga tcaaacctag ctggaagcag ggccaggaaa tataatctaa ggaagacagt  60240
ttttgtagac agtagtagtc tttgcatctg agacatgtag attatcaagc aattaattag  60300
aaaaaatata gccaggtgcg atggctcatg cctgtaatcc cagcactttg ggaggccaag  60360
gggtgtggat cacgaggtca ggcgttcgag accagcctgg ccaacatggt gaaaccccgt  60420
ctctactaaa aatacaaaaa ttagcctggt gtggtggcac gcatctgtaa tcccagtact  60480
caggaggctg aggcagggga atctcttgaa cttgggaggc agaggttgca gtgagccaag  60540
atcacaccac agcactccat cctgggtgac agagcgagac tctgtctcaa aaaaaaaaaa  60600
aaaaaaagga aaggaaaata taatcaagaa tattgacagg taacatttat tcaacactta  60660
ctatgcacca ggcaatacac taagtgtttt acatggatta actcatttaa tcttaacaat  60720
agccctatga agtcagtgct gttattatct ccactttata gataaggaaa ctgaagtaca  60780
gaaaggtcaa gtagagaaat ggccatgctt gcattctcag tttttgaagc aactgttaca  60840
ggaatctggt gtgagaaatg ctctaacaag atgtgagtca ggggttggga ggtactgagt  60900
ctgagttggg cagttgggga tggaaggatg gatgaagaac agcttgacag agaagctgac  60960
acttggcaac tctgtgggac cttgaagggt tagagggact tcaccaaaga aactggtggt  61020
cagggatacg ggagggtcac ggcaaggagg gaaaggaaac tgtaccacag cagagagtct  61080
gaagctacta cagtgtagtt cagcgtataa agaataatta ttttaaggta aacttataac  61140
ctcatgcaaa tataaaatga acacgtgtca aagatcttat ttaatttatt aattaatgag  61200
ggaacctgta agatgttaca gccagttcaa aggataattc aaataaatcc atgcacatat  61260
gtaggcaata aggaatgctg aaatgaattt aaaagtagat gtaaactgat ttatccacag  61320
agaaataatc agttgcattt cacataacaa aattcagttg cttttctaca gaaggaattg  61380
tttgcatcat taccaatttt tctacaacta acagaattat aaaataactc aaacacaatg  61440
aaaggcagat ataacccaca atggtatgat agatacaata tccacatcca ggatgttttt  61500
ttctcatttc aaagtctttc acaagttttc ctgataaggg agtgtcaata atactgtatg  61560
gcaggcaata agactggatg gatggttggg gccaggtttt aaggggtaat aaatgccatg  61620
taaaggtatg tgcatactgt gcaacatgtc ggggaatctc aaattattgg tagagtatgt  61680
aagaaacact tgtggagctt gttaataaat tcaaattccc agacccaact cctcaagggt  61740
ctaatacagt aggtttggag taaagcctga aaatctgcaa ttgtgcaaaa aaaaaaaccc  61800
aggtgattct gatacacttt gagaagcact ggtggaacta atagtcactg aacgtttttg  61860
agcaggggag aaacctgagg acgtctatgt tgcagcagtg gaaacttgat tagaagtagg  61920
agaagatgca tggtcttaaa agaatgcaaa atgatggcta atatttgagt gcttatgatg  61980
ggccaggggc tgtgctaggc gcgtggcaca cattcaatac gatggaagcc tgtaccagtc  62040
agtattagtg gggtatcttt aagagtgacc agaattaagg ggggttttca ccaaagcctg  62100
aggactgagc ctcctcatcc taaattcaga cacaatgctg tacctatgca tttgcctcca  62160
ggctgttcct gggcctccag ggactggccc aggctcctga taaataggga ctcccaacaa  62220
cataaagcct ggattttgga acttcctgaa tgttactcag gctttctagt aactgtggag  62280
atctgaataa taacacaatt ctaagttccc ctactcataa agctgctcat catttagatg  62340
```

-continued

```
gggtaaagca cctgaaatac aatgagcatc actattttca ttcatccatg aaatgaacat  62400
tccggggaga tcagtaagtt gatgtatcac ccttgaacag ggcaaaatga atactcacca  62460
ggaatatgtg gtattttaaa aagaaggcaa agggaagaat agtggggatg gggcaaaaac  62520
tttaaataga ttcccccaat catatatggc aattgaagat aattaaatta tcattttaat  62580
tgagtaagta ctcatagagc cctcactatt tgaaaatgaa ctgcctccta attgttattg  62640
tgcaaatgtg atacattaaa cttaagctat tttaataaaa catccatttt cggaagctgt  62700
agtaggttct cccaggtcag atttgataag ccataaagaa caaatgccaa ctcctatttt  62760
tctatggtgc tgggaaataa gagagaaatg tgtaattcaa agcaatcatt taattttatc  62820
caatagcttg attctcctct ctcttctagc cttttagcta agctgttacc aagtaaccac  62880
actagttggc ttgagtctta ccactgtttc cctgacccca cagtggagag actgcatctg  62940
ttaaagagca gttatgtaac catggctatg ctgagctggg attcccaagg cttaggttct  63000
ttctgtgaat gaccttcacc aagacacctg aggtctgtgt ggaaccacag gcttgtcatc  63060
tctaaggcag agttgataat tccatctgtt tcttgagccc acactgagaa aaagattaca  63120
tgactgcagt tatttgaatg cctcatggaa agacgtctta taaatattat aattaatgtt  63180
atcattaagt aatgcttcaa tgcagatctt ccaagtataa atatcagctg agtaagaagt  63240
caatcttccc tgaagcaaaa ttgaaatttg taaatgcgat ttctgggagc ttattttgta  63300
atacatgatt ccagagtgtc cataacacac acaattgtct tttttcccct acatgggcta  63360
tttacaacaa aattggactt ataatgttta tttccaggga tgactagaac tttaataaca  63420
aaccttgggc caggcatagt ggctcatgcc tataatcaca gcacttcggg aggctgaggc  63480
tggttagatt acttgaggcc aggagtttga gaacagcctg gccaacatgg caaaaccctg  63540
tctctactaa aaatacaaaa attagccggg tgtggtggcg catgccagta atcccagtta  63600
ctaggtaggc tgaggtacga caatcgctgg aacctgggag gcggaggttg cagtgagctg  63660
agattgcact actgcactcc agcctgggtg acagagaaag actctgtctc aaaaaaaaaa  63720
aaaaaataat aataataata ataaaccctg atgaaaggtt tctaaaatgt tttcatctaa  63780
tggttttctt gacaattaaa ttttctatat aatgtcagtt cataaaaaaa ctgagaacga  63840
ccacatgtca tatcgactgc ttaaaagaaa atacgtatat ttacaaacat atacacaata  63900
ctgtcttttg tctggttagt ttagaggtta gataaactgc agtatgttgt agtggacaga  63960
tcatagaact aggagtcagg atgtctggat tcctaggaag caatgaatag gttgcacggt  64020
gcagctcaag gttattcaaa gtgtggtgcc cagaccagca tcatgagtat cctcagggag  64080
cttgttagaa ctgcagatcc tttaactcat tgaatcagaa tccctaggtg tggggccctg  64140
aaatctgtat tttagcaggc tctctgggat tgtgatgtgc cttagagttt gacaaccact  64200
gggtagctga tcctgactta gacttatcag gcatgtgatc ttgaacaagt cacataatct  64260
cactgagttc agttttctta tgtttaaaat aggcccaata atatctattt cacatggatt  64320
gctttgagga ttaggcaaga gatctgtaac agacactgta gaacagtgtc tctggtctac  64380
agctgacctt ccataaatgg tagttgcctt gattctctgc tctgccacat aatagctggt  64440
taactatgag caagtaattt agttcttctc agtttagttt cttcccctgt aaaagaagga  64500
aaataactgt tatactccat ttctgaattg ctataaaagt catttaatta tgggcattga  64560
agctctttgt tcactgtata aggactgtac atctaaggga ttaatgagac caggcttatg  64620
attttaagca tggagtaaat agtaacactg actctgttct atgaaccaca tggaaactct  64680
aaagaatatg cacatttgaa acacaggtat catctgggga aggtgatctg ctcacccaaa  64740
```

-continued

```
ccagttcatg aacatcaatc tccagtggcg tgctggagct agctgtacca gctcatgagg  64800
gccaattgtt tcatttttag gaattttgtt tgctggttaa aaatagtcat tatttaaaat  64860
taaattatgt aaacaataat attagataaa ataagttaaa ataaaaacaa aggaactaat  64920
tatccccaaa ctcttcccca cctaattatt ttactatctg tgccttggga ttatttacat  64980
tgattttatc catatggtga caatactatt catatataaa tggtgtgctt ctcttcataa  65040
ctctacatag cctgatgtca ggctagtagc ttgaaattgg ccacagtggg agtgtgagca  65100
tttgtaccat gaggcttggc caaggctaca aatccagact tttgtttttc cctcctggag  65160
agctgtctgt taaaaattta ccaacacacc actggtctta cctttgttaa tttaccacag  65220
tccaggttct gacctagact tagaaacctg gatttgtcag caagctgagg atagagccat  65280
tatttctaag aaggactcac attacccaag tgcaaagcct gatatatacc ttcagaatat  65340
caatttatta atttacagtg aagaaagcca ccccagggca ttccccaggg gaaggcaaaa  65400
agagctagtt gcacattttg aatgtttgat gacattaggg taaggtgaca cagaatatcc  65460
atttccacaa ctgagatacc tgctgcctta aggaagggac aggcaagtcc ttgggcagga  65520
ccttagattg tcactgtcca tcttgctgta ggactctcct ttccaggcat gacgatggcc  65580
aactctgtcc tcctacccta ctgatgggat tatcttttct tgacacatgg caatgcctcc  65640
aatcagaggc tggtagctat ttttaatctt cagggcagta tttttcaaag ggaagttcat  65700
ggaccatatg catctgtatc atttagatgt atattaaaaa tgcttagtct tccccagtta  65760
tactagatca gaatctctgt tggtggggcc cacgaatcgg tattttcaac aaatcactag  65820
gtaatttctg tatatactat agtgtgaaga ccactgcttg aaggtttctt tgcatatctc  65880
cactaaatat aaaaaatatt gacttctaga tttaactccc aaagcacttg catttttaag  65940
tttctggggg cattatattg tggtacccct ataccactca cactctagtc aggaggtata  66000
ttatggactg aatgtttgtg tccctccaaa actcatatgt tgaagtctta gcttccaatg  66060
tgatagtatt aggagatggt gccttctgga ggtaaaatca agccctcatg aatgggatta  66120
gtgcctttag aaagagagct cgtcactgtc tttccatcaa ttgaagatgc agtgagaagc  66180
tggtagtctt gcatctggaa gagggccctc acacaacctg atcatgctgg cacctggtct  66240
cagactttct gcctccagaa ctatgagatg ataaatttct gttgttcata ccccacccag  66300
gctacaatat taggttgctg caaagtattt gtgatttttg cctttacttt tcagggcaaa  66360
aactgcaatt acttttgtgc caacctaata ttttgttata gcagcccgaa ctaaggcaag  66420
ggagactaca tcagacagtg tagctatgta agtacaaatg tatccctgtt gaaggaaaac  66480
taagttctaa ccctgacttc aggccagtag ccaccttttc aatctctttc atgaagggac  66540
cattatcatt atcactggtg gcaaaaatag agcacgagaa tggaatttgc ttttctgtga  66600
aatctcagtg tatacagatg aagagcaagg gtttgctttc atctctaaga agcaaaagtg  66660
agtacggact ggcacattat cagagaaaga atcattctag ctcggtgggt cttaaccagg  66720
agtgaatttg actccaggga acagttggca atgtctggag acgtttttat ttgttatagc  66780
tgggggatga gtgggtgggt tgctactggc atctagtggg tggagaccag agatgctgtt  66840
aaacatcccg caaagcacag gacagtcccc gacaacaaag aattatctgg ccccaaatat  66900
caatagtgcc aaagttgaga aacctcattc tagcttcctt ttcccttcta cgttctaatc  66960
aactgttgtt ctttcagcat taggattcat ccagcagtct ctttccccag caatttgttg  67020
aaattttttt aaaaatggac tcattttagt gtcacaagaa aaaaatacat tcacaggaaa  67080
```

-continued

```
ggatgggtca ttttgtttaa tgatgttttg cctttcacat agcaaaagct taataaagta  67140
tttttaaata aaatggtgaa tagatcaaaa cattaatttc acatgtgttt taataaataa  67200
caggaagatg gctatattat ataaattgtt cttgtatatg tcttgagtgg atcatcaaac  67260
acaaacgtat ctacatgcct tttcttgtga atagatctaa taataacgct cttctaaaaa  67320
caaattaaat ggatattatt tgctgagaat gtaatgcttg tgtgaataga agccagccct  67380
gaatccaagc ccccagatct atttaaagaa tttgaagaat gtcagaaaag cacgtggctt  67440
caaggttaat gtgtaagact cacagaaact tgaaaaatca ctatgactaa aaagaaagta  67500
tgagctccct gcatgcctgt aaattggaat gacagccaaa accagttaat tataaaaaca  67560
gctaatttaa caggttttca aatttgtttc tttctccaag tagcatatag tcaataatcc  67620
ttaaagagaa agcaaagaag gggaagcact gaaccaaatt tgcttttttg tacctgctca  67680
gctcaaatgc agagttctct acctggaaat tgactgcttc catagtttga tagccacaga  67740
gagatgggaa cagaaggaga ggtataatcc cagacttgat tcagctatag agaatgacaa  67800
tagtgtcaga ggccttccaa ccagagcgac tccatcttga atacgggctg ggtaaaacag  67860
ggctgagacc tactgggctg cattcccagg aggctaagca ttctaagtca caggatgaga  67920
caggaggtca gcacaagacc ttgctgataa aacaggttgt aataaagaag ccagccaaaa  67980
cccaccaaaa ccaagatggc catgagagtt atctgtggtt ggtctcactg ctcattgtat  68040
gctaattata atgtattagc atgttaaaag acactcccac cagtgctatg acagtttaca  68100
ggtacattgg caacttccgg aagttaccct ctatggtcta aaaaggggag gaaccctcac  68160
ctcccagaat tgcccacccc tttcctggaa aacttgtgaa taattcaccc ttgttcagca  68220
tataatcaag aagtaactgt aagtatcctt aggccagaag ctcaggccac tgctctgaat  68280
gtggaatagc cattctttta tcctttactt tcttaataaa cttgctttca ctttactgta  68340
tggacccctg tgaattcttt cttgcaagag atccaaaaac tctctcttgg ggtctggatc  68400
aggacctctt cccagtaaca atagtagtaa ggggtcgggg aaactggaca aaggagttta  68460
agaagcctta gataaagggt cctcatcatt gtcataacat aaaatcatgg actcctagaa  68520
ttttatagct gataggatta gaaatttcaa aattcaattt cattaatttt catctgcgaa  68580
aacagatggc cagagaggcc aaacaatttg ttaaggagca ctgaggcgat ggaacaccac  68640
actggaccgc aaacctccta gcagagtata caaggccttt gatctcctca gtcagaatga  68700
actagagctt tccaggggta ccctttctga ctgtttagca tgtttgccag tctgactaat  68760
tttgaagttg cttaaatatc tgtcatttcc actgtatcat aatctcctca ttcatcttca  68820
atctccaatg ccttgaactc agtaaatgtt agttgaacaa aagtaaattg aacccagaat  68880
ttctgatcat aatctggagc actttaaaat tgtcagctta ctgggaaacg ggataacatg  68940
tgatttgtct ttgatttttt ttttctcata tgctttttcc acctatagat gctacacgaa  69000
tgtttttaaa atctgatata aaaattaaaa ttaaaaaatt aaaaaaagaa aatttgatac  69060
aatgctacat ttagagtgtt gtgattagat tccttaagtg tatcatggtg atctctacat  69120
cacgtggtga tcaaattgct ttgggtttta acacataact gacaaaggct tggggacatg  69180
taagatccca aatacatttt tattgatttt tttttcttgt ttgtcctctt ttaaataact  69240
tttttttgtt ataagaataa ttcatgttca gtggagaaac catagaaaat agtgacaagt  69300
gaaggaataa atttaaaatg acccataatt gtaccataca ttctgatttt ttaaacgctg  69360
aacaaattag ccttgggtaa gtaccaggaa tagagtgcag cattgaaagt taaagtttgg  69420
ggaaggatag ctgacttaag aaattatcta gttagacatt ttttggatgg ggtaattttg  69480
```

-continued

```
cagatgacat tagtgagaga aaggacttgc cactctcaca cagctagtag gggtgtggga  69540
ggatattgga accaagtttc aagtcttcag tgaagaatca agggagaagt tctaaaacct  69600
aacaatatcc ctctggatgg acatttattt tattactaca ataagccaca cggtgagtca  69660
taaggagcat ttcattcttc taatatgtct ctactgtatt tagaatctga taaagcccta  69720
ttagaattca tctctttaag aataaaagaa gctgaggaac taaagagagg gttggaataa  69780
tccactaatt atatccgtta agcttcagtt acgctaataa ggaatatcac atgactgtgg  69840
tgtgtgcttg ttctgaacag taaagtacat gaggaaagat aagattcagg gctgaaatgt  69900
ccttcagcat atgtaggtag tggtgatgaa agtcattaaa agaaaaattg attgaggtat  69960
tttagtaaac aaaagaactc accacttacc catcaggaag tgtattgtta atgcagtgct  70020
gttcagcctt ctggaagaaa aggtttcttc atgcttctct ctttagccta attcttatcc  70080
tgtcactttt caggcaaaat taaaaaaaaa aaaagattga aaacgatgct cctattttat  70140
ttgcttcaaa agaaacaggc tgttgcattg tgcttggaac agtttactct tggccttgat  70200
gtaagtgtga aaggaagccc atgtaattga ctaggcagta tctgaagaag caggaaatac  70260
agtgttaaga aaatgaacag gcatgaaaac catggctatt tgataaaagt aaataatttc  70320
tgcagttcac atgttctcag catattttct ttgatactga cttgcttaat atgacaatag  70380
cagaaccatg gtagcttgta ggcattactt ttcttttaat ttcttttaca ttttgaattt  70440
accagcactc acatttgtat tacttttggg ttatactgag gatctataac ttatagatca  70500
aatacctgac atatatatgc attctctgaa gtcttagggc agaactagaa cattcttgtg  70560
aacatcagta taagatatta aaatggaagt tttgcctaag actgaagaca ataaaaatat  70620
catagtctga aatgaatgcc agcacaccat acaggattta aatatctata catatatatg  70680
tgtgtgtatt atatatattt aatatatatc tgtgtgggat aggaagaggt agggggaaat  70740
cagttttaca attattaagt atttcaccct tgacaagagt atatatattg gaaatcagtt  70800
ggagagtatt ttcaaagata aatgttagtg tgctatgaat gaatccaccc ctaccaccac  70860
tgaggcaggg taggagaggc ctgtgctcct caagcatagt tggaaaagga cctcaacaag  70920
accacttcaa gagtctaatg tgtggagact gttgcttagg gagaccttat ggtctagctt  70980
ctgactcaca gctaagtcag ggagacaggt tggctgctct gatcgtggag tccaaaagat  71040
ggcctgcact gaaaagcctc atgagtgttg acttagggct agtctaagag gtccctggaa  71100
gaagaaacac tcagtaggag agaagctgga ggtaccttca gtgctgaatt ggaactagat  71160
tcattccccc gtggagcaaa ttacatagga aagatgccca gtgatggaga gtgggggtgt  71220
ctctaacaat tacccaccca ctgcccccac cctaagaaaa agaaaatcac atacaaccag  71280
tcagctgtaa acatatgccg agcctagtaa actcagatac taagttacca gggtacctgg  71340
caagtaagaa cattcctgat tcccttcctc tcttctcttt gccctccaac cttagtggct  71400
agcaagatgg ggagaggagg agaagctgta agtggggaaa aaagagcagc tttctctcct  71460
tttcagctgc tggattctcc ctcatcatag gcctgagctg gggaatcagg aagaaggatt  71520
ctttttaaaa ctgaagtaac gttatcattt aattttaaaa cattttaaat tttgacaatg  71580
ttgagattag atatactaat tattaaacta agattatgtt ttgcagcttg aagtgataag  71640
aaaaactctt atctaagagc atccaggaaa gtcgggggtt tcctgaacat ccttttaaat  71700
cctttggaag tcagctttca gagaggattt aaagtgtaga ctgggccttc agaaacttgg  71760
ttaatgtagg ggtttcctat gcagacttgg ggactatacc ttgtgtggaa gagagaaaat  71820
```

-continued

```
aagattatct tacatttttc ccattccttt ttcaaaaaga aagctcagct agcatgaaag  71880
ttaaattcaa aacgtaatgg gtattatttg catattcaaa tctagtgcat atcatgtaag  71940
tactgaatta tggtattcat tatttcaaat gacaagctgg attttttttt ctttcgaatt  72000
tcacaaatta attttccttg gaacctttttg gtttgggctt taagagttta ggctttcatc  72060
acaaagagag gacagccttg aagattaaag tgtgtggctc ttctcaagat gttcttagtc  72120
cagcaaagga ttctatgcat atttgggctt ccttctgtct cataacctgt atttcttgat  72180
attctattta tattctgtaa gatttttttt ttaaaggaaa aattcttcca tggttgaagg  72240
acatgtcaaa aatagaggat acagttttat atcaaaggaa gtttcatgat atgactgtag  72300
aagctcattt gacttaagac acatcatttc ctcatggaag tgttaaacag atctgtacaa  72360
taaggttggc aatctttgtg taaaacagtt tttttctcc tgctctaaag aaagtgtata  72420
tttcaaaatg tgaatgtcag cagtcagaaa atagtatttt tttaacttcg ttttcaaagt  72480
cctcaaaaac ctgtacctaa tcatgaattt tttttcccac agattgtttc ttcttctccc  72540
tcccagaaac tttgaagttt ttctacatga caccaggacc tatgtctttt tttaattaca  72600
cagaaatgaa agaaaaaaag tgtgttgtat cgttaaccaa atatatgaaa tctttaagct  72660
gtatttttat ttttaacttt gttttgcaaa gaggccattc cctttggtta aataatttgt  72720
tattcacagt ttccttgtcc tcatattatc aaggggaaaa ttgtagaaat tttaaaggaa  72780
gctctaggca atgttttcat ccctgaatct ttggagagtt ataaaaacaa acagattact  72840
gaacctgtaa gagaaccaat cgtgaagtca ttacatctaa gcataagcaa aatctcctct  72900
tggatcatta agttatagaa gaaaagaaag cctgcacttt gaaatttaga taaagcttgg  72960
taacttgtaa gtcaaacacg taaaatttta caattcagga atatcgatag cagttgagtt  73020
taatagactt ctcacattcc aaatttaaag cttccttctc tgtgctaata gagatacaat  73080
agcagtaggc gtttaagaag aatgaatcaa caatttaaaa ctataatgtg ttttttattc  73140
atctccctta ttcacatata tttgttttgt tttgagaagg agttctgctc tgtcgcccag  73200
gcaggagtgc tgtggcacga tctcagctca ccgcaacctc tgcctcccgg gttcaagcga  73260
ttctcttgcc tcagcctcct gagtagctgc gattacaggc gtgcgccagc aaccccggct  73320
aatttttgta tttttagtag agacagggtt tcaccacgtt ggacatcttg gtctcgaacc  73380
cctgatctca agtgatcagc ccgcctcggc ctcccaaagt gctgggatta caggcgtgag  73440
ccatcacttc tggcccttat tcgcatacaa tttaaaaatc atcacagaag gtttgaaaga  73500
aggaaggggc agaaaattac ctacttttcc tctccccagc gatctccttc aaatctgtgc  73560
cttttcctca ggcccaggcc tcaatttact gagcagtcac acctcacaga gggaggtctg  73620
ggcaatccac tcttggtcac aggaaagcca ttgaccctcc cacttcctct cctccacctt  73680
gttctcaact cttgactttg ggctttgttt ctgttcaagt cctagaactg gtttctttta  73740
tcaggttaag tgattagttc tctttccctc tagttgctct cactccctga ctcttgcctt  73800
ctgtaacaac tggagacaac tctttcaaaa ccagctccaa gccccagact tctctctggg  73860
ctttagttcg taaggcaggt gccctactga gtgagcctag atcagacaga aacatagctg  73920
ttggcaagga tttaggtgaa tttccttcca ttgtttttct aatacctttt tttttttttt  73980
gtaaatataa ccatgcacct acacacatat ttgaatatcc tgccttttta tttaaaatga  74040
catgataggt ccgggagtgg tggctcatgc ctgtaatccc agcactttgg gaggccgagg  74100
tgggcagatc acctgaggtc aggagttcga gaccagcctg gccaacatgg tgaaactcca  74160
tctctactaa aaatcaaaaa ttagccgggc atggtggcag gctcccagct actcaggagg  74220
```

-continued

```
ctgagatgtg aaaatcgctt gaacccggga ggtagaggtt gcagtgagct gagatcttgc  74280
cattgcattc cagcctgggc aataagagcg aaactccatc tcaaaaaaaa aaaaaaaaaa  74340
aagacaggat aaacattcta gatagtctct ataatggtca tgattaagac aataaaatag  74400
tctgaaattg tcaatatata ttaataataa tttatttggc cattctgcca agtagcagac  74460
acctgtcatt ctgcccactc agcacctctc tttcttttag ggaaatgcta cccactcttt  74520
gcatgggttc tggatggaac tgttgatcac agtgttttca ctccccattt tgcctcacca  74580
gaggtagaca gaagacccaa gccaggccag ttacacacaa tcttcagata attaccgtat  74640
tgatcacagt atcaccccac tcaaggcttg gttggagatg agcagaagag actaaagctg  74700
ggtcatttta attaacacct gtaccccaaa gaaagactgt caatgaggct tttataccga  74760
cactcctggt ttccattctt cctgatgcca ttcatttgac gaactaccca atctttccaa  74820
cagtgtcttt ggaagaaaga tagtcagaaa agaagataga gttgttttct gttctttgca  74880
accaaggaac tctaaatgat agacttgttg ctaggcactt tggttatttt tattatcttg  74940
aatacttctg tgatatactt ctttgtgcat gcctgtttgt acggatgtag ctttttatat  75000
attttatata atttctcaga agtggaatta cttagtcaaa aggtatgaac attttctgat  75060
tcttaatata aattgtgcaa atgcttttta agaagattat accagtttac attttgtgtt  75120
atatataaca gaaagtacta ctgaaaaata ttacaaaaat tgtctctctg ttcaggagga  75180
cttgtaatag atgataaagt acttgaaata ggaacataga gcattttcag tttaaaataa  75240
tttcattggg ttatttacgg aatccttaga attatggcca gacatttata gatgatctgt  75300
accaaaccta gttggttaca taaattgctt attcaactgg cttaaatcta taatagaaag  75360
atgacactta ctgaatgttt aatatacact ttgtcagggg ctttgtatta ttctatgaca  75420
tcttcaaaat gaccctactt tcctatttta taagtaagga caggaaggct tcaagaacat  75480
gactaatttt cccaagggct gtaccaaagc cagaacccaa atctataagg cttttaaacc  75540
tgcattctaa aactgcatct cggccatctt attcctacag aacttaaggt tagaaagcca  75600
gattggagtc ccaatttcac cacttagtaa ccagacaaac ttgaggaatt cactcaacgt  75660
ctttgaatct ccatttccta atctttaaaa ctaaaacaat aatactggcc ctacctattt  75720
cctaaaattt cgtgaggcac atagagctag tgtggtagag tgctgtacag atgtcaagtg  75780
ttagcgtgaa ttacttagat ccctgaacac catggatgaa tgtgtctgac tgctattaga  75840
ggtcataaag aatattgggg ccaggtacat tggcttattc ctataatgcc agcactttgg  75900
gagcctgaga caggaggatc actcgaggcc acaatttcaa gaccggcctg ggcaacatag  75960
tgagacccct tctctacaaa aaaaaaaaag cagccacgtg tagtggcaca cacctgtagt  76020
cccacatact caggagggtg atttgggagg ataactttag tccaggagtt tcaaggtgca  76080
gtgagctgtg attgcaccac tgtactctaa cctggacagc agagtgagac cctgtctcta  76140
aaaaaaaaga aaaaaaaaat aataataata aagaataatg ggccttggga tacccactcc  76200
tctctttctg ctctgagttg tgaagcagtt gagttacata tgcatgtcca atggatgagg  76260
ttgaaaatat caactggatt ggaatgtggc ttacttgcgt ggccacaatg agcttcgtaa  76320
cacttcctga cagggtgaga agacaaactt cctcacccag tcactggcag agctggacac  76380
tctgtgtctc tcccacagaa caacctctta ctgcatggag gtggatgaaa aagtcaaccg  76440
agaacaggct actccaaaaa gcagagcacc aaaggcacca gctggtcagg tccccccttcc  76500
taagtaaaca atcacgtaat tcattcggga caaagccaga gaggtggtgt ggagaaagag  76560
```

-continued

```
agggcagttt cctcccaagt ttttcctgga attctttatg ggaatatgag gtttagggga  76620
ataagacttc cctttaacag tgaagaatcc ccagctctat tggtaatagg aaatcgctta  76680
caaggatcat ggggagtatt tcctcagctc gttctgcctc ctacttggct gagtggaatg  76740
gaaccatctg tggctgctgc atatgatatt gtcaactttg tcattccaca cccactcctt  76800
gacgccctac catgtggtca taagactccc tttaaagtgt tcctttaaaa aacaaaatgt  76860
gttttgtttc tataaaatac agctcaatgt cagaaccctt gtcttgtttg ctctctgatg  76920
taaccctttc acaatgtttg ggcagcttat tctctctatt tccctgtagg gtcccatcca  76980
ggccaaagtg agtgccagcc tcatttgggc agcacatgcc ctgtggaagg gcaggaagag  77040
acgaaagcta attgtaactt tgtgattagc tgtcatggat gcctggtcct gtcaatagcg  77100
ctcaataaag ccagaaggcc aagcgttcgc ttctgcatac tgattgctga gtcagatttc  77160
tcagtgcaga agggctttct aggcagtcaa ttttagaata ttagtcttgg ttcttaagtg  77220
gttaaaatcc ctagctggtc tttaatctga gcctggagaa tttagttagg gctgacattc  77280
tgctgtgata tttttgccct caatatatat gtctttcctc catctcttag atccctgaat  77340
catagagata tatatgttat ataatcaact gtctccagtc tctaagagtg ataagtacac  77400
attgtgtcag gttgagggga caggagaact ttcaaaagcc tttcttgccc ctttttcctt  77460
ctcactgcct cccactaagt ccagccactt attattcagc tgacactatc atcatgacca  77520
tgagtctttt ggggctaccc tggttcggat ccttttggag gtttgttgct taactctgtc  77580
ttcagtccta tggagctgct ttttcaataa gtttctattt tggctaaagt tggccagaat  77640
ctccttgtaa ccaaagaaca aataaaatac cagcttgcaa tgttctatgt tgcttccacc  77700
aaacttatgc agcacttcct atctaatcca cctactagtc tttttttttt ttattttttt  77760
ggagacggag tctcgctctg ttgctcagga tggagtgcaa tggtgcaatc tcggctcact  77820
gcaacctctg cctcccgggt tcaagcaatt ccccggcctc agcctcctga gtagctggga  77880
ctacaggtgc atgccaccac gtccggctaa tttttgtatt tttaggagaga gagggtttca  77940
ccatgttgcc caggctggtc acgaactcct gagctcaggc aatccgccct cctcgggctc  78000
ccaaagtgct gggattacag gagtgagcca cctcacctgg ccccgaccta ctagtcttta  78060
gtgtttgctt ccttctattg ggtaattgtc tgtttatatg catgtcttgt ttcctcaaat  78120
aaaatgtggt cttctcaagg gtattggccc atgttctatc catctgtaga tatcacagca  78180
cctagcagtg tctttcacag aggaagtaca caactggcat tattgattca ttgctccatt  78240
ttttccttct ttatccccag catttctcaa taatttcaaa catctccatt ggagtaccgg  78300
agaaagcagg tagctttact tgcagctatg tttctatccc catagtaact aaaagaggac  78360
ccagagaaac atgtttaaat gctgtcctgt tatcaggacc tcagccttct gatgctccgt  78420
ggcttggggg ttaatgcttg atcatttcct ccccaaccta cactgtgtac ctatgctagt  78480
ctcttcatga ggactaagcc ccatagtaaa agggctagat aaatagaaaa tcattttatg  78540
taattataag aatgagaata ctgagtatta ctggtgtttg tttaggataa gcacatcttt  78600
atttgtatga gaaaaagaaa aagagagtga aaaatatatt aacgtgcata tagttcagga  78660
ccatggattg caagtgacag aaactcaatt caaaccaacg taagtcaaaa ggaaaatata  78720
ttggctcatg taaccttctc acagagaggg caggatggaa ggggctttgg gaacaagaga  78780
attgttctca aattctagga atactaggat tagtccagga tgggtcacct tcctgtccct  78840
gaggtggtgg tagcgatggt agagtcttat gggaggaaag agtgcatgtt aggatgaagg  78900
tagggctaag caaacaaggg caagggccac tatatcatgc taaaaatggt ttttttttgat  78960
```

-continued

```
gtcttcctta atttcacaaa tgcttccaac aaagtagcac acaggaaaaa gaacataggg  79020
actctactgg tgggtgcttt tatcttaagc cttgtacttg cttttcacag cttactcact  79080
gcttgtacct gaggccatat gccctgtaaa agcttctgca gggtttctac taagctgggt  79140
tccttatatg gctctctccc atttctgttg cctcactcta gtgatctttc tcttttcctc  79200
acctctggga ctggtggctg tttgtatgga ctgccttagc tttgctttgg gtttttttcct  79260
ggggacaatg tcttcagatt atcctagacc aaataaacta cagccactgg gccaggctct  79320
tcctcctcca actggaccat gttcccaggg ctcttcacct tagtttaggt caagcattct  79380
tggcaaaaga aaggcctagt taacaataga cattctagca attgattctt tttgacatgt  79440
tgtaagatct attcacattt tgtaattaaa gcattcccct atggaaacca acacgaacta  79500
agctgctcct ggaatgcagg gtggcctcct caatacagga tgttctagag agctgtattt  79560
tgggcactta actattctcc actacttagg gcacagcact gaaattaaca ccactaagtt  79620
tgtcatgtcc atgtagttag tctcaggcag tgcagcctca ggagtggaac tgacctctta  79680
tgtgtgtcca gcctttcttc cttcagaagt cagctgtgtt ttctgctgac tctccatagg  79740
aacatcagtc ctgaatcctc agaccaccat ctggagtagt aagtgctcct gacagtccta  79800
gaagttgtct accgctggat ctccaaagcg tgtgacacac cgtgagagag aaatgagaaa  79860
gctgggctct tcaggtaaat cttgcttttt cacaagcccc ctaattttac tgcataatta  79920
ttttgaattc actgataatt tctacaattt tcccataagt catctacaca caataccctc  79980
tcatgcaaca cttggctttg ctaatacata tctattatga gagctgtgct tcttaagcgt  80040
aaatgtttta tatgcactaa ggctcttggc ttacatataa aaggggtatt gagcaatgtg  80100
atacagaagt cttttctcca caggtctcat atgtaaagaa ttcattagat tggctgaaat  80160
agactgatct gtccatttct ctgctcactt atcataagga agtcattagc taaggaacaa  80220
aaactacaat ctatgtaatt agaagaacaa gctggttttg ctcaatataa aaataagaaa  80280
aagaaaccat gtgaaagtca aaatatttgt ttaatcaggt cattgagaat ctattaaaaa  80340
gtatttgaat tctttatgat gagaactatc ttgactcaag tggacagtgg tgagcttttt  80400
ggcctgtggt ccctacgtag aaaggaggct ttgtcataaa gtcttatatg gtacaggtgc  80460
caagttaagt gcccaagctt gctcttaaaa gcatactgga ttttgtttta gacttttagt  80520
gaactgaagg gaataaacaa atccctctgg gagaacttct cctccatcct tggtgaagtc  80580
attctgccag aattc                                                   80595
```

<210> SEQ ID NO 4
<211> LENGTH: 80246
<212> TYPE: DNA
<213> ORGANISM: Nucleotide sequence of NC-contig

<400> SEQUENCE: 4

```
tggttgattt gtnnataagg aagtttggaa tcaatcccgg aaggaatttt ttttttaaaa     60
aattttttgg aagggtttgg tawtaaaaaa rccaatttgg gtttttaaaa ataggaattt    120
tatgggaaaa aattttccct tttttttttt ttaagtttta gatgttatgt ttccttatac    180
ttaaagtggg tgtcttatag gcagcatata tctgggtctt gatgtattat ttaatctgat    240
aatctcaacc tttttgttgg agtgtttagg ccatttacat ttagtgtaat tatagacatg    300
gtttgatttg ctataccatc ttttcatttg ttttatatgt gagccatctt ttcattgttc    360
ttttttcatc tttgaccatt ttctttagta ctgaatactt tttttgtatt tcattatatc    420
```

-continued

```
tattggcttt ttagttatac ctcttaaaat ttttttttct gttttatgta ggatttataa    480
tatacatctt taacttatca cagattacct tcaaatagta ttttaccagc tcaagtgtaa    540
tgtagaaacc ttacaagagt atattttcat ttctgtctcc taatttttat gctattgtct    600
ataatacatt aggtttgttg ttgtttgttt ttaccttatt gctgttggct ggggtcagca    660
aacattttct gtaaagggct agatagtaca ggcatacctt ggagatactg tgggtttggt    720
tccataccac cacaataata caaatatgca agaagtggat atcacaataa agtgagtcac    780
acaagtcttt tggcttccca gtgcatataa aagttttgct tatactacac tgtagtctgt    840
tcagtgtgca atagtgttat gtctaaaaaa acacatacct taattttaaa atgctttatt    900
actaaaaaat gctaacaatc atttgagcat tcagtgagtt gtaatctttt tgctggtgga    960
aggtcttttc ttattgatga ctgatcgggg gtcaggtgct gaagcttagg gtggctgtgg   1020
cagtttctta aaacaacagt gaagattgca atatcagttg actcttcctt tcatgaaaga   1080
tttctctcta gtgtgtgatg ctttttgata gcattttatg cacagtagaa cttctttgaa   1140
aattggagtc aatcctctca aaccctgctc tgctttaaca acctaagtta atataatatt   1200
ctgaatccat tgttgtcatt tcaacaattt tcacagtgtc ttcaccagga gtagattcca   1260
tctcatttcc tgagatggaa tctttgctca tccataagaa gaaattcctc atctgttcaa   1320
gttttatcat gagattgcag caatacagtc atgtcttcag gcctcacttc acttttaatt   1380
ccagttctct tgctgtttct accacatctg tggttccttc ctccattgaa gtcttgaacc   1440
tctccaagtc atccatgagg gctggaatcg acttcttcca aattcctgtt aatatttata   1500
ttttgacctc ccatgaatca tgaatgttct taatggcacc tggaatggtg aatcctttcc   1560
aaaaggtttt caatttactt agtccagatc catccatcca gaggatccac tttcaatgcc   1620
agttatagcc ttatggaatg tatttcttca ataataaggc ttgaaagttg aaattactcc   1680
ttgatccatt ttctgcaaaa tagatgttgt gttagcaggc atgaaagcaa cattaatctt   1740
tttgtacatg tccatcagag ctcttgggtg accaggtata ttgccagtga gcagtaatac   1800
tttgaaagga attatttttc ttagcagtag gtctcaacaa tgggcttaaa atatttggtc   1860
caccattctg taaactgatg tgctgtcatc taaactttgt agtttcattt atagagcaca   1920
ggcagagtag atgtagcata attcttaagg gacttaggat tttcagaatg gtaaatgaac   1980
attggcatca atttaaatca ctagctgtat tagcccccaa caagagagtc agcctatttt   2040
ttgaagcttt gaagccaagc gtcgacttct cctccctggt tacaaaagtc ctaaatggca   2100
tcttcttcca atataaggct gttttatcta cattgaaaat ctgttgttta gtgtagccac   2160
cttcatcaat gatactatct aaatctcttg gataacttgt gcagcttcta catcagcatt   2220
tgctacttca ccttgtactc ttatgtaatg gagtggcatc tttcctcgta cctcatgaac   2280
caacctctgc tagcttccaa cttttcttct gtagtttcct cgcctctctc agccttcata   2340
gacttgagga tagttagaga cttgctttgg attagatttt ggcttcagga aatgttgtgg   2400
ctggtttgat cttctatcca gaccactaaa actttatcca tatcagcaat aaggctgttt   2460
tgctttctta ttatttgtgt gttcactgga gtagcacttt taatttgctt caagatatat   2520
ttctttgcat tcacaacttg gctgactggt gcaagaggcc tagctttcag actatcttgg   2580
cttttgacat gccttcctca ctaagcttaa tcatttctag cttttgattt aaaatgagag   2640
atgtaggcca ggcacagtgg caggcacagt ggcatatgcc tgtaattcca acacattaag   2700
aggccaaggt gggaggattg cttgaaccca ggaggtggag gttgtagaga tcacaccact   2760
gcattccgtc ctggatgaca gagcaagacc ctttctcaaa ataaaatgag aggtgtgctt   2820
```

-continued

```
cttctttttg tttgagccca tagaagccat agtatgattt ttaattggcc taatttcaat   2880
actgttgtgt ctcagagaat agggaggtct gaagagaggg agagaggtgg gggaatggct   2940
ggtcagtgga gcagtcagaa cacacataac actaataaat tgtttgctgt cttatatgga   3000
tgtggtttgt gatgccccca aacaattaca atagttacag caaatatcac tgatcacaga   3060
tcaccataac agatataaga atcatggaaa agtttgaaat attttgagaa ttagcaaagt   3120
gtgacacaga gaaacaaagt gagcacatgc tgttggaaaa aattggtgtt gatagacttg   3180
ctccatgtaa gtttgccata cgccttcaat ttataaaaaa cacaatatct aggaagttca   3240
ataaagtgaa gtgcaataag atgaagtatg cctgtaaata tttcaggctt tccagaccat   3300
agggtttctg ttgcaactgc tcacctctgc cattatagca tgaaagcagc tatagaaaat   3360
atacataaat gaggcctgta atcccaacac tttgggagcc caaggtggat ggatcacttg   3420
aggtcaggaa ttcgagacca gcttggccaa catggcaaaa ccccgtctct actaaaaata   3480
caaaaatgag ccaggactac gcatgcctgt agtcccagct acttgggagg ctgaggcagg   3540
agaatctctt gaacccggga aggggaggtt acagtgagcc aagattgtgc cactgcactc   3600
cagcctgggc aacagagtga gactgtctca caaaaaaaaa aaaaggaaaa gaaaatacac   3660
ataaatgaat gtatgtggct gtgtaccagt atatcctcat gctctagctt gccaaccctt   3720
gctttacact gtcagttacc ttctaaagag attaaaaatc ataacaatat ctattacgtt   3780
tattcacatc ctagtgtcat ttcttcctta tgtagaatca aatttcattc tggtatcata   3840
tttcttcttt ctaaataatt tcctttaata ttttttatag cacaggtcta atagcaatgc   3900
attatgcaat tcattgctat tagacctgtg ctataaaata gcaatgaatt atgtcagttt   3960
ttatttgtct gaaaaagttt tttgtttttg aaatatactt ttgctgggta tataaatcca   4020
tgttgcataa cttctctttt cttcagcact ttaatgaagt cactcagtta tcttctggct   4080
tgtatagttt ctctggctgc cttcaagatt ttttcattgt ctttaatttt tagcagtttg   4140
atgtgtctag gagtgatttt ctttgtattt atccttttgg gggcctctta atttctttga   4200
tccttttttt cttttttttt ttttttaaac cattttgggt ctttcccccc atttggggtg   4260
aaaaaaaaaa aaaaataaaa tcatagttta aaaaactaat tttggaaaat tttcagctat   4320
catttcttca aatatttatc ctactctatg ctcccctcct cccctttcct tctgtgactc   4380
aaattacagg tatatttaac cattttattt gttcacggca cttggatgct ctgctttctt   4440
attttttgtc tttcattttg gataatttct actgacctat cttcaagttc actgattctt   4500
ttctcagtca tgtctagtgt gctcaacgcc tgttgaagaa atcctttgtc tttaatatca   4560
tgttttttat ttctagcatt ttcatgtaac tctttgttct ggtttccatc tctctactca   4620
cttttttttt tttttttttt tttttttttt tttttttaga cagagtctcg ctctgtcacc   4680
caggctggag tgtagtggcg cgatctcggc tcactgcaac ttccgtcccc tgggttcaag   4740
tgattctcct gcctcatcct cccgaatagt tggaattaca ggtgcccacc accgtggctg   4800
gctaattttt gtattttttt agtggaaaca gggtttcacc atgttggcca ggctggtctt   4860
gaattcctga cctcaggtga tccacctgcc tcagcctccc caattgctga aattactggc   4920
atgaggcact gcacccagct ctgctgacat tttttatctt ttgctgcatt ttgtctacct   4980
tttccatgaa atcctttaac atagtagtca taattacttt caattccttg tctgacagtt   5040
ctgacattca agtctaggtc tgttaatact ttgtgaatct gttaacagct ttttttcatt   5100
cttgtctgtg tgttttgtat ttcttgattg tatgccaaat attgcctgta aaataaactt   5160
```

-continued

```
agataagtca tacttctatc cagaaatagc acatttttttg tgtccagtca ttatgtggag   5220
gagttggggc agtctatcag tggctgaact agtttggatt tgttgatgct atacttagaa   5280
tgcaccagac ttccattcac tgcaagagtg ggctgctgcg ctttgtgatt catgtgaggc   5340
ctgaattgtg gaagggtttt tccttagtgt gtccctccat gctcagattt cagcaagtct   5400
tcatatctgt gccacagaag gaatctgacc catgctcttt ttgacctccc caagtgatca   5460
actgttgctt gttatagctt gtcatggagt aagagggtgt tttttagtt ttcatcctcc   5520
agccttggtc ttgggccctg agctcctaga ctccaggagt ggatggaatc cagtgatttc   5580
tcagtaattc agccccttct ccagtagtgg cagatctctg ctttgtatca gtgcaagatc   5640
ctgggctgag ctcattttct gcccttcctc gagtggcaga cagctcttgc tttcaccctt   5700
ctaccaaagg cagtgcatct tttcttgggc ctctccccat tgaacttatg actttcacat   5760
aagagaaggg ctcatgtatc agagaattct gtgactttgt gccacataca gagtctctca   5820
gttctcttgc cctgccccag tcttttttgt gagcacctag tagagaccct tggagaagag   5880
caaggaagcg agtatggact tcttttgtgt ctgtcgattg ctttgtttct caactgctac   5940
tcttggactt taagaattca ttaaaatttc agctgttttc tttttttctt tcgtttttct   6000
ttttttttt ttttttttt agatggagtc ttgctctgtt gcccaggctg gagtgcagtg   6060
gtgtgatctt ggcttgctgc aacctccgcc tcccgggttc aagcgattct cctgcctcag   6120
cctcccaagt agttgggatt acaggtgccc accaccacac ctggctaatt tttgtatttt   6180
tagtagacac agggtttcac cattttggtc aggcttgtct caaactcctg acctcatgat   6240
ctgcccgcct cagcctccca aagtgctggg attacaggca tgagccaccg cgccaggcct   6300
cagctgttct ctttttacct gctgggatgg ctagttttct gtgtcaactt gactgggcca   6360
tgggatgtcc agatatgtaa ttaaacagta tttctgggtg tttctgtgag ggtgtcttca   6420
gaagagattt gcatttgaat tggtgaacta agtaaagcag agggccctgt ctagtagggg   6480
taggcatcat ccagtctgtt gaggacttga atagaacaaa aggcagggga aggttggaat   6540
tgccccctct ctgcttgagc tgagacatct atcctgccct tggcactcct ggttctcagg   6600
ggttcagacc tggattcctg gtctccacct tgcccatggc agactgtggg acttctcagc   6660
ctcctatcta attaataaat tttttttac acacacacac acacacacac acacacacac   6720
acacacacac acacacccta tgtatccttc tgtttttctg cagaaccata tttaatacac   6780
ctgcttttat gacgattacc tatcgattct gtattctgcc aaaactgaaa acagttcatt   6840
tttccatctc ttctcagaga ggcttgtcag ccattagttc tctgatgggc tcaagaagtt   6900
atgcagtttt ttttttctca ctgttaggat ggaattgata ttctgttgaa actttctata   6960
cctaagtgga aacttgtttt gaggttattt tctctactta cttttgctgg aaatggaaca   7020
ctctgtatct agttaagaca cataaactga cttgtgatac cataatgttg tgttgaattt   7080
tatattctta gaaaatcatc tgtcaaggtg ttaactaatg gcaaagcatt taataaatca   7140
gcattcatgt attcaggtgc tctgaattat ctgactttta aattcttact ttataaatga   7200
gaaaattggg gcatggaaaa gttaactctc ctaaccccga attattacat tattaaggac   7260
aggacttaga ggccagatat cttaagtcat taatattctt tggctcacag aattggcagt   7320
ataacctaaa ggtaataact aggtgatttt cttttatatc aattaaatat gtcagttttc   7380
aaatattcat aagtacctac tgtgcaggga aagaacatgc catacaaaag atgtagtcca   7440
ggcctttaag aaactttcat ttaatgggaa ctcaagaagt gtacatataa ggagggaagt   7500
agcagtatgg tacaagataa tacatacata tcagtgaatg atattgccaa aaagtgctat   7560
```

-continued

```
tgatagagca ataattcatt tctgcaaaca gctgctgatc tcctactgaa aacagaggag   7620
ggagaacagg acgcctcgtg gtcaggatag aagagaaaga ccttgagttg agccttgaac   7680
agtatttaat attcaaaagg ttaagagagg agagcaattg aggaggggag aatagttcca   7740
gcacaaatga tggtgtacaa gatgaacaca gtcagtaaag agcagactgg tctggatgga   7800
gaggaggatt tgcatcattt gggattacgt catttagacc cttgaaagcc aggattgagt   7860
aaagccacag tgaagcgact ggctcgtatg gaagctttat tttaagaaga ttaatctggt   7920
agtgacatgt gccaaaaact gaataggtag aaatgagatg cagagagccc agttagaact   7980
aagtctggtg cagtaatgca ggattgaggc aataaacacc aaactacagt atcaccagat   8040
aatggatgtt tgaacggacg gtttaaagga aaattgatgg tatttggtaa tttattagat   8100
aatccagggc catggaatga gaggggaaaa tgactaacca tagtcatcaa atggtttttc   8160
ttaatgaatc tgaattttgg tgtaagagca acattttctt aggccttgcc tagttggtac   8220
agctgactat gataatgact gctaccatgc ttgttcctct tttagcagct gtgagtcccc   8280
caccagccaa acaatgagcc tcttgaaaag gacgatgcct tttcacttct ctccaagtgc   8340
ttggcaaata ggaggccttt tgaagttact ttatagttag ggttcccag tgagtatttg   8400
aaatattaag tcatgcccgt ggttgacagc atggccctac tgctcatcat cagctattaa   8460
ccttaggcaa gttaatgaac ttttctaagc cccagtctac tcatttataa agtgggatta   8520
ttaataatgt ctacttcata aaattatgaa gcctgagtta ggtcattcag atagtgttta   8580
gtctgattct tcgaacctag taaacagtca gtaaacagaa gcaaatgcca catgcctgat   8640
ttatatccaa ggggagaaag gtaaaagtga aattttcatg atttatggat tcaaattata   8700
catttcaaag atgctttata agctattgtt ttggtaagaa gaattgagct gaaacagaat   8760
tttctgacag cagtgattat taaatggtga aataggctat tgatgtcttt agaggatata   8820
gatgttcacc ttttgcatat aagtgcacaa aaattcacta agtagatatg tctgtctaca   8880
cagagagaga gagcgtgaga gcattaaagt tagtaaacat ccccctcgct tttttttttt   8940
tgagacaggg tcttactctg ttgcctaggc tggagtgcag tggtgcaatc gtggctcact   9000
gcagtctcaa catcctgggc tcaagcgatc ctctcgctca gcctcctgag tagctgaggt   9060
gtgcaccacc acacccggct aatttttaaa tttttttatt gtaaaggtga ggtttcacca   9120
tgttgcccag gtctcaaact cctgagctca agcaatctgc tcacttcagc ctccaaaaat   9180
gctgggatta caggcgtgag ccaccacgcc tggccagtaa accccattca tttacatcat   9240
cttacttgtc cctccaaaat cctgcaaagt aggtaggttc tgtctttatt tgttatttag   9300
gtgaagaact tgaagtggtg ttgaggaata ggtgttttgc caagagtcac gcagctggag   9360
tggcagagct gtatactctt ctgattccac caacgctgtt tacatcacat ctggagaaaa   9420
gtgctctgag gcacagatgt ttagtgggag ggatgagaca caggctgcaa tgcctaaaga   9480
taatcgggaa taaaagcaga aaacaagacg tttgtttctg ttaaaatgag acagaaaata   9540
aggcgtttgt tgtttgggat tgagcacttg gagaagtggg gagcgatttg atttgggtga   9600
gactgctcct ggaatgctgc atctggttct ggactactca ttactaggct tatagaaact   9660
agctggagga ggttcaaaga aaagctccaa aatgattagc gggctgacgg gattgattta   9720
taagaaatat taaaagaatt aaatgtgtat agctcagcta agcaaagatg aaagagacca   9780
gctaaatgta tacaaatatc tgaaacgtgc aaactttaaa aagagagatt aattatttaa   9840
catgatacac gggggcacaa tatgcagtca caggatgaaa atttcagctg agtatctaga   9900
```

-continued

```
agaattcccc gatagtgaat ctgttaaggc tgtctgtagt gtggcctttc cctggagagg   9960
caatagaaat ttcaagtctt acgattttaa aagtttcttg ggaactaggt attagatgat  10020
gttagagaat tattattaat ttggtcaggt atgataatgg tattgtagtt ctataagaaa  10080
aattgtattt tttagagtta cataccctga aatataagca tagaatatga tgtaggagat  10140
ttgctttaaa ataccacagt aaggaaagaa aggaaggagg aagaaaagaa aggaagggga  10200
agaaagggaa aaagaggcaa agaaggaaga gaaggtaaga gaaagaaaaa gaatgaagga  10260
agaaggctgg gcactgtggc tcatgcctat aatcccagca tttaggaggc caagttggga  10320
ggatcactta attaagccca ggagttcaag gctgcagtga gctgtgattg cgccactgca  10380
ctccagcctg ggtggcagag tgaagccctg tctctaaaaa aaaaaaataa gttaaaaaga  10440
aagaaaagga tagatgaagt atggcaagat gttggtaatg ttgaacctga aggaagttaa  10500
tatgtgagtt cactttcctc ttcagtcttc tttatgtatg tttgccaact ttcataataa  10560
acaatttaaa ttatattttc ctgatcaaaa cttagtagca gtattaatcc ctgggcttcc  10620
tgactagaac agcctcatta ccacatgggc agagttctgg ccgaccaggg accacgtagt  10680
ggttcaccat cttgctctgg taatgtggtc tgggctgaag ggccctttct aaggttgtag  10740
atagaaatcc aggaaacttg ttagaactgc agacctatca gggtacctgc aggaggtgag  10800
tctactaagg tgaaaaagca gagggcagag gtcgtgatta gcagctgacc gccccctgct  10860
tttctgtccc tcattcgtgg aaaattgagt ggagctcaat tttgagtgga gctctaagta  10920
gctccacttg tagacattga gtggagctct aagtgtcttc agaatagcaa aacactagtt  10980
ttctttttct tttctttttt tttttttggg agacagagtc ttggtctgtc ccccaggctg  11040
gagtgcaatg gcacgatctc cgctcactga actctgcctc ccgggttcaa gcgactctcc  11100
tgcctcagcc tcccgagtag ctgggattac aggtgcccac caccacgccc agctaatttt  11160
cctattttta gtagagatga ggtttcaccg tgttggccag gctggtctca aactcctggc  11220
ctcaagtgat ccgcctgcct tggcctccca aagtcctggg attacaggtg tgagccacca  11280
cacccagctg caaaacccta tttttcttga atggagaaac actttcccct tatttattga  11340
gtttgggaag caagaagagg ggtaattcat taagtgaaaa tttccaaaat ccagaaaaca  11400
tcgataaagc agcagcttaa tttttttaag gaagaatttt ttaaactatc ttcttttgag  11460
cctctttagg aagacctcac gtccttgcct tgaatgttga gagtgggaaa tccagggagg  11520
ttttggaatg catgccttat gtctgctttt ttgtttgtta gagaaatata aatattttat  11580
ctaggttttg ctgatggcag tcaagcatga acacaaccca ctgtttgaga agctgtaatt  11640
tctgaatttc tgcagagtgc acatctaggc cagcaaatgg cagtaagagt gaggtggatt  11700
tagctcagtg taaggatgaa ctccagaacc atcggctctg actgaaagtg aagcggcagc  11760
cgcgttgtgg gaaagctggc tggagtctct ctcataagca ggcattcttt ttctccagcc  11820
cgtcactgtg ttggtttggg cccacggtaa gcctcctggc ctctaggctg taaccccccac  11880
catcctcctc tgcctcgcct ccagagtgat tgttctgaag cacaactgga tgtcattccc  11940
cttcctgaac tcctagcacc tacagggact ccatcccttg tgccccacat acctcacacg  12000
tagacattcc taatgaagat ttgattgaat tattgtaaac tcagtgcctc ccactcttct  12060
agttgcctct ctgcctgcct ttgtacattt atttatttat ttatttattt atttatttat  12120
gagacagagt cttactgtat cacccaggct ggagtttagt ggcaccatct cagctcactg  12180
caacctctac ctcccagact caagcaatcc tcccacctca gcctcccgag gagctgggac  12240
cataggcacg tgccactatg cccggttaat ttattgtaat ttttgtagag atggggtttc  12300
```

-continued

```
atcgtgttgc ccaggctagt cttgaactcc tggactcagg cgattcgccc gtctcagtct  12360
cccaaagtgc tgggattata ggcgtgagcc accatgccca gccgctagca ctcatcttaa  12420
tcgtatattt acttatctgg ctttcccacc agactgcggg ctcttcaaga gtaaatgcca  12480
tgttttcacc tttatttccc cagtttgtgg cacattctag gcactcgcca tcatgaaata  12540
aacctctgga gctgtgatat tacaaacgtg aaaagatgac gagcactcag caactttcag  12600
tgagtaaaca aaggctttca ttcagcatgt atttattgac tgccctgatc tgggctgctt  12660
cctgtctgtg gttcaaggag agcatagtct acagaaccag agacctggct actctggaag  12720
ttagacttaa gcccaccccg gtccttgaat ggggaaatat ttcccttcat tcctgtgttt  12780
tagggacaga aagatgagta atgcagtgat acatgctgga aatgtttatt ccactacccg  12840
aagctgcctc tcaacttaac aatccatgaa agaaacaaga tggtatataa ctttttctaa  12900
tttgtgatgc ctttgtttat ttgtttccgg ttaaaagagg aggtggcatt gaattgtttg  12960
tttggtttgg tttcttcttc aataagaagc atcttaatat aactagactg gacatctgtc  13020
ccattttcaa aaattacaag tttcgatcat tgctaaattg tacagatccc aatctgtctg  13080
ctctgcatac atttgcattt ataaaagcag aagcagacta gcagtctttc taatgcaatc  13140
ccccaaatgc atgaagtatt agattgcttc tccctattgg ttcatgcatt gctaaaggct  13200
taaaaggatc attgatttta attatttaat gtgtacagca ggctgagctt cctttctttt  13260
ttaagggaag aaccttcagg ggcattgctt tagtttttta atgttaaatc tcatttttct  13320
ttgaaaataa gaagttaaag ctgtattcac acaagctctc aaagtgccag attttcattg  13380
tgtttttaaa ccatctagga aatgtttgat tctaatgaaa cattactgct gaaaattggg  13440
ctgaaattgc tgggctgaaa atattgttat aacttcacat gattccagtg ttgtattatt  13500
atttttctt ttccttttt tgacccgata tagatgaagc gaagagacaa gggagcaatc  13560
ccatgtgtaa taaaaaaagg cagcctgaat tgttgttgct gtttttgaaa tttaagctgg  13620
ttttcaatta aattcagtaa atggtccagg actataaatg ttgaacattt tttaccgtgt  13680
gatttaaaat ttagttttaa tgttttttt ttgggttttt ttttttttga tggtttacat  13740
tttccccatg gaaagcagct atgtcatgtc ggcatgattc atcatggtaa catctcgggt  13800
tattttggtt tgtgttatgt tcagaaagcg gaatgccaaa aataaagagt ggtttgtgat  13860
gtctagtgtg tcttccttta acaaatcaaa ggcttttatt taatccactt aatgggacac  13920
tgcagaaatt taaaaaatgg aagtcccatc cacagaaggc aggtactatg atgtaaaaag  13980
tttaggtggg ggattaatag agtgatcata taatttatga gctaaaccgg aggcactttt  14040
tttttgaga tcgagtctca ctgttgccta ggctggagtg cagtgacgtg atcacagctc  14100
actgcaacct ccgcctcccg ggttcaagcg attctcatgc ctcagcctcc tgagtagctg  14160
ggactatagg cgcccaccac catgcccagc taatttttgt gttttttgta gagatggggt  14220
ttcaccatgt tggccaggct tgtctcaaac tcctgacctc aggtgatccg cccacctcga  14280
cctcctaaac tgctgggatt acaggcgtaa gccaccatgc ctggcccaga gacacttttg  14340
agagtgaaga ggaagctgag aataattcac tgatctacaa ctgggaccat ccagggcaag  14400
ccagatgcca ttaccactag ctagaaagct tgccaaggtc tcatttacct tggtatatag  14460
caaattcttc tttgaattct ggaaattctg gtaagtcatt gaggtagctc tgtgccaagg  14520
agcaatatgg tagaattcta atatttcagg cagtacaaca ctttcctgca tttgtagcag  14580
gtaaagggag gtcagggcag aagacaaaac cactgggact cgacaaaggg cataaacgtc  14640
```

-continued

```
taatgcacct gatgtagctg atggtaaatt gttatcagct aaagatcttt cataataaat  14700
aaacttatca tttgtaggag ggcacagaaa tcgtggaaag ctgggattca ggttgcctgt  14760
ggctttaatt ctggaatcag aaatattagt caaggatatc agtctatgaa gtaagttttc  14820
aatgttatat gccacaagat gcagctgtcc tattttcact tccagtaatt ccttctgaat  14880
taatacacct taaaaatagc tgcagcttct caaatctgtg agaatcgtat gtgctgcttg  14940
ctacactttc ctttttcctg aaggcctctt tgaggtcttt caagaactca attcaattca  15000
gcaacaatta gggggtctaa ggtatacaga cgctgtgcaa gatgctcctg agacacaaag  15060
aggaggtcaa gcccctgcct tcaggcacct ctctataata taggaggaga aagagaagaa  15120
acactaatac acataggtag gtgccattaa aagggtgcat acattaaagc caggtggtag  15180
gtgcaagaag atttgtaacg tgagaatttt ctgcatgttt gaaatatctt ataattttta  15240
aaaattaaaa tgggagatac atatatatgt atttatgtat gtatatatgt atgtacatat  15300
acacacatat atacataaat atatacataa atatgtatat atgtgtatat agacataaat  15360
atgtatatat gtgtatatat acataaatat gtatatatgt gtatatagac ataaatatgt  15420
atatatgtgt atatagacat aaatatgtat atatgtgtat atagacataa atatgtatat  15480
gtgtatatag acataaatat gtatatatgt gtatatagac ataaatatgt atatatgtgt  15540
atatagacat aaatatgtat atatgtgtat atagacataa atatgtatat atgtgtatat  15600
agacataaat atgtatatat gtgtatatag acataaatat gtatatatgt gtatatagac  15660
ataaatatgt atatatgtgt atatagacat aaatatgtat atatgtgtat atagacataa  15720
atatgtatat gtgtgtatat agacataaat atgtatatat gtgtgtatat agacataaat  15780
atgtatatat gtgtgtatat aataatgtgt gtacatatac acacatatat acatacataa  15840
acattctgca ttataccatt cactttgtaa cccatcttcc ctaaaaactg tctcataaag  15900
agtcttcttt tccctgtacc tatgcaatgg taagtagcaa aacacacatt cttttgggtc  15960
cccataacat tccctgtagt ttgcccttaa cagtctttga tgtgaaattt actgtttctg  16020
tcttaacctt gcctgtctcg cgtacatgga gttttggctc ctggctccta gtctgcatct  16080
tcaccccatc ccttgcccaa agaatctggt tatgtgacca ctgctcatct tttctgctgt  16140
cacaactcca gtccaagcca caaacctctc tctcctggac tcctgcgggg agttcctttc  16200
tctccctgca tgagtctatt ctccgcacaa ctggcagagg taagtgagac tgcggaagag  16260
gcaagtttgc aagtccagag gaaatgaaga ctctgcttgt gcacatgctg ggtttgacgg  16320
gtgctggata tccgatggat ggcccttaag gtgagctcaa ggcttaaggg agagataggg  16380
gctgatgatc tgagattcat cagtgtgtgg ctgatgttta aacccagggg acaggataag  16440
aaggttattc cagggagagc gtagataaag aagctaaatg gcttctgggt ccttagtcat  16500
tcaaaatcgg acctctgagg caggaggaaa gcccagaaag agtagattcc tgggactcac  16560
gggataaaga ctttcaaaaa gtgggggctg gccagtgctg ctgaaggaag tagcaggacc  16620
ggaacagaag ggtaatcgtt ggacctggag aacttgaatt tgaattttaa ggttggtaac  16680
cttaaaaaag agcaatttta gataccttt gaaattattt gcaagatttg tttggtatat  16740
gtgttattcc aggcaaaggg accagaaaag taaaaaatac ttactgaaca gttactgcat  16800
gcctggcact gtaacaccct gtttaattct cacggcaacc ctatagagta ggtgtcatca  16860
tccccatctt acagatgagg atatgaggtg cagctagatt aagcagtttg cctcaggtta  16920
caccaactgg ttaacgtaga gctaggattt gaacccggat gggctgatcc cagagctcat  16980
gctttaaatc gctagactgg tgctcacaga agactgggac cgaaaaaaat taataaaaaa  17040
```

-continued

```
aataaggagc cccctgggct agcaaattag gagttgttca gacagatgtg aaaaggaaag 17100
caaggcagag ggaaagtcac tgtacagaag agagagaccc atgacagcag agacagtgag 17160
ctggtaaagt ggctggcgat ctagcccctg aaaatacctc cagagaggca ggctcacgcc 17220
tgtaatccca gcactttggg aggccgaggt gggcagatca cctgaggtca ggagtttgag 17280
accagcctgg ccaatggcga aatcccgtct ctactaaaaa tacaaaaatt agccgagcat 17340
ggtgacaggc acctgtaatc ccagctgttc agttggctga gtcaggagaa tagcctggat 17400
ccgggaagtg gaggttgtag taagccaaga ttgcgccact gcatgccagc ctgggcgaca 17460
gagcaagact tttcttaaaa caaacaaaca aaaaagaaaa aagaaaagga aagaagaaag 17520
agacaaagaa agaaagagag aaggaaagaa aggaaggaag gaagagaagg aaggaaggaa 17580
agaaagaaaa ggaaagaaag aaaaagaaag aagaaagaaa ggaaagaaaa gaaagaaaaa 17640
gaaagaaaga aaatacctcc agagagccag gtctcttagg ccttctgaga aactcacatc 17700
ccttttgatg aacacaaatg cttcacactc tcaatgttat tggtaatcca agttatcaat 17760
atacctaaat cacttagtac tgaatctggc atatagtaat cacctaatga agagataaga 17820
gtcatggagt attctgaagc aattagaatc aatagactca atatacacat ggcaacaaag 17880
ttggatctta aaaaccgacc tgagtgaaaa aggaaaggga aagatacata acacggtacc 17940
attatgtaaa ttgataatat atgcttacac aatttgtaag aacacataca aatagataca 18000
tgtatattaa acatactcga acggttaccc tatggggtgg tggctggagt gggggtaagt 18060
ccgtaagctg taatggaacc taaacaaata catgaaacga gtaggaatca gaaggagtaa 18120
caataaaaat gtgccatgaa ctgaggagtg taaattaatc aactcactgc atctgaggtt 18180
aaaaatagaa agatgataat tgttattctt attactccta ggtcttccac ttgcactcag 18240
ctttacaatg ttggactatc cttcagatgg caccctcctt gcacttgctc aggcaggaga 18300
gctttttcct ccagctttct aggtgattta atatatcagg gaataagtat aaaaaaaggc 18360
acggtgctcc ctgggtagcc tttctggact tcagagctaa attgcaaagt cagttttaca 18420
catgtgattt catctatgaa attagggcaa ggtataaaac tggcacagaa aaaatgtgat 18480
ttattatggt gttactatcc cttacaagcg gagtgtcagc tgcctctttt tgtccactga 18540
tttaaggcaa gatgaactga aagtggctat gatcacgtct tcaaaagcac actctggccc 18600
ctcggctgca ggcgccctgc acattcccca gctgcgtgtc cggtggtgac acagtgcata 18660
attgtggcgc cttcctggtg caaactgtct cacttagctc cgtcttgctg gcacagcaga 18720
aaggaagaaa tcgaaaatgt ttggatttca aaggtaacaa gaagctggaa aacaactact 18780
ggccgagtct gagagtttca gcggagactg gtgcagcctt gtgtttttcc actgacagct 18840
gaaaatgagc ccagcttcag tgaagcttgt ttccttccct cctcaaggtt acccacaatt 18900
ctcagttctc tcaggaaagc caaaaaatga atttgagggt ttaggattgt ggttctttta 18960
tctattacag gattgataat atgttcctcc accagatgtt ctgcttgtaa caatactcac 19020
ttcctgacac tactgcatat gcaggagtgt cactaccaag gtaaacacag aattggctgc 19080
ccaattccaa atccctgaac tgagtgagag aaatcagaat tataataggg gattcaacag 19140
agctggctac ggatgtgcca gtggtcagat actttgctca tcatacgcag gtgctgctgc 19200
tctagcaact gctcactgct tcatttcctg ccttggtctt taaatactgc ttttctcagc 19260
tcaattggct ttcttccctc tggcagtcac gtttctttgg gtcaaacagc aaatgattct 19320
ttagaatcac ctggtactca aaggagctac aagacattgg gcatccactt ccactctctt 19380
```

-continued

```
ggaaaaacaa ttttatggaa gccaaggttg ccatagtgcc tcttgaggtt gtttgctcag  19440
ccaaggccca agctttgtgc ttcaaacatg aaattagaga gcttcagaac aagatccaca  19500
ttttcaatgg cctcacccaa ctggataaaa gaacaattgc catatctcaa tgaccacctt  19560
ttctcaggtg ggatggtaga tgctggaatg ggtcacagca ttgcccaacc aaactttgca  19620
aaaaaggctg gaagctctga ctggggaccc taaatatgca aaagttaata ggctcttcat  19680
tcagaatatg aaccccgtgt atggatatag ctaaagggtt ggcctttatg tttctattcc  19740
ttcacaaacc tggtagaata gatatgcttg tttcccttta aaaaatgtca acaattgcat  19800
ttatgatgct gtgtatagta actcacagat catgctccat gaaaatgctt cagaacccaa  19860
tataaggaga ttttttagcc atgtgtgaca aaagagaggc catttcagtg ttgaaattgt  19920
tcagagaagt atttgattat gttttctcag atctttttat ttttattttt tttgaaacag  19980
tgtctcactt tgtcacccag gctggagtac agtggctgtg gtctcggctc actgcaacct  20040
ttgcctccca ggttcaagcg attctcctgt cagcttcccg aatagctggg attacaggcg  20100
tatgcaccac catgcctaat ttttgtattt ttagtagaga cagagtttcg ccatgttgac  20160
taggcttgcc ttgaactcct gacttcaggt gatccaccca cctcagcctc ccaaagcact  20220
tggattacag gcatgagcca ccgtgcccag cctgttttct cagatcctgt attttgtttc  20280
tgaagccttc atttctatct tcttattcat tttggaagta gtacacctaa gtaaggtttt  20340
taacaatcaa atatctttgg aaaattccct ggttcctttc ttattcctac aaaaatatgt  20400
tcagtatagc tgatgttatg tttctttcaa attattcatt tctctatctc agaatttatc  20460
tcatgcctaa ttgttattga atagtcttca cttcttgtca tccagtttct ggtctcttat  20520
ttcactctaa gtctaattgg ctattagaat aaagagcttg taacagattc tttctccaat  20580
atgtcttatc ttttgactgc atgccagtga caaactgtta actgttttga ttcttcataa  20640
cattccacag aacatgctga ctcctctctt cctgaaagca atgcccaagc acagcattgt  20700
tagatagtat gtacgcaaca gggacatggg tgcatagcaa aaactagaag gaaggaggac  20760
cttccttagc aatgggtgat atggtccctg gacttagact ccaaagggtc gtgaggtgaa  20820
acacacatcg tccataccca ggaagcacac aggtgggatg gaagagctgt gcctaatgaa  20880
acttcatcca cgtggaggtg gaggaggctg cagctgcaag aactcagagc tgccttaccc  20940
agaccaggga ccagggaggg ctttctggag gaaacagcct ctgaactgcc agctgataga  21000
ggagctctac ctcaactctt ctggttcccc agggctgctt ttccacgtcc atttattggc  21060
actgaagttt gaataccttc aggggcccga aagcctgcca ggtcctcttc tctgcagagc  21120
aatcacacca acctgcaaag ggctaggaaa gggctgtcat catctcctac tcagaaactg  21180
gttcactgga aggactcagg ggccactgaa tacatcctgg cagctttcac aagaagggct  21240
tctgactcaa ggatgtttcc atctttgcca ggtcgccttt tctccttctc ttagagtttg  21300
gaggacgcaa atgtgctgag aagtcaacct ttcctgcaag gtgagacaca agggcctttc  21360
ccagcagaaa gaagagagca aatggaaggt ccttcttcct ccagtagagg atggactctg  21420
tctggcagcc acccaacagg aaaagcacaa tgcatgcctg cctgcttccc tccctccctc  21480
cgtttctccc tccctccctc cttcctccct tccattctct tcccttcccc tcccttccct  21540
tcccctccct tcccttcccc tcccctcccc ttcccttctc cctctccttc ccttcctctt  21600
cccttccttc ctcttccctt cctttcccct cccctccctt tcccttcctc cctcccttcc  21660
tcccttcttt ccttcccttc tttccttcct catttcctcc cttccttcct tccttccttc  21720
ctttcttcct actttcctac ctttagggct ctgtgtcttt ggagtccatt ctgattatgc  21780
```

-continued

```
tgtaatgtct gccccttcct cttctctgtc aaaaaatgaa agacatggaa gccacttgcc  21840
ttttactgaa ttaaaaatta gtaaaagagc taaaaattaa tggttaaaaa tgtacgcata  21900
aattatgcag tatactaacc aatgaaaaga tacacttctc ttaattaaaa gctgacaggg  21960
agggaaacaa gaaaagagaa acacaaaaca ataatctaaa tgacctatta gttggaagaa  22020
caacatcaga gaaaatagat actgtgtata gtcatgtgta tgtctatgga ataacatttg  22080
tagagaaatc tggactgatc ctttctgagt aaagagagct gtgggtacaa ttaaggggag  22140
attgaaagga atccaaaagc atagcagatg ctgtgcctca ctggaatggt tgccgatctc  22200
ctccaaacta tgaagtgttt gaggctcaac tttaatataa ttaagataca aagacagaat  22260
gagagaaaga gagaagggag ctcactggaa gaacactcaa gattccttac tactcattct  22320
ctaaaattac aattgttcta gatggaaaag aaaaaaagct tctctgttaa aaaaggagct  22380
tgtgctatag gaggtttaaa atatacttct gacccatctc caacattcta aatccttccc  22440
agaaaagtat gccaatccca agaaatattc aatcaaattg ctggaaagaa aaatacaaaa  22500
tattaaaatg tattaggaag cgacagtaat taaatcagaa ctggagcagg aatagaccag  22560
cagatcaatg agacagacat caagtcccgg aatgtggact tgcaaatgca ttaagtaata  22620
tgatatgcaa taaaggtggc acagtgaacc aatgggaaaa aaattaatct tataataatt  22680
gatattgcaa taattgtcta gtaattgggg gaagaaataa gcttattcct tatctcattt  22740
ctttttttct ttttgagaca gagtctcact ctggtagccc aggctggagt gcagcgatgc  22800
gatctctgcc cactgcaacc ttgctctccc gggctcaggc gattctccca cctcagcctc  22860
ccgagcagct gaactacagg cgtgtgccac cactcccggc aatttttttt tccattttta  22920
gtagaaatgg ggtttcacca tgttgcctgg gctggtcttg aactcctggg ctcaggcaat  22980
ccacccgcct tggcctccca aagtgctagc attacaggca tgagccaccg cgcctggcag  23040
ctcatttttt agactaaata aattggagat ggctaaaaga tttttatgta ggccaactat  23100
gtttttaaaa agtttttttt tttaaggata tctgctggaa ccaatcatgc caccaaccaa  23160
agatgcaaga ctataaaaca tacccagttt ttcaaagcat ttaaaaatta ttctaaaaat  23220
atttttctc cagaaatttt gcattgattc cctgaagaag cattaatatg ggacctgact  23280
tataaaatga tgaactcaat ctccccactc aaggtaggag tctctcagat ttaaaaaata  23340
agcatcctag tcctcttgtc cctgtaaaag ttaaccctta cacctgaaac accaggagac  23400
tggcggttgt ttgcataggg gttacaatta aagttgagct acctctgaca tctattaaca  23460
ccaaaattag taaactatgc atgtatggag acttttatga ttgaacttgt ttattgagtc  23520
aagagatata gtttacaatg aaaatttggg gcatatcaaa atgaccttgg cttagcttag  23580
catttgctga tgttaactat tttcttcatt gggctgattt tagttgctta ggaaaaatac  23640
aaacacacac actttaaaat tatattaaaa tcccgtccta aacctcagag tccagaaccg  23700
catcctaaca ctggtcatgc ataatatgtt taaatttttg tgctttaaaa actacaaata  23760
aggaatgtat taatagttcc acaatcaatg gtcagttagc cgagggaaga ttagcatagt  23820
taaagactta aaatggctta acaacatata tcaaaaggac aaaataaggg gaacagagtc  23880
tagaaatgag gaaactggga cacaggcaaa aaaaaaaaat gagaactggg acatgaataa  23940
cgcaagggat aagactaata cacaaaacac cccaaataaa tagccagcat ttgctgagct  24000
cttactgtga gcctgttcta agcactttac atatattaac tcatttcatc ctcaaggaac  24060
catctgaggc aggcactgtt atcatctcca ttttacagat aaggaataga cccagagagg  24120
```

-continued

```
ctgagcaact gggcctattc cacagctact atggtggaga tgagatttaa atctaatcat  24180
tggctccaga gcccatgcac ccaatggctg cactaagtga atgcatgcgc tatcaacgtt  24240
gccaaaagtg ggccacagct cggatctgcg ttttccagta gccaaagcag agagtgtgat  24300
cagacctcac tttaataagc aagtctcaag ccagagagag gtggtatcag gcagcaaaca  24360
ggctgctagt cgaaatccca cttcttctct gagtggtcca tacagtttta ctctacttgc  24420
ttacagaatg aaaatagctg gagttcaggt gcgctttcaa tgccctgttg tcaggattgg  24480
gcttttcaag tttatttttt gttgttgttt ttaatagact gtacttttta gaaaattttt  24540
agatttacag aaagattgag aggatagtac agagagttcc cgtatacctc acacccagtt  24600
tctgcaatta ttaacctctt acattcatgc ggtacatttg ttacaattaa tgagccaggg  24660
ccggccgggc acagtggttc aggcccctaa tcccagcact ttgggaggca gaggcaagcg  24720
aatcacttga ggtcaggagt tcgagactag cctgaccaac atggtaaacc ctttctgtac  24780
taaaaataca aaaaattagc caggcatggt gctggttgcc tgtattccca gatactcagg  24840
aggctgaggc acaagaattg cttgaaccag ggaggcggag gttgcagtaa gccgagatcg  24900
tgccactgca ctccagcctg ggcaacagag cgagactcca tctcaaaaaa aaaaaaaaaa  24960
aaaagaagga aggaaggaag gaaaattaat gagccaatat tgagacatta ttattactaa  25020
agtccatgct ttatgcagat tttcttagtt tttacctgct gtcatttttc agttccagga  25080
atgcattcag gatgccatac cacatttagt tctcatatct gcttaggctc ctcttggcta  25140
gactgagttt taatctactt tctgcagagc ctgagaactt tagcataatt tccttgaaat  25200
tacagctcaa tattttcaag cacttataca aacagcctaa tgttacgttg gcccataaca  25260
gtgtttcaag gtaataaact tctttgtttt ctgtgccgat tgaaagaact gctgcttagc  25320
ctcctgccag atgatgaact gggtacacac gagcattttt ccaggtaaag catatttcgt  25380
gcgacttctt aagctgcagc cttatatgca ataattgtcc atttacaaga cttatgttcg  25440
aatttcaggc actctgtttt cactaaccat atcttcaact ttgataagta ctgctttaat  25500
cactcagaaa atttaacttg actaattttt tttcaccatc agtttttttt ctgttgactc  25560
tttctccttt ttctgtttgc ccagaaacat gctcaggatt ctctcaggct ttaaaaaatg  25620
aaaaaatgtt tcctgcaatc tagttactcc ttgattctct tgttctgttt atcgctggaa  25680
ttcttgaaag cttggtgtat tagtcttttt tcatgctgct gataaagata tacctgagac  25740
tggataattt ataaagaaaa agaggtttaa tggactcaca gttccacgtg gctgaggaag  25800
cctcacaatc atggtggaag gcaaaaggca tgtcttacat ggcagcagac aagagagaat  25860
gagaaccaag ggatttcccc ttataaaacc atcagatctt gtgagactta ttcactacca  25920
caagaacaat atggggtaaa ccgcccccat gattcaatta tctcccaccg gggccctccc  25980
acaacacgtg ggaattatgg gagctacaat tcaagatgac atttgggtgg ggacatggcc  26040
aaaccatatc acctggccta tagcattatt tccatttctt ccccatcctt ttattcctca  26100
aaccggtaca accagacctc tttttttttt tttctacctg aaactgctct tttgagggta  26160
gctgataagt ccaaaatact gtcacctttt ctcaattccg ttccttctta tgcctttgga  26220
gcaattgact gtgttggttg ccccctcctt taaagtgtct ctcacttggt ttttatgact  26280
aatgatcatg attttctttt tcctctctaa acattccgct atctttttag cttcccttcc  26340
ccctcccatc ccctaaatgt ccttgtttcc cagaatctgc ctcacctctt tgacttctct  26400
atgccctgtc attcactcat gggtctttat tacattattg catctgtgtc aataactctg  26460
gtctttctct taagttccag tctcccattt tcaaatgtcc ccagacattt ccaattgagt  26520
```

-continued

```
atctctccaa tgtatttaac ctgctaaata tctaacacat aatctttccc atcaaatcgt  26580
ttcctcttaa gcttttctta tttcctatta gtactcctgc acttctccca ggagcccaga  26640
cttaaaacct tgaatttctc accataacct ctcttttgtc tcccataatc aattagtagc  26700
aagtgttatc aatgattact tgacaatatc tttttctatt tccctccctg ctatgatcat  26760
tcatctagca agaagagttg gccctttgta tctgtggttt ctgcatccct ggattcaacc  26820
aactgtagat ggaaaatatt tgaagaaaaa agcgtctata ctgagtatga aaaaatttta  26880
tttcttgtca ttattcccta aacaatacag tataacaact acagcattta cactgtagcg  26940
tatagatctt ataatctaga aatgatttca agtacaccat tatatataag ggacttgagc  27000
atctgtgaag tttggtattt gtggggcata ctgggaccaa ttcccccatg gatacagagg  27060
gacaactata tttactcagt gcttactaaa taccagttgg ccaatgtgtt tttctttttc  27120
tgttttcctg tctttagttt gccccttgcc aattaattca atagtgctgc caatgccagg  27180
tgtaccttca gaatattcta ttctaatttt gtcatctcca agcttaaaaa tatttaatgg  27240
gccaggcgca gtggctcaca cttgtaatcc cagcattttg ggaggccaag ggggggtgta  27300
tcacttgagg tcaggagttc cagaccagcc tggccaacat ggcgaaaccc tgtctctaca  27360
aaaaagtata aaagttaacc aggtgctgga gcatttgcct gtggtcccag ctactcacga  27420
ggctgaggca agagaatcgc tttaatctgg gaggtggagt ttgcagtgag ccaagatctc  27480
tccactgcac tccagcctgg gtgacacagc aagactctat ctcaaaacaa caataacaac  27540
aacaacgaaa aacatttaat ggctgcacct tgcctgtgaa aaatgcattt cttggccaga  27600
tgtggtggct caaacctgta atcccaacac tttgggaagc taaggccagg agttcgagac  27660
gagctgggat atataggaag acacaatctc tacaaaaaaa aatccacaaa attagtcagg  27720
cttagtgttc atgcctgtag tcccaggtac tcaggaggct gaggcaggat tcctcaagcc  27780
caggagttca aggcttccgt gagctatgat ggcacaactg cactccatct tgggtgacag  27840
agcaaggtcc tatctctgga gaaaaaaaaa aaagaaggca tttcttagga gagttcttct  27900
ctgtagagtc ctaagggttc catggaactc cttaaaagca tcagagtatg tgagtgcaat  27960
gggaggaagc atttagccag agcagttgtg ctcccattgc atattaattt ttaaaaaaca  28020
aagctataaa aaaaagttga aaactactac gttagcatca gcctgacatt taatggcctc  28080
gtaaatcaaa ccttaattga ctttttagcc agttatgcta ctagccaact acagacaaca  28140
cactttttaa ccaaattaga ctaatagttg tcatcagtgg aaatcaagtt tgccattctt  28200
ccatgccttt gctcacacca ttaccttttc tggaatgtcc tgtactcatc ttcctgtgtt  28260
gaactctata cccaacttta aaaacctagc tcaaagttca acacttccat tccatttcaa  28320
aaagagcttt cctcttcctt aaagtttaag aactcatttt catgaatctt tttggcattt  28380
attgcacaca tgcttgcttt gtgttatttg tgttcatgcc tcatatgccc ccaaggtgtt  28440
ttagactcct taacggcaaa aatgatgctc taaacacctt tctatctttc atagtgtctt  28500
agtctgtttg tgttgctata aaggaatacc tgaggctggg gaatttattt aaaaaagagg  28560
tttatttggc tcacagttct gcagctatat aagaagcata gtgtcagcat ctgcttcagg  28620
tgagggcttc aggaagtttc cacccatggt agaaggcaaa ggggagcagg catcacatat  28680
caagagagga ggaaaaaaag gaaggaagaa aggagggtgc cattctcttt caacaatcag  28740
ttcttgtggg aactaatggg acaagaggct gggcacggtg gctcatgcct gtaatcccag  28800
ccctttggga gaccaaggtg ggtggatcac cagaagtcag aagcctgaga ccagcctggc  28860
```

-continued

```
caatgtggtg aaactccgtc tctactaaag atacataaat tagatctagc tgggcctggt  28920
ggcgtgtacc tgtagtccca gatactcagg aggctgaggt aggataatca cttgaacccg  28980
gaagacagag gttgcagtga gcttgtgcca ctgcactcca gccggggcaa cagagtgaga  29040
cggtctcaaa aaattttaaa aactttaaaa ataatagagc aagaaagcac caagttattc  29100
aggagggatc cacccccaat gactcaaata cctcccacca ggcctcactt ccaacactgg  29160
ggatcaattt ccgtatgaga tttggaggag acaaatatcc aaactatatc acatagtaat  29220
gaacatagta ccttatctat agaaagcaat ggctagacaa ctgttgaatg gctaaccaaa  29280
tctgctttcc tatggtctcg ctctagaggg ggtcagtatg agtttctgtc aaaaggagaa  29340
aaaaaaatgt atagtcagtt ttgtgtgtgt gtgtgttcat gtaaaagaga tcaagagaaa  29400
agaacaagag aaatcatgaa aaggaggggg aatataagaa taatacatag aaaaaagcaa  29460
attatcttgt ttatcagtaa tacccaaggg ggtagaaatg gtaagtaata atccttcttc  29520
actttgtctg tagttcactt ttttgcacct ttattttgat gaattcacat cgaagacatt  29580
aactcattaa ggcttccaat atttttggag ataagaaggg ctgctatgct ctttatagat  29640
ggaaaacttg ggtcattaat aactcaaaca aggacataac aaagaaatgg agcataaact  29700
gccaggtcct gactgtagat ttggattccc agttggtgtc ttgtcaccct ttgttactct  29760
tcctaaagtt atgatctttt cttgtgcata ggaaattcat agtgatttcc catcaccctt  29820
gggattatca tagctccttt aaggtcccct ctatgcactc aataacatca acagtaagtg  29880
ttcttcgagc acttactgag tgtatatcat tgtgttctca cgcagcaccc acagatctca  29940
ccaagaacct agctgaagcc tgtagaatga ataggtaagt actgccatgc caatctggag  30000
tactcaagcg atgcaaatga ttcctttaat tgtacttttg caggcttgtc agttttgctc  30060
atggagaagt ggctactgca tccatgttat atctatgtaa tgttggactg cgaagcatca  30120
cttgactttt tccaagcaga aattacagct gatgacaagc tgctgctgag aaaatggata  30180
tttttctgaa ttcagttcta cgtggaaaca gctgactagt ttccattgct gtaagatggc  30240
tcttttgctc ttggttgatt ttgagtaatg gctttacttc tgtagaaagg agatttcatt  30300
tgaagtccac tcagggattt ggttcaacaa actggagtac aggtttcaga aaatatctct  30360
ttaatcctcc aataataaat tttctcatct ataattcctg gaacacttca tcctttgcag  30420
ccgagcatat agatagattt gttgctcact gtgttctgat tgccactttg acctgctttt  30480
tcaacttagg ttacaaatag aacagaatct ctctgatttt tctcattaat tgtttgaatt  30540
cccacttttc ctcattagca agaagtccag tatcttcctg agaacttcct tttctcaatc  30600
taggaactta cttggtccat aaggtaacag tcttatttct gactatcaag gagagaaata  30660
acaggagcca ttatcatctt catggtgtca cttttgaaaa ctggtcctct gtagatcttc  30720
agattcttgc gttagtccat tcagctgcta taacaaaatt gcatagacag catggcttat  30780
aaataacaga aatgtatttc tgacagttct gaaggctaga aagtcaaaga ttaagacact  30840
ggctgatttg gtgtctggcg aaggcccatt tgctcataga tggacgatga cctttcactc  30900
tgtctgcaca tggcagaagg gcaagagagc tctctgggtc ttttttataa gggcactaat  30960
ctcatttttg aggaccctgc ccccatgact taatcacctc ccaaaggcac tgtctcccaa  31020
taccatcacc ttgagggtta ggatttcaac atatgatttt ggggggacag aaacacgcag  31080
tccatctcgc ttgtccactc catggtggta ttcttgctgg atcagtttcc tccttggggt  31140
gcatttgtgt tccatgtcta acttgcaagt tatagcaggc ccgatagcaa agtattccaa  31200
tgttggtatg cagaggcatt gaataatcag aatgaaccca cgccataaac aactggtaga  31260
```

-continued

```
gctgcagaga gtaccagctg attatgagcc ctgggtaaca gtggttttta gttcctatgt  31320
ccgtcagccc ttttctccca tagtagcccc actgtgttga agtggctgaa tcgacagaag  31380
cttccagctt gggccacatg ctcatggaac caattctcct tatgagccgt acaagagctg  31440
ggttgccatt ctggataccc tctttcttca agagatttta tttcaaggat attttttctt  31500
ttatcaacta cagggattat ttagaatctt agggcagtgg tgcccaacct ttttggcccc  31560
agggacaggt tttgtgggag acaatttttc catggaccag tgtcaggggg ctgggaggca  31620
tggttttggg atgagtcaag tacattacgt ttgttgtata ctttatttct attattatta  31680
tattgtaata tataatgaaa taattacaca actcaccata atgtaggaat cagtggggag  31740
ccctaagttt gttttcctgc aactagacag tcccatctgg gggcaatggg agatagtgac  31800
agatcatcaa gcattagatt ctcataagga gtgctcagcc tagatccccg gcatgtgcag  31860
ttcacaatag gatttgctca cctatgagaa tctaatgcca ctgctgatct gacaggaggt  31920
ggagctcggg cagtaatgcg agggttgggg agcagctgtc aatatagatg aagctttgct  31980
cgctcgcctg ccactcacct cctgctgtgt ggtccacttc ctaacaggtc acagactggt  32040
actggtccat ggccagggag ttgggaccct gtcttaggga gtaggggtgg agttcccttc  32100
acttctagaa ggccctggat tagtatccca gagctgtcat tacagagtat cacaaaccag  32160
gtggctaaaa acagacatga attctctctt atttttgatg gcttggaagt ccaaagtcaa  32220
ggtgctgcca gggccatgct ccctctgaaa tgtgtagggg agaatccttc cttcctcttt  32280
ctagcttctg gtggtttgct ggcaatcact ggcatcgctt ggcttgcagc acttcaacat  32340
ctgcctttac tgtctcatag tgttctcccc tcatgtctcc aggtctctct gtctctcttc  32400
tttgtataag gaaactagtc atattggatt aagggccaac cctactctag tatgacctca  32460
tcttaaggtc acatgcaatg actattccag ataaggtcac attctgaaga actgggagtt  32520
aggacttcat atcttttgaa ggaacacagt tcaaccaata acagcccctg tactgtttta  32580
caaataggta ttcctctcct tcccaaagtt cttcatagca gagacaactt gtaccaaaag  32640
gcaaaatacc ttattatgta accttaacct aggatcatag atccctactt gtctggtgct  32700
tttataagcc acagaaccac ccgggaaatc attattaaga caaggaaagg ccaagtgcag  32760
tggttcatgc ctgtaatccc agcactttgg gaaattgagg cgagtggatc acctgaagtc  32820
aagagtttga gaccaaactg accagcatga cagaacccca tctttactaa aaatacaaaa  32880
attagttggg catggtggca tgtgcctgta atcccagcta ctcaaaagac tgaggcagga  32940
aaatcacttg aaccgaggat gccaagatag cagtgagcca atatcgtgcc actgcactcc  33000
agtctggatg atagagcaag atcctgtctc aaaaaattaa taaataaata aaaagacaag  33060
gaaagccttt tccaaggaga cccttctgct ttgctagttc agagaacttc tctttggaga  33120
aaacaaacac ccagtccatt agcagcaacg tcagggattg aattcttagg gcagcaggct  33180
gggcacagtg gctcatgcct gtaatcccag tactttggga ggctgagatg ggtggatcac  33240
ttgacatcag gtgttcgaga ccagcctggc caacatggtg aaaactcatc tctacaaaaa  33300
atatgaaaaa aaaaaaaaag ctgggtgtgt tggcttatgc ctgtagtctc agctacctgg  33360
gaggctgaag caggagaatc acttgaaccc gggagttgga ggttgcagtg agctgagatt  33420
gccctactgt actccaacct gggtgacaga gagagactcc atctcaaaaa aataaagaat  33480
tcttcgggca gcagtctttc ctccacctca tagaccatgg aggtgagcca gctctgacaa  33540
accatgagaa caatggcaga gacatacctg taacgtaact gactggggca aagacaaagg  33600
```

-continued

```
tgaggaaaat gacaagtttg aggaactatg agaccaggca gtggggaaca ccactagcag  33660
aaatgatgga agttctcaag aataacaaca gagaaataga ccatggccag agtctagaac  33720
cctccaggga aaggagatgg gctccagagg cagaagagga cgttgaaggg aatggggagt  33780
gggtgaaata tatagacgat ggggaccacc caagagcagt cgctattgca aaactgagga  33840
gaaggagagt ctggaggggg tggtgggaag ctgggtctcc taaggaggtt ttgacaaaag  33900
cagtcatgga gcgggcttag aaatcacagt tggggacagg gtaaagttcc tcgggatata  33960
gaggatgaga ttagaagagg ttccaactag ggtagtgtgg agaaaagcac tattgaccca  34020
aaaaggaagg agaatgtggg tggaagtggc agagaaagag gggtttgagc agagagtggt  34080
gatttttcta atgcagagtt gtgggaggtg gagtgcaggg agccaggctg ggtggctgtg  34140
ctgatgtgat taagcactta ctgactgcca ggcaatgggc taagtacctg agatgctttg  34200
tctgttatcc ctcccgaaac ccctctgagc aggtgcagtt attattctca cttcacagat  34260
aaggaaattg aggcacagag aattgagtaa cttacccaag gtgacatagc tcatatatgg  34320
taaagcaggc tttgaactca gtctagctcc cgaacctaag cttgtaacta ctatgctttt  34380
cccaaaaaaa gggggctggc acaaaaagag ctgagggggg ctgggcatgg tggctcatgc  34440
ctgtaatccc agcacttcgg gagactgagg caggtggttc accagaggtc aggagttcga  34500
gaccagcctg gtcaacatgg tgaagccctg tctctactaa aaatacaaaa attagctggg  34560
tgtggtggtg tgcacctgta gtcccagcta ctttgggagg ctgaggcagg agaatcgctt  34620
gaaccccaga ggcggatgtt gtagtgagcc aagatcatgc cactggactc cagcctgggt  34680
gacagagtga gactccatcc aaaaaaaaga agagctgagg tgatggccac catcagcatc  34740
agcctggaag ttatagcagg atgctaagtt tctctaaagc tgtctttctt aggacttgaa  34800
aaagataact tgggtttgta tcccatctct gccattagta gtttactggc tttggataaa  34860
ttacttagcc ttactgaacc aactttggat ttttatagag atactgtaat gaaaggaata  34920
aggtatcagt cttagcagag catccagagt gttcctatta aaacctaaat catatcctgt  34980
cattgctctg ccccaaacca ttcaatggct tcccaactca aagttaaaaa ctcatctttc  35040
cagtggcctg caagagccta tgctatccgg tgtctgacct catctgttgt tcctttctcc  35100
ctccctttct tggctccaga cgcactctgg tctccttgct gttccttgaa tacaccaggc  35160
acactctttt cacctgaaac actttacccc agatatctta gcttactctc tgcctccctc  35220
aattcattga tgaaatgtct cagtgaagtc ttctctctct cctctgtaaa agtatactct  35280
ctgttcccct tctttactgt tctagctact attgctgtgt aacaaatcac tccccaaatt  35340
taatgagtga aaacatcagc catcatctta tttctcacgg tttctgaggg tcaggaattc  35400
tggaagggct cagctgggag gttctggctc tataatctct tatgcagtga gagtcagatg  35460
ctggctaaaa ctgaaacaaa gcagggttct agtagctgag ggctggctgg gtctctcaga  35520
tatagttcag atctcctcca gggggtctct ccacgtgggc tagtctgaac ttcctcacag  35580
catggtggcc tcagggcagt ggactctgca tagtggctga aggcttcgca gctgagtatt  35640
ccagcaagca aagtgggagc tgtattgcct catatgaccc aaccttggaa tccacacagc  35700
atcacttccg tgtattctac gggttgaaaa gtcacaaaaa ccaaccagtt tcaaggagaa  35760
ggaacagaga tcacatttct caattggaga agggtcaaag tcacattgta atcagagcct  35820
atgggatacg aagtattgcg gtcaggtatg aaaaatttga tttgctgcat ctgctttact  35880
ttctccacag cgttcatgat ctgcttctca catgatattg acttacgtca tttctgcatt  35940
tcctgtcttc cacactaaaa tgtcagcctg ttttgttcac tgctgtatcc ccagagccta  36000
```

-continued

```
gcacggagcc cagcatgtag tggtatccaa taaatacttg ttgcatgaat gaattctgtc  36060
ttttaatcct agctataggt ttctaagtta aatattacta taatcatctt acagacgagg  36120
gaaatgaggc tcaagaagat ttggtaactt atgcgggatc actcagccac ataatggaag  36180
agacagcatt gaagtacaca tgcttgctct gtctgctctt ccaagctgct catcacacag  36240
ctgcacctct gaggacttcc ctccccagtc cacctccacc cttacccaga gacacacatg  36300
gccacaatcc actagcagac caaaattcaa tttttcccca gttggttgca ctcaagctga  36360
gagcaaagca attgcacttt aaatcccctt acagcagata tttcagagca tgttcggaag  36420
aacccatcac acttggcttt tagatcttat ttctggtttg ttacaaaaac acaattaaat  36480
gaaaggttag gtagcttttg aatggccagc tcaaagtttt ggcttatttt tgccttgctg  36540
tctttatagg cattttacca atatttatca ctatttccct tagggaaccc ttagatctgt  36600
gatatttgaa ataataaagc ctctccattg gccctttaaa aggtttgtgg taaaaccaca  36660
ccattaacat tcacagttcc ttatttatga ggcctgattg cacttatttc catatttctc  36720
actgtttctc cgatgaggat ttcacataat agtgtttgaa ggctaaagac ttcaaagcag  36780
attctttact atttttatct tgaaaaatat tcaatatttg tgtaattaaa gtgaagtctt  36840
cctagagaaa atgacaactc aaataatctt aaatgtacct ccaagaaaaa agctgtcaaa  36900
gtgacattta gtagtagagt cacattctct aaggcctttg cttctccttc tgagttctta  36960
tcatctttga aggttatgtc atggctgact tcaaatcact tttaaaatta ttatggcctt  37020
ctttaaatgt gagttctgaa ggtgaggggc tttatctttc ttttgctcca gattttttct  37080
accgcgtcat taccaagcat cttaaaacaa aacctaaaaa caaaaatctt ccttgacctg  37140
gtttttccca ctagctaaca tcctattttt atctttccct ttgcactaaa ggtttttaaa  37200
cggatcttta taccctctgt ctccattttc tcatctgcta acttatatgg caaagattac  37260
cactgccttt caacataatt ggccaatcta cagaaagttt tcaagttctc tttttaattg  37320
accacctcct gcctacctcc ccacctttga catcttgctt ctcacttggc accttaccca  37380
gtgttcaaga ttccctcctt taggatgtct tcagagcagc tacacagttg gtactataat  37440
ttatacatcc ttgtacacag ggcttgctgg gatattgatg gagagaagga ggaaactgga  37500
agtagttcag gccagagcta gggaaattga cccatctcca ggtctcaggt ctgcaagggg  37560
agctcacagc ttaacacatg gagtctagaa acttgtgctg gaccttgacc aacaccagcc  37620
catggagtcc aatacagtgc tcaataggga tttccaggaa attgctatat ttattcaaag  37680
agaacttacc aagtgtcagc tacgtgttgg gcattgtgtt aggcacaggg accacaaaga  37740
taagacattg tagctttcct taagttgctc actgagtaaa tagagagaca gaaaggtaaa  37800
caggtaagtg caaaaataca tacaattctg caatagtgtt catagtggct atggagagaa  37860
cgctcactaa ctttgtttaa acagttgttc tttcaaggat ttgacatgga tttgattgga  37920
aaagcatgat accatttttt gcaattaaac acaggaatac ataaataaaa tgcatcagta  37980
ttttttacaa atagctacta agagctacta gaaaacctgg gaattcttaa aaccttacca  38040
tgctacttgc tctaaaatat tttattttat gttattttgt acatttcttt acctacacaa  38100
acaccactgt tttcttcatt tcttagtcta tttaaacctc acacccttc agcatctctt  38160
aattatttac taccatctgt tagttctcct gtcctgaatg aaacaaaaat ggcagaatgt  38220
aaaacgaggg cgaacagatt tttgacagga agtattcaga ggtagaagga aatagtcaag  38280
acacatatga taaacgaaaa caataataac tttatacata acaacttata gacacattta  38340
```

-continued aaaagtttaa gatctcaaga gctatgtctg aatagataga agtaaaaact ctattaagta 38400
attaggaaaa taacaagaac agtgaatttc ttaatgaatg gcatgtaatc aaaactgtac 38460
ttatcgtcta attcataatc ttgaatgttt ttattttatt tatttatttt tttatttttt 38520
gagacagagt cttgctctgt cacccaggct agagtacagt ggcgtgatct cagctcactg 38580
caacctccac ctcccaggtt caagcgattc tgctgcctca gcctcctgag tagctgggat 38640
tacagaggcc tgccactgca cccggctaat ttctgtattt ttagtagaga tggggtttca 38700
ccatcttggc caggctggtc ttgaactcct gacctcatga tccaccagcc ttggcctccc 38760
aaagtgctgg gattacaggc gtgagccacc acgcctggtc gaatgttttt attatttgaa 38820
gagacaacat gggccttaaa tctgtcttct atttgacaga ctttgatgga gtcaaatccc 38880
aatgctgcca cttactgaac ggccttaaat gacttagtct ctctcagctg tctttctgca 38940
tatgtaaggt ggaataatga tggcttcaag gaggaataaa cctatgaaaa gtgttgagga 39000
tagtgtctga tatgaaataa ggattcaaca agtagtagct gctattgaag atttaagagt 39060
tatttattac aactatttaa taaaatttta aaaactaata cacttaaatt attaaagagc 39120
tttgaaatgg gccaggcgca gtagctcctg cctgtaatcc caacactttg ggaggccaag 39180
gtgggcggat cacctgaggt caggagttta agaccagcct ggccaacatg gtgaaaccct 39240
gtctctacta aaaacgcaaa aattagccag gtgtggtggc atgcacctgt agtcccaact 39300
actcaggagg ttgagggagg agaattgctt gaacctagga gctggaggtt gcagtgaccc 39360
gagatgtcac tgcactccag cctggcaaca gagcaagact ccataaagac aacaaaagct 39420
ttgaaattgt gtaaatgagt tgtacctatc ttcatttaag aaattcatct ttgttcatct 39480
atttttactt gacatgagag cttccagcaa tttttaatta agccctcaca gattttatgt 39540
cactggctat gtgataaaca aattatttgc taaaataata ttcttgcttc ttttttaagg 39600
aattgtctcc ctagaaacgg tttgtaccaa acaatacact gactttacac aaaatcagat 39660
ctgattggca acagttgcag atgttttcaa aggattttca tttgagaagg ggcccatttg 39720
ggttatttag attctaagaa ctgaaactgc tttgttctgt ttttctggct tctgggagag 39780
gaggagacat gaattcagtt agcaccttgg tattttcttt atccttcatt tcaatacaga 39840
agatgcttca tatgcacagt ggtgtcaggt cacatcaaaa gaaagagaaa cagtttcttg 39900
gtttttaatt ttcaaccgga aaggaaaggc acccattttg ttccgctcta attagccagt 39960
gcatgactta gagagcaggc agatgctttg aaggcgtggt aacacaggtc ttcattaatc 40020
tccacgcagg acttgcactt ctactatgcc taggctgaag aaaatggctc aggaagatga 40080
acaatctcac agagccctaa ctaactgaag ccaggtgtta taaagcacaa gtcaagaggg 40140
tgagaaacta acgttcttga aatctcccac ttctttctac gtcagaagag ccaagctgat 40200
tattttagtt ggaatttaga aatttttaaa aattattcta aagtcatgaa caagcctaat 40260
tataaagata gttgctgtga aggtgctgaa ataactcgat tttaccaacc ccctcttctg 40320
gaggaagcca gaatggaatc ctgtagaatg ttcactctac caacgaactc ttgtttttct 40380
aatgaggaaa cagaggccca cagtagtaaa ctatcttaac caagacaaaa tgactagtgc 40440
tctggtcctt ttattaagca ctaaaatttt gatccaataa taaatctgtc cagtagaagg 40500
agtttcccta atgtactggt tctaacttgt tcccttcaag ggccagtgt cccgtacaca 40560 tagctaaatg ggacttctct tcaactacca ttacccagag ggcagaacct aaaatgctgt 40620
gaatgacatt ctgctgttca catctcagca gcagtgttgc atttgagctt ctgcagggcc 40680
acccaggacc tatatctgct cagatgttta actcatctaa ttcagtgaac acttcattct 40740

-continued

```
agttaactga acatctactt tgtacaaggc actacagcgg ttcagagatg aataaaatca  40800
tgagattcca ctgtctccta taaaccatca ctttgggaaa ttttagaaat gtgggtaagc  40860
tccagggctt cctgcagcgt agaagtcaca aactcaaatg cctgcagagg cccagctgac  40920
aacataagta aatgattctg gctgggcgga aaacaattac gggtgggtgg gtttccagct  40980
ggggagtgca cgcctgtgtt aaaggacagc tgctactcat ttccagccaa ctgtgttccc  41040
atgtagaact gcggcccagt gtagccagta ccgaagattt ctcagaaaaa gccggagatc  41100
tcaatgttag tgtaaaatct ctcaaatttc caagaggatt atatggggca aaggttctca  41160
gatcagtttg cagtctctta cttagcccat gtgcagagca gtcgtagagg gtagcatgca  41220
gtgtcctaca taataattct tttttatttt attttatgcc ttcctccttc ctgtctctct  41280
ttaacctttc ttcttccctc aggctggctt cttccctcag cctcgtccga ccccagcctg  41340
ggttcaatga acattcggta aaggaacacg gaatgtcaag cgcattagag acaaccttga  41400
gacacattcc tcttgcggta agcacttcac tgtagatttt taattttaaa caagacaatg  41460
tttacgactt gcttctttca gggaagagcg atatcaattt tagtgaacac ttcaaggctg  41520
agatacgcta ggagagtcgt gtggtgttgc acagcaaaga attccacttt gaagcgagtg  41580
ggaaaaaaag catcaaatgc cacatgtaac tcaccgcctg aagggttaca ttggtatgaa  41640
acctgggttt aaaaagggac cgaatagact agccattaaa agacctgcgt acaacctctc  41700
tctctctctt tgagagataa tgtatctgga caataaacat gaacagagtg gagtctatcc  41760
tgtttaaaac attgcctact gtacaggcac caggagctga agggtcagaa tattagcagt  41820
gggagcttga ttagaagttg atgagagatg ggtagtagga ggaaagagtg agatagagga  41880
agaggacatg gggttaccc gtaagtggag agtagaaaag tagaatcagc tggccatcaa  41940
agggcgtggg actgaggaac agtatggcat gtattaaata tactaagcgc tgacattgga  42000
ggagaactag gaaggtaaat gaaatcaata ggggatgatg gagaatagtt aggtgtgcag  42060
ggattagggt tatgatagaa atacatgtga atacatgcag tattgtcctg gaaaatggtt  42120
aacagttggt tctcctgggg ggtgagggga agccctgatt tgtaatattt gcctatttct  42180
gtggtgcaaa tactcccacc atgaccagtt tcaagctatg aatgtgaatc acaaaagcag  42240
gttgggagga gatgcgcaca tttgttcccc ggcaaggtgg aaggtaagga aggtgaaatc  42300
aacaaggtca aagaaaactc aagatttcga ggtgcctcag gtctgagggg caatgaagtc  42360
taggaatggc tgtgctgagg tagctgaaat agaagtgact gcagaggtca tgaagctgaa  42420
gaggtgaaaa cagaaattag aaaggcaaac ccccaccgcc caaccccccac ccctgcagcc  42480
agtttctgag ggtgacaata gaggaaaggg tggagatgga gttcaggtcc agaagccata  42540
gaagcgagtg tgacattgtg ctcaaggtca gcacatgtca gtgtggggtg tcacatgctg  42600
ttgtgaacca tcatttatca ccaattatgg aagacctcct atgggcatct tgccatatgc  42660
attataaaga tgtgtaagaa gacatttccc tccacttggt gaggagaatt agggctgtac  42720
acagatactg tagagtgcca tgtgcctggt acagataagg tgtgttagag gttaaaagat  42780
gaggctctta atattaatga tagatcccac ttacctgagt ctgacttaca atgtgcctag  42840
cattaagtgt tttacctgca ttccctttga ccttcagaac aacccatttt acagataggg  42900
aaattgggtc agaaagtttc agtaacttat ccaaggtcac acaattggca agtgccagag  42960
ctgagccagg aactgaggtc cttctaacac caaacagctt gtctccccaa tcactgtgct  43020
attttccctc cccagaaga taatactctg atggaaatga aggatagtgt aataggagat  43080
```

-continued

```
tcggtgttcc tttttttaaa aaaaattcag cttgcatatt cctaaagagt caattcatgt  43140
ttaaaaaaaa tttcccttgt gcttgcatgt gacatgtatt tttaggatct gctgttagca  43200
agtgtatttt tgtgtgattg agtgggagag tgggaaaagt tttgcagagc tgttgaagcc  43260
agaatgcagg ggggctgcgc agcagagact gtaaaatctc tgccatctca ggtcttggaa  43320
caagcacaaa gagatgtgtt ctcgatttat tattctatgt acatccccag atgaatgact  43380
agttaaaggt attgttaaag cattttaaat gacccacttc cagcagcgaa caaaatcact  43440
tgctgtgcca agccaactgg catttctgag atgataaaac cacaaagtga ggaaaacgtt  43500
aaaactgcta aagcaaaaat gatacacaat aatggagaag gagaaaaatt gagctttatt  43560
gtctgcctag gcagatggct gaccactagg tgggctcggc gtcacgtcca gggtaattgg  43620
ttgctggggt gtttctggcg aggaagattc acgcttcagc tcggtccaca agatcctggc  43680
tcattctttc ctagattcca ttttctgcct cctctccatg actgggtctg atggttgatc  43740
caaacgggca attgaaatca gaaggttacc tttaccttaa aatgcttttc tggaaataaa  43800
aggacatgaa aagtaactaa ggaccggatt tcctagccgt ctttctctcc tgcatgcgca  43860
atttatcccc agatataaaa ttgcctgctt tgataattat accctctaaa tgaggggcaa  43920
gtggctaatt atgcccacat gtggccgatt gcactcccca ttagccaatt atgtgctcaa  43980
ttatttgtgc acatgaataa ttgcactcat ggaaaatagc ggccctcctt tcaaatcctc  44040
gtgcttggag tggctgatgg agtaattgtc acactggaaa tgcacttggt ggggagggaa  44100
agagtatcag ataccaggaa acgcataagt gaccagagct cgcagatgtt cactgccaca  44160
aatggcctta ggagccagag agagcgggaa ggaccacagg atggaacggg ccagcctgtg  44220
agttaggaag cctgcttctg aagttgcctg ggcagctcat gtgcggtgac cttgggcaag  44280
tcattaactt tccttcaggt ctaactggtt ctgcatacac aatgaggatg gtaataacgc  44340
ccaattccca tcactatcgt gggatggatc agactattta aaaggattta caatctgctt  44400
gggtaaaagc tttacataaa tatgaggcat tatcatgtcg cttggtacat ctccaattat  44460
gaaggaaggg taatgaccct ccacagcaat gcaggactcc tggtttggag ggagggaaag  44520
tttgagaagg acaggaagct tgttgcccca gcactgatgt ttctactgag gtaccagaaa  44580
atgtcatgtg gtcatacaga attcatttat tcattcaaca aacatctgtc aattgttaca  44640
ctgtcctgag aatttggaaa aatgatgaaa gactcagtcc tgccttagga ggtcactggc  44700
acattggccc gggcccctgt tttgggcctt ttactctgac ctgtgctgat ttgcaaatag  44760
tgggaaattt tatctcaagt ctaggaaatc tggcatgcat tttcacggtt tgattgccag  44820
gtacattcga tggcaatgag tcttataatg tttggttacc ttcatttacc taaaaactgt  44880
ggttgttgct gtggttgttg tttttgttgt ttttgagacg gagtcttgct ctgtcatcca  44940
ggctggagtg cagtggcatg atctccggtc actgcaaact ccacctccca ggttcaagcg  45000
attctcatgc ctcagccccc tcagtagctg gattacaggc gcgcaccacc atgcccggct  45060
aatttttgta tttttagtgg agacagagtt tcaccatgtt tggccaggct ggtctcgaac  45120
tcctgatctc tggtgatccg cctgcctcgg cctcccaaag tgctgtgatt acaggcgtga  45180
gccactgtgc ccagccagaa ctgtggtttt aatgacaatg ctaaaaagtg gtatatgtca  45240
cagtgtcggg tggggctaag aggcacattg ctgcagtgat ccatcattca tttcccacca  45300
ttctcgcctg gattagcgca gcagctccca gagaggcacc tcactttgac cttcttcctc  45360
aaagacattc tctgtgacct gcctggccct tattacctct ctagctttgc cacttcccta  45420
tgtctccatc tcccctctca cacgtagtaa gaaagagact ctacctccat ggaagttaag  45480
```

-continued gagaggtttc acagaggcag gattgcttat tagtcttcaa agatgaggta tttgctaaat 45540
gaatgagaca aagggattgg ggccacatta caggaaattg aggtatgtaa tagcctggtg 45600
caggttaaga gtgtggactc tgaaaccaga ctcagcctgg aattgaatcc tggctgtgtg 45660
atgttgggcc agtgacttaa cctctctgtg cttttattca ctcttctata aaatggggat 45720
tataataaac ctaccttata aggttattat aagagtcagt aaatataaaa atagaagttt 45780
ttggatgatg actagcacag agtaaacact tgtttgccat tatttttatt acttgactaa 45840
aaatatacca aaaagaccat ccaagaaaag cctttaagct gctagtgcag aaagattccc 45900
cttgtgtttg tgtgctgggg ggtcagtggt gcctgtggcc cactggagag gagacagcta 45960
tggctggagt gattctcaaa cttcagaatg tctaaaatca tcacatggac aacttattaa 46020
ggaaagcaaa tgcctgggct ccatcctcag agagtctcat tcactgggtc aggatagagc 46080
ccaggaatct ttaccttaaa gaaccatccc acctcccacc tcatatgatc cttatgcagg 46140
tgatctgggg gcccacactt tgagaaatag actcaggtca aagtgggctc taactgcatc 46200
tcatttctta cctggcatat ctaatagtag agaagaagac aatgctaaga tttttgttgg 46260
agatcttttg ctgggattgc tgcttcattc attcactcat ttatttattt atttatttat 46320
tttgaaacag agtctcactt tgtcacccag gctggagggc agtggcacaa tctgagctca 46380
ctgcagcctc aggctcctgg gttcaatcga ttctcttgcc tcagcctccc gagtagctgg 46440
gattacagtc atgcaccacc acgcccaact aattcttgta tttttagtag tgacagcgtt 46500
tcaccatgtt agctagactg gtctcgaact cctgacatca ggtaatctgc ctgcctcggc 46560
ctctcaaaat tagtagctgc aattacacgt gtgagctgcc gtgcctggcc tgctgtttct 46620
tttagttggg cctcttctgt aatagagtgt gagaattctg acttgctgca acagtctgct 46680
ttgaagcagg gctgtgttta cactggtcag atgtggaatt gtggggcaca cttagcagct 46740
tccttctcta atttttctgt attttcagga gaacaatttt aaaaaattta ataaaaatgc 46800
cttaaaaatt aacattatta taagatgaat cccatttttc taatcttgta aattaaaaac 46860
aatcataagc atatgagcac ctgcacttag ggaatcaagg tggcaaagct aaacacttcc 46920
agctctaggt gattcgcggc aatacaaatg gagctggact ttggccacag tgcaaaaata 46980
ttgatctgtt gttagatgct ctgaagtttc cacaaagaat tggttctgcc tgctgtgctt 47040
cagtgcttaa gggaagtggt tcctcaaaat gttagttttt aagcccagct ttcttaaata 47100
ggaagattct aatagtagca aaaatataaa ctgcttctag gtttaaaaag gaccagcaca 47160
caatggttat cacacacctt tctcctcagg tgatgagtgg atgagtggcc tggtgtattt 47220
cataacatct cccagggtcc aaatgctaaa gcaattgctg aaaagatacc atgtgtaccg 47280
gaaccttgca gaggtatttt gttggcataa aaagaaatat tgatcatcta tagtaaaaat 47340
ggttctactt taatactact gagaaaagat tttcttttcc cagatctaca tcctgaatct 47400
tcatgaagac aagatcccct aaacttccac taacaccata atgtgtgctg tcctttgtaa 47460
tgtagtccac agatctcata aactgtcaga aatagcagag attgtaaggt catccacttc 47520
ccctgtaagg cctgcgtccc tcacttacat ccctaataac gtcctctaac ctctgctgga 47580
gggcagattt agctgccagc tgggaagagc tctgccctag tcaacatttt tatctgtggc 47640
tttcagatga gaacactgga tgcttatctg aaaaaagctc ctcaggctgg agggagggat 47700
tggctctaac aagatgcaat gtgataagaa taaaagcgaa gccaaactct aggcccaaag 47760
gctctagcaa cacacttttg agaaccttgg agacgagttt tggctgatgc gagcttctcc 47820

-continued

```
gcctgctaaa gtagcccatt ccatttggac ggctctagag gctggcatgt tcttctccac  47880
gttgtgttaa tgtactccag tttcttcctg ccatgaactg gcatgccctg gctcctccta  47940
ccttccccac tttaagtctt ccctccctcc ttctgacctt cccattccag ccacactggc  48000
cttttgtctg gtcctaacaa accatgcctt tcctgcctcc aagccctaca cctgctatcc  48060
atccctctgt ctgagagaca ctcccacccc ttcacaaagc ctgtttctca tccttccagt  48120
tcagatgtct tctcagcttg cctcaactga cctctttcag ctattctcac tctttgtact  48180
ctgttcattt ccttcctggc agtcaccata atttatcttt atttgaatca atttcttagt  48240
tgtattattt agttatttgc acactctgtc tctctgtgcc tttcttattc actgcaggct  48300
ttcttatgta agtaatttat ttacttaaat ttttaaaaat aatttcaact tttggccggg  48360
cacagtggct cacgcctgta atcccagcac tttgggaggc cgaggtgggt agatcagctg  48420
aggtcaggag ttcgagacca gcctggccaa catggtgaaa tcccatctct atttaaaata  48480
caaaaactag ccgggcgtgg tggtatgcac ctgtaatccc agctactcgg gaggttgagg  48540
gaggagaatc acttgaaccg gggaggtgga ggttgcagtg agctgagatc acgccattgc  48600
actccagcct ggggcacgag agtgagactt catctcaaaa aaacaaaaaa caaaaaaccc  48660
ctgcttttca gaggggctga actaatttac attctcacca atagtgtata agcattcccc  48720
tttctctaca gcctcactag catttacttt tttaaaaaac tttttaataa tagccattct  48780
gactggtatg agatggtatc tccttgtggt tttcacttgc aattctctga tgattagtga  48840
tattgagcat tgttttatgt ttgttggctg ttcgtatgtc ttcttttgag aagtgtcttt  48900
tcatatattc tgcccatttt ttgaatggag ttgttttgtg cttgttgaat taagttcctt  48960
atagattcta gatattagac ttttgttgga tgcatagttt gtgaatattt tctcccatcc  49020
tatagttctg tttactctgt tgatagttcc tgttttgtta tgttttgttt ttttgctgta  49080
cagaagctgt ttaatctaat tggtcccact tgtcaatttt tgtttttgtt gcaatggctt  49140
ttgaatttta ataataaatt ctttcctaag gctgatgccc agaacagcat tttctaggtt  49200
ttcttctagg attcttatag ttcaaagtct tatatttaag cttttaatcc acctcaagtt  49260
aatttttata tatagtgaaa tgcaggggtc ctgtttcatt cttttgcatg tggccagcca  49320
gcaatcccag aaccatttat tgaataagga atcttttcct cattgcttat tttgtcaact  49380
ttgtcaaaga tcggatgact gtaggagtgt ggctttttct gggttatcta ctctgttaca  49440
ttggtctatg tgtctgtttt tgtatcagta tcatgctgtt tttgttacta tggtctcata  49500
acatagttta aagttggata atgttatgcc tctgctttgc tgtttttgct taagattgct  49560
ttggctattg aggctctttt ttcacttcat atgaatttta gaatagtttt ttctaattct  49620
ttgaaaaatg accttggcag tttgatagga atagcattga atctatagat tgctttgggc  49680
agtatgctat tttaatgata ttgattcttc ctatccatga gcatggaata tttttccatt  49740
tgtttgtgtc atctactatt tcctttagca atgtttttta gttttccttg tagagatcct  49800
cctaggtatt tcatttttta tgtgactatt ttaaatggga ttgcattctt catgtggctc  49860
tcagcttgaa tgttattggt gtatagaaat gctacagagt tttgtacact gattctgtat  49920
cctgaaacct tactgaagtc atttatcagt tctaggagcc tttggcaaag tctgtagtgt  49980
tttctaggta tagaatcata tcattagcaa agaaagatag tttgacttct tcttttccta  50040
tttgaatgcc ttttatttct ttcccttgtc tgattgctct tccagtacta cgttgaatag  50100
gagtgctgag agtgagcatc cttgtcttgt tccacctctc aagggaaatg gttccagctt  50160
ttgcccattc aatatgatgt tggccatggg tttgtcacag atggctctta ttattttgag  50220
```

-continued

```
gtgtattcct ttgatgccta gtttgtcaaa ggcctttatc atgaagggat gttggatttt  50280
attgaaagct ttttctgggt cttatttggt gaattgcatt tattgaattg tgcatgttga  50340
gccaaacttc catcccaggg attaaaccta cttaatcatg gtgttaactt tttgatgtgc  50400
tgctggattt ggtttgctaa tttttttttt ttttttaaaa tggattctcc ctctgtcccc  50460
caggctggat tgcagtggtg tgatcttggc tcactgcaag ctccacctcc cgatttcatg  50520
ccattctcct gcctcagcct cccgattagc tgggactaca ggcacccgct accataccca  50580
gctaattttt gtatttttta gtaaaaacag gatttcacca tgttagccag gatggtcttg  50640
atctcctgac ctcgtgatct gcctgcctca gcctcccaaa gtggctagta tttttttaat  50700
tactattttt tctcaccctt gctgccatct tatgattttc tagtattttg ttgaagattt  50760
ttgcatctat tttcatcagg gatattggcc tgtaattttc ttttttcatt tcatctttac  50820
cacatttttg tatcaggttc atactggctt catagaatga gttcaggaat ggtccctcct  50880
cctcgaattt tctctgtaga attagtacca gctctttgtg tgtctgggag aagttgtatg  50940
ccaataattt aaatgcagtt aatatttact ggacaatttc ctccagataa ttgtatatga  51000
tttttggtcc accctgagtt gatacatgta ttttaattgt atcatggtat gaaaagagca  51060
agagtatttg gtcacctagt cttgcctata gatgtgccta atgattcaaa gtagatattt  51120
tgggagccta acaggtgccg tgactaggca gttttgtttt tttttttttt tgagacagag  51180
tctcgttatg ctgcccaggc tggagtgcag tggcatgatc tcggctcact gcaacatccg  51240
cctcctgggt tcaagcaatt atactgcctc agcctcccca gtagctggga ctacaggctc  51300
acgccaccac gcctggctaa tttttgtatt tttagtagag atggggtttc accatattgg  51360
ccaggctggt gttgaactcc tggcctcatg atccacccgc ctcggcctcc caatgtgctg  51420
ggcttacagg cgtgagccac cgcacccgga gattaggcaa ttttatattc ccaaatatcc  51480
aactcttctg acccgctttc tcagcctggg tgtatcaggc acaaggcctg ttcagattat  51540
gtggtctctg aagatatggc tctccagggt tgacaatgtg gataaggatt cacctggttt  51600
aggatttaca cattcgcctt gaatgtctgt tgcatcaagt agacagtcca tcccaacttg  51660
gccatttggt cagagctgta aggagacaag gaggtgggca gccgctgctg tgaactgctt  51720
ggacaaagac tgccaaatag ctatcagaca gtgttaacaa cagctgattt aggtttgaag  51780
ggggcagtct cttgggccac ttactatgct gcatcatcct ctttggaaaa tgctcttcag  51840
gtaactgcct aacagactga gaaaataaaa tgctcacaga gaaaaaagac ccggaaagtc  51900
tgacttctca gagctcagtg tttaggtgca gaactggatt gtgaaaggat ttttaaattt  51960
tttatattca ttgcagggaa cattcattta ttccatcctt ctccactccc acctgtctgt  52020
cgttgtcttt gtctctgtct ccccacctct ctctctagac acacacacac acacacacac  52080
acacacacac acacacacac acacacacac acacacacac acacacacac acacacccct  52140
attcattgcc aacagtaata gagttgcttc tttacttctt ggagagaaaa gcctcaatct  52200
gaggaagctg tgctgactag ccttgctctt aatcatggag acaatgcttt atgcctttat  52260
ctttgcacag ctgaaagcca tggcagaagc agtcctctaa acgaaataaa atagaaaggt  52320
tcctgctaag ccctggcaaa tgcagccttc tatccctccc ccaacactca cagcttctga  52380
gcaagatgta gctgccttcc aggaggctgg gtgatgggca ataatgagca gagccacgtg  52440
aaggaaagat gggtgaagaa atgtgtgtgg aggtcatgct ggctgcactg accatgaaac  52500
aaaggatcta cccctctagt aactgcccta ctcctttggt aactgttctg aaattataac  52560
```

-continued

```
ttgccagaag ttcagaagga cctagtgcag gtattagagg aaattcgtaa gattgagcca  52620
tttattcctg cacagataca taataatgga cacgggccat ggtggccagc attcttgctc  52680
ttgacaatgg tgaagggaag ggttgtaggt catggctatg ctctcagaat tataatggaa  52740
agaaacagct cctgagtgtt tactatgagc caagggctgt gctaaacact ttaccatatg  52800
atgacatctt tttctcacag gtatcaaaaa acaataggac ataccggata gctacaatct  52860
ttgggcccct gcaaacacaa taatgtgtat tctcttcttc aaatcctaca tattgctaca  52920
aactgtatcc ctgaggcata ttcattgtaa aataaaaaca tataaagtac tacttttgtt  52980
ttttgagatg gagtctcgct ctgtcaccca gactggagtg caatagcatg atcgtggctc  53040
actgcaaccc cctgctcctg ggctcaagtg attctcctga ctcagcctct caagtagctg  53100
ggattacagg cgcacgcccc catgcctggc taatttttgt acttttaata gagaccaggt  53160
ttcaccatgt tggccaggct ggtctcaaac tcctgacctc aagtgatcca cctgcctcgg  53220
ccttccaaag tgctggcatt acagatgtga gccactgcac ccggcccata taaagtacta  53280
ctaatgtaac agggtgctag tccagacagt gaccacacgt ggtgttcatt gaaggctgga  53340
ctaacaactc cagcctctcc gccatcacag agtgatgact gccttccctg aagcaaagct  53400
tctggttcaa ggaaaggcca gtaagtgact gctctttgtt gtatacatgt tagatgatca  53460
ggcctcaaga aaagtataaa gagatctttg tgctctctgg gactcaaaaa gctgcactct  53520
ttgggggaag gatagccagg taaaagtggc ccaggtaaag agggcctggt acacctggtt  53580
ctgcaagatg gtagacacaa aaatgagagc cacatttgga gcttatgtgc ccctaactct  53640
gtacataacc tgcaagatct aattactaac aactggaatc ttggaaacac ctgtagtaca  53700
tccttggcta aggttagccc caacagagag ggctctcctc ttacagagaa ccattacatt  53760
tgtgccttca tcctagagta gaaaaggcat gatcagacta ctaaaaagac atcaggaaag  53820
ggcctgtgac atctgaggga agtggttgcc ctctctggga tgttggttcg ggaagagggg  53880
catggaggag tgcctgcttt agatggtcat tcaggaaccc aggctgatag tgagaggtga  53940
agccagctgg gcttctgggc tagggggac ttggagaact tttgtgtcta gctaaaggat  54000
tgtaaatgca ccaatcagca ctctgtaaaa tggaccaatc agcactctgt aaaatggacc  54060
aatcagcagg atgtgggcag ggccaaataa gggaataaaa gctggccacc agagccagca  54120
gtggcaaact gctcaggtcc ccttccacgc tgtggaagct ttgttctttt gctcttcaca  54180
ataaatcttg ctgctgctca ctctttgggt ctgcactatc tttatgagct gtaacactca  54240
ccgtgagggt ctgtggcttc attcctgaag tcagtgagac cacaaaccca ctgggaggaa  54300
caaacaactc tggacacgcc aactttaaga gctgtaacat tcactgcgaa ggtctgcggc  54360
ttcacctctg aagtcagcga gactatgaac ccactggaag gaagaaactc cagacacatc  54420
tgaacatctg aaggaagaaa ctccagacac accatcttta agagctgtaa cactcactgc  54480
aagggtctgc ggcttcattc ttgaagtcag caagaccaag aacccactgg aaggaaacaa  54540
ttccggacac attttggtga cccagatggg actatcacca agtggtgagt accatcaacc  54600
cctttcactt gttattctgt cctatttttc cttagaattc gggggctaaa tattgggcac  54660
ctgtcagcca gttaaaagcg actagcatgg ctgccagact taagagacta aagacacggg  54720
tgtcagactt tctgggaaag ggctctctaa taacccccaa ctctttggag ttgggagcgt  54780
tggtttgcct ggaaccagct tccacatttc ctgtacttct gggctgagac gagggtcaac  54840
agagaggaaa gccattcagc tctggggtcc cgacagcaag ttggttgacc ctgtggccat  54900
gaacagaact ctcgaagtca tgttgcccaa gcgagactca cccatctatc ctatctatcc  54960
```

-continued tgactcttgc ttcctgggtc ctaatgcctg gaagacaaaa cttcctcttg tctctgttct 55020
ccaaggctag tcccacttct aaaaaccact ccctgtctct ggtgcttttc tagtttctcc 55080
tataagaatg atttctagta taaactccag gactctattc tcttctttag gcacccgggc 55140
tcaccaatca gaaagccata atttttgccc aaagccccat cttagggggg actatctgga 55200
attttaggat ccctcctcag acaagcaggc ctaacaaaag ctattcctga agctaggata 55260
tggggagcct cagaaatgat atccttccta ttcaagtgag gacaaaaggc atcactcttc 55320
caattctgga aatcccttcc ctccctcagg gtatggccct ccacttcact tttggggcat 55380
aacgtcttta taggacacgg gtaaagtccc aatgctaaca ggagaatgtt taggactcta 55440
acaggttttc aagaatgtgt cggtaagggc cactaaatcc gatttttctc agtcctcttt 55500
gtggtctagg aggacaggta agggtgcagg ttttcaaaaa tgtgttggta agggccacta 55560
aatctgacat tccttggtcc tccttgtggt ctaggaggaa aactagtgtt tctgctgctg 55620
catcagtgag cgcaactatt ccaatcaaca gggtccaggg accattgtgg gttcttgggc 55680
aagaggtgtt tctgctgctg cattggtggg ctcaactatt ccaatcagca gggtccagtg 55740
acctttgcgg gttcttgggt cggggggtgg ggggaacaaa cagaccaaaa ctgggggcag 55800
ttttgtcttt cagatgggaa acactcaggc accaacaggc tcacccttga aatgtatcct 55860
aagccattgg gactaatttg acccgcaaac cctgaaaaag agtggctcat tttattctgc 55920
actatggcct ggtcccaata ttctctctct gatggggaaa aatggccacc tgaaggaagt 55980
ataaattaca atactatcct gcagcttgac cttttctgta agaaggaaag caaatggagt 56040
gaaatacctt atgtccaaac tttcttttca ttaaaggaaa atccacaact atgcaaaact 56100
tacaattcac atcccacaag aggacctctc agcttacccc catatcatag cttccctata 56160
gctccccttc ctattaatga taagcctcct taatctcccc cacccagaag gaaacaagca 56220
aagaaatctc caaaggacca caaaaacccc tgggctatcg gttatgtccc cttcaagctg 56280
tagcggggga ggggaatttg gcccaaccca ggtacatgtc cccttctccc tctctgattt 56340
aaagcagatc aaggcagacc aggggaagct ttcagatgat cctgataggt atacagatgt 56400
cctacagggt ctagggcaaa ccttcaatct cacttggaga gatgtcatgc tattgttaga 56460
tcaaaccctg gcctttaatt taaagaatgt ggctttagcc acagcccgag agtttggaga 56520
tacctggtat cttagtcaag taaatgatag aatgacagct ggggaaaggg acaaagtctc 56580
tcccggtcag caagccatcc ctagtgtgga tccccactgg gacctagact cagatcattg 56640
ggactggagt cgcaaacatc tgttgacctg tgttctagaa agactaagga gaattaggaa 56700
agagcctatg aattattcaa tgatgtccac cataactcag gaaaaggaag aaagtcttgc 56760
cttcccttga gtggctacag ggaggcctta aggaaaatat aactcccctg tcacccaact 56820
cacttcaagg gttaattgat tctaaaagat atgtttatta ctcaatcagc tgcagatatc 56880
aggagaaagc tccaaaagca agcccttggc cctgaacaaa atctggaggc attattaaac 56940
ctggcaacct tggtgttcta taatagggc caagaggagc aggccaaaat ggaaaagcga 57000
gataagagaa aggccacagc cttagtcatg gccctcagac aaacaaacct tggtggttca 57060
gagaggacag aaaatggagc aggccaatca cccagtaggg cttgttgtca gtgtggtttg 57120
caaggacagt ttaaaaaaga ttgtcctatg agaaacaagc tgccccctca cccatgtcca 57180
ctatgctgaa gcaatcactg gaagccacac tgccccaaag gacaaagatt atctgggcca 57240
gaagccccca agcagatgat ccaaccacag gactgagggt gctcagggtt agcgccagct 57300

-continued

```
catgtcatca ccctcactga gccctgggta catttaacca ttgagggcca ggaaattgac  57360
ttcctactgg acactggtgc ggctttctca gtgttaacct cctgtcctgg acagctgtcc  57420
tcaaggtctg ttaccatccg aggaatcctg ggacagccta tatccaggta tttctcccac  57480
ctcctcagtt gtaactggga gactttgcta cagatagtaa gtatgcttac ctaatcctac  57540
atgcccatgc tgcgatatgg aaagaaaggg aattcctaac ttctgggtga acccccatta  57600
aatatcacaa ggaaactatg gagttattgc acacagtgca aaaacccaag gaggtggcgg  57660
tcttacattg ccgaagccat caaaagggga aggagagggg agaactgcag cataagtggc  57720
tggcagaggc agggaaagac aagcagaaag gaaagagaga aagagcagaa agtgagagag  57780
aaagagagat aggaagtgat agcaaagagg gagtccgaaa gaaaagagag aggagagaga  57840
gagggggaaa gacagagaga gacagaggaa gagacagaga gacagaaaga gagaagcaaa  57900
gagaggaaga gacaaagaag gagtcaaaga gagggaaaga gaagtagtaa agaaaaaaca  57960
gtgtacccta ttcctttaaa agccaggtta aatttaaaac ctataattga taattgaagg  58020
ccttttctgt aaccctataa tactccaata ccaccttgtt gtcagtgtaa acaagggtat  58080
agcccaaaag cactgaggcc actgacaacc cgtagccttc ttatcaaaaa tccttaacac  58140
agcaggtttc ctaacaggga atctaaatct taaggtcgga ccagacatag gaggaactgc  58200
cttcaggaca ggatgataga tggttcctcc caggtgatta aggaaaaaga cacaatgggt  58260
attcagtaag tgataaggaa actcttatag aagcagagtt aggaaaattg cctaataagt  58320
ggtctgctca aacgttgaag ctgtttgctg tttgcactca gctaaacctt aaagtactta  58380
cagaatcagg aaggagccat ctataccaat tctaagttaa tatggactga acgaggtttt  58440
attaatagca aagaaaatta aaatctcaaa cttacaaggt tttcaactaa agtaaagttt  58500
gctaaaagtt aacagcgtaa catgtattat cctactacct cacactctct caaaggattt  58560
ctcagacagt ttgcaaaaaa gaacgaaatc tgtccttact ctacaatccc aaatagactc  58620
tttggcagca gtgactctcc aaaaccgctg aggcctagac tctcttactg ctgagaaagg  58680
aagattctgc acttcttagg ggtagagtgt tgtttttata ctaaccagtc agggataata  58740
tgagatacca cccagtgttt acaggaaaag gcttctgaaa tcagacaatg cctttcaaac  58800
tcttatacca acctctggag ttgggcgaca tggcttctcc cctttctagg tcctgtgaca  58860
gccatcttgc taatagtcgc atttgggccc tgtattttta acctcttggt caaatttgtt  58920
tcctctagga tcgaggccat caagctacag atgatcttac aaatgtaacc ccaaatgagc  58980
tcaactaaca acttctgctg aggacccctg gaccgacccg ctggcccttt caatggccta  59040
aagagctccc ctctggagga cactaccact gcagggcccc ttcttcaccc ctatccagca  59100
ggaagtagct acagcggtca tcgccaaatc ccaacagcag ctggggtgtc ctgtttggag  59160
gggggattga gaggtgaagc cagctgggct tctgggtcag gtggggactt ggagaacttt  59220
tgtgtctagc taaaggattg taaatgcacc aatcagcact ctgtgtctag ctaaaggatt  59280
gtaaatgcac caatcagcac tctgtaaaat ggaccaatca gcaggatgtg ggcggggtca  59340
aataagggag taaaaactgg ccacccgagc cagcagtggc aacccactcg ggtccccttc  59400
cacactgtgg aagctttgtt cttttgctct tcacaataaa tcttgctgct gctcattctt  59460
tgtgtccaca ctacctttat gagctgtaac actcactgcg agggtctgtg gcttcattcc  59520
tgaagtcaac agaccacgaa cccactggaa ggaacaaaga actcccgatg tgctgccttt  59580
aagagctgta acactcactg cgaagctctg cagcttcact cctgaagtca gtgagaccac  59640
aaacccacca gaaggaagaa actctggaca cacctgaata tctgaaggaa caaactccag  59700
```

-continued acacaccatc tttcagagct gtaacactca ccgcaagggt ctgtggcttc attcttgaag 59760
tcagcaagac caagaaccca ccggaaggaa caaattccag acacagtagg aaatctgtat 59820
ttttgatctg tggcttccag ggttactcca gtcattgaag tctccattgc agccttaagg 59880
aaacagagaa tggtttggag gagcacatgt gggaattgtt atggaccagg cttgagatgc 59940
acatagggca tttctgatca aacctagctg gaagcagggc caggaaatat aatctaagga 60000
agacagtttt tgtagacagt agtagtcttt gcatctgaga catgtagatt atcaagcaat 60060
taattagaaa aaatatagcc aggtgcgatg gctcatgcct gtaatcccag cactttggga 60120
ggccaagggg tgtggatcac aaggtcaggc gttcgagacc agcctggcca acatggtgaa 60180
accccgtctc tactaaaaat acaaaaatta gcctggtgtg gtggcacgca tctgtaatcc 60240
cagtactcag gaggctgagg caggggaatc tcttgaactt gggaggcaga ggttgcagtg 60300
agccaagatc acaccacagc actccatcct gggtgacaga gcgagactct gtctcaaaaa 60360
aaaaaaaaaa aaaaggaaag gaaaatataa tcaagaatat tgacaggtaa catttattca 60420
acacttacta tgcaccaggc aatacactaa gtgttttaca tggattaact catttaatct 60480
taacaatagc cctatgaagt cagtgctgtt attatctcca ctttatagat aaggaaactg 60540
aagtacagaa aggtcaagta gagaaatggc catgcttgca ttctcagttt ttgaagcaac 60600
tgttacagga atctggtgtg agaaatgctc taacaagatg tgagtcaggg gttgggaggt 60660
actgagtctg agttgggcag ttggggatgg aaggatggat gaagaacagc ttgacagaga 60720
agctgacact tggcaactct gtgggacctt gaagggttag agggacttca ccaaagaaac 60780
tggtggtcag ggaaacggga gggtcacggc aaggagggaa aggaaactgt accacagcag 60840
agagtctgaa gctactacag tgtagttcag cgtataaaga ataattattt taaggtaaac 60900
ttataacctc atgcaaatat aaaatgaaca cgtgtcaaag atcttattta atttattaat 60960
taatgaggga acctgtaaga tgttacagcc agttcaaagg ataattcaaa taaatccatg 61020
cacatatgta ggcaataagg aatgctgaaa tgaatttaaa agtagatgta aactgattta 61080
tccacagaga aataatcagt tgcatttcac ataacaaaat tcagttgctt ttctacagaa 61140
ggaattgttt gcatcattac caatttttct acaactaaca gaattataaa ataactcaaa 61200
cacaatgaaa ggcagatata acccacaatg gtatgataga tacaatatcc acatccagga 61260
tgttttttc tcatttcaaa gtctttcaca agttttcctg ataagggagt gtcaataata 61320
ctgtatggca ggcaataaga ctggatggat ggttggggcc aggttttaag gggtaataaa 61380
tgccatgtaa aggtatgtgc atactgtgca acatgtcggg ggaatctcaa attattggta 61440
gagtatgtag gaaacacttg tgggagcttg ttaataaatt caaattccca gacccaactc 61500
ctcaaggggt ctaatacagt aggtttggag taaagcctga aaatctgcaa ttgtgcaaaa 61560
aaaaaaccca ggtgattctg atacactttg agaagcactg gtggaactaa tagtcactga 61620
acgtttttga gcaggggaga aacctgagga cgtctatgtt gcagcagtgg aaacttgatt 61680
agaagtagga gaagatgcat ggtcttaaaa gaatgcaaaa tgatggctaa tatttgagtg 61740
cttatgatgg gccaggggct gtgctaggcg cgtggcacac attcaatacg atggaagcct 61800
gtaccagtca gtattagtgg ggtatcttta agagtgacca gaattaaggg gggttttcac 61860
caaagcctga ggactgagcc tcctcatcct aaattcagac acaatgctgt acctatgcat 61920
ttgcctccag gctgttcctg ggcctccagg gactggccca ggctcctgat aaatagggac 61980
tcccaacaac ataaagcctg gattttggaa cttcctgaat gttactcagg ctttctagta 62040

-continued

```
actgtggaga tctgaataat aacacaattc taagttcccc tactcataaa gctgctcatc  62100
atttagatgg ggtaaagcac ctgaaataca atgagcatca ctattttcat tcatccatga  62160
aatgaacatt ccggggagat cagtaagttg atgtatcacc cttgaacagg gcaaaatgaa  62220
tactcaccag gaatatgtgg tattttaaaa agaaggcaaa gggaagaata gtggggatgg  62280
ggcaaaaact ttaaatagat tcccccaatc atatatggca attgaagata attaaattat  62340
cattttaatt gagtaagtac tcatagagcc ctcactattt gaaaatgaac tgcctcctaa  62400
ttgttattgt gcaaatgtga tacattaaac ttaagctatt ttaataaaac atccattttc  62460
ggaagctgta gtaggttctc ccaggtcaga tttgataagc cataaagaac aaatgccaac  62520
tcctattttt ctatggtgct gggaaataag agagaaatgt gtaattcaaa gcaatcattt  62580
aattttatcc aatagcttga ttctcctctc tcttctagcc ttttagctaa gctgttacca  62640
agtaaccaca ctagttggct tgagtcttac cactgtttcc ctgaccccac agtggagaga  62700
ctgcatctgt taaagagcag ttatgtaacc atggctatgc tgagctggga ttcccaaggc  62760
ttaggttctt tctgtgaatg accttcacca agacacctga ggtctgtgtg gaaccacagg  62820
cttgtcatct ctaaggcaga gttgataatt ccatctgttt cttgagccca cactgagaaa  62880
aagattacat gactgcagtt atttgaatgc ctcatggaaa gacgtcttat aaatattata  62940
attaatgtta tcattaagta atgcttcaat gcagatcttc caagtataaa tatcagctga  63000
gtaagaagtc aatcttccct gaagcaaaat tgaaatttgt aaatgcgatt tctgggagct  63060
tattttgtaa tacatgattc cagagtgtcc ataacacaca caattgtctt ttttcccta  63120
catgggctat ttacaacaaa attggactta taatgtttat ttccagggat gactagaact  63180
ttaataacaa accttgggcc aggcatagtg gctcatgcct ataatcacag cacttcggga  63240
ggctgaggct ggtagattac ttgaggccag gagtttgaga acagcctggc caacatggca  63300
aaaccctgtc tctactaaaa atataaaaat tagccgggtg tggtggcgca tgccagtaat  63360
cccagttact aagtaggctg aggtacgaca atcgctggaa cctgggaggc ggaggttgca  63420
gtgagctgag attgcactac tgcactccag cctgggtgac agagaaagac tctgtctcaa  63480
aaaaaaaaaa aaaaaataat aataataata aaccctgatg aaaggtttct aaaatgtttt  63540
catctaatgg ttttcttgac aattaaattt tctatataat gtcagttcat aaaaaaactg  63600
agaacgacca catgtcatat cgactgctta aaagaaaata cgtatattta caaacatata  63660
cacgatactg tcttttgtct ggttagttta gaggttagat aaactgcagt atgttgtagt  63720
ggacagatca tagaactagg agtcaggatg tctggattcc taggaagcaa tgaataggtt  63780
gcacggtgca gaccagcatc atgagtatcc tcagggagct tgttagaact gcagatcctt  63840
taactcattg aatcagaatc cctaggtgtg gggccctgaa atctgtattt tagcaggctc  63900
tctgggattg tgatgtgcct tagagtttga caaccactgg gtagctgatc ctgacttaga  63960
cttatcaggc atgtgatctt gaacaagtca cataatctca ctgagttcag ttttcttatg  64020
cttaaaatag gcccaataat atctatttca catggactgc tttgaggatt aggcaagaga  64080
tctgtaacag acactgtaga acagtgtctc tggtctacag ctgaccttcc ataaatggta  64140
gttgccttga tctctgctct gccacataat agctggttaa ctatgagcaa gtaatttagt  64200
tcttctcagt ttagtttctt cacctgtaaa agaaggaaaa taactgttat actcaatttc  64260
tgaagtggct ataaaaatca gtttaaatta tgggcattga agctctttgt acactgtata  64320
aggactgtac atctaaggga ttaatgagac caggcttatg attttaagca tggagtaaat  64380
agtaacactg actctgttct atgaaccaca tggaaactct aaagaatatg cacatttgaa  64440
```

-continued

```
acacaggtat catctgggga aggtgatctg ctcacccaaa ccagttcatg aacatcaatc  64500
tccagtggcg tgctggagct agctgtacca gctcatgagg gccaattgtt tcatttttag  64560
gaattttgtt tgctggttaa aaatagtcat tatttaaaat taaattatgt aaacaataat  64620
attagataaa ataagttaaa ataaaaacaa aggaactaat tatccccaaa ctcttcccca  64680
cctaattatt ttactatctg tgccttggga ttatttacat tgattttatc catatggtga  64740
caatactatt catatataaa tggtgtgctt ctcttcataa ctctacatag cctgatgtca  64800
ggctagtagc ttgaaattgg ccacagtggg agtgtgagca tttgtaccat gaggcttggc  64860
caaggctaca aatccagact tttgtttttc cctcctggag agctgtctgt taaaaattta  64920
ccaacacacc actggtctta cctttgttaa tttaccacag tccaggttct gacctagact  64980
tagaaacctg gatttgtcag caagctgagg atagagccat tatttttaag aaggactcac  65040
attacccaag tgcaaagcct gatatatacc ttcagaatat caatttatta atttacagtg  65100
aagaaagcca ccccagggca ttccccaggg gaaggcaaaa agagctagtt gcacattttg  65160
aatgtttgat gacattaggg taaggtgaca cagaatatcc atttccacaa ctgagatacc  65220
tgctgcctta aggaagggac aggcaagtcc ttgggcagga ccttagattg tcactgtcca  65280
tcttgctcta ggactctcct ttccaggcat gacgatggcc aactctgtcc tcctacccta  65340
ctgatgggat tatcttttct tgacacatgg caatgcctcc aatcagaggc tggtagctat  65400
ttttaatctt cagggcagta tttttcaaag ggaagttcat ggaccatatg catctgtatc  65460
atttagatgt atattaaaaa tgcttagtct tccccagtta tactagatca gaatctctgt  65520
tggtggggcc cacgaatcgg tattttcaac aaatcactag gtaatttctg tatatactat  65580
agtgtgaaga ccactgcttg aaggtttctt tgcatatctc cactaaatat aaaaaatatt  65640
gacttctaga tttaactccc aaagcacttg catttttaag tttctgggg cattatattg  65700
tggtacccct ataccactca cactctagtc aggaggtata ttatggactg aatgtttgtg  65760
tccctccaaa actcatatgt tgaagtctta gcttccaatg tgatagtatt aggagatggt  65820
gccttctgga ggtaaaatca agccctcatg aatgggatta gtgcctttag aaagagagct  65880
ccgtcactgt ctttccatca attgaagatg cagtgagaag ctggtagtct tgcatctgga  65940
agagggccct cacacaacct gatcatgctg gcacctggtc tcagactttc tgcctccaga  66000
actatgagat gataaatttc tgttgttcat accccaccca ggctacaata ttaggttgct  66060
gcaaagtatt tgtgattttt gcctttactt ttcagggcaa aaactgcaat tacttttgtg  66120
ccaacctaat attttgttat agcagcccga actaaggcaa gggagactac atcagacagt  66180
gtagctatgt aagtacaaat gtatccctgt tgaggaaaac taagttctaa ccctgacttc  66240
aggccagtag ccacctttc aatctctttc atgaagggac cattatcatt atcactggtg  66300
gcaaaaatag aggcacgaga atggaatttg cttttctgtg aaatctcagt gtatacagat  66360
tgaagagcaa gggtttgctt tcatctctaa gaagcaaaag tgagtacgga ctggcacatt  66420
atcagagaaa gaatcattct agctcggtgg gtcttaacca ggagtgaatt tgactccagg  66480
gaacagttgg caatgtctgg agacgttttt atttgttata gctgggggat gagtgggtgg  66540
gttgctactg gcatctagtg ggtggagacc agagatgctg ttaaacatcc cgcaaagcac  66600
aggacagtcc ccgacaacaa agaattatct ggccccaaat atcaatagtg ccaaagttga  66660
gaaacctcat tctagcttcc ttttcccttc tacgttctaa tcaactgttg ttctttcagc  66720
attaggattc atccagcagt ctctttcccc agcaatttgt tgaaattttt ttaaaaatgg  66780
```

-continued

```
actcatttta gtgtcacaag aaaaaaatac attcacagga aaggatgggt cattttgttt  66840
aatgatgttt tgcctttcac atagcaaaag cttaataaag tatttttaaa taaaatggtg  66900
aatagatcaa aacattaatt tcacatgtgt tttaataaat aacaggaaga tggctatatt  66960
atataaattg ttcttgtata tgtcttgagt ggatcatcaa acacaaacgt atctacatgc  67020
cttttcttgt gaatagatct aataataacg ctcttctaaa aacaaattaa atggatatta  67080
tttgctgaga atgtaatgct tgtgtgaata gaagccagcc ctgaatccaa gcccccagat  67140
ctatttaaag aatttgaaga atgtcagaaa agcacgtggc ttcaaggtta atgtgtaaga  67200
ctcacagaaa cttgaaaaat cactatgact aaaaagaaag tatgagctcc ctgcatgcct  67260
gtaaattgga atgacagcca aaaccagtta attataaaaa cagctaattt aacaggtttt  67320
caaatttgtt tctttctcca agtagcatat agtcaataat ccttaaagag aaagcaaaga  67380
aggggaagca ctgaaccaaa tttgcttttt tgtacctgct cagctcaaat gcagagttct  67440
ctacctggaa attgactgct tccatagttt gatagccaca gagagatggg aacagaagga  67500
gaggtataat cccagacttg attcagctat agagaatgac aatagtgtca gaggccttcc  67560
aaccagagcg actccatctt gaatacgggc tgggtaaaac agggctgaga cctactgggc  67620
tgcattccca ggaggctaag cattctaagt cacaggatga gacaggaggt cagcacaaga  67680
ccttgctgat aaaacaggtt gtaataaaga agccagccaa aacccaccaa aaccaagatg  67740
gccatgagag ttatctgtgg ttggtctcac tgctcattgt atgctaatta taatgtatta  67800
gcatgttaaa agacactccc accagtgcta tgacagttta caggtacatt ggcaacttcc  67860
ggaagttacc ctctatggtc taaaaagggg aggaaccctc acctcccaga attgcccacc  67920
cctttcctgg aaaacttgtg aataattcac ccttgttcag catataatca agaagtaact  67980
gtaagtatcc ttaggccaga agctcaggcc actgctctga atgtggaata gccattcttt  68040
tatcctttac tttcttaata aacttgcttt cactttactg tatggactcc ctgtgaattc  68100
tttcttgcaa gagatccaag aactctctct tggggtctgg atcaggacct ctttccagta  68160
acaatagtag taaggggtca gggagactgg acaaaggagt ttaagaagcc ttagataaag  68220
ggtcctcatc attgtcataa cataaaatca tggactccta gaattttata gctgatagga  68280
ttagaaattt caaaattcaa tttcattaat tttcatctgc gaaaacagat ggccagagag  68340
gccaaacaat ttgttaagga gcactgaggg cagaccacac tggaacgcaa acctcttagc  68400
agagtataca aggcctttga tctcctcagt cagaatgaac tagagctttc cagggtaccc  68460
tttctgactg tttagcatgt ttgccagtct gactaatttt gaagttgctt aaatatctgt  68520
catttccact gtatcataat ctcctcattc atcttcaatc tccaatgcct tgaactcagt  68580
aaatgttagt tgaacaaaag taaattgaac ccagaatttc tgatcataat ctggagcact  68640
ttaaaattgt cagcttactg ggaaacggga taacatgtga tttgtctttg attttttttt  68700
tctcatatgc tttttccacc tatagatgct acacgaatgt ttttaaaatc tgatataaaa  68760
attaaaatta aaaaattaaa aaaagaaaat ttgatacaat gctacattta gagtgttgtg  68820
attagattcc ttaagtgtat catggtgatc tctacatcac gtggtgatca aattgctttg  68880
ggttttaaca cataactgac aaaggcttgg ggacatgtaa gatcccaaat acatttttat  68940
tgattttttt ttcttgtttg tcctctttta aataactttt ttttgttata agaataattc  69000
atgttcagtg gagaaaccat agaaaatagt gacaagtgaa ggaataaatt taaaatgacc  69060
cataattgta ccatacattc tgattttta aacgctgaac aaattagcct tgggtaagta  69120
ccaggaatag agtgcagcat tgaaagttaa agtttgggga aggatagctg acttaagaaa  69180
```

-continued

```
ttatctagtt agacattttt tgatggggta attttgcaga tgacattagt gagagaaagg  69240
acttgccact ctcacacagc tagtaggggt gtgggaggat attggaacca agtttcaagt  69300
cttcagtgaa gaatcaaggg agaagttcta aaacctaaca atatccctct ggatggacat  69360
ttattttatt actacaataa gccacacggt gagtcataag gagcatttca ttcttctaat  69420
atgtctctac tgtatttaga atctgataaa gcccctatta gaattcatct ctttaagaat  69480
aaaagaagct gaggaactaa agagagggtt ggaataatcc actaattata tccgttaagc  69540
ttcagttacg ctaataagga atatcacatg actgtggtgt gtgcttgttc tgaacagtaa  69600
agtacatgag gaaagataag attcagggct gaaatgtcct tcagcatatg taggtagtgg  69660
tgatgaaagt cattaaaaga aaaattgatt gaggtatttt agtaaacaaa agaactcacc  69720
acttacccat caggaagtgt attgttaatg cagtgctgtt cagccttctg gaagaaaagg  69780
tttcttcatg cttctctctt tagcctaatt cttatcctgt cacttttcag gcaaaattaa  69840
aaaaaaaaaa agattgaaaa cgatgctcct attttatttg cttcaaaaga aacaggctgt  69900
tgcattgtgc ttggaacagt ttactcttgg ccttgatgta agtgtgaaag gaagcccatg  69960
taattgacta ggcagtatct gaagaagcag gaaatacagt gttaagaaaa tgaacaggca  70020
tgaaaaccat ggctatttga taaaagtaaa taatttctgc agttcacatg ttctcagcat  70080
attttctttg atactgactt gcttaatatg acaatagcag aaccatggta gcttgtaggc  70140
attactttc ttttaatttc ttttacattt tgaatttacc agcactcaca tttgtattac  70200
ttttgggtta tactgaggat ctataactta tagatcaaat acctgacata tatatgcatt  70260
ctctgaagtc ttagggcaga actagaacat tcttgtgaac atcagtataa gatattaaaa  70320
tggaagtttt gcctaagact gaagacaata aaaatatcat agtctgaaat gaatgccagc  70380
acaccataca ggatttaaat atctatacat atatatgtgt gtgtattata tatatttaat  70440
atatatctgt gtgggatagg aagaggtagg gggaaatcag ttttacaatt attaagtatt  70500
tcacccttga caagagtata tatattggaa atcagttgga gagtattttc aaagataaat  70560
gttagtgtgc tatgaatgaa tccacccta ccaccactga ggcagggtag gagaggcctg  70620
tgctcctcaa gcatagttgg aaaaggacct caacaagacc acttcaagag tctaatgtgt  70680
ggagactgtt gcttagggag accttatggt ctagcttctg actcacagct aagtcaggga  70740
gacaggttgg ctgctctgat cgtggagtcc aaaagatggc ctgcactgaa aagcctcatg  70800
agtgttgact tagggctagt ctaagaggtc cctggaagaa gaaacactca gtaggagaga  70860
agctggaggt accttcagtg ctgaattgga acctagattc attcccccgt ggagcaaatt  70920
acataggaaa gatgcccagt gatggagagt gggggtgtct ctaacaatta cccacccacc  70980
tgcccccacc cctaagaaaa agaaaatcac atacaaccag tcagctgtaa acatatgccg  71040
agcctagtaa actcagatac taagttacca gggtacctgg caagtaagaa cattcctgat  71100
tcccttccct cctcttcctc tttgccctcc aaccttagtg gctagcaaga tggggagagg  71160
aggagaagct gtaagtgggg aaaaaagagc agctttctct ccttttcagc tgctggattc  71220
tccctcatca taggcctgag ctggggaatc aggaagaagg attcttttta aaactgaagt  71280
aacgttatca tttaatttta aaacatttta aattttgaca atgttgagat tagatatact  71340
aattattaaa ctaagattat gttttgcagc ttgaagtgat aagaaaaacc tcttatctaa  71400
gagcatccag gaaagtcggg ggtttcctga acatcctttt aaatcctttg gaagtcagct  71460
ttcagagagg atttaaagtg tagactgggc cttcagaaac ttggttaatg taggggtttc  71520
```

-continued

```
ctatgcagac ttggggacta taccttgtgt ggaagagaga aaataagatt atcttacatt  71580
tttcccattc ctttttcaaa aagaaagctc agctagcatg aaagttaaat tcaaaacgta  71640
atgggtatta tttgcatatt caaatctagt gcatatcatg taagtactga attatggtat  71700
tcattatttc aaatgacaag ctggattttt ttttctttcg aatttcacaa attaattttc  71760
cttggaacct tttggtttgg gctttaagag tttaggcttt catcacaaag agaggacagc  71820
cttgaagatt aaagtgtgtg gctcttctca agatgttctt agtccagcaa aggattctat  71880
gcatatttgg gcttccttct gtctcataac ctgtatttct tgatattcta tttatattct  71940
gtaagatttt ttttttaaag gaaaaattct tccatggttg aaggacatgt caaaaaataga  72000
ggatacagtt ttatatcaaa ggaagtttca tgatatgact gtagaagctc atttgactta  72060
agacacatca tttcctcatg gaagtgttaa acagatctgt acaataaggt tggcaatctt  72120
tgtgtaaaac agtttttttt ctcctgctct aaagaaagtg tatatttcaa aatgtgaatg  72180
tcagcagtca gaaaatagta tttttttaac ttcgttttca aagtcctcaa aaacctgtac  72240
ctaatcatga attttttttc ccacagattg tttcttcttc tccctcccag aaactttgaa  72300
gtttttctac atgacaccag gacctatgtc tttttttaat tacacagaaa tgaaagaaaa  72360
aaagtgtgtt gtatcgttaa ccaaatatat gaaatcttta agctgtattt ttatttttaa  72420
ctttgttttg caaagaggcc attccctttg gttaaataat ttgttattca cagtttcctt  72480
gtcctcatat tatcaagggg aaaattgtag aaattttaaa ggaagctcta ggcaatgttt  72540
tcatccctga atctttggag agttataaaa acaaacagat tactgaacct gtaagagaac  72600
caatcgtgaa gtcattacat ctaagcataa gcaaaatctc ctcttggatc attaagttat  72660
agaagaaaag aaagcctgca ctttgaaatt taaataaagc ttggtaactt gtaagtcaaa  72720
cacgtaaaat tttacaattc aggaatatcg atagcagttg agtttaatag acttctcaca  72780
ttccaaattt aaagcttcct tctctgtgct aatagagata caatagcagt aggcgtttaa  72840
gaagaatgaa tcaacaattt aaaactataa tgtgtttttt attcatctcc cttattcaca  72900
tatatttgtt ttgttttgag aaggagttct gctctgtcgc ccaggcagga gtgctgtggc  72960
acgatctcag ctcaccgcaa cctctgcctc ccgggttcaa gcgattctct tgcctcagcc  73020
tcctgagtag ctgcgattac aggcgtgcgc cagcaacccc ggctaatttt tgtattttta  73080
gtagagacag ggtttcacca cgttggccag gttggtctcg aacccctgat ctcaagtgat  73140
cagcccgcct cggcctccca aagtgctggg attacaggcg tgagccatca cttctggccc  73200
ttattcgcat acaatttaaa aatcatcaca gaaggtttga aagaaggaag gggcagaaaa  73260
ttacctactt ttcctctccc cagcgatctc cttcaaatct gtgccttttc ctcaggccca  73320
ggcctcaatt tactgagcag tcacacctca cagagggagg tctgggcaat ccactcttgg  73380
tcacaggaaa gccattgacc ctcccacttc ctctcctcca ccttgttctc aactcttgac  73440
tttgggcttt gtttctgttc aagtcctagg aactggtttc ttttatcagg ttaagtgatt  73500
agttctcttt ccctctagtt gctctcactc cctgactctt gccttctgta acaactggag  73560
acaactcttt caaaaccagc tccaagcccc agacttctct ctgggcttta gttcgtaagg  73620
caggtgccct actgagtgag cctagatcag acagaaacat agctgttggc aatgatttag  73680
gtgaatttcc ttccattgtt tttctaatac cttctttttt ttgtaaatat aaccatgcac  73740
atacacacat atttgaatat cctgcctttt tatttaaaat gacaataggt ccgggagtgg  73800
tggctcatgc ctgtaatccc agcactttgg gaggccgagg tgggcaatca cctgaggtca  73860
ggagttcgag accagcctgg ccaacatggt gaaactccat ctctactaaa aatcaaaaat  73920
```

-continued

```
tagccgggca tggtggcagg ctcccagcta ctcaggaggc tgagatgtga aaatcgcttg  73980
aacccgggag gtagaggttg cagtgagctg agatcttgcc attgcactcc aacctgggca  74040
ataagagcga aactccatct catggaaaaa aaaaaaaaaa agacaggata aacattctag  74100
atagtctcta taatggtcat gattaagaca ataaaatagt ctgaaattgt caatatatat  74160
taataataat ttatttggcc attctgccaa gtagcagaca cctgtcattc tgcccactca  74220
gcacctctct ttcttttagg gaaatgctac ccactctttg catgggttct ggatggaact  74280
gttgatcaca gtgttttcac tccccatttt gcctcaccag aggtagacag aagacccaag  74340
ccaggccagt tacacacaat cttcagataa ttaccgtatt gatcacagta tcaccccact  74400
caaggcttgg ttggagatga gcagaagaga ctaaagctgg gtcattttaa ttaacacctg  74460
taccccaaag aaagactgtc aatgaggctt ttataccgac actcctggtt tccattcttc  74520
ctgatgccat tcatttgacg aactacccaa tctttccaac agtgtctttg gaagaaagat  74580
agtcagaaaa gaagatagag ttgttttctg ttctttgcaa ccaaggaact ctaaatgata  74640
gacttgttgc taggcacttt ggttattttt attatcttga atacttctgt gatatacttc  74700
tttgtgcatg cctgtttgta cggatgtagc tttttatata ttttatataa tttctcagaa  74760
gtggaattac ttagtcaaaa ggtatgaaca tttttctgat tcttaatata aattgtgcaa  74820
atgcttttta agaggattat accagtttac attttgtgtt atatataaca gaaagtacta  74880
ctgaaaaaat attacaaaaa tttgtctctc tgttcaggag gaccttgtaa tagatgataa  74940
agtacttgaa ataggaacat agagcatttt cagtttaaaa taatttcatt gggttattta  75000
cggaatcctt agaattatgg ccagacattt atagatgatc tgtaccaaac ctaggttggt  75060
tacataaatt gcttattcaa ctggcttaaa tctataatag aaagatgaca cttactgaat  75120
gtttaatata cactttgtca ggggctttgt attattctat gacatcttca aaatgaccct  75180
actttcctat tttataagta aggacaggaa ggcttcaaga acatgactaa ttttcccaag  75240
ggctgtacca aagccagaac ccaaatctat aaggctttta aacctgcatt ctaaaactgc  75300
atctcggcca tcttattcct acagaactta aggttagaaa gccagattgg agtcccaatt  75360
tcaccactta gtaaccagac aaacttgagg aattcactca acgtctttga atcttcattt  75420
tctaatcttt aaaactaaaa caataatact tgctctacct atgtcctaag atttcgtgag  75480
gcacatagag atagtgtgga agagtgctgt acagatgtca agtgttagcg tgattactta  75540
gatccctgaa caccatggat gaatgtctct gactgctatt agaggtcata aagaatattg  75600
gggccaggta cattggctta ttcctataat gccagcactt tgggagcctg agacaggagg  75660
atcactcgag gccacgagtt caagaccggc ctgggcaaca tagtgagacc ccttctctac  75720
aaaaaaaaaa gcagccacgt gtagtggcac acacctgtag tcccacatac tcaggagggt  75780
gagttgggag gataacttta gtccaggagt ttcaaggtgc agtgagctgt gattgcacca  75840
ctgtactcta acctggacag cagagtgaga ccctgtctct aaaaaaaaag aaaaaaaaat  75900
aataataata aagaataatg gggccttggg atacccactc ctctctttct gctctgagtt  75960
gtgaagcagt tgagttacat atgcatgtcc aatggatgag gttgaaaata tcaactggat  76020
tggaatgtgg cttacttgcg tggccacaat gagcttcgta acacttcctg acagggtgag  76080
aagacaaact tcctcaccca gtcactggca gagctggaca ctctgtgtct ctcccacaga  76140
acaacctctt actgcatgga ggtggatgaa aaagtcaacc gagaacaggc tactccaaaa  76200
agcagagcac caaaggcacc agctggtcag gtccccccttc ctaagtaaac aatcacgtaa  76260
```

-continued

```
ttcattcggg acaaagccag agaggtggtg tggagaaaga gagggcagtt tcctcccaag  76320
tttttcctgg aattctttat gggaatatga ggtttagggg aataagactt ccctttaaca  76380
gtgaagaatc cccagctcta ttggtaatag gaaatcgctt acaaggatca tggggagtat  76440
ttcctcagct cgttctgcct cctacttggc tgagtggaat ggaaccatct gtggctgctg  76500
catatgatat tgtcaacttt gtcattccac acccactcct tgacgcccta ccatgtggtc  76560
ataagactcc ctttaaagtg ttcctttaaa aaacaaaatg tgttttgttt ctataaaata  76620
cagctcaatg tcagaaccct tgtcttgttt gctctctgat gtaacccttt cacaatgttt  76680
gggcagctta ttctctctat ttccctgtag ggtcccatcc aggccaaagt gagtgccagc  76740
ctcatttggg cagcagatgc cctgtggaag ggcaggagga gacgagagct aattgtaact  76800
ttgtgattag ctgtcatgga tgcctggtcc tgtcaatagc gctcaataaa gccagaaggc  76860
caagcgttcg cttctgcata ctgattgctg agtcagattt ctcagtgcag aagggctttc  76920
taggcagtca attttagaat attagtcttg gttcttaagt ggttaaaatc cctagctggt  76980
ctttaatctg agcctggaga atttagttat ggctgacatt ctgctgtgat atttttgccc  77040
tcaatatata tgtctttcct ccatctctta gatccctgaa tcatagagat atatatgtta  77100
tataatcaac tgtctccagt ctctaagagt gataagtaca cattgtgtca ggttgagggg  77160
acaggagaac tttcaaaagc ctttcttgcc cctttttcct tctcactgcc tcccactaag  77220
tccagccact tattattcag ctgacactat catcatgacc atgaggtctt ttggggctac  77280
cctggttcgg atccttctgg aggtttgttg cttaactctg tcttcagtcc tatgagctgc  77340
tttttcaata agtttctatt ttggctaaag ttggccagaa tctccttgta accaaagaac  77400
aaataaaata ccagcttgca atgttctatg ttgcttccac caaacttatg cagcacttcc  77460
tatctaatcc acctactagt cttttttttt tttatttttt ttgagacgga gtctcgctct  77520
gttgctcagg atggagtgca atggtgcaat ctcggctcac tgcaacctct gcctcccggg  77580
ttcaagcaat tccccggcct cagcctcctg agtagctggg actacaggtg catgccacca  77640
cgtccggcta atttttgtat tttaggagag agagggtttc accatgttgc ccaggctggt  77700
cacgaactcc tgagctcagg caatccgccc tcctcgggct cccaaagtgc tgggattaca  77760
ggagtgagcc acctcacctg gccccgacct actagtcttt agtgtttgct tccttctatt  77820
gggtaattgt ctgtttatat gcatgtcttg tttcctcaaa taaaatgtgg tcttctcaag  77880
ggtattggcc catgttctat ccatctgtag atatcacagc acctagcagt gtctttcaca  77940
gaggaagtac acaactggca ttattgattc attgctccat tttttccttc tttatcccca  78000
gcatttctca ataatttcaa acatctccat tggagtaccg gagaaagcag gtagctttac  78060
ttgcagctat gtttctatcc ccatagtaac taaaagagga cccagagaaa catgtttaaa  78120
tgctgtcctg ttatcaggac ctcagccttc tgatgctccg tggcttgggg gttattgctt  78180
gatcatctcc tccccaacct acactgtgta cctatgctag tctcttcatg aggactaagc  78240
cccatagtaa aagggctaga taaatagaaa atcattttat gtaattataa gaatgagaat  78300
actgagtatt ctggtgtttg tttaggataa gcacatcttt atttgtatga gaaaaagaaa  78360
aagagagtga aaaatatatt aacgtgcata ttgttcagaa cccttggatt gcaagtgaca  78420
gaaactcaat tcaaaccaac gtaagtcaaa aggaaaatat attggctcat gtaaccttct  78480
cacagagagg gcaggatgga aggggctttg ggaacaagag aattgttctc aaattctagg  78540
aatactagga ttagtccagg atgggtcacc ttcctgtccc tgaggtggtg gtagcgatgg  78600
tagagtctta tgggaggaaa gagtgcatgt taggatgaag gtagggctaa gcaaacaagg  78660
```

-continued gcaagggcca ctatatcatg ctaaaaatgg tttttttga tgtcttcctt aatttcacaa 78720
atgcttccaa caaagtagca cacaggaaaa agaacatagg gactctactg gtgggtgctt 78780
ttatcttaag ccttgtactt gcttttcaca gcttactcac tgcttgtacc tgaggccata 78840
tgccctgtaa aagcttctgc agggtttcta ctaagctggg ttccttatat ggctctctcc 78900
catttctgtt gcctcactct agtgatcttt ctcttttcct cacctctggg actggtggct 78960
gtttgtatgg actgccttag ctttgctttg ggtttttcc tggggacaat gtcttcagat 79020
tatcctagac caaataaact acagccactg ggccaggctc ttcctcctcc aactggacca 79080
tgttcccagg gctcttcacc ttagtttagg tcaagcattc ttggcaaaag aaaggcctag 79140
ttaacaatag acattctagc aattgattct ttttgacatg ttgtaagatc tattcacatt 79200
ttgtaattaa agcattcccc tatggaaacc aacacgaact aagctgctcc tggaatgcag 79260
ggtggcctcc tcaatacagg atgttctaga gagctgtatt ttgggcactt aactattctc 79320
cactacttag ggcacagcac tgaaattaac accactaagt ttgtcatgtc catgtagtta 79380
gtctcaggca gtgcagcctc aggagtggaa ctgacctctt atgtgtgtcc agcctttctt 79440
ccttcagaag tcagctgtgt tttctgctga ctctccatag gaacatcagt cctgaatcct 79500
cagaccacca tctggagtag taagtgctcc tgacagtcct agaagttgtc taccgctgga 79560
tctccaaagc gtgtgacaca ccgtgagaga gaaatgagaa agctgggctc ttcaggtaaa 79620
tcttgctttt tcacaagccc cctaatttta ctgcataatt attttgaatt cactgataat 79680
ttctacaatt ttcccataag tcatctacac acaataccct ctcatgcaac acttggcttt 79740
gctaatacat atctattatg agagctgtgc ttcttaagcg taaatgtttt atatgcacta 79800
aggctcttgg cttacatata aaaggggtat tgagcaatgt gatacagaag tcttttctcc 79860
acaggtctca tatgtaaaga attcattaga ttggctgaaa tagactgatc tgtccatttc 79920
tctgctcact tatcataagg aagtcattag ctaaggaaca aaaactacaa tctatgtaat 79980
tagaagaaca agctggtttt gctcaatata aaaataagaa aaagaaacca tgtgaaagtc 80040
aaaatatttg tttaatcagg tcattgagaa tctattaaaa agtatttgaa ttctttatga 80100
tgagaactat cttgactcaa gtggacagtg gtgagctttt tggcctgtgg tccctacgta 80160
gaaaggaggc tttgtcataa agtcttatat ggtacaggtg ccaagttaag tgcccaagct 80220
tgctcttaaa agcatactgg attttg 80246

<210> SEQ ID NO 5
<211> LENGTH: 5596
<212> TYPE: DNA
<213> ORGANISM: BAC-F2 contig 1

<400> SEQUENCE: 5
tatggacata ttgtcgttag aacgcggcta caattaatac ataaccttat gtatcataca 60
catacgattt aggtgacact atagaaccag atctgatatc gaatgaattc tttcttgcaa 120
gagatccaag aactctctct tggggtctgg atcaggacct ctttccagta acaatagtag 180
taaggggtca gggagactgg acaaaggagt ttaagaagcc ttagataaag ggtcctcatc 240
attgtcataa cataaaatca tggactccta gaattttata gctgatagga ttagaaattt 300
caaaattcaa tttcattaat tttcatctgc gaaaacagat ggccagagag gccaaacaat 360
ttgttaagga gcactgaggg cagaccacac tggaacgcaa acctcttagc agagtataca 420
aggcctttga tctcctcagt cagaatgaac tagagctttc cagggtaccc tttctgactg 480

-continued

```
tttagcatgt ttgccagtct gactaatttt gaagttgctt aaatatctgt catttccact    540
gtatcataat ctcctcattc atcttcaatc tccaatgcct tgaactcagt aaatgttart    600
tgaacaaaag taaattgaac ccagaatttc tgatcataat ctggagcact ttaaaattgt    660
cagcttactg ggaaacggga taacatgtga tttgtctttg attttttttt tctcatatgc    720
tttttccacc tatagatgct acacgaatgt ttttaaaatc tgatataaaa attaaaatta    780
aaaaattaaa aaaagaaaat ttgatacaat gctacattta gagtgttgtg attagattcc    840
ttaagtgtat catggtgatc tctacatcac gtggtgatca aattgctttg ggttttaaca    900
cataactgac aaaggcttgg ggacatgtaa gatcccaaat acatttttat tgattttttt    960
ttctkgtttg tcctctttta aataactttt ttttgttata agaataattc atgttcagtg   1020
gagaaaccat agaaaatagt gacaagtgaa ggaataaatt taaaatgacc cataattgta   1080
ccatacattc tgatttttta aacgctgaac aaattagcct tgggtaagta ccaggaatag   1140
agtgcagcat tgaaagttaa agtttgggga aggatagctg acttaagaaa ttatctagtt   1200
agacattttt tggatggggt aattttgcag atgacattag tgagagaaag gacttgccac   1260
tctcacacag ctagtagggg tgtgggagga tattggaacc aagtttcaag tcttcagtga   1320
agaatcaagg gagaagttct aaaacctaac aatatccctc tggatggaca tttattttat   1380
tactacaata agccacacgg tgagtcataa ggagcatttc attcttctaa tatgtctcta   1440
ctgtatttag aatctgataa agcccctatt agaattcatc tctttaagaa taaaagaagc   1500
tgaggaacta aagagagggt tggaataatc cactaattat atccgttaag cttcagttac   1560
gctaataagg aatatcacat gactgtggtg tgtgcttgtt ctgaacagta aagtacatga   1620
ggaaagataa gattcagggc tgaaatgtcc ttcagcatat gtaggtagtg gtgatgaaag   1680
tcattaaaag aaaaattgat tgaggtattt tagtaaacaa aagaactcac cacttaccca   1740
tcaggaagtg tattgttaat gcagtgctgt tcagccttct ggaagaaaag gtttcttcat   1800
gcttctctct ttagcctaat tcttatcctg tcacttttca ggcaaaatta aaaaaaaaaa   1860
aagattgaaa acgatgctcc tattttattt gcttcaaaag aaacaggctg ttgcattgtg   1920
cttggaacag tttactcttg gccttgatgt aagtgtgaaa ggaagcccat gtaattgact   1980
aggcagtatc tgaagaagca ggaaatacag tgttaagaaa atgaacaggc atgaaaacca   2040
tggctatttg ataaaagtaa ataatttctg cagttcacat gttctcagca tattttcttt   2100
gatactgact tgcttaatat gacaatagca gaaccatggt agcttgtagg cattactttt   2160
cttttaattt cttttacatt ttgaatttac cagcactcac atttgtatta cttttgggtt   2220
atactgagga tctataactt atagatcaaa tacctgacat atatatgcat tctctgaagt   2280
cttagggcag aactagaaca ttcttgtgaa catcagtata agatattaaa atggaagttt   2340
tgcctaagac tgaagacaat aaaaatatca tagtctgaaa tgaatgccag cacaccatac   2400
aggatttaaa tatctataca tatatatgtg tgtgtattat atatatttaa tatatatctg   2460
tgtgggatag gaagaggtag ggggaaatca gttttacaat tattaagtat ttcacccttg   2520
acaagagtat atatattgga aatcagttgg agagtatttt caaagataaa tgttagtgtg   2580
ctatgaatga atccacccct accaccactg aggcagggta ggagaggcct gtgctcctca   2640
agcatagttg gaaaaggacc tcaacaagac cacttcaaga gtctaatgtg tggagactgt   2700
tgcttaggga gaccttatgg tctagcttct gactcacagc taagtcaggg agacaggttg   2760
gctgctctga tcgtggagtc caaaagatgg cctgcactga aaagcctcat gagtgttgac   2820
ttagggctag tctaagaggt ccctggaaga agaaacactc agtaggagag aagctggagg   2880
```

-continued

```
taccttcagt gctgaattgg aacctagatt cattcccccg tggagcaaat tacataggaa   2940
agatgcccag tgatggagag tgggggtgtc tctaacaatt acccacccac ctgcccccac   3000
ccctaagaaa aagaaaatca catacaacca gtcagctgta aacatatgcc gagcctagta   3060
aactcagata ctaagttacc agggtacctg gcaagtaaga acattcctga ttcccttccc   3120
tcctcttcct ctttgccctc caaccttagt ggctagcaag atggggagag gaggagaagc   3180
tgtaagtggg gaaaaaagag cagctttctc tccttttcag ctgctggatt ctccctcatc   3240
ataggcctga gctggggaat caggaagaag gattcttttt aaaactgaag taacgttatc   3300
atttaatttt aaaacatttt aaattttgac aatgttgaga ttagatatac taattattaa   3360
actaagatta tgttttgcag cttgaagtga taagaaaaac ctcttatcta agagcatcca   3420
ggaaagtcgg gggtttcctg aacatccttt taaatccttt ggaagtcagc tttcagagag   3480
gatttaaagt gtagactggg ccttcagaaa cttggttaat gtaggggttt cctatgcaga   3540
cttggggact ataccttgtg tggaagagag aaaataagat tatcttacat ttttcccatt   3600
cctttttcaa aaagaaagct cagctagcat gaaagttaaa ttcaaaacgt aatgggtatt   3660
atttgcatat tcaaatctag tgcatatcat gtaagtactg aattatggta ttcattattt   3720
caaatgacaa gctggatttt tttttctttc gaatttcaca aattaatttt ccttggaacc   3780
ttttggtttg ggctttaaga gtttaggctt tcatcacaaa gagaggacag ccttgaagat   3840
taaagtgtgt ggctcttctc aagatgttct tagtccagca aaggattcta tgcatatttg   3900
ggcttccttc tgtctcataa cctgtatttc ttgatattct atttatattc tgtaagattt   3960
tttttttaaa ggaaaaattc ttccatggtt gaaggacatg tcaaaaatag aggatacagt   4020
tttatatcaa aggaagtttc atgatatgac tgtagaagct catttgactt aagacacatc   4080
atttcctcat ggaagtgtta aacagatctg tacaataagg ttggcaatct ttgtgtaaaa   4140
cagttttttt tctcctgctc taaagaaagt gtatatttca aaatgtgaat gtcagcagtc   4200
agaaaatagt atttttttaa cttcgttttc aaagtcctca aaaacctgta cctaatcatg   4260
aatttttttt cccacagatt gtttcttctt ctccctccca gaaactttga agtttttcta   4320
catgacacca ggacctatgt cttttttttaa ttacacagaa atgaaagaaa aaaagtgtgt   4380
tgtatcgtta accaaatata tgaaatcttt aagctgtatt tttattttta actttgtttt   4440
gcaaagaggc cattcccttt ggttaaataa tttgttattc acagtttcct tgtcctcata   4500
ttatcaaggg gaaaattgta gaaattttaa aggaagctct aggcaatgtt ttcatccctg   4560
aatctttgga gagttataaa aacaaacaga ttactgaacc tgtaagagaa ccaatcgtga   4620
agtcattaca tctaagcata agcaaaatct cctcttggat cattaagtta tagaagaaaa   4680
gaaagcctgc actttgaaat ttaaataaag cttggtaact tgtaagtcaa acacgtaaaa   4740
ttttacaatt caggaatatc gatagcagtt gagtttaata gacttctcac attccaaatt   4800
taaagcttcc ttctctgtgc taatagagat acaatagcag taggcgttta agaagaatga   4860
atcaacaatt taaaactata atgtgttttt tattcatctc ccttattcac atatatttgt   4920
tttgttttga gaaggagttc tgctctgtcg cccaggcagg agtgctgtgg cacgatctca   4980
gctcaccgca acctctgcct cccgggttca agcgattctc ttgcctcagc ctcctgagta   5040
gctgcgatta caggcgtgcg ccagcaaccc cggctaattt ttgtattttt agtagagaca   5100
gggtttcacc acgttggcca ggttggtctc gaacccctga tctcaagtga tcagcccgcc   5160
tcggcctccc aaagtgctgg gattacaggc gtgagccatc acttctggcc cttattcgca   5220
```

-continued

```
tacaatttaa aaatcatcac agaaggtttg aaagaaggaa ggggcagaaa attacctact   5280

tttcctctcc ccagcgatct ccttcaaatc tgtgcctttt cctcaggccc aggcctcaat   5340

ttactgagca gtcacacctc acagagggag gtctgggcaa tccactcttg gtcacaggaa   5400

agccattgac cctcccactt cctctcctcc accttgttct caactcttga ctttgggctt   5460

tgtttctgtt caagtcctag gaactggttt cttttatcag gttaagtgat tagttctctt   5520

tccctctagt tgctctcact ccctgactcg gggcatccac tagttctaga gcggccgcca   5580

ccgcgtggac tcacag                                                   5596
```

<210> SEQ ID NO 6
<211> LENGTH: 18443
<212> TYPE: DNA
<213> ORGANISM: BAC-F2 contig 2

<400> SEQUENCE: 6

```
gagggcggga accccctttc caaaaaaaaa gaaacaaaga caggataaac attctagata     60

gtctctataa tggtcatgat taagacaata aaatagtctg aaattgtcaa tatatattaa    120

taataattta tttggccatt ctgccaagta gcagacacct gtcattctgc ccactcagca    180

cctctctttc ttttagggaa atgctaccca ctctttgcat gggttctgga tggaactgtt    240

gatcacagtg ttttcactcc ccattttgcc tcaccagagg tagacagaag acccaagcca    300

ggccagttac acacaatctt cagataatta ccgtattgat cacagtatca ccccactcaa    360

ggcttggttg gagatgagca gaagagacta aagctgggtc attttaatta acacctgtac    420

cccaaagaaa gactgtcaat gaggctttta taccgacact cctggtttcc attcttcctg    480

atgccattca tttgacgaac tacccaatct ttccaacagt gtctttggaa gaaagatagt    540

cagaaaagaa gatagagttg ttttctgttc tttgcaacca aggaactcta aatgatagac    600

ttgttgctag gcactttggt tatttttatt atcttgaata cttctgtgat atacttcttt    660

gtgcatgcct gtttgtacgg atgtagcttt ttatatattt tatataattt ctcagaagtg    720

gaattactta gtcaaaaggt atgaacattt ttctgattct taatataaat tgtgcaaatg    780

ctttttaaga ggattatacc agtttacatt ttgtgttata tataacagaa agtactactg    840

aaaaaatatt acaaaaattt gtctctctgt tcaggaggac cttgtaatag atgataaagt    900

acttgaaata ggaacataga gcattttcag tttaaaataa tttcattggg ttatttacgg    960

aatccttaga attatggcca gacatttata gatgatctgt accaaaccta ggttggttac   1020

ataaattgct tattcaactg gcttaaatct ataatagaaa gatgacactt actgaatgtt   1080

taatatacac tttgtcaggg gctttgtatt attctatgac atcttcaaaa tgaccctact   1140

ttcctatttt ataagtaagg acaggaaggc ttcaagaaca tgactaattt tcccaagggc   1200

tgtaccaaag ccagaaccca aatctataag gcttttaaac ctgcattcta aaactgcatc   1260

tcggccatct tattcctaca gaacttaagg ttagaaagcc agattggagt cccaatttca   1320

ccacttagta accagacaaa cttgaggaat tcactcaacg tctttgaatc ttcattttct   1380

aatctttaaa actaaaacaa taatacttgc tctacctatg tcctaagatt tcgtgaggca   1440

catagagata gtgtggaaga gtgctgtaca gatgtcaagt gttagcgtga ttacttagat   1500

ccctgaacac catggatgaa tgtctctgac tgctattaga ggtcataaag aatattgggg   1560

ccaggtacat tggcttattc ctataatgcc agcactttgg gagcctgaga caggaggatc   1620

actcgaggcc acgagttcaa gaccggcctg ggcaacatag tgagacccct tctctacaaa   1680

aaaaaaagca gccacgtgta gtggcacaca cctgtagtcc cacatactca ggagggtgag   1740
```

-continued

```
ttgggaggat aactttagtc caggagtttc aaggtgcagt gagctgtgat tgcaccactg   1800
tactctaacc tggacagcag agtgagaccc tgtctctaaa aaaaaagaaa aaaaaataat   1860
aataataaag aataatgggg ccttgggata cccactcctc tctttctgct ctgagttgtg   1920
aagcagttga gttacatatg catgtccaat ggatgaggtt gaaaatatca actggattgg   1980
aatgtggctt acttgcgtgg ccacaatgag cttcgtaaca cttcctgaca gggtgagaag   2040
acaaacttcc tcacccagtc actggcagag ctggacactc tgtgtctctc ccacagaaca   2100
acctcttact gcatggaggt ggatgaaaaa gtcaaccgag aacaggctac tccaaaaagc   2160
agagcaccaa aggcaccagc tggtcaggtc ccccttccta agtaaacaat cacgtaattc   2220
attcgggaca aagccagaga ggtggtgtgg agaaagagag ggcagtttcc tcccaagttt   2280
ttcctggaat tctttatggg aatatgaggt ttaggggaat aagacttccc tttaacagtg   2340
aagaatcccc agctctattg gtaataggaa atcgcttaca aggatcatgg ggagtatttc   2400
ctcagctcgt tctgcctcct acttggctga gtggaatgga accatctgtg gctgctgcat   2460
atgatattgt caactttgtc attccacacc cactccttga cgccctacca tgtggtcata   2520
agactccctt taaagtgttc ctttaaaaaa caaaatgtgt tttgtttcta taaaatacag   2580
ctcaatgtca gaacccttgt cttgtttgct ctctgatgta accctttcac aatgtttggg   2640
cagcttattc tctctatttc cctgtagggt cccatccagg ccaaagtgag tgccagcctc   2700
atttgggcag cagatgccct gtggaagggc aggaggagac gagagctaat tgtaactttg   2760
tgattagctg tcatggatgc ctggtcctgt caatagcgct caataaagcc agaaggccaa   2820
gcgttcgctt ctgcatactg attgctgagt cagatttctc agtgcagaag ggctttctag   2880
gcagtcaatt ttagaatatt agtcttggtt cttaagtggt taaaatccct agctggtctt   2940
taatctgagc ctggagaatt tagttatggc tgacattctg ctgtgatatt tttgccctca   3000
atatatatgt ctttcctcca tctcttagat ccctgaatca tagagatata tatgttatat   3060
aatcaactgt ctccagtctc taagagtgat aagtacacat tgtgtcaggt tgaggggaca   3120
ggagaacttt caaaagcctt tcttgcccct ttttccttct cactgcctcc cactaagtcc   3180
agccacttat tattcagctg acactatcat catgaccatg aggtcttttg ggctaccct   3240
ggttcggatc cttctggagg tttgttgctt aactctgtct tcagtcctat gagctgcttt   3300
ttcaataagt ttctatttg gctaaagttg gccagaatct ccttgtaacc aaagaacaaa   3360
taaaatacca gcttgcaatg ttctatgttg cttccaccaa acttatgcag cacttcctat   3420
ctaatccacc tactagtctt tttttttttt attttttttg agacggagtc tcgctctgtt   3480
gctcaggatg gagtgcaatg gtgcaatctc ggctcactgc aacctctgcc tcccgggttc   3540
aagcaattcc ccggcctcag cctcctgagt agctgggact acaggtgcat gccaccacgt   3600
ccggctaatt tttgtatttt aggagagaga gggtttcacc atgttgccca ggctggtcac   3660
gaactcctga gctcaggcaa tccgccctcc tcgggctccc aaagtgctgg gattacagga   3720
gtgagccacc tcacctggcc ccgacctact agtctttagt gtttgcttcc ttctattggg   3780
taattgtctg tttatatgca tgtcttgttt cctcaaataa aatgtggtct tctcaagggt   3840
attggcccat gttctatcca tctgtagata tcacagcacc tagcagtgtc tttcacagag   3900
gaagtacaca actggcatta ttgattcatt gctccatttt ttccttcttt atccccagca   3960
tttctcaata atttcaaaca tctccattgg agtaccggag aaagcaggta gctttacttg   4020
cagctatgtt tctatcccca tagtaactaa aagaggaccc agagaaacat gtttaaatgc   4080
```

-continued

```
tgtcctgtta tcaggacctc agccttctga tgctccgtgg cttgggggtt attgcttgat   4140
catctcctcc ccaacctaca ctgtgtacct atgctagtct cttcatgagg actaagcccc   4200
atagtaaaag ggctagataa atagaaaatc attttatgta attataagaa tgagaatact   4260
gagtattctg gtgtttgttt aggataagca catctttatt tgtatgagaa aaagaaaaag   4320
agagtgaaaa atatattaac gtgcatattg ttcagaaccc ttggattgca agtgacagaa   4380
actcaattca aaccaacgta agtcaaaagg aaaatatatt ggctcatgta accttctcac   4440
agagagggca ggatggaagg ggctttggga acaagagaat tgttctcaaa ttctaggaat   4500
actaggatta gtccaggatg ggtcaccttc ctgtccctga ggtggtggta gcgatggtag   4560
agtcttatgg gaggaaagag tgcatgttag gatgaaggta gggctaagca aacaagggca   4620
agggccacta tatcatgcta aaaatggttt tttttgatgt cttccttaat ttcacaaatg   4680
cttccaacaa agtagcacac aggaaaaaga acatagggac tctactggtg ggtgctttta   4740
tcttaagcct tgtacttgct tttcacagct tactcactgc ttgtacctga ggccatatgc   4800
cctgtaaaag cttctgcagg gtttctacta agctgggttc cttatatggc tctctcccat   4860
ttctgttgcc tcactctagt gatctttctc ttttcctcac ctctgggact ggtggctgtt   4920
tgtatggact gccttagctt tgctttgggt tttttcctgg ggacaatgtc ttcagattat   4980
cctagaccaa ataaactaca gccactgggc caggctcttc ctcctccaac tggaccatgt   5040
tcccagggct cttcacctta gtttaggtca agcattcttg gcaaaagaaa ggcctagtta   5100
acaatagaca ttctagcaat tgattctttt tgacatgttg taagatctat tcacattttg   5160
taattaaagc attcccctat ggaaaccaac acgaactaag ctgctcctgg aatgcagggt   5220
ggcctcctca atacaggatg ttctagagag ctgtattttg ggcacttaac tattctccac   5280
tacttagggc acagcactga aattaacacc actaagtttg tcatgtccat gtagttagtc   5340
tcaggcagtg cagcctcagg agtggaactg acctcttatg tgtgtccagc ctttcttcct   5400
tcagaagtca gctgtgtttt ctgctgactc tccataggaa catcagtcct gaatcctcag   5460
accaccatct ggagtagtaa gtgctcctga cagtcctaga agttgtctac cgctggatct   5520
ccaaagcgtg tgacacaccg tgagagagaa atgagaaagc tgggctcttc aggtaaatct   5580
tgctttttca caagccccct aattttactg cataattatt ttgaattcac tgataatttc   5640
tacaattttc ccataagtca tctacacaca ataccctctc atgcaacact tggctttgct   5700
aatacatatc tattatgaga gctgtgcttc ttaagcgtaa atgttttata tgcactaagg   5760
ctcttggctt acatataaaa ggggtattga gcaatgtgat acagaagtct tttctccaca   5820
ggtctcatat gtaaagaatt cattagattg gctgaaatag actgatctgt ccatttctct   5880
gctcacttat cataaggaag tcattagcta aggaacaaaa actacaatct atgtaattag   5940
aagaacaagc tggttttgct caatataaaa ataagaaaaa gaaaccatgt gaaagtcaaa   6000
atatttgttt aatcaggtca ttgagaatct attaaaaagt atttgaattc tttatgatga   6060
gaactatctt gactcaagtg gacagtggtg agctttttgg cctgtggtcc ctacgtagaa   6120
aggaggcttt gtcataaagt cttatatggt acaggtgcca agttaagtgc ccaagcttgm   6180
tcttaaaagc atactggatt ttgttttaga cttttagtga actgaaggga ataaacaaat   6240
ccctctggga gaacttctcc tccatccttg gtgaagtcat tctgccagaa ttctatctgg   6300
tagttacctt ctccgattca ttaaatgttg tcccatggtc cgacatgggt aatttttctc   6360
tcatttgtga ttagttccac tacaaggaat taaatattca acttcttgcc ttctgggata   6420
tactcagcct tatcacagag ctcctccagg gaaggaactt agattctttg aagaacttcc   6480
```

-continued

```
ctgctcttac ccaaaccgat tcagttgtta attctgtcca ccttgctcca ttttcagtgc   6540
aggagaaaaa gcatttgtgg caagtctgac cttacaaagg ctcgttaatg ctcaataact   6600
gtgaggacct gctataagtc atgcctttta agaaaaaata cacacatgca cacactcacg   6660
acaagactgc aacacaactg tgatggcagc ttgcatattg aaccagctgt ttccctaaaa   6720
catttgattc ggcatccttt gtagacagta aatgcaaaag acttaggttg gaaaagtgca   6780
ttaggttttg attaacgatt ggatgagggc cagttaaatt tttaaatctg aatgagcttg   6840
ctgactcagg agccttagca gcataatgga cagacagtcc tcaaagcttt cattaaaagg   6900
gtttctggta actgatgtct aragaaatga gttgaaatac aattcactga accactcagc   6960
tttcatctaa aacagaatat gtaatctcaa agaactcaac tggtctcttg aaatattcag   7020
gtaaaattaa atgtaaagaa gctagagctt aaatattttg aggaaaggaa gcctcctgta   7080
gctttgtgac tatatcactt tatccttttg aatgccgtat ttaattatgt taattgcatt   7140
ttaagtatag ctggagtcac cgatctgctg aaaacaaact ctasaatggt ttgtgggagg   7200
tgctcaggat gtatcagaga ctgatttgat ttgcatttta tttttaactt tagttcctct   7260
ctgaactctg ccttctcatg tttgtttttt wtgttgttgt tgcttaatac agtcatgtgc   7320
cacctaatga cagggatatg ttctgagaaa tgcattatta ggtgattttg ccattgtgca   7380
aacatcacag tgtacttaca caaacctaga tggcatagcc tactacacac gtctgctata   7440
tggtagagcc tattgcttcc agactacaaa cctgtatagc atgttactgt actaactact   7500
gtaggcagtt gtaacactgg tatttgtgta tctaaaccta tctaaacata gaaaaggtac   7560
aataaaaata cagtattata atcttatggg accactgcta tatatgcagt ccatcattga   7620
ctgaaacatt atgtggtgca tgactataat aggatcaaac tatgcctttg cagaaatccc   7680
cctggaaagc ctctgaaact accctgatct tagaggcagt tttataaatc acggccaatg   7740
attctcagcc tttgggttgt gccagagatg tgtccgctct ccttttgcaa tgaccctaga   7800
ggtaaaggtg ctctttcttc ttctgcttct catgaaaaaa tgtaaatgtt gtattttagc   7860
ttcttttccc agtctagtaa tatcttgtta aatttacaag attgtagcgg tgcctccaaa   7920
aggggatagc aatagttact ttgaaaatgg gtgagttctt tgcaaccatc tctgagttga   7980
acagttcttg tataatctgt cttcccagtt aggctgtgag ccgcctgaag gcagcaagtg   8040
tatctttcac tcttctctga tctcctcagc cactcttctg ccccacaatt ccaaaaatca   8100
gttaccaagc cattgtaatt ccttttctga aatgtgtagt agactccttt tagggtattt   8160
gcccagttca caaagacccc tgccctcttt ggaaatctgt ccttgcagcc atatatggtt   8220
tttgtttgtt tgtttgtttg agacagagtt tcactctgtc gcccaggctg gagtgcagtg   8280
gtgcgatctc ggctcactgc aagctccccc tcccgggttc acgccattct cctgcctcag   8340
cctcccaagt agctgggact acaggcgcct gccaccatac ccagttaatt tttttgtatt   8400
tttagtagag acgggctttc accatgttag ccaggatggt ctcgatctcc tgacctcgtg   8460
atctgcccgc tttggcctcc caaagtgctg ggattacagg cgtgagccac tgcacccggc   8520
agccatatat gttctatatg actctttctg agacaatagc tgattagaac agtgattaga   8580
actgtgattt ctgagacaat agctgatttc tgagacaata gctgattaga acagttgcca   8640
cgagctggac caatcatatt aatattctct atctctctct tttgctctcg aaatctcaaa   8700
ttgagattca gaaacagcta tgtagtctct gtttgtggct agaactgtaa catatgaacc   8760
cagagctaga gagatgcaat attctatcaa gcagagagag aagcagagga agccggtcgg   8820
```

-continued

```
cacagacgga atgcagtagc acacagagag aagcagacac tcggagatgt ctgacacctt   8880
tctgcttaga ttccagtcag ttcagaggcc cagacgcatt cctgtctgga agcattctga   8940
tcctgttttg taaatcaaca ataaatccct tgccaccctc tttgcgtgtt agcttaagtt   9000
gtcttgctct taaaaatcta aagagttcta aatgatatga aatgtctgtt atacagaaag   9060
tagaatgaca attgccaggg gctgagagga gagggaaatg gaaaattgct caatggttat   9120
agttttagct ttgcaagagg aaaaagttgt ggatattggt ggcacaacaa tgcgaatata   9180
cttaccacta ctgagctcta tgcttagata cggttaagat ggtaaatttt atgttatgta   9240
tattttatcg ctgtttttaa aaaagtttaa aatagcctgt tgtagtcagc ttccttgtct   9300
tccttactac tgcagccata ttcaggtctc catggcccaa ggtatggaca actgtagtca   9360
ccaaactggt ctccccactt ccaccccttg gaatttggtc cccagcaatc taccctacat   9420
gcatggagca atcaatatta cccataaagc actaacgctg tgctgtactc caaaatgcaa   9480
accttcatgg tgtcccattg aattcaggat caagttcata ctccccagct tgtcatacag   9540
gacccagtga tcctttccaa ccttctgacc tactgattcc cagtaggaag caaaccctag   9600
caagactggt ctgcctcatc ccagaacagt acttactcat gctgtttcct tgccatgatt   9660
accttccttc tcctcaccac atcttatctt tctttcactt gatcttagtc caaatgccga   9720
gaagcaatct tatcttactt tcaaagccca ggttcagacc catcaattct ataaaacatt   9780
tctgaccaca ctagtcctcc atggacattt atttgaattg aacttcttag catttaaata   9840
tacacagttt cttattcatc tgtcttgttc ttctgctagt ttataaattg cttgattata   9900
gaacatgagc ttgataatct ttgatttttc ctggatactg tgttcttgct aggctgttaa   9960
taatgcttgt tgaatgaaat gagaaatgaa gaacggctgc tttaccagtt tgtctcttct  10020
gccaactttt ttacatggat tttacacgtc aactttttta cacaatgatt aaatatacct  10080
aatttgatca tcccaacaac actagtaaat atatatgatc attatcctca tactacagat  10140
gaggaaacac aggcacacat cgtttgtttg tttttttttt tgagacggag tcttgctctg  10200
ttgcccaggc tggagtacag tagcacgatc ttggctcact gcaacctctg ctcctgggtt  10260
caggccatty tcctgcytca gcctcccgag tagctgggac tacaggcatg tgccacaatg  10320
cctggctaat ttttgtactt tcagtagaga tggggtttca ctatgttggc caggctgatc  10380
tcgaactcct gacctgatga tctgcctgct tcggactccc aaagtgctgg gattacaagc  10440
atgaaccact gtgctgggcc aagcacacat agttaaataa cttgcaaaaa aaaaaaaatc  10500
gtatctattt gtaggaggca gagtcgtgat tctgagctga atctatttgg ctcctaagct  10560
tatgcttttt ctacagtatc accacatatc ccatactcta ttgttattgt tggctttatt  10620
gcctgttttt cctgtgaatt ttaaccttcc caaaagcagg aatcttatct cagtatatca  10680
cagagaatca ctaagtatct atagaggaaa ggaaggagag aaggaaagaa gaaaaggaag  10740
aaggaaagga gggaagaaag gaagaaggaa aggagggaag aaaggaagga aggaaggagg  10800
gaaggcaaga gggcaggaag acagaaaaga aggaaggaag aaggaaggaa gggagggagg  10860
aaggaaagaa gggagggagg gaggaacgga taggagggca gaaactctgg aaaggagctt  10920
gtcttactcc taagcttggt aaagatcagt cttgcaaggg gcttgactag aaaacactgg  10980
cttatctcac tgaaccatat tcccaatgtc attgactcct ttcccctggg gagtaattca  11040
accatgtgtt cactgtatgg atcagagttg atgatgaata ttctcttgcc tcagtctctt  11100
ttggccagag ttccttggct tccagcctgc tccttgcttg ttttgaacga ataatatatg  11160
actttccttc ttaactggca aatgctgaac tgtggcctct cttaaccctc aagtctcccg  11220
```

-continued

```
ataaaaagca aaatattaga ttcgctgacc agcgctactc cttaccccgg ctgatttcac  11280
atgaagagct atatatgggg tggtaacata ggtttaagga tggatgtgca tataactcct  11340
ggataccgtt cctgaaaata tactattggg gattatttct ttggttgaag agtcccttca  11400
ctaccacatg tcagtcccct tacctataaa atgggaacct tagggttgtt ataaggatta  11460
aatgagttaa tgtgtataat gtgcttagca cagtacctgc cactcaatgc tattattgtt  11520
gttgttgtta ttattattgg tagtagtagt agcagtagtt gttgtatgaa gatgcatgat  11580
ttcctgggaa aggtagcaca ttaaggcagg atcagtcatg agttacctca agcagattaa  11640
tttactagcc ctttcatgct atttcccaaa gggatggttt atcaagttga ggaagatgta  11700
gatgtgattt atgatggatt tgaggttagt actgtgtatc caggttgtgt gtgagaagac  11760
aagaaggaac tgagggcaca gctgtactta ggaagaactc tggtttgcaa ggtacataag  11820
ctaattcaga cgagtttaaa ccataggaga ttttgttaca aaggcactag gtaactgcag  11880
ggaccaggga gcagggtgtc cactctcatt ccagattctt ttgaattctg tatattttat  11940
tctctttcca caaacagact ttctatccac ggtggtgatg ataaccaata acatttcctt  12000
cagtctcacc cttgtagctc tgtgaccaaa aatgcaaagc tgctgcttct ccagcttcaa  12060
aatttaataa gaatcacagg gcagaacatt tattggctag gcctgagttg catgtctaac  12120
cttggagaac tcactttgaa taggggaatt cagaactagg attggtggct ccacaaatct  12180
cacaaaaatg gagcaaarta ggaactcatc aaacagaaat caatagatct ccactggctt  12240
tatagtacgt ggttctggga atccagatat tcagagccta ggtgaacctg aacatttccc  12300
tttaggcaga tggaaatcca cgttcttcta gctaaaattt ttccattctc tttgagggga  12360
gtttccatgg agaggctagc tttgtgggag agagtgggaa raaacaactc atgctgtttt  12420
tcattgggga ccattcttat tgctacttta gtccagtcct gcccacggat cacacattat  12480
tccttactct tgttgcttct gggctttttc tttttccttt gcatgctgct tatattccct  12540
tccctaaaag ctactctatt aagagggaga ttaggcaagt aggctggttt gattatgtgc  12600
tggtttaacc cataatcaca tacctcaaaa agaaaatgtc agacacacta taatagctcc  12660
agatacaaaa catgaagtac gaagacctct tcagaaaact gcaggcttgc tactcaccca  12720
cagacaaata gagctgattc tattagaaca gtgaggaaag aacacagtaa agaatggcat  12780
ttaagatcaa ttgtggcaat gtctaatttt gtctgggaag accatggcag tgagggatgc  12840
aaagggatga catcaagttt tcagaacagt gcctatatgt ttaggacgaa gagttaaata  12900
atgagagaaa acaaatgcaa tacaatttca ttggctacct ggttagacct agcatgaact  12960
gtgtctgtga tggtgctatt aatttgtgat ggagacattg gatattgtct ttccctattt  13020
ggtaagagct tgattcaggt agagagaaac aataattatt ttacagtgta caaagcactt  13080
tcttatacga tatattattt tcatcctccc aactagtttg ataggcagta atattattcc  13140
catttcacag agggggaaac ctgggttagg gcccaggaac ttggctggtg agtttggaaa  13200
gcttgaatag caatgattat aatcttggtg cacagaagca gccagtgaaa ttctgaaatg  13260
catatttctg ttctctactt ccagagggtc tgattgagtt agcttgggga agggcctaag  13320
aaatggaatc ttttttattc acaccaggtg attttgaagc atggggtcta ctgagtatgc  13380
ttatgaaaca ttaactttag gtcctaggca ctggcttagt tgactgtgag aaactgaagc  13440
acaaaattgt gtgaccaagt tctttctgag cctcagtttc ctcacctgaa aaatgaatga  13500
tgatgataaa aataactagg ctccatgcca agtgatttac atatttcccc tcaaatcatc  13560
```

-continued

```
tttcttacaa acctaggagt tcggaggcat tgttgttcct atgctatggg actcaaaccc  13620
aaatcatttc tactcactct tcctttcata attgtcagga agattagaca tagaaagtat  13680
ctagcacata ttcctgatgt tgaaggaata gcagcagctg ttataactac tactaaaact  13740
gacaatactg accatacagc caccactaaa atgytggggt tgaattcaga taatctctaa  13800
ggttcttccc agctccacca taccctgatt tcagcatttc aaatatatgc tgtatttgtg  13860
ggggggggttc ctagaaagag tgtggcagta actgaactca actatacaaa agaccgaatt  13920
cttcctttag ttggagattt attgattttt gtaagtgagt ttatagacaa aaacgaggaa  13980
gatacagaga aaaaagagaa gaattactgt gctttgatag tagggctatg ggtgattatt  14040
ttatttttaa aattttattt tttatacatt aatgtggttt ctataacaaa cacaaattta  14100
gaataaaagt aagatatttc tcttgtgctt ccaatttacc atatacttct taaatgtatt  14160
tgtatcataa tcatcagctg taagtttact attaaaaaaa atcaacaaaa gaacaatatc  14220
agagctaaag gacttcaggc ctgatgaacc taagtctagt ttctgtgctc actagccttg  14280
gcttatccca aaatattaaa agtaaaatat gatccaatct gcatctcttg cacatgtcat  14340
gttttgtaaa tagaaagttc ttggaacaat ctgtaacatc gttgaagtac ttcattcaat  14400
tcttgggcat taaattttat cttctgttcc tgcctcatat cattaaacag taccttcacc  14460
tacattgcag tcaactatgg aggactaatg ctctattttt tttatgttga acatgaagca  14520
taaacatgta cagctctgaa cctgagtttt ccttgcttta gaaataagag gtgttgatga  14580
aagaggaaat ccctgagact ctgtaaacct wacctgcagg tatgagaata caatctgtgt  14640
ttwatttatk gtattcttwa gcaaaattat agtaaaatta gtatttttct tttcatttgc  14700
tctcgaatta tcctttagta acagagtgaa cttgtatgtc catattttgg gtttaaagaa  14760
catggttact gtagcaaaga aggggctagc ccatgtatta aggtcctgga ttatactgtt  14820
gctcacagga gagcatgggt ttgaagatga ggctgcatag taaagtaggt aaaagtttgg  14880
accttggggc caaactgcct aagctcaaat catggtcctg ccagtactct ctgttcgacc  14940
tttagcaagt tacttaatcc ttgtagacct ctgatttggt ctcttcaaaa tagggatagc  15000
aataatgcct gtcttataga gacattgtga ggattcaatg aattgatatt tgtagaagaa  15060
tattgagttg gttttgctag aagatattaa gtgcgcagtc tttctaaaat aactaaatgc  15120
tacaaaaagc aaaatagcca ttctgcaaag agcagtgatt gaagcaggaa aaatgcctgc  15180
cttcataaag cttacattat aaggagagaa aaataagcaa aacaaactac gtggtatata  15240
tgtaaaataa aaataaagag ggggaagcat ggggtggggc agatattgca gttataaata  15300
gaatggtcat tggaggcttt attgaaaagg ggacatttga gcaaagtctt caagggggta  15360
tggaagtgag ccatgtgagt attttggtgt agggaaggaa aaacatcctt ctaccctctt  15420
aggtttggtg gctaacctaa gaattaaaac aacatagatt aacaagagaa aagcatgcac  15480
atttatttaa tgtttttatg tatacatggg agtcctcaga gaaaaatgaa gacccaaaga  15540
agactttatg ccccaaagct tatatacatt ttttacacaa agaatgataa actgtggaga  15600
tgtgacaaga caaaaggcct tgggctagaa gcagtaaatt gtgggagtaa gggatataca  15660
ggcgaaacta gtggaaaatg aggatgattt tagttttttt ttacaggtcc atttcgatga  15720
taactccagt catctctggt gatactattc ttctcttcct ggcacaagga gggcaccttt  15780
ctcatgggaa attttatgac ctgctttttg gtagaaaggg gaagtctgag agctcttcct  15840
gcccctagtg tttctcaagc gccttcagct caaaataatc attatgccaa agtggcatat  15900
tttgaggtgg catgttctga gccatttcat ggggtaagga tattccaggc tgaaggaact  15960
```

-continued

```
gggaatgcaa aggcccttag acaggaacat gcctggtata ttcaagagac atctgggaag  16020
ccaaggtaat gaatgacagc agagcatgag ggtgtgggtg gcaggagatg aggagatggt  16080
acaggaggca caaatcaggc agcatgttat tgatcaccgg cagagctcca ggtttcattc  16140
cattctgagt gacatgaacg gccatcaaag gtgtttgagt agaggagtga ctgtgtttag  16200
aatggactgc aggggaataa gggtagaagc gggaagacca gttagaaact gttagagatg  16260
atagtggctt agacctgagt gacagcagta gaataggtaa gagatggatt atgagtgtgt  16320
ctggctgatt cactcttata tcccctatgc taaggcatca tgcttggcac atagtaggga  16380
ctcaataaat acttgcagag cgaatgaata aatgggagtt caacttgggt aaggcaactt  16440
ctctaaggct ctgtttcctc atctctaaaa tgagggtaag aaaaatatta atagatctac  16500
ctccaacggt tattgtggag attaaatgag gtcattccca tgcattgctt agcatagtaa  16560
ctgaaacata agatagggct aagatgtata catacacata aatataaagc atttttgcaa  16620
gagtttacct ttggagacat ggaggaaggt agacttttat tcttcatttt atgaactaaa  16680
agcaaaagaa gaaaacaagt gttgaaatta tgagtcattt tcaagttctt tttgtacttt  16740
tcactaccat ttggaatttt cctataatga atatgcgagg caaagacaga aatgaaagga  16800
taagatcact cagaatttca ggtttttata aagcatcaga aatgtaagac tttttctgc  16860
tactgcatgg cccatttctc tgactctttg aatgtgggta ttattctcat ctttctccct  16920
cctcttctct ttttggttaa aagtaaagag agcttttgaa gctattatgg aacaagaaca  16980
acagcctagt tcatcctcac attttggagc ctcttattcc ttccaaagaa caaacacatc  17040
tatttagtgg ctaagagtct cttgagctga aaccattcat caccataact acattcaaac  17100
tgtctgaggt atacattata actaagaaaa tggggttcct cattggaatt tacaaactaa  17160
atattcaaag aagggttctg atgcttttaa aataggggcg ccaccaaaag gtaaagtaag  17220
acatgtggtt gaagacacag gaaagggcag aggtcaccag aaaagttggt tgtcacgcct  17280
gatcttaggg cctcataaag aaataattat ggcagaatga gccctaagaa gcaagcactt  17340
tagcatggct ctccctggac aaagtggaga ggcccttcca ccctaactta tcctattgtc  17400
ctggtcttca gtctttcctg tctgtttgcc tttcctggtg ttaatatact tgttcctaag  17460
gttttcaccc tgctgacttt tagctcttct tgctaagatt cctggctgta cattagaaaa  17520
ctcctgagca actaaacaca aaaaaatatt tggcaggggg atagggggtg cttctaggcc  17580
ctaactaaga cctgttaaat tagagtctct ttcgggtggc tcctgggcat tggggttttt  17640
ttgtcctttt tttttttttt tttaaatcta aagcttccca gttgattcca atatgtagcc  17700
agaattgaga ccagaaagct gttaataccc aagtagtata ctaatattaa taatgatcat  17760
aatagattaa taactaacat tgaatgaact ttaaatgtgt tagctgattt aattctcaat  17820
gactctgagg cagttactat tattattaat gtaccccttc tacagatgaa gaattcaaga  17880
taccaaaaat ctacataatt tggcaaacaa gtaaatgcta aagttggaat tcaaacacag  17940
gtagtttagt gtccgagccc acactcttca ccaccacact ggtggattgc ccacctgcaa  18000
tgttaaaaat cgcagaggat agtgatgata ctgcagacac actgcctgca ttttatctcc  18060
tccttgttag gctgagccat tcatacctca gtggtccaca ccttaaaggc aggatataaa  18120
ggtaaatata tgtaccttct ctgatatgaa ctagagactc catcccttct ttttaagtaa  18180
tgtaaatgat taaccagctt tctgttattc ctttcagaat ctcattcata gaataaattc  18240
ctggcataaa ttagtatcat aagttttcta ttattgctca ttaatcagta tgtgatgtaa  18300
```

-continued

```
gatcaagcag taagagttcc ccccaacccc aaagaatggt ctttctgttt gtgacaaatt  18360

attcttggca atgtaattag ccagttgggt tattgagggg gatccactag ttctagagcg  18420

gccgccaccg cggtggacta gat                                          18443
```

<210> SEQ ID NO 7
<211> LENGTH: 11811
<212> TYPE: DNA
<213> ORGANISM: BAC-F2 contig 3

<400> SEQUENCE: 7

```
cctgttaaag tttaccttgt atcttaaaac ttgccctaac cggattaatt ttctggccaa     60

atagggaggc tgaatgaaag tttcacataa accttagata ctcctaatta actgtttttt    120

atgtctgttt ttctaggaca catgttcaaa gagcataatt aactttttaa aagaagctag    180

taagtactga aatagttttt taagtttttt ctacaagaat agaggaagaa aggaaacatg    240

gaattctgaa gggctactta gcaagctgct tatggcataa tctggggtgg gggtgcatag    300

taaaggattt gcattttact gagaccgata catgtcaagg gaatggtatt taaaattagt    360

gatatgtgtt gatttttcaa ggactatagc ccatcaacta caataggctc caaaaaattc    420

tggtgaaatt agcttcttgg agccttccag tttacctact atgttattcc cactataaaa    480

tattctcaac ttttggggtt ttagccactt aagtttttta ttttctctaa tgtctctagt    540

atctgcttta gtttcctgtc aatgctagac tctgtggttc agcagttcat ccattctctt    600

cccagtactc aacctcgttg cttatagttt cattacattc atctagcaaa accttaattc    660

tgtatgtttg ccataccatt agtgcttaga gcatttttc agaaaagaat cctggaaaaa     720

tggatcttat ctcacctggg ccctcaggac tgctgggctg cctggtgtca gcacttcccg    780

ccatttctca tagcaccagt attattctta atactttaaa aaaccaccag gcacggtggc    840

tcacgcctgg aatcccagca ctttgggagg ccaaggtggg cggatcacaa ggtcaggaga    900

tcaagaccat cctggctaac acggtgaaac cctgtctgta ctaaaaatag aaaaaaatta    960

gctgggcgtg gtggcatgca cctgtagtcc cagctgctgg ggaggctgag gcaggagaat   1020

ggcgtgaacc cgggaggcgg agcttgcagt gagccgagat tgcaccactg cactccagcc   1080

tgggtgacag agcgagactc cgtctcaaaa aaaaaaagta aataaaaata aaaaaccata   1140

tcccactatc tccccccttct ctctttgcct gtgatcttgc tgcatactta tggggaaatc  1200

tttaagatgt cagatttcag ttctctcact tttctacaac ttctcccact tttgcctttc   1260

ttatgtacct tcccttcctt cccatctgat tccttatcag tatttacaca tgattagttc   1320

ttgcctaacc taatagaccc tttcttgagt gcaaatcagt ggctattttt gctagggtat   1380

aaaaattacc tatctaatca ccttgacaaa gttaccctgt tatttccaat aacttacttc   1440

ctatggattc ttgtagattt tctttttttt ttttttaatt tttttatttt cagatgtttt   1500

ctcgctttgt caccatgcct ggcctaaatt ctcgtaggtt ttctatgtaa acaatcagat   1560

tttctgcaag tattagtctc ctttctaatt gttataattt taatttcttt ttctttttaa   1620

aatttttcgt agagacaagg ttttgctatg ttgtccagcc tggtcttgaa ctcctgggct   1680

caagcaatcc tcccatctca gcctcccaaa gtgccattac agtggcatga gccactgtgc   1740

ctggccaaat ttcttttctt gttgcgaagg cagacttttc atacaatact gaatagaagt   1800

gatagtagat tactttattt ctgattttca aaggaatgct ttccgtttct ctctgttgaa   1860

gataattgcg tattgttttt ttttttaaat agtaactttt atcaggttaa ggaaggtttc   1920

ttctatttct atttaaaagg attttttaaa atcttgaatt catatgtttt tatctaatgc   1980
```

-continued

```
attttctaca tcagttgaaa tggttgtatg aactctttta atatgggtga attatattta   2040
tagattttat gttaaaatat ccttgtatat cttggataaa ctcaactgga tcatgattta   2100
tctttttat atgctagatt caatttgttg atactttgtt atgatttttg aatatatatt   2160
attgtgtaaa agtgagcctg tgattttctt tcttgtaatg tttctgtcca gttttggtgc   2220
ctggttttgc tctctcctta gaatgagctg ggaactagtc actcttgttt tctcacctat   2280
aatagcatct gggtccagtg ttttttatgt gggacaaatt tgaacttgtg gtcaacctct   2340
ttaattgtaa gaatattcag gtcttttgtt cttcctgggc tagtttttta ttctttttct   2400
agagattcgt tcatttttct tagttttatt tgcctataat tgtggataat ctgtttttta   2460
tctgctactt ctgtaattat ttccacattt gatttataat attaacttgt gggccaggcg   2520
tcgtggctca cacctgtaat cccagcactt tgggaggccg aggcgggcgg atcacgaggt   2580
caagagatcg agaccatcct ggcccatggt gaaaccccgt ctctactaaa aatacaaaga   2640
aaaaaattag ccgggcgtgg tggcaggcac ctgtagtccc agctactcag aaggctgagg   2700
caggagaatg gcgtgaaccc aggaggcgga ggttgcagtg agccgagatc gcaccactgc   2760
actccagcct gggcgacaga gcgagactcc atctcaaaaa aaaaaaaaat ttacttgtgt   2820
cttctctttt tacctgtttg ttaatttatc aaataactac ttttggcttt gtttcatttt   2880
tattatacaa taaaatgaaa ttcttttcat tgtatttctt ttcattgatt attcctataa   2940
ttcttaaaca actttataat tgatgtaaca ataacctgta cacatttaaa gtgtaaaatt   3000
tattacattt tgatccatgt atatagcagg gaaatatcac cacaacaaga gtgtgaacat   3060
ataatctctc cccaaagttt tcttgtgtct tttataatca ctgcctcttg cccctgccca   3120
ctccctcatc cttaagcaac cattggtctg ttttctgcca ctatagatta gattgtattt   3180
tctagagttt tatacaagtg aaatcatgta gtatagtatt aaccatgtgt ttgtttgttt   3240
gtttgtttct ttctttcttt cttttttttt tagacggagt ctcgctttgt cacccaggct   3300
aaagtgcagt ggggcgatct cggcttactg ccagctccga ctccggggtt cacaccattc   3360
tcctacctct gcctcccgag tagctgggac tccaggcgtg cccgccacca cgcccagcta   3420
gtttttgtat ttttagtaga gacggggttt caccatgtta gccaggatgg tctcgatctc   3480
ctgacctcgt gatccgccca cctcagcctc ccaaagcgct gggattacag gcaggagcca   3540
ctgcgcccag caactatgtg tttctgatcc tttgtcaggg ctagccaatt cctagagaca   3600
gtgaataact cactcataat ctagctgcct cctttatgtc gctctcatag gactttgaca   3660
cctctctgct acaatccacc tgccctgttc atttcaagat caggtaccag gaaactcggg   3720
acatccctat gctgcagaac tcactgaaat tattcaaact agccagtcct aaacatgctt   3780
accctgcctt gcccattcct tccgctgaaa ccacataaag gctcttgccc atgttttcat   3840
cccattccat tgacctcctt actgacccta gctagtgctt cctcatgtgg cccctgcatg   3900
gcatggtgtg caccttcctc ttcggaactg cgagtaactg tcttgtcagc ggcaatcatc   3960
ttgtgatctg ttggcctcat catatttgaa taacaataaa atctgtttta aggctgggcg   4020
cggtggctca tgcctgtaat cccagcactt tgggaggcca aggcaggcgg atcacgaggt   4080
caagagattg aggtgaaacc ccctctctac taaaagtaga aaaattagct gggcatggtg   4140
gtgcgtgcct gtaatcccag ctactcagga gactgaggca gggaatctct tgaacccagg   4200
aggcagaggt tgcggtgagc caagattgca ccacggcact ccagcctggt gacagagcga   4260
gactccatct caaaaaaaga aaaaaaaaaa actgtcaaat gatactccaa aatggttgta   4320
```

-continued

```
ccattttata tttgcaacaa caatgtctga gggtactgat tgctccatat ccttgacagc   4380
acttggtata gctgatcttt taattttagt cactttagtg ggcatatact ggtattttat   4440
gttttacttt ttattttcct aatgattaat agtttgcagc atctttcatg tgcttatttc   4500
cctttcatat atcttctttg ataaaaatat ctgttcaaat attttgccca ttattttgtt   4560
ggaatactta ttttcttact gttgagcttt gagagttctt tatatatctg gataccaatc   4620
ctttgtcaga tatatttttt gcaaaatttt ttcccagcct gtgatttagt ttgttattct   4680
catgtctttt aaaaaaaatt gtagttaaaa tatacacata atacaaaatt taacatttta   4740
actctttgta agtatacagt tttgtggtat taagcatagt cacattgttg tgcaaccatc   4800
accgccatcc atctctggaa ctttttcatc ctccctgact gaaattctgt acccatttaa   4860
acactaactt ctcattcccc cttactccag cccctggcaa ccatcgttct gttttccttc   4920
tctatgagtt tgactgctct aagtacttca tataagtgga gtcatacaat attttcattt   4980
tgtgactggc ttattagtat aatgtcttca agtttcatcc atgtggtagc atgtgtcaga   5040
atttccttcc tttttaaggc taacattcca tcctatgtat ataccacatt ttatccattc   5100
atctgttgat ggacatttaa gttgcttcct cctttttggct attgtgaata atgctgctgt   5160
gaatgttgtt gtataaatat ctgttcgagt tcctgctttc aattcttttg agtatgttcc   5220
caaaagtaga attgctgggt catatgttaa tactgtattt agttttttga ggaattgcca   5280
tactgatttc tatagtagtg gtaccattta cattccaacc agcagtgttc agggttccaa   5340
tttgttaaca ttcttgccaa cccttgttgt tttctggatt ttttttattt tggggttttt   5400
tattttattt atttattttt tttttgaggc agagtctcac tctgtcaccc aggctgaagt   5460
gtagtggcgc aatctcggct cactgcaacc tctgcccccc gggttcaagc gattctcctg   5520
cctcagcctc cgagtagctg ggactacagg cgcgcgttac cacgcctggc taattttttg   5580
tatttttagt agaggtgggg tttcactgtg ttaatcagga tggtctcgat ctccggacct   5640
tgtgattcac ccgcctcagc ctcccgaagt gctgggatta caggcgtgag cactatgcct   5700
ggccattttt tatttttaaa caatagccat cctaatgggt atgaaatagg ttttttggtg   5760
ttttgttttt tttttttgag acagaatctt gctgtgttgc cctggctgga gtttagtgac   5820
gtgatctcgg ctcacctcaa cctccgtctc ctgggttcaa gcacttctcc tgcctcagac   5880
ttccaagtgg ctgggactac aggcgcccgc caccacaccc agctagtttt tgtattttta   5940
gtagagatgg ggtttcactg tgttggccag gctggtccac gatccatcca ccttggcctc   6000
ccaaagtgtt gggattacag gggtgagcca ccatgcacag ccagggtttt gttttgtttt   6060
gtttttacta tttttttttt tttttagaga caagctgtct cccaagctgt agtgcagtgg   6120
caccattcgt atctcactgt aacctcaaaa tcctggaccc aagcaatcct cctgcctcag   6180
ccttccatgt agctacctct acagggaatt gcccccatac cccgggaaat tttttttttt   6240
tttttttttt gagagttttg ctcttgttgc ccaggctgga gtgcaatggc atgatcttgg   6300
ctcactgcaa cctcctcttc ctgggttcaa gtgattttcc tgcctcagcc tcctgagtag   6360
ctgggattac aggcgcccgc caccacgcct ggctaatttt ttgtattttt agtagagatg   6420
ggtttcacc atgttggcca ggctgggctc gaactcctga cctcaggtga tccacccacc    6480
ttgacctccc aaagggctgg gattacaggc gtgcgccacc acacctggcc cccagctaac   6540
ttttaaatgt attttgtaga gatgaggtct cactgtgttg gccaggctgg tcttgaactt   6600
ctgagctcaa gtcattctcc cacctcggcc tcccaaagtg ctgggattac aggcatgagc   6660
caccacacct ggcccctttg cccattttaa aaattaggtt gtttttgttg ttgttgagtt   6720
```

-continued gtaggagctc tttgtatatt ctgcatttcg gttccttatt ggatatgtga ttggcataca 6780
ttttttccca tccatggatt gctttttcat tctgttatag tatccttgat tcacagaagt 6840
ttttaatatt gatgaggtcc tgcttagtct gtgttttgtt ttgttgcttg tgcttttggt 6900
gttatatcca agaaattttt gccaaatcca aagtcatgaa gctttgccct ctgtttcctt 6960
ctgagtttta tagttttagg acttaaattt aggttttcga cccattttta gttaattttt 7020
gcaagtggta taagggaggg gtccagcgtt attgtttcac gtgtagatat acagttttct 7080
gagtaccatt tgatgaaaag gctgtccatt gaattgcttt tgcaactttt atttgggcat 7140
atttatgtga gtctgttact ggttctatat tttactccat tgatctatgt gtctattcct 7200
ctgctaatac tgtcttaaat atggtagcta tatagtaagc cttaacactg agtagataga 7260
tttctcccct ttttttgttc tttttcaaaa ttgtcactgg tttgttttta ttttttactt 7320
tatgcagata atctgtacta tactttggtt tcatgtatca agtagtttgt tccaagttgt 7380
gctttaagca gaacaaataa attttcatat tgttctttgt gttaatctgc aatataaacc 7440
tataccaaat tctattttgt gtatttgttt attgtagtaa tctgactgac tcttttgcct 7500
ccagactcat ctctttcaag gtccccaact gaatcttgtt ttaggtggaa cttagaagca 7560
gtagaagtta agaatctatt tcacagcctt agtagtctag tttcattctc tatataatgt 7620
tgtctatgca agtgagctgc tctccagtgc cttagtttca ctaatgttgg ggaaggtctc 7680
ttctcttgtt ttggacttct ctatcacatt gcctttctca agagaagaca tataatgaaa 7740
gttgatatct ggtgttctag gacttcttca gaagcttgcc agtttttcaa gctgatttct 7800
ctcactggca actcttcaga gtgctgttcc tactccaccc tcccctggtg gtatgtatca 7860
gtttctact catcagcacc cacctactcc tgcctactgt gtttctcaga tgtctgctgc 7920
ctggctagct cattgctgct tttgtcactc atagagctgt cttcttccct ttttttggct 7980
ttctgcctga cttccagggc agctgctctg tcattgcctg tctgccattc tgtctttttt 8040
ccccctaccc cccacagata caacatctac tctaatacca cacattctcc atgttcaaac 8100
taacctcatc actttcccca ccacattccc caaaactggt catcctccag cttatagcat 8160
tgcagttcac tgaagttaga catctgggcc ttgcttacct ccaacatctc attagccttc 8220
gattctaccc ctataaatcc tcttctcagt ctcctttaga tattcctgcc ctgctgtgag 8280
atccatctgg tttattggct agattacttc agaaagcttc agtcagtgac cctccttact 8340
tcaaacccca ccagttgatc cttcactctg ccatcagtca ttgcttctaa aatctaaatt 8400
gttccattta accttgctgt gataaaacct ttggtagttc ttcagtgtgt tcagtggtaa 8460
gttaaaactt tcactgtaat gtacaggccc cttcatgata tgatcgctgc ctcctcgagc 8520
ctcattgtgt gcatttcccc gccccaccct ttcctcaccc accctagtct ttcatgtctg 8580
ccatttttac attcatttag cagatattta ttgaagcccc ctgtgatgtc cttacctagg 8640
tctttcttgt tgccaggacc agacaggctt tttcaagctt ccaagtcatc tcagtttgaa 8700
agactatgtc tgacccttgt cttggccaat tactctttat ccttccaagt tcaatgattg 8760
tcccactgca ctccaaccag agtgagagag caagaccctg tctcagtaaa taaaaataaa 8820
taaataaata aataaataaa taaataaatc agccataatt tatttaatca tgtctctctc 8880
ccccattgat agacgttaag ggtatttcca gtattcttct cttgaaaaca atgctacatt 8940
gaataacctt gtacatgggt cactttgaaa gtatggatat gtatccgtgg aataagtttc 9000
cagaagtgga attgtgtcag aggggttgtg catttgtaat tctgatgaat atttatagat 9060

-continued

```
tatatgagag tacctgttta ctcaaactct tgccaatgca gcattatcaa agtttttttat   9120
gttcgccagt gtgatagatt aaaaaatggt atctcagcca ggcgcagtgg ctcacgcctg   9180
taatcccagc actttgggag gctgaggcgg gcagatcacg gggtcaggag atcgagacca   9240
tcctggccaa cacagtgaaa ccctgtctct actaaaaata caaaaaatta tccaggcgtg   9300
gtggcgggca cctgtagtcc cagctactcg gaaggctgag gcaggagaat ggcatgaacc   9360
tgggaggcgg agcttgcact gagccgagat cgcgccacaa cattcgagcc tgggcgacag   9420
agcgagactc cgtctcaaat aataaaaaaa aaagatggta tctcagcatt gatttctttg   9480
atcatcagtg aggttgagca tcttttcata gatttaagag aactgtatgg tttttttgtga   9540
gttatgtttc atatcgttta cccattttac ttttaggctg gaagcagctg ttttagtgga   9600
atggtggaac aagaagccag attgccatgg agagacaact ctttctagag atttggctat   9660
gaagcagagt agagacaatg atagctgaag gattgatgta gatgcaaaga aatttttcat   9720
cttctttgaa aacttaattg tgttaaaaac tggtatgaaa gggaggggtt aaagctagag   9780
atggtggtag aaaaaaatgc agggttccta aaggactgag attcctggat ggaatttcag   9840
ggaaggggaa aatttctgga tatagtgact ggggagttaa gggtgtctag tccaatggct   9900
tttattttct tggaagggta ggcaaggcca acagccacat gtgtgggagg agatggttag   9960
aggggagagg aggtttgaag gcaccgctat ggagaattgg agagagctaa ggaaagacag  10020
aaagactgca gaaagtgctt agggttccac tgaagcggaa atagtgattt gtagtgatac  10080
aacccttatg agttatttga tttttttttt tttttaagca gcatctggca gtccaagtat  10140
agggctgaca gtttgggatt tttctttcca tgttggtgta aaagaagaac agtgtagtga  10200
aggaagttag gacaaaagaa tgattgaact gacaccaagt tttcttgatt tggtagaaaa  10260
ggaaataaag atagagcaga gatattgaaa agaattagag aggggttcaa gagactgaag  10320
gcctgggtga ggtcagagag caggtgtggt agacataaca gagagaacta caaggataga  10380
aagtgtggtt ggagagtggg aaggcaagat ttattcagta tgggggcttt tctgggtgat  10440
gacagcatct ggagtacagc cattgtcgtg agtggcccaa gtgtagcaga gataaagcgt  10500
tgttggagtg aaggaagtca aggaactgag aggctggcct agatggggat tttggttgtc  10560
atccatgagg atattgaagt catccaggag aatagcaggc ctgggggaca ggaaggaaac  10620
tgagccactt acagtgtctt cagtgatagg aaagcacagg gcaaaaagct ttcaagaaca  10680
gggactgtta agccgggtac agtggctcac acctataatc ctagcatttt gggaggccaa  10740
ggcgggtgga tcacttgagg tcaggagttc aagaccagcc tggccaacat ggtgaaaccc  10800
catctctact aaaaatacaa aaattagcca ggcatggtgg cacgcgcctg taatcccagc  10860
tacttgggag gctgaggcag gagaattgct tgaacctagg aggcggaggt ggcagtgagc  10920
ctagatcgcg cccttggctg cgatccagac ttcactccag cctgggtgac agagcaagac  10980
tctgtctcaa aaaaaaaaaa gaaaatcaga ctcttaatat ttgtaaagaa gtagtccttg  11040
agctactact taagtctaga aagagttgat attcttgttt taagagtgtt agggcacttt  11100
gggaggctga ggcaggtgga tcacttgagc ccaggagttc cagaccagcc tgagcaatat  11160
ggggaaacct tgtctctact aaaaatacaa aaattaacca ggcatgtggt acgtacctgt  11220
agtcccagcc acttgggacg ctgaggtggg aggatcacct gagcccagga aatggaggtt  11280
gcagtgagcc aagattgcgt gactgtactc tagcctgggc aacagagcaa gactctgtct  11340
caaaaaaaaa aagggcgggg attatcatag tgccattatt attatgagtt tatgatggct  11400
ttctctaagc accttttaca ttcggcattt attcagtacc tattaagcat caaggagtcc  11460
```

-continued

```
agaaaaaatt ttatatataa atatatataa aatatgtaaa tatatatatg catatgcttc  11520

cctatctcag gaaggaaata tgtgaacatc aggaaccgaa gtctactcag ttacatgcca  11580

ttggatatat cacacaaagt gctgagggaa ctcagaaggc tcattatatc tggggagtgg  11640

gaaggaggca cagagatgtg ctttgggaag tttaaattaa aatagcaaat ggggaaaatg  11700

aagacacacc agacagggca caagcaaaga gacatgaaag agtaagtcat gtgtttgagg  11760

atctggggat ccactagttc tagagcggcc gccaccgcgt agcagttacg g           11811
```

<210> SEQ ID NO 8
<211> LENGTH: 1241
<212> TYPE: DNA
<213> ORGANISM: BAC-F2 contig 4

<400> SEQUENCE: 8

```
tcgtgatgcg gtattttctc cttacgcatc tgtgcggtat ttcacaccgc atagatccgt     60

cgagttcaag agaaaaaaaa agaaaaagca aaaagaaaaa aggaaagcgc gcctcgttca    120

gaatgacacg tatagaatga tgcattacct tgtcatcttc agtatcatac tgttcgtata    180

catacttact gacattcata ggtatacata tatacacatg tatatatatc gtatgctgca    240

gctttaaata atcggtgtca ctacataaga acacctttgg tggagggaac atcgttggta    300

ccattgggcg aggtggcttc tcttatggca accgcaagag ccttgaacgc actctcacta    360

cggtgatgat cattcttgcc tcgcagacaa tcaacgtgga gggtaattct gctagcctct    420

gcaaagcttt caagaaaatg cgggatcatc tcgcaagaga gatctcctac tttctccctt    480

tgcaaaccaa gttcgacaac tgcgtacggc ctgttcgaaa gatctaccac cgctctggaa    540

agtgcctcat ccaaaggcgc aaatcctgat ccaaaccttt ttactccacg cacggcccct    600

agggcctctt taaaagcttg accgagagca atcccgcagt cttcagtggt gtgatggtcg    660

tctatgtgta agtcaccaat gcactcaacg attagcgacc agccggaatg cttggccaga    720

gcatgtatca tatggtccag aaaccctata cctgtgtgga cgttaatcac ttgcgattgt    780

gtggcctgtt ctgctactgc ttctgcctct ttttctggga agatcgagtg ctctatcgct    840

aggggaccac cctttaaaga gatcgcaatc tgaatcttgg tttcatttgt aatacgcttt    900

actagggctt tctgctctgt catctttgcc ttcgtttatc ttgcctgctc attttttagt    960

atattcttcg aagaaatcac attactttat ataatgtata attcattatg tgataatgcc   1020

aatcgctaag aaaaaaaaag agtcatccgc taggtggaaa aaaaaaaatg aaaatcatta   1080

ccgaggcata aaaaaatata gagtgtacta gaggaggcca agagtaatag aaaaagaaaa   1140

ttgcgggaaa ggactgtgtt atgacttccc tgactaatgc cgtgttcaaa cgatacctgg   1200

cagtgactcc tagcgctcac caagctctta aaacgggaat t                       1241
```

<210> SEQ ID NO 9
<211> LENGTH: 1701
<212> TYPE: DNA
<213> ORGANISM: BAC-F2 contig 5

<400> SEQUENCE: 9

```
ataaaaaaca gttaattagg agtatctagg ttatgtgaag cattcatcac cyycctaytg     60

rcagaaawtw tcgwtaggca aattttatat twtaagtaac tttaacatga acacttctta    120

aactttggct cataatttca caaaaattag gctgcaagtc accatattca tcagatactg    180

gcagacacta acttctgcgg ctatgacacc aagcaatact gaaatctctt atctttccag    240
```

-continued

```
gggggttgtt catgtattca gtgtttgcaa agagttcctg ctgagctaaa cacagtccac    300

tgtgcactct acgaaagagt ccatgagaca agcatggggg agggtaggaa gtttaatact    360

ttcacaatgc ctgtggagac gctggcagtg atgaaagcct agaaaactca tgaaaggacc    420

ttttatgagc agggtgaatg tagagcacaa aagcaaagtc agatgaccca cttaaagctt    480

tgcctttact gatgagaatt cattctcatt ccagattagt ctctctctag aaaaagcaaa    540

ccttatataa gagttggaaa attaagatac aggaagtata attctactaa attccagttt    600

ttccttctca aatatcagcc taagtcctaa ggtctgtggc caaagacaga aaatacaagg    660

cgctgagaaa tatgctattt atcttggtgt aacaatctct gactgttggg gtttgaggaa    720

atttaagctc tacaatccat agatcagacc agaagtttag ggtagtaata ttatgagagg    780

aaatagtttc tttctggaac ttatataaag caaataactg gtaaacctga tttgcaaggt    840

aatgacagtc caagttcctt caaagcagag aaccacttat ttgctcattc attcaactaa    900

gttccttgtc ttgtgccagg ctggagagag aaagcagctc ctgtcctcaa ggagctcaca    960

tctcaggcat cttctcaccc tcctttctca tgttaaccaa aacatttcag gttcatcaat   1020

gaaactcttc atccaggagg cagataaaat ggcttctctt cattttgatt catttactct   1080

ttcttttatt tattttatta ttattatttt tttttttct gagaaggagt ctcgctctgt   1140

tgcccaggct ggagtgcagt ggcgtgatct cggctcactg caacctctgc ctcccgggtt   1200

caagcgattc tcctgcctca gcctcccaag tagctgggat tacaggcatg cgccaccacg   1260

cccggctaat tttgtaatt ttagtagaga tggggtttca ccatgttggt caggctggtg   1320

tcaaactcct gaccttgtga tccgcctgcc tcagcctccc aaagtgctgg gattacaggt   1380

gtgagccacc atgcccggcc tactctttct tttaaacaga gaaataagat ggaatatttt   1440

tatcccatct tttcttctgt aattaaaaaa ggaatacgaa gaaacttgac atagtctctc   1500

tcctcatgtg ctctcttact tcccatccca attccatgtt tgctctcttt ttcctctctc   1560

cttctgtttt gttgtgaatg aagaattagg taactagtcc aaaactacag agctacacct   1620

ggagcctaga ttcactggta gcaaatcact aattttctga aggtaaatgg gagaaaatgg   1680

gggtgggggg aaactcatta a                                             1701
```

<210> SEQ ID NO 10
<211> LENGTH: 1293
<212> TYPE: DNA
<213> ORGANISM: BAC-F2 contig 6

<400> SEQUENCE: 10

```
ggagataata agtatacact atgtgtgaag ggggtgtctc tattgttgtt gtggcgatta     60

ggtgagtaat tttacacctg gttgtgaata aagtccgaga ttgggggact cacgctttgt    120

agagtctccc aggacaatgg gttttgcccc cgtgcccaat taatagttaa aggttggggg    180

cttttcgatt cccttattcc aactggatag ggctcttgaa atgcccccaa aaaaggttga    240

ccctttcccc acacgtcaaa gagggaattc tcccgctaga ctacccttga acctgaagtg    300

cagtccctac agggtattct agcttgttag catcccccac tgtgaatcaa tcccttaaaa    360

taaacctata taagatgtat gtaatagagg actaatcttt aatataataa gcatatattt    420

aatataattt cggtactacc cccttatctg gggggggggt ggggggatat gttccaagac    480

tcccagtaga tgcctgaaac cacagatggt actgaaccct acgtaaactg tatttcattc    540

ctatacatgc aggctatgtg ttgtaatctg tagggtaacc actaaaagaa cagggtctat    600

aacttggcaa gagggaaaaa agctaggata gtaaaaaagt ctatcaatcc aaaaagcaag    660
```

-continued

```
aaaaaagaga aaaaggaaca tgctggcata ttattataag tattgtattt tattattagt    720

tattgttaat tttttactgt gcctaattta taaattaaac tttatcacag ctatgtatgt    780

ataggaaaat atatatctgt ggttttaggc atccactggg ggtcttggaa tataatgctt    840

cccccagata agaaggtact actgtaatta tattatatgt catattaagt atacattaat    900

tctactaggt agtagccaca ttatatatta attatattaa atatatatca tatagaatta    960

ttttaaggaa ttgactcata atagaagagg ctggcaggct ggagattcag ggaggagttg   1020

catttcaagt gcaaaggcag actgccagag aattccctct tgcttggggg aggtcagcct   1080

tttgttctat tcaaatcttt gaggaaaata gaaagcaaag aatatattaa ctatattaaa   1140

caaactaaat gttccaatta aaatacaaaa attataaagc ctaataataa aagccctcaa   1200

ttatatgctg tttaaaagag acatttttaa gcttaaggat atagaaaagt tgaacataca   1260

agcatggaat aaaataagca tgcaaaatac tag                                1293
```

<210> SEQ ID NO 11
<211> LENGTH: 529
<212> TYPE: DNA
<213> ORGANISM: BAC-F2 contig 7

<400> SEQUENCE: 11

```
gctgaggtgc atcgcggtgg cggacgctct agaactagtg gatccccaaa caaaacctgt     60

ccctgctaat gatggtagac ccaatcagat ccccggagaa gccgaaatac ggaaaccata    120

tcagcatacg catggcatac atagaacccc atacatggat tgcttactca gccagatata    180

gaaatctatc ttcacgatag agatatatat atatagacac actgcatata cagatgtgag    240

atggaggctc actctgccac ccgtgctgga tctacagtgg cacaagctca gtccacagtc    300

acgtcgatct gccgggcgtg accgactgag atgcagcggc ctcgggcgta gctgtgagta    360

cacgcaccag tcatcgcgac tggctgcaag tggtataagc ggaggggaca gggttacagc    420

atgacggcta ggcaggccgc aaactgagga ccacaagagt gccacgctgc ccgaacgcat    480

gcagtggcga gattacatgg ggcagccact agagccgccg tatcagaaa               529
```

<210> SEQ ID NO 12
<211> LENGTH: 18073
<212> TYPE: DNA
<213> ORGANISM: BAC-F2 contig 8

<400> SEQUENCE: 12

```
agcgcgtgcg ccgctctaga actagtggat cccccgagga gtgaggagga cctcaaccct     60

acttcctgaa atggagctct gagatgttgg agtagaaatt tggaaaccag agagagaagt    120

aagggtagtg ttgttgcaac atgcattgta tatgggggt cgggaagtca caggagtttg    180

cctcaaagtc tttctcggag acggatgagg ttttcactgt gattttcctg gtcgtggtct    240

atggatatag tacctgttag tgacatggat cttcttaact tctgatgtgt cttttcctcc    300

ctagtgtacg cataccaatt ctctccacag cttccatcac catgcatttg ttcttttccc    360

ttgttcttgt attacctttc tggaaaggaa tttttattgt aggctaattg ttactcccac    420

cagtatttaa ccactggata tttcatatga ttgatctctt ctgatttgga aaataaaaat    480

gtaatctcat tatattcatt tgattagtgg ggacagtcaa cacttctttg tgtattttct    540

tagctgttcg tttttctcgt ctgtaaatta tctgtttagg tccttcagat ttttcaaaat    600

tggactgtta tgttttcagt attgttatga gttcttgttt caattattta tgacagttca    660
```

-continued

```
ttttcttttt taaaatagac tttttttttc ttagagaaat aagaaaaaat aaaaattaaa     720
atagactttg tgttttagag agtttcaggt tcacagcaaa attgatcaaa aagtatggag     780
agttccggcc aggcgcggtg gctcacacct gtaatcccag cactttggaa ggccaaggtg     840
ggcagatcac aaggtcagga gtttaagacc agcctggcca atatgatgaa accccatgtc     900
tactaacaat acacaaatta gctgggtgtg gtggtgcaca cctgtaactg tacctactca     960
ggaggctgag gcagaagaat ctcttgaacc tgggaggtgg aggttacagt gagccacagt    1020
catgcccctg cactccagcc tgggcaacag agtgagactc cgtcctaaaa aaagaaagaa    1080
agaaaatata gagcattcct aaataccacc tgtccccaac acctgcacag cctcctcatt    1140
atccacatcc tacaccactg tggtaccttt gttgcaattg atggaccaac attgactcct    1200
cattatcacc caagctttgg tgttgtacat tctgtagatt tggacaaatg tataatgaca    1260
tgtgtctacc attgtagtat catacagaag aatttgactg ccctgacagt cctctgctcc    1320
acctgcttac tcctctctcc cttttcctaa ctgcacaacc actgattttt tttttttttt    1380
tttgagaggg ggtctcactc tgtcccccag gccggagtgc agtggggcca tttggggtca    1440
ctgaaagctc cacctccggg gttaatgcaa ttctccggcc tcagcctccc gggtaactgg    1500
gattaaaggg gcccgccacc aaatcggggt aatttttgga atttgaagta aaaagggggt    1560
ttccccattt tagccaggat ggtctcgatc tcctgacctc gtgatccgcc cacctcggcc    1620
tcccaaagct gggattacag gcatgagcca ccacgcccta cctttttttt aaaaaacaag    1680
gtcttgctct gtcacccagg cctgagtgca gtgatgatca ctcctcactg aagcgtcgac    1740
ctcccaggct caagtgatcc tcccacctca gcctcctaaa tagctgagac tacacacaca    1800
caccaccatg cccagctaag ttttgtattt tttatagaaa tgtggtcttg ctgtgttgtc    1860
caggctggtc ttgaactcct gagttcaagc aatttgcctg ccttggcctc tcaaggtgtt    1920
gggattacag gcatgagtca ccgcacctgg cctttttat tttctttttt ttttttaac      1980
cagtgatctt ttactgtctc catggttttt cacattggct tctgtcactt agtaatatat    2040
gtttaagttt cttctacgta ttttcatgtt tttagcttat ttctttttag cagtgagtaa    2100
tatttcattg tctggatgtg ccatcactta tttatccatt cgcctgctga aggatatctt    2160
gattgctccc agtcgtggca attataaata aagttgctgt aaacatccat gtgcaggttt    2220
tttttaagtg gcataagttt tcatctcatt tggttaaata ccaaggagca caattgctgg    2280
atcatatggt aagagcttat ttattttttt gagagactac caagctgcct tccaaagtgg    2340
atgtaccatt ttgcattccc accagcagtg aatgagagtt cctgctgctc catattctta    2400
caaacatgta gtattgtcaa atgttttgga ttttaaaacc aaaatccatt ttcatagatg    2460
tgtagtggta tcccgtttta atttgcaatt acctaatgac ttgatgttct gtgtcttttc    2520
agatgcttat ttgccgtact gtttatcttc tttggtgagg tgtctattca ggtcttttgc    2580
ccatttttaa tctggttgtt atttttcttg ttgagtttaa gaattctctg tcctttgtca    2640
gatctatctt ttgcaaatat tttctcctag tctgtggctt atcctctgat tctcttggca    2700
ttgtctttca cagagtagac attttatatt ttaatgaagt ccagactatc aattatgttc    2760
tcatggatca tgcctttgat gttatatcta aaaagttctc gccataccca aagtcatcta    2820
gattttctcc tgttatcttc ttggcatttt atagtcttat gattgatatt taggtctatg    2880
attcattttt agttaaattt ttgtgaaaga taataaggtc tgatatggat taatttttct    2940
atatgtagct gtcccgttcc agtatcattt gttgaaaaga ctatcttgct ccattttatt    3000
gcctttgctc ctttgtcagt tgactatatt tatgtgggtc tgtttatgat ctctgttccg    3060
```

-continued ttccattgat ctgtttgcct tttcttttgc taataccaca gtcttaatta ccatagcttt 3120
aaagtaagtc ttgaagtcca atagcattaa tctttgactc ttctttaata ttgagttgcc 3180
ccttcagaat cttaatgtct ctccatgtaa actttagaat cagcattttt atattcacaa 3240
aataacttgc tgagattatg attgagattg cattgaatct ataggcttat ttgggaataa 3300
ctgacatctt gacaatattg agtcttcctg tccataaaca ttatttatga tgggcttctt 3360
ctttatgttt aggagctttt gttttttctg tcagatattc cacttctacc tttatgattt 3420
cttaattgcc ttttatgctt agaaagtttt tcctcatcct gagctcacat attcatttat 3480
tttcttttaa aatgtgtttt caagcattta atttttaaac ctatgtggaa tttattttgg 3540
tatatggaat gaggtggtgg tctaactccc tcctctcaaa tatgtagtta tttttcccaa 3600
aaccattttc tattaattta tcaagaatag acatgtatac atatacatat ataatagtca 3660
gccttccact tgttgtttga cccttgtgaa ggaaattgta tgagtttcca attttggatt 3720
aggctcaggt agtaattgag ctgggttctg ccagagatcc atgttaattc actatccaaa 3780
cagagttata aaatgtaagt tttatgaaaa tctaacagta tatcactggt ttaatgatca 3840
cagcctagga agaatgggga aattgtcaaa atcttctgtg gatgcacctg aaggccactg 3900
ctgaacccat ttccctgcta ggcacggctg ctggtaccag gggcaaactc ctggagtata 3960
tatgaaccac ctacatctcc ttctcttccc cccctaccct tgagattttc atgtgtccct 4020
taaggatgtg tgtcctactt cccttggaga gtcactacca cattgaacac tttagactgt 4080
gagtcctgtg aagatggggc tcatgagtgt attgctcccc agttgtttct ctagcactag 4140
ctcagtatag ggcataaaaa tctgaatgga tgaacaaacc actattactg gtggggacat 4200
gctactatct tacatggttc gaggtggaat aaaggttgag aacagctata taatgtgttc 4260
cttgaagggc agcagtacat cagtgcaatc agcctacctt ctccatactt ctcactctga 4320
aaactgtaaa gctgcaccta gcaatcaact tgggagcttt aaaagggact gctccctagc 4380
tctcacccac aaagctgtag tctagcacag gtgacttttt taaaaaagtt ttttggtcca 4440
gatgtgatga ctcacgcctg taatcccagc acttcgggag gctgaggctg ggaggtcacc 4500
tggggtcagg agtttgagac cagcgtgacc aacatggaga aaccccatct ctactaaaaa 4560
tttgccgggc atggtggcac atgcctctaa tctcagctac tcgggaggct gaggcaggag 4620
aattgcttga acccgggagg cggaggttgc cgtgagccaa gatcacacca ttgcactcca 4680
gcccgggcga cagtgcaaga ctccgtctca aaaaaaaata aaaaaggagt cctattaaga 4740
cttattttta caggttggat atctctaatc ccaaaatctg aaatgctcca aaatttgaaa 4800
ctttttgagc gcagacatga tgctcaaaaa aatgctcact gggacatttt ggatttcaaa 4860
atttggatta gggactaggt gtgggagctc acacctgtaa tcatagcact ttgggaagtt 4920
gaagcaagag gatcagttga acccaagagt ttgagagcag cctagacaac atagtgagac 4980
gccgtctcta cagaaaattt taaaaattag ccaggcatcg tagtacatgc ctatagtccc 5040
agctactcag gaggctgaga cagaaggatc acttgagtcc aggaggtaga ggctgcactg 5100
agctatgatc ataaccactg tctccatcct gggcaacaga gcaagaccct atctcttaaa 5160
aaaaatctga aacactgcta gtcctcaaga taagggatag tcagtcttta taaagactca 5220
attagttatt ggatatctga ggaagcatgc atatcaggct cccaaaagat cattggttta 5280
ggcacacatt ttaatagctt ggaaatccag aatactcttc tggtgaccag ctcagacata 5340
gtcctgataa tataggacct catctaacat gactccctat tttccagata agcatggatt 5400

-continued

```
cctggttcat tcttgttctg ctcggcagtg gtctgatatg tgtcagtgcc aacaatgcta   5460
ccacaggtaa attgtcattt gataaggctg ctatttgaaa tgaaattttg ctttcacatt   5520
taatgagcca catttgaaaa ccgagatggt atttgaagaa aggaatataa aaattttatt   5580
caaagtgatg gtaaaatagg tgtcttcaga aatcttggaa ttgaatgctc agcattgttt   5640
ttcatacata cataactgct ttaaataaat caaagagatt atgtgttctt tcctgaaaag   5700
taaaataaat tgttgacatt tacaactcta tatatggttt ctgaggaact aagtgaagaa   5760
tcttgtgtct ttctccctta aaccgtagtc ctttggagga ggtaggaaag gtccagcatg   5820
agataaaaac gtagggggtg ggtggtgttg agggggattg gtctttgctt ggtctccata   5880
tgtttgagag tttattaagg cttgctgctt tgtgtctcac agctttttag cctcacattc   5940
ttcatgtgct atttccttgt tttttggtgt ttgtagttgc accttctgta ggaattacaa   6000
gattaattaa ctcatcaacg gcagaaccag ttaaagaaga ggccaaaact tcaaatccaa   6060
cttcttcact aacttctctt tctgtggcac caacattcag cccaaatata actctgggac   6120
ccacctattt aaccactgtc aattcttcag actctgacaa tgggaccaca agaacagcaa   6180
gcaccaattc tataggcatt acaatttcac caaatggaac gtggcttcca gataaccagt   6240
tcacggatgc cagaacagaa ccctgggagg ggaattccag caccgcagca accactccag   6300
aaactttccc tccttcaggt actagagatg attctgtttg ttcttttgct ctttgagttt   6360
agtcttcctt ttattatctt gtttgtgttt tctagcctta aaatttcttc aaataagtaa   6420
aattgctcaa gtgaagtaat gaaacctgta tgtggaattt ttgggttagc atgagtgaag   6480
aggaaagaag aaagattctg gagaatatct ttctgctagg tgggatcctg gttagattga   6540
gaggacttaa atgtgtttaa aggtagagaa gaaggcttaa aaagacaaga gaaatagagg   6600
agctcattga cgatgcaaga gactgaagat gaaaagatac agagaatgag taataagatt   6660
aggtttggaa agggagggat ccgtggagac catggaaagg agaatgggta ttgatgtcca   6720
tgacagttag atgtgagata cagagaatga gtaataagat taggtttgga aagggaggga   6780
tccatggaga ccatggaaag gagaatggac attgatgtcc atgacagtta gatatggagt   6840
ggcaggccag tggccagggg tggcatcagg ctctgggaaa tggttacatt gcagtgccag   6900
ttgttcaggg cctcaggttg aagcagtagt cccaaggaga aaatcagaga cgtggatctg   6960
agaccagggc aggtaagaca agtttctgac ctctttgaac cttaggtacc ttgtctgtaa   7020
aagaggatta gagataccct caaagggctt ctatgaggag taaaggaaat aatcattacc   7080
tgattgctat gtaactgtca tccctttct agcaaaaatc actctttcct cttctgtgtt   7140
cccagttaga tggtgagtgc ccctaagcag aatcacatct cgctcatgtg gaacattcag   7200
gaactgtttg ctcagttgat tctcatttgt tactacagat gatatctttt actgcgcctt   7260
ataactcaga cccttcacct gccagctttt ccccatattt tctaccgtaa agacaagaca   7320
gcatttgcag ttaagagcac agtcttcagt gccacactga gtttgaatcc cagctcttcc   7380
ataaaccagc catgtttatg gcatagctgg cttactttat ctctctacct cggtttgttc   7440
atctgtgaaa caagaatgag tgatagtaat agttcttacc tcatagagga gatattagga   7500
ttaaacaagt taatatgggt aaagcactta taaaggtgcc tacacatggt aagcactatt   7560
tttaagtgtg agctgttagt attgttgtgg ttattgctct gatagttacc agtaaaatat   7620
atgaaggtac ctttaatgca gatggcatcc cactattctt gatgagatag gggactgcag   7680
acaaataatg tctgatactt gctttgtgct ttagagttaa tgtagttttg tcatagttat   7740
tactgtgtgc taggcatcgt actaagagtt ttctagaata atcctatgaa ttaagttcta   7800
```

-continued

```
ttttatgttt tataggtgaa agtattttac aatgatgaaa ccataatttg tggaatgttt   7860
ttcagtgtac aggtcatgac acaattcatg aaatcacttt agcaggccac cactagttgt   7920
ttgttttgtt ttattttaat ggatgatcca gttccatgtt tattctttta atgttacata   7980
caatttttttg aaattttagt aacaacataa aatgttgggt tgtggccatt gcttagggag   8040
aaaggcagga taacttgtac aaactgtatg agtgaatgga aaaggtggag actgtaacac   8100
aggcctgact gactgaacag cccatgttct attgtgtact gtctttcatt taacagttct   8160
gtgacatgac catggataat catctccttt taacagatgc ttgatttcag actgtatata   8220
gaggttaaat gatttgtttt agatctcaag gctgacaaat taggcctatt tctcactttt   8280
gcggtctttc cactctgctt gtagggaact tagttttcca taaactgact taggtccaaa   8340
ttgtgccaca gctaagaatc tagttattgt acatttaaca cagttcacgt cataggaggc   8400
tgagactatg tttctctagt ggcgtttatt caagatgagt aaaacacaag aaaccattat   8460
cgcacatggg aatttcatag tcttaaaccc cacatcccac ttatcaccac catttaccag   8520
tcctcctgta acagttacaa ttttttatta aatcagtatt tgatgtatat tattgtaatt   8580
atgaaatatt cattgctgag ctataagtat aaatggattg tttttcttgt acagtttttt   8640
ttctggattt aatacttacc ttattttttg tttatttagt tttctattta gtcaggccag   8700
gcacactggc taacacctgt aatcccagca ctttgggagg ccaaggtgga cagatcactt   8760
gagctcaaga gtttgagacc agcctgggga acatggtgaa accccatctc tacaaaaaat   8820
acaaaaatta gctgggcatg ggtgcatgtg cttgtagtcc cagctactca ggagcctgag   8880
gtgggaggat tgcttaagcc caggaggttg aggctgcagt gagctgtgtt cataccactg   8940
cactccagcc tgggtgacaa agcgagacca tgtctcaaaa aagttattgc tactcaattc   9000
ttaccatgct ctccagagcc tctcaaaaca gctttctaca aagtgagatc tgttagataa   9060
tctatttctt ttttacctct agaaattcct cctgagccct ccattgtctt attccagtct   9120
aggcttgtcg atctctaggg ctactacaca gatacatcag cctgagattt cccttctctg   9180
tcattctggg aattcccctt gctgctgctt cctgacttcc atattgtctt cctttttgtc   9240
ttctcatcat tcggtagatt cctgagaaaa ggggtccatg ggaggcaaat tgcatcctta   9300
catatctaaa aatatcttta gggctgtgca tagaatttga ggaatatttt tcccccagaa   9360
tttttaaagt aatgccctaa ctgacacctg tttaccaggt ttggaggatt ttactgctat   9420
cttaatccct aattgtttgt atgctttcta ggatcttctc tttatcatca gtatcctgaa   9480
atttcacaga gatgtatctt gatgtgggtc tttttcgttc attattatgg atacttaata   9540
ggccctttag agccttgatc ttgcatttct gaaaattttc tcccatttct ttgaaacctt   9600
ctccccctct tccttttttt tttttctcaa attcttaata tttggatatt ggatgtatcc   9660
tgaattaatt ctttaatctt taaaattttt cctttctgtt gatctttgct ttgagtcttt   9720
ttctcctttt aaaaataaac aaaggccagc taggcacagt ggcttatatc tgtaattcca   9780
gcactttggg aggctgaagc aggaggatcg cttaagcccg ggagtttgag accagcctaa   9840
gcatcgcagc aaaacctcat ctctacaaat gatttagaaa ttagcagggc ctaatggctc   9900
atgcctgtgg tcccagctac tcagggctga ggcaggagga ttacttgagg cctggcagtt   9960
gaggctgctg cagtgagctg tgatcgcacc accgtactcc agtctgggca acagagggag  10020
acctcatctc aaaaataaat aggcctggtg tggtggctca ctcctgtaat cccagcactt  10080
tgggaggcca aggcaggtgg atcacttgaa gccaggagct caagaccagc ctagccgaca  10140
```

-continued

```
tggcaaaacc ctctgtctac ctactaaaaa taaaaaaatt agtcaaacgt gttggcatat  10200
acttgtaatc ccagctactt gggaggctga gacatgagaa ttgcttgaac ctgggaggtg  10260
gaggttgcag tgagtcaagt ccctgcacta tagcctgggg aacagagtga gacccgagac  10320
tctatctcaa aaaaaaaaaa tcagtgacaa gtaaaaaggt agaatacctt tttttttttc  10380
tttgagacag tctcaccctg tcgcccagtc tggagtgcaa tggcgcagtc tcggcatact  10440
gcaaactctg ccttcagggt tcaaacaatt ctcctgcctc agcctcctga gtagctggga  10500
ttacacatgc ccacgaccac acccagcttt tttttgtatt tttagtagag acaggtttca  10560
ccatgttggc catgctggtc tcgaactcct gacctcatga tccacctgcc ccggcctccc  10620
aaagtgctgg tattacaggc gtgagccact gcgcccagcc tagaatacct tttaaaaata  10680
aataaatagg ccgggcgcgg cggctcatgc ctgtaatccc agcactttgg gaggctgagg  10740
cgggcagatc acgaggtcag gagatcaaga ccctcctggc taacatggtg aaccccatct  10800
ctactaaaaa atacaaaaaa aaattagctg ggcgtggtgg caggtgcctg tagtcccagc  10860
tactctggag gctgaggcag gagaatggcg tgaacccagg aggtggagct tgcagtgagc  10920
cgagattgcg ccactacact ccagcctggg caacagagca agactctctc tctaaataaa  10980
taataaataa ataaataaat aaataaataa ctccttttac aaaagcatat atattcattt  11040
tttccattta taatataaat aatagatatg ctgagttgat ttctgcatat tgctttttca  11100
gttaccctat catacttgct ctttgtttta gtaaagagct gctgtattga aggatatacc  11160
ttaatctctt tatccagttt ccccatcagt ggacactaag attgttttca gagtactctt  11220
ataaacaata cagtttgtca tttcagacac atatgagaat attagcagga tgaattattt  11280
taagtctgca tttataaatt tatggatatt gccacattta cctctgctag gaagtctatt  11340
cctattaaca atatgtcaaa gtgcctattt ttctaaactc tcttcagtgt ggtgaattgt  11400
taaacttggg gatctctgcc aatctgacag gtgaaaaata acatctcagt gtaagtttaa  11460
tttgcatttt gctgagattg agcaattttg tgtaatttaa aagatcattt atttttctga  11520
gcattctctg ttgatattct ttacccattt ttattagagt gtcaaggttt tcctgactcg  11580
tttgtagatg ttctttgtac gtttgggaaa tgagtccttt gcctatggta aaactgcaaa  11640
tgttgttccc taggtggtca tctagatttt ctgcattgca gaagatatca ttagctattt  11700
ttaatttttt taatttaaat atttctcagt ttaggttttc taggaattgg gtcatatcta  11760
ggaaggcttt ccttactcca agattataaa aataattttc ttctggactt ctatggtttc  11820
gtgtgtgtgt gtgtgtgtgt gtacacgcac ttaagtctgt ctcgaattta ttctgatgca  11880
gagtgagcta tggatctgtt tttccccaaa tatctaactt gtcccaatac cccttaataa  11940
tttatttttc ctcattgatt tgaaatgcca cctatcttat atattgaatt cagatattta  12000
tttacctctt catatgtatt tgagtatttg ggaacattca ttttattttc tattaatctt  12060
tttctctgtc catgtgcaaa gcctcactgt ctcaataatt gtaactttgt aaagtattta  12120
atatccagta aaatgagtca ttccttgtta attttatttt tcagaatttt gttagcaatt  12180
cttattataa acattagaat taacttgtct agcaggaaaa aaagtttgta ttgatcatgt  12240
taaatacgta gattaacaga gaaaatggca tcttacagat gttgagtcta actatccaag  12300
aatgcaatat attccatttt ctgaagtctt tttttttaa atcttctgtt tttgtaatta  12360
taaatggagc attttcttcc atcagatctt ctaactggct gctgttgggg atatgaaggc  12420
tactgatttt tgtagagaca ttttgtactg gccaccttaa actctcttag tattggaagt  12480
aattttcttc attaattttt atggcttcaa gtcatctcat ctgcatatat cttccaaatt  12540
```

-continued

```
tttagaactt tctttttctt ctgtttaatc gcattgatga atacctccag aacaaagtta  12600
agcagctggt aaatgcagac agcattctct tgtatctgac actaaggagg acactttcag  12660
tggtttttca ttatacgtgg tactgactct tgagttgaga taaacatatt ttattgtgtt  12720
caggatttaa tgagcgttta tgttaggaat gggtgttaaa ttttgccagt tgcctgttca  12780
ggatcaatga gaaagatctg aatgattttt tttctctttt ggtctgtttc tatggtggat  12840
tctattccta ggtttgtttg tttgtttgtt tattttgaga tggagtctgt taccaggctg  12900
gagtgcagtg gcgccatctc agctcactgc aacctccacc tcgcgggttc aagtgattcc  12960
cctgcctcag cctccgagta gctgggacta caggcacgca ccaccatgcc cggctaattt  13020
tttgtatttt agtagagacg tggtttcacc atgttggcca acctggtctc gaactcctga  13080
ccccatgatc ctgcctcagc ctcccaaagt gctgggatta taggtgtgag ccactgcgcc  13140
ctgccagttt ttatttattc attttttaga gacagggtct tgctctgaat taattcttta  13200
atcttcttaa tttttctttt ctgttgacct ttgctttgct ttaagtcttt tcctttgagt  13260
catccaggct gaagtacagt ggcacgatca tggctcactg taaccttgaa ctcccagact  13320
taagcaaacc ccacctcaga cttctgagta gctaaggact ataggcgcat gtcaccacgc  13380
ccagctaatt tttaaatttt ctcagaaaca gggactcact gtgttgccca gactggtcat  13440
gaactcctgg cctcaagcag tcctcagcct tagccttcca aagcactggg attataggca  13500
tgagccaagg ccgcccaaac atattgtatc gttcctgtaa caagctgttg cagtctattt  13560
gatattattt cttatttttt tcatttagaa ttttctctgt ctagatattc tcaaattatc  13620
tctaaatgag attgatctat gtttttcctt tgtgtgtgta ttctttttga taagttttag  13680
tttttagtgt tttgttttgc tacatggaaa ggatttgaaa gtttacacta aaaaatatgc  13740
tttttttttt taagacaggc tttttcactg ttgcctagtg ctggagtgca gtggcatgat  13800
ctcggctcat tgcggcctgc acctcctggg ctcaggtgat cctctcacct cagcctccca  13860
agtagctggg attacaggtg tgttccacca tgcccagcta atttttttgta tttttttgta  13920
gagatggggt ttcgccatgt tgcccaggct ggtcttgaac tcctgggctc acatgattct  13980
cctgtcttag cctcccaaag tgctaggatt acaggtgtga gccaccacat ctggccattt  14040
cattcatgtt ttcaaatgta tttgaatgag gaaaagttct cccttgtgat tatttattat  14100
aatagcctac agagctatta atttttaaat tttgtttact ttatgtctcc tttttttttt  14160
tgtttaggct gaataaccat ttatttcata ggtttattgc ctttttttctt ccaaagaact  14220
tgctattgtg catttatagt ccttttatgt ttacgttttc tatttcattg attttaactt  14280
tctaccttct ttagatttat tttgttcttt ttctatcttc ttgaattgag tgtgctttaa  14340
ttgcattctt tccagttaat taacatattt agtgctgtga attttgaaca agcacagctt  14400
tagccacatc ccataggtgt ttctataggc agttgtatta ggatgcgcta taagctgctc  14460
tgacaaagat accaaaattc agtgacttaa ataagaccaa agtgtctttc tctccccagt  14520
tacattccag aggtagacag ggccttcgtc tcagtaggga ccaaattcct ttcctcttgt  14580
ggccctgcca tcctaacaat attgccctta tctgtttggt tagagatagt tctcaccatt  14640
gggttctagt tccaaccact gcgaaggaca aacaaaggga ataggggcca tttctcttcc  14700
aaaagatgtg acctggaagt tactcacatt gctttagctc acatcccgtt ggctagaatt  14760
catcacatga ccacacctag cacaaaggag tctcaaatat agtctgccag gagagcttgg  14820
tgctcagcta aaaaacaaag gttctgtatc aaggcaagaa gagaaagaga ctgatctgag  14880
```

-continued

```
gggaggagag ttggcaggtt ctgtcacaaa acttctcgtc attgttattt ttaaggtatt  14940
tttccatttt gggtttttttg tttgtctgat tttttttttt tttttgaga tggagtctcg  15000
ctctgttgcc caggctggag tgcagtggcg tgatctctgc tcaccgcaag ctctgcctcc  15060
tggttcacgc cattctcctg cctcagcctc ccaagtagct gggactacag gcgtacacca  15120
ccacgcctgg ctaatttttt ttttgtattt ttattagaga cagggtttca ctgtgttacc  15180
caggatggtc tcattctcct gactttgtga tctgcccact tcggcctccc aaagtgttag  15240
gattacaggc gtgagccacc gcgcccggcc gtctgtttga tttttgagat ggaatctcac  15300
tctgcccccc ttctggagta cagtggtgtg atcttgggtc actgcaacct ctaccctccc  15360
aggtttaagc aattcttgtg cctcagcctc ccaaagtgct gggattaaag acgtgagcca  15420
ctgtgcccag cccattttgg ttttgatttt tttttttctt tgaaatagag tctcgctctg  15480
ttacctaggc tggagtacag tggcatgatc tcggctcact gcaacctccc cctcctgggt  15540
tcaagtgatt ctcgtgcctc agcctcccaa gtagctggga ttataggcac ccaccaccac  15600
gcccagctaa tttgttttgt atttttagta gagacggggt tttaccatgt tggccaggct  15660
ggtctcgaac tcctgacctc aggtgatcca ctgcacccgg cctcattttg gttttgattt  15720
ttattttcaa atgttttctt actttgtcaa tttctaattt tattgcattg ggacaaaaga  15780
atattgtact ctttctactg ttggggttta taagggctgt ggatatttca ctcgcctttg  15840
aaaagaaggt ttctctgttt agtctgtaga gtttggtatg taccaattag attttattac  15900
ttatcatttt ggtcttttgt atccttactt aattttgtcc tcttgaattt taatggagca  15960
aaagacataa agtcctctaa taacatgcgt tctgtttgca ttctcatact ttttatgaat  16020
attgatgctg cactatttgt gtacccaggg agaaggccag accactgtcc aaagtttagt  16080
gaatctgggc agccttgttt cccagttgtt ggaggatgcc tcatggagga aagcattcct  16140
aatcctggag cttgttttgt tgtactctaa ttgaattgta atgtgtttct ttaacctgaa  16200
tgaatgtttc tattttttac ttattacaca ggtaattctg actcgaagga cagaagaggt  16260
gagctgctca ccttatatct gttgttcctt ttacacagtg tacagtattc atttatttcc  16320
tctgctcaca gtctgtggta accgtgtgca tctgtggctg tgttgtttgt ttactttccc  16380
ttaagttatt tccatgttaa tctcatggag aagagcaata gaaacaagta ctgtattcag  16440
tatgtttttt aatatagact atggattcta acagctatga tgtattttaa caagtaacaa  16500
aatatatctt actttgacat gtcactttgt taacattact ttttggtgat attaggtcat  16560
aatttctata ccattagtta cttctgattt ctaggccaca gttcccttta aatattcttt  16620
gtgttgtttt tcccctagtg tataaaatgt caaccctttg tggctttata tggattttat  16680
ggattttcag cccttaaatg taaagtctct atggcctgag atgttgtgtc tgtggtttaa  16740
gctggactgc tgagtccctg gtcactagag agtaggggga catgggtact tgtctgcaga  16800
agtgtggcac attttgccta gaatgacagt aaggctgcta tcaaagagca tgagagaaag  16860
agaaagagat catctaacat tctaagaagt gattattaca tttgagtttt aaaaatgtta  16920
ctattcgaag cagtgttttt atcataattt tctattttat caaatcagac ttgagttttt  16980
tttctgattc tgttatttaa ccatacacaa ttttccctgt gtaattaagt aatggaacac  17040
ttggaggcat atgaagtccc actaagtagg gagcatttga gtcagaaaag tgggtactct  17100
cttcctttat gtgatgtcca tctgccattg tatttggtaa ggaatagtga ggtgttacca  17160
tactgtgtac agatttccct cacttttcca cctctcactt tcctaaactt gggaactaaa  17220
cattggatta atacagtgtc tttgctgttc agattcactt gccagatttt atcaaatgta  17280
```

-continued gacttaaata ggttttattg tgatagatat ttacttgctc cctaaaactg ctctcttaac 17340
cagccttaca ataaagtcaa aagtcaaagt ggtaggcttc aagatgaaac ataagatctg 17400
ttgactcctt cctctattta gtatatattt tcataatatt cagccttttc ttgccccaga 17460
tatcatatct attttaccta cccaatattt aagtagtttc catgttgtga ttaagaaaac 17520
aaaattacca taattaccta gattattgct aattgtgaca tatgtaaagt ctattaatgt 17580
aataaatctc ctttcttaag tcaaaaaata attttgtgta attccaaaca ggaaactgaa 17640
aaggcatagg tattctcagc agtctctaaa gtcccaaaat ctaatggcaa ttttaccaga 17700
gcagatcttt agaagtattg ctataaattt ggatatccca ttctaatttt aagccaaatg 17760
ctttttgaga aataagccag ctgtttggaa atgcttgtat tataatcggt ttgataagca 17820
gttatgtctt atgcagatga attaggggct acctgttttt atgcactggt ctttggggtg 17880
cttttgaaca gtagtgtctg atgttttaat tgtcaaagca aaaagaaatg agagggaggg 17940
caacttttct tcctcttctg aattccagga aactggttat tttctcatgc catatgattt 18000
taaaatatat tcccagccag gtgcagtggg tcacgcttgt aatcccagat tttgggatg 18060 ccaagcgggg gga 18073

<210> SEQ ID NO 13
<211> LENGTH: 7505
<212> TYPE: DNA
<213> ORGANISM: BAC-F2 contig 9

<400> SEQUENCE: 13
tccgagctcc acgcggtggc ggccgctcta gaactagtgg atccctctgg tggcccattg 60
agaatcaaaa cttgcagtga gtgactctat aaaatggaaa attgaatcaa gtctgaaaat 120
gatccacata gttctacagc agggctggac accgtggtca ggacctcaat atattctgct 180
tccacagaat tcagacagtt cagagtttgg tgaattaacc tcaaaggcag caagatatct 240
gtcccgggag tcagcaggta agcatagcag aaatggctgg agcagcggga gcctgctttc 300
cttctgttgg ctgctagcgt ccactccatt atagctcctg atggaagatt tctacagagt 360
gatgcctcag aatcttcctt ataccttttct tccatgatcc ttgcacctct ttttctagat 420
ttgcccacat tcttatgtgc aagtaactag atatacatta tcagacaagc tagcagacct 480
gcatatatcc acttccctac ttttcctata atttcttcac ctgaacctct atcattcttc 540
tctttctgtg ttgactctgg tgttaacctt gcaggcaagt tgagcgtggg tttggtgtca 600
cagtgaagga ctaagggaat agttagcctt ctatttatta acaaatcttc cctttgatgt 660
ctggatcagt gtctctctaa taggaattat tggcatgtta aggcaaagaa catatgctta 720
ttgagtgctg actgattggg gttaatacta atttgatact attaaggtgt ggggcccagg 780
aatgccaaaa ttctacctca atgtagagcc accattcccc ttgaggtaac ctaggtggga 840
tagatatacg tgtaagggct aatggaagat agggaatcaa agtatcactt tattttttat 900
ttttattttt tatttaattt ttttgagatg gagtcttgct ctgttgctag gctgtagcgc 960
agtggcacaa tgaaagtatc actttattat tatctgagct tgtgccctaa acttcactgc 1020
agaatatgct ggtaaaatgg actggattac aggatttaga ggcaaggtcc acaggtcagg 1080
ataagaggta aagagggaaa tctttctctc ttcctaagcc caaaccctcc atgacaattg 1140
agattaaaaa aaaaaaataa actgatgaga gaatccaagc acagttgatc aaagaggaaa 1200
gagaaatgat gatgtttccc tctttctttt tcatgagaaa gtggctctct tattgatcgg 1260

-continued

```
ctacttgatt agagaaacag tgggggaaag aactgccata tccacatgtg caattttttta   1320
aaacacacag tgattctgaa cactagtata aattcccagt cagtgttctg gccatctgac   1380
tactcaggtt ataataccta atttttacaa gggagttggg aagtgtgcca aacctgtaga   1440
agtctatatc tactgtattc agattttata tgcattattt tatataacct tttgacctct   1500
ctcctctatc atcacttgag tgatttcatc cagcgtcatc atttaacata ttttaaataa   1560
ctctatatac tgataattcc caaatttata tctccatccc cgattgttct cctaacctcc   1620
agcctctaat atccaactgc ctactcaagc ctcagcaatg gtgagcgccc ctgccccagc   1680
ctcgctgctg ccttgcagct cgatctcaga ctgctgtgct ggcaatgagc gaggctccgt   1740
gggcgtggga ccttccgagc caggcgcagg atataatctc ctggtgtgct gtttgctaag   1800
accgttggaa aagcacagta ttagggtggg agtgacccaa ttttccaggt gtcgtctgtc   1860
acagctttgc ttggctacga aagggaattc gctgacccct tgcacttcct gggtgaggca   1920
atgcctcgcc ctgcttcggc tcatgctcag tgcgctgcac ccactgtcct gcacccagtg   1980
tccgacgagc cccagtggga tgaacccggt acctcagttg gaaatacaga aatcacccgt   2040
cttctgtgtc cctcatgctg ggagctgtag actggagctg ttcctatttg gccatcttgg   2100
aactgccttg cattcagttt ttaatatcca actgcctata cgatatcttc acttggattt   2160
tgaataggca tatcaaactt gtcatgttca aaagtgaggt tctaatcttc cctcccaaac   2220
ctgcttctcc catggctttc cccatctcag taaataggaa tttcatcctt ccaattgctc   2280
atgccaaaaa tttgggagtt atccttgact cttctctttc tcacacccca cattcaatcc   2340
atcaccacat tctgatgcct ctatcttcaa gatatactta gactttcacc acttttcttc   2400
actctgcaat taccactttg gtccaagcca ctgttatctc tttcttggat tattgtaata   2460
gcttcctaat aatttgtccc ctttcttcca cctttgtttc ccctacagta taatcttaac   2520
gaagcagcca gaatggttgc ctacaaacct ttaaaatggt aagccagaac atgtaggtat   2580
attcaaaacc ttccaatggc ttgtcatgga actaaaagtc tctacattgg cctataagac   2640
cctatgtcat ctacccctag tctcctcctt tctaacttca tctcctgcta tgctgtcctt   2700
caactcactc tgctccaggt gctctggcct cctcaaacac accacacaca cttgcagctc   2760
acagtcttgg cacttgctgt tcttctcctc taggaccttc ttcctccaac tgtctggttc   2820
acccacccct tccttctgga tttctgctct gatgtcattt tatcagtggg cacttcccaa   2880
tttctctatt taagaccaca attccaggcc agggtggtgg ttcatgcctg taatcccagc   2940
actttgggaa gccgaggtgg gcagatcatg aggtcaagaa ttcgagacca gcttggccaa   3000
catggtgaaa ccccatctct actaaaaata caaaaaaaat tagccaggtg tggtggcaca   3060
tgcctgtaat ctcagctact taggaggctg aggcaggaga atcgcttgaa cctgggggc    3120
agaggttgta gtgagccgag attgcgccac tgcacttcag cctgggcaat agagcgagac   3180
tctgtctcaa aaaaaaaaaa aaatttgctg ttatttccta tactattttt gtaaggcaag   3240
gaccttatta ttttccttga taatacctct cacactttat aattacatat ttgactttgt   3300
tgattaatga atatccctcc tttatagcat aaattccaca agagcaagga ttacatgtct   3360
gcttcattct cactgtacac ctaaaaccta gcacagggtc tcacacataa caggcacaaa   3420
acaaacaatg gattacgttg agccaaagaa caaaaaaaaa tagtaattta tcactaaatg   3480
tctttgttaa attccaacaa caggggggcag tatatcaggt attataagaa agtaattagg   3540
cacatcccag cactttggga ggccgaggcg ggtggatcac aaggtcagga gttcaagacc   3600
agcctggcca atatggtgaa accccgtctc tgctaaaaat acaaaattag cgggtgtggt   3660
```

-continued

```
ggcacacccc tctggtccca gctactcagg aggctgaggc aggagaatcg cttgtaccca   3720
ggaggcggag gtttcagtga gccaagatcg tgccactgca ctccagcctg ggtgacggag   3780
cgagactctg cctcaaaaaa aaaaaaaaaa agaagaagaa gaaagtaatt aggcaccttt   3840
ggcttaagac actgggctaa atccatgaat ttacttcatc ttcccccaaa gcacactgac   3900
atggtagaag aaatataaaa atactaatga atcaacagca tatctgaaag gcagcaaacg   3960
gtggcatatg tagatcagaa tctttgagag atttctggaa gacaaaacag accagactcg   4020
atgtccaaga gatcaaacag agccaaagag cctccagctg aaaactaagt actagttcta   4080
ccagtttggg cctggaaaca cctcaagctc agagggaatt gggactgggg ttgaaagtgg   4140
accttgaggt accaggatgg tacttaagca aaggcctgcc aacccagcac cagtacaccc   4200
acagcccaaa tgacaagcgg ggcttcccat ctagactcag ctggaaaaac agtgctctac   4260
acagagtaga gagtttgtca cagagactgg taagggcttc tttttacaa aacatatgct    4320
gcatatatat tttctcaacg tcacactaat gacattttgg gctatacaat tctctgttat   4380
gtgggtctgt catgtgcact gtaggacatt taacaatatc cctagcctct aattattaga   4440
tgtctgtagc aaattcccaa ttttgatgac caaaagtatc tccaagcatt gctaaatgcc   4500
tttgtggggg aaatagcccc cagtaaggaa ccactggtct atactcacgc cattctaact   4560
gaattctttt aaggcaaatc cgagacctag catttcaaat gcaattactt aggtatgtat   4620
caccaagaga tcaagattct taacataaac ataatactat tatccaattt aaaaagtaac   4680
actaattcct tagtatcatc taatattatt cagttactgc ttgaatttcc ctgagtgtct   4740
cataaatgct tttttttgt tttggttaga attgacacca gagcaggtct acactgcata    4800
tgattgttaa gtatattggg tccacagaag gtctcctggg gcctgcagac agaaaaaaac   4860
catagtagtg cccaagctaa ttctaggcaa ccacaagaga ggaaaggaaa aagaaaacgg   4920
cagctcgcct agaggataac tgcaccctgc cccgattttc ctgagccatc actgaacccc   4980
ttcctggttt aggacgtatg tccatgtttg tcttctgaag ggatgaaggg acacctattg   5040
tgagcacagt ctaagccact caatggtcca gggcatagct caaacagagc aacagtagcc   5100
ctgggaaatg gaggtgacaa aagaaacaga ataaatcttt caaaatatac tgcaatttgt   5160
gcaacaggat gccatattga tttaaaaaaa ttttttttct taaatttttt gtagagatgg   5220
ggggaggggg tcttgttgtt gcccaggctg gtcttgaact cttggtctca agtgatcttc   5280
ttgccttggc ctcccaaaat gctatgatta tgtgcgtgag ccactgctgc attgcgtttt   5340
tttttctttt ctcgagacgg agtctcactc cgtcacccag gctgaagtgc actggcgtga   5400
tcttggttca ctgcaacggc ctcctggttc gagcgatcct cacaccttag cctccctagt   5460
agctggaact gcaggcctgg ctaagttttg tatttttagt agagacaggg tttcactatg   5520
ttggccagcc tggtcttgaa ctcctgacct caggtgatca gcctgcctca gcctcccaaa   5580
gtgctgggat tataggtgtg agccactgtg cccagcctac attgatattt tttaaaagcc   5640
actatttaaa aaggagtaat ctgagtagta agaaggagtt ctttaaaaac tggccgggca   5700
tggtggctca cgcctgtaat cccaacactt tgggaggccg aggcaggcag atcacctgag   5760
gttggtagtt taagagcagc ctgaccaaca tagagaaacc ccatctctac taaaaataca   5820
aaattagcca ggtgtggtgg cacatgcctg taatcccagc tactctgggg gctgaggcag   5880
gagaatcgtt tgaacctgga aggcagaggt tgcggtgaac cgagatcgtg ccattgcaca   5940
ccagcttggg caacaagagc aaaactccgt ctcaaaacaa aacaaaacaa aaatgaaaac   6000
```

-continued

```
aaacaaaaaa acaccaacat gattaggagg gaaaaaatct agatagaaag gcttaacagg   6060

gccgggcacg gtggctcatg cctgtaagcc caacactttg ggaggccagg gtgggaggac   6120

tgcttgaggc caggagtttg agaccagcct gggcaactta gcgagactct ggtagtctgt   6180

ctctaccaaa caaacaaaca aacacctgat tagctgggca tggtggcata tgcctatagt   6240

cccagctacc cgggaggctg aggctggagg atcgcttgag tcccagaggt caaggctgca   6300

gtgagctgtg atcaggccac tgcactccag cctgggcgac agagcatgag tctgccccag   6360

ccctgcctcc aaaaaaagaa aggctaaata ggagaactga tataactgaa aaccaaatta   6420

gttgtgtgaa agagcaactg tcctggaagc tcccagaaca cagagcaata agagatgaaa   6480

aatatgacag catagaaaag aaaggaactg gataggtcca ggagatccaa tacctgtgca   6540

acaggagagt ccaaagaaga aaccagtaag aagggagaga agtaatacaa gaaagttcct   6600

gagttatcag gccaaaagaa ataatctagt ttgtggagta atattgacaa aaaaatcttt   6660

acacctagat gtattctgaa aaaattctta aattctaatt gaaatcaacc aacgaaccac   6720

aggccagcct tagaaaacca tttccagggc atggggtttt agggtctgac agacctgaag   6780

ttcaaattcc tactatccta acttactagt agtgtgataa tctcttagaa caatgtatga   6840

aatggaagca taatagcacc ctccaccttt tagagttaat gggagatcta aaagaggtaa   6900

catttgcaaa gtgtctgaca tgaagggaag agattggctt tggcatccac aagttcacac   6960

actagcagag aacctcagtc cagcttccta cgctcaggca gttctttgcc tagaagaggg   7020

gtcggcaaac tatagcccaa atttagccca ctgcctgttt ttgtaaataa aatgctatca   7080

gaacatggcc atgttcattc atttacatac catctatggc tgcttttaca ttacaaaggc   7140

agagctgagt agatgagaca gagacagtat ggttacaaac cgaaactgtt tcaaccccaa   7200

cttcattcca gcaaagtttt actttctaga ttcaggccag ggagcaagca tgaaaatgaa   7260

aaccactaaa atggtgtccc gggacaacag atacctactt gctataactt ctttccttga   7320

aaacaaaggg ccatattaat tgaagggctc acctctaaac aggtgagtga cttaaggact   7380

tcagacacac actggtcaac tacaaactag tcagtaaagg aatagccata gtcctatagc   7440

cccagttcct atggcccagg gggatccact agttctagag cggccgccac cgcggtggac   7500

tccag                                                               7505
```

<210> SEQ ID NO 14
<211> LENGTH: 529
<212> TYPE: DNA
<213> ORGANISM: BAC-F2 contig 15

<400> SEQUENCE: 14

```
gctgaggtgc atcgcggtgg cggacgctct agaactagtg gatccccaaa caaaacctgt     60

ccctgctaat gatggtagac ccaatcagat ccccggagaa gccgaaatac ggaaaccata    120

tcagcatacg catggcatac atagaacccc atacatggat tgcttactca gccagatata    180

gaaatctatc ttcacgatag agatatatat atatagacac actgcatata cagatgtgag    240

atggaggctc actctgccac ccgtgctgga tctacagtgg cacaagctca gtccacagtc    300

acgtcgatct gccgggcgtg accgactgag atgcagcggc ctcgggcgta gctgtgagta    360

cacgcaccag tcatcgcgac tggctgcaag tggtataagc ggaggggaca gggttacagc    420

atgacggcta ggcaggccgc aaactgagga ccacaagagt gccacgctgc ccgaacgcat    480

gcagtggcga gattacatgg ggcagccact agagccgccg tatcagaaa               529
```

-continued

<210> SEQ ID NO 15
<211> LENGTH: 635
<212> TYPE: DNA
<213> ORGANISM: BAC-F2 contig 33

<400> SEQUENCE: 15
taccacgcgg tagcgccgct ctagaactag tggatcgggt aatccagcac tttgggaggc 60
caaggagggc agatcacctg aagtcaggag tttgagacca gcctggccaa catggtgaaa 120
ctccatctct actaaaatta caaaaattag ccgggcgtgg tggcgcatgc ctgtaatccc 180
agctactcga gaggctgcgg catgacagtc actcaagccc gggaggtaga ggttgcagtg 240
agctgagatt gtgccactgc actccagcct gggtggcaga gtgagaccct gtctaaaaaa 300
aaaaaaaaaa aaaggcccat taggggaccc aaacggttcc ccagctttgt tggatttccc 360
caaatttggg gccaattttt ggagggttgt cccttaaaaa tttaaatttg ggggtttttt 420
tccaggcgcc cattagaaat gggttccgaa aattttttgg ccaaaaaaat ttggtttaac 480
cgcggaccaa aatcctaagg tttaactttt tcctaaacct tttagaattt aaagtttccg 540
gggtttctca ggagggggta acccttcacc ccaatataac tcggaaaccc cccttttttta 600 ggaaaagggg aattagtggt gctttccggg ccaaa 635

<210> SEQ ID NO 16
<211> LENGTH: 938
<212> TYPE: DNA
<213> ORGANISM: BAC-F2 contig 39

<400> SEQUENCE: 16
cccagggacc aagcgagtgc gaccgctcta gaactagtgg atcccccttg aagactatat 60
ttcttttcat cacgtgctat aaaaataatt ataatttaaa ttttttaata taaatatata 120
aattaaaaat agaaagtaaa aaaagaaatt aaagaaaaaa tagtttttgg tttccgaaga 180
tgtataatag gttgaaagtt agaaattatt attataatag caaaaaaaat ttaaagttag 240
aaattagaat ttaaggctct acacacgttt acgatgatat tggacgaacg acacgattag 300
acagttgtag gttgtgtgtt gtgatgtttt tgagtgattt gtagtgttta accttgtggt 360
ttggaaaggt ngtatgagta ttaatctcgg gcttattggg aggtttatgt gcaatgcatt 420
ttgtggtttt tttataatgt tgtgtttagg gttaaaacct gttgtgtata ttgtgttggt 480
ttgttgcttg tttgtacatt ggtatgatgc ctntttttgct tatgggttng gtgtttggtt 540
ttggttgtgt tttttgtggt gtgttgtttg atagttttag cggttgtttt tgggttgttg 600
ttttatgttg tggtggtgtt ttgtgtgtag agttgtggtt tgtgtgtttt gttggttgtg 660
ttgtggtatt gtttatgttt gtcgtgtgta tggtttgttg ttagtcgttg ttgtaggctt 720
gtgtgttgtg tgttgtgtgt gcgtgtggtc tagtttgggt ggtattgttg atttagtgtg 780
atagtctgtt agagtttggg ttgttgtgtg tattgggttt gtctgtgtgt ggtttttttg 840
tgggtgtaga tgatgatttg tgtatgtggg tgaggtatat gttatttgtg gtatttcggt 900
tgtgatgtgt tggttattat gtgtttgtta tgtgtatt 938

<210> SEQ ID NO 17
<211> LENGTH: 1145
<212> TYPE: DNA
<213> ORGANISM: BAC-F2 contig 41

<400> SEQUENCE: 17
gtctccgagc tcaccgcggt ggcggccgct ctagaactag tggatccccc gctctcactc 60

-continued

```
cctgactctt gccttctgta acaactggag acaactcttt caaaaccagc tccaagcccc    120
agacttctct ctgggcttta gttcgtaagg caggtgccct actgagtgag cctagatcag    180
acagaaacat agctgttggc aaggatttag gtgaatttcc ttccattgtt tttctaatac    240
ctttttttttt ttttggaaaa tataaccatg cacctacaca catatttgaa tatcctgcct    300
ttttatttaa aatgacatga taggtccggg agtggtggct catgcctgta atcccagcac    360
tttgggaggc cgaggtgggc agatcacctg aggtcaggag ttcgagacca gcctggccaa    420
catggtgaaa ctccatctct actaaaaatc aaaaattagc cgggcatggt ggcaggctcc    480
cagctactca ggaggctgag atgtgaaaat cgcttgaacc cgggaggtag aggttgcagt    540
gagctgagat cttgccattg cactccagcc tgggcaataa gagcgaaact ccatctcaaa    600
aaaaaaaaaa aaaacccagg gataaacttt ccaaaaggcc ccaaaaaggg gcatgattaa    660
gacaataaat tagtcgaaaa ttgtcaatat aaatgaataa taattttttt ggccattctg    720
ccaagtggca taaccctgtc attctgccca ttcggcaact ctttttcctc ccggggaatc    780
gctcccactt tttgcatggg ttttggatgg aactgttggt cacaggtttt tcacccccat    840
ttggccctcc cagaggtgta caaagtaccc cagcctggcc ctttttcacc caattttccc    900
aggtatattc ccccggtttt ggtcccaggt tttaaccccc ccctccaaag ggctttgggt    960
tttggaagga ttaagtcctc gaaataggcc cctcataata cctggggggg ggaccttttt   1020
caaagttgtg ggcacctctt gtgtcgcccc cacgggggac tgatgtattt acgccccntt   1080
ggggnntaat atggattgnt atgtattggg cgaggagaaa atatttttga tggggttttt   1140
ctctt                                                               1145
```

<210> SEQ ID NO 18
<211> LENGTH: 852
<212> TYPE: DNA
<213> ORGANISM: BAC-F2 contig 42

<400> SEQUENCE: 18

```
tcaccgcggt ggcggccgct ctagaactag tggatccccc gttttgctct ctccttagaa     60
tgagctggga actagtcact cttgttttct cacctataat agcatctggg tccagtgttt    120
tttatgtggg acaaatttga acttgtggtc aacctcttta attgtaagaa tattcaggtc    180
ttttgttctt cctgggctag ttttttattc tttttctaga gattcgttca tttttcttag    240
ttttatttgc ctataattgt ggataatctg ttttttatct gctacttctg taattatttc    300
cacatttgat ttataatatt aacttgtggg ccaggcgtcg tggctcacac ctgtaatccc    360
agcactttgg gaggccgagg cgggcggatc acgaggtcaa gagattgagg tgaaaccccc    420
tctctactaa aagtagaaaa attagctggg catggtggtg cgtgcctgta atcccagcta    480
ctcaggagac tgaggcaggg aatctcttga acccaggagg cagaggttgc ggtgagccaa    540
gattgcacca cggcactcca gcctggtgac agagcgagac tccatctcaa aaaaagaaaa    600
aaaaaaaact gtcaaatgat actccaaaat ggttgtacca ttttatattt gcaacaacaa    660
tgtctgaggg tactgattgc tccatatcct tgacagcact tggtatagcc gatcctttaa    720
ttttaggcac tttaaggggg caaatacctg ggattttaaa ggtttaacct ttttattttc    780
ccaaatgggt taataggttc tcagcaactt ttcaaggggc ctaattcccc ccttcaaaat    840
aacctcccct gg                                                        852
```

<210> SEQ ID NO 19
<211> LENGTH: 1854

-continued

<212> TYPE: DNA
<213> ORGANISM: BAC-F2 contig 44

<400> SEQUENCE: 19
ccggcactca ccgcggtggc ggccgctcta gaactagtgg atccccggaa atgttacttc 60
caacatttta gaactgaaat gattcttagt ctggtgataa atgtcaatta aaatagttct 120
cctttcacag agaaaattaa gaaaaaatta gttcaagaaa atatcaatca tgattgccag 180
cggaaatttg tttctgcagt aaaacaagca aaacaaatca aatccattaa aactagcaac 240
agactgtctt ctaaagtcaa gttcacatct ggagattttt ataaacttta ttggaaaagt 300
tctggttatc tatattttta gcatagcaaa atattcttct tgtttgttga atttgatata 360
aaatgttatt tttagccaag tcctggggca actcctacat ggctggaaaa tgttctcggt 420
gttaacaaag atgcaaagat cttaaatatt aatgttatca atcaactgga tactcttaag 480
tattatttgt aattatgtcc aatgtcatca ccacagggct gaccaacaag caaagagctg 540
acagtagtag caaaatgtag aaatctctgg taagcatgtt gtgtttatca atcctcttca 600
aatagatgaa attaaattgc atttaaagaa tgttacttat attaggcatt ttttgtgaaa 660
gacgttttaa actatggtgt cagaaaacag aaatactaaa cagaatgcat ttaacaggac 720
cttgaaatca ctgaatactc acctgtgtaa aagtcaaagt tcagataatt gaaatgttct 780
tactagtctc aagatgtctt ttggttacat agaaatttcc atgctgaatt ttgatttttt 840
taaaaagcca ttaatatgag tcaaaatcca ttatttcaca agtaaatgac ctttttatta 900
aaaaaaaaaa agagagagag agaagagcaa ggaaccaccc acatctaacc tcttaaatct 960
gagatcaata tatcaaaatt ttaatgtaca ttgaaaacat tttcatttta ttccacacac 1020
taccttttct tcataatttc ttattctgga catatagcag ttttttttgt cttttaaaac 1080
aggaaaaata aacaaacatg gtcttattat tgttactaag tcacaggtag taaagatggg 1140
accaggagaa ccttggagga ctagaaactt ctcaagagta gttagatttc acattcagag 1200
ggaggactca gagtcctgcc tgggacatac atttgcattc taggctcaag agcaaatatg 1260
tcagctttcc tttggtcaaa caatctttgc tacaggtcct aggtagttat atcagtggaa 1320
cctactaaag atgatggaat ttgtggtatt tcagggtagg aggtaaagtc ttagcaggct 1380
caactataca tgatcttaaa actaaatttg aaatgcagat gttctatgag ttagttggat 1440
attgtagtta tcccatctat caactgatca catttggtat gagcttgtta gttctgatta 1500
ggactcatct caacataata agaagggtgg catttagggc ccagtgtggg ggcctagtga 1560
tcactgctgg gacactgctt ctaaatcaac ataactaacc tctctaggat ggcaggctga 1620
ggctgctcaa gtacttcctg tctggcatct gggacagggc tgagtctctg ggtgggaaga 1680
tgggtgggag gactgaggct gatgagtata tgatataaat gagagccatt ggaatggctc 1740
cacatacagg acatgttgat aaatcatttt aacatatttt gctttctctc tctggtggcc 1800
cattgagaat caaaaggggg atccactagt tctagagcgg ccgccaccgc ggta 1854

<210> SEQ ID NO 20
<211> LENGTH: 1101
<212> TYPE: DNA
<213> ORGANISM: BAC-F2 contig 47

<400> SEQUENCE: 20
ccaccttttc aattcatcat ttttttttta ttcttttttt tgatttcggt ttccttgaaa 60
tttttttgat tcggtaatct ccgaacagaa ggaagaacga aggaaggagc acagacttag 120

-continued attggtatat atacgcatat gtagtgttga agaaacatga aattgcccag tattcttaac 180
ccaactgcac agaacaaaaa cctgcaggaa acgaagataa atcatgtcga aagctacata 240
taaggaacgt gctgctactc atcctagtcc tgttgctgcc aagctattta atatcatgca 300
cgaaaagcaa acaaacttgt gtgcttcatt ggatgttcgt accaccaagg aattactgga 360
gttagttgaa gcattaggtc ccaaaatttg tttactaaaa acacatgtgg atatcttgac 420
tgatttttcc atggagggca cagttaagcc gctaaaggca ttatccgcca agtacaattt 480
tttactcttc gaagacagaa aatttgctga cattggtaat acagtcaaat tgcagtactc 540
tgcgggtgta tacagaatag cagaatgggc agacattacg aatgcacacg gtgtggtggg 600
cccaggtatt gttagcggtt tgaagcaggc ggcagaagaa gtaacaaagg aacctagagg 660
ccttttgatg ttagcagaat tgtcatgcaa gggctcccta tctactggag aatatactaa 720
gggtactgtt gacattgcga agagcgacaa agattttgtt atcggcttta ttgctcaaag 780
agacatgggt ggaagagatg aaggttacga ttggttgatt atgacacccg gtgtgggttt 840
agatgacaag ggagacgcat tgggtcaaca gtatagaacc gtggatgatg tggtctctac 900
aggatctgac attattattg ttggaagagg actatttgca aagggaaggg atgctaaggt 960
agagggtgaa cgttacagaa aagcaggctg ggaagcatat ttgagaagat gcggccagca 1020
aaactaaaaa actgtattat aagtaaatgc atgtatacta aactcacaaa ttagagcttc 1080
aatttaatta tatcagttat t 1101

<210> SEQ ID NO 21
<211> LENGTH: 120
<212> TYPE: DNA
<213> ORGANISM: BAC-F2 contig 47 fragment 1

<400> SEQUENCE: 21
aactaatgta tcccccgggc tgcaggaaca cgatataaag ccttaaaatt gtgcgaatgt 60
grtaagtcga tccaatctca actgctatct rtgtaccaga atagtttcat aattacgtgt 120

<210> SEQ ID NO 22
<211> LENGTH: 300
<212> TYPE: DNA
<213> ORGANISM: BAC-F2 contig 47 fragment 2

<400> SEQUENCE: 22
gaattctctg wkattakaac tatcttgmct caaattsact tggtgagcta acctggcctg 60
tggtcccttg gctttaatgg aggctttgtc atatagatca tmtgtggtac tkgtgcctag 120
ttgtagtgcc ctgccttgct sttctwggct tactkgattt wggggtatac atcwatktaa 180
ytsaaaggtc tttctcctcc cgyygggaga atttctcctc ctccctcgga gaactctttc 240
tsccgaaatt ctattccggg ctgggtctcc attctgctta cctcccacac ttttaatmaa 300

<210> SEQ ID NO 23
<211> LENGTH: 599
<212> TYPE: DNA
<213> ORGANISM: BAC-F2 contig 47 fragment 3

<400> SEQUENCE: 23
gaattccctc ttgcttgggg gaggtcagcc ttttgttcta ttcaaatctt tgaggaaaat 60
agaaagcaaa gaatatatta actatattaa acaaactaaa tgttccaatt aaaatacaaa 120
aattataaag cctaataata aaagccctca attatatgct gtttaaaaga gacattttta 180
agcttaagga tatagaaaag ttgaaaataa aagaatggaa taaaataagc catgaaaata 240

-continued

```
ctagtataac actgatgtca aaatctgaca aagcacacaa aaaagaaaat aactttaact    300

gcaaaatctt aaaatcctag caaagaaaaa gcagcatatg ttataattat accacaacct    360

gatcaagtaa ggcttacttc aaaaatttaa ccatggtcca ttattggaaa acatattaat    420

aaaaatcctc acaaaaataa ttcaaaatat aaaaagccat atgataagcc tgatgaatgc    480

tggtttacag aactggtttt ctttaaaaag gcaatcattg ggaaataac ccgcttactc    540

agtatttact atgtgctagc cctgttcctt ctactagaaa ttagtgaaca aattctaac     599
```

<210> SEQ ID NO 24
<211> LENGTH: 330
<212> TYPE: DNA
<213> ORGANISM: BAC-F2 contig 47 fragment 4

<400> SEQUENCE: 24

```
aagctttcaa gaacagggac tgttaagccg ggtacagtgg ctcacaccta taatcctagc     60

attttgggag gccaaggcgg gtggatcact tgaggtcagg agttcaagac cagcctggcc    120

aacatggtga aaccccatct ctactaaaaa aaaaaaaaaa aaaaaaaaaa aaagaaatwc    180

maaaattacc caggcatggt ggcacgcgcc tgtaatccca kctacttggg aggctgaggc    240

aggaaaattg cttgaaccta ggaggcggag gtggcagtga cctaatcaca ccactgttct    300

ccatcctggg caacagaacg aaactgtttc                                     330
```

<210> SEQ ID NO 25
<211> LENGTH: 258
<212> TYPE: DNA
<213> ORGANISM: BAC-F2 contig 47 fragment 5

<400> SEQUENCE: 25

```
aagcttgggt gataatgagg agtcaatgtt ggtccatcaa ttgcaacaaa ggtaccacag     60

tggtgtagga tgtggataat gaggaggctg tgcacgtgtt ggggacaggt ggtatttacg    120

aatgctctat attttctttc tctctttttt taggacggag tctcactctg ttgcccacgc    180

tggaatgcay gggcatgact gtggctcact gtacccccca ctccccatgt tcaagagatt    240

ctcttgcctc acctcctg                                                  258
```

<210> SEQ ID NO 26
<211> LENGTH: 622
<212> TYPE: DNA
<213> ORGANISM: BAC-F2 contig 47 fragment 6

<400> SEQUENCE: 26

```
ctcgagtcca ccgcggtggc ggccgctcta gaactagtgg atcccccgat ttatttaaag     60

cagttatgta tgtatgaaaa acaatgctga gcattcaatt ccaagatttc tgaagacacc    120

tattttacca tcactttgaa taaaattttt atattccttt cttcaaatac catctcggtt    180

ttcaaatgtg gctcattaaa tgtgaaagca aaatttcatt tcaaatagca gccttatcaa    240

atgacaattt acctgtggta gcattgttgg cactgacaca tatcagacca ctgccgagca    300

gaacaagaat gaaccaggaa tccatgctta tctggaaaat agggagtcat gttagatgag    360

gtcctatatt atcaggacta tgtctgagct ggtcaccaga agagtattct ggatttccaa    420

gctattaaaa tgtgtgccta aaccaatgat cttttgggag cctgatatgc atgcttcctc    480

agatatccaa taactaattg agtctttata aagactgact atcccttatc ttgaggacta    540

gcagtgtttc agattttttt taagagatag ggtcttgctc tgttgccagg atggagacag    600
```

-continued

```
tggttatgat catagctcag tg                                          622


<210> SEQ ID NO 27
<211> LENGTH: 602
<212> TYPE: DNA
<213> ORGANISM: BAC-F2 contig 47 fragment 7

<400> SEQUENCE: 27

tcggactcca ccgcggtggc ggccgctcta gaactagtgg atcccccggg ccctcaggac    60

tgctgggctg cctggtgtca gcacttcccg ccattttcta tagcaccagt attattctta   120

atactttaaa aaaccaccag gcacggtggc tcacgcctgg aatcccagca ctttgggagg   180

ccaaggtggg cggatcacaa ggtcaggaga tcaagaccat cctggctaac acggtgaaac   240

cctgtctgta ctaaaaatag aaaaaaatta gctgggcgtg gtggcatgca cctgtagtcc   300

cagctgctgg ggaggctgag gcaggagaat ggcgtgaacc cgggaggcgg acttgcagtg   360

agccgagatt gcaccactgc actccagcct gggtgacaga gcgagacccc gtctcaaaaa   420

aaaaaagtaa ataaaaataa aaaaccatat cccactatct ccccttctc tctttgcctg   480

tgactannng gcatacttat ggggaaatct ttaagatgtc agatttcagt tctctcactt   540

ttctacaact tctccccatt ttgcctttct taggaacttc ccttcttccc atctgattcc   600

tn                                                                 602


<210> SEQ ID NO 28
<211> LENGTH: 546
<212> TYPE: DNA
<213> ORGANISM: BAC-F2 contig 47 fragment 8

<400> SEQUENCE: 28

tatcaaggcg gagtccacgg tggcggccgc tctagaacta gtggatcccc gaaccaggaa    60

tccatgctta tctggaaaat agggagtcat gttagatgag gtcctatatt atcaggacta   120

tgtctgagct ggtcaccaga agagtattct ggatttccaa gctattaaaa tgtgtgccta   180

aaccaatgat cttttgggag cctgatatgc atgcttcctc agatatccaa taactaattg   240

agtctttata aagactgact atcccttatc ttgaggacta gcagtgtttc agattttttt   300

taagagatag ggtcttgctc tgttgcccag gatggagaca gtggttatga tcatagctca   360

gtgcagcctc tacctcctgg actcaagtga tccttctgtc tcagcctcct gagtagctgg   420

gactataggc atgtactacg atgcctggct aatttttaaa attttctgta gagacggcgt   480

ctcactatgt tgtctaggct gctctcaaac tcttgggttc aactgatctc ttgcttcaac   540

ttccag                                                             546


<210> SEQ ID NO 29
<211> LENGTH: 498
<212> TYPE: DNA
<213> ORGANISM: BAC-F2 contig 47 fragment 9

<400> SEQUENCE: 29

gtggattcag acgcggtggc ggccgctcta gaactagtgg atcccccgag cagaggttgc    60

agtgagccaa gatcgtgcta ctgtactcca gcctgggcaa cagagcaaga ctccgtctca   120

aaaaaaaaaa caaacaaacg atgtgtgcct gtgtttcctc atctgtagta tgaggataat   180

gatcatatat atttactagt gttgttggga tgatcaaatt aggtatattt aatcattgtg   240

taaaaaagtt gacgtgtaaa atccatgtaa aaaagttggc agaagagaca aactggtaaa   300

gcagccgttc ttcatttctc atttcattca acaagcatta ttaacagcct agcaagaaca   360
```

-continued

```
cagtatccag gaaaaatcaa agattatcaa gctcatgttc tataatcaag caatttataa    420

actagcagaa gaacaagaca gatgaataag aacttgggta tatttaaatg ctaagaagtt    480

caattcaaat aaatgtcc                                                  498
```